United States Patent
Rana et al.

(10) Patent No.: US 11,136,301 B2
(45) Date of Patent: Oct. 5, 2021

(54) BROAD SPECTRUM ANTIVIRAL COMPOUNDS AND USES THEREOF

(71) Applicants: The Regents Of The University Of California, Oakland, CA (US); The University of Miami, Miami, FL (US)

(72) Inventors: Tariq M. Rana, San Diego, CA (US); Mario Stevenson, Miami, FL (US)

(73) Assignee: The Regents of the University of California, A California Corporation et al., Oakland, CA (US)

( * ) Notice: Subject to any disclaimer, the term of this patent is extended or adjusted under 35 U.S.C. 154(b) by 110 days.

(21) Appl. No.: 15/754,877

(22) PCT Filed: Aug. 31, 2016

(86) PCT No.: PCT/US2016/049744
§ 371 (c)(1),
(2) Date: Feb. 23, 2018

(87) PCT Pub. No.: WO2017/040693
PCT Pub. Date: Mar. 9, 2017

(65) Prior Publication Data
US 2018/0297963 A1    Oct. 18, 2018

Related U.S. Application Data

(60) Provisional application No. 62/334,682, filed on May 11, 2016, provisional application No. 62/329,848, filed on Apr. 29, 2016, provisional application No. 62/212,499, filed on Aug. 31, 2015.

(51) Int. Cl.
| | | |
|---|---|---|
| *C07D 271/07* | (2006.01) | |
| *C07D 271/06* | (2006.01) | |
| *C07D 249/06* | (2006.01) | |
| *C07D 271/107* | (2006.01) | |
| *C07D 413/04* | (2006.01) | |
| *A61P 31/18* | (2006.01) | |

(52) U.S. Cl.
CPC ............ *C07D 271/07* (2013.01); *A61P 31/18* (2018.01); *C07D 249/06* (2013.01); *C07D 271/06* (2013.01); *C07D 271/107* (2013.01); *C07D 413/04* (2013.01)

(58) Field of Classification Search
CPC .............. C07D 271/07; C07D 271/107; C07D 249/06; C07D 413/04
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |

| | | |
|---|---|---|
| 2005/0154012 A1 | 7/2005 | Cai et al. |
| 2008/0255216 A1* | 10/2008 | Aster ...................... A61P 25/28 514/383 |
| 2011/0015149 A1 | 1/2011 | Almond et al. |

OTHER PUBLICATIONS

STN Registry entry for CAS RN 1348842-36-3, Entered STN Dec. 5, 2011, Accessed Sep. 18, 2018.*
STN Registry database entry for CAS RN 1973508-62-1, entry date Aug. 16, 2016; Accessed Mar. 4, 2019.*
Ito et al. in Cancer Science 94(1), 3-8 (2003).*
STN Registry database entry for CAS RN 1337553-40-8, entry date Oct. 19, 2011; Accessed Feb. 25, 2020.*
STN Registry database entry for CAS RN 852851-58-2, entry date Jun. 23, 2005; Accessed Feb. 25, 2020.*
Mohammed et al., J. Med. Chem., 2016, 59, p. 7677-7682.*
Bishop, K.N. et al. (Dec. 2008, e-published Dec. 5, 2008). "APOBEC3G inhibits elongation of HIV-1 reverse transcripts," *PLoS Pathog* 4(12):e1000231.
Borg, S. et al. (Oct. 21, 1999). "Design, synthesis, and evaluation of Phe-Gly mimetics: heterocyclic building blocks for pseudopeptides," *J Med Chem* 42(21):4331-4342.
Cullen, B.R. (Feb. 2006). "Role and mechanism of action of the APOBEC3 family of antiretroviral resistance factors," *J Virol* 80(3):1067-1076.
Goff. S.P. et al. (Dec. 22, 2004). "Retrovirus restriction factors," *Mol Cell* 16(6):849-859.
Grimes, K.D. et al. (May 1, 2010). "Copper(II)-Catalyzed Conversion of Aryl/Heteroaryl Boronic Acids, Boronates, and Trifluoroborates into the Corresponding Azides: Substrate Scope and Limitations," *Synthesis* 2010(9):1441-1448.
Hicks, C. et al. (Apr. 1, 2009). "Raltegravir: the first HIV type 1 integrase inhibitor," *Clin Infect Dis* 48(7):931-939.
Jäger, S. et al. (Jan. 2012). "Vif hijacks CBF-beta to degrade APOBEC3G and promote HIV-1 infection," Nature 481(7381):371-375.
Johnson, V.A. et al. (Dec. 2010). "Update of the drug resistance mutations in HIV-1: Dec. 2010," *Top HIV Med* 18(5):156-163.
Kwong, F.Y. et al. (Oct. 3, 2002). "A general, efficient, and inexpensive catalyst system for the coupling of aryl iodides and thiols," *Org Lett* 4(20):3517-3520.
Lee, W.G. et al. (Oct. 13, 2014). "Picomolar Inhibitors of HIV-1 Reverse Transcriptase: Design and Crystallography of Naphthyl Phenyl Ethers," ACS Med Chem Lett 5(11)1259-1262.
Liang, G-B. et al. (Sep. 1996). "An improved oxadiazole synthesis using peptide coupling reagents," *Tetrahedron Letters* 37(37):6627-6630.
Luo, K. et al. (Jul. 2007, e-published Apr. 11, 2007). "Cytidine deaminases APOBEC3G and APOBEC3F interact with human immunodeficiency virus type 1 integrase and inhibit proviral DNA formation," *J Virol* 81(13):7238-7248.
Malim, M.H. et al. (May 2012). "HIV Restriction Factors and Mechanisms of Evasion," *Cold Spring Harb Perspect Med* 2(5):a006940.
Manetsch, R. et al. (Oct. 13, 2004). "In situ click chemistry: enzyme inhibitors made to their own specifications," *J Am Chem Soc* 126(40):12809-12818.

(Continued)

*Primary Examiner* — Alicia L Otton
(74) *Attorney, Agent, or Firm* — Fish & Richardson P.C.

(57) ABSTRACT

Disclosed herein, inter alia, are agents having antiviral activity and methods of use thereof.

16 Claims, 40 Drawing Sheets

Specification includes a Sequence Listing.

(56) References Cited

OTHER PUBLICATIONS

Mehle, A. et al. (Feb. 27, 2004, e-published Dec. 13, 2003). "Vif overcomes the innate antiviral activity of APOBEC3G by promoting its degradation in the ubiquitin-proteasome pathway," *J Biol Chem* 279(9):7792-7798.
Mohammed, I. et al. (Jun. 14, 2012). "SAR and Lead Optimization of an HIV-1 Vif-APOBEC3G Axis Inhibitor," *ACS Med Chem Lett* 3(6):465-469.
Prochnow, C. et al. (2009). "The prosecpect of APOBEC3G for the future of HIV therapy," *HIV Ther.* 2009, 3(1):7-10.
Ren, J. et al. (Jun. 2008, e-published Mar. 3, 2008). "Structural basis for drug resistance mechanisms for non-nucleoside inhibitors of HIV reverse transcriptase," Virus Res 134(1-2):157-170.
Rostovtsev, V.V. et al. (Jul. 15, 2002). "A stepwise huisgen cycloaddition process: copper(I)-catalyzed regioselective "ligation" of azides and terminal alkynes.," *Angew Chem Int Ed Engl* 41(14):2596-2599.
Samant, R.S. et al. (May 6, 2014, e-published Apr. 23, 2014). "E3 ubiquitin ligase Cullin-5 modulates multiple molecular and cellular responses to heat shock protein 90 inhibition in human cancer cells," *PNAS USA* 111(18):6834-6839.
Shaabani, A. et al. (Dec. 6, 2004). "Green oxidations. The use of potassium permanganate supported on manganese dioxide," *Tetrahedron* 60(50):11415-11420.
Sheehy, A.M. et al. (Aug. 8, 2002, e-published Jul. 14, 2002). "Isolation of a human gene that inhibits HIV-1 infection and is suppressed by the viral Vif protein," *Nature* 418(6898):646-650.
Sonogashira, K. et al. (1975). "A convenient synthesis of acetylenes: catalytic substitutions of acetylenic hydrogen with bromoalkenes, iodoarenes and bromopyridines," *Tetrahedron Letters* 16(50):4467-4470.
Sperotto, E. et al. (Jul. 18, 2008, e-published Jun. 21, 2008). "Ligand-free copper-catalyzed C-S coupling of aryl iodides and thiols," *J Org Chem* 73(14):5625-5628.
Tam, A. et al. (Oct. 24, 2007, e-published Oct. 3, 2007). "Protein prosthesis: 1,5-disubstituted[1,2,3]triazoles as cis-peptide bond surrogates," *J Am Chem Soc* 129(42):12670-12671.
Tang, J. et al. (Apr. 14, 2011, e-published Mar. 7, 2011). "3-Hydroxypyrimidine-2,4-diones as an inhibitor scaffold of HIV integrase," *J Med Chem* 54(7):2282-2292.
Tao, C-Z. et al. (May 14, 2007). Copper-catalyzed synthesis of aryl azides and 1-aryl-1,2,3-triazoles from boronic acids, *Tetrahedron Letters* 48(20):3525-3529.
Thompson, M.A. et al. (Jul. 21, 2010). "Antiretroviral treatment of adult HIV infection: 2010 recommendations of the International AIDS Society-USA panel," *JAMA* 304(3):321-333.
Tornøe, C. et al. (May 3, 2002). "Peptidotriazoles on solid phase: [1,2,3]-triazoles by regiospecific copper(i)-catalyzed 1,3-dipolar cycloadditions of terminal alkynes to azides," *J Org Chem* 67(9):3057-3064.
Tron, G.C. et al. (Mar. 2008). "Click chemistry reactions in medicinal chemistry: applications of the 1,3-dipolar cycloaddition between azides and alkynes," *Med Res Rev* 28(2):278-308.
Turelli, P. et al. (Mar. 19, 2004). "Inhibition of hepatitis B virus replication by APOBEC3G," *Science* 303(5665):1829.
Valverde, I.E. et al. (Aug. 19, 2013, e-published Jul. 5, 2013). "1,2,3-Triazoles as amide bond mimics: triazole scan yields protease-resistant peptidomimetics for tumor targeting," *Angew Chem Int Ed Engl* 52(34):8957-8960.
Volberding, P.A. et al. (Jul. 3, 2010). "Antiretroviral therapy and management of HIV infection," *Lancet* 376(9734):49-62.
Yu, Y. et al. (Dec. 1, 2004). "Selective assembly of HIV-1 Vif-Cul5-ElonginB-ElonginC E3 ubiquitin ligase complex through a novel SOCS box and upstream cysteines," *Genes Dev* 18(23):2867-2872.
Zhang, L. et al. (Nov. 23, 2005). "Ruthenium-catalyzed cycloaddition of alkynes and organic azides," *J Am Chem Soc* 127(46):15998-15999.
Zhang, W. et al. (Jan. 19, 2012). "T-cell differentiation factor CBF-beta regulates HIV-1 Vif-mediated evasion of host restriction," *Nature* 481:376-379.
International Search Report dated Nov. 17, 2016, for PCT Application No. PCT/US2016/049744, filed Aug. 31, 2016, 3 pages.
Written Opinion dated Nov. 17, 2016, for PCT Application No. PCT/US2016/049744, filed Aug. 31, 2016, 3 pages.
Albin et al., "Interactions of host APOBEC3 restriction factors with HIV-1 in vivo: implications for therapeutics," Expert Rev. Mol. Med., 2010, 12:e4.
Ali et al., "Synthesis and structure-activity relationship studies of HIV-1 virion infectivity factor (Vif) inhibitors that block viral replication," ChemMedChem, 2012, 7:1217-1229.
Al-Muhammed, "In-vivo studies on dexamethasone sodium phosphate liposomes," J. Microencapsul., 1996, 13:293-306.
Altman et al., "HIV-1 Protease Inhibitors from Inverse Design in the Substrate Envelope Exhibit Subnanomolar Binding to Drug-Resistant Variants," J. Am. Chem. Soc., 2008, 130, 6099.
Arhel et al., "Host Proteins Involved in HIV Infection: New Therapeutic Targets," Biochim. Biophysic. Acta, 2010, 1802:313.
Berge et al., "Pharmaceutical Salts", Journal of Pharmaceutical Science, 1977, 66, 1-19.
Bergeron et al., "The SOCS-box of HIV-1 Vif interacts with ElonginBC by induced-folding to recruit its Cul5-containing ubiquitin ligase complex," PLoS pathogens, 2010, 6:e1000925.
Bishop et al., "APOBEC3G Inhibits Elongation of HIV-1 Reverse Transcripts," PLoS Pathogens, 2008, 4:e1000231.
Blagosklonny, "Hsp-90-associated oncoproteins: multiple targets of geldanamycin and its analogs," Leukemia, 2002, 16:455-462.
Borg et al., "Design, Synthesis, and Evaluation of Phe-Gly Mimetics: Heterocyclic Building Blocks for Pseudopeptides," J. Med. Chem. 1999, 42:4331.
Cai et al., "Decomposing the Energetic Impact of Drug Resistant Mutations in HIV-1 Protease on Binding DRV," J. Chem. Theory Comput. 2010, 6:1358.
Chonn et al., "Recent Advances in Liposomal Drug-Delivery Systems," Curr. Opin. Biotechnol., 1995, 6:698-708.
Ehrlich et al., "Regulation of Hsp90 client proteins by a Cullin5-RING E3 ubiquitin ligase," Proceedings of the National Academy of Sciences of the United States of America, 2009, 106:20330-20335.
Eyles, "Oral Delivery and Fate of Poly(lactic acid) Microsphere-encapsulated Interferon in Rats," J. Pharm. Pharmacol., 1997, 49:669-674.
Gabuzda et al., "Role of vif in replication of human immunodeficiency virus type 1 in CD4+ T. lymphocytes," J. Virol., 1992, 66:6489-6495.
Gao et al., "Controlled Release of a Contraceptive Steroid From Biodegradable and Injectable Gel Formulations: In Vitro Evaluation," Pharm. Res., 1995, 12:857-863.
Ghosh et al., "Design and Synthesis of Potent HIV-1 Protease Inhibitors Incorporating Hexahydrofuropyranol-derived High Affinity P2 ligands: Structure-activity Studies and Biological Evaluation," Med. Chem., 2011, 54:622.
Karagoz et al., "Hsp90 interaction with clients," Trends in biochemical sciences, 2015, 40:117-125.
Ko et al., "Universal Peptidomimetics," J. Am. Chem. Soc. 2011, 133:462.
Kumar et al., "Synthesis and Anticancer Activities of Novel 3,5-disubstituted-1,2,4-oxadiazoles," Bioorg. Med. Chem. Lett., 2009, 19:2739.
Lewis et al., Angew. Chem. Int. Ed. 2009, 41:1053.
Luo et al., "Cytidine Deaminases APOBEC3G and APOBEC3F Interact With Human Immunodeficiency Virus Type 1 Integrase and Inhibit Proviral DNA Formation," J. Virol. 2007, 81:7238.
Marin et al., "HIV-1 Vif protein binds the editing enzyme APOBEC3G and induces its degradation," Nature Med., 2003, 9:1398-1403.
Meanwell, "Synopsis of Some Recent Tactical Application of Bioisosterism in Drug Design," J. Med. Chem., 2011, 54:2529-2591.
Mehellou et al., "Twenty-Six Years of Anti-HIV Drug Discovery: Where Do We Stand and Where Do We Go?" J. Med. Chem., 2010, 53:521-538.

(56) References Cited

OTHER PUBLICATIONS

Mehle et al, "Phosphorylation of a novel SOCS-box regulates assembly of the HIV-1 Vif-Cul5 complex that promotes APOBEC3G degradation," Genes Dev., 2004, 18:2861-2866.

Mohammed, I. et al., "SAR and Lead Optimization of an HIV-1 Vif-APOBEC3G Axis Inhibitor," Acs Medicinal Chemistry Letters, 2012, 3:465-469.

Nathans et al., "Small-molecule inhibition of HIV-1 Vif," Nat. Biotechol. 2008, 26:1187-1192.

Navarro et al., "Recent insights into HIV-1 Vif," Curr. Opin. Immunol., 2004, 16:477-482.

Neil et al,. "Human Immunodeficiency Virus, Restriction Factors, and Interferon," Interferon Cytokine Res., 2009, 29, 569.

Ostro, "Use of liposomes as injectable-drug delivery systems," Am. J. Hosp. Pharm., 1989, 46:1576-1587.

Parai et al., "Design, Synthesis, and Biological and Structural Evaluations of Novel HIV-1 Protease Inhibitors to Combat Drug Resistance ," J. Med. Chem., 2012, 55, 6328.

Prohaska et al., "The multifaceted roles of RNA binding in APOBEC cytidine deaminase functions," Wiley interdisciplinary reviews. RNA, 2014, 5:493-508.

Rao, "Recent Developments of Collagen-Based Materials for Medical Applications and Drug Delivery Systems," J. Biomater Sci. Polym. Ed., 1995, 7:623-645.

Ren, "Structural Basis for Drug Resistance Mechanisms for Non-Nucleoside Inhibitors of HIV Reverse Transcriptase," Virus Res. 2008, 134:157.

Rostovtsev et al., "A Stepwise Huisgen Cycloaddition Process: copper(I)-catalyzed Regioselective "Ligation" of Azides and Terminal Alkynes," Angew. Chem. Int. Ed. 2002, 41:2596.

Sheehy et al., "The antiretroviral enzyme APOBEC3G is degraded by the proteasome in response to HIV-1 Vif," Nature Med., 2003, 9, 1404-1407.

Spekowitz, "AIDS—the First 20 Years ," N. Engl. J. Med., 2001, 344:1764.

Sperotto et al., "Ligand-free Copper-Catalyzed C-S Coupling of Aryl Iodides and Thiols ," J. Org. Chem. 2008, 73, 5625.

Stopak et al., "HIV-1 Vif blocks the antiviral activity of APOBEC3G by impairing both its translation and intracellular stability," Mol. Cell, 2003, 12:591-601.

Strebel et al., "The HIV A (sor) gene product is essential for virus infectivity," Nature 1987, 328:728-730.

Taipale et al., "HSP90 at the hub of protein homeostasis: emerging mechanistic insights. Nature reviews," Molecular cell biology, 2010, 11:515-528.

Tornøe et al., "Peptidotriazoles on Solid Phase: [1,2,3]-triazoles by Regiospecific Copper(i)-Catalyzed 1,3-dipolar Cycloadditions of Terminal Alkynes to Azides ," J. Org. Chem. 2002, 67:3057.

Trepel et al., "Targeting the dynamic HSP90 complex in cancer," Nature reviews, Cancer, 2010, 10:537-549.

Wolf et al., "Host restriction factors blocking retroviral replication," Annual review of genetics, 2008, 42:143-163.

Yu et al., "Induction of APOBEC3G ubiquitination and degradation by an HIV-1 Vif-Cul5-SCF complex," Science, 2003, 302:1056-1060.

\* cited by examiner

BROAD SPECTRUM ANTIVIRAL COMPOUNDS AND USES THEREOF

CROSS REFERENCES TO RELATED APPLICATIONS

This application is a national stage application filed under 35 U.S.C. § 371, of International Patent Application No. PCT/US2016/049744, filed Aug. 31, 2016, which claims the benefit of and priority under 35 U.S.C. § 119(e) to U.S. Provisional Application No. 62/212,499, filed Aug. 31, 2015, 62/329,848, filed Apr. 29, 2016, and 62/334,682, filed May 11, 2016, each of which are incorporated herein by reference and for all purposes.

STATEMENT AS TO RIGHTS TO INVENTIONS MADE UNDER FEDERALLY SPONSORED RESEARCH AND DEVELOPMENT

This invention was made with Government support under grant number 1 P01 MH100942 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048537-564N01US_ST25.TXT, created on Feb. 22, 2018, 6,278 bytes, machine format IBM-PC, MS-Windows operating system, is hereby incorporated by reference.

BACKGROUND

Vif is necessary for the replication of HIV-1 and promotes viral replication by neutralizing a host antiviral protein known as apobec 3. This host protein is a cytidine deaminase that introduces catastrophic levels of G to A hypermutations in viral cDNA. As such, those viral genomes are biologically incompetent. Vif eliminates apobec 3 proteins by linking them to the proteasornal machinery such that apobec 3 proteins are prematurely ubiquitylated and degraded in the proteasome.

Without wishing to be bound by any theory, agents that interfere with the action of Vif would be expected to preserve apobec 3 levels in the cell and render those cells resistant to HIV-1 infection.

Current antiretroviral agents target enzymatic functions of the virus. These include reverse transcription, protease processing of viral polyproteins and integration. HIV-1 encodes accessory proteins including Vif, vpu and nef and these proteins counteract cellular antiviral factors that otherwise would restrict viral replication. In the case of Vif, its function is to target the host factor Apobec 3 for proteasomal degradation. As viral replication is absolutely dependent on the ability of Vif to neutralize apobec 3 proteins, the Vif-apobec axis is an attractive antiviral target.

Provided herein, inter alia, are solutions to these and other problems in the art.

SUMMARY

In an aspect is provided a compound, or a pharmaceutically acceptable salt thereof, having the formula:

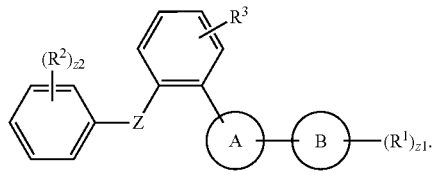

Ring A is a substituted or unsubstituted 5 membered heteroaryl. Ring B is a phenyl or 6 membered heteroaryl. $R^1$ is independently hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-NHNR^{1A}R^{1B}$, $-N(O)_{m1}$, $-NR^{1A}R^{1B}$, $-C(O)R^{1C}$, $-RC(O)OR^{1C}$, $-C(O)NR^{1A}R^{1B}$, $-ONR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $X^1$ is independently $-F$, $-Cl$, $-Br$, or $-I$. $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-NHNR^{2A}R^{2B}$, $-N(O)_{m2}$, $-NR^{2A}R^{2B}$, $-C(O)R^{2C}$, $C(O)OR^{2C}$, $-C(O)NR^{2A}R^{2B}$, $-ONR^{2A}R^{2B}$, $-OR^{2D}$, $-N^{RA}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $X^2$ is independently $-F$, $-Cl$, $-Br$, or $-I$. $R^3$ is independently hydrogen, halogen, $-CX^3_3$, $-CH-X^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-NHNR^{3A}R^{3B}$, $-N(O)_{m3}$, $-NR^{3A}R^{3B}$, $-C(O)R^{3C}$, $-C(O)OR^{3C}$, $-C(O)NR^{3A}R^{3B}$, $-ONR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^3$ is independently $-F$, $-Cl$, $-Br$, or $-I$. Each $R^{1A}$, $R^{1B}$, $R^{1C}$, $R^{1D}$, $R^{2A}$, $R^{2B}$, $R^{2C}$, $R^{2D}$, $R^{3A}R^{3B}$, $R^{3C}$, and $R^{3D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl. Each X is independently —F, —Cl, —Br, or —I. The symbols n1, n2, and n3 are independently an integer from 0 to 4. The symbols m1, m2, m3, v1, v2, and v3 are independently an integer from 1 to 2. Z is —S— or —SO$_2$—. z1 and z2 are independently an integer from 0 to 5.

In an aspect is provided a pharmaceutical composition including a compound (e.g., as described herein), or a pharmaceutically acceptable salt thereof, and a pharmaceutically acceptable excipient.

In an aspect is provided a method of treating a viral (e.g., HIV, Zika virus, Ebola virus, hepatitis virus (e.g., hepatitis A, hepatitis B, or hepatitis C)) infection in a subject in need thereof, the method including administering to the subject an effective amount of a compound (e.g., as described herein), or a pharmaceutically acceptable salt thereof.

In an aspect is provided a method of treating HIV infection in a subject in need thereof, the method including administering to the subject an effective amount of a compound (e.g., as described herein), or a pharmaceutically acceptable salt thereof.

In an aspect is provided a method of treating a hepatitis (e.g., hepatitis A, hepatitis B, or hepatitis C)) infection in a subject in need thereof, the method including administering to the subject an effective amount of a compound (e.g., as described herein), or a pharmaceutically acceptable salt thereof.

In an aspect is provided a method of treating Zika virus infection in a subject in need thereof, the method including administering to the subject an effective amount of a compound (e.g., as described herein), or a pharmaceutically acceptable salt thereof.

In an aspect is provided a method of treating Ebola virus infection in a subject in need thereof, the method including administering to the subject an effective amount of a compound (e.g., as described herein), or a pharmaceutically acceptable salt thereof.

In another aspect is provided a method of treating cancer in a subject in need thereof, the method including administering to the subject an effective amount of a compound (e.g., as described herein), or a pharmaceutically acceptable salt thereof.

In an aspect is provided a method of inhibiting (e.g., compared to control) Vif protein activity in a subject in need thereof, the method including administering an effective amount of a compound (e.g., as described herein), or a pharmaceutically acceptable salt thereof, to the subject.

In an aspect is provided a method of reducing (e.g., compared to control) the level of Vif protein in a subject in need thereof, the method including administering an effective amount of a compound (e.g., as described herein), or a pharmaceutically acceptable salt thereof, to the subject.

In an aspect is provided a method of increasing (e.g., compared to control) the level of an APOBEC3 family protein (e.g., a plurality of different APOBEC3 family protein members, or one member of the APOBEC3 family of proteins) activity in a subject in need thereof, the method including administering an effective amount of a compound (e.g., as described herein), or a pharmaceutically acceptable salt thereof, to the subject. In embodiments, the method includes reducing the association of an APOBEC3 protein with a degradation complex (e.g., as described herein) (e.g., compared to control).

In an aspect is provided a method of increasing (e.g., compared to control) the level of an APOBEC3 family protein (e.g., a plurality of different APOBEC3 family protein members, or one member of the APOBEC3 family of proteins) in a subject in need thereof, the method including administering an effective amount of a compound (e.g., as described herein), or a pharmaceutically acceptable salt thereof, to the subject. In embodiments, the method includes reducing the association of an APOBEC3 protein with a degradation complex (e.g., as described herein) (e.g., compared to control).

In an aspect is provided a method of inhibiting (e.g., compared to control) degradation of an APOBEC3 family protein (e.g., a plurality of different APOBEC3 family protein members, or one member of the APOBEC3 family of proteins) in a subject in need thereof, the method including administering an effective amount of a compound (e.g., as described herein), or a pharmaceutically acceptable salt thereof, to the subject. In embodiments, the method includes reducing the association of an APOBEC3 protein with a degradation complex (e.g., as described herein) (e.g., compared to control).

In an aspect is provided a method of increasing (e.g., compared to control) the level of APOBEC3G activity in a subject in need thereof, the method including administering an effective amount of a compound (e.g., as described herein), or a pharmaceutically acceptable salt thereof to the subject. In embodiments, the method includes reducing the association of APOBEC3G protein with a degradation complex (e.g., as described herein) (e.g., compared to control).

In an aspect is provided a method of increasing (e.g., compared to control) the level of APOBEC3G protein in a subject in need thereof, the method including administering an effective amount of a compound (e.g., as described herein), or a pharmaceutically acceptable salt thereof to the subject. In embodiments, the method includes reducing the association of APOBEC3G protein with a degradation complex (e.g., as described herein) (e.g., compared to control).

In an aspect is provided a method of inhibiting (e.g., compared to control) degradation of APOBEC3G protein in a subject in need thereof, the method including administering an effective amount of a compound (e.g., as described herein), or a pharmaceutically acceptable salt thereof, to the subject. In embodiments, the method includes reducing the association of APOBEC3G protein with a degradation complex (e.g., as described herein) (e.g., compared to control).

In an aspect is provided a method of inhibiting a degradation complex (e.g., as described herein) activity in a subject in need thereof, the method including administering an effective amount of a compound (e.g., as described herein), or a pharmaceutically acceptable salt thereof, to the subject (e.g., compared to control).

In another aspect, there is provided a method for inhibiting Vif protein activity in a subject in need thereof. The method includes administering an effective amount of a compound of Formula (I) to the subject (e.g., a compound described herein, including in embodiments).

In another aspect, there is provided a method for treating a viral infection. The method includes administering to a subject in need thereof a therapeutically effective amount of a compound according to Formula (I), and embodiments thereof.

In embodiments, the viral infection is HIV-1, Ebola virus or Zika virus infection, as known in the art. In embodiments, the viral infection is HIV-1. In embodiments, the viral infection is Ebola virus. In embodiments, the viral infection is Zika virus.

BRIEF DESCRIPTION OF THE DRAWINGS

FIG. 1A, Structures of the Vif antagonist RN-18, affinity probes, and control molecules used in the ViTAP experimental strategy. FIG. 1B, HSP90 is a target of Vif inhibitors. 293FT cells co-expressing HA-A3G and pNLA1-Vif or pNLA1-ΔVif were treated with 1% DMSO (vehicle), 10 μM IMD55, or 10 μM IMD64 for 16 h, then fresh compounds were added again for a further 30 min. Cells were UV irradiated to crosslink IMD55 and IMD64 to associated proteins. Compound-protein complexes were isolated by streptavidin affinity purification, resolved by SDS-PAGE, and subjected to silver staining. The 90 kDa protein co-purified from IMD55-treated cells was identified as HSP90 by mass spectrometry. FIG. 1C, HSP90 is targeted by IMA82. Experiments were performed as described for FIG. 1B, except cells were not UV irradiated. FIG. 1D, The RN-18 affinity probe, IMD40, binds HSP90. Experiments were performed as described for FIG. 1C, and the identity of HSP90 was confirmed by immunoblotting. FIG. 1E, HSP90 is required for Vif antagonist activity. H9 cells were transduced with pLKO-1-HSP90α, β, or shNT control shRNA lentiviruses for 48 h. Cells were treated with IMA82 for 16 h prior to infection with HIV-1 and grown for 48 h post infection with IMA82. Total cell lysates were analyzed by immunoblotting with antibodies against HSP90, A3G, and Vif. GAPDH was probed as a loading control. FIG. 1F, experiments were performed as described for FIG. 1E, After 48 h of transduction, the cells were grown in presence and absence of RN18 and infected with HIV-1. The supernatants were collected at 2 day intervals and analyzed for HIV-1 reverse transcriptase activity.

FIG. 2A-2B: 293FT cells were transfected with HA-A3G and GFP-Vif or GFP-ΔVif for 4 h, treated with DMSO, IMA8, IMA82, IMD55, or IMD64 for 16 h, and then incubated with proteasome inhibitor ALLN for 4 h. FIG. 2A, Vif antagonists inhibit A3G ubiquitination. Cell lysates were immunoprecipitated with anti-HA (A3G) and immunoblotted with anti-ubiquitin. FIG. 2B, Vif antagonists induce Vif ubiquitination. Cell lysates were immunoprecipitated with anti-GFP (Vif) and immunoblotted with anti-ubiquitin. FIGS. 2C-2E: IMA82 induces Cul5-mediated degradation of Vif. 293FT cells co-expressing HA-A3G and GFP-Vif were transfected with control (siNT) or Cul5-specific SMARTpool siRNA before incubation with IMA82. FIG. 2C: Cell lysates were analyzed by immunoblotting with antibodies to Cul5, HA (A3G), and GFP (Vif). GAPDH was probed as a loading control. Cell lysates were immunoprecipitated with anti-HA (A3G) (FIG. 2D) or anti-GFP (Vif) (FIG. 2E) and immunoblotted with anti-ubiquitin antibody.

FIG. 5A: 293FT cells were co-transfected with HA-A3G and GFP-Vif or ΔVif. Four hours later, the indicated concentrations of 17-AAG were added and the cells were incubated for a further 16 h. Cell lysates were analyzed by immunoblotting with antibodies to HSP90, HA (A3G), and GFP (Vif). GAPDH was probed as a loading control. FIG. 5B: Non-permissive (H9) cells were exposed to 17-AAG for 16 h, infected with wild-type HIV-1 and cultured for 72 h in the presence of the same concentrations of 17-AAG. Cell lysates were analyzed by immunoblotting with antibodies to HSP90, A3G, Vif, p24, and β-actin. An uninfected cell lysate served as a control. FIG. 5C: H9 cells were treated with 17-AAG for 16 h and cell lysates were analyzed by immunoblotting with antibodies to HSP90, A3G, and β-actin. FIG. 5D: 293FT cells were transfected with HA-A3G and GFP-Vif or ΔVif. After 4 h, cells were incubated with 17-AAG for 16 h and then with ALLN or DMSO for a further 4 h. Cell lysates were immunoprecipitated with anti-HA antibody and immunoblotted with anti-ubiquitin antibody. FIG. 5E: 293FT cells were transfected with FLAG-HSP90 and HA-A3G. After 4 h, cells were incubated with and without 17-AAG or IMA82 for 16 h. Cell lysates were immunoprecipitated with anti-FLAG antibody and immunoblotted with anti-HA or anti-FLAG antibody.

FIG. 8A: Schematic representation of the ViTAP experimental strategy. 293FT cells co-expressing HA-A3G and pNLA1-Vif, pNLA1-ΔVif, or pEGFP-C1-Vif were treated with RN-18-based probes and exposed to UV irradiation (IMD55 and IMD64). The crosslinked compound-protein complexes were affinity purified and resolved by SDS-PAGE. Unique bands were analyzed by mass spectrometry. FIG. 8B: Structures and synthetic schemes for the compounds used in this study. Reagents (a) 4-nitrothiophenol, $K_2CO_3$, 5 mol % CuI, 100° C., 6 h. (b) Lithium hydroxide hydrate, THF/MeOH/$H_2O$ (4:2:1), R.T., 5 h. (c) $SOCl_2$, cat. DMF, Benzene, 60° C., 2 h. (d) Methyl 4-amino-3-methoxybenzoate, $Et_3N$, Benzene, 75° C., 5 h. (e) Amine-$PEG_3$-Biotin, EDCI, HOBT, dry $CH_2Cl_2$, R.T., 12 h. FIG. 8C: Reagents (a) 4-fluoronitrobenzene, $K_2CO_3$, DMF, 110° C., 8 h. (b) $SOCl_2$, cat. DMF, Benzene, 60° C., 2 h. (c) Methyl 4-amino-3-methoxybenzoate, $Et_3N$, Benzene, 75° C., 5 h. (d) $(CH_3)_3SnOH$, 1-2-DCE, 80° C., 6 h. (e) Amine-$PEG_3$-Biotin, EDCI, HOBT, dry $CH_2Cl_2$, R.T., 12 h.

FIG. 10A: 293FT cells co-expressing HA-A3G and pNLA1-Vif or pNLA1-ΔVif were treated with 1% DMSO or the indicated concentrations of IMA82 for 16 h. Cell lysates were analyzed by immunoblotting with antibodies to HSP90, HA (A3G), Vif, and CBF-β. β-actin was probed as a loading control. FIG. 10B: Non-permissive (H9) cells were treated with 1% DMSO or the indicated concentrations of IMA82 for 16 h, infected with wild-type HIV-1$_{LAI}$ (2×10$^5$ C.P.M.) and incubated for a further 72 h with the same concentrations of IMA82. Cell lysates were analyzed by immunoblotting with antibodies to HSP90, A3G, Vif, CBF-β, p24, and β-actin. Uninfected H9 cell lysates served as controls. FIG. 10C: Permissive (MT4) cells were treated and processed as described for b. Cell lysates were analyzed by immunoblotting with antibodies to HSP90, A3G, Vif, p24, and β-actin.

FIG. 11A: H9 cells were transuded with shHSP90α or β as mentioned in FIG. 1E. Total RNA was isolated from the cells and the relative expression of HSP90 was analyzed by RT-qPCR. 293FT cells co-expressing HA-A3G and pNLA1-Vif or pNLA1-ΔVif were also transfected with non-targeting (NT) SMARTpool siRNA or siRNA targeting HSP90α or β isoforms prior to incubation with 10 μM IMA82. After 16 h incubation, Total RNA and total proteins were isolated separately. FIG. 11B: Total RNA was analyzed by RT-qPCR for relative expression of HSP90. FIG. 11C: Total cell lysates were analyzed by immunoblotting with antibodies to HSP90, HA (A3G), and Vif. GAPDH was probed as a loading control. FIG. 11D: Twenty-four hour post transfection of HSP90 siRNAs, HA-A3G and GFP-Vif, the cells were over expressed with FLAG-HSP90 followed by treatment of IMA82. Total HSP90, HA-A3G and GFP-Vif protein expression was analyzed by western blot.

FIG. 12A: 293FT cells expressing the indicated FLAG-HSP90 constructs were incubated with 25 μM IMA82 and the indicated concentrations of RN18 or IMD70 for 16 h. Cells were re-exposed to the same concentrations of IMA82 and either RN18 or IMD70 for 30 min. IMA82 was then affinity purified from the cell lysates and samples were immunoblotted with anti-FLAG antibody. FIG. 12B: 293 FT cells were co-transfected with HA-A3G and GFP-Vif or ΔVif. Four hours later, the cells were exposed to IMA82 or DMSO for 16 h and were re-exposed for 30 min before harvesting. Proteins associated with IMA82 were affinity purified, resolved by SDS-PAGE, and analyzed by immunoblotting with antibodies to HSP90, HA (A3G), GFP (Vif), or Cul5.

DETAILED DESCRIPTION

1. Definitions

Figure 1A:
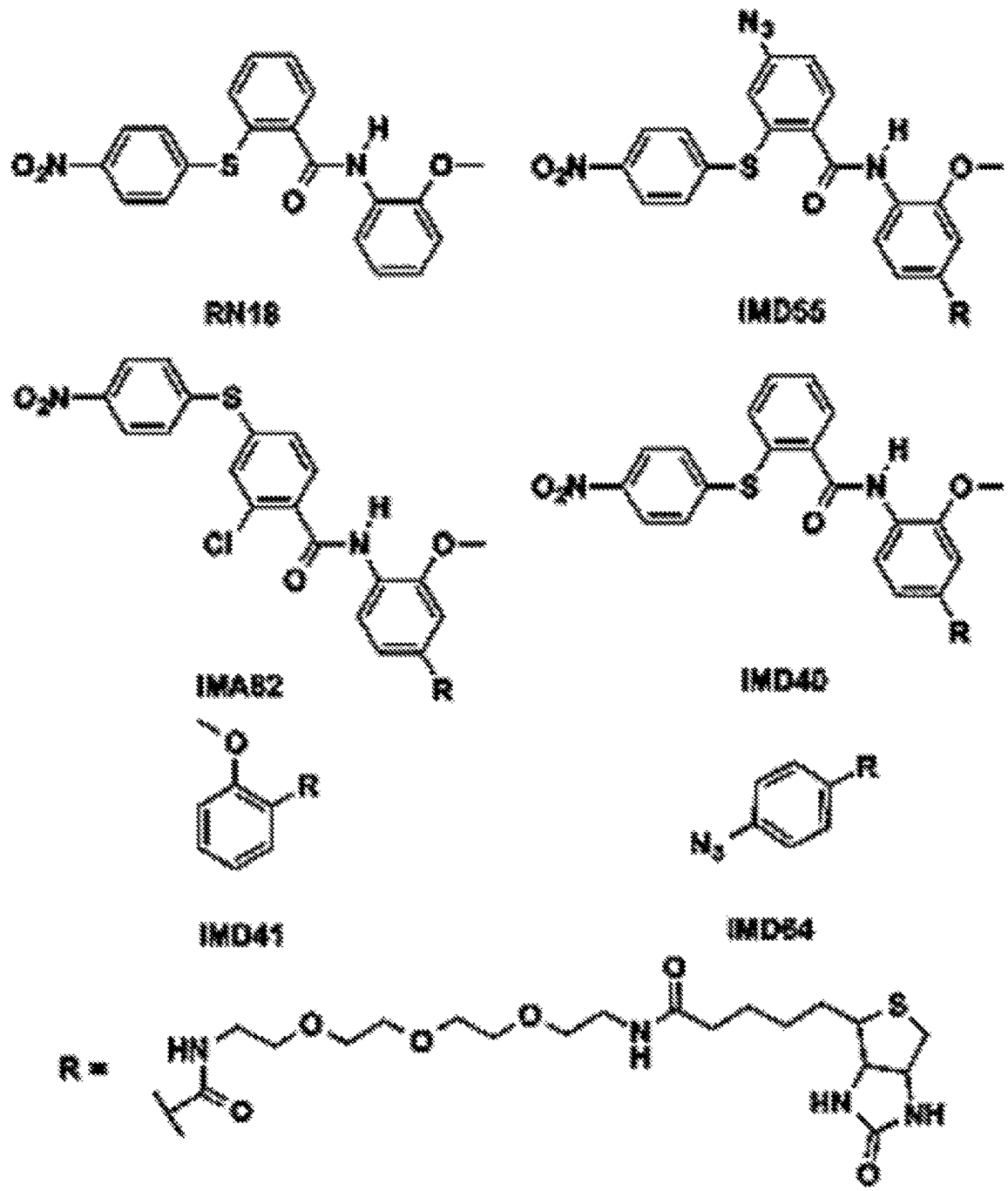
FIGS. 1A-1F. Vif antagonists bind to HSP90.

The following definitions are provided to facilitate understanding of certain terms used frequently herein and are not meant to limit the scope of the present disclosure. The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., selected from the group consisting of O, N, P, Si, and S), and wherein the nitrogen and sulfur atoms may optionally be oxidized, and the nitrogen heteroatom may optionally be quaternized. Heteroalkyl is not cyclized. The heteroatom(s) (e.g., O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, monophosphate (or derivatives thereof), diphosphate (or derivatives thereof), triphosphate (or derivatives thereof), in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

Certain complexes and compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol " $\sim\!\sim\!\sim$ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus, a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Analog," or "analogue" are used in accordance with plain ordinary meaning within Chemistry and Biology and refer to a chemical compound that is structurally similar to another compound (i.e., a so-called "reference" compound)

but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

The term "pharmaceutically acceptable salts" is meant to include salts of active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds disclosed herein contain both basic and acidic functionalities that allow the compounds to be converted into either base or acid addition salts.

Thus, the compounds disclosed herein may exist as salts, such as with pharmaceutically acceptable acids. The compounds disclosed herein include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, there are provided compounds which are in a prodrug form. Prodrugs of the compounds described herein include those compounds that readily undergo chemical or enzymatic changes under physiological conditions to provide the compounds disclosed herein. Additionally, prodrugs can be converted to the compounds disclosed herein by chemical or biochemical methods in an ex vivo environment. For example, prodrugs can be slowly converted to the compounds disclosed herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope disclosed herein. Certain compounds disclosed herein may exist in multiple crystalline or amorphous forms. In general, all physical forms are equivalent for the uses disclosed herein and are intended to be within the scope of the compounds and methods disclosed herein.

As used herein, the term "salt" refers to acid or base salts of the compounds used in the methods disclosed herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g., achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the methods disclosed herein should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions disclosed herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein. One of skill in the art will recognize that other pharmaceutical excipients are useful in the compositions and methods disclosed herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions disclosed herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polvm. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions disclosed herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions disclosed herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds disclosed herein. Adjustment and manipulation of established dosages (e.g., frequency and duration) are well within the ability of those skilled in the art.

The compounds described herein can be used in combination with one another, with other active drugs known to be useful in treating a disease or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances.

Co-administration includes administering one active agent within 0.5, 1, 2, 4, 6, 8, 10, 12, 16, 20, or 24 hours of a second active agent. Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g., toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK 1, MEK2, or MEK1 and MEK2) inhibitors (e.g. XL518, CI-1040, PD035901, selumetinib/AZD6244, GSK1120212/ trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab, dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor, leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibixf), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is prostate cancer, liver cancer, intestinal cancer, breast cancer, pancreastic cancer, bladder cancer, gall bladder cancer, or colon cancer. In some embodiments, the disease is a disease associated with a viral infection (e.g., hepatitis A, hepatitis B, hepatitis C, HIV, Zika virus, Ebola virus; or an RNA virus).

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "apolipoprotein B mRNA editing enzyme, catalytic polypeptide-like 3G" or "APOBEC3G" refers to a cytidine deaminase protein belonging to the APOBEC superfamily of proteins and to the APOBEC3 family of proteins, which are involved in innate anti-viral immunity. The term "APOBEC3G" may refer to the nucleotide sequence or protein sequence of human APOBEC3G (e.g., Entrez 60489, Uniprot Q9HC 16, RefSeq NM_021822, or RefSeq NP_068594) (SEQ ID NO:1). The term "APOBEC3G" includes both the wild-type form of the nucleotide sequences or proteins as well as any mutants thereof. In some embodiments, "APOBEC3G" is wild-type APOBEC3G. In some embodiments, "APOBEC3G" is one or more mutant forms. The term "APOBEC3G" XYZ refers to a nucleotide sequence or protein of a mutant APOBEC3G wherein the Y numbered amino acid of APOBEC3G that normally has an X amino acid in the wildtype, instead has a Z amino acid in the mutant. In embodiments, an APOBEC3G is the human APOBEC3G. In embodiments, the APOBEC3G has the nucleotide sequence corresponding to reference number GI: 304282223 (SEQ ID NO:2). In embodiments, the APOBEC3G has the nucleotide sequence corresponding to RefSeq NM_021822.3 (SEQ ID NO:2). In embodiments, the APOBEC3G has the protein sequence corresponding to reference number GI: 13399304 (SEQ ID NO: 1). In embodiments, the APOBEC3G has the amino acid sequence corresponding to RefSeq NP_068594.1. In embodiments, the APOBEC3G has the following amino acid sequence:

```
                                              (SEQ ID NO: 1)
MKPHFRNTVERMYRDTFSYNFYNRPILSRRNTVWLCYEVKTKGPSRPP

LDAKIFRGQVYSELKYHPEMRFFHWFSKWRKLHRDQEYEVTWYISWSP

CTKCTRDMATFLAEDPKVTLTIFVARLYYFWDPDYQEALRSLCQKRDG

PRATMKIMNYDEFQHCWSKFVYSQRELFEPWNNLPKYYILLHIMLGEI

LRHSMDPPTFTFNFNNEPWVRGRHETYLCYEVERMHNDTWVLLNQRRG

FLCNQAPHKHGFLEGRHAELCFLDVIPFWKLDLDQDYRVTCFTSWSPC

FSCAQEMAKFISKNKHVSLCIFTARIYDDQGRCQEGLRTLAEAGAKIS

IMTYSEFKHCWDTFVDHQGCPFQPWDGLDEHSQDLSGRLRAILQNQEN.
```

In embodiments, the APOBEC3G is a mutant APOBEC3G. In embodiments, the mutant APOBEC3G is associated with a disease that is not associated with wildtype APOBEC3G. In embodiments, the APOBEC3G includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above. The APOBEC3 family of proteins is those APOBEC superfamily proteins most similar to APOBEC3G, and include the human APOBEC3A, APOBEC3B, APOBEC3C, APOBEC3D (APOBEC3E), APOBEC3F, APOBEC3G, and APOBEC3H proteins.

The term "degradation complex" refers to an assembly of molecules ("degradation complex components") (e.g., proteins, nucleic acids, lipids, carbohydrates, biomolecules, or small molecules) that collectively function to increase the degradation of a target protein. In embodiments, a degradation complex binds a ubiquitin moiety to a target protein (e.g., a ubiquitin ligase degradation complex). In embodiments, the target protein is an APOBEC family protein. In embodiments, the target protein is an APOBEC3G protein. Non-limiting examples of a degradation complex include Cullin-RING ubiquitin ligases (CRLs), which are degradation complexes that target proteins for ubiquitin-mediated degradation (e.g., proteasome-mediated degradation). Examples of degradation complex components include Cullins (e.g., human CUL1 (e.g., Entrez 8454, UniProt Q13616), CUL2 (e.g., Entrez 8453, UniProt Q13617), CUL3 (e.g., Entrez 8452, UniProt Q13618), CUL4A (e.g., Entrez 8451, UniProt Q13619), CUL4B (e.g., Entrez 8450, UniProt Q13620), CUL5 (e.g., Entrez 8065, UniProt Q93034, RefSeq NM_003478, RefSeq NP_003469.2), CUL7 (e.g., Entrez 9820, UniProt Q14999), or CUL9), $RBX^2$ (e.g., UniProt Q9UBF6), E2 (e.g., ubiquitin conjugating enzyme), APOBEC3 family protein, CBF-beta, ELOB-ELOC, ELOB, ELOC, DCAF1, DDB1, SAMHD1, ROC, RBX1 (e.g., Entrez 9978, UniProt P62877), SKP1, FOXSKP2, SCF, HSP90 (e.g., heat shock protein 90), E3 (ubiquitin ligase), or the proteasome. Examples of degradation complexes include the Cullin5-RING ubiquitin ligase. Examples of degradation complexes include the SCF complex, which is a degradation complex including SKP1, CUL1, RBX1, and F-BOX protein and is a multi-protein E3 ubiquitin ligase complex. Examples of degradation complexes include ECS complex (Elongin C-CUL2-SOCS-box). Examples of degradation complexes include CUL3-BTB complex. In embodiments, a degradation complex includes CUL5, $RBX^2$, E2, APOBEC3G, ELOC, and ELOB. In embodiments, a degradation complex includes CUL5, $RBX^2$, E2, APOBEC3G, Vif, ELOC, and ELOB. In embodiments, a degradation complex includes CUL5, $RBX^2$, E2, APOBEC3G, ELOB, ELOC, and CBF-beta. In embodiments, a degradation complex includes CUL5, $RBX^2$, E2, APOBEC3G, ELOB, ELOC, CBF-beta, and Vif. In embodiments, a degradation complex includes CUL4A, RBX1, E2, SAMHD1, DCAF1, and DDB1. In embodiments, a degradation complex includes CUL4A, RBX1, E2, SAMHD1, DCAF1, DDB1, and Vpx. In embodiments, the degradation complex is a proteasomal degradation complex (i.e., degradation includes proteasome activity). In embodiments, the degradation complex and the degradation complex components are a human degradation complex and human degradation complex components respectively. In embodiments a degradation complex includes human and viral degradation complex components (e.g, HIV Vif or another viral molecule). In embodiments, the degradation complex is an E3 ubiquitin ligase complex. In embodiments, the degradation complex is as described in Malim, M. H. and Bieniasz, P. D., Cold Spring Harbor Perspectives in Medicine 2012; 2:a006940 or Malim, M. H., Ringside Views Nature Jan. 9, 2014, vol. 505, p. 167-68, the contents of which are incorporated herein by reference in their entirety for all purposes.

II. Compounds

In an aspect is provided a compound, or a pharmaceutically acceptable salt thereof, having the formula:

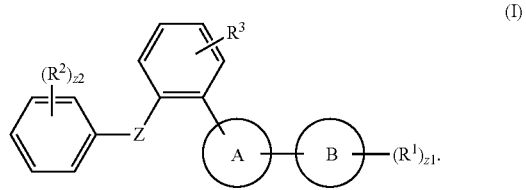

(I)

Ring A is a substituted or unsubstituted 5 membered heteroaryl. Ring B is a phenyl or 6 membered heteroaryl. $R^1$ is independently hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-NHNR^{1A}R^{1B}$, $-N(O)_{m1}$, $-NR^{1A}R^{1B}$, $-C(O)R^{1C}$, $-C(O)OR^{1C}$, $-C(O)NR^{1A}R^{1B}$, $-ONR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $X^1$ is independently $-F$, $-Cl$, $-Br$, or $-I$. $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{n2}NR^{2A}R^{2B}$, $-NHC(O)NR^{2A}R^{2B}$, $-NHNR^{2A}R^{2B}$, $-N(O)_{m2}$, $-NR^{2A}R^{2B}$, $-C(O)R^{2C}$, $-C(O)OR^{2C}$, $-C(O)NR^{2A}R^{2B}$, $-ONR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $X^2$ is independently $-F$, $-Cl$, $-Br$, or $-I$. $R^3$ is independently hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3D}$, $-SO_{v3}NR^{3A}R^{3B}$, $-NHC(O)NR^{3A}R^{3B}$, $-NHNR^{3A}R^{3B}$, $-N(O)_{m3}$, $-N^{3A}R^{3B}$, $-C(O)R^{3C}$, $-C(O)OR^{3C}$, $-C(O)NR^{3A}R^{3B}$, $-ONR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $X^3$ is independently $-F$, $-Cl$, $-Br$, or $-I$. Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, and $R^{3D}$ is independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl. Each X is independently $-F$, $-Cl$, $-Br$, or $-I$. The symbols n1, n2, and n3 are independently an integer from 0 to 4. The symbols m1, m2, m3, v1, v2, and v3 are independently an integer from 1 to 2. Z is $-S-$ or $-SO_2-$. z1 and z2 are independently an integer from 0 to 5.

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-NHNR^{1A}R^{1B}$, $-N(O)_{m1}$, $-NR^{1A}R_{1B}$, $-C(O)R^{1C}$, $-C(O)OR^{1C}$, $-C(O)NR^{1A}R^{1B}$, $-ONR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^1$ is independently halogen, $-CX^1_3$, $-CHX^1_2$, $-CH_2X^1$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently halogen, $-CX^1_3$, $-CHX^1_2$, $-CH_2X^1$, $-OH$, $-SH$, $-OCX^1_3$, $-OCHX^1_2$, $-OCH_2X^1$, substituted or unsubstituted $C_1$-$C_4$ alkyl, substituted or unsubstituted 2 to 4 membered heteroalkyl. In embodiments, $R^1$ is independently $-F$, $-CH_3$, or $-OCH_3$.

In embodiments, $R^1$ is independently $-OCH_3$. In embodiments, $R^1$ is independently $-COOH$. In embodiments, $R^1$ is independently $-COO^-$. In embodiments, $R^1$ is independently a salt of $-COO^-$. In embodiments, $R^1$ is independently a choline salt of $-COO^-$. In embodiments, $R^1$ is independently a $-COO^-(HOCH_2CH_2N(CH_3)_3^+)$. In embodiments, $R^1$ is independently $-CONH_2$. In embodiments, $R^1$ is independently $-CONHCH_3$. In embodiments, $R^1$ is independently $-CONHCH_2CH_3$. In embodiments, $R^1$ is independently $-CONHC(CH_3)_2$. In embodiments, $R^1$ is independently $-CONHC(CH_3)_3$. In embodiments, $R^1$ is independently $-COOCH_3$. In embodiments, $R^1$ is independently $-COOCH_2CH_3$. In embodiments, $R^1$ is independently $-COOC(CH_3)_2$. In embodiments, $R^1$ is independently $-COOC(CH_3)_3$. In embodiments, $R^1$ is independently $-OCH_2CH_3$. In embodiments, $R^1$ is independently $-OCH(CH_3)_2$. In embodiments, $R^1$ is independently $-OC(CH_3)_3$. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted butyl. In embodiments, $R^1$ is independently unsubstituted n-propyl. In embodiments, $R^1$ is independently unsubstituted iso-propyl. In embodiments, $R^1$ is independently unsubstituted n-butyl. In embodiments, $R^1$ is independently unsubstituted iso-butyl. In embodiments, $R^1$ is independently unsubstituted methoxy. In embodiments, $R^1$ is independently unsubstituted ethoxy. In embodiments, $R^1$ is independently unsubstituted propoxy. In embodiments, $R^1$ is independently unsubstituted butoxy. In embodiments, $R^1$ is independently unsubstituted —F. In embodiments, $R^1$ is independently unsubstituted —Cl. In embodiments. $R^1$ is independently unsubstituted —I. In embodiments, $R^1$ is independently unsubstituted —Br. In embodiments, $R^1$ is independently unsubstituted —NO$_2$. In embodiments, $R^1$ is independently —CF$_3$. In embodiments, $R^1$ is independently —CCl$_3$. In embodiments, $R^1$ is independently —Cl$_3$. In embodiments, $R^1$ is independently —CBr$_3$. In embodiments, $R^1$ is independently —NH$_2$.

In embodiments, $R^1$ is independently halogen. In embodiments, $R^1$ is independently oxo. In embodiments, $R^1$ is independently —$CX^1_3$. In embodiments, $R^1$ is independently —$CHX^1_2$. In embodiments, $R^1$ is independently —$CH_2X$. In embodiments, $R^1$ is independently —$OCX^1_3$. In embodiments, $R^1$ is independently —$OCH_2X$. In embodiments, $R^1$ is independently —$OCHX^1_2$. In embodiments, $R^1$ is independently —CN. In embodiments, $R^1$ is independently —$SO_{n1}R^{1D}$. In embodiments, $R^1$ is independently —$SO_{v1}NR^{1A}R^{1B}$. In embodiments, $R^1$ is independently —$NHC(O)NR^{1A}R^{1B}$. In embodiments, $R^1$ is independently —$NHNR^{1A}R^{1B}$. In embodiments, $R^1$ is independently —$N(O)_{m1}$. In embodiments, $R^1$ is independently —$NR^{1A}R^{1B}$. In embodiments, $R^1$ is independently —$C(O)R^{1C}$. In embodiments, $R^1$ is independently —$C(O)OR^{1C}$. In embodiments, $R^1$ is independently —$C(O)NR^{1A}R^{1B}$. In embodiments, $R^1$ is independently —$OR^{1D}$. In embodiments, $R^1$ is independently —$NR^{1A}SO_2R^{1D}$. In embodiments, $R^1$ is independently —$NR^{1A}C(O)R^{1C}$. In embodiments, $R^1$ is independently —$NR^A C(O)OR^{1C}$. In embodiments, $R^1$ is independently —$NR^{1A}OR^{1C}$. In embodiments, $R^1$ is independently —OH. In embodiments, $R^1$ is independently —NH$_2$. In embodiments, $R^1$ is independently —COOH. In embodiments, $R^1$ is independently —CONH$_2$. In embodiments, $R^1$ is independently —NO$_2$. In embodiments, $R^1$ is independently —SH. In embodiments, $R^1$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 2 to 3 membered, 4 to 6 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^1$ is —F, —Cl, —Br, or —I. In embodiments, $R^1$ is independently hydrogen. In embodiments, $R^1$ is independently methyl. In embodiments, $R^1$ is independently ethyl. In embodiments, $R^1$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 2 to 3 membered, 4 to 6 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^1$ is independently

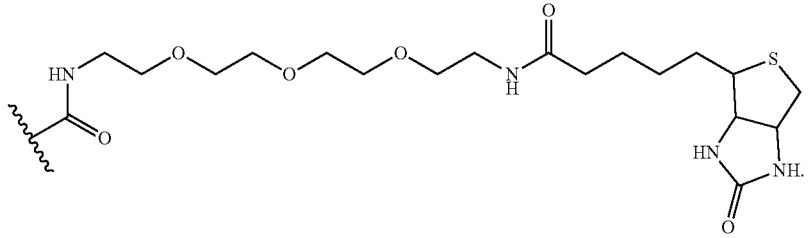 [SMILES: *C(=O)NCCOCCOCCOCCNC(=O)CCCCC1SCC2NC(=O)NC21]

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). $X^1$ is —F, —Cl, —Br, or —I. In embodiments, $R^1$ is independently hydrogen. In embodiments, $R^1$ is independently methyl. In embodiments, $R^1$ is independently ethyl. In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, two adjacent $R^1$ substituents may optionally be joined to form an $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, two adjacent $R^1$ substituents may optionally be joined to form an unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{20}$ is independently oxo, halogen, $-CX^{20}_3$, $-CHX^{20}_2$, $-CH_2X^{20}$, $-OCX^{20}_3$, $-OCH_2X^{20}$, $-OCHX^{20}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 or 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 6 membered, 4 to 6 membered, 4 to 5 membered, or 5 to 6 membered), $R^{21}$-substituted or unsubstituted aryl (e.g., $C_6$-$C_{10}$ or phenyl), or $R^{21}$-substituted or unsubstituted heteroaryl (e.g., 5 to 10 membered, 5 to 9 membered, or 5 to 6 membered). $X^{20}$ is $-F$, $-Cl$, $-Br$, or $-I$. In embodiments, $R^{20}$ is independently oxo, halogen, $-CX^{20}_3$, $-CHX^{20}_2$, $-CH_2X^{20}$, $-OCX^{20}_3$, $-OCH_2X^{20}$, $-OCHX^{20}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21}$ is independently oxo, halogen, $-CX^{21}_3$, $-CHX^{21}_2$, $-CH_2X^{21}$, $-OCX^{12}_3$, $-OCH_2X^{21}$, $-OCHX^{21}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 or 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered). $X^{21}$ is $-F$, $-Cl$, $-Br$, or $-I$. In embodiments, $R^{21}$ is independently oxo, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22}$ is independently oxo, halogen, $-CX^{22}_3$, $-CHX^{22}_2$, $-CH_2X^{22}$, $-OCX^{22}_3$, $-OCH_2X^{22}$, $-OCHX^{22}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22}$ is $-F$, $-Cl$, $-Br$, or $-I$.

In embodiments, $R^{1A}$ is independently hydrogen, $-CX^{1A}_3$, $-CN$, $-COOH$, $-CONH_2$, $-CHX^{1A}_2$, $-CH_2X^{1A}$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 or 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 6 membered, 4 to 6 membered, 4 to 5 membered, or 5 to 6 membered), $R^{20A}$-substituted or unsubstituted aryl (e.g., $C_6$-$C_{10}$ or phenyl), or $R^{20A}$-substituted or unsubstituted heteroaryl (e.g., 5 to 10 membered, 5 to 9 membered, or 5 to 6 membered). $X^{1A}$ is $-F$, $-Cl$, $-Br$, or $-I$. In embodiments, $R^{1A}$ is independently hydrogen. In embodiments, $R^A$ is independently methyl. In embodiments, $R^{1A}$ is independently ethyl. In embodiments, $R^{1A}$ is independently hydrogen. $-CX^{1A}_3$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{1A}$ and $R^{1B}$ substituents bonded to the same nitrogen atom may optionally be joined to form a $R^{20A}$-substituted or unsubstituted heterocycloalkyl or $R^{20A}$-substituted or unsubstituted heteroaryl. In embodiments, $R^{1A}$ and $R^{1B}$ substituents bonded to the same nitrogen atom may optionally be joined to form a $R^{20A}$-substituted or unsubstituted 3 to 6 membered heterocycloalkyl or $R^{20A}$-substituted or unsubstituted 5 to 6 membered heteroaryl. In embodiments, $R^{1A}$ and $R^{1B}$ substituents bonded to the same nitrogen atom may optionally be joined to form an unsubstituted 3 to 6 membered heterocycloalkyl or unsubstituted 5 to 6 membered heteroaryl. In embodiments, $R^{1A}$ and $R^{1B}$ substituents bonded to the same nitrogen atom may optionally be joined to form a $R^{20A}$-substituted or unsubstituted piperazinyl. In embodiments, $R^{1A}$ and $R^{1B}$ substituents bonded to the same nitrogen atom may optionally be joined to form a $R^{20A}$-substituted or unsubstituted piperidinyl. In embodiments, $R^{1A}$ and $R^{1B}$ substituents bonded to the same nitrogen atom may optionally be joined to form a $R^{20A}$-substituted or unsubstituted pyrrolidinyl. In embodiments, $R^{1A}$ and $R^{1B}$ substituents bonded to the same nitrogen atom may optionally be joined to form a $R^{20A}$-substituted or unsubstituted azetidinyl. In embodiments, $R^{1A}$ and $R^{1B}$ substituents bonded to the same nitrogen atom may optionally be joined to form a $R^{20A}$-substituted or unsubstituted morpholinyl. In embodiments, $R^{1A}$ and $R^{1B}$ substituents bonded to the same nitrogen atom may optionally be joined to form a $R^{20A}$-substituted or unsubstituted azeridinyl.

$R^{20A}$ is independently oxo, halogen, —$CX^{20A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{20A}_2$, —$CH_2X^{20A}$, —$OCX^{20A}_3$, —$OCH_2X^{20A}$, —$OCHX^{2A}_2$, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 or 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 6 membered, 4 to 6 membered, 4 to 5 membered, or 5 to 6 membered), $R^{21A}$-substituted or unsubstituted aryl (e.g., $C_6$-$C_{10}$ or phenyl), or $R^{21A}$-substituted or unsubstituted heteroaryl (e.g., 5 to 10 membered, 5 to 9 membered, or 5 to 6 membered). $X^{20A}$ is —F, —Cl, —Br, or —I. In embodiments, $R^{20A}$ is independently oxo, halogen, —$CX^{2A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{20A}_2$, —$CH_2X^{20A}$, —$OCX^{20A}_3$, —$OCH_2X^{20A}$, —$OCHX^{20A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21A}$ is independently oxo, halogen, —$CX^{21A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21A}_2$, —$CH_2X^{21A}$, —$CX^{21A}_3$, —$OCH_2X^{21A}$, —$OCHX^{21A}_2$, $R^{22A}$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 or 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 6 membered, 4 to 6 membered, 4 to 5 membered, or 5 to 6 membered), $R^{22A}$-substituted or unsubstituted aryl (e.g., $C_6$-$C_{10}$ or phenyl), or $R^{22A}$-substituted or unsubstituted heteroaryl (e.g., 5 to 10 membered, 5 to 9 membered, or 5 to 6 membered). $X^{21A}$ is —F, —Cl, —Br, or —I. In embodiments, $R^{21A}$ is independently oxo, halogen, —$CX^{21A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21A}_2$, —$CH_2X^{21A}$, —$OCX^{21A}_3$, —$OCH_2X^{21A}$, —$OCHX^{21A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22A}$ is independently oxo, halogen, —$CX^{22A}_3$, —CN, —OH, —$NH_2$, —COOH, —$CONH_2$, —SH, —$NHNH_2$, —$ONH_2$, —NHC(O)$NHNH_2$, NHC(O)$NH_2$, —NHC(O)H, —NHC(O)OH, —NHOH, —$CHX^{22A}_2$, —$CH_2X^{22A}$, —$OCX^{22A}_3$, —$OCH_2X^{22A}$, $OCHX^{22A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22A}$ is —F, —Cl, —Br, or —I.

In embodiments, $R^{1B}$ is independently hydrogen, —$CX^{1B}_3$, —CN, —COOH, —$CONH_2$, —$CHX^{1B}_2$, —$CH_2X^{1B}$, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 or 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$-substituted or unsubstituted heterocycloalkyl (e.g., 3 to 6 membered, 4 to 6 membered, 4 to 5 membered, or 5 to 6 membered), $R^{20B}$-substituted or unsubstituted aryl (e.g., $C_6$-$C_{10}$ or phenyl), or $R^{20B}$-substituted or unsubstituted heteroaryl (e.g., 5 to 10 membered, 5 to 9 membered, or 5 to 6 membered). $X^{1B}$ is —F, —Cl, —Br, or —I. In embodiments, $R^{1B}$ is independently hydrogen. In embodiments, $R^{1B}$ is independently methyl. In embodiments, $R^{1B}$ is independently ethyl. In embodiments, $R^{1B}$ is independently hydrogen, —$CX^{1B}_3$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{1B}$ and $R^{1A}$ substituents bonded to the same nitrogen atom may optionally be joined to form a $R^{20B}$-substituted or unsubstituted heterocycloalkyl or $R^{20B}$-substituted or unsubstituted heteroaryl. In embodiments, $R^{1B}$ and $R^{1A}$ substituents bonded to the same nitrogen atom may optionally be joined to form a $R^{20B}$-substituted or unsubstituted 3 to 6 membered heterocycloalkyl or $R^{20B}$-substituted or unsubstituted 5 to 6 membered heteroaryl. In embodiments, $R^{1B}$ and $R^{1A}$ substituents bonded to the same nitrogen atom may optionally be joined to form an unsubstituted 3 to 6 membered heterocycloalkyl or unsubstituted 5 to 6 membered heteroaryl. In embodiments, $R^{1B}$ and $R^{1A}$ substituents bonded to the same nitrogen atom may optionally be joined to form a $R^{20B}$-substituted or unsubstituted piperazinyl. In embodiments, $R^{1B}$ and $R^{1A}$ substituents bonded to the same nitrogen atom may optionally be joined to form a $R^{20B}$-substituted or unsubstituted piperidinyl. In embodiments, $R^{1B}$ and $R^{1A}$ substituents bonded to the same nitrogen atom may optionally be joined to form a $R^{20B}$-substituted or unsubstituted pyrrolidinyl. In embodiments, $R^{1B}$ and $R^{1A}$ substituents bonded to the same nitrogen atom may optionally be joined to form a $R^{20}$-substituted or unsubstituted azetidinyl. In embodiments, $R^{1B}$ and $R^{1A}$ substituents bonded to the same nitrogen atom may optionally be joined to form a $R^{20B}$-substituted or unsubstituted morpholinyl. In embodiments, $R^{1B}$ and $R^{1A}$ substituents bonded to the same nitrogen atom may optionally be joined to form a $R^{20B}$-substituted or unsubstituted azeridinyl.

$R^{20B}$ is independently oxo, halogen, —$CX^{20B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{20B}_2$, —$CH_2X^{20B}$, —$OCX^{20B}_3$, —$OCH_2X^{20B}$, —$OCHX^{2B}_2$, $R^{21B}$-substituted or unsubstituted alkyl (e.g., $C_1$-$C_8$, $C_1$-$C_6$, $C_1$-$C_4$, or $C_1$-$C_2$), $R^{21B}$-substituted or unsubstituted heteroalkyl (e.g., 2 to 8 membered, 2 to 6 membered, 4 to 6 membered, 2 or 3 membered, or 4 to 5 membered), $R^{21B}$-substituted or unsubstituted cycloalkyl (e.g., $C_3$-$C_8$, $C_3$-$C_6$, $C_4$-$C_6$, or $C_5$-$C_6$), $R^{21B}$-substituted or unsubstituted heterocycloalkyl (e.g., 3 to 6 membered, 4 to 6 membered, 4 to 5 membered, or 5 to 6 membered), $R^{21B}$-substituted or unsubstituted aryl (e.g., $C_6$-$C_{10}$ or phenyl), or $R^{21B}$-substituted or unsubstituted heteroaryl (e.g., 5 to 10 membered, 5 to 9 membered, or 5 to 6 membered). $X^{20}$B is —F, —Cl, —Br, or —I. In embodiments, $R^{20B}$ is independently oxo, halogen, —$CX^{20B}{}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{20B}{}_2$, —$CH_2X^{20B}$, —$OCX^{20B}{}_3$, —$OCH_2X^{20B}$, —$OCHX^{20B}{}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21B}$ is independently oxo, halogen, —$CX^{21B}{}_3$, —CN, —OH, —$NH_2$, —COOH, —$CONH_2$, —SH, —$NHNH_2$, —$ONH_2$, —NHC(O)$NHNH_2$, NHC(O)$NH_2$, —NHC(O)H, —NHC(O)OH, —NHOH, —$CHX^{21B}{}_2$, —$CH_2X^{21B}$, —$OCX^{21B}{}_3$, —$OCH_2X^{21B}$, —$OCHX^{21B}{}_2$, $R^{22B}$-substituted or unsubstituted alkyl (e.g., $C_1$-$C_8$, $C_1$-$C_6$, $C_1$-$C_4$, or $C_1$-$C_2$), $R^{22B}$-substituted or unsubstituted heteroalkyl (e.g., 2 to 8 membered, 2 to 6 membered, 4 to 6 membered, 2 or 3 membered, or 4 to 5 membered), $R^{22B}$-substituted or unsubstituted cycloalkyl (e.g., $C_3$-$C_8$, $C_3$-$C_6$, $C_4$-$C_6$, or $C_5$-$C_6$), $R^{22B}$-substituted or unsubstituted heterocycloalkyl (e.g., 3 to 6 membered, 4 to 6 membered, 4 to 5 membered, or 5 to 6 membered), $R^{22B}$-substituted or unsubstituted aryl (e.g., $C_6$-$C_{10}$ or phenyl), or $R^{22B}$-substituted or unsubstituted heteroaryl (e.g., 5 to 10 membered, 5 to 9 membered, or 5 to 6 membered). $X^{21B}$ is —F, —Cl, —Br or —I. In embodiments, $R^{21B}$ is independently oxo, halogen, —$CX^{21B}{}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21B}{}_2$, —$CH_2X^{21B}$, —$OCX^{21B}{}_3$, —$OCH_2X^{21B}$, —$OCHX^{21B}{}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22B}$ is independently oxo, halogen, —$CX^{22B}{}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{22B}{}_2$, —$CH_2X^{22B}$, —$OCX^{22B}{}_3$, —$OCH_2X^{22B}$, —$OCHX^{22B}{}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered. 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22B}$ is —F, —Cl, —Br, or —I.

In embodiments, $R^{1C}$ is independently hydrogen. —$CX^{1C}{}_3$, —CN, —COOH, —$CONH_2$, —$CHX^{1C}{}_2$, —$CH_2X^{1C}$, $R^{20C}$-substituted or unsubstituted alkyl (e.g., $C_1$-$C_8$, $C_1$-$C_6$, $C_1$-$C_4$, or $C_1$-$C_2$), $R^{20C}$-substituted or unsubstituted heteroalkyl (e.g., 2 to 8 membered, 2 to 6 membered, 4 to 6 membered, 2 or 3 membered, or 4 to 5 membered), $R^{20C}$-substituted or unsubstituted cycloalkyl (e.g., $C_3$-$C_8$, $C_3$-$C_6$, $C_4$-$C_6$, or $C_5$-$C_6$), $R^{2C}$-substituted or unsubstituted heterocycloalkyl (e.g., 3 to 6 membered, 4 to 6 membered, 4 to 5 membered, or 5 to 6 membered), $R^{20C}$-substituted or unsubstituted aryl (e.g., $C_6$-$C_{10}$ or phenyl), or $R^{20C}$-substituted or unsubstituted heteroaryl (e.g., 5 to 10 membered, 5 to 9 membered, or 5 to 6 membered). $X^{1C}$ is —F, —Cl, —Br, or —I. In embodiments, $R^{1C}$ is independently hydrogen. In embodiments, $R^{1C}$ is independently methyl. In embodiments, $R^{1C}$ is independently ethyl. In embodiments, $R^{1C}$ is independently hydrogen. —$CX^{1C}{}_3$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{20C}$ is independently oxo, halogen, —$CX^{20C}{}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{20C}{}_2$, —$CH_2X^{20C}$, —$OCX^{20C}{}_3$, —$OCH_2X^{20C}$, —$OCHX^{20C}{}_2$, $R^{21C}$-substituted or unsubstituted alkyl (e.g., $C_1$-$C_8$, $C_1$-$C_6$, $C_1$-$C_4$, or $C_1$-$C_2$), $R^{21C}$-substituted or unsubstituted heteroalkyl (e.g., 2 to 8 membered, 2 to 6 membered, 4 to 6 membered, 2 or 3 membered, or 4 to 5 membered), $R^{21C}$-substituted or unsubstituted cycloalkyl (e.g., $C_3$-$C_8$, $C_3$-$C_6$, $C_4$-$C_6$, or $C_5$-$C_6$), $R^{21C}$-substituted or unsubstituted heterocycloalkyl (e.g., 3 to 6 membered, 4 to 6 membered, 4 to 5 membered, or 5 to 6 membered), $R^{21C}$-substituted or unsubstituted aryl (e.g., $C_6$-$C_{10}$ or phenyl), or $R^{21C}$-substituted or unsubstituted heteroaryl (e.g., 5 to 10 membered, 5 to 9 membered, or 5 to 6 membered). $X^{20C}$ is —F, —Cl, —Br, or —I. In embodiments, $R^{20C}$ is independently oxo, halogen, —$CX^{20C}{}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{20C}{}_2$, —$CH_2X^{20C}$, —$OCX^{20C}{}_3$, —$OCH_2X^{20C}$, —$OCHX^{20C}{}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered. 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21C}$ is independently oxo, halogen, —$CX^{21C}{}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{21C}{}_2$, —$CH_2X^{21C}$, —$OCX^{21C}{}_3$, —$OCH_2X^{21C}{}_3$, —$OCHX^{21C}{}_2$, $R^{22C}$-substituted or unsubstituted alkyl (e.g., $C_1$-$C_8$, $C_1$-$C_6$, $C_1$-$C_4$, or $C_1$-$C_2$), $R^{22C}$-substituted or unsubstituted heteroalkyl (e.g., 2 to 8 membered, 2 to 6 membered, 4 to 6 membered, 2 or 3 membered, or 4 to 5 membered), $R^{22C}$-substituted or unsubstituted cycloalkyl (e.g., $C_3$-$C_8$, $C_3$-$C_6$, $C_4$-$C_6$, or $C_5$-$C_6$), $R^{22C}$-substituted or unsubstituted heterocycloalkyl (e.g., 3 to 6 membered, 4 to 6 membered, 4 to 5 membered, or 5 to 6 membered), $R^{22C}$-substituted or unsubstituted aryl (e.g., $C_6$-$C_{10}$ or phenyl), or $R^{22C}$-substituted or unsubstituted heteroaryl (e.g., 5 to 10 membered, 5 to 9 membered, or 5 to 6 membered). $X^{21C}$ is —F, —Cl, —Br, or —I. In embodiments, $R^{21C}$ is independently oxo, halogen, —$CX^{21C}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{21C}_2$, —$CH_2X^{21C}$, —$OCX^{21C}_3$, —$OCH_2X^{21C}$, —$OCHX^{21C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22C}$ is independently oxo, halogen, —$CX^{22C}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{22C}_2$, —$CH_2X^{22C}$, —$OCX^{22C}_3$, —$OCH_2X^{22C}$, —$OCHX^{22C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22C}$ is —F, —Cl, —Br, or —I.

In embodiments, $R^{1D}$ is independently hydrogen, —$CX^{1D}_3$, —CN, —COOH, —$CONH_2$, —$CHX^{1D}_2$, —$CH_2X^{1D}$, $R^{20D}$-substituted or unsubstituted alkyl (e.g., $C_1$-$C_8$, $C_1$-$C_6$, $C_1$-$C_4$, or $C_1$-$C_2$), $R^{20D}$-substituted or unsubstituted heteroalkyl (e.g., 2 to 8 membered, 2 to 6 membered, 4 to 6 membered, 2 or 3 membered, or 4 to 5 membered), $R^{20D}$-substituted or unsubstituted cycloalkyl (e.g., $C_3$-$C_8$, $C_3$-$C_6$, $C_4$-$C_6$, or $C_5$-$C_6$), $R^{20D}$-substituted or unsubstituted heterocycloalkyl (e.g., 3 to 6 membered, 4 to 6 membered, 4 to 5 membered, or 5 to 6 membered), $R^{20D}$-substituted or unsubstituted aryl (e.g., $C_6$-$C_{10}$ or phenyl), or $R^{20D}$-substituted or unsubstituted heteroaryl (e.g., 5 to 10 membered, 5 to 9 membered, or 5 to 6 membered). $X^{1D}$ is —F, —Cl, —Br, or —I. In embodiments, $R^{1D}$ is independently hydrogen. In embodiments, $R^{1D}$ is independently methyl. In embodiments, $R^{1D}$ is independently ethyl. In embodiments, $R^{1D}$ is independently hydrogen, —$CX^{1D}_3$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{20D}$ is independently oxo, halogen, —$CX^{20D}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{20D}_2$, —$CH_2X^{20D}$, —$OCX^{20D}_3$, —$OCH_2X^{20D}$, —$OCHX^{20D}_2$, $R^{21D}$-substituted or unsubstituted alkyl (e.g., $C_1$-$C_8$, $C_1$-$C_6$, $C_1$-$C_4$, or $C_1$-$C_2$), $R^{21D}$-substituted or unsubstituted heteroalkyl (e.g., 2 to 8 membered, 2 to 6 membered, 4 to 6 membered, 2 or 3 membered, or 4 to 5 membered), $R^{21D}$-substituted or unsubstituted cycloalkyl (e.g., $C_3$-$C_8$, $C_3$-$C_6$, $C_4$-$C_6$, or $C_5$-$C_6$), $R^{21D}$-substituted or unsubstituted heterocycloalkyl (e.g., 3 to 6 membered, 4 to 6 membered, 4 to 5 membered, or 5 to 6 membered), $R^{21D}$-substituted or unsubstituted aryl (e.g., $C_6$-$C_{10}$ or phenyl), or $R^{21D}$-substituted or unsubstituted heteroaryl (e.g., 5 to 10 membered, 5 to 9 membered, or 5 to 6 membered). $X^{20D}$ is —F, —Cl, —Br, or —I. In embodiments, $R^{20D}$ is independently oxo, halogen, —$CX^{20D}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{20D}_2$, —$CH_2X^{20D}$, —$OCX^{20D}_3$, —$OCH_2X^{20D}$, —$OCHX^{20D}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{21D}$ is independently oxo, halogen, —$CX^{21D}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{21}'2$, —$CH_2X^{21D}$, —$OCX^{21D}_3$, —$OCH_2X^{21D}$, —$OCHX^{21D}_2$, $R^{22D}$-substituted or unsubstituted alkyl (e.g., $C_1$-$C_8$, $C_1$-$C_6$, $C_1$-$C_4$, or $C_1$-$C_2$), $R^{22D}$-substituted or unsubstituted heteroalkyl (e.g., 2 to 8 membered, 2 to 6 membered, 4 to 6 membered, 2 or 3 membered, or 4 to 5 membered), $R^{22D}$-substituted or unsubstituted cycloalkyl (e.g., $C_3$-$C_8$, $C_3$-$C_6$, $C_4$-$C_6$, or $C_5$-$C_6$), $R^{22D}$-substituted or unsubstituted heterocycloalkyl (e.g., 3 to 6 membered, 4 to 6 membered, 4 to 5 membered, or 5 to 6 membered), $R^{22D}$-substituted or unsubstituted aryl (e.g., $C_6$-$C_{10}$ or phenyl), or $R^{22D}$-substituted or unsubstituted heteroaryl (e.g., 5 to 10 membered, 5 to 9 membered, or 5 to 6 membered). $X^{21D}$ is —F, —Cl, —Br, or —I. In embodiments, $R^{21D}$ is independently oxo, halogen, —$CX^{21D}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{21D}_2$, —$CH_2X^{21D}$, —$OCX^{21D}_3$, —$OCH_2X^{21D}$, —$OCHX^{21D}2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{22D}$ is independently oxo, halogen, —$CX^{22D}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{2D}_2$, —$CH_2X^{22D}$, —$OCX^{22D}_3$, —$OCH_2X^{22D}$, —$OCHX^{22D}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22D}$ is —F, —Cl, —Br, or —I.

In embodiments, $R^2$ is independently halogen, —$CX^2_3$, —$CHX^2_2$, —$CH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^2_3$, —$OCHX^2_2$, —$OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is halogen, —$CX^2_3$, —$CHX^2_2$, —$CH_2X^2$, —OH, —$NH_2$, —COOH, —$CONH_2$, —$NO_2$, —SH, —$OCX^2_3$, —$OCHX^2_2$, —$OCH_2X^2$, substituted or unsubstituted $C_1$-$C_4$ alkyl, substituted or unsubstituted 2 to 4 membered heteroalkyl; or a pharmaceutically acceptable salt thereof. In embodiments, $R^2$ is —$CF_3$, —$NH_2$, —COOH, —$COOCH_3$, —$NO_2$, —$OCH_3$, —$OCHX^2_2$, —$OCH_2X^2$, or —$COO^-$($HOCH_2CH_2N(CH_3)_3^+$).

In embodiments, $R^2$ is independently halogen. In embodiments, $R^2$ is independently oxo. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^2_2$. In embodiments, $R^2$ is independently —CN. In embodiments, $R^2$ is independently —$SO_2R^{2D}$. In embodiments, $R^2$ is independently —$SO_{v2}NR^{2A}R^{2B}$. In embodiments, R is independently —$NHC(O)NR^{2A}R^{2B}$. In embodiments, $R^2$ is independently —$NHNR^{2A}R^{2B}$. In embodiments, $R^2$ is independently —$N(O)_{m2}$. In embodiments, $R^2$ is independently —$NR^{2A}R^{2B}$. In embodiments, $R^2$ is independently —$C(O)R^{2C}$. In embodiments, $R^2$ is independently —$C(O)OR^{2C}$. In embodiments, $R^2$ is independently —$C(O)NR^{2A}R^{2B}$. In embodiments, $R^2$ is independently —$OR^{2D}$. In embodiments, $R^2$ is independently —$NR^{2A}SO_2R^{2D}$. In embodiments, $R^2$ is independently —$NR^{2A}C(O)R^{2C}$. In embodiments, $R^2$ is independently —$NR^{2A}C(O)OR^{2C}$. In embodiments, $R^2$ is independently —$NR^{2A}OR^{2C}$. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$NO_2$. In embodiments, $R^2$ is independently —SH. In embodiments, $R^2$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^2$ is —F, —Cl, —Br, or —I. In embodiments, $R^2$ is independently hydrogen. In embodiments, $R^2$ is independently methyl. In embodiments, $R^2$ is independently ethyl. In embodiments, $R^2$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^2$ is independently —$OCH_3$. In embodiments, $R^2$ is independently —COOH. In embodiments, $R^2$ is independently —$COO^-$. In embodiments, $R^2$ is independently a salt of —$COO^-$. In embodiments, $R^2$ is independently a choline salt of —$COO^-$. In embodiments, $R^2$ is independently a —$COO^-$($HOCH_2CH_2N(CH_3)_3^+$). In embodiments, $R^2$ is independently —$CONH_2$. In embodiments, $R^2$ is independently —$CONHCH_3$. In embodiments, $R^2$ is independently —$CONHCH_2CH_3$. In embodiments, $R^2$ is independently —$CONHC(CH)_2$. In embodiments, $R^2$ is independently —$CONHC(CH_3)_3$. In embodiments, $R^2$ is independently —$COOCH_3$. In embodiments, $R^2$ is independently —$COOCH_2CH_3$. In embodiments, $R^2$ is independently —$COOC(CH_3)_2$. In embodiments, $R^2$ is independently —$COOC(CH_3)_3$. In embodiments, $R^2$ is independently —$OCH_2CH_3$. In embodiments, $R^2$ is independently —$OC(CH_3)_2$. In embodiments, $R^2$ is independently —$OC(CH_3)_3$. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted butyl. In embodiments, $R^2$ is independently unsubstituted n-propyl. In embodiments, $R^2$ is independently unsubstituted iso-propyl. In embodiments, $R^2$ is independently unsubstituted n-butyl. In embodiments, $R^2$ is independently unsubstituted iso-butyl. In embodiments, $R^2$ is independently unsubstituted methoxy. In embodiments, $R^2$ is independently unsubstituted ethoxy. In embodiments, $R^2$ is independently unsubstituted propoxy. In embodiments, $R^2$ is independently unsubstituted butoxy. In embodiments, $R^2$ is independently —F. In embodiments, $R^2$ is independently —Cl. In embodiments, $R^2$ is independently —I. In embodiments, $R^2$ is independently —Br. In embodiments, $R^2$ is independently —$NO_2$. In embodiments, $R^2$ is independently —$CF_3$. In embodiments, $R^2$ is independently —$CCl_3$. In embodiments, $R^2$ is independently —$Cl_3$. In embodiments, $R^2$ is independently —$CBr_3$. In embodiments, $R^2$ is independently —$NH_2$.

$R^2$ is independently halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$NHNR^{2A}R^{2B}$, —$N(O)_{m2}$, —$NR^{2A}R^{2B}$, —$C(O)R^{2C}$, —$C(O)OR^{2C}$, —$C(O)NR^{2A}R^{2B}$, —$ONR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —NHC(O)—OH, —NHOH, $R^{23}$-substituted or unsubstituted alkyl (e.g., $C_1$-$C_8$, $C_1$-$C_6$, $C_1$-$C_4$, or $C_1$-$C_2$), $R^{23}$-substituted or unsubstituted heteroalkyl (e.g., 2 to 8 membered, 2 to 6 membered, 4 to 6 membered, 2 or 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 6 membered, 4 to 6 membered, 4 to 5 membered, or 5 to 6 membered), $R^{23}$-substituted or unsubstituted aryl (e.g., $C_6$-$C_{10}$ or phenyl), or $R^{23}$-substituted or unsubstituted heteroaryl (e.g., 5 to 10 membered, 5 to 9 membered, or 5 to 6 membered). $X^2$ is —F, —Cl, —Br, or —I. In embodiments, $R^2$ is independently hydrogen. In embodiments, $R^2$ is independently methyl. In embodiments, $R^2$ is independently ethyl. In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered. 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered. 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, two adjacent $R^2$ substituents may optionally be joined to form an $R^{23}$ substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 6 membered, 4 to 6 membered, 4 to 5 membered, or 5 to 6 membered), $R^{23}$-substituted or unsubstituted aryl (e.g., $C_6$-$C_{10}$ or phenyl), or $R^{23}$-substituted or unsubstituted heteroaryl (e.g., 5 to 10 membered, 5 to 9 membered, or 5 to 6 membered). In embodiments, two adjacent $R^2$ substituents may optionally be joined to form an unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 or 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered). $X^{23}$ is —F, —Cl, —Br, or —I. In embodiments, $R^{23}$ is independently oxo, halogen, —$CX^{23}_3$, —$CHX^{23}_2$, —$CH_2X^{23}$, —$OCX^{23}_3$, —$OCH_2X^{23}$, —$OCHX^{23}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, 2 or 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{25}$-substituted or unsubstituted heterocycloalkyl (e.g., 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered). $X^{24}$ is —F, —Cl, —Br, or —I. In embodiments, $R^{24}$ is independently oxo, halogen, —$CX^{24}_3$, —$CHX^{24}_2$, —$CH_2X^{24}$, —$OCX^{24}_3$, —$OCH_2X^{24}$, —$OCHX^{24}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{25}$ is independently oxo, halogen, —$CX^{25}_3$, —$CHX^2_2$, —$CH_2X^{25}$, —$OCX^{25}_3$, —$OCH_2X^{25}$, —$OCHX^{25}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25}$ is —F, —Cl, —Br, or —I.

In embodiments, $R^{2A}$ is independently hydrogen, —$CX^{2A}_3$, —CN, —COOH, —$CONH_2$, —$CHX^{2A}_2$, —$CH_2X^{2A}$, $R^{23A}$-substituted or unsubstituted alkyl (e.g., $C_1$-$C_8$, $C_1$-$C_6$, $C_1$-$C_4$, or $C_1$-$C_2$), $R^{23A}$-substituted or unsubstituted heteroalkyl (e.g., 2 to 8 membered, 2 to 6 membered, 4 to 6 membered, 2 or 3 membered, or 4 to 5 membered), $R^{23A}$-substituted or unsubstituted cycloalkyl (e.g., $C_3$—C, $C_3$-$C_6$, $C_4$-$C_6$, or $C_5$-$C_6$), $R^{23A}$-substituted or unsubstituted heterocycloalkyl (e.g., 3 to 6 membered, 4 to 6 membered, 4 to 5 membered, or 5 to 6 membered), $R^{23A}$-substituted or unsubstituted aryl (e.g., $C_6$-$C_{10}$ or phenyl), or $R^{23A}$-substituted or unsubstituted heteroaryl (e.g., 5 to 10 membered, 5 to 9 membered, or 5 to 6 membered). $X^{2A}$ is —F, —Cl, —Br, or —I. In embodiments, $R^{2A}$ is independently hydrogen. In embodiments, $R^{2A}$ is independently methyl. In embodiments, $R^{2A}$ is independently ethyl. In embodiments, $R^{2A}$ is independently hydrogen, —$CX^{2A}_3$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{2A}$ and R$^{2B}$ substituents bonded to the same nitrogen atom may optionally be joined to form a R$^{23A}$-substituted or unsubstituted heterocycloalkyl or R$^{23A}$-substituted or unsubstituted heteroaryl. In embodiments, R$^{2A}$ and R$^{2B}$ substituents bonded to the same nitrogen atom may optionally be joined to form a R$^{23A}$-substituted or unsubstituted 3 to 6 membered heterocycloalkyl or R$^{23A}$-substituted or unsubstituted 5 to 6 membered heteroaryl. In embodiments, R$^{2A}$ and R$^{2B}$ Substituents bonded to the same nitrogen atom may optionally be joined to form an unsubstituted 3 to 6 membered heterocycloalkyl or unsubstituted 5 to 6 membered heteroaryl. In embodiments, R$^{2A}$ and R$^{2B}$ substituents bonded to the same nitrogen atom may optionally be joined to form a R$^{23A}$-substituted or unsubstituted piperazinyl. In embodiments, R$^{2A}$ and R$^{2B}$ substituents bonded to the same nitrogen atom may optionally be joined to form a R$^{23A}$-substituted or unsubstituted piperidinyl. In embodiments, R$^{2A}$ and R$^{2B}$ substituents bonded to the same nitrogen atom may optionally be joined to form a R$^{23A}$-substituted or unsubstituted pyrrolidinyl. In embodiments, R$^{2A}$ and R$^{2B}$ substituents bonded to the same nitrogen atom may optionally be joined to form a R$^{23A}$-substituted or unsubstituted azetidinyl. In embodiments, R$^{2A}$ and R$^{2B}$ substituents bonded to the same nitrogen atom may optionally be joined to form a R$^{23A}$-substituted or unsubstituted morpholinyl. In embodiments, R$^{2A}$ and R$^{2B}$ substituents bonded to the same nitrogen atom may optionally be joined to form a R$^{23A}$-substituted or unsubstituted azeridinyl.

R$^{23A}$ is independently oxo, halogen, —CX$^{23A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{23A}_2$, —CH$_2$X$^{23A}$, —OCX$^{23A}_3$, —OCH$_2$X$^{23A}$, —OCHX$^{23A}_2$, R$^{24A}$-substituted or unsubstituted alkyl (e.g., C$_1$-C$_8$, C$_1$-C$_6$, C$_1$-C$_4$, or C$_1$-C$_2$), R$^{24A}$-substituted or unsubstituted heteroalkyl (e.g., 2 to 8 membered, 2 to 6 membered, 4 to 6 membered, 2 or 3 membered, or 4 to 5 membered), R$^{24A}$-substituted or unsubstituted cycloalkyl (e.g., C$_3$-C$_8$, C$_3$-C$_6$, C$_4$-C$_6$, or C$_5$-C$_6$), R$^{24A}$-substituted or unsubstituted heterocycloalkyl (e.g., 3 to 6 membered, 4 to 6 membered, 4 to 5 membered, or 5 to 6 membered), R$^{24A}$-substituted or unsubstituted aryl (e.g., C$_6$-C$_{10}$ or phenyl), or R$^{24A}$-substituted or unsubstituted heteroaryl (e.g., 5 to 10 membered, 5 to 9 membered, or 5 to 6 membered). X$^{23A}$ is —F, —Cl, —Br, or —I. In embodiments, R$^{23A}$ is independently oxo, halogen, —CX$^{23A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{23A}_2$, —CH$_2$X$^{23A}$, —OCX$^{23A}_3$, —OCH$_2$X$^{23A}$, —OCHX$^{23A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{24A}$ is independently oxo, halogen, —CX$^{24A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{24A}_2$, —CH$_2$X$^{24A}$, —OCX$^{24A}_3$, —OCH$_2$X$^{24A}$, —OCHX$^{24A}_2$, R$^{25A}$-substituted or unsubstituted alkyl (e.g., C$_1$-C$_8$, C$_1$-C$_6$, C$_1$-C$_4$, or C$_1$-C$_2$), R$^{25A}$-substituted or unsubstituted heteroalkyl (e.g., 2 to 8 membered, 2 to 6 membered, 4 to 6 membered, 2 or 3 membered, or 4 to 5 membered), R$^{25A}$-substituted or unsubstituted cycloalkyl (e.g., C$_3$-C$_8$, C$_3$-C$_6$, C$_4$-C$_6$, or C$_5$-C$_6$), R$^{25A}$-substituted or unsubstituted heterocycloalkyl (e.g., 3 to 6 membered. 4 to 6 membered, 4 to 5 membered, or 5 to 6 membered), R$^{25A}$-substituted or unsubstituted aryl (e.g., C$_6$-C$_{10}$ or phenyl), or R$^{25A}$-substituted or unsubstituted heteroaryl (e.g., 5 to 10 membered, 5 to 9 membered, or 5 to 6 membered). X$^{24A}$ is —F, —Cl, —Br, or —I. In embodiments, R$^{24A}$ is independently oxo, halogen, —CX$^{24A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{24A}_2$, —CH$_2$X$^{24A}$, —OCX$^{24A}_3$, —OCH$_2$X$^{24A}$, —OCHX$^{4A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, Or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{25A}$ is independently oxo, halogen, —CX$^{25A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{25A}_2$, —CH$_2$X$^{25A}$, —OCX$^{25A}_3$, —OCH$_2$X$^{25A}$, —OCHX$^{25A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{25A}$ is —F, —Cl, —Br, or —I.

In embodiments, R$^{2B}$ is independently hydrogen, —CX$^{2B}_3$, —CN, —COOH, —CONH$_2$, —CHX$^{2B}_2$, —CH$_2$X$^{2B}$, R$^{23B}$-substituted or unsubstituted alkyl (e.g., C$_1$-C$_8$, C$_1$-C$_6$, C$_1$-C$_4$, or C$_1$-C$_2$), R$^{23B}$-substituted or unsubstituted heteroalkyl (e.g., 2 to 8 membered, 2 to 6 membered, 4 to 6 membered, 2 or 3 membered, or 4 to 5 membered), R$^{23B}$-substituted or unsubstituted cycloalkyl (e.g., C$_3$-C$_8$, C$_3$-C$_6$, C$_4$-C$_6$, or C$_5$-C$_6$), R$^{21B}$-substituted or unsubstituted heterocycloalkyl (e.g., 3 to 6 membered, 4 to 6 membered, 4 to 5 membered, or 5 to 6 membered), R$^{23B}$-substituted or unsubstituted aryl (e.g., C$_6$-C$_{10}$ or phenyl), or R$^{23B}$-substituted or unsubstituted heteroaryl (e.g., 5 to 10 membered, 5 to 9 membered, or 5 to 6 membered). X$^{2B}$ is —F, —Cl, —Br, or —I. In embodiments, R$^{2B}$ is independently hydrogen. In embodiments, R$^{2B}$ is independently methyl. In embodiments. R$^{2B}$ is independently ethyl. In embodiments. R$^{2B}$ is independently hydrogen, —CX$^{2B}_3$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{2B}$ and $R^{2A}$ substituents bonded to the same nitrogen atom may optionally be joined to form a $R^{23B}$-substituted or unsubstituted heterocycloalkyl or $R^{23B}$-substituted or unsubstituted heteroaryl. In embodiments, $R^{2B}$ and $R^{2A}$ substituents bonded to the same nitrogen atom may optionally be joined to form a $R^{23B}$-substituted or unsubstituted 3 to 6 membered heterocycloalkyl or $R^{23B}$-substituted or unsubstituted 5 to 6 membered heteroaryl. In embodiments, $R^{2B}$ and $R^{2A}$ substituents bonded to the same nitrogen atom may optionally be joined to form an unsubstituted 3 to 6 membered heterocycloalkyl or unsubstituted 5 to 6 membered heteroaryl. In embodiments, $R^{2B}$ and $R^{2A}$ substituents bonded to the same nitrogen atom may optionally be joined to form a $R^{23B}$-substituted or unsubstituted piperazinyl. In embodiments, $R^{2B}$ and $R^{2A}$ substituents bonded to the same nitrogen atom may optionally be joined to form a $R^{23B}$-substituted or unsubstituted piperidinyl. In embodiments, $R^{2B}$ and $R^{2A}$ substituents bonded to the same nitrogen atom may optionally be joined to form a $R^{23B}$-substituted or unsubstituted pyrrolidinyl. In embodiments, $R^{2B}$ and $R^{2A}$ substituents bonded to the same nitrogen atom may optionally be joined to form a $R^{23B}$-substituted or unsubstituted azetidinyl. In embodiments, $R^{2B}$ and $R^{2A}$ substituents bonded to the same nitrogen atom may optionally be joined to form a $R^{2B}$-substituted or unsubstituted morpholinyl. In embodiments, $R^{2B}$ and $R^{2A}$ substituents bonded to the same nitrogen atom may optionally be joined to form a $R^{23B}$-substituted or unsubstituted azeridinyl.

$R^{23B}$ is independently oxo, halogen, —$CX^{23B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{23B}_2$, —$CH_2X^{23B}$, —$OCX^{23B}_3$, —$OCH_2X^{23B}$, —$OCHX^{23B}_2$, $R^{24B}$-substituted or unsubstituted alkyl (e.g., $C_1$-$C_8$, $C_1$-$C_6$, $C_1$-$C_4$, or $C_1$-$C_2$), $R^{24B}$-substituted or unsubstituted heteroalkyl (e.g., 2 to 8 membered, 2 to 6 membered, 4 to 6 membered, 2 or 3 membered, or 4 to 5 membered), $R^{24B}$-substituted or unsubstituted cycloalkyl (e.g., $C_3$-$C_8$, $C_3$-$C_6$, $C_4$-$C_6$, or $C_5$-$C_6$), $R^{24B}$-substituted or unsubstituted heterocycloalkyl (e.g., 3 to 6 membered, 4 to 6 membered, 4 to 5 membered, or 5 to 6 membered), $R^{24B}$-substituted or unsubstituted aryl (e.g., $C_6$-$C_{10}$ or phenyl), or $R^{24B}$-substituted or unsubstituted heteroaryl (e.g., 5 to 10 membered, 5 to 9 membered, or 5 to 6 membered). $X^{23B}$ is —F, —Cl, —Br, or —I. In embodiments, $R^{23B}$ is independently oxo, halogen, —$CX^{23B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{23}_{82}$, —$CH_2X^{23B}$, —$OCX^2_3$, —$OCH_2X^{23B}$, —$OCHX^{23B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{24B}$ is independently oxo, halogen, —$CX^{24B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{24B}_2$, —$CH_2X^{24B}$, —$OCX^{24B}_3$, —$OCH_2X^{24B}$, —$OCHX^{24B}_2$, $R^{25B}$-substituted or unsubstituted alkyl (e.g., $C_1$-$C_8$, $C_1$-$C_6$, $C_1$-$C_4$, or $C_1$-$C_2$), $R^{25B}$-substituted or unsubstituted heteroalkyl (e.g., 2 to 8 membered, 2 to 6 membered, 4 to 6 membered, 2 or 3 membered, or 4 to 5 membered), $R^{25B}$-substituted or unsubstituted cycloalkyl (e.g., $C_3$-$C_8$, $C_3$-$C_6$, $C_4$-$C_6$, or $C_5$-$C_6$), $R^{25B}$-substituted or unsubstituted heterocycloalkyl (e.g., 3 to 6 membered, 4 to 6 membered, 4 to 5 membered, or 5 to 6 membered), $R^{25B}$-substituted or unsubstituted aryl (e.g., $C_6$-$C_{10}$ or phenyl), or $R^{25B}$-substituted or unsubstituted heteroaryl (e.g., 5 to 10 membered, 5 to 9 membered, or 5 to 6 membered). $X^{24B}$ is —F, —Cl, —Br, or —I. In embodiments, $R^{24B}$ is independently oxo, halogen, —$CX^{24B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{24B}_2$, —$CH_2X^{24B}$, —$OCX^{24B}_3$, —$OCH_2X^{24B}$, —$OCHX^{24B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{25B}$ is independently oxo, halogen, —$CX^{25B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{25B}_2$, —$CH_2X^{25B}$, —$OCX^{25B}$, —$OCH_2X^{25B}$, —$OCHX^{25B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25B}$ is —F, —Cl, —Br, or —I.

In embodiments, $R^{2C}$ is independently hydrogen, —$CX^{2C}_3$, —CN, —COOH, —$CONH_2$, —$CHX^{2C}_2$, —$CH_2X^{2C}$, $R^{23C}$-substituted or unsubstituted alkyl (e.g., $C_1$-$C_8$, $C_1$-$C_6$, $C_1$-$C_4$, or $C_1$-$C_2$), $R^{23C}$-substituted or unsubstituted heteroalkyl (e.g., 2 to 8 membered, 2 to 6 membered, 4 to 6 membered, 2 or 3 membered, or 4 to 5 membered), $R^{23C}$-substituted or unsubstituted cycloalkyl (e.g., $C_3$-$C_8$, $C_3$-$C_6$, $C_4$-$C_6$, or $C_5$-$C_6$), $R^{23C}$-substituted or unsubstituted heterocycloalkyl (e.g., 3 to 6 membered, 4 to 6 membered, 4 to 5 membered, or 5 to 6 membered), $R^{23C}$-substituted or unsubstituted aryl (e.g., $C_6$-$C_{10}$ or phenyl), or $R^{23C}$-substituted or unsubstituted heteroaryl (e.g., 5 to 10 membered, 5 to 9 membered, or 5 to 6 membered). $X^{2C}$ is —F, —Cl, —Br, or —I. In embodiments, $R^{2C}$ is independently hydrogen. In embodiments, $R^{2C}$ is independently methyl. In embodiments, $R^{2C}$ is independently ethyl. In embodiments, $R^{2C}$ is independently hydrogen, —$CX^{2C}_3$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{23C}$ is independently oxo, halogen, —$CX^{23C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)

H, —NHC(O)OH, —NHOH, —CHX$^{23C}_2$, —CH$_2$X$^{23C}$, —OCX$^{23C}_3$, —OCH$_2$X$^{23C}$, —OCHX$^{23C}_2$, R$^{24C}$-substituted or unsubstituted alkyl (e.g., C$_1$-C$_8$, C$_1$-C$_6$, C$_1$-C$_4$, or C$_1$-C$_2$), R$^{24C}$-substituted or unsubstituted heteroalkyl (e.g., 2 to 8 membered, 2 to 6 membered, 4 to 6 membered, 2 or 3 membered, or 4 to 5 membered), R$^{24C}$-substituted or unsubstituted cycloalkyl (e.g., C$_3$-C$_8$, C$_3$-C$_6$, C$_4$-C$_6$, or C$_5$-C$_6$), R$^{24C}$-substituted or unsubstituted heterocycloalkyl (e.g., 3 to 6 membered, 4 to 6 membered, 4 to 5 membered, or 5 to 6 membered), R$^{24C}$-substituted or unsubstituted aryl (e.g., C$_6$-C$_{10}$ or phenyl), or R$^{24C}$-substituted or unsubstituted heteroaryl (e.g., 5 to 10 membered, 5 to 9 membered, or 5 to 6 membered). X$^{23C}$ is —F, —Cl, —Br, or —I. In embodiments, R$^{23C}$ is independently oxo, halogen, —CX$^{23C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{23C}_2$, —CH$_2$X$^{23C}$, —OCX$^{23C}_3$, —OCH$_2$X$^{23C}$, —OCHX$^{23C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{24C}$ is independently oxo, halogen, —CX$^{24C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{24C}_2$, —CH$_2$X$^{24C}$, —OCX$^{24C}_3$, —OCH$_2$X$^{24C}$, —OCHX$^{24C}_2$, R$^{25C}$-substituted or unsubstituted alkyl (e.g., C$_1$-C$_8$, C$_1$-C$_6$, C$_1$-C$_4$, or C$_1$-C$_2$), R$^{25C}$-substituted or unsubstituted heteroalkyl (e.g., 2 to 8 membered, 2 to 6 membered, 4 to 6 membered, 2 or 3 membered, or 4 to 5 membered), R$^{25C}$-substituted or unsubstituted cycloalkyl (e.g., C$_3$-C$_8$, C$_3$-C$_6$, C$_4$-C$_6$, or C$_5$-C$_6$), R$^{25C}$-substituted or unsubstituted heterocycloalkyl (e.g., 3 to 6 membered, 4 to 6 membered. 4 to 5 membered, or 5 to 6 membered), R$^{25C}$-substituted or unsubstituted aryl (e.g., C$_6$-C$_{10}$ or phenyl), or R$^{25C}$-substituted or unsubstituted heteroaryl (e.g., 5 to 10 membered, 5 to 9 membered, or 5 to 6 membered). X$^{24C}$ is —F, —Cl, —Br, or —I. In embodiments, R$^{24C}$ is independently oxo, halogen, —CX$^{24C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{24C}_2$, —CH$_2$X$^{24C}$, —OCX$^{24C}_3$, —OCH$_2$X$^{24C}$, —OCHX$^{24C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{25C}$ is independently oxo, halogen, —CX$^{25C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{25C}_2$, —CH$_2$X$^{25C}$, —OCX$^{25C}_3$, —OCH$_2$X$^{25C}$, —OCHX$^{25C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{25C}$ is —F, —Cl, —Br, or —I.

In embodiments, R$^{2D}$ is independently hydrogen, —CX$^{2D}_3$, —CN, —COOH, —CONH$_2$, —CHX$^{2D}_2$, —CH$_2$X$^{2D}$, R$^{23D}$-substituted or unsubstituted alkyl (e.g., C$_1$-C$_8$, C$_1$-C$_6$, C$_1$-C$_4$, or C$_1$-C$_2$), R$^{23D}$-substituted or unsubstituted heteroalkyl (e.g., 2 to 8 membered, 2 to 6 membered, 4 to 6 membered, 2 or 3 membered, or 4 to 5 membered), R$^{23D}$-substituted or unsubstituted cycloalkyl (e.g., C$_3$-C$_8$, C$_3$-C$_6$, C$_4$-C$_6$, or C$_5$-C$_6$), R$^{23D}$-substituted or unsubstituted heterocycloalkyl (e.g., 3 to 6 membered, 4 to 6 membered, 4 to 5 membered, or 5 to 6 membered), R$^{23D}$-substituted or unsubstituted aryl (e.g., C$_6$-C$_{10}$ or phenyl), or R$^{23D}$-substituted or unsubstituted heteroaryl (e.g., 5 to 10 membered, 5 to 9 membered, or 5 to 6 membered). X$^{2D}$ is —F, —Cl, —Br, or —I. In embodiments, R$^{2D}$ is independently hydrogen. In embodiments, R$^{2D}$ is independently methyl. In embodiments. R$^{2D}$ is independently ethyl. In embodiments, R$^{2D}$ is independently hydrogen, —CX$^{2D}_3$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{23D}$ is independently oxo, halogen, —CX$^{23D}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{23D}_2$, —CH$_2$X$^{23D}$, —OCX$^{23D}_3$, —OCH$_2$X$^{23D}$, —OCHX$^{23D}_2$, R$^{24D}$-substituted or unsubstituted alkyl (e.g., C$_1$-C$_8$, C$_1$-C$_6$, C$_1$-C$_4$, or C$_1$-C$_2$), R$^{24D}$-substituted or unsubstituted heteroalkyl (e.g., 2 to 8 membered, 2 to 6 membered, 4 to 6 membered, 2 or 3 membered, or 4 to 5 membered), R$^{24D}$-substituted or unsubstituted cycloalkyl (e.g., C$_3$-C$_8$, C$_3$-C$_6$, C$_4$-C$_6$, or C$_5$-C$_6$), R$^{24D}$-substituted or unsubstituted heterocycloalkyl (e.g., 3 to 6 membered, 4 to 6 membered, 4 to 5 membered, or 5 to 6 membered), R$^{24D}$-substituted or unsubstituted aryl (e.g., C$_6$-C$_{10}$ or phenyl), or R$^{24D}$-substituted or unsubstituted heteroaryl (e.g., 5 to 10 membered, 5 to 9 membered, or 5 to 6 membered). X$^{23D}$ is —F, —Cl, —Br, or —I. In embodiments, R$^{23D}$ is independently oxo, halogen, —CX$^{23D}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{23D}_2$, —CH$_2$X$^{23D}$, —OCX$^{23D}_3$, —OCH$_2$X$^{23D}$, —OCHX$^{23D}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{24D}$ is independently oxo, halogen, —CX$^{24D}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{24D}_2$, —CH$_2$X$^{24D}$, —OCX$^{24D}_3$, —OCH$_2$X$^{24D}$, —OCHX$^{24D}_2$, R$^{25D}$-substituted or unsubstituted alkyl (e.g., C$_1$-C$_8$, C$_1$-C$_6$, C$_1$-C$_4$, or C$_1$-C$_2$), R$^{25D}$-substituted or unsubstituted heteroalkyl (e.g., 2 to 8 membered, 2 to 6 membered, 4 to 6 membered, 2 or 3 membered, or 4 to 5 membered), $R^{25D}$-substituted or unsubstituted cycloalkyl (e.g., $C_3$-$C_8$, $C_3$-$C_6$, $C_4$-$C_6$, or $C_5$-$C_6$), $R^{25D}$-substituted or unsubstituted heterocycloalkyl (e.g., 3 to 6 membered, 4 to 6 membered, 4 to 5 membered, or 5 to 6 membered), $R^{25D}$-substituted or unsubstituted aryl (e.g., $C_6$-$C_{10}$ or phenyl), or $R^{25D}$-substituted or unsubstituted heteroaryl (e.g., 5 to 10 membered, 5 to 9 membered, or 5 to 6 membered). $X^{24D}$ is —F, —Cl, —Br, or —I. In embodiments, $R^{24D}$ is independently oxo, halogen, —$CX^{24D}{}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{24D}{}_2$, —$CH_2X^{24D}$, —$OCX^{24D}{}_3$, —$OCH_2X^{24D}$, —$OCHX^{24D}{}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{25D}$ is independently oxo, halogen, —$CX^{25D}{}_3$, —CN, —OH, —$NH_2$, —COOH, —$CONH_2$, —SH, —$NHNH_2$, —$ONH_2$, —$NHC(O)NHNH_2$, $NHC(O)NH_2$, —NHC(O)H, —NHC(O)OH, —NHOH, —$CHX^{25D}{}_2$, —$CH_2X^{25D}$, —$OCX^{25D}{}_3$, —$OCH_2X^{25D}$, $OCHX^{25D}{}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25D}$ is —F, —Cl, —Br, or —I.

In embodiments, $R^3$ is hydrogen, halogen, —$CX^3{}_3$, —$CHX^3{}_2$, —$CH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^3{}_3$, —$OCHX^2$, —$OCH_2X^3$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is hydrogen.

In embodiments, $R^3$ is independently halogen. In embodiments, $R^3$ is independently oxo. In embodiments, $R^3$ is independently —$CX^3{}_3$. In embodiments, $R^3$ is independently —$CHX^3{}_2$. In embodiments, $R^3$ is independently —$CH_2X^3$. In embodiments. $R^3$ is independently —$OCX^3{}_3$. In embodiments, $R^3$ is independently —$OCH_2X^3$. In embodiments, $R^3$ is independently —$OCHX^3{}_2$. In embodiments, $R^3$ is independently —CN. In embodiments, $R^3$ is independently —$SO_{n3}R^{3D}$. In embodiments, $R^3$ is independently —$SO_{v3}NR^{3A}R^{3B}$. In embodiments, $R^3$ is independently —$NHC(O)NR^{3A}R^{3B}$. In embodiments, $R^3$ is independently —$NHNR^{3A}R^{3B}$. In embodiments, $R^3$ is independently —$N(O)_{m3}$. In embodiments, $R^3$ is independently —$NR^{3A}R^{3B}$. In embodiments, $R^3$ is independently —C(O)$R^{3C}$. In embodiments, $R^1$ is independently —C(O)$OR^{3C}$. In embodiments, $R^3$ is independently —C(O)$NR^{3A}R^{3B}$. In embodiments, $R^3$ is independently —$OR^{3D}$. In embodiments, $R^3$ is independently —$NR^{3A}SO_2R^{3D}$. In embodiments, $R^3$ is independently —$NR^{3A}C(O)R^{3C}$. In embodiments, $R^3$ is independently —$NR^{3A}C(O)OR^{3C}$. In embodiments, $R^3$ is independently —$NR^{3A}OR^{3C}$. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —$NO_2$. In embodiments, $R^3$ is independently —SH. In embodiments, $R^3$ is independently —$N_3$. In embodiments, $R^3$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^3$ is —F, —Cl, —Br, or —I. In embodiments, $R^3$ is independently hydrogen. In embodiments, $R^3$ is independently methyl. In embodiments, $R^3$ is independently ethyl. In embodiments, $R^3$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^3$ is independently —$OCH_3$. In embodiments, $R^3$ is independently —COOH. In embodiments, $R^3$ is independently —$COO^-$. In embodiments, $R^3$ is independently a salt of —$COO^-$. In embodiments, $R^3$ is independently a choline salt of —$COO^-$. In embodiments, $R^3$ is independently a —$COO^-(HOCH_2CH_2N(CH_3)_3)$. In embodiments, $R^3$ is independently —$CONH_2$. In embodiments, $R^3$ is independently —$CONHCH_3$. In embodiments, $R^3$ is independently —$CONHCH_2CH_3$. In embodiments, $R^3$ is independently —$CONHC(CH_3)_2$. In embodiments, $R^3$ is independently —$CONHC(CH_3)_3$. In embodiments, $R^3$ is independently —$COOCH_3$. In embodiments, $R^3$ is independently —$COOCH_2CH_3$. In embodiments, $R^3$ is independently —$COOC(CH_3)_2$. In embodiments, $R^3$ is independently —$COOC(CH_3)_3$. In embodiments, $R^3$ is independently —$OCH_2CH_3$. In embodiments, $R^3$ is independently —$OC(CH_3)_2$. In embodiments, $R^3$ is independently —$OC(CH_3)_3$. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted butyl. In embodiments, $R^3$ is independently unsubstituted n-propyl. In embodiments. $R^3$ is independently unsubstituted iso-propyl. In embodiments, $R^3$ is independently unsubstituted n-butyl. In embodiments, $R^3$ is independently unsubstituted iso-butyl. In embodiments, $R^3$ is independently unsubstituted methoxy. In embodiments, $R^3$ is independently unsubstituted ethoxy. In embodiments, $R^3$ is independently unsubstituted propoxy. In embodiments, $R^3$ is independently unsubstituted butoxy. In embodiments, $R^3$ is independently —F. In embodiments, $R^3$ is independently —Cl. In embodiments, $R^3$ is independently —I. In embodiments, $R^3$ is independently —Br. In embodiments, $R^3$ is independently —$NO_2$. In embodiments, $R^3$ is independently —$CF_3$. In embodiments, $R^3$ is independently —$CCl_3$. In embodiments, $R^3$ is independently —$Cl_3$. In embodiments, $R^3$ is independently —$CBr_3$. In embodiments, $R^3$ is independently —$NH_2$. In embodiments, $R^3$ is independently —$N_3$.

In embodiments, $R^3$ is independently hydrogen, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{26}$-substituted or unsubstituted alkyl (e.g., $C_1$-$C_8$, $C_1$-$C_6$, $C_1$-$C_4$, or $C_1$-$C_2$), $R^{26}$-substituted or unsubstituted heteroalkyl (e.g., 2 to 8 membered, 2 to 6 membered, 4 to 6 membered, 2 or 3 membered, or 4 to 5 membered), $R^{26}$-substituted or unsubstituted cycloalkyl (e.g., $C_3$-$C_8$, $C_3$-$C_6$, $C_4$-$C_6$, or $C_5$-$C_6$), $R^{26}$-substituted or unsubstituted heterocycloalkyl (e.g., 3 to 6 membered, 4 to 6 membered, 4 to 5 membered, or 5 to 6 membered), $R^{26}$-substituted or unsubstituted aryl (e.g., $C_6$-$C_{10}$ or phenyl), or $R^{26}$-substituted or unsubstituted heteroaryl (e.g., 5 to 10 membered, 5 to 9 membered, or 5 to 6 membered). $X^3$ is —F, —Cl, —Br, or —I. In embodiments, $R^3$ is independently hydrogen. In embodiments, $R^3$ is independently methyl. In embodiments, $R^3$ is independently ethyl. In embodiments, $R^3$ is independently hydrogen, halogen, —$CX^3_3$, —$CHX^3_2$, —$CH_2X^3$, —$OCX^3_3$, —$OCH_2X^3$, —$OCHX^3_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered. 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{26}$ is independently oxo, halogen, —$CX^{26}_3$, —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 or 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 6 membered, 4 to 6 membered, 4 to 5 membered, or 5 to 6 membered), $R^{27}$-substituted or unsubstituted aryl (e.g., $C_6$-$C_{10}$ or phenyl), or $R^{27}$-substituted or unsubstituted heteroaryl (e.g., 5 to 10 membered, 5 to 9 membered, or 5 to 6 membered). $X^{26}$ is —F, —Cl, —Br, or —I. In embodiments, $R^{26}$ is independently oxo, halogen, —$CX^{26}_3$. —$CHX^{26}_2$, —$CH_2X^{26}$, —$OCX^{26}_3$, —$OCH_2X^{26}$, —$OCHX^{26}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

unsubstituted aryl (e.g., $C_6$-$C_1$ or phenyl), or unsubstituted heteroaryl (e.g., 5 to 10 membered, 5 to 9 membered, or 5 to 6 membered).

$R^{27}$ is independently oxo, halogen, —$CX^{27}_3$, —$CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 or 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered). $X^{27}$ is —F, —Cl, —Br, or —I. In embodiments, $R^{27}$ is independently oxo, halogen, —$CX^{27}_3$, —$CHX^{27}_2$, —$CH_2X^{27}$, —$OCX^2_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{28}$ is independently oxo, halogen, —$CX^{28}_3$, —$CHX^{28}_2$, —$CH_2X^{28}$, —$OCX^{28}_3$, —$OCH_2X^{28}$, —$OCHX^{28}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28}$ is —F, —Cl, —Br, or —I.

In embodiments, $R^{3A}$ is independently hydrogen, —$CX^{3A}_3$, —CN, —COOH, —$CONH_2$, —$CHX^{3A}_2$, —$CH_2X^{3A}$, $R^{26A}$-substituted or unsubstituted alkyl (e.g., $C_1$-$C_8$, $C_1$-$C_6$, $C_1$-$C_4$, or $C_1$-$C_2$), $R^{26A}$-substituted or unsubstituted heteroalkyl (e.g., 2 to 8 membered, 2 to 6 membered, 4 to 6 membered, 2 or 3 membered, or 4 to 5 membered), $R^{26A}$-substituted or unsubstituted cycloalkyl (e.g., $C_3$-$C_8$, $C_3$-$C_6$, $C_4$-$C_6$, or $C_5$-$C_6$), $R^{26A}$-substituted or unsubstituted heterocycloalkyl (e.g., 3 to 6 membered. 4 to 6 membered, 4 to 5 membered, or 5 to 6 membered), $R^{26A}$-substituted or unsubstituted aryl (e.g., $C_6$-$C_{10}$ or phenyl), or $R^{26A}$-substituted or unsubstituted heteroaryl (e.g., 5 to 10 membered, 5 to 9 membered, or 5 to 6 membered). $X^{3A}$ is —F, —Cl, —Br, or —I. In embodiments, $R^{3A}$ is independently hydrogen. In embodiments, $R^{3A}$ is independently methyl. In embodiments. $R^{3A}$ is independently ethyl. In embodiments, $R^{3A}$ is independently hydrogen, —$CX^{3A}_3$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{3A}$ and R$^{3B}$ substituents bonded to the same nitrogen atom may optionally be joined to form a R$^{26A}$-substituted or unsubstituted heterocycloalkyl or R$^{26A}$-substituted or unsubstituted heteroaryl. In embodiments, R$^{3A}$ and R$^{3B}$ substituents bonded to the same nitrogen atom may optionally be joined to form a R$^{26A}$-substituted or unsubstituted 3 to 6 membered heterocycloalkyl or R$^{26A}$-substituted or unsubstituted 5 to 6 membered heteroaryl. In embodiments, R$^{3A}$ and R$^{3B}$ substituents bonded to the same nitrogen atom may optionally be joined to form an unsubstituted 3 to 6 membered heterocycloalkyl or unsubstituted 5 to 6 membered heteroaryl. In embodiments, R$^{3A}$ and R$^{3B}$ substituents bonded to the same nitrogen atom may optionally be joined to form a R$^{26A}$-substituted or unsubstituted piperazinyl. In embodiments, R$^{3A}$ and R$^{3B}$ substituents bonded to the same nitrogen atom may optionally be joined to form a R$^{26A}$-substituted or unsubstituted piperidinyl. In embodiments, R$^{3A}$ and R$^{3B}$ substituents bonded to the same nitrogen atom may optionally be joined to form a R$^{26A}$-substituted or unsubstituted pyrrolidinyl. In embodiments, R$^{3A}$ and R$^{3B}$ substituents bonded to the same nitrogen atom may optionally be joined to form a R$^{26A}$-substituted or unsubstituted azetidinyl. In embodiments, R$^{3A}$ and R$^{3B}$ substituents bonded to the same nitrogen atom may optionally be joined to form a R$^{26A}$-substituted or unsubstituted morpholinyl. In embodiments, R$^{3A}$ and R$^{3B}$ substituents bonded to the same nitrogen atom may optionally be joined to form a R$^{26A}$-substituted or unsubstituted azeridinyl.

R$^{26A}$ is independently oxo, halogen, —CX$^{26A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{26A}_2$, —CH$_2$X$^{26A}$, —OCX$^{26A}_3$, —OCH$_2$X$^{26A}$, —OCHX$^{26A}_2$, R$^{27A}$-substituted or unsubstituted alkyl (e.g., C$_1$-C$_8$, C$_1$-C$_6$, C$_1$-C$_4$, or C$_1$-C$_2$), R$^{27A}$-substituted or unsubstituted heteroalkyl (e.g., 2 to 8 membered, 2 to 6 membered, 4 to 6 membered, 2 or 3 membered, or 4 to 5 membered), R$^{27A}$-substituted or unsubstituted cycloalkyl (e.g., C$_3$-C$_8$, C$_3$-C$_6$, C$_4$-C$_6$, or C$_3$-C$_6$), R$^{27A}$-substituted or unsubstituted heterocycloalkyl (e.g., 3 to 6 membered, 4 to 6 membered, 4 to 5 membered, or 5 to 6 membered), R$^{27A}$-substituted or unsubstituted aryl (e.g., C$_6$-C$_{10}$ or phenyl), or R$^{27A}$-substituted or unsubstituted heteroaryl (e.g., 5 to 10 membered, 5 to 9 membered, or 5 to 6 membered). X$^{26A}$ is —F, —Cl, —Br, or —I. In embodiments, R$^{26A}$ is independently oxo, halogen, —CX$^{26A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{26A}_2$, —CH$_2$X$^{26A}$, —OCX$^{26A}_3$, —OCH$_2$X$^{26A}$, —OCHX$^{26A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{27A}$ is independently oxo, halogen, —CX$^{27A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{27A}_2$, —CH$_2$X$^{27A}$, —OCX$^{27A}_3$, —OCH$_2$X$^{27A}$, —OCHX$^{27A}_2$, R$^{28A}$-substituted or unsubstituted alkyl (e.g., C$_1$-C$_8$, C$_1$-C$_6$, C$_1$-C$_4$, or C$_1$-C$_2$), R$^{28A}$-substituted or unsubstituted heteroalkyl (e.g., 2 to 8 membered, 2 to 6 membered, 4 to 6 membered, 2 or 3 membered, or 4 to 5 membered), R$^{28A}$-substituted or unsubstituted cycloalkyl (e.g., C$_3$-C$_8$, C$_3$-C$_6$, C$_4$-C$_6$, or C$_5$-C$_6$), R$^{28A}$-substituted or unsubstituted heterocycloalkyl (e.g., 3 to 6 membered, 4 to 6 membered, 4 to 5 membered, or 5 to 6 membered), R$^{28A}$-substituted or unsubstituted aryl (e.g., C$_6$-C$_{10}$ or phenyl), or R$^{28A}$-substituted or unsubstituted heteroaryl (e.g., 5 to 10 membered, 5 to 9 membered, or 5 to 6 membered). X$^{27A}$ is —F, —Cl, —Br, or —I. In embodiments, R$^{27A}$ is independently oxo, halogen, —CX$^{27A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{27A}_2$, —CH$_2$X$^{27A}$, —OCX$^{27A}_3$, —OCH$_2$X$^{27A}$, —OCHX$^{27A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{28A}$ is independently oxo, halogen, —CX$^{28A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{28A}_2$, —CH$_2$X$^{28A}$, —OCX$^{28A}_3$, —OCH$_2$X$^{28A}$, —OCHX$^{28A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{28A}$ is —F, —Cl, —Br, or —I.

In embodiments, R$^{3B}$ is independently hydrogen, —CX$^{3B}_3$, —CN, —COOH, —CONH$_2$, —CHX$^{3B}_2$, —CH$_2$X$^{3B}$, R$^{26B}$-substituted or unsubstituted alkyl (e.g., C$_1$-C$_8$, C$_1$-C$_6$, C$_1$-C$_4$, or C$_1$-C$_2$), R$^{26B}$-substituted or unsubstituted heteroalkyl (e.g., 2 to 8 membered, 2 to 6 membered, 4 to 6 membered, 2 or 3 membered, or 4 to 5 membered), R$^{26B}$-substituted or unsubstituted cycloalkyl (e.g., C$_3$-C$_8$, C$_3$-C$_6$, C$_4$-C$_6$, or C$_5$-C$_6$), R$^{6B}$-substituted or unsubstituted heterocycloalkyl (e.g., 3 to 6 membered, 4 to 6 membered, 4 to 5 membered, or 5 to 6 membered), R$^{26B}$-substituted or unsubstituted aryl (e.g., C$_6$-C$_{10}$ or phenyl), or R$^{26B}$-substituted or unsubstituted heteroaryl (e.g., 5 to 10 membered, 5 to 9 membered, or 5 to 6 membered). X$^{3B}$ is —F, —Cl, —Br, or —I. In embodiments, R$^{3B}$ is independently hydrogen. In embodiments, R$^{3B}$ is independently methyl. In embodiments, R$^{3B}$ is independently ethyl. In embodiments, R$^{3B}$ is independently hydrogen. —CX$^{3B}_3$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{3B}$ and $R^{3A}$ substituents bonded to the same nitrogen atom may optionally be joined to form a $R^{26B}$-substituted or unsubstituted heterocycloalkyl or $R^{26B}$-substituted or unsubstituted heteroaryl. In embodiments, $R^{3B}$ and $R^{3A}$ substituents bonded to the same nitrogen atom may optionally be joined to form a $R^{26B}$-substituted or unsubstituted 3 to 6 membered heterocycloalkyl or $R^{26B}$-substituted or unsubstituted 5 to 6 membered heteroaryl. In embodiments, $R^{3B}$ and $R^{3A}$ substituents bonded to the same nitrogen atom may optionally be joined to form an unsubstituted 3 to 6 membered heterocycloalkyl or unsubstituted 5 to 6 membered heteroaryl. In embodiments, $R^{3B}$ and $R^{3A}$ substituents bonded to the same nitrogen atom may optionally be joined to form a $R^{26B}$-substituted or unsubstituted piperazinyl. In embodiments, $R^{3B}$ and $R^{3A}$ substituents bonded to the same nitrogen atom may optionally be joined to form a $R^{26B}$-substituted or unsubstituted piperidinyl. In embodiments, $R^{3B}$ and $R^{3A}$ substituents bonded to the same nitrogen atom may optionally be joined to form a $R^{26B}$-substituted or unsubstituted pyrrolidinyl. In embodiments, $R^{3B}$ and $R^{3A}$ substituents bonded to the same nitrogen atom may optionally be joined to form a $R^{26B}$-substituted or unsubstituted azetidinyl. In embodiments, $R^{3B}$ and $R^{3A}$ substituents bonded to the same nitrogen atom may optionally be joined to form a $R^{26B}$-substituted or unsubstituted morpholinyl. In embodiments, $R^{3B}$ and $R^{3A}$ substituents bonded to the same nitrogen atom may optionally be joined to form a $R^{26B}$-substituted or unsubstituted azeridinyl.

$R^{26B}$ is independently oxo, halogen, —$CX^{26B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —$NHC(O)$H, —$NHC(O)OH$, —NHOH, —$CHX^{26B}_2$, —$CH_2X^{26B}$, —$OCX^{26B}_3$, —$OCH_2X^{26B}$, —$OCHX^{26B}_2$, $R^{27B}$-substituted or unsubstituted alkyl (e.g., $C_1$-$C_8$, $C_1$-$C_6$, $C_1$-$C_4$, or $C_1$-$C_2$), $R^{27B}$-substituted or unsubstituted heteroalkyl (e.g., 2 to 8 membered, 2 to 6 membered, 4 to 6 membered, 2 or 3 membered, or 4 to 5 membered), $R^{27B}$-substituted or unsubstituted cycloalkyl (e.g., $C_3$-$C_8$, $C_3$-$C_6$, $C_4$-$C_6$, or $C_5$-$C_6$), $R^{27B}$-substituted or unsubstituted heterocycloalkyl (e.g., 3 to 6 membered, 4 to 6 membered, 4 to 5 membered, or 5 to 6 membered), $R^{27B}$-substituted or unsubstituted aryl (e.g., $C_6$-$C_{10}$ or phenyl), or $R^{27B}$-substituted or unsubstituted heteroaryl (e.g., 5 to 10 membered, 5 to 9 membered, or 5 to 6 membered). $X^{26B}$ is —F, —Cl, —Br, or —I. In embodiments, $R^{26B}$ is independently oxo, halogen, —$CX^{26B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —$NHC(O)H$, —$NHC(O)OH$, —NHOH, —$CHX^{26B}_2$, —$CH_2X^{26B}$, —$OCX^{26B}_3$, $OCH_2X^{26B}$, —$OCHX^{26B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{27B}$ is independently oxo, halogen, —$CX^{27B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —$NHC(O)$H, —$NHC(O)OH$, —NHOH, —$CHX^{27B}_2$, —$CH_2X^{27B}$, —$OCX^{27B}_3$, —$OCH_2X^{27B}$, —$OCHX^{27B}_2$, $R^{28B}$-substituted or unsubstituted alkyl (e.g., $C_1$-$C_8$, $C_1$-$C_6$, $C_1$-$C_4$, or $C_1$-$C_2$), $R^{28B}$-substituted or unsubstituted heteroalkyl (e.g., 2 to 8 membered, 2 to 6 membered, 4 to 6 membered, 2 or 3 membered, or 4 to 5 membered), $R^{28B}$-substituted or unsubstituted cycloalkyl (e.g., $C_3$-$C_8$, $C_3$-$C_6$, $C_4$-$C_6$, or $C_5$-$C_6$), $R^{28B}$-substituted or unsubstituted heterocycloalkyl (e.g., 3 to 6 membered, 4 to 6 membered, 4 to 5 membered, or 5 to 6 membered), $R^{28B}$-substituted or unsubstituted aryl (e.g., $C_6$-$C_{10}$ or phenyl), or $R^{28B}$-substituted or unsubstituted heteroaryl (e.g., 5 to 10 membered, 5 to 9 membered, or 5 to 6 membered). $X^{27B}$ is —F, —Cl, —Br, or —I. In embodiments, $R^{27B}$ is independently oxo, halogen, —$CX^{27B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —$NHC(O)H$, —$NHC(O)OH$, —NHOH, —$CHX^{27B}_2$, —$CH_2X^{27B}$, —$OCX^{27B}$, —$OCH_2X^{27B}$, —$OCHX^{27B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered. 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{28B}$ is independently oxo, halogen, —$CX^{28B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —$NHC(O)$H, —$NHC(O)OH$, —NHOH, —$CHX^{28B}_2$, —$CH_2X^{28B}$, —$OCX^{28B}_3$, —$OCH_2X^{28B}$, —$OCHX^{28B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2RB}$ is —F, —Cl, —Br, or —I.

In embodiments, $R^{3C}$ is independently hydrogen, —$CX^{3C}_3$, —CN, —COOH, —$CONH_2$, —$CHX^{3C}_2$, —$CH_2X^{3C}$, $R^{26C}$-substituted or unsubstituted alkyl (e.g., $C_1$-$C_8$, $C_1$-$C_6$, $C_1$-$C_4$, or $C_1$-$C_2$), $R^{26C}$-substituted or unsubstituted heteroalkyl (e.g., 2 to 8 membered, 2 to 6 membered, 4 to 6 membered, 2 or 3 membered, or 4 to 5 membered), $R^{26C}$-substituted or unsubstituted cycloalkyl (e.g., $C_3$-$C_8$, $C_3$-$C_6$, $C_4$-$C_6$, or $C_5$-$C_6$), $R^{26C}$-substituted or unsubstituted heterocycloalkyl (e.g., 3 to 6 membered. 4 to 6 membered, 4 to 5 membered, or 5 to 6 membered), $R^{26C}$-substituted or unsubstituted aryl (e.g., $C_6$-$C_{10}$ or phenyl), or $R^{26C}$-substituted or unsubstituted heteroaryl (e.g., 5 to 10 membered, 5 to 9 membered, or 5 to 6 membered). $X^{3C}$ is —F, —Cl, —Br, or —I. In embodiments, $R^{3C}$ is independently hydrogen. In embodiments, $R^{3C}$ is independently methyl. In embodiments, $R^{3C}$ is independently ethyl. In embodiments, $R^{3C}$ is independently hydrogen, —$CX^{3C}_3$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{26C}$ is independently oxo, halogen, —$CX^{26C}_3$, —CN, —OH, —$NH_2$, —COOH, —$CONH_2$, —SH, —$NHNH_2$, —$ONH_2$, —$NHC(O)NHNH_2$, —$NHC(O)NH_2$, —$NHC(O)$ H, —NHC(O)OH, —NHOH, —CHX$^{26C}_2$, —CH$_2$X$^{26C}$, —OCX$^{26C}_3$, —OCH$_2$X$^{26C}$, —OCHX$^{26C}_2$, R$^{27C}$-substituted or unsubstituted alkyl (e.g., C$_1$-C$_8$, C$_1$-C$_6$, C$_1$-C$_4$, or C$_1$-C$_2$), R$^{27C}$-substituted or unsubstituted heteroalkyl (e.g., 2 to 8 membered, 2 to 6 membered, 4 to 6 membered, 2 or 3 membered, or 4 to 5 membered), R$^{27C}$-substituted or unsubstituted cycloalkyl (e.g., C$_3$-C$_8$, C$_3$-C$_6$, C$_4$-C$_6$, or C$_5$-C$_6$), R$^{27C}$-substituted or unsubstituted heterocycloalkyl (e.g., 3 to 6 membered, 4 to 6 membered, 4 to 5 membered, or 5 to 6 membered), R$^{27C}$-substituted or unsubstituted aryl (e.g., C$_6$-C$_{10}$ or phenyl), or R$^{27C}$-substituted or unsubstituted heteroaryl (e.g., 5 to 10 membered, 5 to 9 membered, or 5 to 6 membered). X$^{26C}$ is —F, —Cl, —Br, or —I. In embodiments, R$^{26C}$ is independently oxo, halogen, —CX$^{26C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{26C}_2$, —CH$_2$X$^{26C}$, —OCX$^{26C}_3$, —OCH$_2$X$^{26C}$, —OCHX$^{26C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{27C}$ is independently oxo, halogen, —CX$^{27C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{27C}_2$, —CH$_2$X$^{27}$, —OCX$^{27C}_3$, —OCH$_2$X$^{27}$C, —OCHX$^{27C}_2$, R$^{28C}$-substituted or unsubstituted alkyl (e.g., C$_1$-C$_8$, C$_1$-C$_6$, C$_1$-C$_4$, or C$_1$-C$_2$), R$^{28C}$-substituted or unsubstituted heteroalkyl (e.g., 2 to 8 membered, 2 to 6 membered, 4 to 6 membered, 2 or 3 membered, or 4 to 5 membered), R$^{28C}$-substituted or unsubstituted cycloalkyl (e.g., C$_3$-C$_8$, C$_3$-C$_6$, C$_4$-C$_6$, or C$_5$-C$_6$), R$^{28C}$-substituted or unsubstituted heterocycloalkyl (e.g., 3 to 6 membered, 4 to 6 membered, 4 to 5 membered, or 5 to 6 membered), R$^{28C}$-substituted or unsubstituted aryl (e.g., C$_6$-C$_{10}$ or phenyl), or R$^{28C}$-substituted or unsubstituted heteroaryl (e.g., 5 to 10 membered, 5 to 9 membered, or 5 to 6 membered). X$^{27C}$ is —F, —Cl, —Br, or —I. In embodiments, R$^{27C}$ is independently oxo, halogen, —CX$^{27C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{27C}_2$, —CH$_2$X$^{27C}$, —OCX$^{27C}_3$, —OCH$_2$X$^{27}$C, —OCHX$^{27C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{28C}$ is independently oxo, halogen, —CX$^{28C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{28C}_2$, —CH$_2$X$^{28C}$, —OCX$^{28C}_3$, —OCH$_2$X$^{28C}$, —OCHX$^{28C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{28C}$ is —F, —Cl, —Br, or —I.

In embodiments, R$^{3D}$ is independently hydrogen, —CX$^{3D}_3$, —CN, —COOH, —CONH$_2$, —CHX$^{3D}_2$, —CH$_2$X$^{3D}$, R$^{26D}$-substituted or unsubstituted alkyl (e.g., C$_1$-C$_8$, C$_1$-C$_6$, C$_1$-C$_4$, or C$_1$-C$_2$), R$^{26D}$-substituted or unsubstituted heteroalkyl (e.g., 2 to 8 membered, 2 to 6 membered, 4 to 6 membered, 2 or 3 membered, or 4 to 5 membered), R$^{26D}$-substituted or unsubstituted cycloalkyl (e.g., C$_3$-C$_8$, C$_3$-C$_6$, C$_4$-C$_6$, or C$_5$-C$_6$), R$^{26D}$-substituted or unsubstituted heterocycloalkyl (e.g., 3 to 6 membered, 4 to 6 membered, 4 to 5 membered, or 5 to 6 membered), R$^{26D}$-substituted or unsubstituted aryl (e.g., C$_6$-C$_{10}$ or phenyl), or R$^{26D}$-substituted or unsubstituted heteroaryl (e.g., 5 to 10 membered, 5 to 9 membered, or 5 to 6 membered). X$^{3D}$ is —F, —Cl, —Br, or —I. In embodiments, R$^{3D}$ is independently hydrogen. In embodiments, R$^{3D}$ is independently methyl. In embodiments, R$^{3D}$ is independently ethyl. In embodiments, R$^{3D}$ is independently hydrogen, —CX$^{3D}_3$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{26D}$ is independently oxo, halogen, —CX$^{26D}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{26D}_2$, —CH$_2$X$^{26D}$, —OCX$^{26D}_3$, —OCH$_2$X$^{26D}$, —OCHX$^{26D}_2$, R$^{27D}$-substituted or unsubstituted alkyl (e.g., C$_1$-C$_8$, C$_1$-C$_6$, C$_1$-C$_4$, or C$_1$-C$_2$), R$^{27D}$-substituted or unsubstituted heteroalkyl (e.g., 2 to 8 membered, 2 to 6 membered, 4 to 6 membered, 2 or 3 membered, or 4 to 5 membered), R$^{27D}$-substituted or unsubstituted cycloalkyl (e.g., C$_3$-C$_8$, C$_3$-C$_6$, C$_4$-C$_6$, or C$_5$-C$_6$), R$^{27D}$-substituted or unsubstituted heterocycloalkyl (e.g., 3 to 6 membered, 4 to 6 membered, 4 to 5 membered, or 5 to 6 membered), R$^{27D}$-substituted or unsubstituted aryl (e.g., C$_6$-C$_{10}$ or phenyl), or R$^{27D}$-substituted or unsubstituted heteroaryl (e.g., 5 to 10 membered, 5 to 9 membered, or 5 to 6 membered). X$^{26D}$ is —F, —Cl, —Br, or —I. In embodiments, R$^{26D}$ is independently oxo, halogen, —CX$^{26D}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{26D}_2$, —CH$_2$X$^{26D}$, —OCX$^{26D}_3$, —OCH$_2$X$^{26D}$, —OCHX$^{26D}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{27D}$ is independently oxo, halogen, —CX$^{27D}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{27D}_2$, —CH$_2$X$^{27D}$, —OCX$^{27D}_3$, —OCH$_2$X$^{27D}$, —OCHX$^{27D}_2$, R$^{28D}$-substituted or unsubstituted alkyl (e.g., C$_1$-C$_8$, C$_1$-C$_6$, C$_1$-C$_4$, or C$_1$-C$_2$), R$^{28D}$-substituted or unsubstituted heteroalkyl (e.g., 2 to 8 membered, 2 to 6 membered, 4 to 6 membered, 2 or 3 membered, or 4 to 5 membered), $R^{28D}$-substituted or unsubstituted cycloalkyl (e.g., $C_3$-$C_8$, $C_3$-$C_6$, $C_4$-$C_6$, or $C_5$-$C_6$), $R^{28D}$-substituted or unsubstituted heterocycloalkyl (e.g., 3 to 6 membered, 4 to 6 membered, 4 to 5 membered, or 5 to 6 membered), $R^{28D}$-substituted or unsubstituted aryl (e.g., $C_6$-$C_{10}$ or phenyl), or $R^{28D}$-substituted or unsubstituted heteroaryl (e.g., 5 to 10 membered, 5 to 9 membered, or 5 to 6 membered). $X^{27D}$ is —F, —Cl, —Br, or —I. In embodiments, $R^{27D}$ is independently oxo, halogen, —$CX^{27D}_3$, —CN, —OH, —$NH_2$, —COOH, —$CONH_2$, —SH, —$NHNH_2$, —$ONH_2$, —$NHC(O)NHNH_2$, —NHC$(O)NH_2$, —NHC(O)H, —NHC(O)OH, —NHOH, —$CHX^{27D}_2$, —$CH_2X^{27D}$, —$OCX^{27D}_3$, —$OCH_2X^{27D}$, —$OCHX^{27D}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{28D}$ is independently oxo, halogen, —$CX^{28D}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{28D}_2$, —$CH_2X^{28D}$, —$OCX^{28D}_3$, —$OCH_2X^{28D}$, —$OCHX^{28D}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28D}$ is —F, —Cl, —Br, or —I.

In embodiments, Ring A is an oxadiazolyl. In embodiments, Ring A is a substituted or unsubstituted oxadiazolyl. In embodiments, Ring A is an unsubstituted oxadiazolyl. In embodiments, Ring A is an 1,3,4-oxadiazolyl. In embodiments, Ring A is a substituted or unsubstituted 1,3,4-oxadiazolyl. In embodiments, Ring A is an unsubstituted 1,3,4-oxadiazolyl. In embodiments, Ring A is an 1,2,4-oxadiazolyl. In embodiments, Ring A is a substituted or unsubstituted 1,2,4-oxadiazolyl. In embodiments, Ring A is an unsubstituted 1,2,4-oxadiazolyl. In embodiments, Ring A is a triazolyl. In embodiments, Ring A is a substituted or unsubstituted triazolyl. In embodiments, Ring A is an unsubstituted triazolyl. In embodiments. Ring A is a 1,2,3-triazolyl. In embodiments, Ring A is a substituted or unsubstituted 1,2,3-triazolyl. In embodiments, Ring A is an unsubstituted 1,2,3-triazolyl.

In embodiments, Ring A is an oxadiazolylene. In embodiments, Ring A is a substituted or unsubstituted oxadiazolylene. In embodiments, Ring A is an unsubstituted oxadiazolylene. In embodiments, Ring A is an 1,3,4-oxadiazolylene. In embodiments, Ring A is a substituted or unsubstituted 1,3,4-oxadiazolylene. In embodiments, Ring A is an unsubstituted 1,3,4-oxadiazolylene. In embodiments, Ring A is an 1,2,4-oxadiazolylene. In embodiments, Ring A is a substituted or unsubstituted 1,2,4-oxadiazolylene. In embodiments, Ring A is an unsubstituted 1,2,4-oxadiazolylene. In embodiments, Ring A is a triazolylene. In embodiments, Ring A is a substituted or unsubstituted triazolylene. In embodiments. Ring A is an unsubstituted triazolylene. In embodiments, Ring A is a 1,2,3-triazolylene. In embodiments, Ring A is a substituted or unsubstituted 1,2,3-triazolylene. In embodiments, Ring A is an unsubstituted 1,2,3-triazolylene. In embodiments, Ring A is a divalent oxadiazolyl. In embodiments, Ring A is a divalent substituted or unsubstituted oxadiazolyl. In embodiments, Ring A is a divalent unsubstituted oxadiazolyl. In embodiments, Ring A is a divalent 1,3,4-oxadiazolyl. In embodiments, Ring A is a divalent substituted or unsubstituted 1,3,4-oxadiazolyl. In embodiments, Ring A is a divalent unsubstituted 1,3,4-oxadiazolyl. In embodiments, Ring A is a divalent 1,2,4-oxadiazolyl. In embodiments, Ring A is a divalent substituted or unsubstituted 1,2,4-oxadiazolyl. In embodiments, Ring A is a divalent unsubstituted 1,2,4-oxadiazolyl. In embodiments, Ring A is a divalent triazolyl. In embodiments, Ring A is a divalent substituted or unsubstituted triazolyl. In embodiments, Ring A is a divalent unsubstituted triazolyl. In embodiments, Ring A is a divalent 1,2,3-triazolyl. In embodiments, Ring A is a divalent substituted or unsubstituted 1,2,3-triazolyl. In embodiments, Ring A is a divalent unsubstituted 1,2,3-triazolyl.

In embodiments, Ring A is

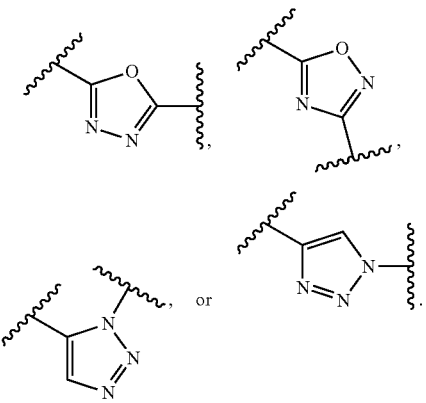

embodiments, Ring A is

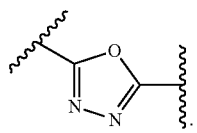 [SMILES: *c1nnc(*)o1]

In embodiments, Ring A is

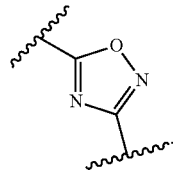 [SMILES: *c1noc(*)n1]

In embodiments, Ring A is

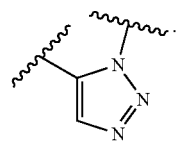 [SMILES: *c1cnnn1*]

In embodiments, Ring A is

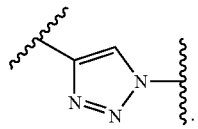 [SMILES: *c1cn(*)nn1]

In embodiments, Ring B is a phenyl. In embodiments, Ring B is a 6 membered heteroaryl. In embodiments, Ring B is a pyridyl. In embodiments, Ring B is a pyridin-2-yl. In embodiments, Ring B is a pyridin-3-yl. In embodiments, Ring B is a pyridin-4-yl. In embodiments, Ring B is a pyrazinyl. In embodiments, Ring B is pyrimidinyl. In embodiments, Ring B is pyridazinyl. In embodiments, Ring B is triazinyl. In embodiments, Ring B is 1,2,3-triazinyl. In embodiments, Ring B is 1,2,4-triazinyl. In embodiments, Ring B is 1,3,4-triazinyl.

In embodiments, X is —F. In embodiments, X is —Cl. In embodiments, X is —Br. In embodiments, X is —I. In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, X is —F. In embodiments, X is —Cl. In embodiments, X is —Br. In embodiments, X is —I.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4.

In embodiments, m1 is 1. In embodiments, m1 is 2. In embodiments, m2 is 1. In embodiments, m2 is 2. In embodiments, m3 is 1. In embodiments, m3 is 2.

In embodiments, v1 is 1. In embodiments, v1 is 2. In embodiments, v2 is 1. In embodiments, v2 is 2. In embodiments, v3 is 1. In embodiments, v3 is 2.

In embodiments, Z is —S—. In embodiments, Z is —$SO_2$—.

In embodiments, z1 is 0. In embodiments z1 is 1. In embodiments, z1 is 2. In embodiments, z1 is 3. In embodiments, z1 is 4. In embodiments, z1 is 5. In embodiments, z2 is 0. In embodiments, z2 is 1. In embodiments, z2 is 2. In embodiments, z2 is 3. In embodiments, z2 is 4. In embodiments, z2 is 5.

In embodiments, the compound has the formula:

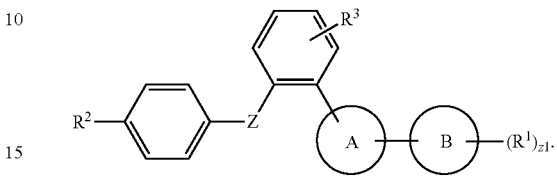

(II)

$R^1$, $R^2$, $R^3$, ring A, ring B, Z, and z1, are as described herein, including in embodiments.

In embodiments, the compound has the formula:

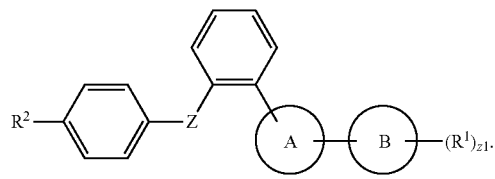

(IIa)

$R^1$, $R^2$, ring A, ring B, Z, and z1 are as described herein, including in embodiments.

In embodiments, the compound has the formula:

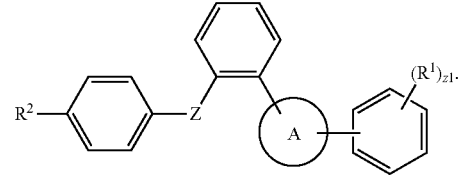

(IIb)

$R^1$, $R^2$, ring A, Z, and z1 are as described herein, including in embodiments.

In embodiments, the compound has the formula:

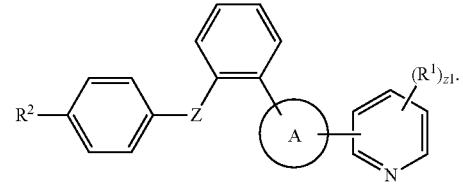

(IIc)

$R^1$, $R^2$, ring A, Z, and z1 are as described herein, including in embodiments.

In embodiments, the compound has the formula:

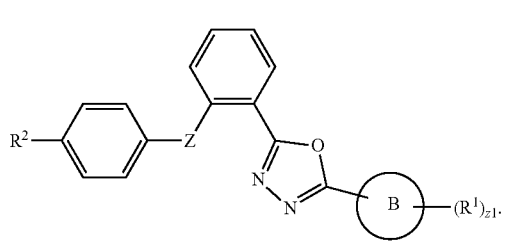
(IId)

$R^1$, $R^2$, ring B, Z, and z1 are as described herein, including in embodiments.

In embodiments, the compound has the formula:

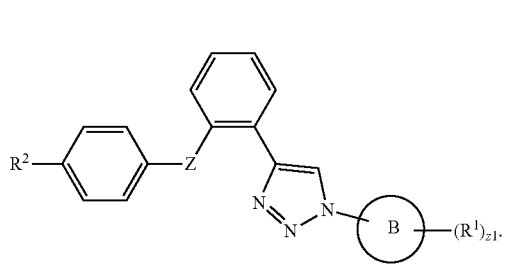
(IIe)

$R^1$, $R^2$, ring B, Z, and z1 are as described herein, including in embodiments.

In embodiments, the compound has the formula:

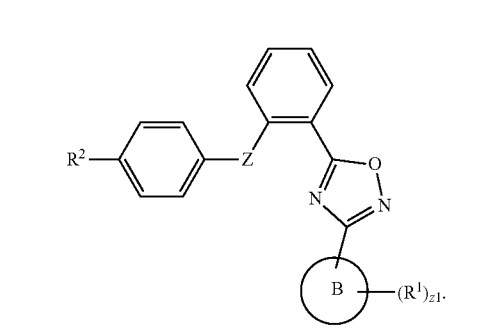
(IIf)

$R^1$, $R^2$, ring B, Z, and z1 are as described herein, including in embodiments.

In embodiments, the compound has the formula:

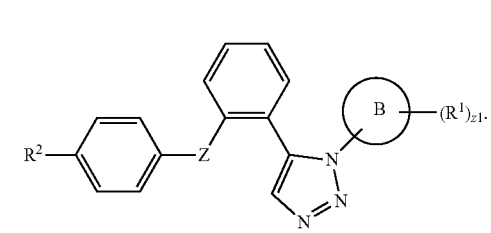
(IIg)

$R^1$, $R^2$, ring B, Z, and z1 are as described herein, including in embodiments.

In embodiments, the compound has the formula:

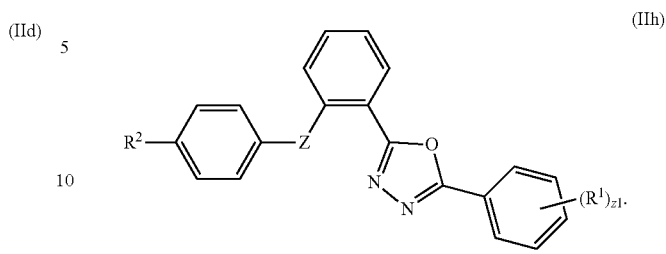
(IIh)

$R^1$, $R^2$, Z, and z1 are as described herein, including in embodiments.

In embodiments, the compound has the formula:

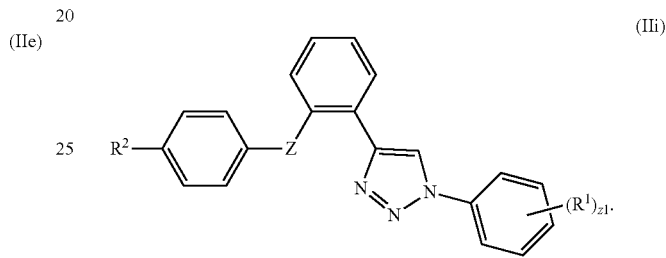
(IIi)

$R^1$, $R^2$, Z, and z1 are as described herein, including in embodiments.

In embodiments, the compound has the formula:

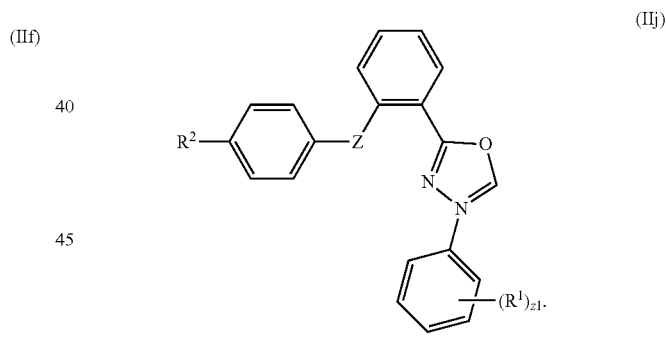
(IIj)

$R^1$, $R^2$, Z, and z1 are as described herein, including in embodiments.

In embodiments, the compound has the formula:

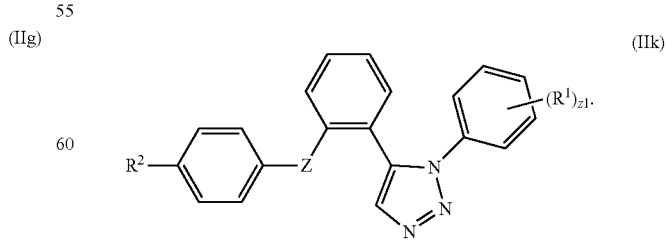
(IIk)

$R^1$, $R^2$, Z, and z1 are as described herein, including in embodiments.

In embodiments, the compound has the formula:

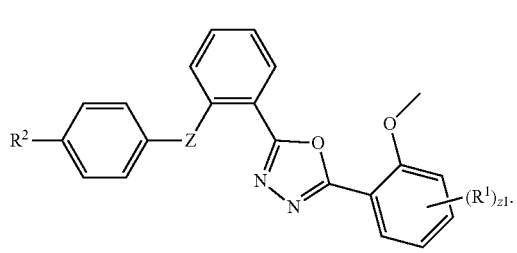
(III)

$R^1$, $R^2$, and Z are as described herein, including in embodiments. In embodiments, z1 is an integer from 0 to 4.

In embodiments, the compound has the formula:

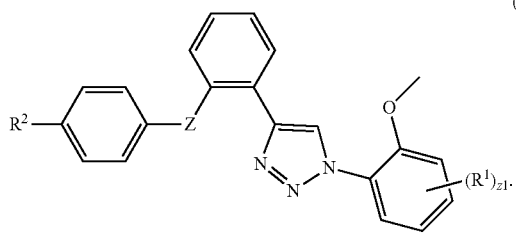
(IIm)

$R^1$, $R^2$, and Z are as described herein, including in embodiments. In embodiments, z1 is an integer from 0 to 4.

In embodiments, the compound has the formula:

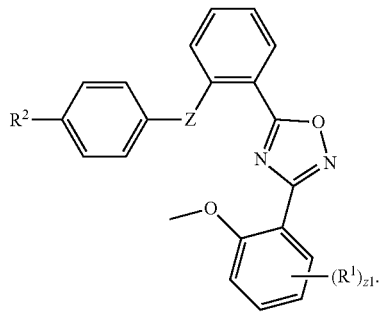
(IIn)

$R^1$, $R^2$, and Z are as described herein, including in embodiments. In embodiments, z1 is an integer from 0 to 4.

In embodiments, the compound has the formula:

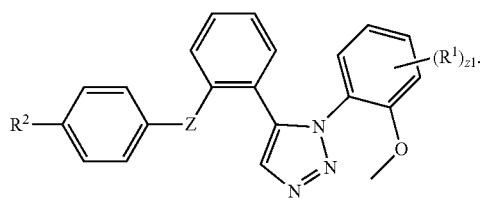
(IIo)

$R^1$, $R^2$, and Z are as described herein, including in embodiments. In embodiments, z1 is an integer from 0 to 4.

In embodiments, the compound has the formula:

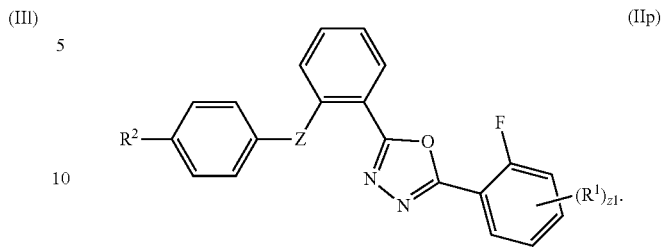
(IIp)

$R^1$, $R^2$, and Z are as described herein, including in embodiments. In embodiments, z1 is an integer from 0 to 4.

In embodiments, the compound has the formula:

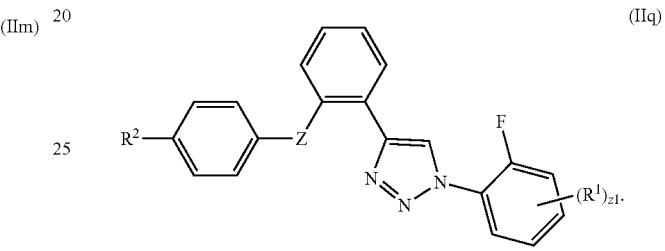
(IIq)

$R^1$, $R^2$, and Z are as described herein, including in embodiments. In embodiments, z1 is an integer from 0 to 4.

In embodiments, the compound has the formula:

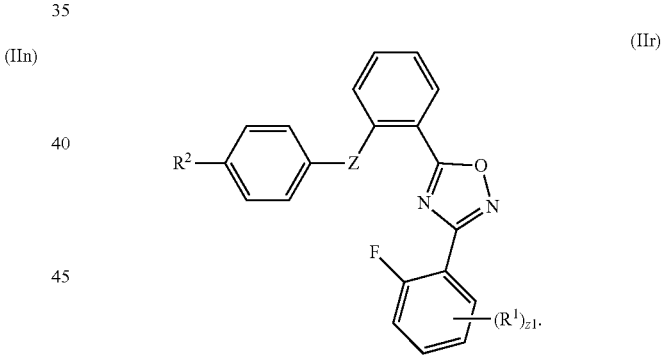
(IIr)

$R^1$, $R^2$, and Z are as described herein, including in embodiments. In embodiments, z1 is an integer from 0 to 4.

In embodiments, the compound has the formula:

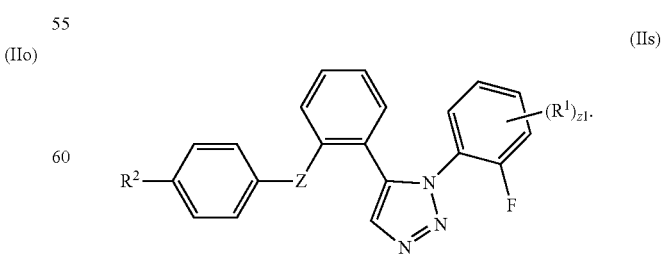
(IIs)

$R^1$, $R^2$, and Z are as described herein, including in embodiments. In embodiments, z1 is an integer from 0 to 4.

In embodiments, the compound has the formula:

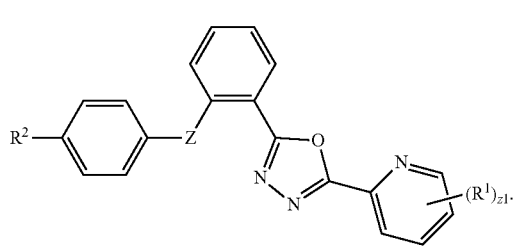
(IIt)

$R^1$, $R^2$, Z, and z1 are as described herein, including in embodiments.

In embodiments, the compound has the formula:

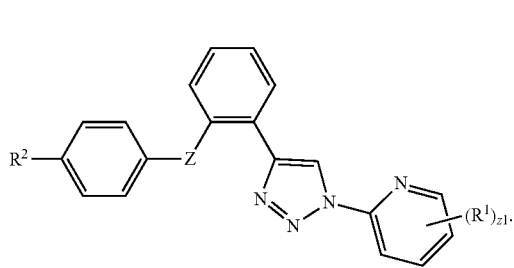
(IIu)

$R^1$, $R^2$, Z, and z1 are as described herein, including in embodiments. In embodiments, z1 is an integer from 0 to 4.

In embodiments, the compound has the formula:

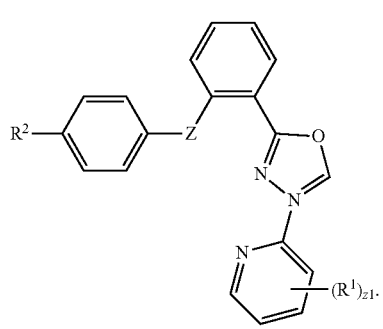
(IIv)

$R^1$, $R^2$, Z, and z1 are as described herein, including in embodiments.

In embodiments, the compound has the formula:

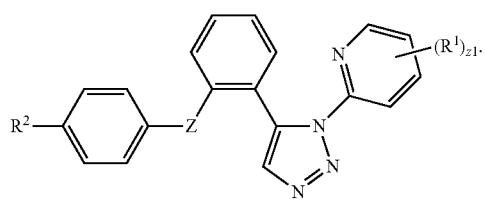
(IIw)

$R^1$, $R^2$, Z, and z1 are as described herein, including in embodiments. In embodiments, z1 is an integer from 0 to 4.

In embodiments, the compound has the formula:

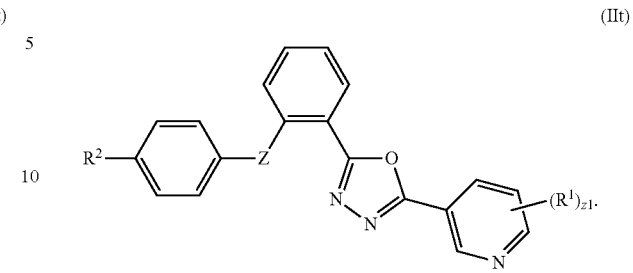
(IIt)

$R^1$, $R^2$, Z, and z1 are as described herein, including in embodiments.

In embodiments, the compound has the formula:

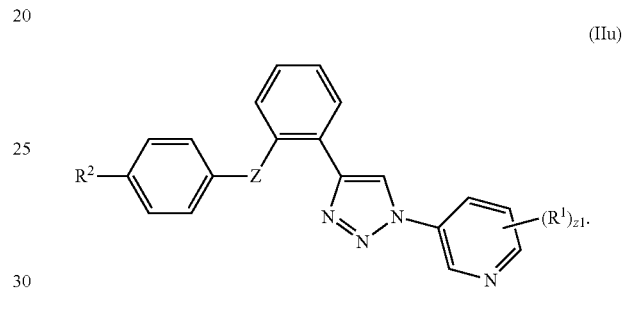
(IIu)

$R^1$, $R^2$, Z, and z1 are as described herein, including in embodiments.

In embodiments, the compound has the formula:

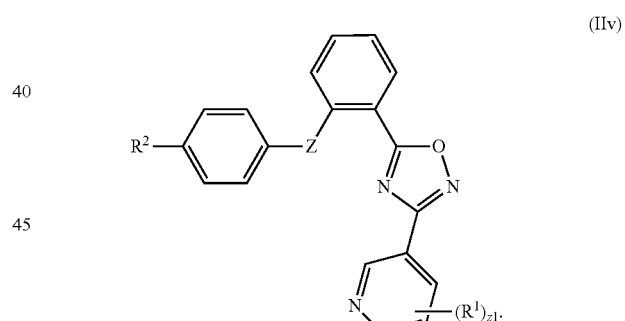
(IIv)

$R^1$, $R^2$, Z, and z are as described herein, including in embodiments.

In embodiments, the compound has the formula:

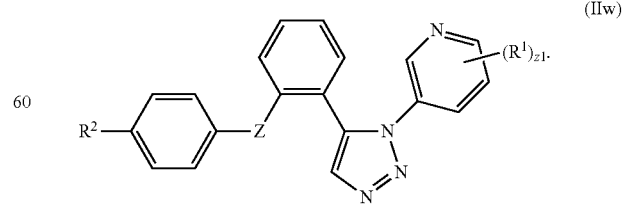
(IIw)

$R^1$, $R^2$, Z, and z1 are as described herein, including in embodiments.

In embodiments, the compound has the formula:

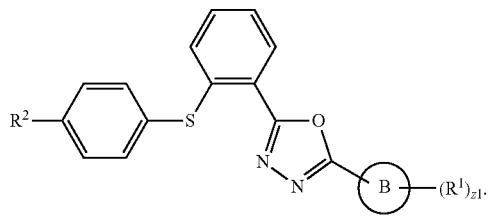
(IIx)

$R^1$, $R^2$, ring B, and z1 are as described herein, including in embodiments.

In embodiments, the compound has the formula:

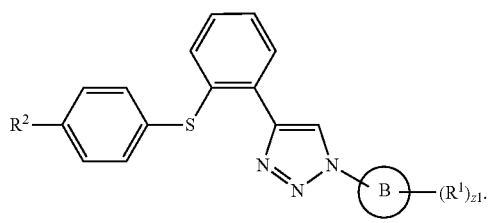
(IIy)

$R^1$, $R^2$, ring B, and z1 are as described herein, including in embodiments.

In embodiments, the compound has the formula:

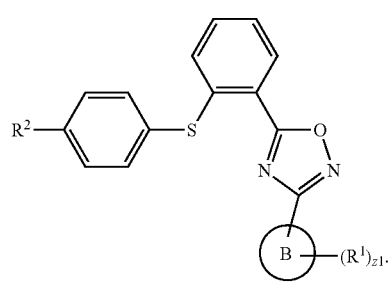
(IIz)

$R^1$, $R^2$, ring B, and z1 are as described herein, including in embodiments.

In embodiments, the compound has the formula:

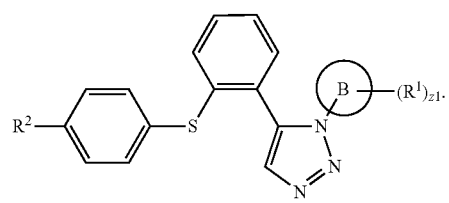
(IIaa)

$R^1$, $R^2$, ring B, and z1 are as described herein, including in embodiments.

In embodiments, the compound has the formula:

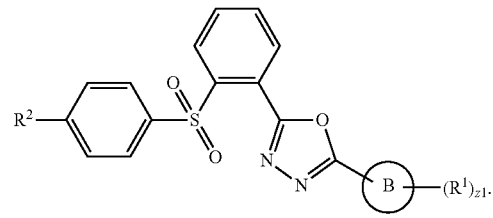
(IIab)

$R^1$, $R^2$, ring B, and z1 are as described herein, including in embodiments.

In embodiments, the compound has the formula:

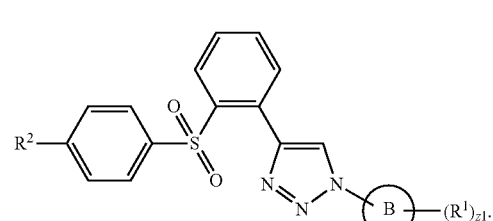
(IIac)

$R^1$, $R^2$, ring B, and z1 are as described herein, including in embodiments.

In embodiments, the compound has the formula:

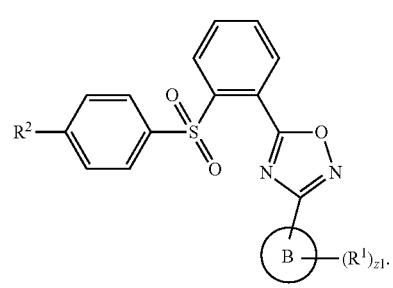
(IIad)

$R^1$, $R^2$, ring B, and z1 are as described herein, including in embodiments.

In embodiments, the compound has the formula:

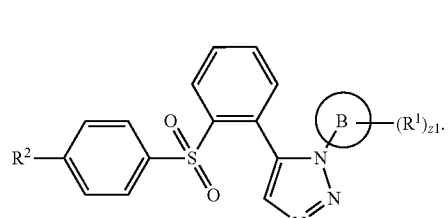
(IIae)

$R^1$, $R^2$, ring B, and z1 are as described herein, including in embodiments.

In embodiments, the compound has the formula:

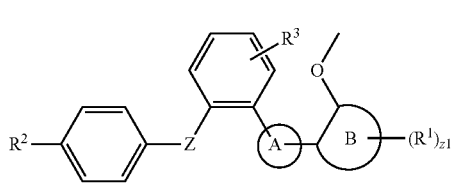
(III)

wherein z1 is an integer from 0 to 4. $R^1$, $R^2$, $R^3$, ring A, ring B, Z, and z1 are as described herein, including in embodiments.

In embodiments, the compound has the formula:

(IIIa)

wherein z1 is an integer from 0 to 4. $R^1$, $R^2$, ring A, ring B, Z, and z1 are as described herein, including in embodiments.

In embodiments, the compound has the formula:

(IIIb)

wherein z1 is an integer from 0 to 4. $R^1$, $R^2$, ring A, ring B, and z1 are as described herein, including in embodiments.

In embodiments, the compound has the formula:

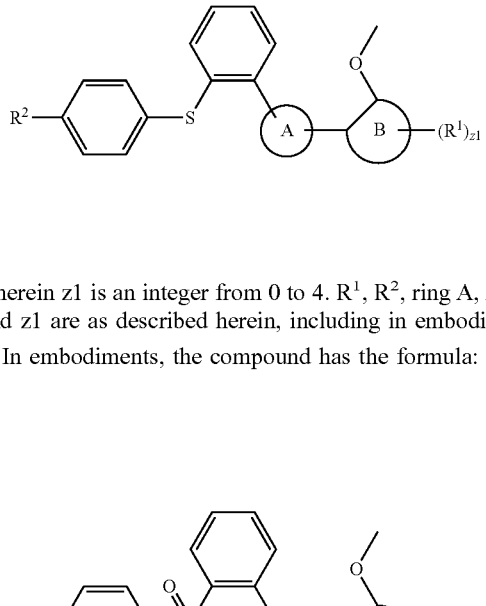
(IIIc)

wherein z1 is an integer from 0 to 4. $R^1$, $R^2$, ring A, ring B, and z1 are as described herein, including in embodiments.

In embodiments, the compound has the formula:

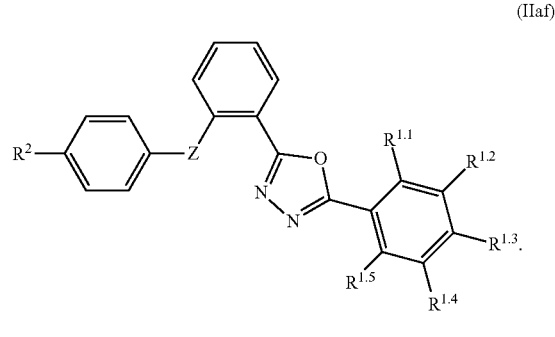
(IIaf)

$R^2$ and Z are as described herein, including in embodiments. $R^{1.1}$, $R^{1.2}$, $R^{1.3}$, $R^{1.4}$, and $R^{1.5}$ are each independently an $R^1$ substituent as described herein (e.g., in an embodiment).

In embodiments, the compound has the formula:

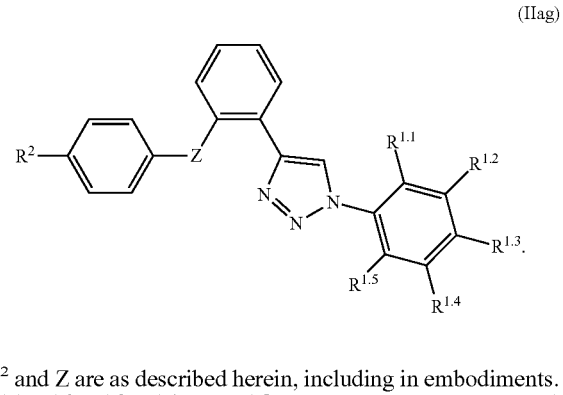
(IIag)

$R^2$ and Z are as described herein, including in embodiments. $R^{1.1}$, $R^{1.2}$, $R^{1.3}$, $R^{1.4}$, and $R^{1.5}$ are each independently an $R^1$ substituent as described herein (e.g., in an embodiment).

In embodiments, the compound has the formula:

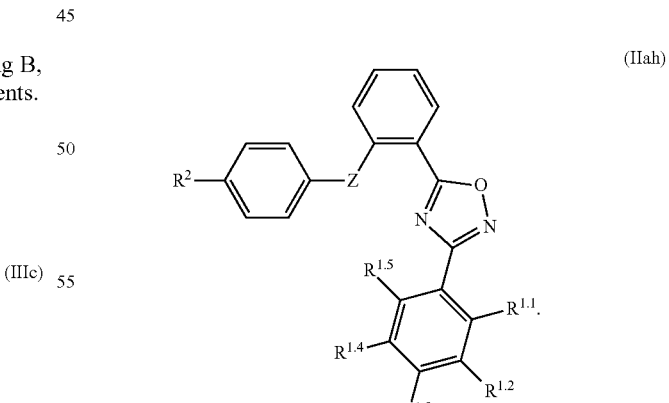
(IIah)

$R^2$ and Z are as described herein, including in embodiments. $R^{1.1}$, $R^{1.2}$, $R^{1.3}$, $R^{1.4}$, and $R^{1.5}$ are each independently an $R^1$ substituent as described herein (e.g., in an embodiment).

In embodiments, the compound has the formula:

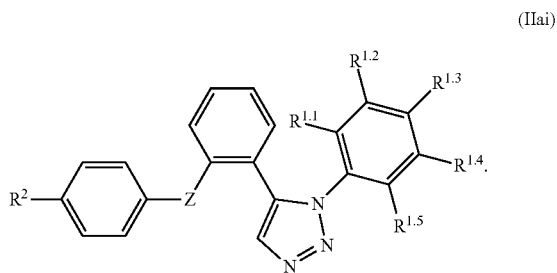

(IIai)

$R^2$ and Z are as described herein, including in embodiments. $R^{1.1}$, $R^{1.2}$, $R^{1.3}$, $R^{1.4}$, and $R^{1.5}$ are each independently an $R^1$ substituent as described herein (e.g., in an embodiment).

In embodiments, $R^{1.1}$ is independently hydrogen, halogen, —$CX^{1.1}_3$, —$CHX^{1.1}_2$, —$CH_2X^{1.1}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCX^{1.1}_3$, —$OCHX^{1.1}_2$, —$OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1.1}$ is independently hydrogen, halogen, —$CX^{1.1}_3$, —$CHX^{1.1}_2$, —$CH_2X^{1.1}$, —OH, —SH, —$OCX^{1.1}_3$, —$OCHX^{1.1}_2$, —$OCH_2X^{1.1}$, substituted or unsubstituted $C_1$-$C_4$ alkyl, substituted or unsubstituted 2 to 4 membered heteroalkyl. In embodiments, $R^{1.1}$ is independently —F, —$CH_3$, or —$OCH_3$. In embodiments, $R^{1.1}$ is independently hydrogen.

In embodiments, $R^{1.1}$ is independently —$OCH_3$. In embodiments, $R^{1.1}$ is independently —COOH. In embodiments, $R^{1.1}$ is independently —$COO^-$. In embodiments, $R^{1.1}$ is independently a salt of —$COO^-$. In embodiments, $R^{1.1}$ is independently a choline salt of —$COO^-$. In embodiments. $R^{1.1}$ is independently a —$COO^-$(HOCH$_2$CH$_2$N(CH$_3$)$_3$+). In embodiments, $R^{1.1}$ is independently —$CONH_2$. In embodiments, $R^{1.1}$ is independently —$CONHCH_3$. In embodiments, $R^{1.1}$ is independently —$CONHCH_2CH_3$. In embodiments, $R^{1.1}$ is independently —CONHC(CH)$_2$. In embodiments, $R^{1.1}$ is independently —CONHC(CH$_3$)$_3$. In embodiments, $R^{1.1}$ is independently —$COOCH_3$. In embodiments, $R^{1.1}$ is independently —$COOCH_2CH_3$. In embodiments, $R^{1.1}$ is independently —COOC(CH$_3$)$_2$. In embodiments, $R^{1.1}$ is independently —COOC(CH$_3$)$_3$. In embodiments, $R^{1'}$ is independently —$OCH_2CH_3$. In embodiments, $R^{1.1}$ is independently —OC(CH$_3$)$_2$. In embodiments, $R^{1.1}$ is independently —OC(CH$_3$)$_3$. In embodiments, $R^{1.1}$ is independently unsubstituted methyl. In embodiments, $R^{1.1}$ is independently unsubstituted ethyl. In embodiments, $R^{1.1}$ is independently unsubstituted propyl. In embodiments, $R^{1.1}$ is independently unsubstituted butyl. In embodiments, $R^{1.1}$ is independently unsubstituted n-propyl. In embodiments, $R^{1.1}$ is independently unsubstituted iso-propyl. In embodiments, $R^{1.1}$ is independently unsubstituted n-butyl. In embodiments, $R^{1.1}$ is independently unsubstituted iso-butyl. In embodiments, $R^{1.1}$ is independently unsubstituted methoxy. In embodiments, $R^{1.1}$ is independently unsubstituted ethoxy. In embodiments, $R^{1.1}$ is independently unsubstituted propoxy. In embodiments, $R^{1.1}$ is independently unsubstituted butoxy. In embodiments, $R^{1.1}$ is independently —F. In embodiments, $R^{1.1}$ is independently —Cl. In embodiments, $R^{1.1}$ is independently —I. In embodiments, $R^{1.1}$ is independently —Br. In embodiments, $R^{1.1}$ is independently —$NO_2$. In embodiments, $R^{1.1}$ is independently —$CF_3$. In embodiments, $R^{1.1}$ is independently —$CCl_3$. In embodiments, $R^{1.1}$ is independently —$CI_3$. In embodiments, $R^{1.1}$ is independently —$CBr_3$. In embodiments, $R^{1.1}$ is independently —$NH_2$.

In embodiments, $R^{1.1}$ is independently halogen. In embodiments, $R^{1.1}$ is independently oxo. In embodiments, $R^{1.1}$ is independently —$CX^{1.1}_3$. In embodiments, $R^{1.1}$ is independently —$CHX^{1.1}_2$. In embodiments, $R^{1.1}$ is independently —$CH_2X^{1.1}$. In embodiments, $R^{1.1}$ is independently —$OCX^{1.1}_3$. In embodiments, $R^{1.1}$ is independently —$OCH_2X^{1.1}$. In embodiments, $R^{1.1}$ is independently —$OCHX^{1.1}_2$. In embodiments, $R^{1.1}$ is independently —CN. In embodiments, $R^{1.1}$ is independently —OH. In embodiments, $R^{1.1}$ is independently —$NH_2$. In embodiments, $R^{1.1}$ is independently —COOH. In embodiments, $R^{1.1}$ is independently —$CONH_2$. In embodiments, $R^{1.1}$ is independently —$NO_2$. In embodiments, $R^{1.1}$ is independently —SH. In embodiments, $R^{1.1}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{1.1}$ is —F, —Cl, —Br, or —I. In embodiments, $R^{1.1}$ is independently hydrogen. In embodiments, $R^{1.1}$ is independently methyl. In embodiments, $R^{1.1}$ is independently ethyl. In embodiments, $R^{1.1}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$ or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1.1}$ is —F, —Cl, —Br, or —I. In embodiments, $R^{1.1}$ is independently halogen, —$CX^{1.1}_3$, —$CHX^{1.1}_2$, —$CH_2X^{1.1}$, —$OCX^{1.1}_3$, —$OCH_2X^{1.1}$, —$OCHX^{1.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^{1.1}$ is independently hydrogen, halogen, —$CX^{1.1}_3$, —$CHX^{1.1}_2$, —$CH_2X^{1.1}$, —$OCX^{1.1}_3$, —$OCH_2X^{1.1}$, —$OCHX^{1.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{1.2}$ is independently hydrogen, halogen, —$CX^{1.2}_3$, —$CHX^{1.2}_2$, —$CH_2X^{1.2}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{1.2}_3$, —$OCHX^{1.2}_2$, —$OCH_2X^{1.2}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1.2}$ is independently hydrogen, halogen, —$CX^{1.2}_3$, —$CHX^{1.2}_2$, —$CH_2X^{1.2}$, —OH, —SH, —$OCX^{1.2}_3$, —$OCHX^{1.2}_2$, —$OCH_2X^{1.2}$, substituted or unsubstituted $C_1$-$C_4$ alkyl, substituted or unsubstituted 2 to 4 membered heteroalkyl. In embodiments, $R^{1.2}$ is independently —F, —$CH_3$, or —$OCH_3$. In embodiments, $R^{1.2}$ is independently hydrogen.

In embodiments, $R^{1.2}$ is independently —$OCH_3$. In embodiments, $R^{1.2}$ is independently —COOH. In embodiments, $R^{1.2}$ is independently —$COO^-$. In embodiments, $R^{1.2}$ is independently a salt of —$COO^-$. In embodiments, $R^{1.2}$ is independently a choline salt of —$COO^-$. In embodiments, $R^{1.2}$ is independently a —$COO^-$($HOCH_2CH_2N(CH_3)_3$). In embodiments, $R^{1.2}$ is independently —$CONH_2$. In embodiments, $R^{1.2}$ is independently —$CONHCH_3$. In embodiments, $R^{1.2}$ is independently —$CONHCH_2CH_3$. In embodiments, $R^{1.2}$ is independently —$CONHC(CH_3)_2$. In embodiments, $R^{1.2}$ is independently —$CONHC(CH)_3$. In embodiments, $R^{1.2}$ is independently —$COOCH_3$. In embodiments, $R^{1.2}$ is independently —$COOCH_2CH_3$. In embodiments, $R^{1.2}$ is independently —$COOC(CH_3)_2$. In embodiments. $R^{1.2}$ is independently —$COOC(CH_3)_3$. In embodiments, $R^{1.2}$ is independently —$OCH_2CH_3$. In embodiments, $R^{1.2}$ is independently —$OC(CH_3)_2$. In embodiments, $R^{1.2}$ is independently —$OC(CH_3)_3$. In embodiments, $R^{1.2}$ is independently unsubstituted methyl. In embodiments, $R^{1.2}$ is independently unsubstituted ethyl. In embodiments, $R^{1.2}$ is independently unsubstituted propyl. In embodiments, $R^{1.2}$ is independently unsubstituted butyl. In embodiments, $R^{1.2}$ is independently unsubstituted n-propyl. In embodiments, $R^{1.2}$ is independently unsubstituted iso-propyl. In embodiments, $R^{1.2}$ is independently unsubstituted n-butyl. In embodiments, $R^{1.2}$ is independently unsubstituted iso-butyl. In embodiments, $R^{1.2}$ is independently unsubstituted methoxy. In embodiments, $R^{1.2}$ is independently unsubstituted ethoxy. In embodiments, $R^{1.2}$ is independently unsubstituted propoxy. In embodiments, $R^{1.2}$ is independently unsubstituted butoxy. In embodiments, $R^{1.2}$ is independently —F. In embodiments, $R^{1.2}$ is independently —Cl. In embodiments, $R^{1.2}$ is independently —I. In embodiments, $R^{1.2}$ is independently —Br. In embodiments, $R^{1.2}$ is independently —$NO_2$. In embodiments, $R^{1.2}$ is independently —$CF_3$. In embodiments, $R^{1.2}$ is independently —$CCl_3$. In embodiments, $R^{1.2}$ is independently —$CI_3$. In embodiments, $R^{1.2}$ is independently —$CBr_3$. In embodiments, $R^{1.2}$ is independently —$NH_2$.

In embodiments, $R^{1.2}$ is independently halogen. In embodiments, $R^{1.2}$ is independently oxo. In embodiments, $R^{1.2}$ is independently —$CX^{1.2}_3$. In embodiments, $R^{1.2}$ is independently —$CHX^{1.2}_2$. In embodiments, $R^{1.2}$ is independently —$CH_2X^{1.2}$. In embodiments, $R^{1.2}$ is independently —$OCX^{1.2}_3$. In embodiments, $R^{1.2}$ is independently —$OCH_2X^{1.2}$. In embodiments, $R^{1.2}$ is independently —$OCHX^{1.2}_2$. In embodiments, $R^{1.2}$ is independently —CN. In embodiments, $R^{1.2}$ is independently —OH. In embodiments, $R^{1.2}$ is independently —$NH_2$. In embodiments, $R^{1.2}$ is independently —COOH. In embodiments, $R^{1.2}$ is independently —$CONH_2$. In embodiments, $R^{1.2}$ is independently —$NO_2$. In embodiments, $R^{1.2}$ is independently —SH. In embodiments, $R^{1.2}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{1.2}$ is —F, —Cl, —Br, or —I. In embodiments, $R^{1.2}$ is independently hydrogen. In embodiments, $R^{1.2}$ is independently methyl. In embodiments, $R^{1.2}$ is independently ethyl. In embodiments, $R^{1.2}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1.2}$ is —F, —Cl, —Br, or —I. In embodiments, $R^{1.2}$ is independently halogen, —$CX^{1.2}_3$, —$CHX^{1.2}_2$, —$CH_2X^{1.2}$, —$OCX^{1.2}_3$, —$OCH_2X^{1.2}$, —$OCHX^{1.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered. 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^{1.2}$ is independently hydrogen, halogen, —$CX^{1.2}_3$, —$CHX^{1.2}_2$, —$CH_2X^{1.2}$, —$OCX^{1.2}_3$, —$OCH_2X^{1.2}$, —$OCHX^{1.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{1.3}$ is independently hydrogen, halogen, —$CX^{1.3}{}_3$, —$CHX^{1.3}{}_2$, —$CH_2X^{1.3}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{1.3}{}_3$, —$OCHX^{1.3}{}_2$, —$OCH_2X^{1.3}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1.3}$ is independently hydrogen, halogen, —$CX^{1.3}{}_3$, —$CHX^{1.3}{}_2$, —$CH_2X^{1.3}$, —OH, —SH, —$OCX^{1.3}{}_3$, —$OCHX^{1.3}{}_2$, —$OCH_2X^{1.3}$, substituted or unsubstituted $C_1$-$C_4$ alkyl, substituted or unsubstituted 2 to 4 membered heteroalkyl. In embodiments, $R^{1.3}$ is independently —F, —$CH_3$, or —$OCH_3$. In embodiments, $R^{1.3}$ is independently hydrogen.

In embodiments, $R^{1.3}$ is independently —$OCH_3$. In embodiments, $R^{1.3}$ is independently —COOH. In embodiments, $R^{1.3}$ is independently —$COO^-$. In embodiments, $R^{1.3}$ is independently a salt of —$COO^-$. In embodiments, $R^{1.3}$ is independently a choline salt of —$COO^-$. In embodiments, $R^{1.3}$ is independently a —$COO^-$($HOCH_2CH_2N(CH_3)_3$). In embodiments, $R^{1.3}$ is independently —$CONH_2$. In embodiments, $R^{1.3}$ is independently —$CONHCH_3$. In embodiments, $R^{1.3}$ is independently —$CONHCH_2CH_3$. In embodiments, $R^{1.3}$ is independently —$CONHC(CH_3)_2$. In embodiments, $R^{1.3}$ is independently —$CONHC(CH_3)_3$. In embodiments, $R^{1.3}$ is independently —$COOCH_3$. In embodiments, $R^{1.3}$ is independently —$COOCH_2CH_3$. In embodiments, $R^{1.3}$ is independently —$COOC(CH_3)_2$. In embodiments, $R^{1.3}$ is independently —$COOC(CH_3)_3$. In embodiments, $R^{1.3}$ is independently —$OCH_2CH_3$. In embodiments, $R^{1.3}$ is independently —$OC(CH_3)_2$. In embodiments, $R^{1.3}$ is independently —$OC(CH_3)_3$. In embodiments, $R^{1.3}$ is independently unsubstituted methyl. In embodiments, $R^{1.3}$ is independently unsubstituted ethyl. In embodiments, $R^{1.3}$ is independently unsubstituted propyl. In embodiments, $R^{1.3}$ is independently unsubstituted butyl. In embodiments, $R^{1.3}$ is independently unsubstituted n-propyl. In embodiments, $R^{1.3}$ is independently unsubstituted iso-propyl. In embodiments, $R^{1.3}$ is independently unsubstituted n-butyl. In embodiments, $R^{1.3}$ is independently unsubstituted iso-butyl. In embodiments, $R^{1.3}$ is independently unsubstituted methoxy. In embodiments, $R^{1.3}$ is independently unsubstituted ethoxy. In embodiments, $R^{1.3}$ is independently unsubstituted propoxy. In embodiments, $R^{1.3}$ is independently unsubstituted butoxy. In embodiments, $R^{1.3}$ is independently —F. In embodiments, $R^{1.3}$ is independently —Cl. In embodiments, $R^{1.3}$ is independently —I. In embodiments, $R^{1.3}$ is independently —Br. In embodiments, $R^{1.3}$ is independently —$NO_2$. In embodiments, $R^{1.3}$ is independently —$CF_3$. In embodiments, $R^{1.3}$ is independently —$CCl_3$. In embodiments, $R^{1.3}$ is independently —$CI_3$. In embodiments, $R^{1.3}$ is independently —$CBr_3$. In embodiments, $R^{1.3}$ is independently —$NH_2$.

In embodiments, $R^{1.3}$ is independently halogen. In embodiments, $R^{1.3}$ is independently oxo. In embodiments, $R^{1.3}$ is independently —$CX^{1.3}{}_3$. In embodiments, $R^{1.3}$ is independently —$CHX^{1.3}{}_2$. In embodiments, $R^{1.3}$ is independently —$CH_2X^{1.3}$. In embodiments, $R^{1.3}$ is independently —$OCX^{1.3}{}_3$. In embodiments, $R^{1.3}$ is independently —$OCH_2X^{1.3}$. In embodiments, $R^{1.3}$ is independently —$OCHX^{1.3}{}_2$. In embodiments, $R^{1.3}$ is independently —CN. In embodiments, $R^{1.3}$ is independently —OH. In embodiments, $R^{1.3}$ is independently —$NH_2$. In embodiments, $R^{1.3}$ is independently —COOH. In embodiments, $R^{1.3}$ is independently —$CONH_2$. In embodiments, $R^{1.3}$ is independently —$NO_2$. In embodiments, $R^{1.3}$ is independently —SH. In embodiments, $R^{1.3}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered. 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{1.3}$ is —F, —Cl, —Br, or —I. In embodiments, $R^{1.3}$ is independently hydrogen. In embodiments, $R^{1.3}$ is independently methyl. In embodiments, $R^{1.3}$ is independently ethyl. In embodiments, $R^{1.3}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1.3}$ is —F, —Cl, —Br, or —I. In embodiments, $R^{1.3}$ is independently halogen, —$CX^{1.3}{}_3$, —$CHX^{1.3}{}_2$, —$CH_2X^{1.3}$, —$OCX^{1.3}{}_3$, —$OCH_2X^{1.3}$, —$OCHX^{1.3}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^{1.3}$ is independently hydrogen, halogen, —$CX^{1.3}{}_3$, —$CHX^{1.3}{}_2$, —$CH_2X^{1.3}$, —$OCX^{1.3}{}_3$, —$OCH_2X^{1.3}$, —$OCHX^{1.3}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{1.3}$ is independently

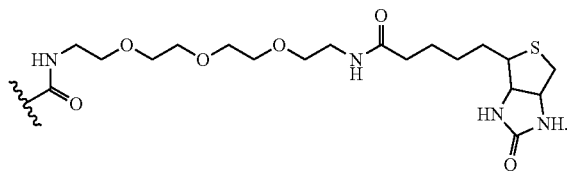 [SMILES: *C(=O)NCCOCCOCCOCCNC(=O)CCCCC1SCC2NC(=O)NC21]

In embodiments, $R^{1.4}$ is independently hydrogen, halogen, $-CX^{1.4}_3$, $-CHX^{1.4}_2$, $-CH_2X^{1.4}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{1.4}_3$, $-OCHX^{1.4}_2$, $-OCH_2X^{1.4}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1.4}$ is independently hydrogen, halogen, $-CX^{1.4}_3$, $-CHX^{1.4}_2$, $-CH_2X^{1.4}$, $-OH$, $-SH$, $-OCX^{1.4}_3$, $-OCHX^{1.4}_2$, $-OCH_2X^{1.4}$, substituted or unsubstituted $C_1$-$C_4$ alkyl, substituted or unsubstituted 2 to 4 membered heteroalkyl. In embodiments, $R^{1.4}$ is independently $-F$, $-CH_3$, or $-OCH_3$. In embodiments, $R^{1.4}$ is independently hydrogen.

In embodiments, $R^{1.4}$ is independently $-OCH_3$. In embodiments, $R^{1.4}$ is independently $-COOH$. In embodiments, $R^{1.4}$ is independently $-COO$. In embodiments, $R^{1.4}$ is independently a salt of $-COO^-$. In embodiments, $R^{1.4}$ is independently a choline salt of $-COO^-$. In embodiments, $R^{1.4}$ is independently a $-COO^-(HOCH_2CH_2N(CH_3)_3+)$. In embodiments, $R^{1.4}$ is independently $-CONH_2$. In embodiments, $R^{1.4}$ is independently $-CONHCH_3$. In embodiments, $R^{1.4}$ is independently $-CONHCH_2CH_3$. In embodiments, $R^{1.4}$ is independently $-CONHC(CH_3)_2$. In embodiments, $R^{1.4}$ is independently $-CONHC(CH_3)_3$. In embodiments, $R^{1.4}$ is independently $-COOCH_3$. In embodiments, $R^{1.4}$ is independently $-COOCH_2CH_3$. In embodiments, $R^{1.4}$ is independently $-COOC(CH_3)_2$. In embodiments, $R^{1.4}$ is independently $-COOC(CH_3)_3$. In embodiments, $R^{1.4}$ is independently $-OCH_2CH_3$. In embodiments, $R^{1.4}$ is independently $-OC(CH_3)_2$. In embodiments, $R^{1.4}$ is independently $-OC(CH)_3$. In embodiments, $R^{1.4}$ is independently unsubstituted methyl. In embodiments, $R^{1.4}$ is independently unsubstituted ethyl. In embodiments, $R^{1.4}$ is independently unsubstituted propyl. In embodiments, $R^{1.4}$ is independently unsubstituted butyl. In embodiments, $R^{1.4}$ is independently unsubstituted n-propyl. In embodiments, $R^{1.4}$ is independently unsubstituted iso-propyl. In embodiments, $R^{1.4}$ is independently unsubstituted n-butyl. In embodiments, $R^{1.4}$ is independently unsubstituted iso-butyl. In embodiments, $R^{1.4}$ is independently unsubstituted methoxy. In embodiments, $R^{1.4}$ is independently unsubstituted ethoxy. In embodiments, $R^{1.4}$ is independently unsubstituted propoxy. In embodiments, $R^{1.4}$ is independently unsubstituted butoxy. In embodiments, $R^{1.4}$ is independently $-F$. In embodiments, $R^{1.4}$ is independently $-Cl$. In embodiments, $R^{1.4}$ is independently $-I$. In embodiments, $R^{1.4}$ is independently $-Br$. In embodiments, $R^{1.4}$ is independently $-NO_2$. In embodiments, $R^{1.4}$ is independently $-CF_3$. In embodiments, $R^{1.4}$ is independently $-CCl_3$. In embodiments, $R^{1.4}$ is independently $-CI_3$. In embodiments, $R^{1.4}$ is independently $-CBr_3$. In embodiments, $R^{1.4}$ is independently $-NH_2$.

In embodiments, $R^{1.4}$ is independently halogen. In embodiments, $R^{1.4}$ is independently oxo. In embodiments. $R^{1.4}$ is independently $-CX^{1.4}_3$. In embodiments. $R^{1.4}$ is independently $-CHX^{1.4}_2$. In embodiments, $R^{1.4}$ is independently $-CH_2X^{1.4}$. In embodiments, $R^{1.4}$ is independently $-OCX^{1.4}_3$. In embodiments, $R^{1.4}$ is independently $-OCH_2X^{1.4}$. In embodiments, $R^{1.4}$ is independently $-OCHX^{1.4}_2$. In embodiments, $R^{1.4}$ is independently $-CN$. In embodiments, $R^{1.4}$ is independently $-OH$. In embodiments, $R^{1.4}$ is independently $-NH_2$. In embodiments, $R^{1.4}$ is independently $-COOH$. In embodiments, $R^{1.4}$ is independently $-CONH_2$. In embodiments, $R^{1.4}$ is independently $-NO_2$. In embodiments, $R^{1.4}$ is independently $-SH$. In embodiments, $R^{1.4}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{1.4}$ is $-F$, $-Cl$, $-Br$, or $-I$. In embodiments, $R^{1.4}$ is independently hydrogen. In embodiments, $R^{1.4}$ is independently methyl. In embodiments, $R^{1.4}$ is independently ethyl. In embodiments, $R^{1.4}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1.4}$ is $-F$, $-Cl$, $-Br$, or $-I$. In embodiments, $R^{1.4}$ is independently halogen, $-CX^{1.4}_3$, $-CHX^{1.4}_2$, $-CH_2X^{1.4}$, $-OCX^{1.4}_3$, $-OCH_2X^{1.4}$, $-OCHX^{1.4}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^{1.4}$ is independently hydrogen, halogen, $-CX^{1.4}_3$, $-CHX^{1.4}_2$, $-CH_2X^{1.4}$, $-OCX^{1.4}_3$, $-OCH_2X^{1.4}$, $-OCHX^{1.4}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^2$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, $R^{1.5}$ is independently hydrogen, halogen, —$CX^{1.5}{}_3$, —$CHX^{1.5}{}_2$, —$CH_2X^{1.5}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^{1.5}{}_3$, —$OCHX^{1.5}{}_2$, —$OCH_2X^{1.5}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{1.1}$ is independently hydrogen, halogen, —$CX^{1.5}{}_3$, —$CHX^{1.5}{}_2$, —$CH_2X^{1.5}$, —OH, —SH, —$OCX^{1.5}{}_3$, —$OCHX^{1.5}{}_2$, —$OCH_2X^{1.5}$, substituted or unsubstituted $C_1$-$C_4$ alkyl, substituted or unsubstituted 2 to 4 membered heteroalkyl. In embodiments, $R^{1.5}$ is independently —F, —$CH_3$, or —$OCH_3$. In embodiments, $R^{1.5}$ is independently hydrogen.

In embodiments, $R^{1.5}$ is independently —$OCH_3$. In embodiments, $R^{1.5}$ is independently —COOH. In embodiments, $R^{1.5}$ is independently —COO$^-$. In embodiments, $R^{1.5}$ is independently a salt of —COO$^-$. In embodiments, $R^{1.5}$ is independently a choline salt of —COO$^-$. In embodiments, $R^{1.5}$ is independently a —COO$^-$(HOCH$_2$CH$_2$N(CH$_3$)$_3$). In embodiments, $R^{1.5}$ is independently —$CONH_2$. In embodiments, $R^{1.5}$ is independently —$CONHCH_3$. In embodiments, $R^{1.5}$ is independently —$CONHCH_2CH_3$. In embodiments, $R^{1.5}$ is independently —$CONHC(CH_3)_2$. In embodiments, $R^{1.5}$ is independently —$CONHC(CH_3)_3$. In embodiments, $R^{1.5}$ is independently —$COOCH_3$. In embodiments, $R^{1.5}$ is independently —$COOCH_2CH_3$. In embodiments, $R^{1.5}$ is independently —$COOC(CH_3)_2$. In embodiments, $R^{1.5}$ is independently —$COOC(CH_3)_3$. In embodiments, $R^{1.5}$ is independently —$OCH_2CH_3$. In embodiments, $R^{1.5}$ is independently —$OC(CH_3)_2$. In embodiments, $R^{1.5}$ is independently —$OC(CH_3)_3$. In embodiments, $R^{1.5}$ is independently unsubstituted methyl. In embodiments, $R^{1.5}$ is independently unsubstituted ethyl. In embodiments, $R^{1.5}$ is independently unsubstituted propyl. In embodiments, $R^{1.5}$ is independently unsubstituted butyl. In embodiments, $R^{1.5}$ is independently unsubstituted n-propyl. In embodiments, $R^{1.5}$ is independently unsubstituted iso-propyl. In embodiments, $R^{1.5}$ is independently unsubstituted n-butyl. In embodiments, $R^{1.5}$ is independently unsubstituted iso-butyl. In embodiments, $R^{1.5}$ is independently unsubstituted methoxy. In embodiments, $R^{1.5}$ is independently unsubstituted ethoxy. In embodiments, $R^{1.5}$ is independently unsubstituted propoxy. In embodiments, $R^{1.5}$ is independently unsubstituted butoxy. In embodiments, $R^{1.5}$ is independently —F. In embodiments, $R^{1.5}$ is independently —Cl. In embodiments, $R^{1.5}$ is independently —I. In embodiments, $R^{1.5}$ is independently —Br. In embodiments, $R^{1.5}$ is independently —$NO_2$. In embodiments, $R^{1.5}$ is independently —$CF_3$. In embodiments, $R^{1.5}$ is independently —$CCl_3$. In embodiments, $R^{1.5}$ is independently —$CI_3$. In embodiments, $R^{1.5}$ is independently —$CBr_3$. In embodiments, $R^{1.5}$ is independently —$NH_2$.

In embodiments, $R^{1.5}$ is independently halogen. In embodiments, $R^{1.5}$ is independently oxo. In embodiments, $R^{1.5}$ is independently —$CX^{1.5}{}_3$. In embodiments, $R^{1.5}$ is independently —$CHX^{1.5}{}_2$. In embodiments, $R^{1.5}$ is independently —$CH_2X^{1.5}$. In embodiments, $R^{1.5}$ is independently —$OCX^{1.5}{}_3$. In embodiments, $R^{1.5}$ is independently —$OCH_2X^{1.5}$. In embodiments, $R^{1.5}$ is independently —$OCHX^{1.5}{}_2$. In embodiments, $R^{1.5}$ is independently —CN. In embodiments, $R^{1.5}$ is independently —OH. In embodiments, $R^{1.5}$ is independently —$NH_2$. In embodiments, $R^{1.5}$ is independently —COOH. In embodiments, $R^{1.5}$ is independently —$CONH_2$. In embodiments, $R^{1.5}$ is independently —$NO_2$. In embodiments, $R^{1.5}$ is independently —SH. In embodiments, $R^{1.5}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $X^{1.5}$ is —F, —Cl, —Br, or —I. In embodiments, $R^{1.5}$ is independently hydrogen. In embodiments, $R^{1.5}$ is independently methyl. In embodiments, $R^{1.5}$ is independently ethyl. In embodiments, $R^{1.5}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 or 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1.5}$ is —F, —Cl, —Br, or —I. In embodiments, $R^{1.5}$ is independently halogen, —$CX^{1.5}{}_3$, —$CHX^{1.5}{}_2$, —$CH_2X^{1.5}$, —$OCX^{1.5}{}_3$, —$OCH_2X^{1.5}$, —$OCHX^{1.5}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered). In embodiments, $R^{1.5}$ is independently hydrogen, halogen, —$CX^{1.5}{}_3$, —$CHX^{1.5}{}_2$, —$CH_2X^{1.5}$, —$OCX^{1.5}{}_3$, —$OCH_2X^{1.5}$, —$OCHX^{1.5}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 or 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 6 membered, 4 to 6 membered, 4 to 5 membered, or 5 to 6 membered), $R^{20}$-substituted or unsubstituted aryl (e.g., $C_6$-$C_{10}$ or phenyl), or $R^{20}$-substituted or unsubstituted heteroaryl (e.g., 5 to 10 membered, 5 to 9 membered, or 5 to 6 membered).

In embodiments, the compound has the formula:

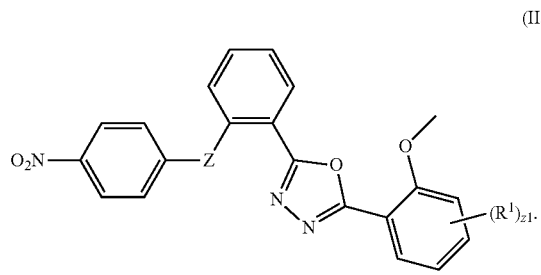
(IIak)

$R^1$ and Z are as described herein, including in embodiments. In embodiments, z1 is an integer from 0 to 4.

In embodiments, the compound has the formula:

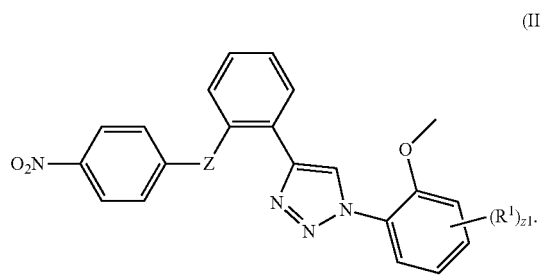
(IIal)

$R^1$ and Z are as described herein, including in embodiments. In embodiments, z1 is an integer from 0 to 4.

In embodiments, the compound has the formula:

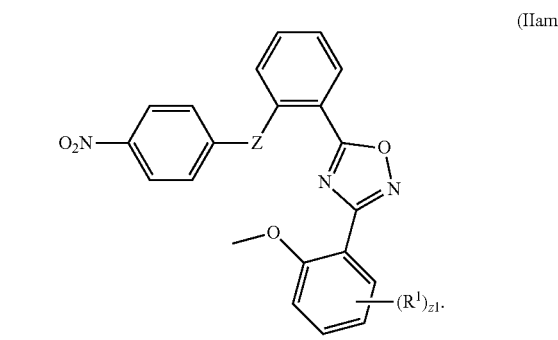
(IIam)

$R^1$ and Z are as described herein, including in embodiments. In embodiments, z1 is an integer from 0 to 4.

In embodiments, the compound has the formula:

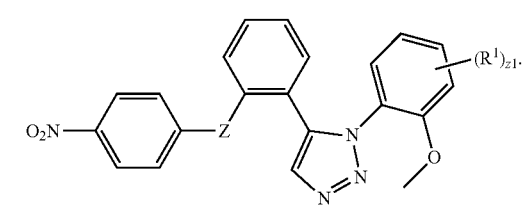
(IIan)

$R^1$ and Z are as described herein, including in embodiments. In embodiments, z1 is an integer from 0 to 4.

In embodiments, the compound has the formula:

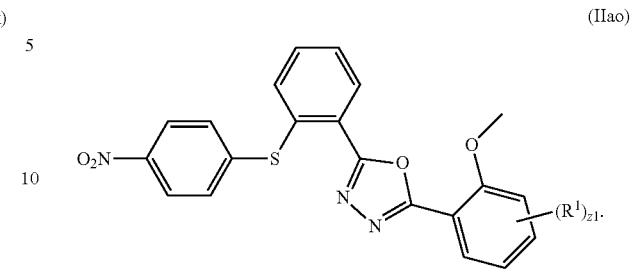
(IIao)

$R^1$ is as described herein, including in embodiments. In embodiments, z1 is an integer from 0 to 4.

In embodiments, the compound has the formula:

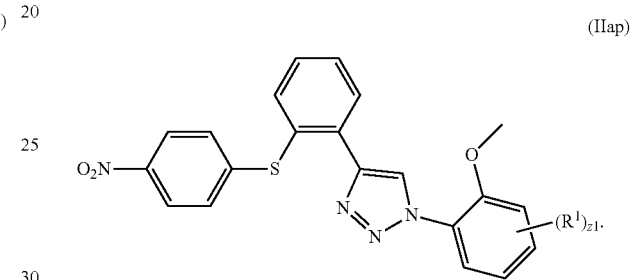
(IIap)

$R^1$ is as described herein, including in embodiments. In embodiments, z1 is an integer from 0 to 4.

In embodiments, the compound has the formula:

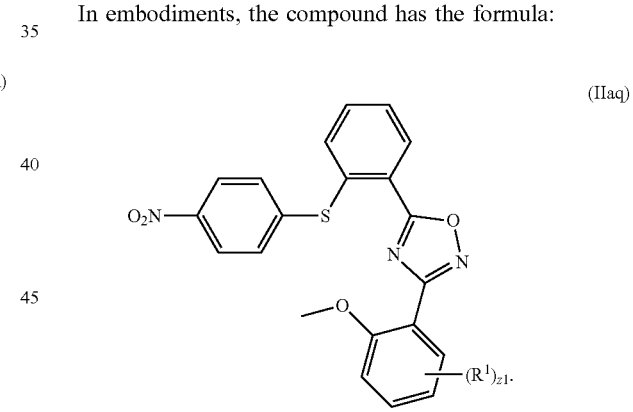
(IIaq)

$R^1$ is as described herein, including in embodiments. In embodiments, z1 is an integer from 0 to 4.

In embodiments, the compound has the formula:

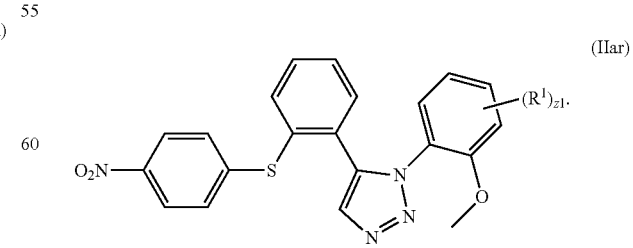
(IIar)

$R^1$ is as described herein, including in embodiments. In embodiments, z1 is an integer from 0 to 4.

In embodiments, the compound has the formula:
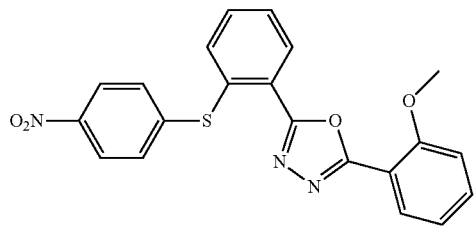
(IIas)
In embodiments, the compound has the formula:
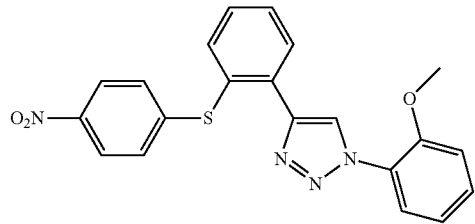
(IIat)
In embodiments, the compound has the formula:
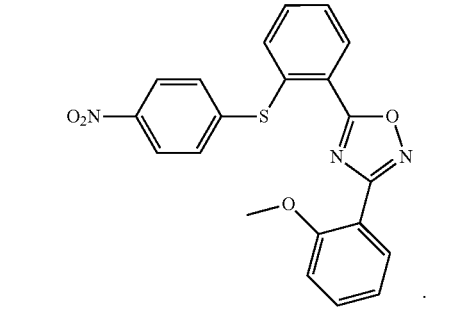
(IIau)
In embodiments, the compound has the formula:
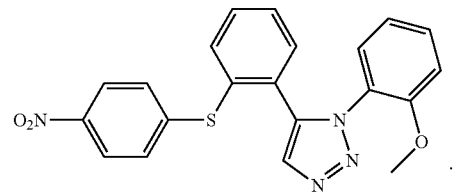
(IIav)
In embodiments, the compound is
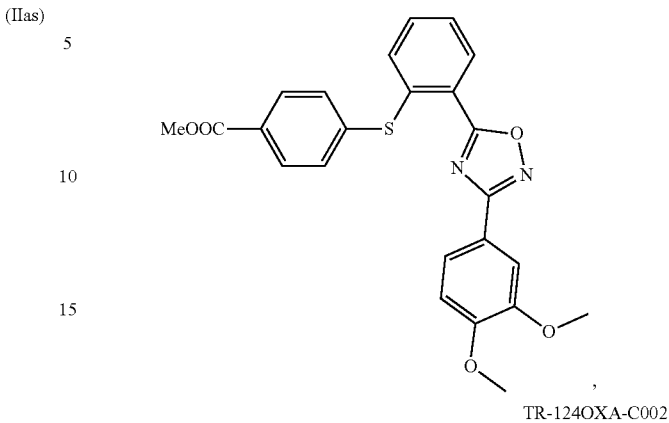
TR-124OXA-C001
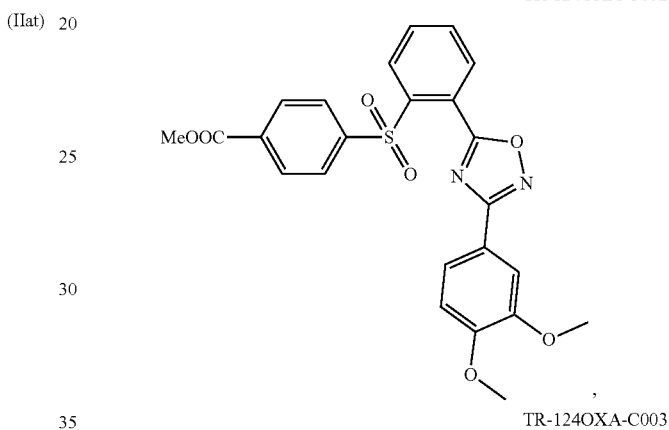
TR-124OXA-C002
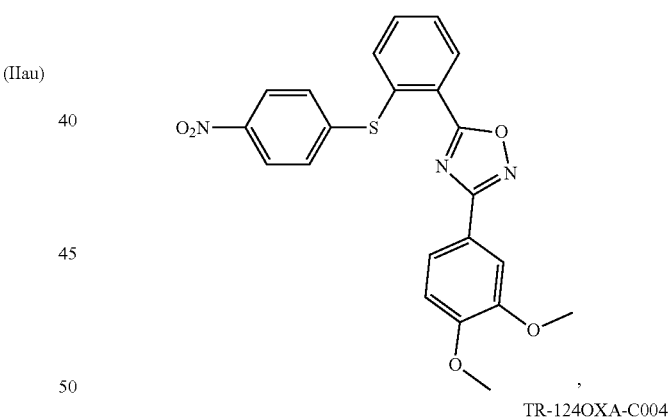
TR-124OXA-C003
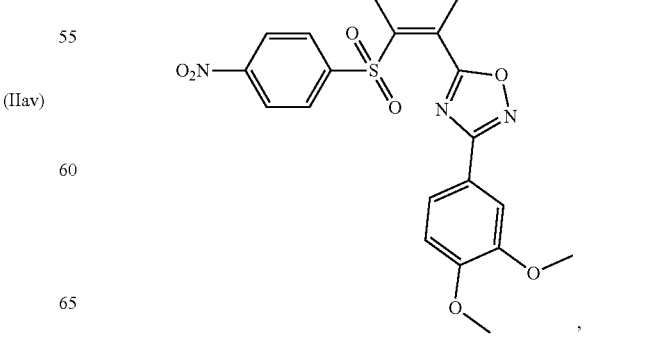
TR-124OXA-C004

TR-124OXA-C005
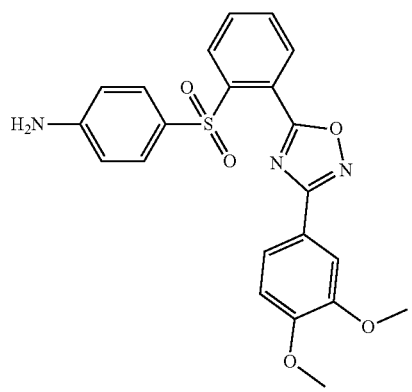
TR-124OXA-C006
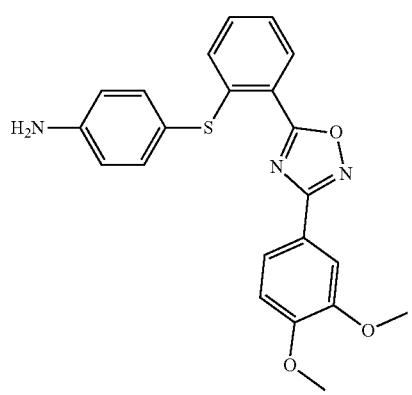
TR-124OXA-C007
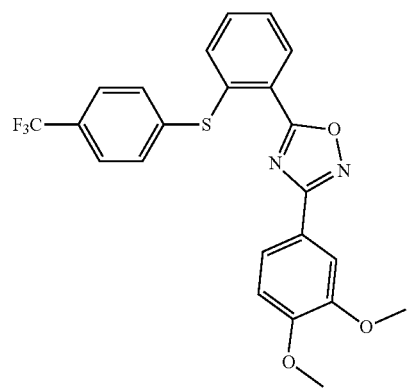
TR-124OXA-C008
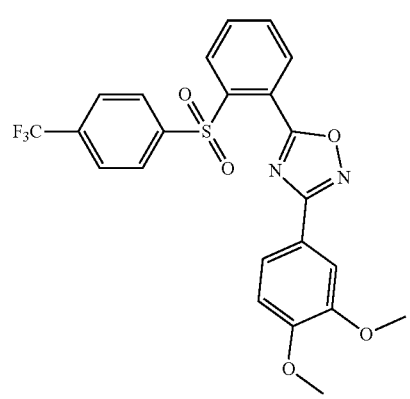
TR-124OXA-C009
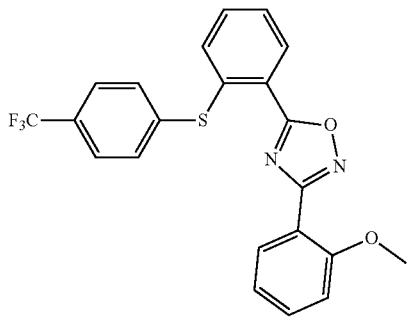
TR-124OXA-C010
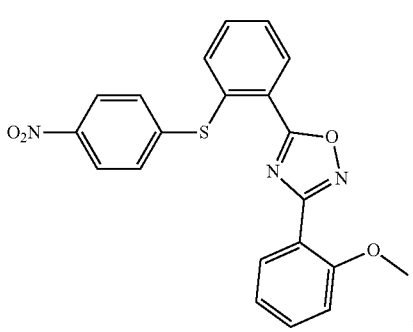
TR-124OXA-C011
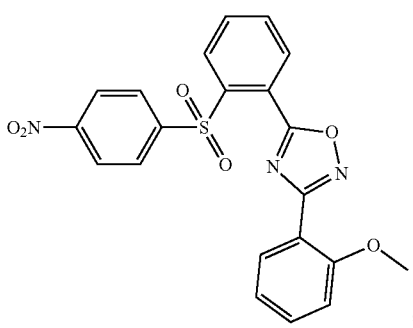
TR-124OXA-C012
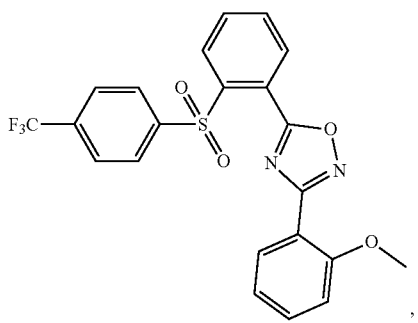

-continued
TR-124OXA-C013
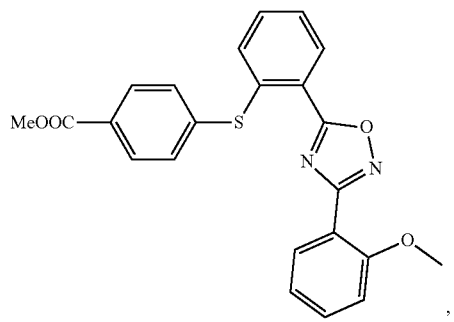
TR-124OXA-C014
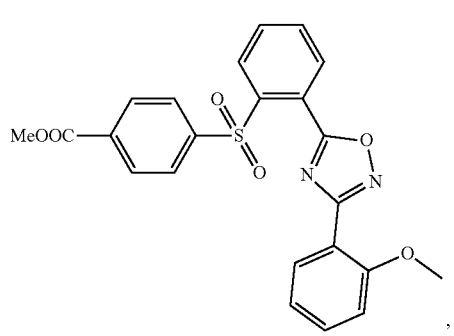
TR-124OXA-C015
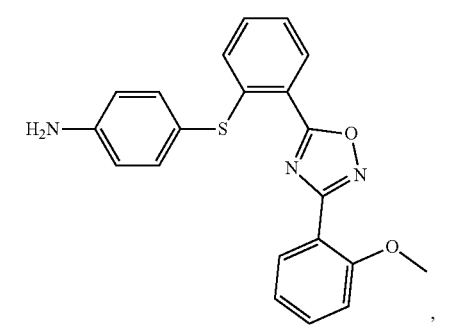
TR-124OXA-C016
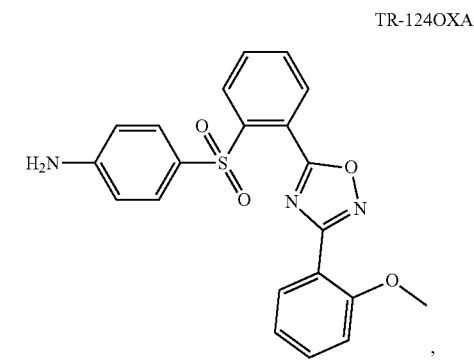
TR-124OXA-C017
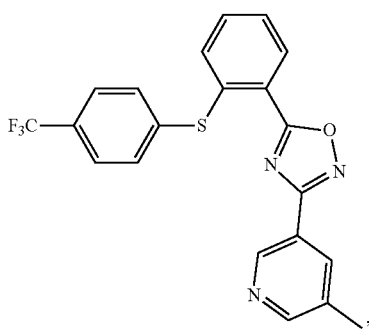
TR-124OXA-C018
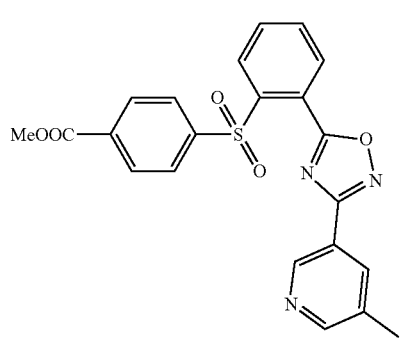
TR-124OXA-C019
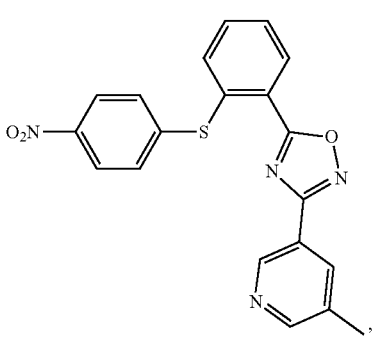
TR-124OXA-C020
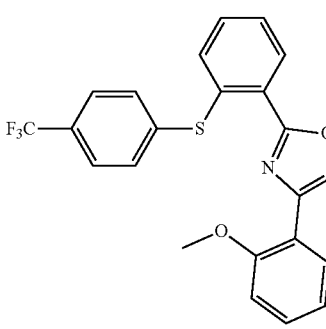

TR-124OXA-C021
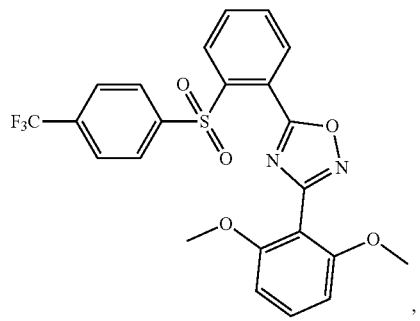
TR-124OXA-C025
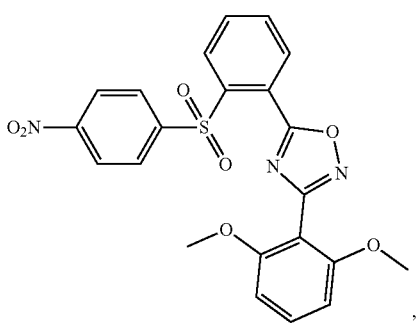
TR-124OXA-C022
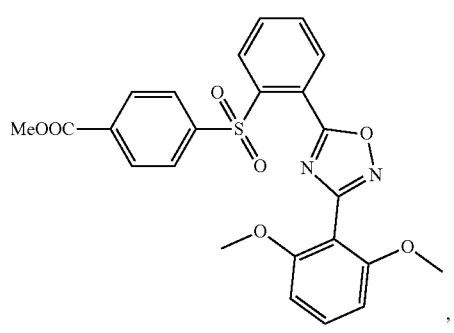
TR-124OXA-C026
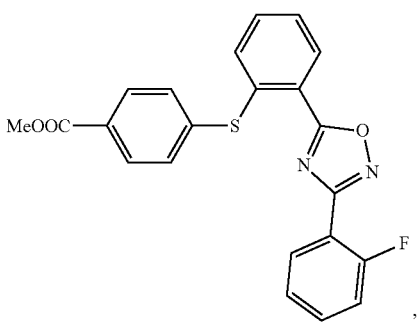
TR-124OXA-C023
TR-124OXA-C027
TR-124OXA-C024
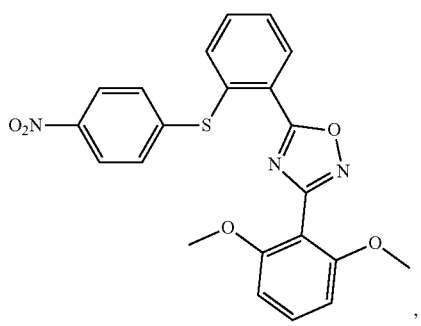
TR-124OXA-C028
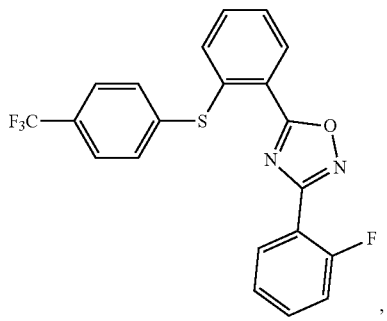

TR-124OXA-C029
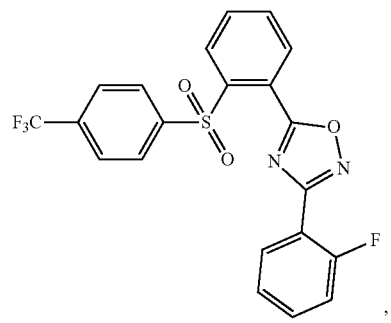
TR-124OXA-C033
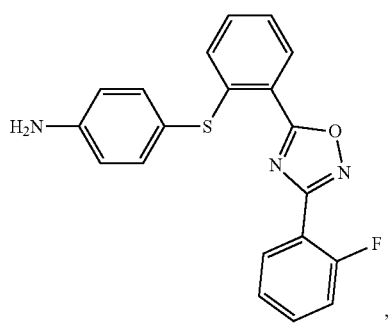
TR-124OXA-C030
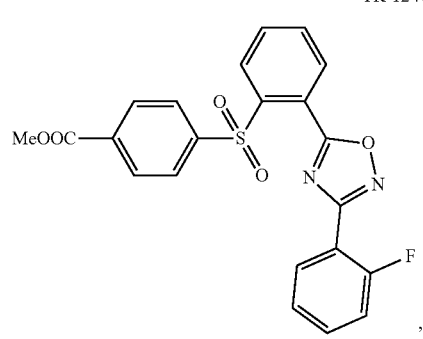
TR-124OXA-C034
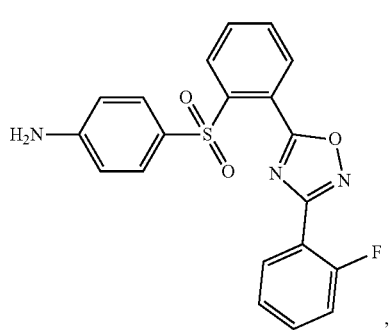
TR-124OXA-C031
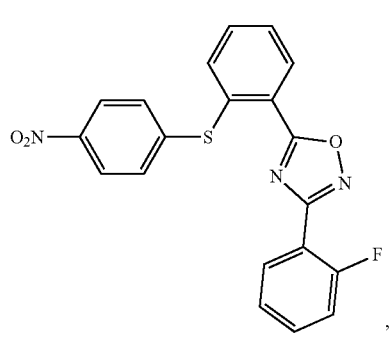
TR-124OXA-C035
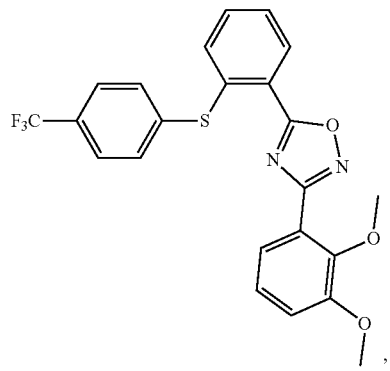
TR-124OXA-C032
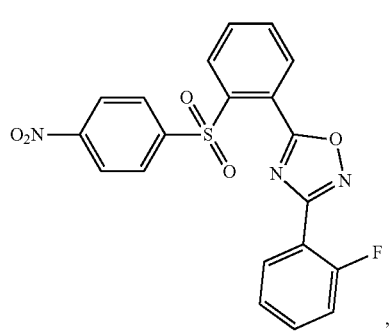
TR-124OXA-C036
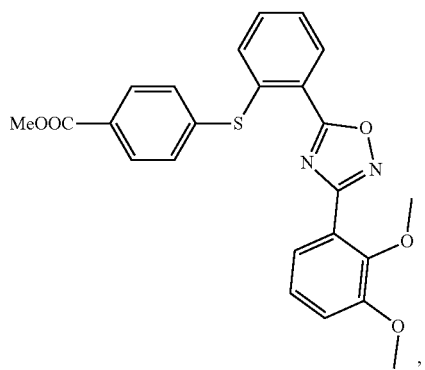

-continued
TR-124OXA-C037
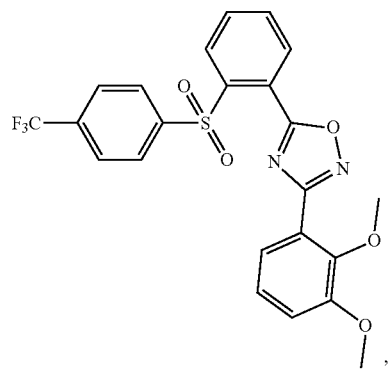
TR-124OXA-C038
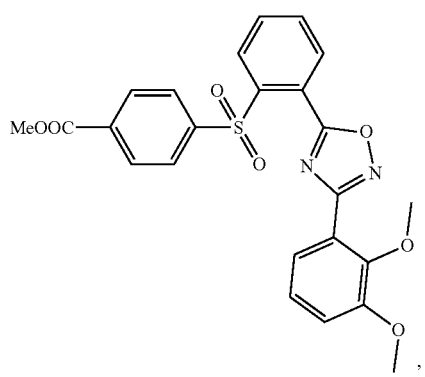
TR-124OXA-C039
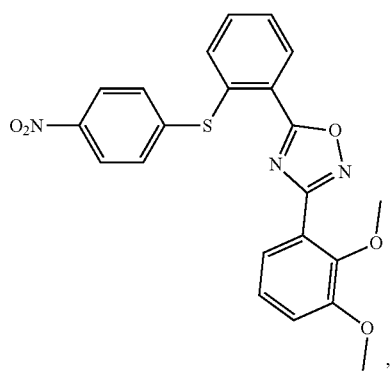
TR-124OXA-C040
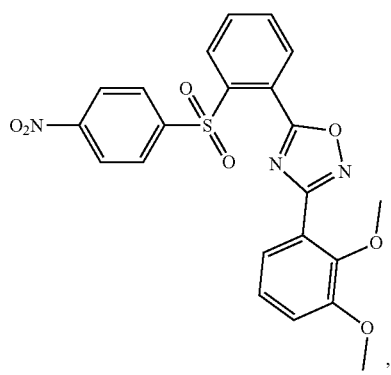
-continued
TR-124OXA-C041
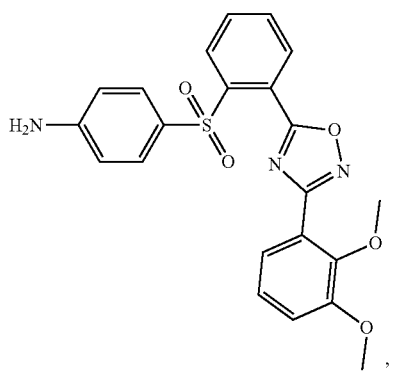
TR-124OXA-C042
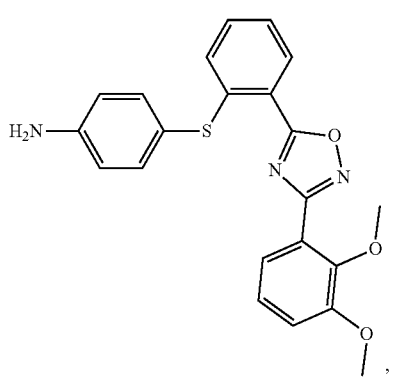
TR-124OXA-C043
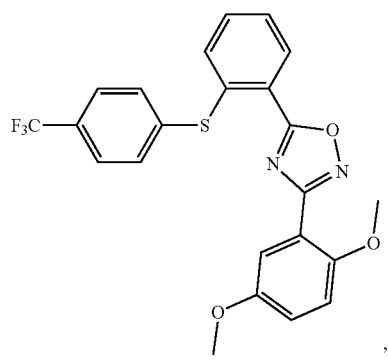
TR-124OXA-C044
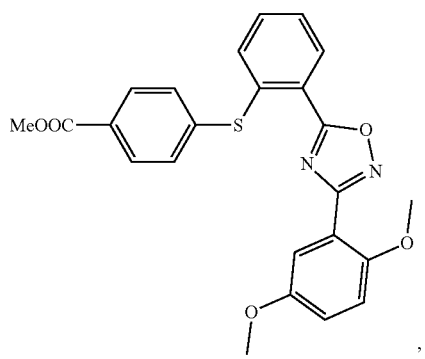

TR-124OXA-C045
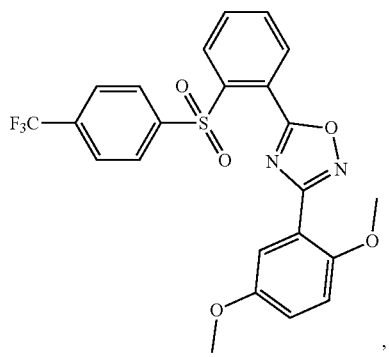

TR-124OXA-C046
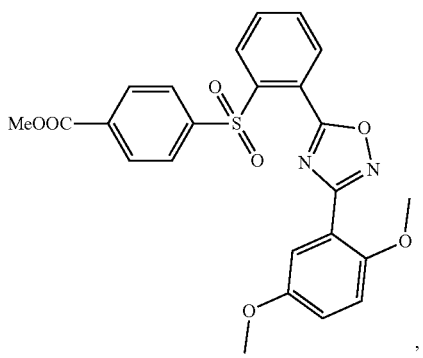

TR-124OXA-C047
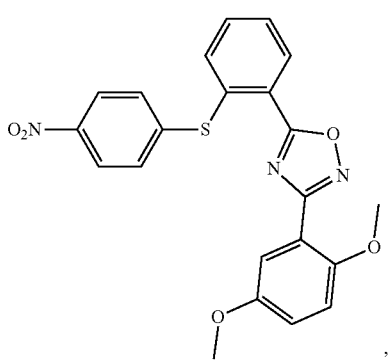

TR-124OXA-C048
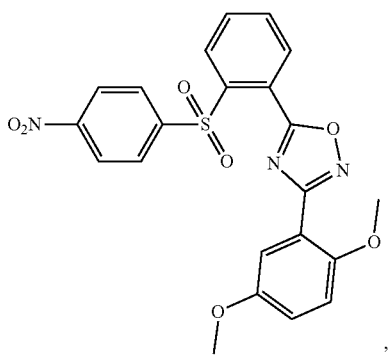

TR-124OXA-C049
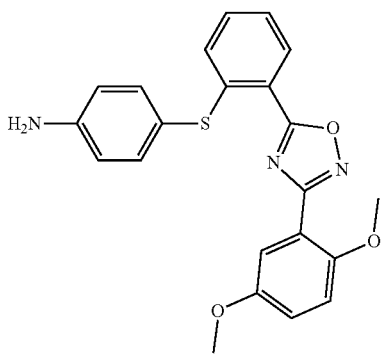

, or

TR-124OXA-C050
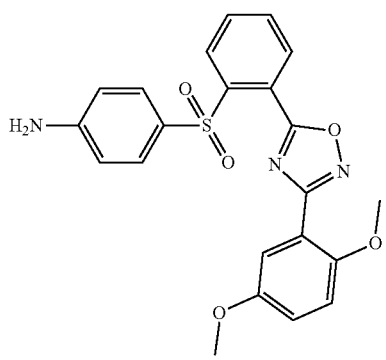

.

In embodiments, the compound, or a pharmaceutically acceptable salt thereof, is 2ax. In embodiments, the compound, or a pharmaceutically acceptable salt thereof, is 2bx. In embodiments, the compound, or a pharmaceutically acceptable salt thereof, is 2cx. In embodiments, the compound, or a pharmaceutically acceptable salt thereof, is 2dx. In embodiments, the compound, or a pharmaceutically acceptable salt thereof, is 2ex. In embodiments, the compound, or a pharmaceutically acceptable salt thereof, is 2fx. In embodiments, the compound, or a pharmaceutically acceptable salt thereof, is 2gx. In embodiments, the compound, or a pharmaceutically acceptable salt thereof, is 2ay. In embodiments, the compound, or a pharmaceutically acceptable salt thereof, is 2by. In embodiments, the compound, or a pharmaceutically acceptable salt thereof, is 2cy. In embodiments, the compound, or a pharmaceutically acceptable salt thereof, is 2dy. In embodiments, the compound, or a pharmaceutically acceptable salt thereof, is 2ey. In embodiments, the compound, or a pharmaceutically acceptable salt thereof, is 2fy. In embodiments, the compound, or a pharmaceutically acceptable salt thereof, is 2gy.

In embodiments, the compound, or a pharmaceutically acceptable salt thereof, is 3ax. In embodiments, the compound, or a pharmaceutically acceptable salt thereof, is 3bx. In embodiments, the compound, or a pharmaceutically acceptable salt thereof, is 3cx. In embodiments, the compound, or a pharmaceutically acceptable salt thereof, is 3dx. In embodiments, the compound, or a pharmaceutically acceptable salt thereof, is 3ex. In embodiments, the compound, or a pharmaceutically acceptable salt thereof, is 3fx. In embodiments, the compound, or a pharmaceutically acceptable salt thereof, is 3gx. In embodiments, the compound, or a pharmaceutically acceptable salt thereof, is 3ay. In embodiments, the compound, or a pharmaceutically acceptable salt thereof, is 3by. In embodiments, the compound, or a pharmaceutically acceptable salt thereof, is 3cy. In embodiments, the compound, or a pharmaceutically acceptable salt thereof, is 3dy. In embodiments, the compound, or a pharmaceutically acceptable salt thereof, is 3ey. In embodiments, the compound, or a pharmaceutically acceptable salt thereof, is 3fy. In embodiments, the compound, or a pharmaceutically acceptable salt thereof, is 3gy.

In embodiments, the compound, or a pharmaceutically acceptable salt thereof, is 4ax. In embodiments, the compound, or a pharmaceutically acceptable salt thereof, is 4bx. In embodiments, the compound, or a pharmaceutically acceptable salt thereof, is 4cx. In embodiments, the compound, or a pharmaceutically acceptable salt thereof, is 4dx. In embodiments, the compound, or a pharmaceutically acceptable salt thereof, is 4ex. In embodiments, the compound, or a pharmaceutically acceptable salt thereof, is 4fx. In embodiments, the compound, or a pharmaceutically acceptable salt thereof, is 4gx. In embodiments, the compound, or a pharmaceutically acceptable salt thereof, is 4ay. In embodiments, the compound, or a pharmaceutically acceptable salt thereof, is 4by. In embodiments, the compound, or a pharmaceutically acceptable salt thereof, is 4cy. In embodiments, the compound, or a pharmaceutically acceptable salt thereof, is 4dy. In embodiments, the compound, or a pharmaceutically acceptable salt thereof, is 4ey. In embodiments, the compound, or a pharmaceutically acceptable salt thereof, is 4fy. In embodiments, the compound, or a pharmaceutically acceptable salt thereof, is 4gy.

In embodiments, the compound, or a pharmaceutically acceptable salt thereof, is 5ax. In embodiments, the compound, or a pharmaceutically acceptable salt thereof, is 5bx. In embodiments, the compound, or a pharmaceutically acceptable salt thereof, is 5cx. In embodiments, the compound, or a pharmaceutically acceptable salt thereof, is 5dx. In embodiments, the compound, or a pharmaceutically acceptable salt thereof, is 5ex. In embodiments, the compound, or a pharmaceutically acceptable salt thereof, is 5fx. In embodiments, the compound, or a pharmaceutically acceptable salt thereof, is 5gx. In embodiments, the compound, or a pharmaceutically acceptable salt thereof, is 5ay. In embodiments, the compound, or a pharmaceutically acceptable salt thereof, is 5by. In embodiments, the compound, or a pharmaceutically acceptable salt thereof, is 5cy. In embodiments, the compound, or a pharmaceutically acceptable salt thereof, is 5dy. In embodiments, the compound, or a pharmaceutically acceptable salt thereof, is 5ey. In embodiments, the compound, or a pharmaceutically acceptable salt thereof, is 5fy. In embodiments, the compound, or a pharmaceutically acceptable salt thereof, is 5gy.

In embodiments, the compound, or a pharmaceutically acceptable salt thereof, is 6ax. In embodiments, the compound, or a pharmaceutically acceptable salt thereof, is 6bx. In embodiments, the compound, or a pharmaceutically acceptable salt thereof, is 6cx. In embodiments, the compound, or a pharmaceutically acceptable salt thereof, is 6dx. In embodiments, the compound, or a pharmaceutically acceptable salt thereof, is 6ex. In embodiments, the compound, or a pharmaceutically acceptable salt thereof, is 6fx. In embodiments, the compound, or a pharmaceutically acceptable salt thereof, is 6gx. In embodiments, the compound, or a pharmaceutically acceptable salt thereof, is 6ay. In embodiments, the compound, or a pharmaceutically acceptable salt thereof, is 6by. In embodiments, the compound, or a pharmaceutically acceptable salt thereof, is 6cy. In embodiments, the compound, or a pharmaceutically acceptable salt thereof, is 6dy. In embodiments, the compound, or a pharmaceutically acceptable salt thereof, is 6ey. In embodiments, the compound, or a pharmaceutically acceptable salt thereof, is 6fy. In embodiments, the compound, or a pharmaceutically acceptable salt thereof, is 6gy.

In embodiments, the compound, or a pharmaceutically acceptable salt thereof, is 7ax. In embodiments, the compound, or a pharmaceutically acceptable salt thereof, is 7bx. In embodiments, the compound, or a pharmaceutically acceptable salt thereof, is 7cx. In embodiments, the compound, or a pharmaceutically acceptable salt thereof, is 7dx. In embodiments, the compound, or a pharmaceutically acceptable salt thereof, is 7ex. In embodiments, the compound, or a pharmaceutically acceptable salt thereof, is 7fx. In embodiments, the compound, or a pharmaceutically acceptable salt thereof, is 7gx. In embodiments, the compound, or a pharmaceutically acceptable salt thereof, is 7ay. In embodiments, the compound, or a pharmaceutically acceptable salt thereof, is 7by. In embodiments, the compound, or a pharmaceutically acceptable salt thereof, is 7cy. In embodiments, the compound, or a pharmaceutically acceptable salt thereof, is 7dy. In embodiments, the compound, or a pharmaceutically acceptable salt thereof, is 7ey. In embodiments, the compound, or a pharmaceutically acceptable salt thereof, is 7fy. In embodiments, the compound, or a pharmaceutically acceptable salt thereof, is 7gy.

In embodiments, the compound is TR-1240XA-C001. In embodiments, the compound is TR-1240XA-C002. In embodiments, the compound is TR-1240XA-C003. In embodiments, the compound is TR-1240XA-C004. In embodiments, the compound is TR-1240XA-C005. In embodiments, the compound is TR-1240XA-C006. In embodiments, the compound is TR-1240XA-C007. In embodiments, the compound is TR-1240XA-C008. In embodiments, the compound is TR-1240XA-C009. In embodiments, the compound is TR-1240XA-C010. In embodiments, the compound is TR-1240XA-C011. In embodiments, the compound is TR-1240XA-C012. In embodiments, the compound is TR-1240XA-C013. In embodiments, the compound is TR-1240XA-C014. In embodiments, the compound is TR-1240XA-C015. In embodiments, the compound is TR-1240XA-C016. In embodiments, the compound is TR-1240XA-C017. In embodiments, the compound is TR-1240XA-C018. In embodiments, the compound is TR-1240XA-C019. In embodiments, the compound is TR-1240XA-C020. In embodiments, the compound is TR-1240XA-C021. In embodiments, the compound is TR-1240XA-C022. In embodiments, the compound is TR-1240XA-C023. In embodiments, the compound is TR-1240XA-C024. In embodiments, the compound is TR-1240XA-C025. In embodiments, the compound is TR-1240XA-C026. In embodiments, the compound is TR-1240XA-C027. In embodiments, the compound is TR-1240XA-C028. In embodiments, the compound is TR-1240XA-C029. In embodiments, the compound is TR-1240XA-C030. In embodiments, the compound is TR-1240XA-C031. In embodiments, the compound is TR-1240XA-C032. In embodiments, the compound is TR-1240XA-C033. In embodiments, the compound is TR-1240XA-C034. In embodiments, the compound is TR-1240XA-C035. In embodiments, the compound is TR-1240XA-C036. In embodiments, the compound is TR-1240XA-C037. In embodiments, the compound is TR-1240XA-C038. In embodiments, the compound is TR-1240XA-C039. In embodiments, the compound is TR-1240XA-C040. In embodiments, the compound is TR-1240XA-C041. In embodiments, the compound is TR-1240XA-C042. In embodiments, the compound is TR-1240XA-C043. In embodiments, the compound is TR-1240XA-C044. In embodiments, the compound is TR-1240XA-C045. In embodiments, the compound is TR-1240XA-C046. In embodiments, the compound is TR-1240XA-C047. In embodiments, the compound is TR-1240XA-C048. In embodiments, the compound is TR-1240XA-C049. In embodiments, the compound is TR-1240XA-C050.

In embodiments, the compound has the formula:

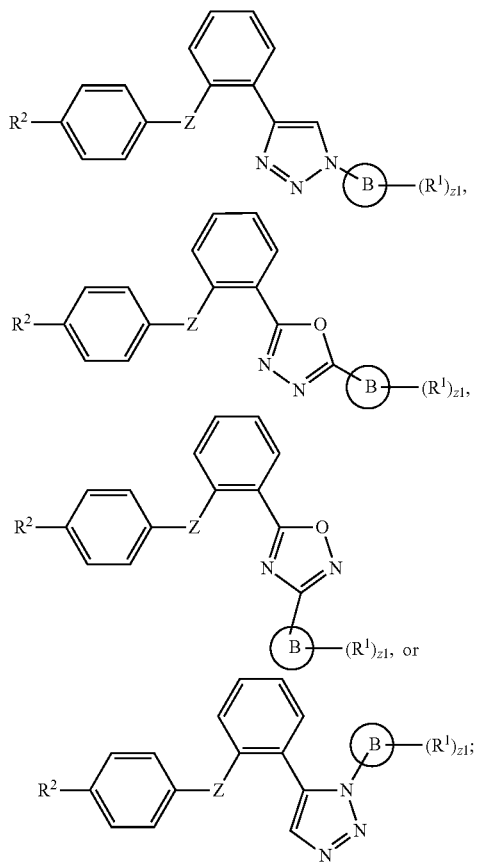

wherein Z is as described herein; Ring B is as described herein. In embodiments, the compound has the formula:

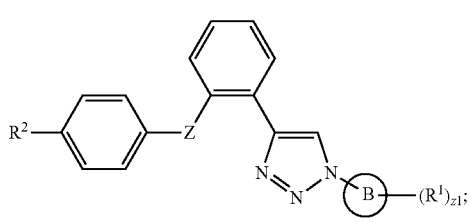

wherein Z is as described herein; Ring B is as described herein; wherein $R^1$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered); $R^2$ is halogen, —$CX^2_3$, —$CHX^2_2$, —$CH_2X^2$, —OH, —$NH_2$, —COOH, —$CONH_2$, —$NO_2$, —SH, —$OCX^2_3$, —$OCHX^2_2$, —$OCH_2X^2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 or 3 membered, or 4 to 5 membered); and z1 is 1 or 2. In embodiments, $R^2$ is —$CF_3$, —$NH_2$, —COOH, —$COOCH_3$, —$NO_2$, or —$C(O)O(C_1$-$C_6$ alkyl). In embodiments, $R^1$ is —$CH_3$, —$OCH_3$, —$OCH_2CH_3$, —$OCH(CH_3)_2$, —$OC(CH_3)_3$, unsubstituted methyl, unsubstituted ethyl, unsubstituted propyl, unsubstituted butyl, unsubstituted n-propyl, unsubstituted iso-propyl, unsubstituted n-butyl, unsubstituted iso-butyl, unsubstituted methoxy, unsubstituted ethoxy, unsubstituted propoxy, or unsubstituted butoxy. In embodiments, $R^1$ is independently unsubstituted methoxy and $R^2$ is —$COOCH_3$. In embodiments, $R^1$ is independently unsubstituted methoxy and $R^2$ is —$COO^-$. In embodiments, $R^1$ is independently unsubstituted methoxy and $R^2$ is —$NH_2$. In embodiments, $R^1$ is independently unsubstituted methoxy and $R^2$ is —$NO_2$. In embodiments, $R^1$ is independently unsubstituted methoxy and z1 is 2.

In embodiments, the compound has the formula:

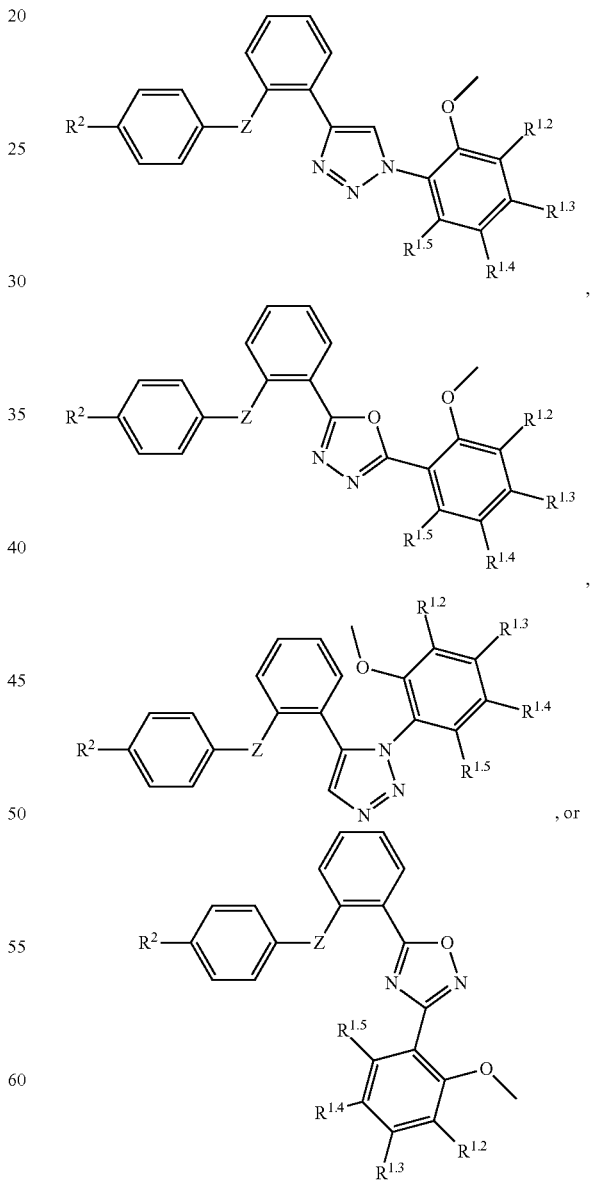

wherein $R^2$, Z, and z2 are as described herein. In embodiments, the compound has the formula:

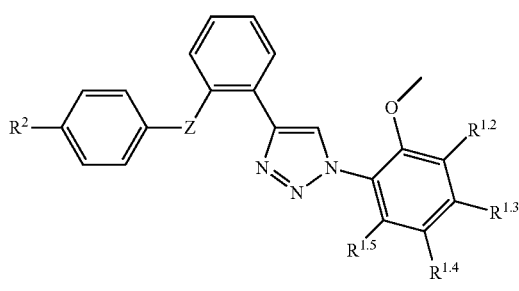

wherein $R^2$, Z, and z2 are as described herein, including in embodiments. $R^{1.2}$, $R^{1.3}$, $R^{1.4}$, and $R^{1.5}$ are each independently an $R^1$ substituent as described herein (e.g., in an embodiment). In embodiments, $R^{1.3}$, $R^{1.4}$, and $R^{1.5}$ are each independently hydrogen and $R^{1.2}$ is —$OCH_3$. In embodiments, $R^{1.2}$, $R^{1.4}$, and $R^{1.5}$ are each independently hydrogen and $R^{1.3}$ is —$OCH_3$. In embodiments, $R^{1.2}$, $R^{1.3}$, and $R^{1.5}$ are each independently hydrogen and $R^{1.4}$ is —$OCH_3$. In embodiments, $R^{1.2}$, $R^{1.3}$, and $R^{1.4}$ are each independently hydrogen and $R^{1.5}$ is —$OCH_3$. In embodiments, $R^2$ is C(O)$OCH_3$. In embodiments, $R^{1.3}$, $R^{1.4}$, and $R^{1.5}$ are each independently hydrogen and $R^{1.2}$ is unsubstituted $C_1$-$C_4$ alkoxy. In embodiments, $R^{1.2}$, $R^{1.4}$, and $R^{1.5}$ are each independently hydrogen and $R^{1.3}$ is unsubstituted $C_1$-$C_4$ alkoxy. In embodiments, $R^{1.2}$, $R^{1.3}$, and $R^{1.5}$ are each independently hydrogen and $R^{1.4}$ is unsubstituted $C_1$-$C_4$ alkoxy. In embodiments, $R^{1.2}$, $R^{1.3}$, and $R^{1.4}$ are each independently hydrogen and $R^{1.5}$ is unsubstituted $C_1$-$C_4$ alkoxy. In embodiments, $R^2$ is C(O)$OCH_3$. In embodiments, $R^2$ is C(O)O(unsubstituted $C_1$-$C_4$). In embodiments, $R^2$ is —C(O)$OCH_3$ or —$NO_2$. In embodiments, $R^2$ is —$NO_2$. In embodiments, $R^2$ is —$NH_2$. In embodiments, $R^2$ is —NH(unsubstituted $C_1$-$C_4$). In embodiments, $R^2$ is —N(unsubstituted $C_1$-$C_4$)$_2$. In embodiments, $R^2$ is —N($CH_3$)$_2$.

In embodiments, the compound has the formula:

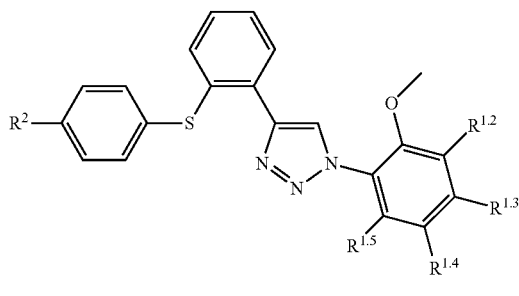

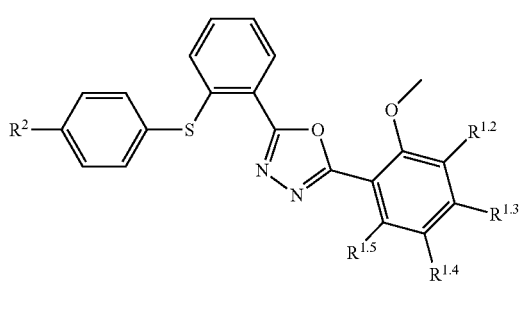

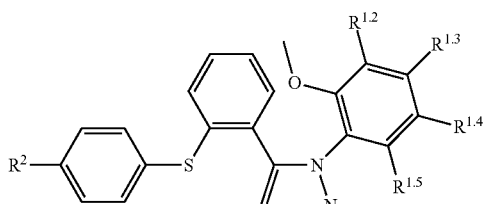

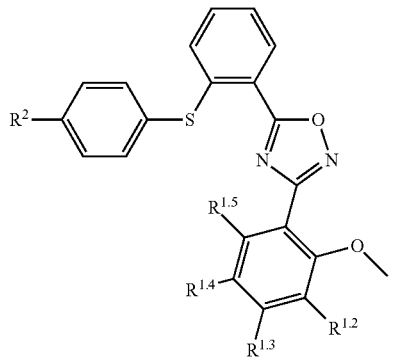

wherein $R^2$ is as described herein. In embodiments, the compound has the formula:

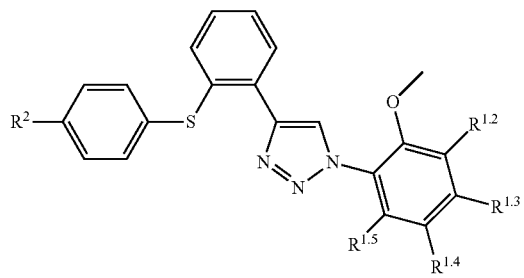

$R^2$ is as described herein, including in embodiments. $R^{1.2}$, $R^{1.3}$, $R^{1.4}$, and $R^{1.5}$ are each independently an $R^1$ substituent as described herein (e.g., in an embodiment). In embodiments, $R^{1.3}$, $R^{1.4}$, and $R^{1.5}$ are each independently hydrogen and $R^{1.2}$ is —$OCH_3$. In embodiments, $R^{1.2}$, $R^{1.4}$, and $R^{1.5}$ are each independently hydrogen and $R^{1.3}$ is —$OCH_3$. In embodiments, $R^{1.2}$, $R^{1.3}$, and $R^{1.5}$ are each independently hydrogen and $R^{1.4}$ is —$OCH_3$. In embodiments, $R^{1.2}$, $R^{1.3}$, and $R^{1.4}$ are each independently hydrogen and $R^{1.5}$ is —$OCH_3$. In embodiments, $R^2$ is —$NO_2$. In embodiments, $R^{1.3}$, $R^{1.4}$, and $R^{1.5}$ are each independently hydrogen and $R^{1.2}$ is unsubstituted $C_1$-$C_4$ alkoxy. In embodiments, $R^{1.2}$, $R^{1.3}$, and $R^{1.5}$ are each independently hydrogen and $R^{1.3}$ is unsubstituted $C_1$-$C_4$ alkoxy. In embodiments, $R^{1.2}$, $R^{1.3}$, and $R^{1.5}$ are each independently hydrogen and $R^{1.4}$ is unsubstituted $C_1$-$C_4$ alkoxy. In embodiments, $R^{1.2}$, $R^{1.3}$, and $R^{1.4}$ are each independently hydrogen and $R^{1.5}$ is unsubstituted $C_1$-$C_4$ alkoxy. In embodiments, $R^2$ is C(O)$OCH_3$. In embodiments, $R^2$ is C(O)O(unsubstituted $C_1$-$C_4$). In embodiments. $R^2$ is —NH(unsubstituted $C_1$-$C_4$). In embodiments, $R^2$ is —N(unsubstituted $C_1$-$C_4$)$_2$. In embodiments, $R^2$ is —N($CH_3$)$_2$. In embodiments, $R^2$ is —COO$^-$. In embodiments, $R^2$ is —COO$^-$HOC(O)O$CH_2$$CH_2$N($CH_3$)$_3$$^+$).

In embodiments, the compound has the formula:
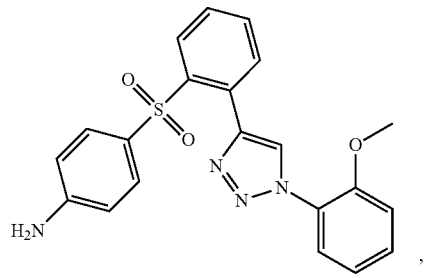
(2ey)
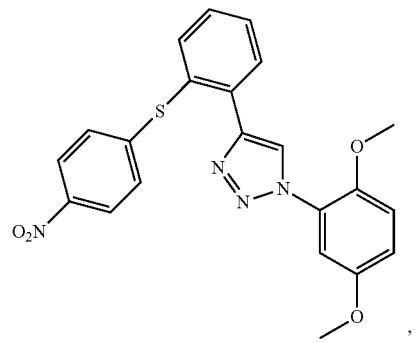
(5ax)
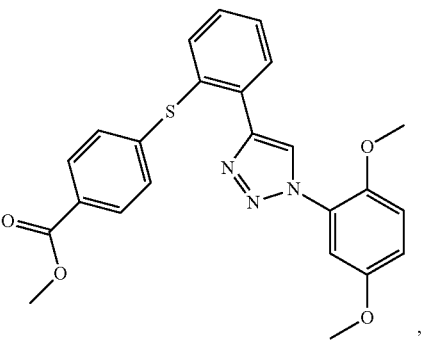
(5bx)
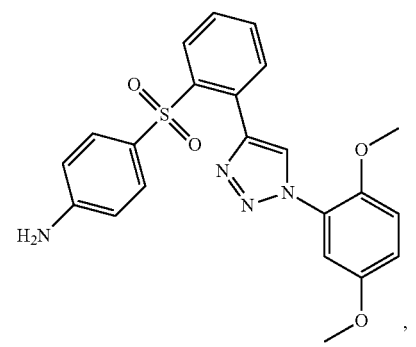
(5ey)
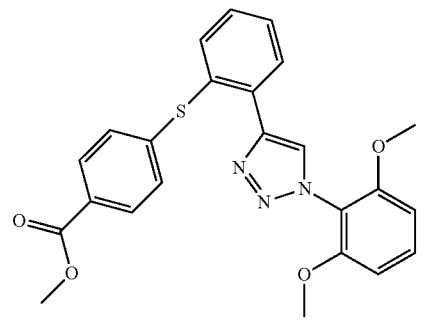
(6bx)
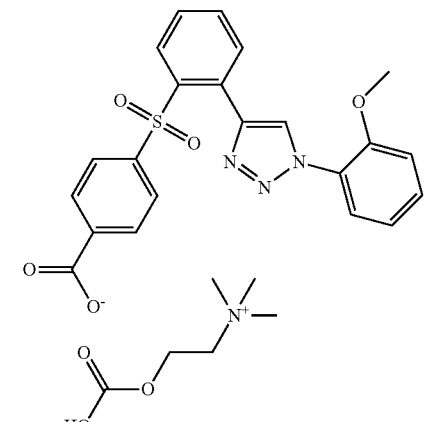
(2gy)
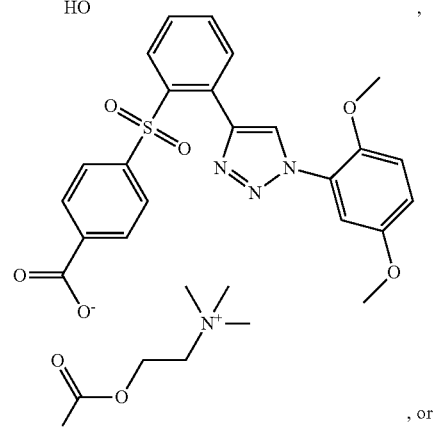
(5gy)
, or
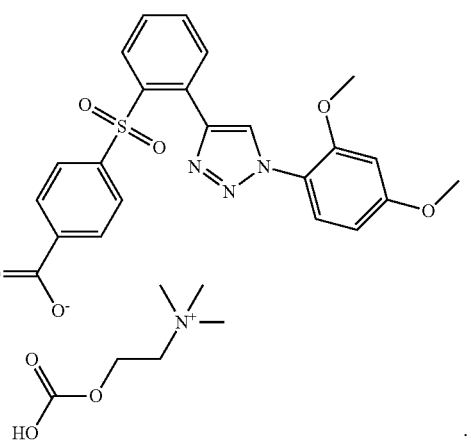
(4gy)

In embodiments, the compound has the formula:

(2ey)
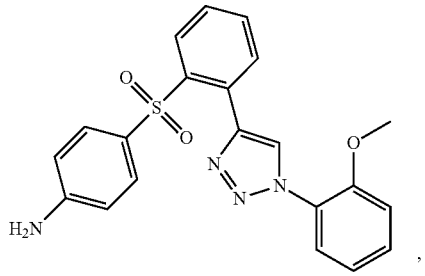

(5ax)
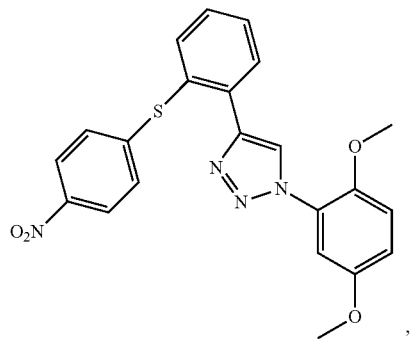

(5bx)
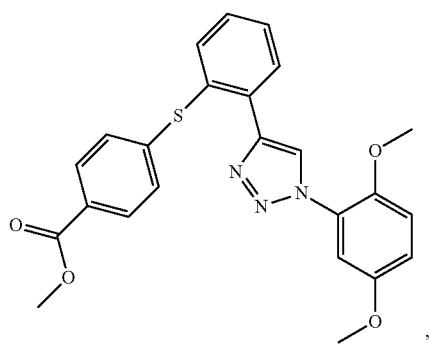

(5ey)
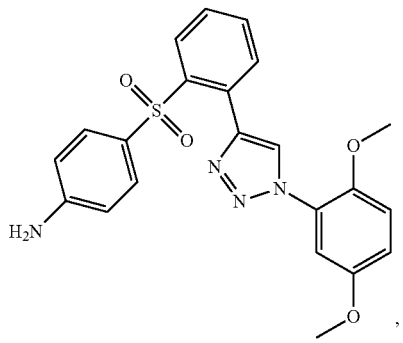

-continued (6bx)
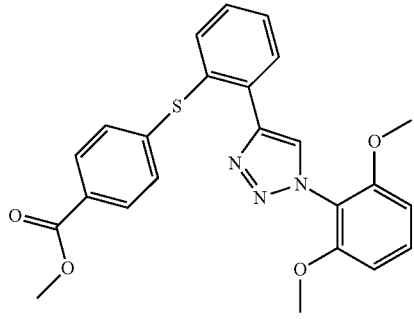

In embodiments, the compound has the formula:

(5ax)
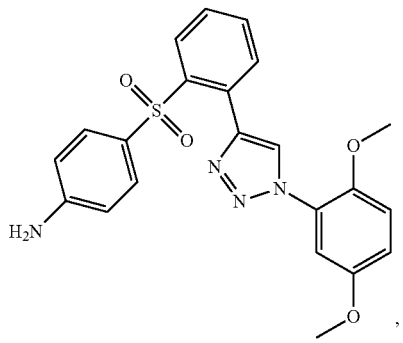

In embodiments, the compound is 5ax, 2ey, 5bx, 5ey, 6bx, 2ax, 2dx, 2ex, 2fx, 3ax, 3dx, 3fx, 3fy, 5ay, 6ex, 6fx, 6ey, 6fy, 2gy, 4gy or 5gy. In embodiments, the compound is 5ax, 2ey, 5bx, 5ey, 6bx, 2ax, 2dx, 2ex, 2fx, 3ax, 3dx, 3fx, 3fy, 5ay, 6ex, 6fx, 6ey, or 6fy. In embodiments, the compound is 5ax, 2ey, 5bx, 5ey, or 6bx. In embodiments, the compound is 2gy, 4gy or 5gy.

In embodiments, the compound has the formula:

(4bx)
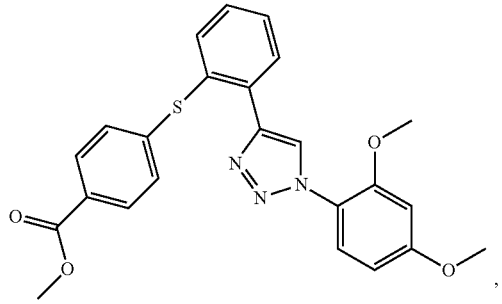

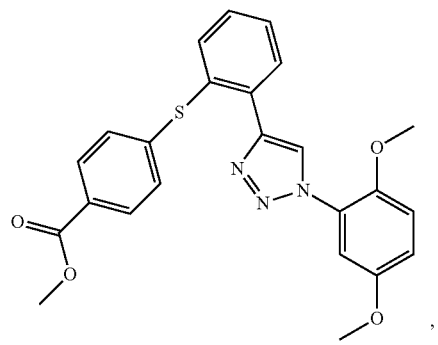
(5bx)
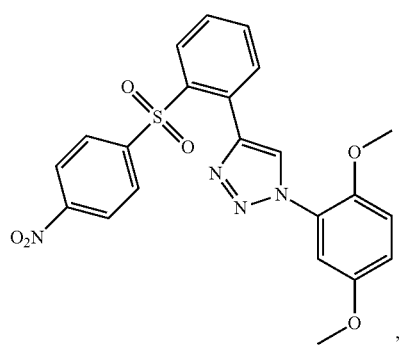
(5ay)
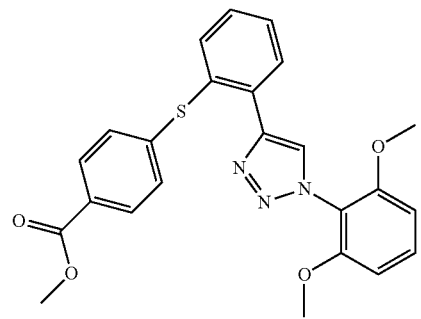
(6bx)
In embodiments, the compound has the formula:
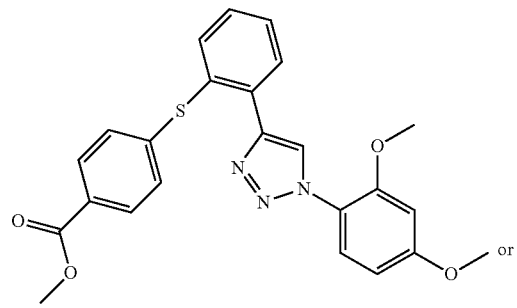
(4bx)
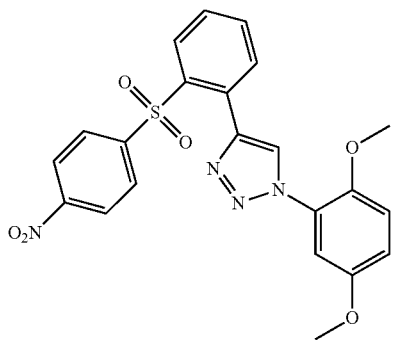
(5ay)
In embodiments, the compound has the formula:
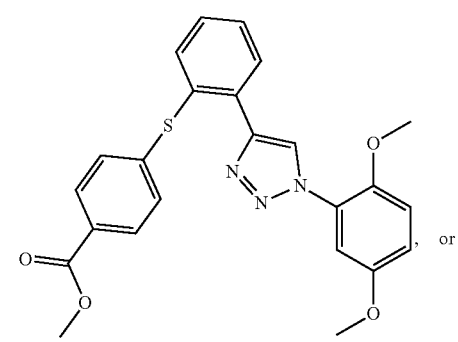
(4bx)
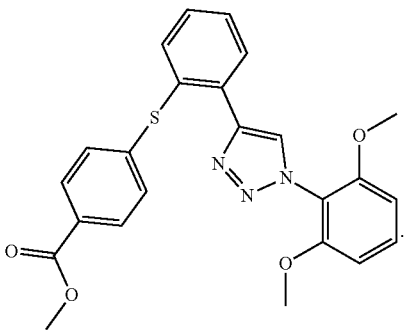
(5bx), or
(6bx)

In embodiments, the compound has the formula:

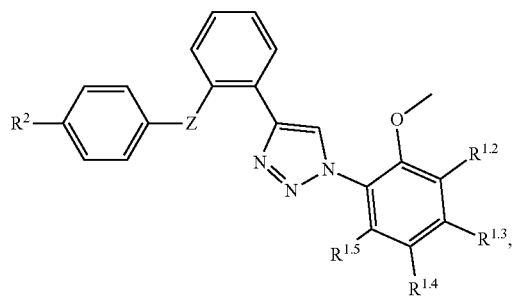

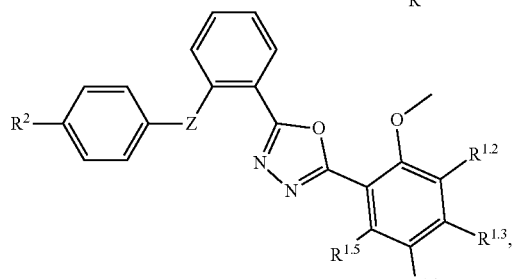

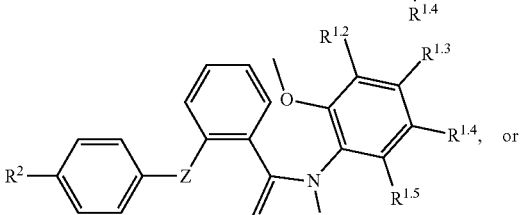

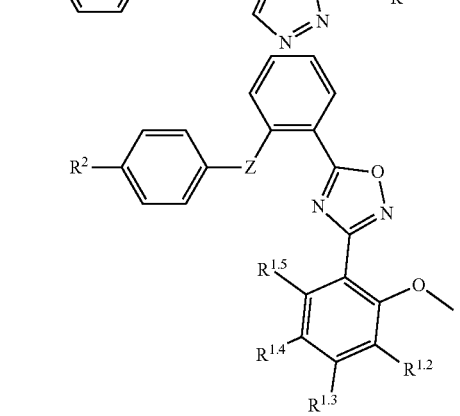

wherein $R^2$, Z, and z2 are as described herein. In embodiments, the compound has the formula:

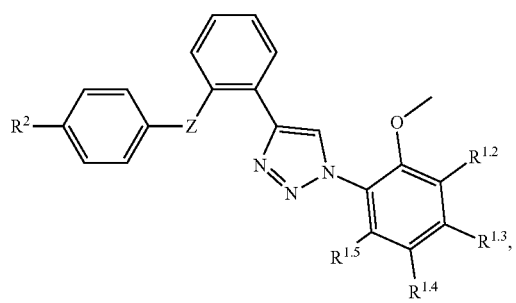

wherein $R^2$, Z, and z2 are as described herein, including in embodiments. $R^{1.2}$, $R^{1.3}$, $R^{1.4}$, and $R^{1.5}$ are each independently an $R^1$ substituent as described herein (e.g., in an embodiment). In embodiments, $R^{1.2}$ and $R^{1.5}$ are hydrogen; $R^{1.3}$ and $R^{1.4}$ are each independently hydrogen or unsubstituted $C_1$-$C_4$ alkoxy (e.g., unsubstituted methoxy); $R^2$ is —C(O)O(unsubstituted $C_1$-$C_4$) or —$NO_2$. In embodiments, $R^{1.2}$ and $R^{1.5}$ are hydrogen; $R^{1.3}$ and $R^{1.4}$ are each independently hydrogen or halogen-substituted $C_1$-$C_4$ alkoxy (e.g., —$OCF_3$, —$OCH_2F$, or —$OCHF_2$); $R^2$ is —C(O)O(unsubstituted $C_1$-$C_4$) or —$NO_2$. In embodiments, $R^{1.2}$ and $R^{1.5}$ are hydrogen; $R^{1.3}$ and $R^{1.4}$ are each independently hydrogen or halogen-substituted or unsubstituted $C_1$-$C_3$ alkoxy (e.g., —$OCH_3$, —$OCF_3$, —$OCH_2F$, or —$OCHF_2$); $R^2$ is —C(O)O(unsubstituted $C_1$-$C_2$) or —$NO_2$.

In embodiments, the compound has the formula:

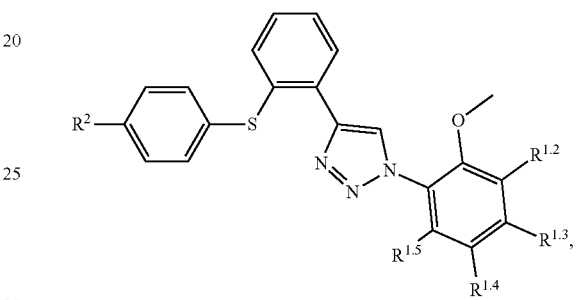

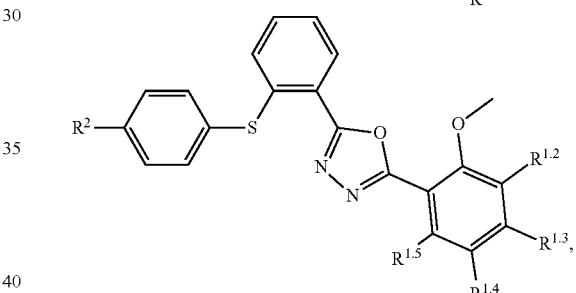

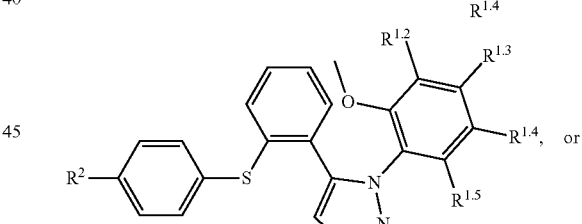

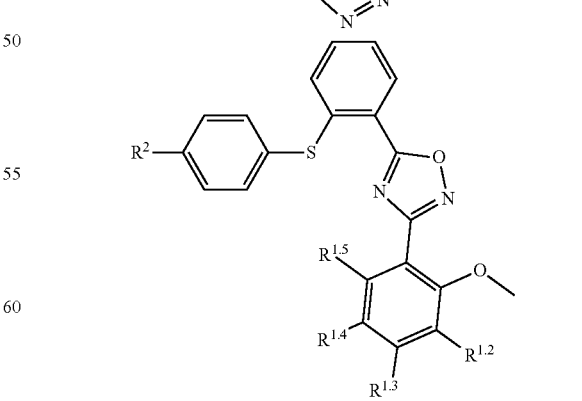

wherein $R^2$ is as described herein. In embodiments, the compound has the formula:

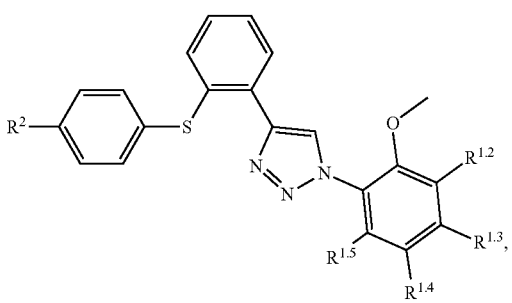

$R^2$ is as described herein, including in embodiments. $R^{1.2}$, $R^{1.3}$, $R^{1.4}$, and $R^{1.5}$ are each independently an $R^1$ substituent as described herein (e.g., in an embodiment). In embodiments, $R^{1.2}$ is hydrogen; $R^{1.3}$, $R^{1.4}$, and $R^{1.5}$ are each independently hydrogen or unsubstituted $C_1$-$C_4$ alkoxy (e.g., unsubstituted methoxy); $R^2$ is —C(O)O(unsubstituted $C_1$-$C_4$). In embodiments, $R^{1.2}$ is hydrogen; $R^{1.3}$, $R^{1.4}$, and $R^{1.5}$ are each independently hydrogen or halogen-substituted $C_1$-$C_4$ alkoxy (e.g., —OCF$_3$, —OCH$_2$F, or —OCHF$_2$); $R^2$ is —C(O)O(unsubstituted $C_1$-$C_4$). In embodiments, $R^{1.2}$ is hydrogen; $R^{1.3}$, $R^{1.4}$, and $R^{1.5}$ are each independently hydrogen or halogen-substituted or unsubstituted $C_1$-$C_3$ alkoxy (e.g., —OCH$_3$, —OCF$_3$, —OCH$_2$F, or —OCHF$_2$); $R^2$ is —C(O)O(unsubstituted $C_1$-$C_2$).

In embodiments, the compound is a compound described herein (e.g., in an aspect, embodiment, example, figure, table, or claim).

III. Pharmaceutical Compositions

In an aspect is provided a pharmaceutical composition including a compound (e.g., as described herein), or a pharmaceutically acceptable salt thereof, and a pharmaceutically acceptable excipient.

In embodiments of the pharmaceutical compositions, the compound, or a pharmaceutically acceptable salt thereof, is included in a therapeutically effective amount.

In embodiments, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the second agent is an anti-infectious disease agent. In embodiments, the second agent is an anti-viral agent. In embodiments, the second agent is an anti-HIV agent. In embodiments, the anti-viral agent is an HIV reverse transcriptase inhibitor, HIV protease inhibitor, HIV integrase inhibitor, HIV fusion inhibitor, or HIV entry inhibitor. In embodiments, the second agent is abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat. In embodiments, the second agent is a combination of two or more anti-HIV agents (e.g., a combination of two or more of abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat). In embodiments, the pharmaceutical composition includes a second and third agent (e.g. therapeutic agents). In embodiments, the pharmaceutical composition includes a second, third, and fourth agent (e.g. therapeutic agents). In embodiments, the pharmaceutical composition includes a second, third, fourth, and fifth agent (e.g. therapeutic agents). In embodiments, the pharmaceutical composition includes a second, third, fourth, fifth, and sixth agent (e.g. therapeutic agents). In embodiments, the second agent is an agent for treating a Ebola virus infection. In embodiments, the second agent is an agent for treating a Zika virus infection. In embodiments, the second agent is an agent for treating a hepatitis (e.g., hepatitis A, hepatitis B, or hepatitis C) infection. In embodiments, the second agent is adefovir, dipivoxil, entecavir, interferon, lamivudine, peginterferon, telbivudine, tenofovir, ribavirin, boceprevir, teleprevir, simeprevir, or sofosbuvir. In embodiments of the pharmaceutical compositions, the second agent is an agent for treating cancer. In embodiments, the second agent is an anti-cancer agent. In embodiments, the second agent is a chemotherapeutic.

IV. Methods of Use

In an aspect is provided a method of treating a viral (e.g., HIV, Zika virus, Ebola virus, hepatitis virus (e.g., hepatitis A, hepatitis B, or hepatitis C)) infection in a subject in need thereof, the method including administering to the subject an effective amount of a compound (e.g., as described herein), or a pharmaceutically acceptable salt thereof. In embodiments, the method includes a decrease of the severity or frequency of the symptoms of a viral infection, or elimination of the symptoms of a viral infection (e.g., compared to control). In embodiments, the method includes reducing the level of virions (e.g., compared to control). In embodiments, the method includes decreasing the level of viable virus genomes (e.g., by introducing mutations) (e.g., compared to control). In embodiments, the viral infection is associated with an RNA virus.

In an aspect is provided a method of treating HIV infection in a subject in need thereof, the method including administering to the subject an effective amount of a compound (e.g., as described herein), or a pharmaceutically acceptable salt thereof. In embodiments, the method includes a decrease of the severity or frequency of the symptoms of an HIV infection, or elimination of the symptoms of an HIV infection (e.g., compared to control). In embodiments, the HIV is HIV-1.

In an aspect is provided a method of treating a hepatitis (e.g., hepatitis A, hepatitis B, or hepatitis C) infection in a subject in need thereof, the method including administering to the subject an effective amount of a compound (e.g., as described herein), or a pharmaceutically acceptable salt thereof. In embodiments, the method includes a decrease of the severity or frequency of the symptoms of a hepatitis (e.g., hepatitis A, hepatitis B, or hepatitis C) infection, or elimination of the symptoms of a hepatitis (e.g., hepatitis A, hepatitis B, or hepatitis C) infection (e.g., compared to control). In embodiments, the hepatitis infection is a hepatitis A infection. In embodiments, the hepatitis infection is a hepatitis B infection. In embodiments, the hepatitis infection is a hepatitis C infection.

In an aspect is provided a method of treating Zika virus infection in a subject in need thereof, the method including administering to the subject an effective amount of a compound (e.g., as described herein), or a pharmaceutically acceptable salt thereof. In embodiments, the method includes a decrease of the severity or frequency of the symptoms of a Zika virus infection, or elimination of the symptoms of a Zika virus infection (e.g., compared to control). In embodiments, the compound is IMC-58 (4bx), IMC-38 (6bx), or IMC-60 (5bx). In embodiments, the compound has the formula:

independently hydrogen or unsubstituted $C_1$-$C_4$ alkoxy (e.g., unsubstituted methoxy); $R^2$ is —C(O)O(unsubstituted $C_1$-$C_4$). In embodiments, $R^{1.2}$ is hydrogen; $R^{1.3}$, $R^{1.4}$, and $R^{1.5}$ are each independently hydrogen or halogen-substituted $C_1$-$C_4$ alkoxy (e.g., —OCF$_3$, —OCH$_2$F, or —OCHF$_2$); $R^2$ is —C(O)O(unsubstituted $C_1$-$C_4$). In embodiments, $R^{1.2}$ is hydrogen; $R^{1.3}$, $R^{1.4}$, and $R^{1.5}$ are each independently hydrogen or halogen-substituted or unsubstituted $C_1$-$C_3$ alkoxy (e.g., —OCH$_3$, —OCF$_3$, —OCH$_2$F, or —OCHF$_2$); $R^2$ is —C(O)O(unsubstituted $C_1$-$C_2$).

In an aspect is provided a method of treating Ebola virus infection in a subject in need thereof, the method including administering to the subject an effective amount of a compound (e.g., as described herein), or a pharmaceutically acceptable salt thereof. In embodiments, the method includes a decrease of the severity or frequency of the symptoms of an Ebola virus infection, or elimination of the symptoms of an Ebola virus infection (e.g., compared to control). In embodiments, the compound is IMC-58 (4bx) or IMC-68 (5ay). In embodiments, the compound has the formula:

wherein $R^2$ is as described herein. In embodiments, the compound has the formula:

$R^2$ is as described herein, including in embodiments. $R^{1.2}$, $R^{1.3}$, $R^{1.4}$, and $R^{1.5}$ are each independently an $R^1$ substituent as described herein (e.g., in an embodiment). In embodiments, $R^{1.2}$ is hydrogen; $R^{1.3}$, $R^{1.4}$, and $R^{1.5}$ are each wherein $R^2$, Z, and z2 are as described herein. In embodiments, the compound has the formula:

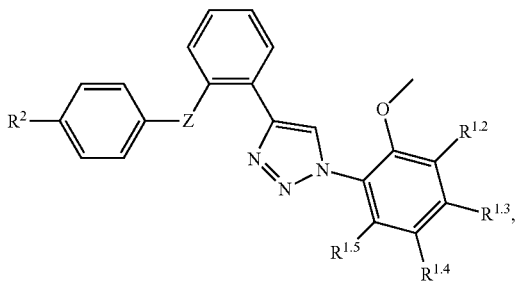

wherein $R^2$, Z, and z2 are as described herein, including in embodiments. $R^{1.2}$, $R^{1.3}$, $R^{1.4}$, and $R^{1.5}$ are each independently an $R^1$ substituent as described herein (e.g., in an embodiment). In embodiments, $R^{1.2}$ and $R^{1.5}$ are hydrogen; $R^{1.3}$ and $R^{1.4}$ are each independently hydrogen or unsubstituted $C_1$-$C_4$ alkoxy (e.g., unsubstituted methoxy); $R^2$ is —C(O)O(unsubstituted $C_1$-$C_4$) or —NO$_2$. In embodiments, $R^{1.2}$ and $R^{1.5}$ are hydrogen; $R^{1.3}$ and $R^{1.4}$ are each independently hydrogen or halogen-substituted $C_1$-$C_4$ alkoxy (e.g., —OCF$_3$, —OCH$_2$F, or —OCHF$_2$); $R^2$ is —C(O)O(unsubstituted $C_1$-$C_4$) or —NO$_2$. In embodiments, $R^{1.2}$ and $R^{1.5}$ are hydrogen; $R^{1.3}$ and $R^{1.4}$ are each independently hydrogen or halogen-substituted or unsubstituted $C_1$-$C_3$ alkoxy (e.g., —OCH$_3$, —OCF$_3$, —OCH$_2$F, or —OCHF$_2$); $R^2$ is —C(O)O(unsubstituted $C_1$-$C_2$) or —NO$_2$.

In another aspect is provided a method of treating cancer in a subject in need thereof, the method including administering to the subject an effective amount of a compound (e.g., as described herein), or a pharmaceutically acceptable salt thereof. In embodiments, the method includes a decrease of the severity or frequency of the symptoms of a cancer, or elimination of the symptoms of a cancer (e.g., compared to control).

In embodiments, the method includes administering a second agent (e.g. therapeutic agent). In embodiments, the method includes administering a second agent (e.g. therapeutic agent) in a therapeutically effective amount. In embodiments, the second agent is an anti-infectious disease agent. In embodiments, the second agent is an anti-viral agent. In embodiments, the second agent is an anti-HIV agent. In embodiments, the anti-viral agent is an HIV reverse transcriptase inhibitor, HIV protease inhibitor, HIV integrase inhibitor, HIV fusion inhibitor, or HIV entry inhibitor. In embodiments, the second agent is abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat. In embodiments, the second agent is a combination of two or more anti-HIV agents (e.g., a combination of two or more of abacavir, didanosine, emtricitabine, lamivudine, stavudine, tenofovir disoproxil fumarate, zidovudine, efavirenze, etravirine, nevirapine, rilpivirine, atazanavir, darunavir, fosamprenavir, indinavir, nelfinavir, ritonavir, saquinavir, tipranavir, enfuvirtide, maraviroc, dolutegravir, elvitegravir, raltegravir, or cobicistat). In embodiments, the method includes administering a second and third agent (e.g. therapeutic agents). In embodiments, the method includes administering a second, third, and fourth agent (e.g. therapeutic agents). In embodiments, the method includes administering a second, third, fourth, and fifth agent (e.g. therapeutic agents). In embodiments, the method includes administering a second, third, fourth, fifth, and sixth agent (e.g. therapeutic agents). In embodiments, the second agent is an agent for treating a Ebola virus infection. In embodiments, the second agent is an agent for treating a Zika virus infection. In embodiments, the second agent is an agent for treating a hepatitis (e.g., hepatitis A, hepatitis B, or hepatitis C) infection. In embodiments, the second agent is adefovir, dipivoxil, entecavir, interferon, lamivudine, peginterferon, telbivudine, tenofovir, ribavirin, boceprevir, teleprevir, simeprevir, or sofosbuvir.

In an aspect is provided a method of inhibiting (e.g., compared to control) Vif protein activity in a subject in need thereof, the method including administering an effective amount of a compound (e.g., as described herein), or a pharmaceutically acceptable salt thereof, to the subject.

In an aspect is provided a method of reducing (e.g., compared to control) the level of Vif protein in a subject in need thereof, the method including administering an effective amount of a compound (e.g., as described herein), or a pharmaceutically acceptable salt thereof, to the subject.

In an aspect is provided a method of increasing (e.g., compared to control) the level of an APOBEC3 family protein (e.g., a plurality of different APOBEC3 family protein members, a member of the APOBEC3 protein family) activity in a subject in need thereof, the method including administering an effective amount of a compound (e.g., as described herein), or a pharmaceutically acceptable salt thereof, to the subject. In embodiments, the method includes reducing the association of an APOBEC3 protein with a degradation complex (e.g., as described herein) (e.g., compared to control). In embodiments, the method includes reducing the association of an APOBEC3 protein with a degradation complex component (e.g., as described herein).

In an aspect is provided a method of increasing (e.g., compared to control) the level of an APOBEC3 family protein (e.g., a plurality of different APOBEC3 family protein members, a member of the APOBEC3 protein family) in a subject in need thereof, the method including administering an effective amount of a compound (e.g., as described herein), or a pharmaceutically acceptable salt thereof, to the subject. In embodiments, the method includes reducing the association of an APOBEC3 protein with a degradation complex (e.g., as described herein) (e.g., compared to control). In embodiments, the method includes reducing the association of an APOBEC3 protein with a degradation complex component (e.g., as described herein).

In an aspect is provided a method of inhibiting degradation (e.g., compared to control) of an APOBEC3 family protein (e.g., a plurality of different APOBEC3 family protein members, a member of the APOBEC3 protein family) in a subject in need thereof, the method including administering an effective amount of a compound (e.g., as described herein), or a pharmaceutically acceptable salt thereof, to the subject. In embodiments, the method includes reducing (e.g., compared to control) the association of an APOBEC3 protein with a degradation complex component (e.g., as described herein).

In an aspect is provided a method of increasing (e.g., compared to control) the level of APOBEC3G activity in a subject in need thereof, the method including administering an effective amount of a compound (e.g., as described herein), or a pharmaceutically acceptable salt thereof, to the subject. In embodiments, the method includes reducing the association of APOBEC3G protein with a degradation complex (e.g., as described herein) (e.g., compared to control).

In embodiments, the method includes reducing (e.g., as described herein) the association of an APOBEC3 protein with a degradation complex component.

In an aspect is provided a method of increasing (e.g., as described herein) the level of APOBEC3G protein in a subject in need thereof, the method including administering an effective amount of a compound (e.g., as described herein), or a pharmaceutically acceptable salt thereof, to the subject. In embodiments, the method includes reducing the association of APOBEC3G protein with a degradation complex (e.g., as described herein) (e.g., compared to control). In embodiments, the method includes reducing (e.g., as described herein) the association of an APOBEC3 protein with a degradation complex component (e.g., as described herein).

In an aspect is provided a method of inhibiting degradation (e.g., as described herein) of APOBEC3G protein in a subject in need thereof, the method including administering an effective amount of a compound (e.g., as described herein), or a pharmaceutically acceptable salt thereof, to the subject. In embodiments, the method includes reducing the association of APOBEC3G protein with a degradation complex (e.g., as described herein) (e.g., compared to control). In embodiments, the method includes reducing (e.g., as described herein) the association of an APOBEC3 protein with a degradation complex component (e.g., as described herein).

In an aspect is provided a method of inhibiting (e.g., as described herein) a degradation complex (e.g., as described herein) activity in a subject in need thereof, the method including administering an effective amount of a compound (e.g., as described herein), or a pharmaceutically acceptable salt thereof, to the subject. In an aspect is provided a method of inhibiting (e.g., as described herein) a degradation complex component (e.g., as described herein) activity in a subject in need thereof, the method including administering an effective amount of a compound (e.g., as described herein), or a pharmaceutically acceptable salt thereof, to the subject.

In embodiments, the modulation (e.g., inhibition, reduction, increase, or activation) of a variable (e.g., of a level of activity, level of protein, disease, or symptom) is in comparison to a control. In embodiments, the control is an equivalent subject or experiment not being administered an effective amount (e.g., not being administered any amount) of a compound (e.g., as described herein). In embodiments, the control is an average amount (e.g., level of activity, level of protein, disease, or symptom) of a plurality of subjects (e.g., similar subjects or equivalent subjects to the subject being administered the compound) not being administered an effective amount (e.g., not being administered any amount) of the compound (e.g., as described herein).

In another aspect, there is provided a method for inhibiting Vif protein activity in a subject in need thereof. The method includes administering an effective amount of a compound of Formula (I) to the subject (e.g. a compound described herein).

In another aspect, there is provided a method for treating a viral infection. The method includes administering to a subject in need thereof a therapeutically effective amount of a compound according to Formula (I), and embodiments thereof.

In embodiments, the viral infection is HIV-1 Ebola virus or Zika virus infection, as known in the art. In embodiments, the viral infection is HIV-1 virus. In embodiments, the viral infection is Ebola virus. In embodiments, the viral infection is Zika virus.

EXAMPLES

Example 1. Vif Antagonists Rescue HIV-1 Host Restriction by Disrupting HSP90-APOBEC3G Interactions in the Vif-Proteasomal Complex The HIV-1 accessory protein Vif, which is essential for viral replication, counteracts the host defense by targeting APOBEC3G restriction factor for polyubiquitination and proteasomal degradation. The RN-18-based class of small molecule Vif antagonists reduce viral infectivity by restoring antiviral restriction. Here, by using a chemical biology strategy, we identified the heat shock protein HSP90, which acts as a molecular chaperone for diverse client proteins, as a unique target for this class of compounds. We demonstrate that HSP90 interacts directly with APOBEC3G and is a component of the Vif-APOBEC3G-Cul5-CBF-β E3 ubiquitin ligase complex. Direct interaction of Vif antagonists to HSP90 disrupted E3 ligase complex assembly by removing APOBEC3G from the complex, thereby preventing proteasomal degradation of APOBEC3G while enhancing the ubiquitination and degradation of Vif. Thus, disrupting the interaction between HSP90 and APOBEC3G in E3-ligase complex represents a new strategy to develop antiviral therapeutics targeting Vif function.

To combat viral infections, mammalian cells express several classes of proteins, termed restriction factors, that directly inhibit virus replication[1-3]. The human APOBEC3 cytidine deaminases are restrictions factors for a variety of retroviruses, including human immunodeficiency virus type 1 (HIV-1)[4-8]. The HIV-1 accessory protein Viral infectivity factor, Vif, which is essential for viral replication, counteracts the host defense by interacting with an E3 ubiquitin ligase complex composed of cullin5, elongin B, elongin C, CBF-β, and a RING-box protein, and targeting APOBEC3G (A3G) for polyubiquitination and degradation[9-16]. Small molecule Vif antagonists that disrupt the complex restore antiviral restriction, but the mechanisms by which this occurs remain unclear[17-19]. The RN-18-based class of small molecule Vif antagonists reduce viral infectivity by enhancing APOBEC3G-dependent Vif degradation, increasing APOBEC3G incorporation into virions, and enhancing cytidine deamination of the viral genome[17-19]. Here, we identified the cellular target and mechanism of action of RN-18-based Vif antagonists. Using a chemical biology strategy coupled with affinity purification-mass spectrometry, we isolated cellular proteins that interacted with RN-18 analogs and identified the heat shock protein HSP90, which acts as a molecular chaperone for diverse client proteins, as a unique target for this class of compounds. Our results show that HSP90 directly binds A3G and assembles into a Vif-A3G-Cul5-CBF-β E3 ubiquitin ligase complex. Vif antagonists targets non-catalytic region of HSP90 and disrupted Vif-E3 ligase complex assembly by removing A3G from the complex. Consequently, Vif inhibitors prevented proteasomal degradation of A3G while enhancing the polyubiquitination and degradation of Vif. These studies highlight the power of chemical biology strategies to identify drug targets in living cells and provide evidence that interfering with HSP90 and A3G binding in the Vif-A3G-E3 ligase complex may lead to the development of new AIDS therapies.

Identification of Cellular Target of Vif Antagonists.

Figure 1B:
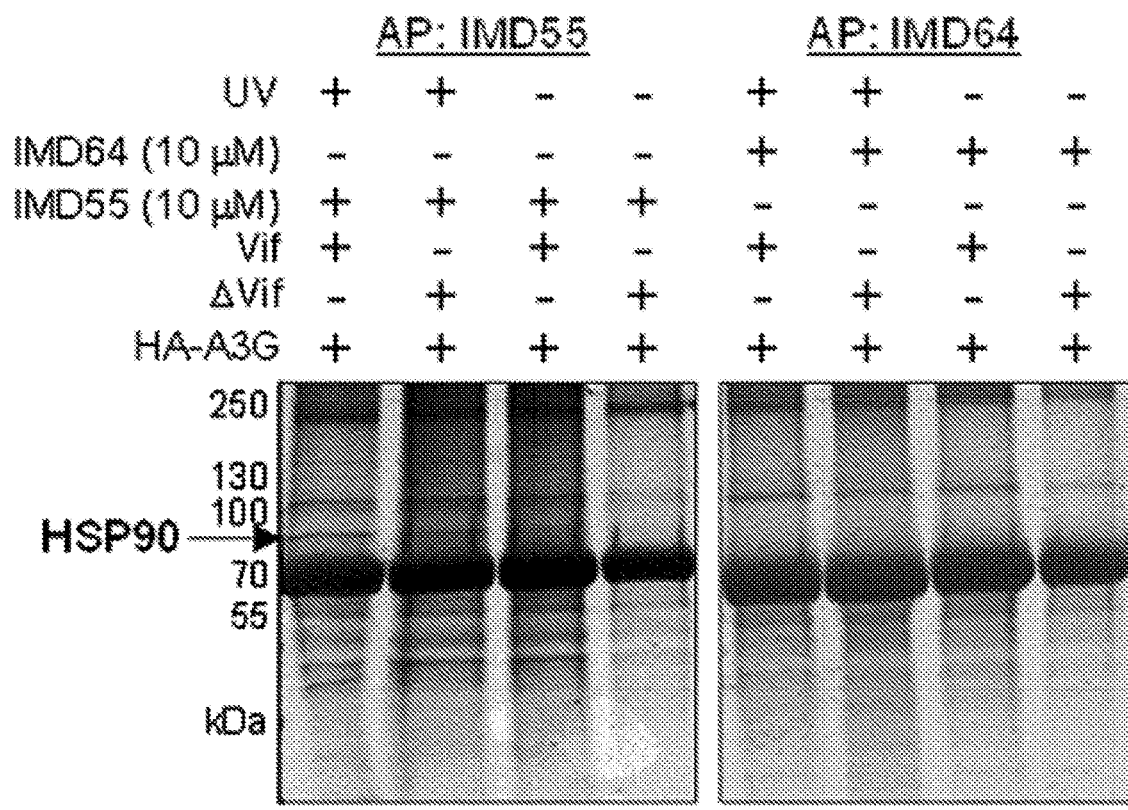
Figure 1C:
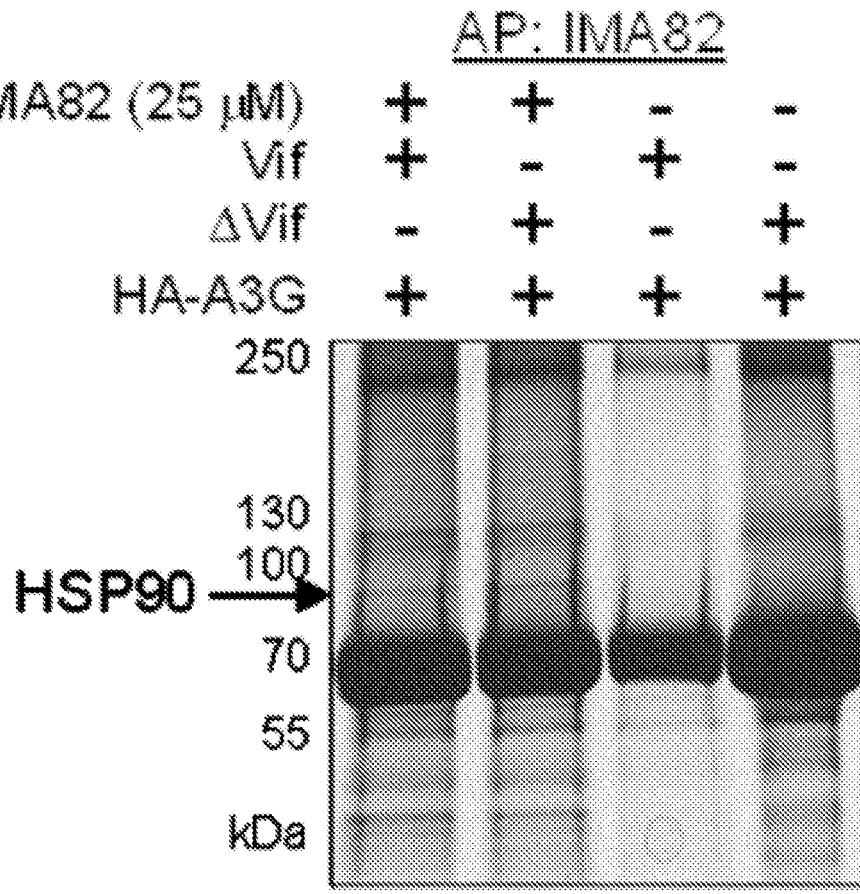
Figure 1D:
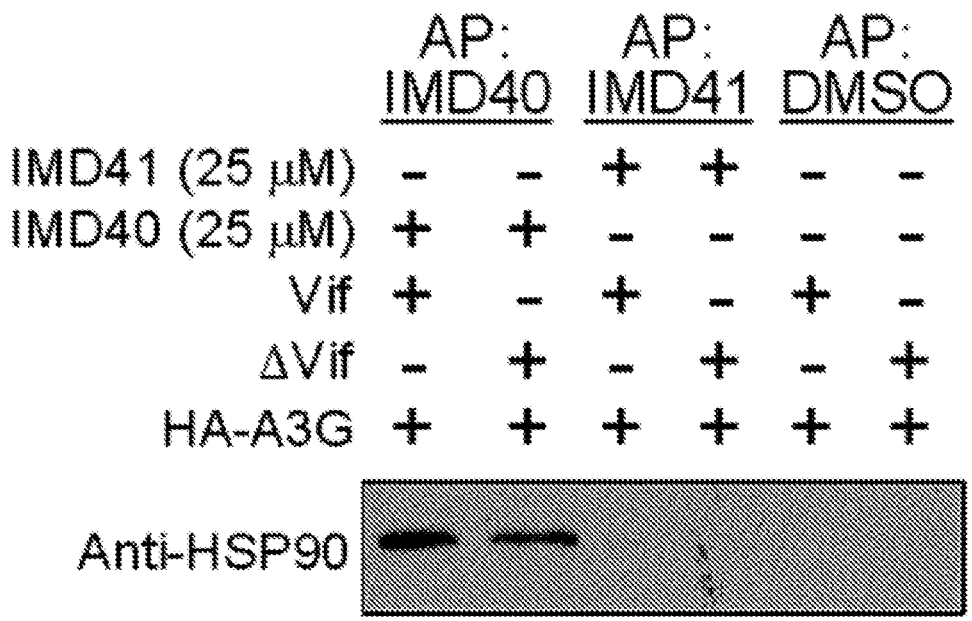
Figure 8A:
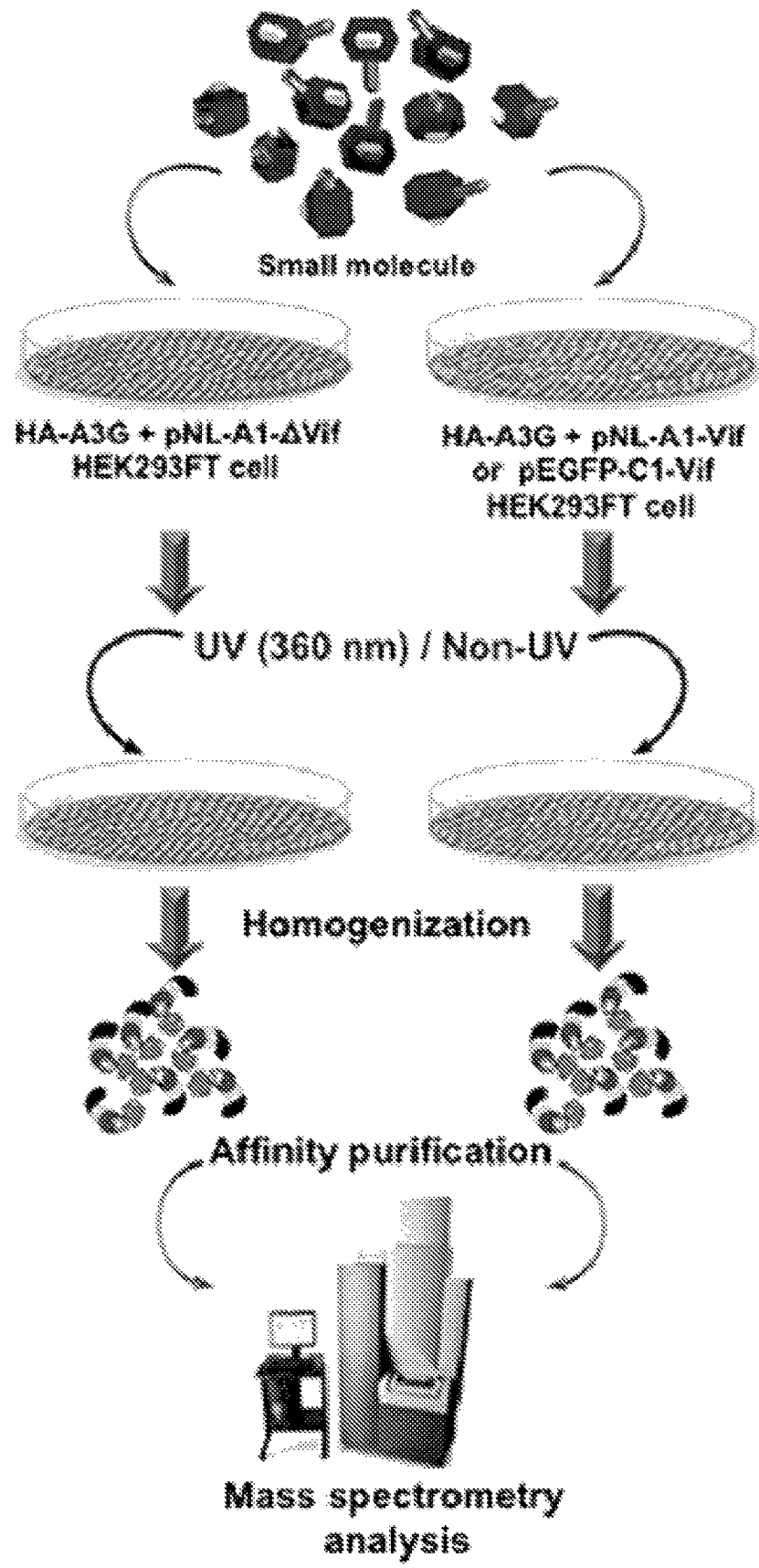
FIG. 8A-8C. ViTAP: Vif inhibitor Target Affinity Purification.
Figure 8B:
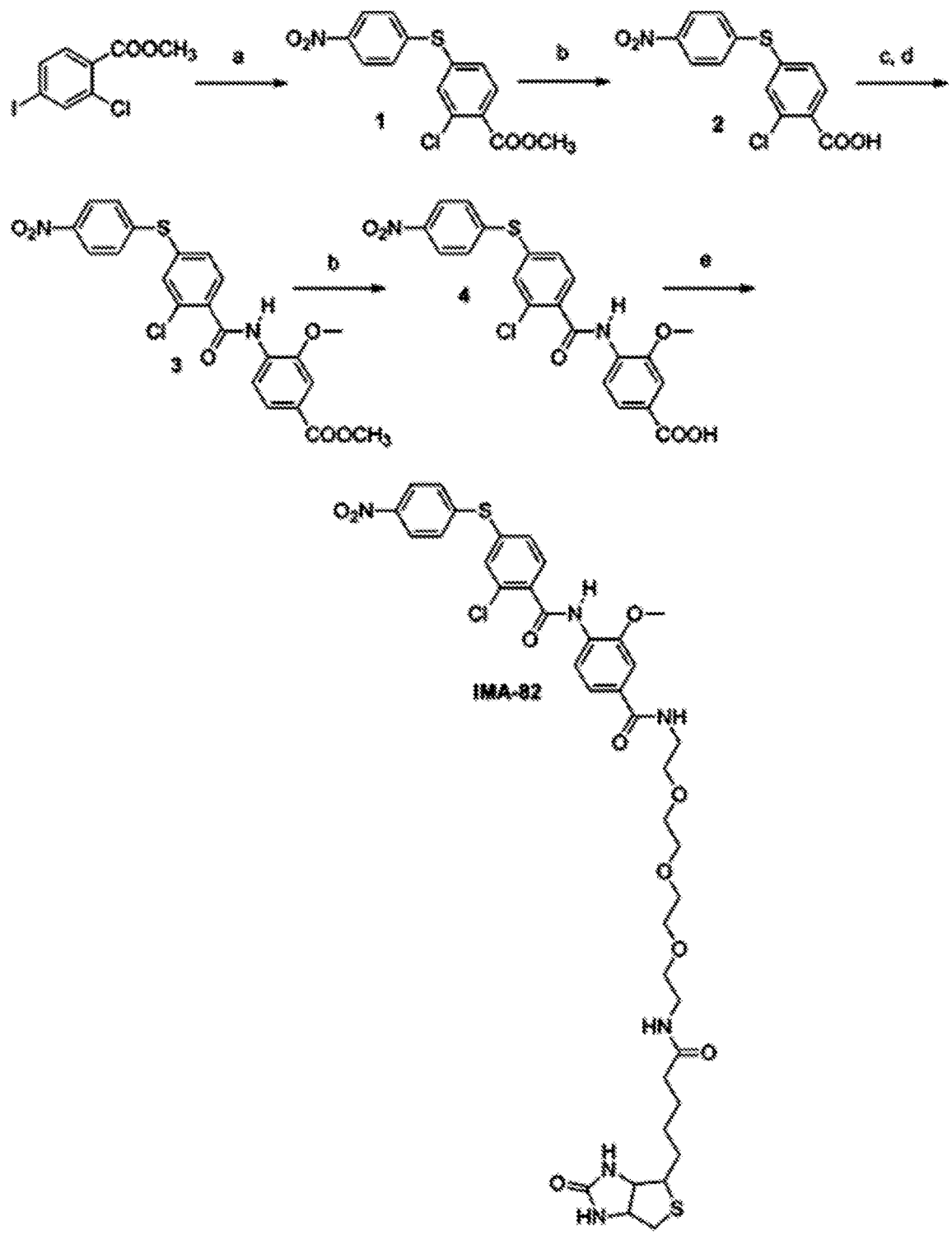
Figure 8C:
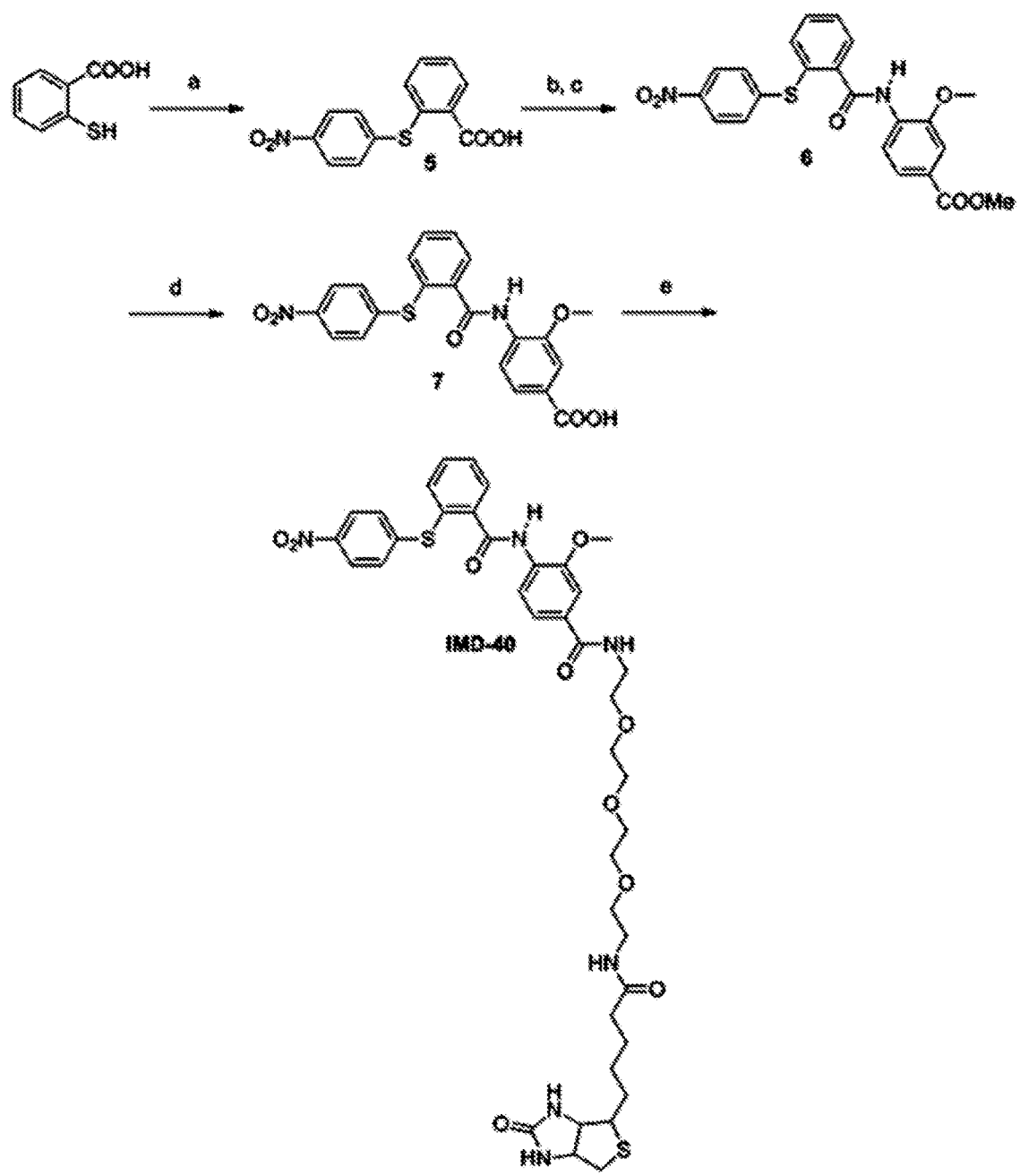
Figure 9A:
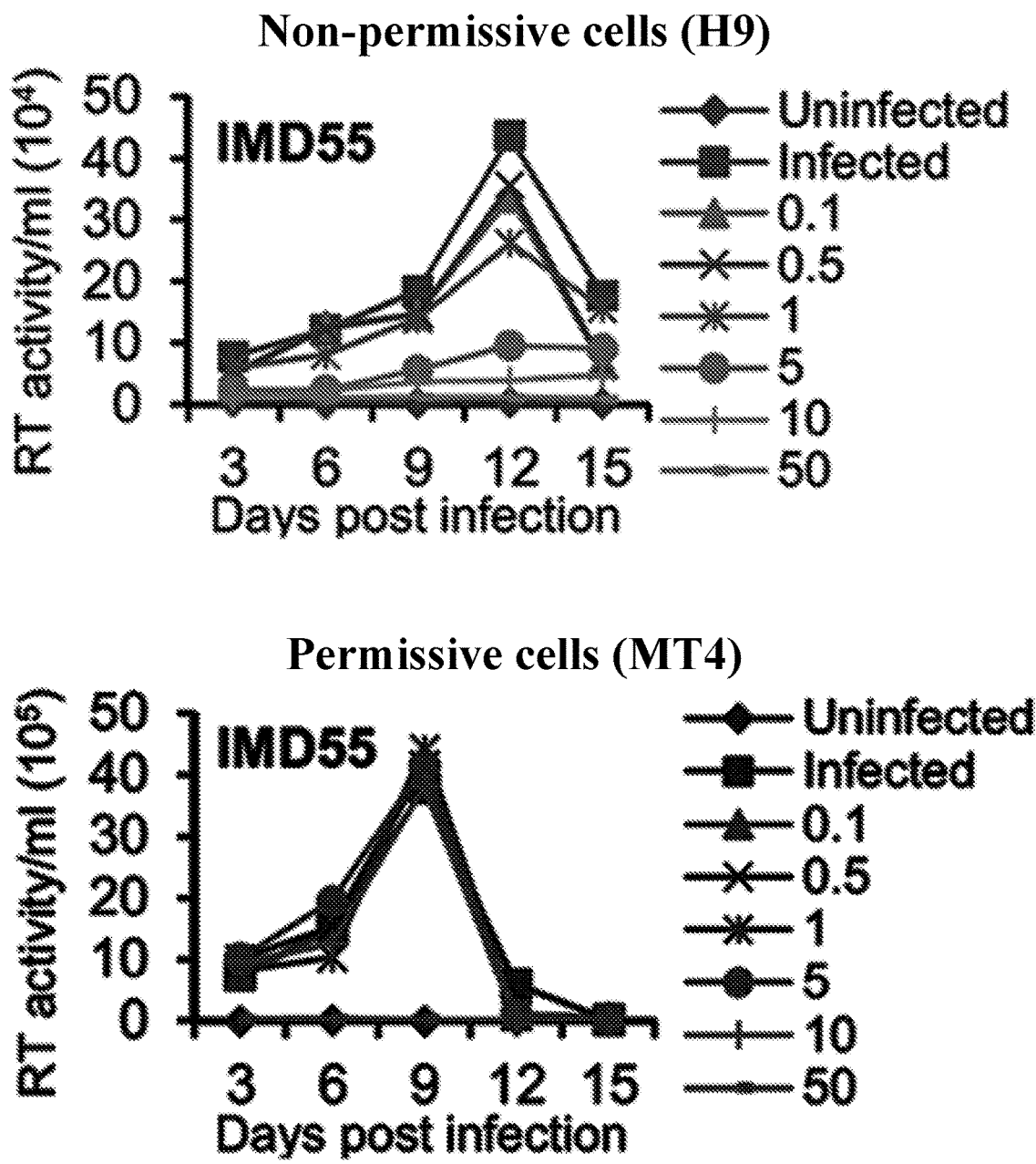
FIGS. 9A-9E. Vif antagonists inhibit HIV-1 replication in non-permissive but not permissive host cells. Non-permissive (H9) and permissive (MT4) cells were exposed to the indicated concentrations of IMD55 (FIG. 9A), IMD64 (FIG. 9B), IMA82 (FIG. 9C), IMD40 (FIG. 9I)), or IMD41 (FIG. 9E) for 16 h and then infected with wild-type HIV-$1_{LAI}$ ($2 \times 10^5$ C.P.M.). Cells were cultured with the indicated concentrations of compounds for 15 days. Every 3 days, the culture supernatants were collected and analyzed for reverse transcriptase activity. Uninfected cells or infected cells treated with 1% DMSO served as controls.
Figure 9B:
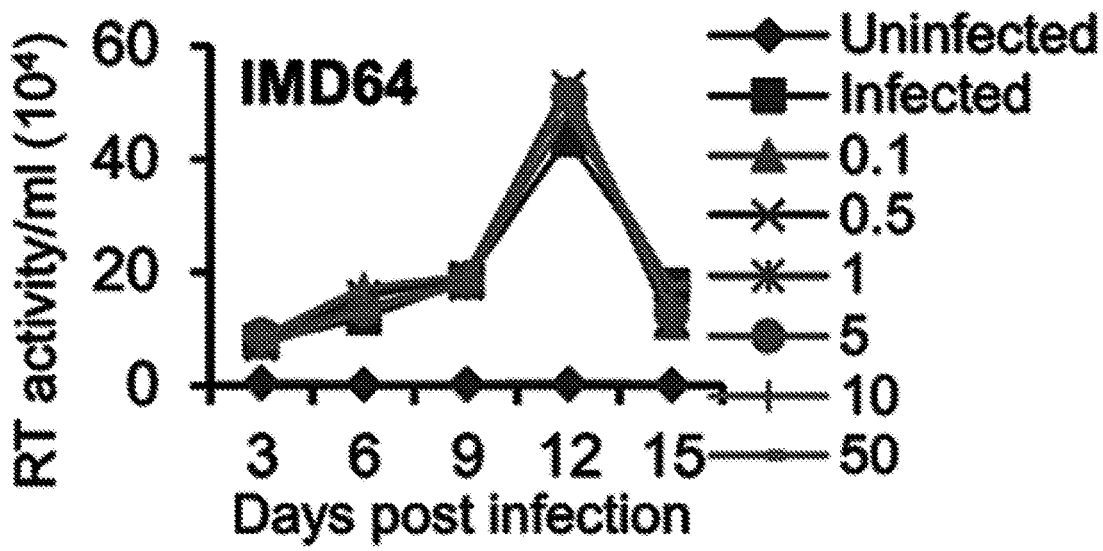
Figure 9B:
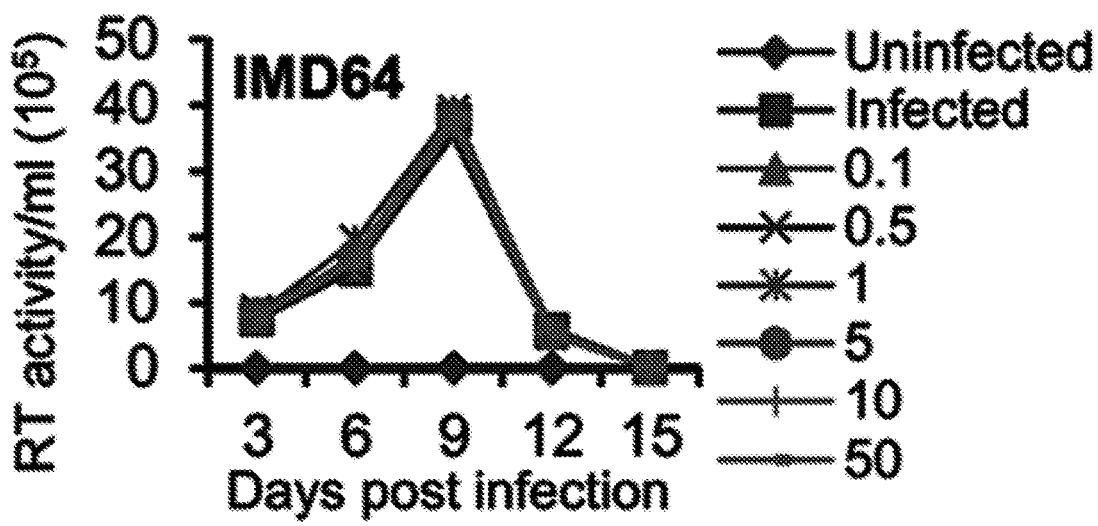
Figure 9C:
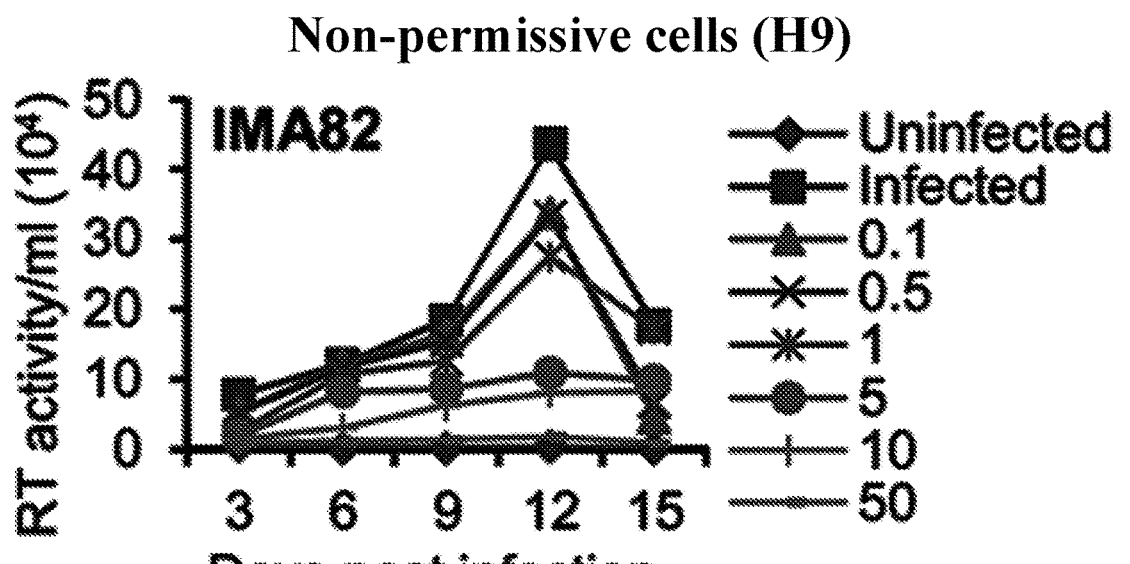
Figure 9C:
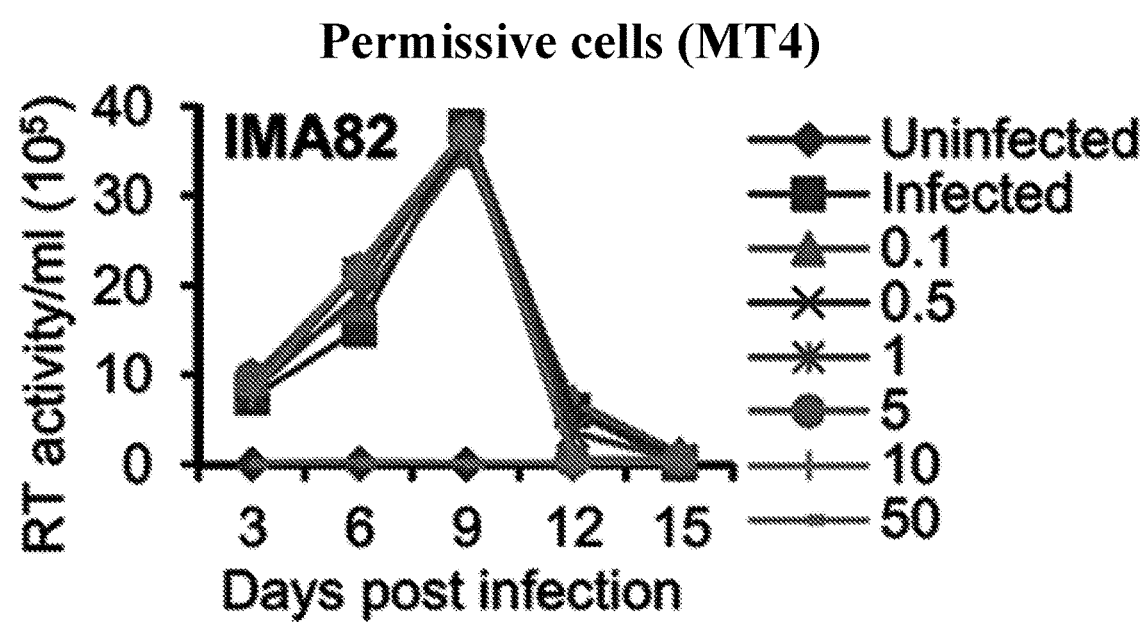
Figure 9D:
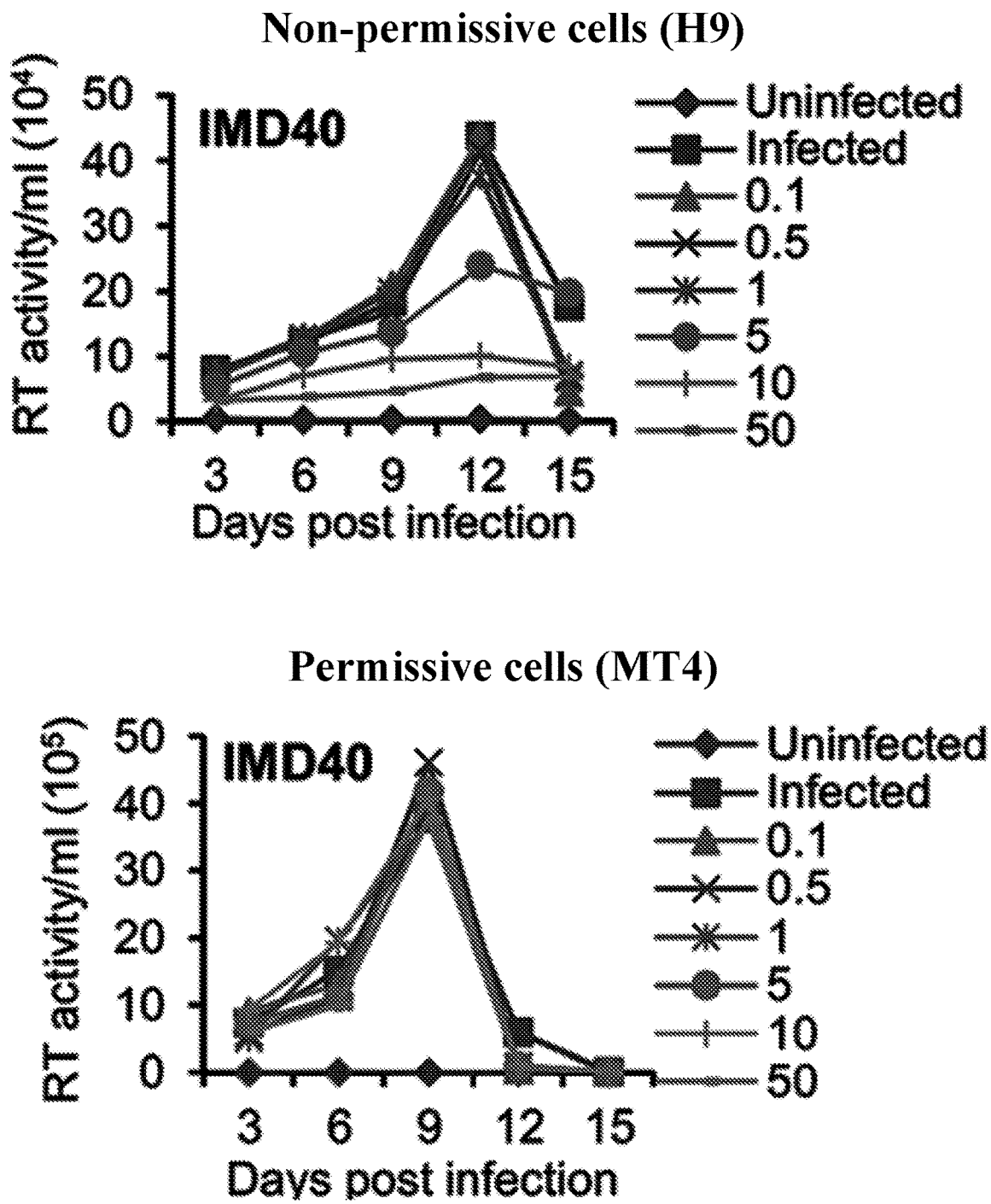
Figure 9E:
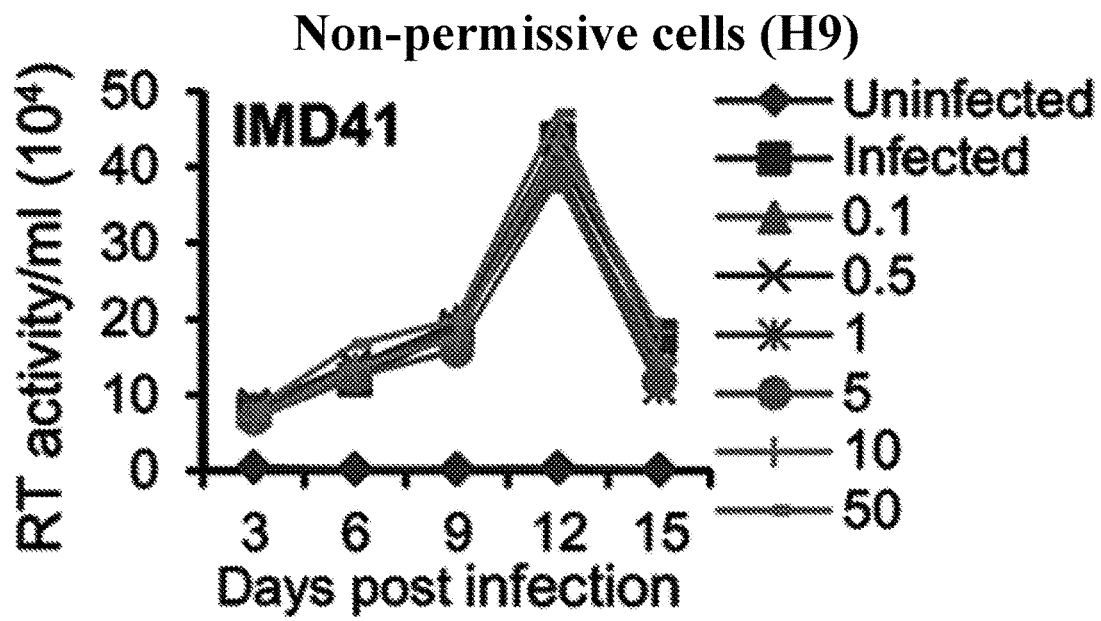
Figure 9E:
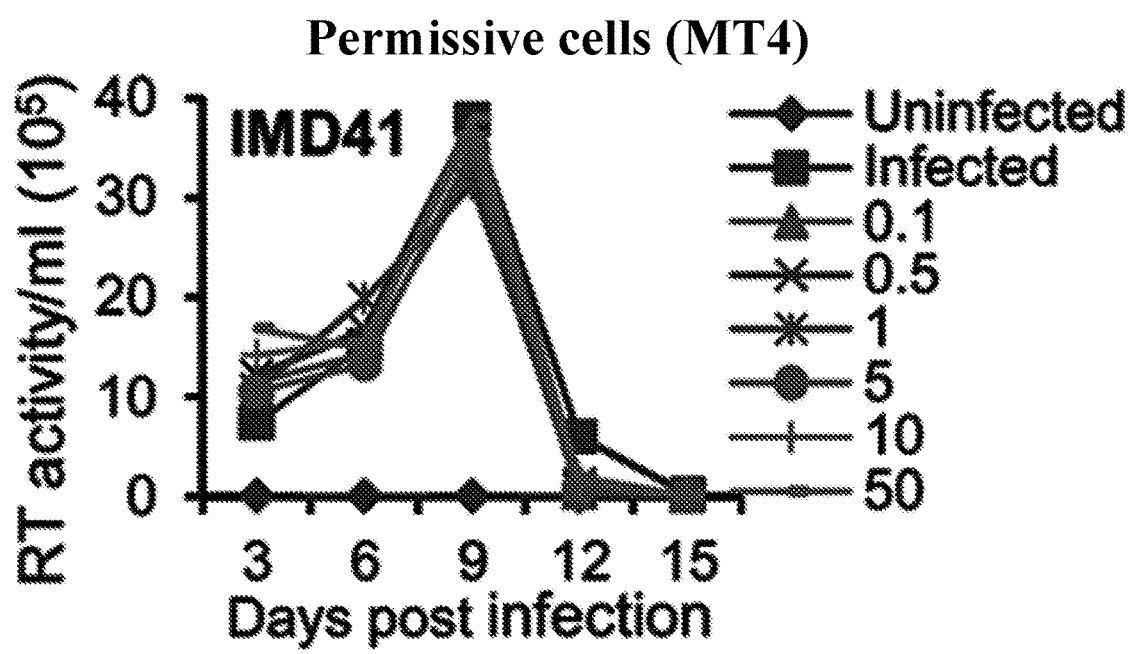

To identify the cellular target(s) of the RN-18-based Vif antagonists and to understand the mechanism of action of this new class of HIV-1 inhibitors, we devised a chemical biology strategy termed ViTAP (Vif inhibitor Target Affinity Purification; FIG. 8A) in which proteins interacting with the antagonists are affinity purified and identified by mass spectrometry (MS). We designed an RN-18 analog containing a photoactivatable —$N_3$ group to enable UV crosslinking of bound proteins, and a biotin group to allow streptavidin-mediated purification of the compound-protein complexes (IMD55, FIG. 1A). Previous large-scale structure-activity relationship studies of RN-18 indicated that the modified sites would not affect the Vif-antagonistic properties of the compounds[17-19]. To ensure specificity, a negative control analog was synthesized that contained the —$N_3$ group and biotin moiety but lacked the critical 3-ring structure of RN-18 required for activity (IMD64, FIG. 1A). To isolate IMD55-interacting proteins, we transfected 293FT cells with vectors encoding hemagglutinin (HA)-conjugated APOBEC3G (HA-A3G) and either pNLA1-Vif or pNLA1-ΔVif, respectively. Cells were treated with IMD55, IMD64, or DMSO vehicle and exposed to UV irradiation to induce crosslinking of compound-associated proteins. Following affinity purification with streptavidin beads, proteins were resolved by SDS-PAGE and visualized by silver staining (FIGS. 1B and 8A). An~90 kDa protein was found to specifically co-purify with IMD55, but not with IMD64, in both 293FT-A3G-Vif and 293FT-A3G-ΔVif cells, establishing that IMD55 binding to the protein did not require Vif Although UV irradiation increased the recovery of the IMD55-bound 90 kDa protein, it was not essential for co-purification, suggesting that the affinity of the intermolecular interaction was high and did not require covalent conjugation of the compound. As expected, the 90 kDa protein did not associate with the control compound IMD64 under any conditions (FIG. 1B). Mass Spectrometry (MS) analysis of the isolated 90 kDa protein revealed it to be the heat shock protein HSP90, a molecular chaperone that plays an important role in protein folding and degradation[20]. To confirm the specificity and affinity of the HSP90-Vif antagonist association, we synthesized further biotinylated analogs but omitted the photo-crosslinking —$N_3$ group. Compounds IMA82 (FIGS. 1A, 1C) and IMD40 (FIGS. 1A, 1D) also purified a specific 90 kDa protein from transfected 293FT cells, which was confirmed to be HSP90 by MS and immunoblotting, respectively. HSP90 did not co-purify with the negative control compound IMD41 under any conditions (FIG. 1D).

Vif Antagonists Inhibit Viral Replication by Restoring A3G Levels and Degrading Vif.

We confirmed that the analogs retained the antiviral activity of the parent compound RN-18 by examining their effect on HIV-1 replication in H9 (non-permissive) and MT4 (permissive) CD4+ T cell lines. Vif is essential for HIV-1 replication in A3G-expressing H9 cells but not in A3G-deficient MT4 cells. H9 and MT4 cells were infected with HIV-1$_{LAI}$ and incubated with up to 50 μM of the analogs for 15 days. Viral replication was monitored by periodically measuring reverse transcriptase activity in the supernatants (FIGS. 9A-9E). The functionally active analogs IMD55, IMA82, and IMD40 dose-dependently inhibited viral replication in H9 cells but not in MT4 cells (FIGS. 9A-9E), establishing that the analogs inhibited Vif-dependent HIV-1 replication, consistent with our previous observations with RN-18[17-19]. As expected, the inactive analogs IMD64 and IMD41 had no effect on viral replication in either H9 or MT4 cells. Taken together, these results indicate that the RN-18-based affinity probes specifically bind to HSP90 in a Vif-independent manner and inhibit HIV-1 replication only in non-permissive cells. Because the functional activities of IMD40, IMD55, and IMA82 were similar, further structural and functional studies were performed with IMA82.

Figure 10A:
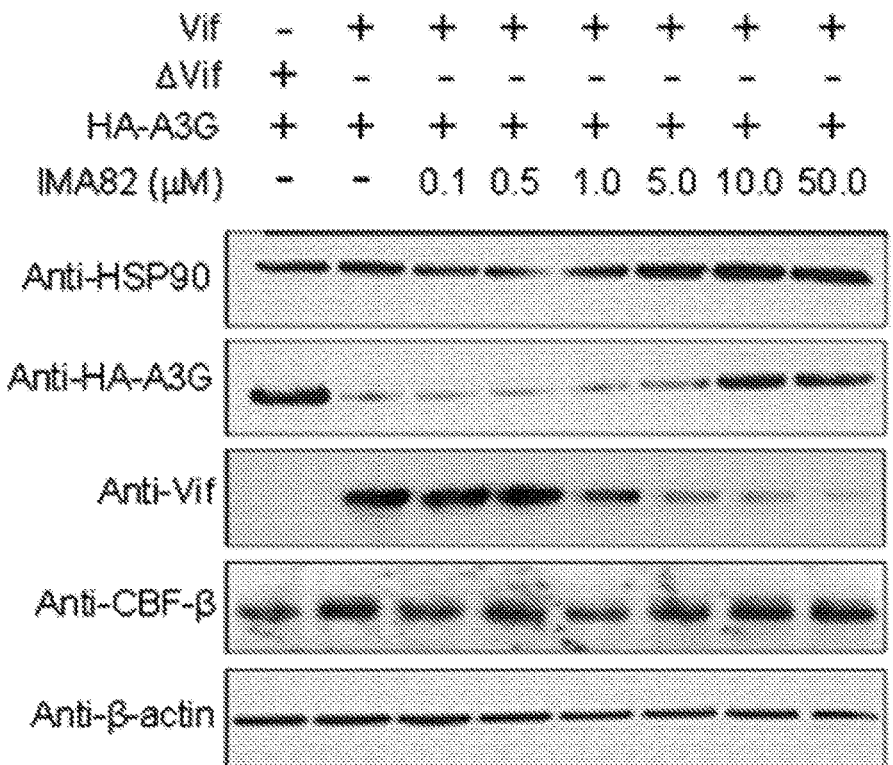
FIGS. 10A-10C. IMA82 enhances APOBEC3G expression and reduces Vif expression.
Figure 10B:
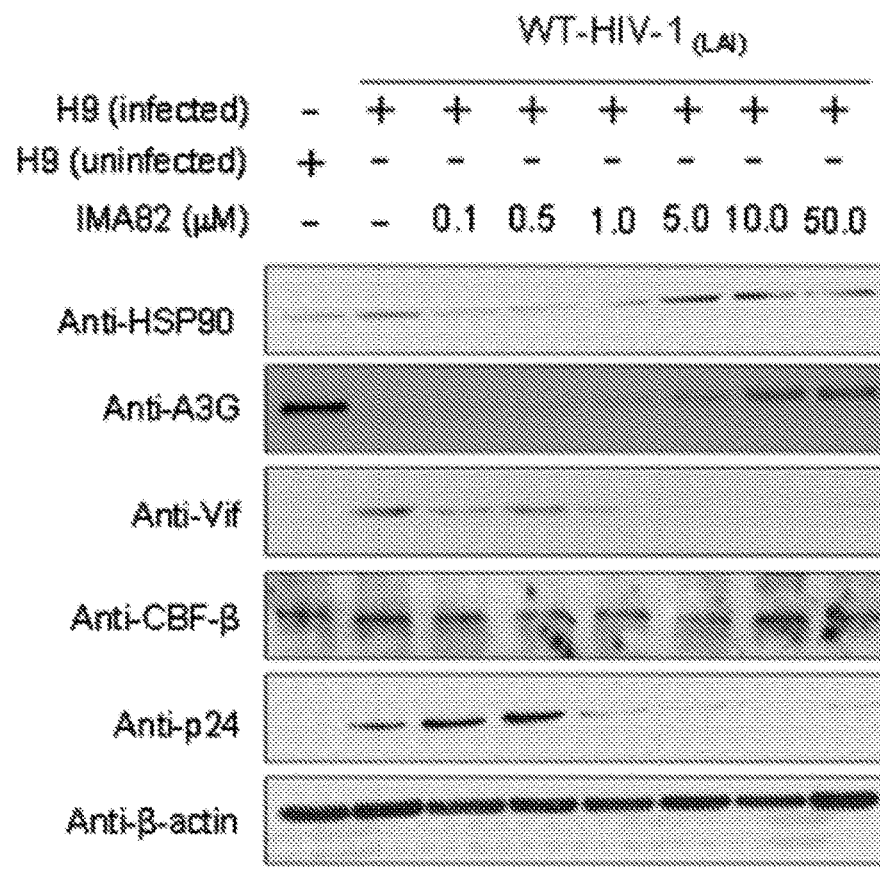
Figure 10C:
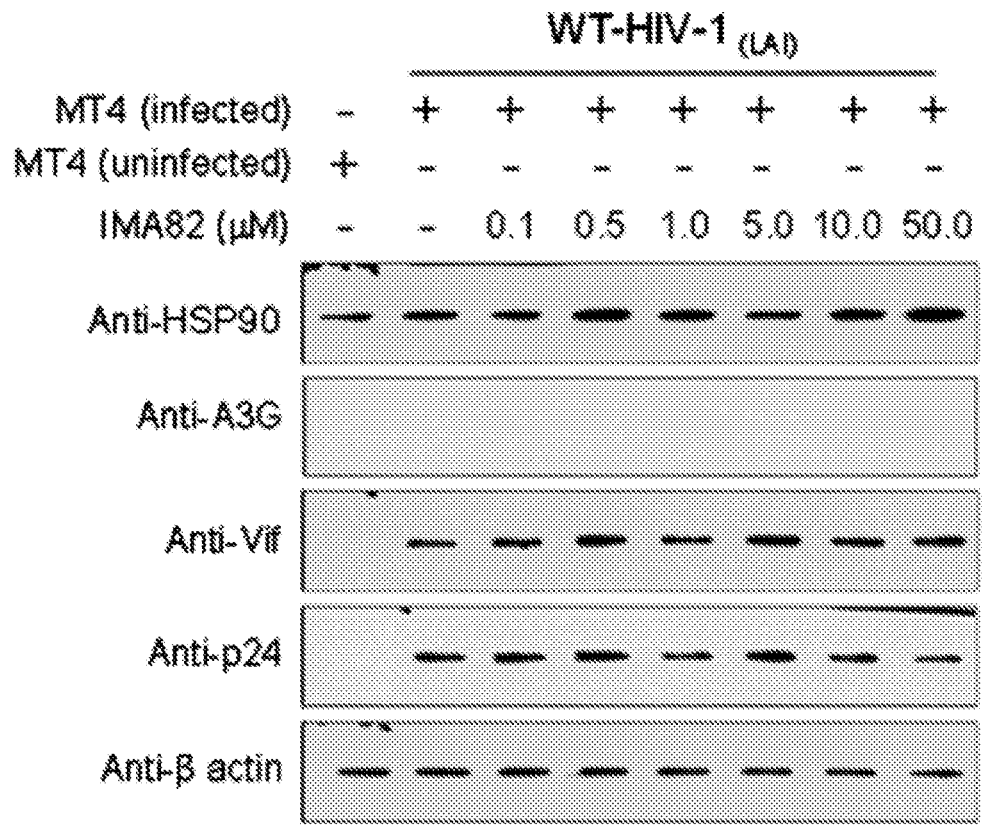

We previously showed that the RN-18-based Vif antagonists inhibit HIV-1 replication, at least in part, by attenuating Vif-dependent downregulation of A3G[19]. We therefore examined the effect of IMA82 treatment on expression of A3G, Vif, and HSP90 in transfected 293FT cells (FIG. 10A). As expected, untreated 293FT-A3G-Vif cells had markedly reduced A3G levels compared with 293FT-A3G-ΔVif cells. However, treatment with IMA82 dose-dependently restored A3G expression and concomitantly enhanced Vif degradation, an effect previously observed for RN-18[19]. IMA82 did not significantly affect expression of HSP90 protein (FIG. 10A) or mRNA (data not shown), and interestingly, had no effect on levels of CBF-β, a recently described component of the E3 ligase complex that promotes Vif activity for proteosomal degradation of A3G[21,22] (FIG. 10A). These results suggested that the IMA82-HSP90 interaction inhibits A3G degradation and promotes Vif degradation in a CBF-β-independent manner. To confirm that this occurs in IMA82-treated CD4+ T cells during active HIV-1 infection, we examined the expression of HSP90, A3G, Vif, and p24 in HIV-1$_{LAI}$-infected H9 and MT4 cells. HIV-1 p24 levels were reduced in IMA82-treated H9 cells, but not MT4 cells, confirming the antiviral efficacy of IMA82 (FIGS. 10B-10C). IMA82 treatment also restored A3G levels and decreased Vif levels, but did not affect the expression of either HSP90 or CBF-β, consistent with the observations in transfected 293FT cells (FIGS. 10A-10B).

HSP90 is Required for Vif Antagonist Function.

Figure 1E:
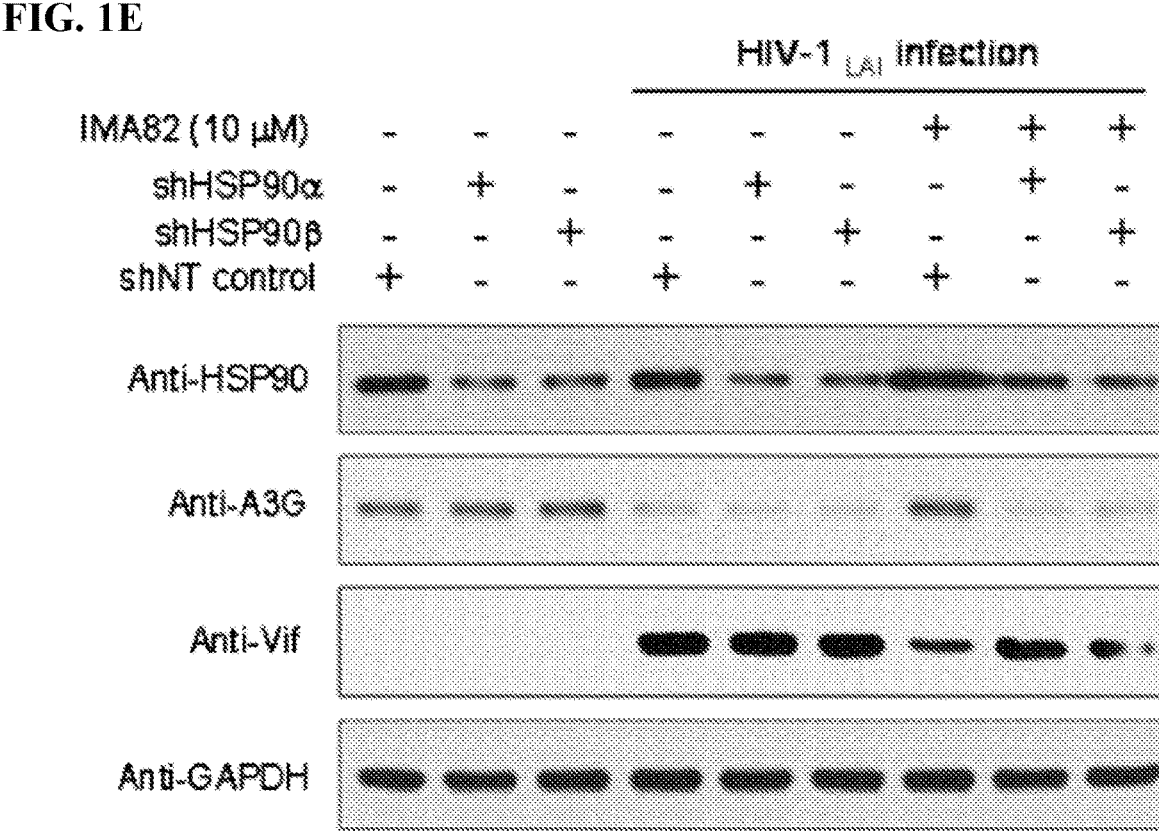
Figure 1F:
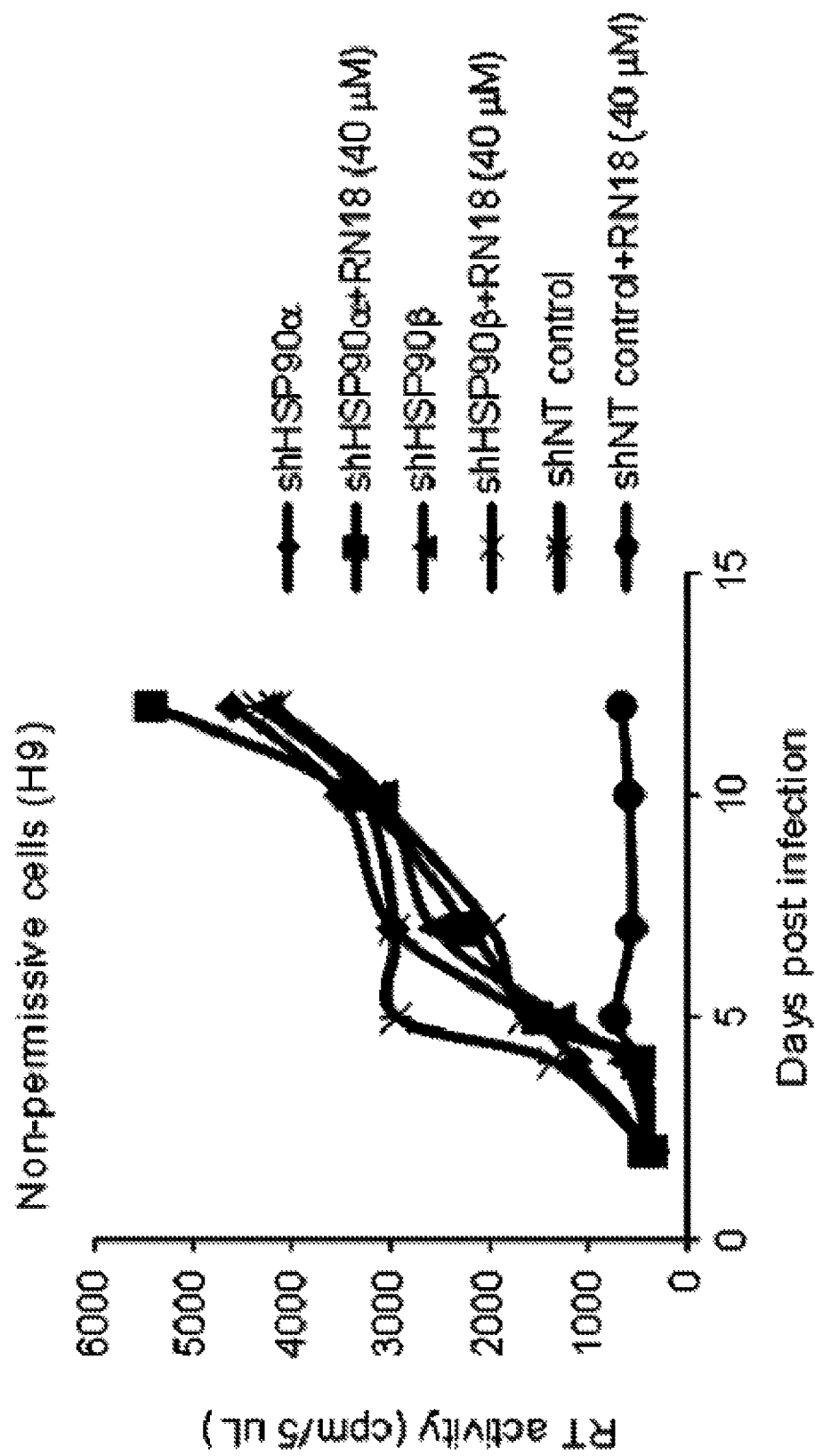
Figure 11A:
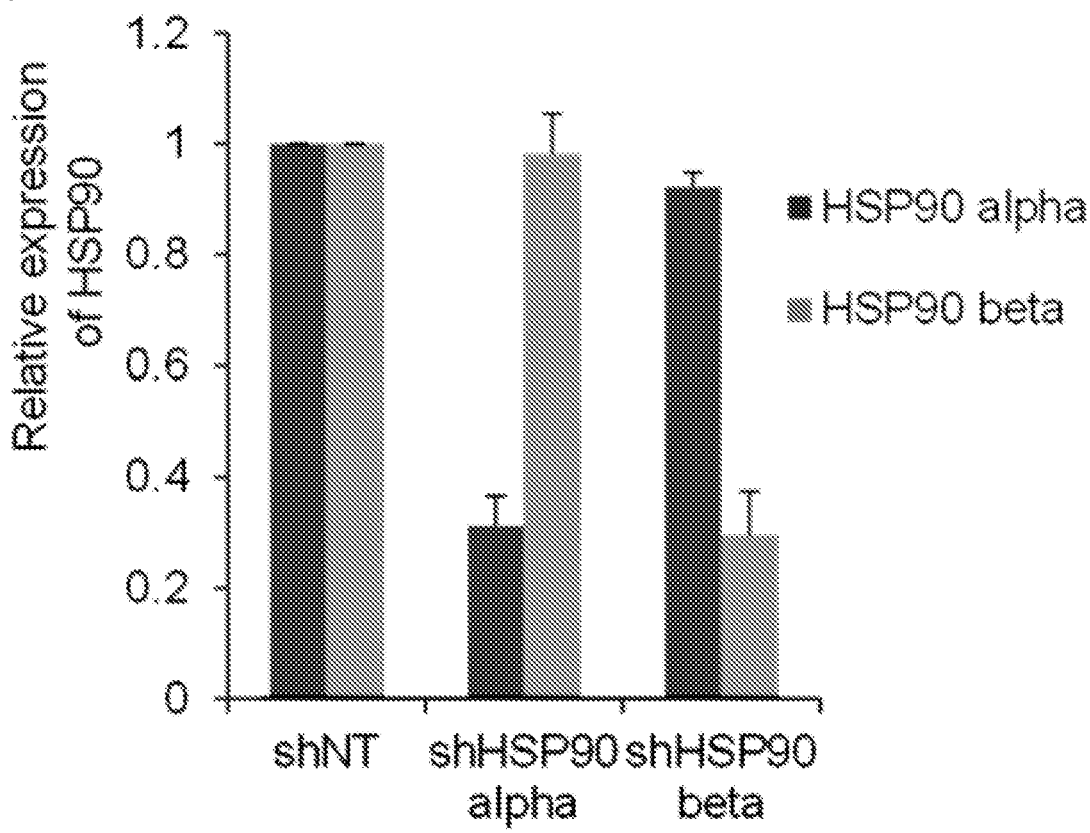
FIGS. 11A-11D. HSP90 is required for Vif antagonist activity.
Figure 11B:
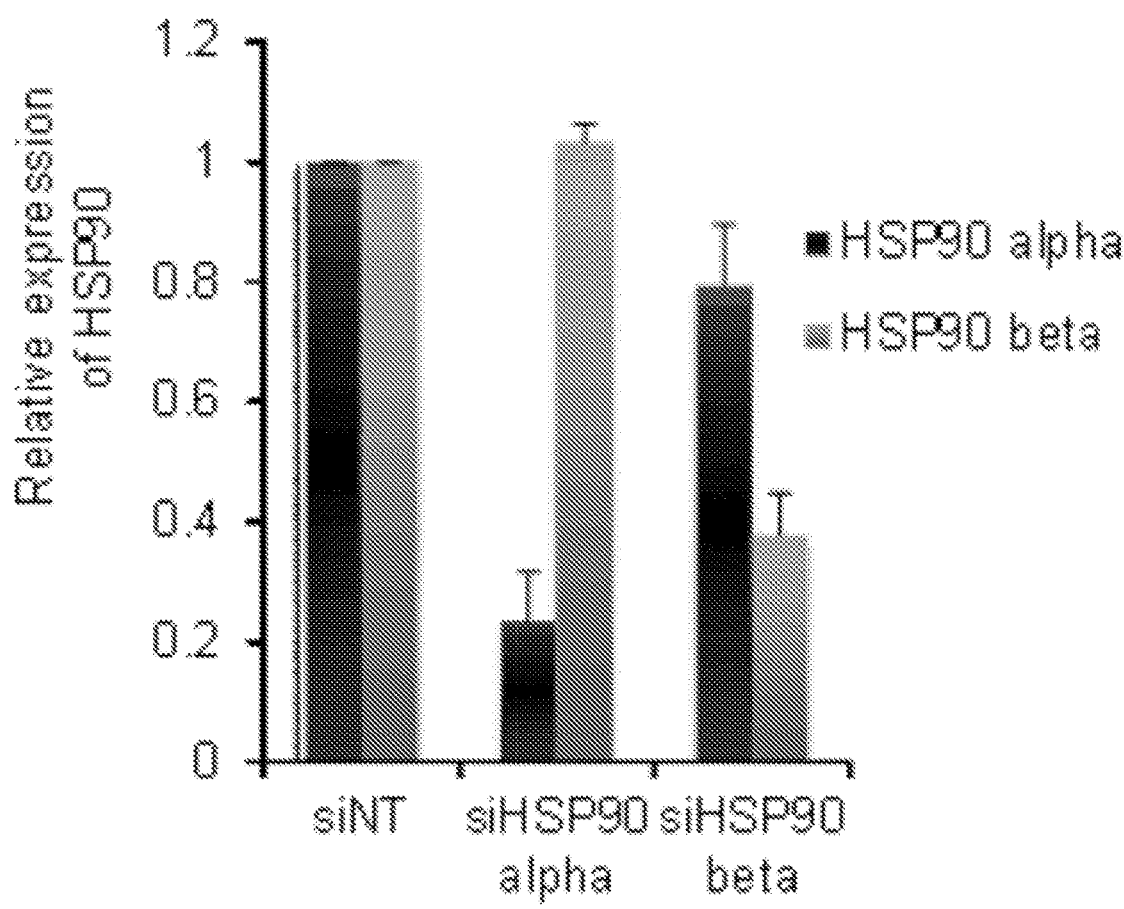
Figure 11C:
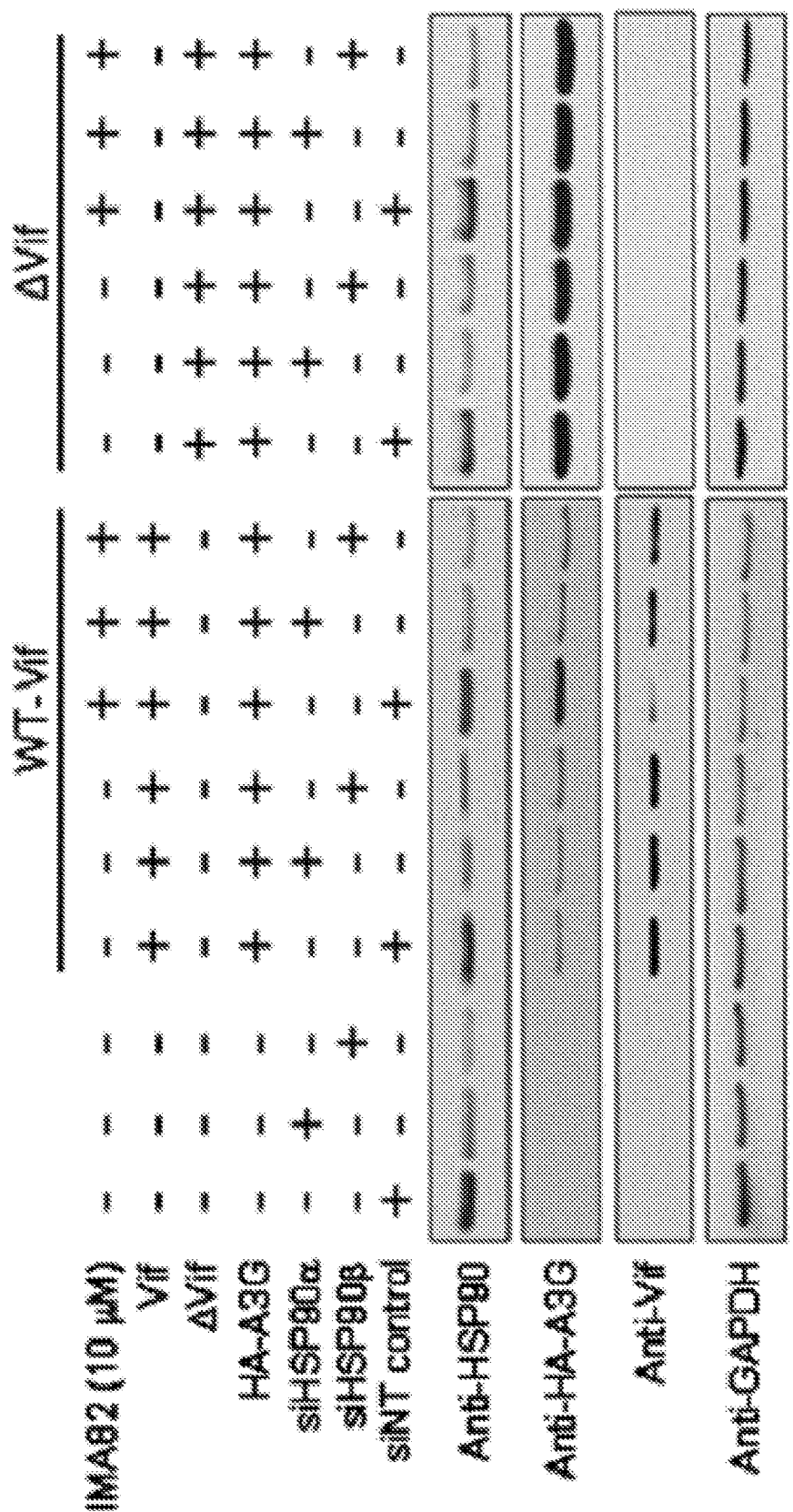
Figure 11D:
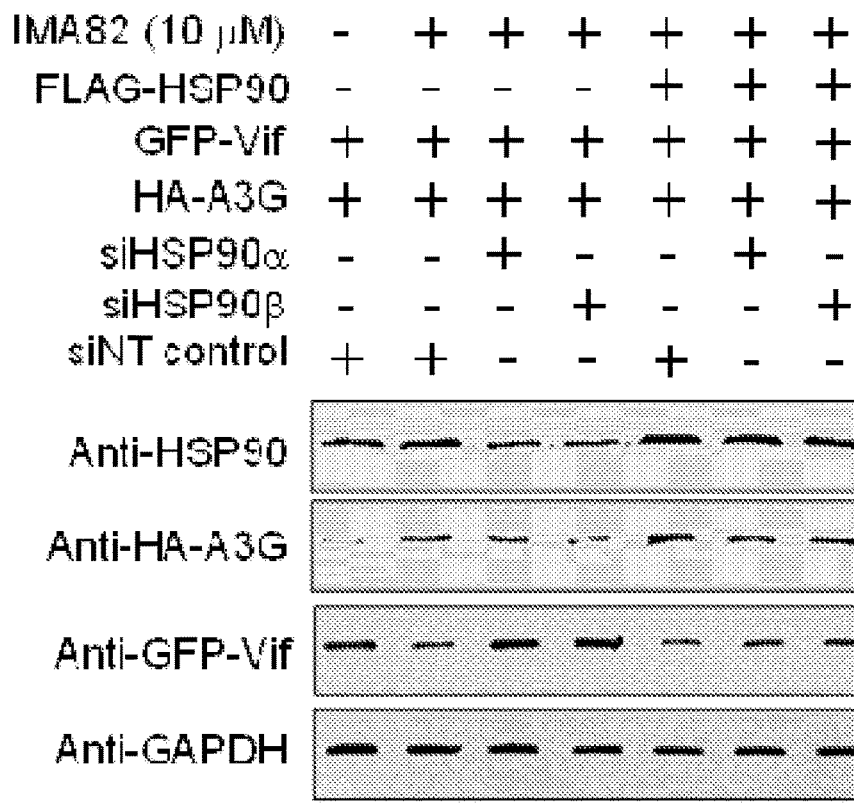

Because HSP90 levels were unaltered by IMA82 treatment, we asked whether the antiviral activity of IMA82 required HSP90. To address the essential role of HSP90 in IMA82 activity, we knockdown HSP90 expression by lentiviral transduction of HSP90α and HSP90 shRNA in H9 cells. This transduction reduced HSP90 expression by approximately 60%, as shown by western blotting (FIG. 1E) and qRT-PCR (FIG. 11A). Cells transduced with non-targeting shRNA (shNT) and HSP90 knockdown cells were then infected with HIV-1$_{LAI}$ and treated with IMA82. As expected, IMA82 treatment of control shNT-transduced cells rescued A3G from Vif-mediated proteasomal degradation and reduced Vif levels accordingly (FIG. 1E). We further silenced HSP90 expression in 293 cells with SMART poll siRNAs targeting HSP90α and HSP90β. This treatment reduced HSP90 expression by approximately 70%, as shown by immunoblotting (FIG. 1D) and qRT-PCR (FIG. 11B). Cells treated with non-targeting siRNA (siNT) and HSP90 knockdown were transfected with HA-A3G and pNLA1 Vif or GFP-Vif or pNLA1 ΔVif and incubated with IMA82. Similar result was observed as FIG. 1E. We found that IMA82 had no effect on A3G or Vif levels in HSP90 knockdown cells (FIGS. 1E, 11C), establishing that HSP90 was required for IMA82 to stabilize A3G and increase Vif turnover. The HSP90 knockdown (as described in FIG. 1E) H9 cells were grown in the presence or absence of RN-18 for 15 days and viral replication was monitored by periodically measuring reverse transcriptase activity in the supernatants (FIG. 1F). RN-18 inhibited viral replication in shNT control cells but had no effect in HSP90 knockdown cells. To further validate HSP90 mediated specific activity of RN-18, we first knockdown endogenous HSP90 and then overexpressed FLAG-HSP90 in cells to restore the protein expression. Treatment of IMA82 in these cells rescued A3G expression and downregulate Vif (FIG. 11D), indicating that HSP90 is essential for RN-18 mediated stabilization of A3G and inhibition of viral replication by downregulating Vif protein.

Vif Antagonist Stabilizes A3G and Degrades Vif by Altering Ubiquitination Specificity.

Figure 2A:
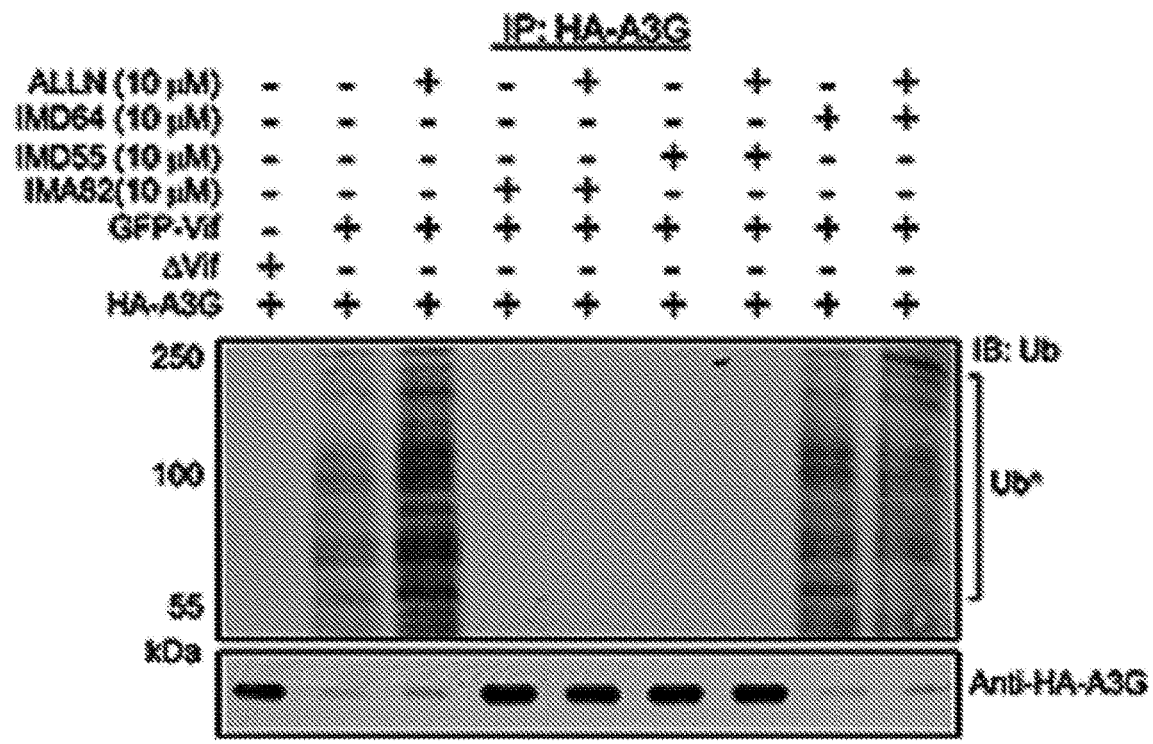
FIGS. 2A-2E. Vif antagonists inhibit Vif-mediated polyubiquitination of APOBEC3G but induce polyubiquitination and Cul5-mediated degradation of Vif.
Figure 2B:
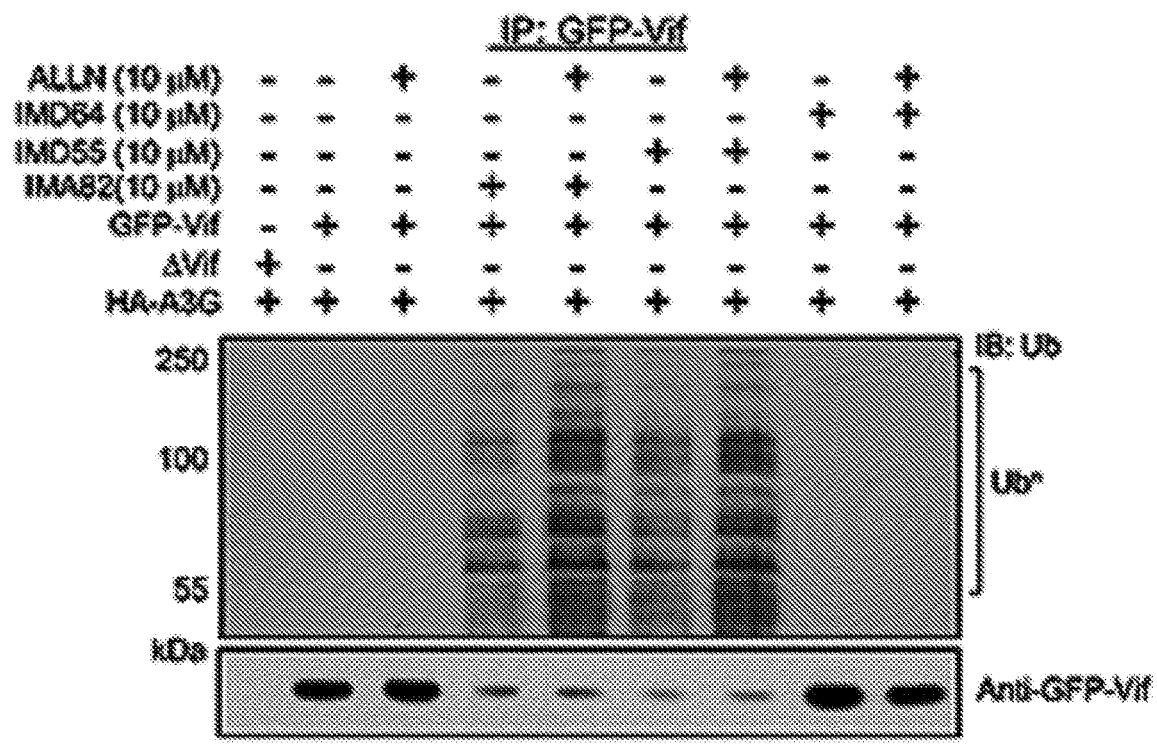

We next examined the polyubiquitination status of A3G and Vif in transfected 293FT cells exposed to the analogs. These experiments were performed in the presence of a proteasome inhibitor, ALLN, to enhance detection of ubiquitinated proteins[10]. A3G was immunoprecipitated from drug treated or untreated cells and subjected to ubiquitin-specific immunoblotting. A3G from cells treated with vehicle or the inactive analog IMD64 was found to be extensively ubiquitinated, but this was not observed in cells treated with either IMA82 or IMD55 (FIG. 2A). The pattern of Vif ubiquitination in these cells was reversed: immunoprecipitated Vif was ubiquitinated only in cells treated with the active Vif antagonists IMA82 and IMD55 (FIG. 2B). As expected, treatments that induced ubiquitination also reduced the absolute levels of A3G and Vif protein, and vice versa (FIGS. 2A,2B). Thus, the Vif antagonists restore A3G levels and reduce Vif levels by inhibiting or promoting ubiquitin-directed proteosomal degradation, respectively.

Figure 2C:
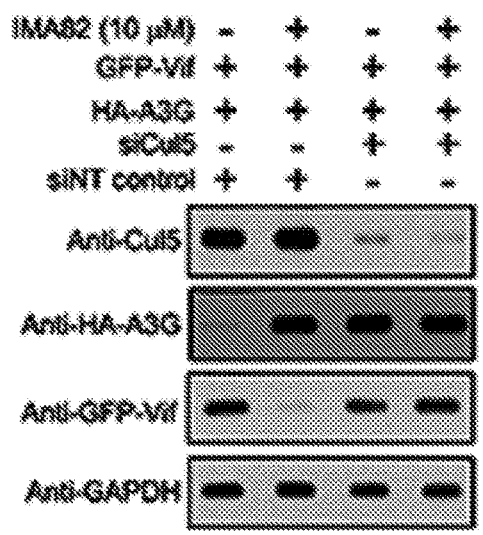
Figure 2D:
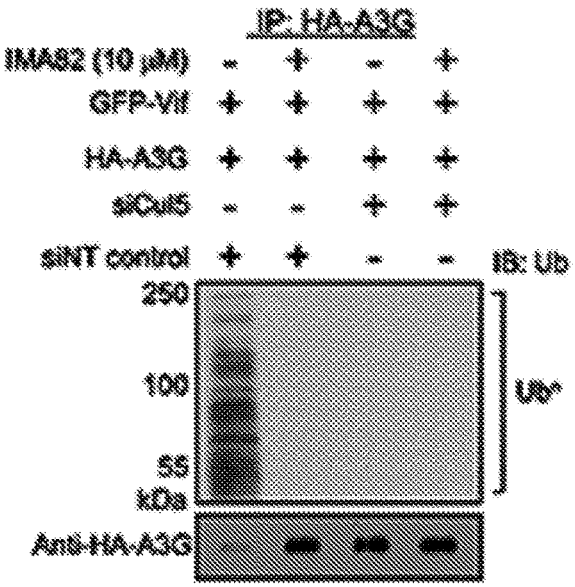
Figure 2E:
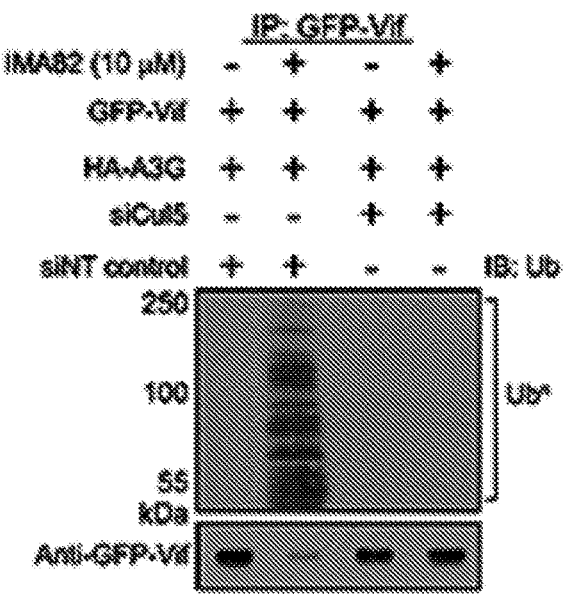

Vif protein induces proteasomal degradation of A3G by recruiting the Cul5-E3 ubiquitin ligase complex[9-15]. To determine if IMA82 modulates A3G and Vif levels through this complex, we used SMART poll siRNA to deplete Cul5 in 293FT-A3G-Vif cells and then treated the cells with vehicle or IMA82. As shown in FIG. 2C, lysates from cells treated with control siRNA (siNT) showed the expected rescue of A3G levels upon IMA82 treatment (FIG. 2C). However, A3G levels were high in Cul5-depleted cells, and IMA82 treatment had no further effect on A3G or Vif levels (FIG. 2C). To examine their ubiquitination state under these conditions, A3G and Vif were immunoprecipitated and analyzed by immunoblotting. Ubiquitination of A3G and Vif was reduced and increased, respectively, by IMA82 treatment of siNT-treated cells, but neither protein was ubiquitinated in Cul5-depleted cells (FIGS. 2D, 2E). Thus, Vif antagonists modulate A3G and Vif ubiquitination through the Cul5-E3 ligase complex.

Vif Antagonist's Interaction with HSP90 Disrupts A3G Incorporation into the E3 Ligase Complex.

Figure 3A:
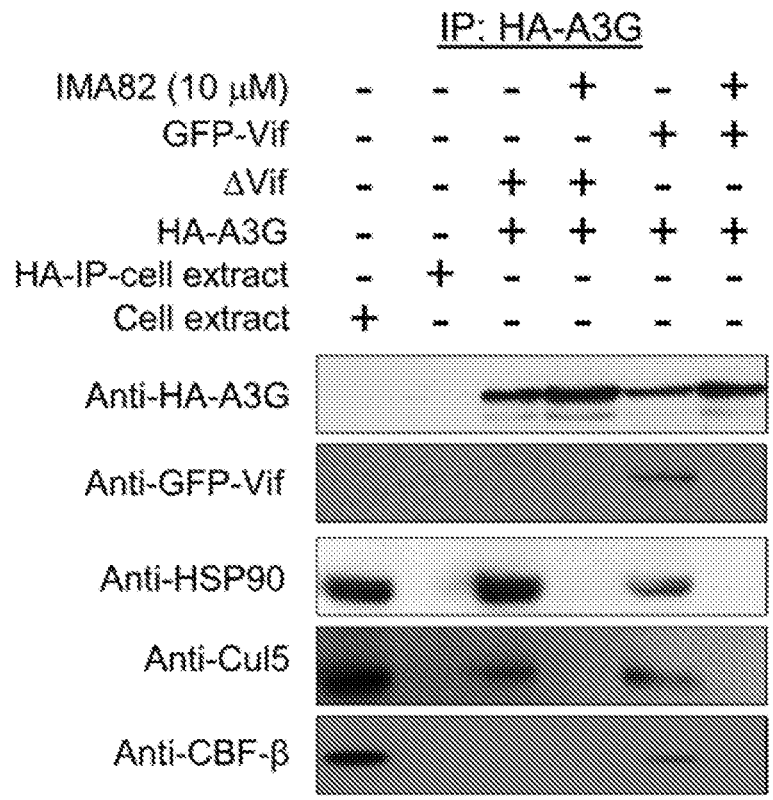
FIGS. 3A-3D. Binding of IMA82 to HSP90 prevents APOBEC3G association with the Vif-APOBEC3G-HSP90-Cul5-CBF-β complex. 293FT cells co-expressing HA-A3G and GFP-Vif or ΔVif were incubated with IMA82 or DMSO. Lysates were immunoprecipitated (IP) with antibodies to HA (A3G) (FIG. 3A), GFP (Vif) (FIG. 3B), HSP90 (FIG. 3C), and Cul5 (FIG. 3D) and immunoblotted with the indicated antibodies. Untreated cell lysates and IP of untreated cell lysates served as specificity controls for immunoblotting and IP, respectively.
Figure 3B:
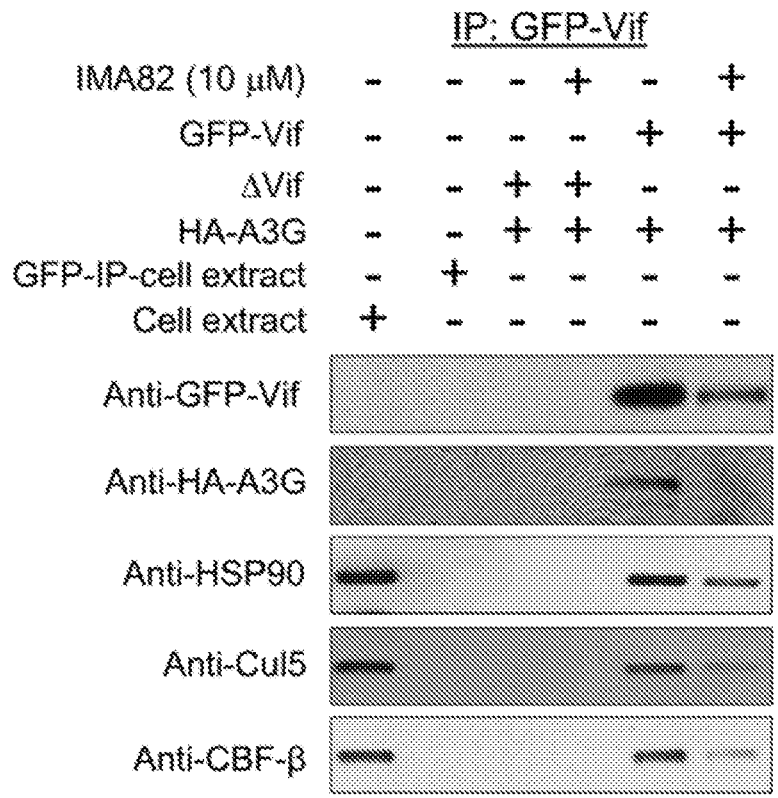
Figure 3C:
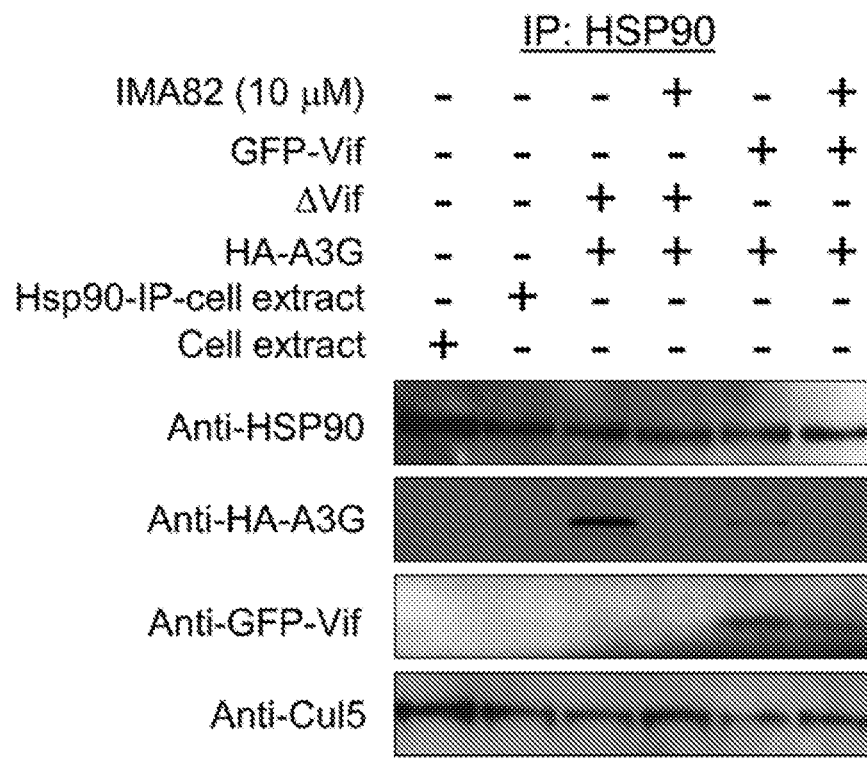
Figure 3D:
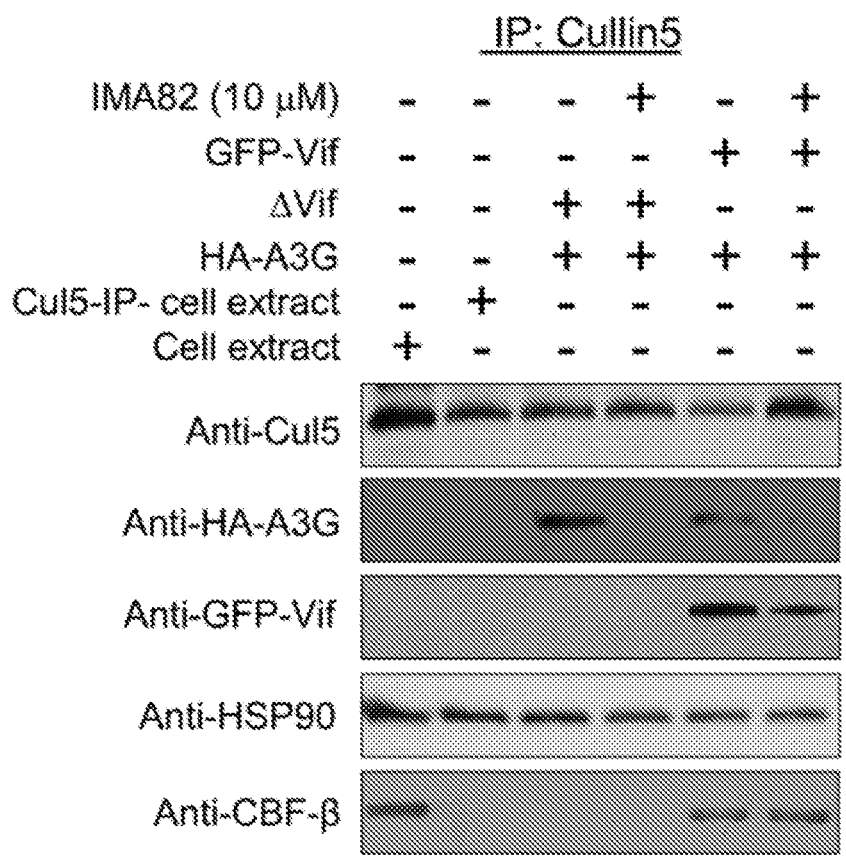
Figure 12A:
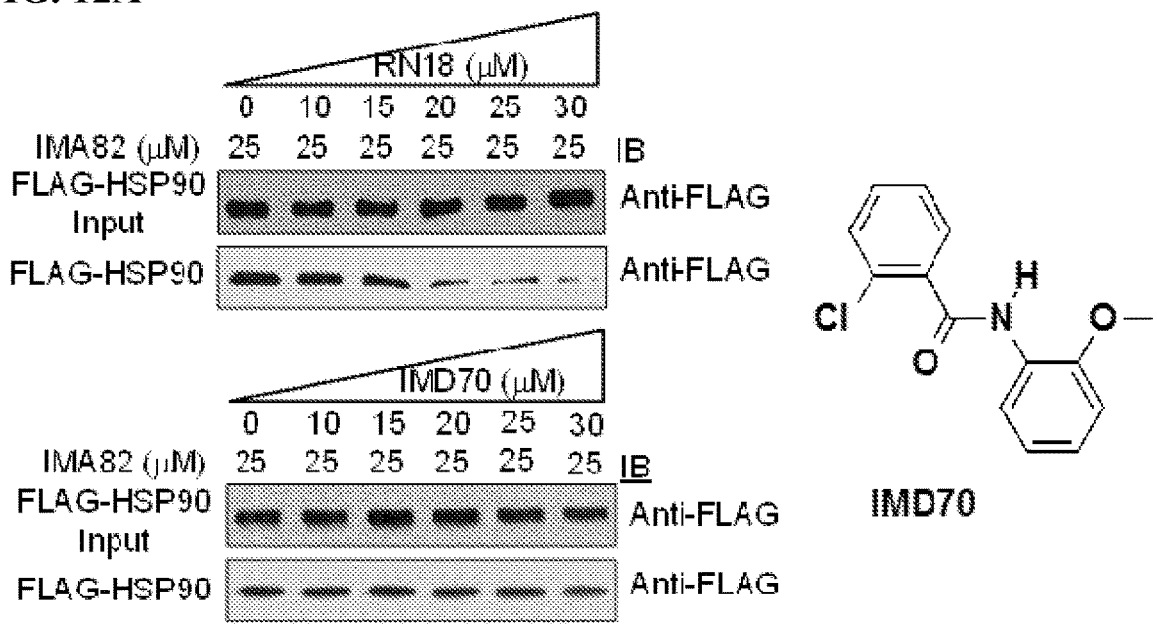
FIGS. 12A-12B. The Vif antagonist IMA82 specifically interacts with HSP90 in Vif, and Cul5 containing E3 complex.
Figure 12B:
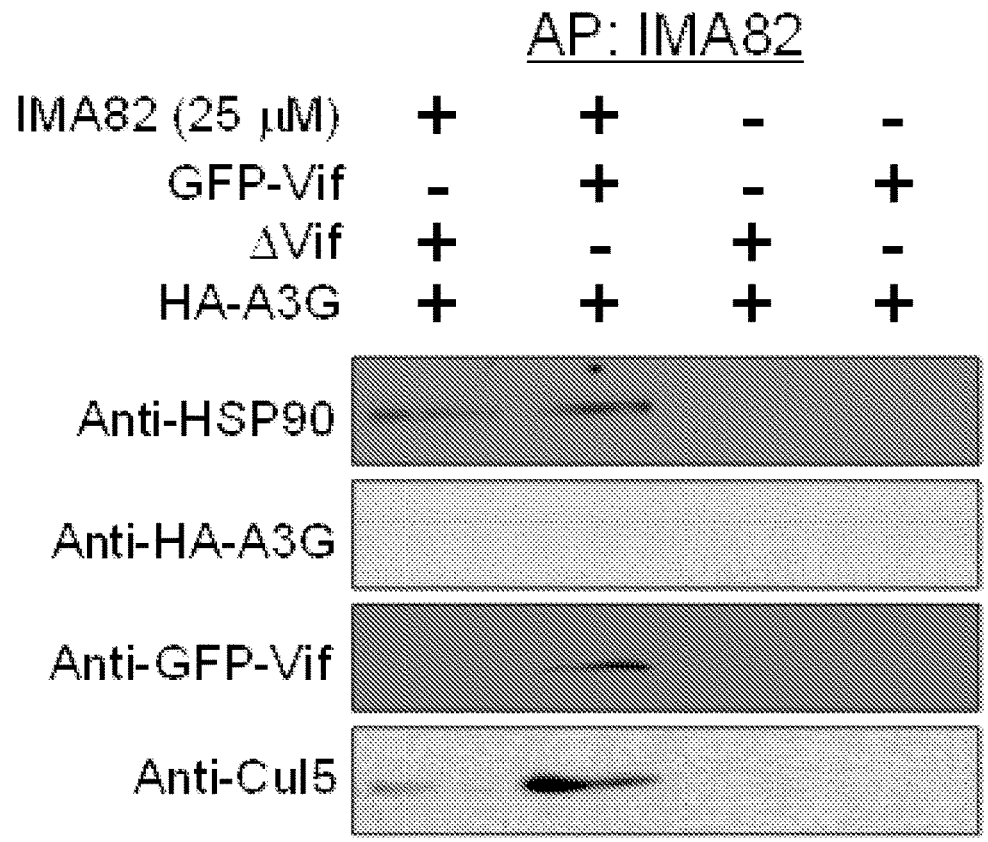

To confirm the specificity of Vif antagonist IMA82 binding with HSP90, we performed competitive binding experiments with the parental, non-biotinylated compound, RN-18. We expressed FLAG-tagged full-length HSP90 in 293FT cells and incubated with a fixed concentration (25 µM) of IMA82 in the presence of increasing concentrations (0-30 µM) of RN18 or an inactive IMA82 analog, IMD70[18]. Subsequent affinity purification and FLAG immunoblotting revealed that IMA82 binding to HSP90 was dose-dependently inhibited by the unlabeled analog, RN-18, but not by the control compound IMD70 (FIG. 12A), demonstrating the specificity of IMA82 binding to FLAG-tagged HSP90. We next asked if IMA82 and HSP90 co-purify with components of the Cul5-E3 ligase complex. IMA82-associating proteins were affinity purified from 293FT cells expressing A3G-Vif and A3G-ΔVif and probed for the presence of HSP90, A3G, Vif, and Cul5 (FIG. 12B). HSP90 and Cul5 co-purified with IMA82 from both Vif- and ΔVif-expressing cells, and in Vif-expressing cells, IMA82 co-purified with HSP90, Cul5, and Vif (FIG. 12B). These results suggest that HSP90 is a component of the Cul5-E3 ligase complex, and associates independently of Vif. Interestingly, we did not detect A3G in the IMA82-associated complex (FIG. 12B). To determine whether A3G association with the HSP90-Cul5-Vif complex might be modulated by IMA82, we immunoprecipitated A3G, Vif, HSP90, and Cul5 from 293FT-A3G-Vif and 293FT-A3G-ΔVif cells, and performed immunoblotting to identify the associated proteins. Consistent with our hypothesis, immunoprecipitation of HA-A3G from vehicle-treated cells also pulled down Vif, HSP90, Cul5, and CBF-β (FIG. 3A). Similarly, immunoprecipitation of GFP-Vif (FIG. 3B), HSP90 (FIG. 3C), and Cul5 (FIG. 3D) from the same cells pulled down the remaining members of the E3 ligase complex. Remarkably, A3G was not present in any of the complexes immunoprecipitated from cells treated with IMA82 (FIGS. 3A-3D). This was not a consequence of disruption of the entire complex by IMA82, because A3G was the only component absent from the complexes in these cells. Collectively, these results provide evidence that HSP90 is a novel component of the Vif-A3G-Cul5-CBF-β E3 ligase complex, and further suggest that IMA82 binding to HSP90 actively prevents A3G from associating with the complex.

Vif Antagonist Directly Inhibits HSP90 and A3G Interactions.

Figure 4:
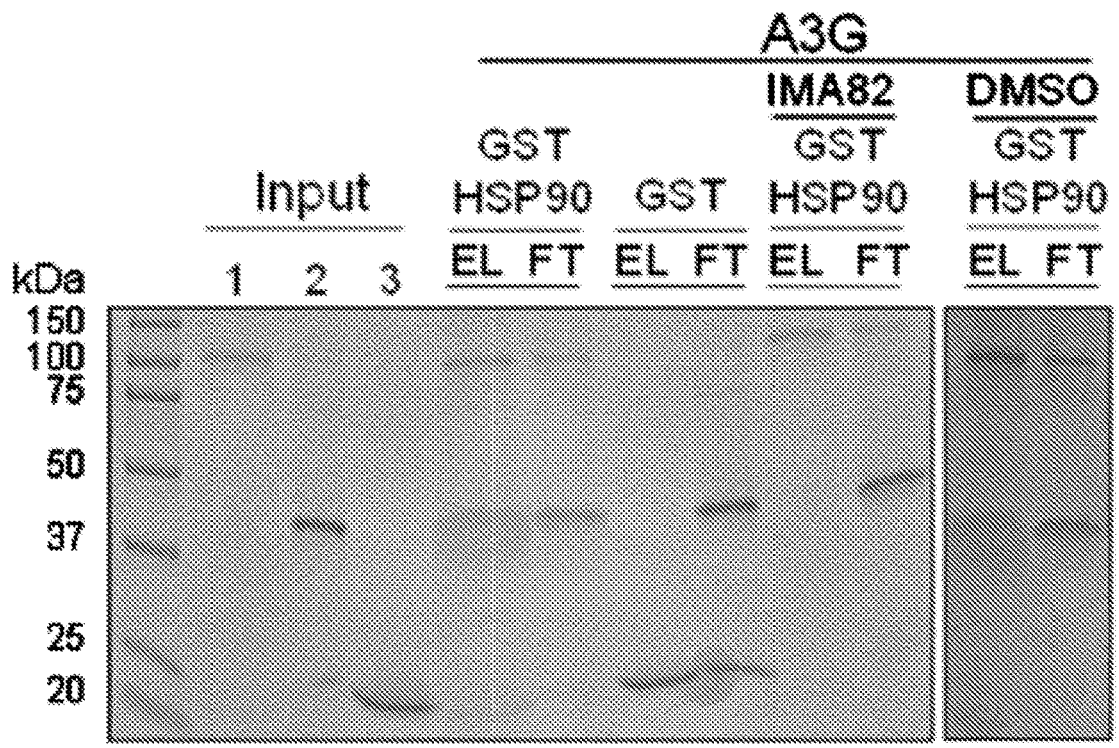
FIG. 4. IMA82 binds HSP90 to block APOBEC3G association. Purified GST-HSP90, and GST were incubated with A3G protein in the presence or absence of IMA82. Samples were precipitated with GSH-SEPHAROSE® beads. After extensive washing, the proteins were eluted by boiling with SDS sample buffer. The purified input protein, flow through (FT), and eluted proteins (EL) were analyzed by SDS-PAGE. The input proteins are shown in lanes 1-3: purified GST-HSP90 (lane 1), A3G (lane 2), and GST (lane 3).

To determine the interaction status of HSP90 and A3G, we examined binding between purified A3G and HSP90 proteins in vitro. For these experiments, we expressed and purified GST-tagged full-length HSP90 in E. Coli. The A3G used in these experiments was a commercially obtained C-terminal Myc-DDK-tagged protein purified from HEK293 cells. After co-incubation of the purified proteins, the A3G-HSP90 complexes were isolated by glutathione affinity chromatography and analyzed by SDS-PAGE. The experiment revealed that A3G was directly interacting with GST-HSP90 but not with control GST proteins (FIG. 4). Furthermore, addition of IMA82 to the in vitro binding reactions inhibited A3G binding to GST-HSP90 (FIG. 4). Collectively, these data demonstrate that HSP90 directly interact with A3G and IMA82 binding to the HSP90 disrupts the complex formation.

A3G is a Client Protein of HSP90.

Figure 5A:
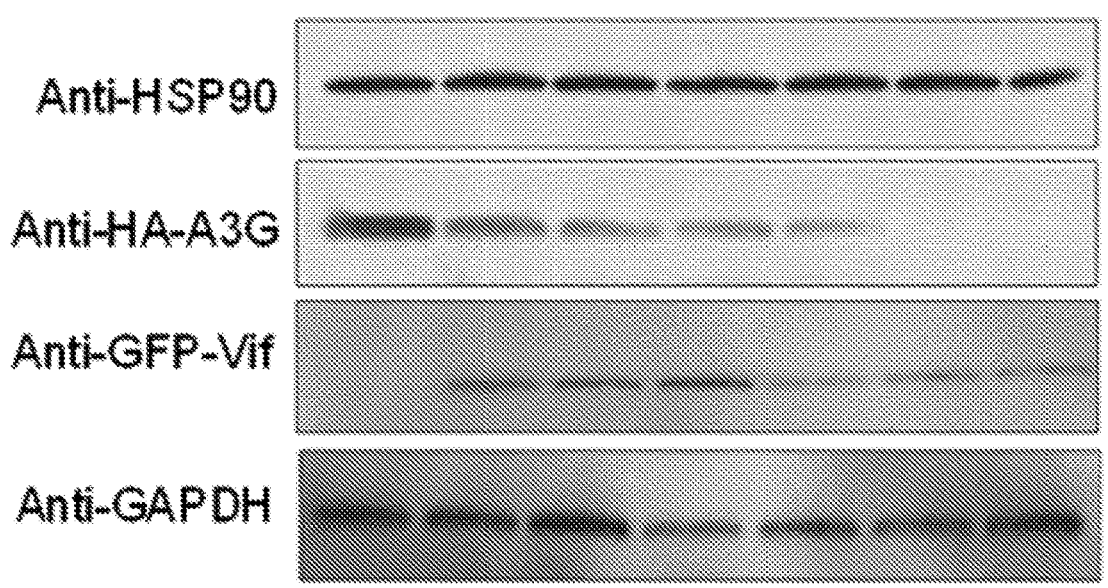
FIGS. 5A-5E. APOBEC3G is a client protein of HSP90.
Figure 5B:
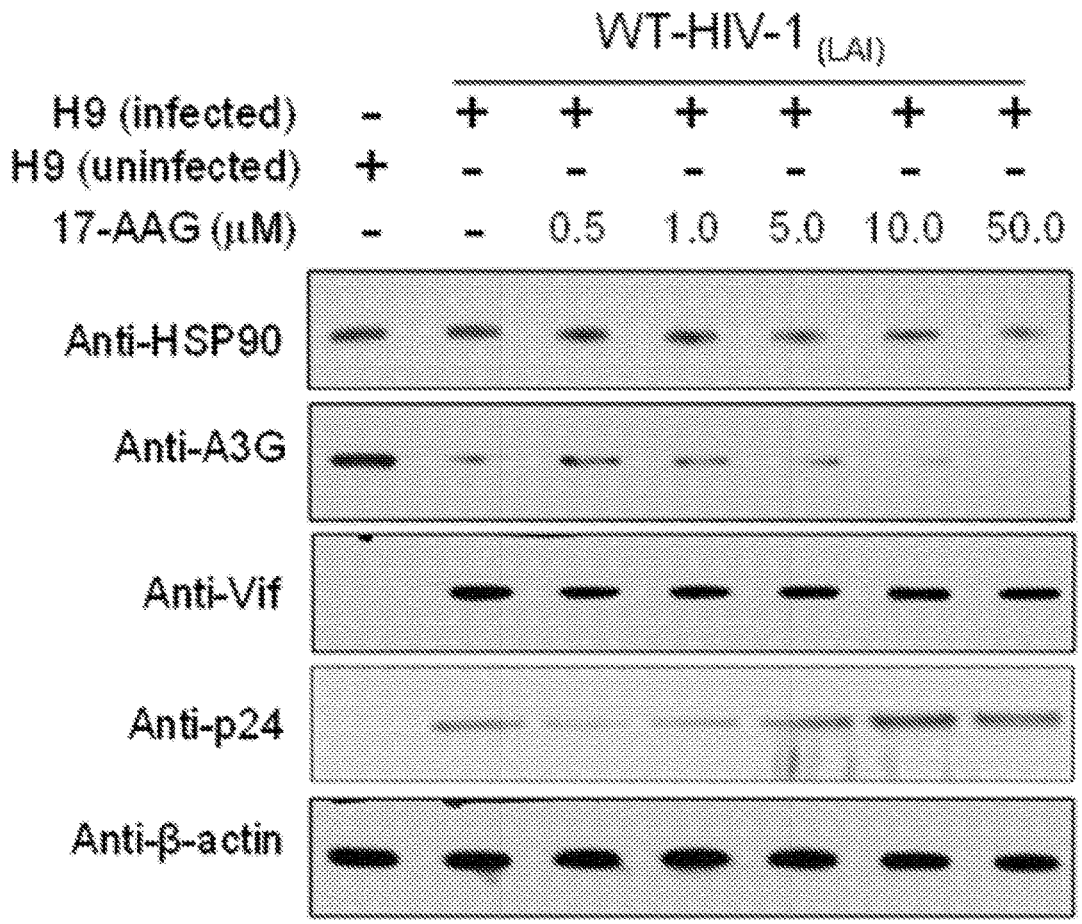
Figure 5C:
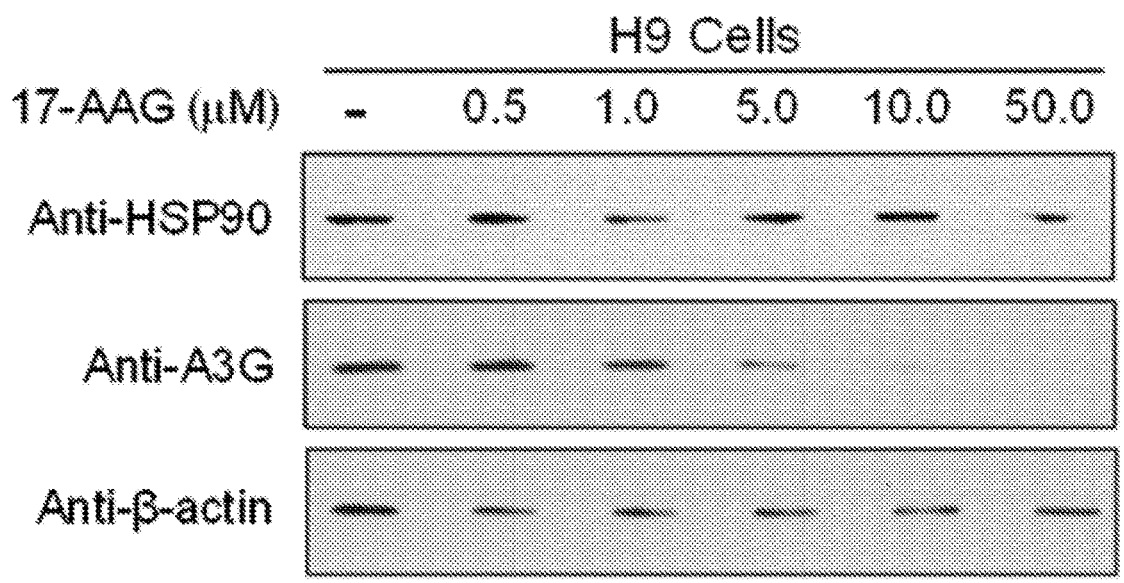
Figure 5D:
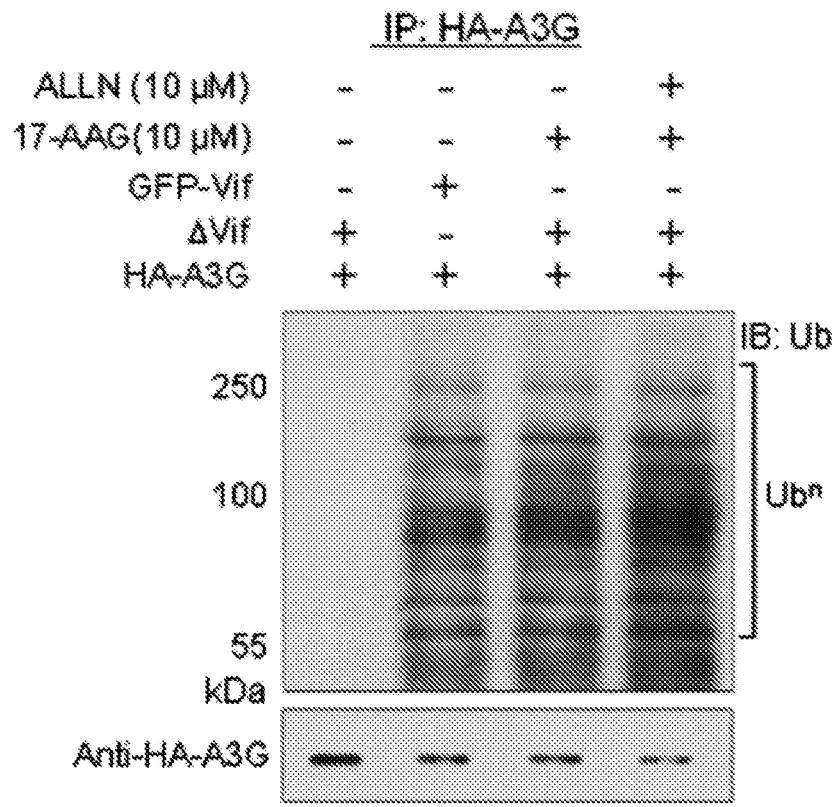
Figure 5E:
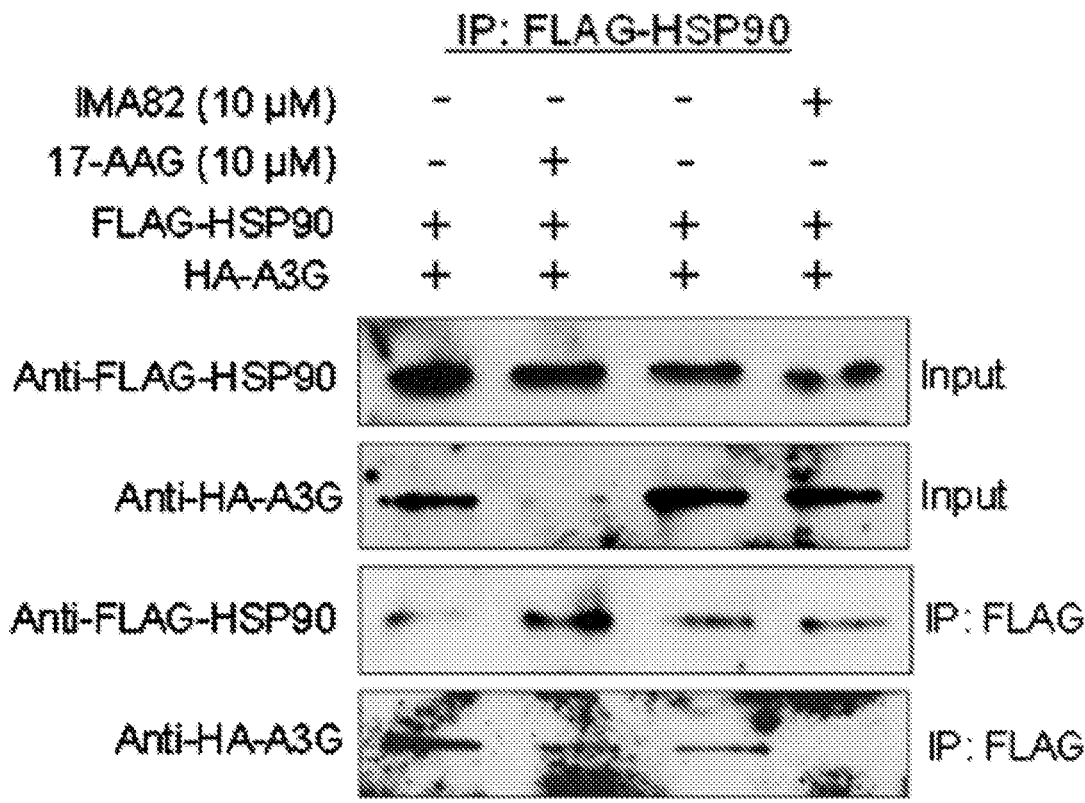
Figure 6:
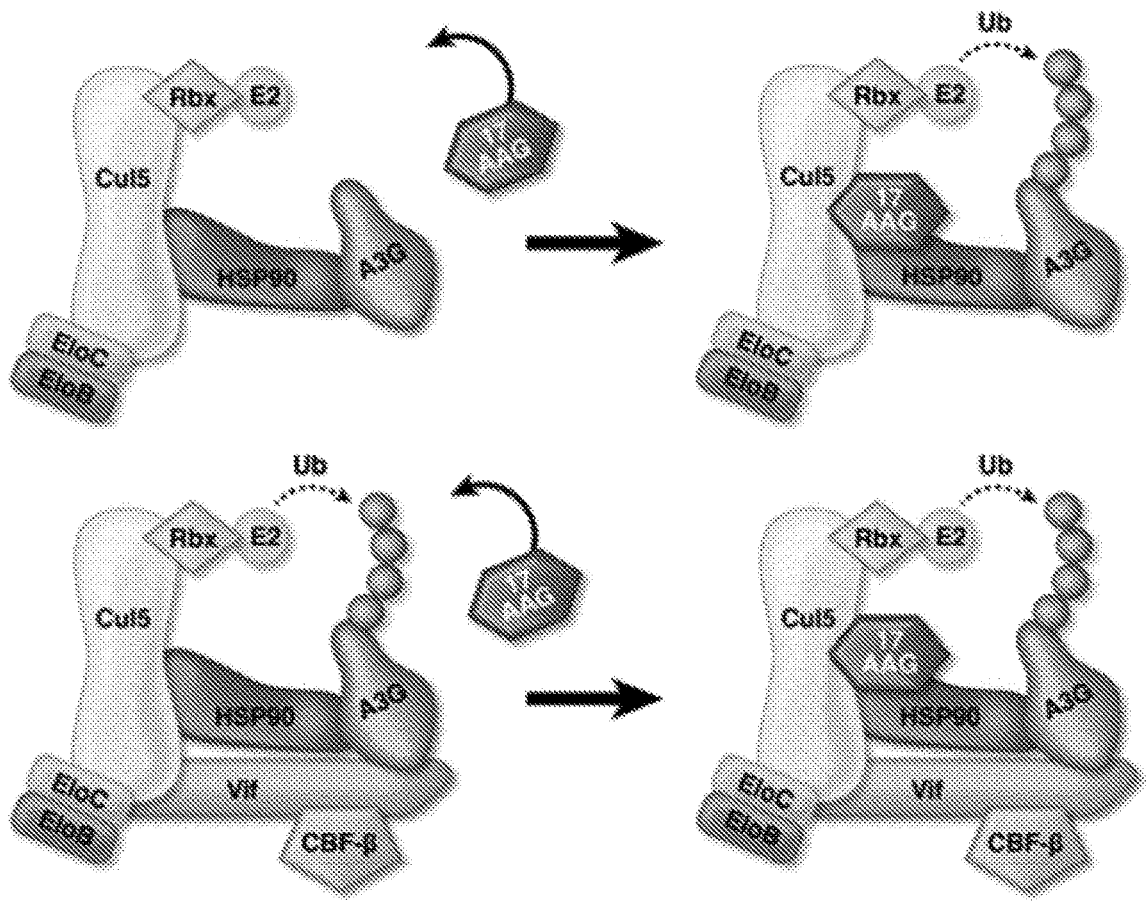
FIG. 6. APOBEC3G and HSP90 interactions and proteasomal degradation. A cartoon model proposed for HSP90 inhibition and its interactions with A3G in Cul5 polyubiquitination and degradation complex. HSP90 inhibitors destabilize A3G in the presence and absence of Vif.

These findings raise the possibility that A3G might be a client protein of HSP90. HSP90 acts as a molecular chaperone to fold and stabilize proteins in an ATP-dependent manner[20,23]. Because our results are consistent with such a role for HSP90 in preventing A3G ubiquitination, we examined the fate of A3G when HSP90 function was inhibited with 17-N-Allylamino-17-demethoxygeldanamycin (17-AAG), a competitive inhibitor of ATP binding that increases the degradation of HSP90 client proteins[24,25]. Indeed, incubation of 293FT-A3G-Vif and 293FT-A3G-ΔVif cells with 17-AAG dose-dependently decreased A3G expression but had no effect on HSP90 levels (FIG. 5A). Moreover, Vif expression was also unaffected by 17-AAG treatment, demonstrating that the decrease in A3G levels was not secondary to increased Vif expression, but was due to inhibition of the protection afforded by HSP90 binding (FIG. 5A). The same effect was observed in HIV-1-infected H9 cells, in which 17-AAG dose-dependently decreased the expression of A3G without affecting Vif expression (FIG. 5B). Notably, A3G expression was also decreased by 17-AAG treatment of uninfected H9 cells (FIG. 5C), confirming that the loss in A3G protein was due to inhibition of the chaperone activity of HSP90. To determine if loss of HSP90 protection induced A3G ubiquitination by the E3 ligase complex, we examined the ubiquitination status of A3G immunoprecipitated from 17-AAG-treated 293FT-A3G-Vif or 293FT-A3G-ΔVif cells. A3G was ubiquitinated in Vif-expressing cells as expected, and was also ubiquitinated in cells lacking Vif but treated with 17-AAG (FIG. 5D). Addition of the proteasome inhibitor ALLN did not further affect A3G polyubiquitination indicating that the 17-AAG caused the maximum level of A3G ubiquitination (FIG. 5D). Affinity purification using FLAG-HSP90 further showed that IMA82 inhibited interactions of HSP90 and A3G while HSP90 remained in complexes with A3G in 17-AAG treated cells (FIG. 5E). Altogether, these results demonstrate that Cul5-E3 ligase complex mediates HSP90-A3G polyubiquitination and degradation in the presence of 17-AAG (FIG. 6). These results are in consistent with previous reports indicating HSP90-Cul5 connection in both structural and functional aspects of the interactions. For example, Cul5 interacts with HSP90 chaperone complex and the HSP90 client proteins such as ErbB2 and Hif1-alpha[26]. In addition, Cul5 recruitment to the site of ErbB2 at the plasma membrane leads to polyubiquitination and degradation[26]. More recently, a focused functional genomics screen using RNAi targeting 28 Cullin-ring ligases found that Cul5 and Rbx2 were required for degradation of several HSP90 client proteins in cancer cells treated with HSP90 inhibitor 17-AAG[27]. In summary, previous findings together with our results suggest that Cul5 mediated E3 ligation complex is recruited to HSP90 and its client protein complexes for subsequent polyubiquitination and degradation of the client proteins by inhibition of HSP90 activity.

Figure 13:
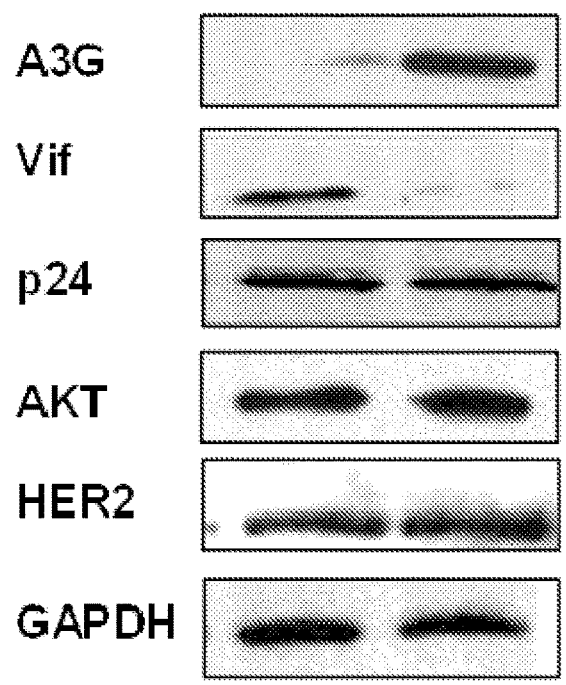
FIG. 13. The Vif inhibitor, RN-18, specifically restores APOBEC3G and does not affect the levels of cellular Hsp90 substrates. 293T cells were co-transfected with HIV-1 (pLAI2) and HA-tagged APOBEC3G vectors and cultured for 24 h in the presence (+) or absence (−) of 50 μM RN-18. Cell lysates were collected and used for Western blot analysis with antibodies against the viral and cellular proteins indicated. Levels of cellular GAPDH were used as a loading control.

Both RN-18 and 17-AAG interact with HSP90 in Cul5 mediated E3 ligase complex. Previous studies show that 17-AAG treatment destabilizes the expression of HSP90 client proteins such as AKT and HER2 by inhibition of HSP90 activity[26 27 28]. To determine whether RN-18 had an effect on cellular substrates of HSP90, 293T cells were co-transfected with HIV-1 (pLAI2) and HA-tagged A3G vectors and cultured for 24 h in the presence (+) or absence (−) of 50 µM RN-18. Cell lysates were prepared and various viral and cellular protein levels were analyzed by immunoblotting (FIG. 13). Levels of cellular GAPDH were used as loading controls. These results showed that RN-18 restored A3G while enhanced degradation of Vif, as expected, while had no effect on AKT and HER2 levels. Thus, these data indicate that RN-18 is not a general HSP90 inhibitor and specifically regulate A3G-Vif interactions and their protein expression levels.

Figure 7:
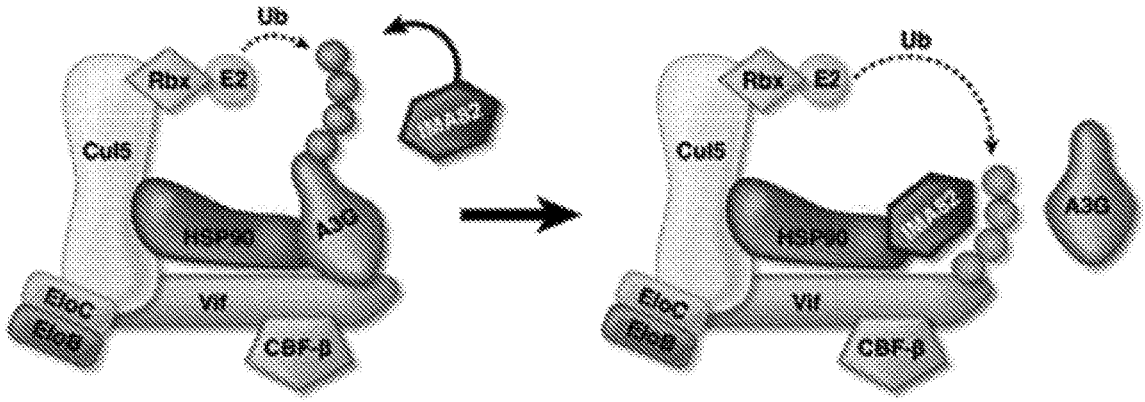
FIG. 7. Proposed model for the mechanisms of action of Vif antagonists. RN-18 analog IMA82 binds to M domain of HSP90 in the Cul5 mediated E3 ubiquitin ligase complex and replace A3G from the complex. Replacement of A3G from the complex, A3G escaped from poly-ubiquitination and stabilized from proteosomal degradation. Stable expression of A3G down regulates Vif through poly-ubiquitination and proteasomal degradation.

Collectively, our study used an affinity-directed chemical biology strategy to identify the cellular target of RN-18-based Vif antagonists and to elucidate the molecular interactions by which they inhibit HIV-1 replication. We have identified HSP90-A3G interactions in the Vif-A3G-Cul5-CBF-β E3 ligase complex, which is required for Vif-induced ubiquitination and proteasomal degradation of A3G. In addition, we show that the Vif antagonists disrupt the HSP90-A3G interaction by binding to HSP90. Our findings are consistent with a model (FIG. 7) in which HSP90 and A3G interact to form a complex with Cul5, Vif, CBF-β, Rbx, and elongins B and C. During HIV-1 infection, Vif induces A3G ubiquitination and degradation, but IMA82 binding to HSP90 releases A3G from the E3 ubiquitin ligase complex and induces Vif ubiquitination and subsequent degradation. It is quite possible that chaperone activity of HSP90 is involved in the proper folding of A3G and its association with A3G is exploited by the Vif-E3 ligase complex, which is disrupted by RN-18 analogues resulting in A3G rescue from ubiquitination and Vif-mediated degradation. Thus, targeting the HSP90-A3G interactions may provide a new strategy to develop antiviral therapeutics.

HIV-1$_{LAI}$ Production, Cell Infection, and Small Molecule Treatment.

293T cells ($7\times10^6$) were transfected with 35 µg of a pro-viral HIV-1$_{LAI}$ plasmid using LIPOFECTAMINE™ 2000 (Invitrogen) in OPTI-MEM® medium. Three hours later, complete medium was added and the cells were cultured for 48 h in a humidified 5% $CO_2$ incubator at 37° C. The virus supernatant was then harvested and reverse transcriptase activity was measured.

Non-permissive (H9) and permissive (MT4) cells ($2\times10^5$/well) were cultured in 24-well plates in RPMI 1640 medium containing 10% FBS, penicillin (100 units/ml), and streptomycin (100 µg/ml). Cells were exposed for 16 h to 0.1-50 µM of IMD55, IMD64, IMA82, IMD40, or IMD41, as indicated in the figures. The medium was removed by centrifugation of cells at 1000 rpm for 5 min. The cells were resuspended in fresh medium, HIV-1$_{LAI}$ ($2\times10^5$ C.P.M.) was added to each well and the cells were incubated at 37° C. for 5 h. The virus supernatant was removed by centrifugation and the cells were washed three times in PBS, resuspended in medium, and incubated with compounds for a further 15 days. Every 3 days, 20% of the supernatant volume was removed and replaced with fresh medium containing the appropriate concentration of compound. The supernatant sample was assayed for reverse transcriptase activity to monitor viral replication. Each compound was tested in an individual experiment.

Protein Analysis.

Affinity purification, immunoprecipitation, and immunoblotting were performed on total cell lysates prepared with M-PER or IP lysis buffer (both Thermo Scientific) containing a protease inhibitor cocktail (Roche).

For affinity purification, aliquots of cell lysates (200 µg protein) were rotated with 50 µl of streptavidin beads at room temperature (RT) for 1 h. The beads were washed three times with PBS containing 0.05% BSA, and proteins were eluted by boiling with SDS-PAGE sample buffer followed by centrifugation at 12,000 rpm for 2 min. Samples were resolved by 4%-20% SDS-PAGE (Lonza) and the gels were stained using a Silver Stain Plus Kit (Bio-Rad).

For immunoblotting, the affinity-purified proteins or cell lysates were boiled with SDS-PAGE sample buffer, resolved by SDS-PAGE, (Lonza), and transferred to PVDF membranes using a semi-dry electroblotter (Bio-Rad). The membranes were blocked with 5% non-fat dry milk in Tris-buffered saline Tween-20 (TBST) buffer for 2 h and then exposed to primary antibodies as indicated in the figure legends. The following primary antibodies were used. Rabbit polyclonal anti-ubiquitin (1:1000 dilution, Cell Signaling); rabbit polyclonal anti-A3G (1:500 dilution, Santa Cruz Biotechnology), rabbit polyclonal anti-HA (1:1000 dilution, Cell Signaling); mouse monoclonal anti-HIV-1 Vif (1:1000 dilution, #319, NIH AIDS Research and Reference Reagent Program, Division of AIDS, NIAID, NIH); polyclonal anti-GFP (1:500 dilution, Wako); polyclonal anti-Hsp90 (1:1000 dilution, Cell Signaling); rabbit polyclonal anti-Cul5 (1:1000 dilution, Millipore); polyclonal anti-Cul5 (1:500 dilution, Santa Cruz Biotechnology), monoclonal anti-FLAG (1:1000 dilution, Cell Signaling); polyclonal anti-CBF-β (1:1000 dilution, Sigma); polyclonal anti-β-actin (1:2000 dilution. Santa Cruz Biotechnology), mouse monoclonal anti-HIV p24 (1:500, Millipore), and rabbit polyclonal anti-GAPDH (1:1000 dilution, Cell Signaling)

Knockdown of Hsp[90] and Cul5.

SMARTpool siRNAs specific for Hsp90α, Hsp90β, or Cul5 were purchased from Thermo Scientific-Dharmacon. 293FT cells ($1\times10^6$/well) were seeded into 6-well plates. Specific or nontargeting siRNAs (50 nM) were mixed with HA-A3G and pNLA1-Vif or pNLA1-ΔVif plasmids (for Hsp90 knockdown) or HA-A3G and GFP-Vif (for Cul5 knockdown), and co-transfected into 293FT cells using LIPOFECTAMINE™ 2000 in OPTI-MEM® medium for 4 h. The transfection mixture was then replaced with complete DMEM medium without geneticin. Cells were treated with 10 μM IMA82 and incubated at 37° C. overnight (Hsp90 knockdown) or for 16 h (Cul5 knockdown). Total cellular RNA was isolated from Hsp90 knockdown cells using TRIZOL® reagent (Invitrogen), and cDNA was synthesized using Superscript III and random primers according to the manufacturer's instructions (Invitrogen). Real-time qPCR of Hsp90α and Hsp90β was performed using SYBR green (Abgene) and a Roche LightCycler480 II. GAPDH was measured as an internal control. Hsp90 knockdown cell lysates were immunoblotted with antibodies to Hsp90, HA (A3G), Vif, and GAPDH proteins. Cul5 knockdown cell lysates were immunoblotted with antibodies to Cul5, HA (A3G), GFP (Vif), or ubiquitin.

Ubiquitination Assay.

293FT cells were co-transfected with HA-A3G and pEGFP-C1-Vif or pNL-A1-ΔVif plasmids for 4 h. Cells were incubated with or without 10 μM of IMA82, IMD55, or IMD64 for 16 h, and then with or without 10 μM of the calpain inhibitor ALLN for 4 h. The cells were washed once with PBS and lysed. Samples of 200 μg protein were immunoprecipitated by the addition of rat anti-HA (Roche) or mouse anti-GFP (Wako) antibodies (7 μg) and 50 μl protein G DYNABEADS® (Invitrogen) and rotated at RT for 2 h. The beads were washed three times with PBS containing 0.05% Tween 20 and boiled in 5×SDS sample buffer. The denatured proteins were resolved and electroblotted onto PVDF membranes. The membranes were probed with rabbit anti-ubiquitin, rabbit anti-HA, or rabbit anti-GFP antibodies, as described above.

Protein Analysis of HIV-1 Infected Cells.

Non-permissive (H9) and permissive (MT4) cells were treated with 1% DMSO, IMA82, or 17-DMAG overnight and then infected with HIV-1$_{LAI}$ for 5 h. Cells were washed three times with PBS and cultured in medium for 72 h in the presence of the same concentrations of DMSO, IMA82, or 17-DMAG. Total cell lysates were prepared with M-PER buffer containing 0.5% Triton X-100, 150 mM NaCl, 5 mM EDTA, and protease inhibitor cocktail. Protein concentrations were determined with the DC protein assay kit (Bio-Rad). Immunoblotting was performed as described above.

Immunoprecipitation of IMA82-Interacting Proteins.

293FT cells were co-transfected with HA-A3G and pEGFP-C1-Vif or pNL-A1-ΔVif plasmid (1.5:4 molar ratio) for 4 h, then treated with 1% DMSO or 10 μM IMA82 for 16 h. Cells were washed twice with PBS and lysed in IP lysis buffer (Thermo) or in a buffer composed of 50 mM Tris-HCl (pH 7.2), 150 mM NaCl, 1% NP-40, 10% glycerol, and protease inhibitor cocktail. Cell lysates (100 Mg) were incubated with 5 μl of rat anti-HA (Roche), rabbit anti-GFP (Cell Signaling), mouse anti-Hsp90 (Millipore), or rabbit anti-Cul5 (Sigma) plus 30 μl of protein A or G DYNA-BEADS® (Invitrogen) and rotated at RT for 2 h. The beads were washed three times with PBS containing 0.05% Tween 20. Each lysate was immunoprecipitated in triplicate and the beads were combined. Immune complexes were eluted by boiling in 5×SDS sample buffer. The proteins were separated by SDS-PAGE and analyzed by immunoblotting with antibodies to HA (A3G), GFP (Vif), Hsp90, Cul5, and CBF-β, as described above.

In Vitro Binding Studies.

The recombinant human A3G used for in vitro binding studies was purchased from OriGene. According to the manufacturer, the recombinant protein was expressed in HEK293 cells and purified by anti-DDK (FLAG) affinity chromatography. GST, GST-Hsp90, or GST-Hsp90 domain deletion mutants (1 μg each) were incubated with recombinant A3G (1 μg) for 1 h at RT in 50 mM sodium phosphate buffer (pH 7.2) containing 150 mM NaCl, in the presence or absence of IMA82 (50 μM in 1% DMSO). To capture GST fusion proteins, GSH-SEPHAROSE® beads were added to the reaction mixture and incubated at RT for 1 h. The GSH beads were collected by centrifugation and washed three times with 50 mM sodium phosphate buffer (pH 7.2) containing 150 mM NaCl. The bound proteins were eluted with SDS sample buffer and analyzed by 4%-20%, SDS-PAGE.

Materials.

Commercial reagents and solvents (HPLC grade for purifications and anhydrous solvents for reactions) were purchased from Sigma-Aldrich, Thermo Scientific, Acros Organics, Alfa Aesar, EMD, Combiblocks, Oakwoods, Toronto Research Chemicals Inc., Astatech Inc., etc. and were used without further purification.

All reactions were performed in oven-dried round-bottom flasks and air sensitive reactions were performed under positive pressure of nitrogen. Moisture sensitive reactions were performed using calcium sulphate protected guard tubes. Stainless steel syringes were used to transfer dry solvents or moisture/air sensitive liquids. Column chromatography was performed using SINGLE StEP™ Pump and SINGLE StEP™ columns Intro Packs of various sizes made by Thomson Instrument Company. Silica gel used was 60° pore size, 40 μm, supplied by Fisher Scientific and amines were purified using neutral alumina Brockmann I of Sigma-Aldrich. Analytical thin-layer chromatography (TLC) was performed using TLC silica gel 60 F$_{254}$ aluminum sheets of EMD. TLC plates were visualized by exposure to ultraviolet light (254 nm), iodine adsorbed on silica gel and by exposure to an ethanolic solution of phosphomolybdic acid (PMA) or an acidic solution of p-anisaldehyde, or a slightly basic solution of potassium permanganate. Organic extracts or solutions or eluents were concentrated using Heidolph's Hei-VAP Advantage vacuo rotavapor at temperatures below 38-40° C. Dry-ice was used for low temperature baths in different organic solvents. $^1$H (proton) and $^{13}$C (carbon) nuclear magnetic spectra were recorded using 400 MHz Jeol JNM-ECS spectrometer with a 5 mm proton/multi-frequency auto-tune and auto sample changer. Proton and carbon nuclear magnetic resonance spectra are reported in parts per million (ppm) on the δ scale using the internal standard of reference as trimethylsilane (TMS). Electron-Spray Mass spectroscopy (ESI MS) was performed on Waters micromass Model ZQ 4000 using methanol solvent to dissolve samples. Qualitative and preparative HPLC was performed using Waters 2695 Separation Module having Waters 996 photodiode array detector.

N-(2-methoxyphenyl)-2-((4-nitrophenyl)thio)benzamide (RN-18)

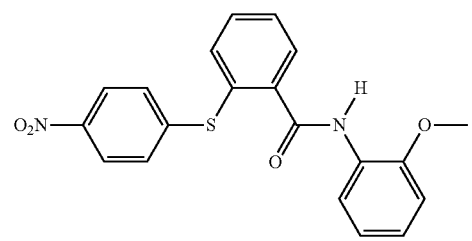

RN-18

$^1$H NMR (400 MHz, CDCl$_3$, TMS) δ: 3.71 (s, 3H), 6.77-6.81 (m, 1H), 6.86-6.92 (m, 1H), 6.96-7.02 (m, 1H), 7.21 (d, 2H, J=9.16 Hz), 7.40-7.50 (m, 3H), 7.69-7.73 (dd, 1H, J$_1$=1.83 Hz, J$_2$=7.32 Hz), 7.99 (d, 2H, J=9.16 Hz), 8.31 (s, 1H), 8.33 (d, 1H, J=7.93 Hz). $^{13}$C NMR (100 MHz, CDCl$_3$, TMS) δ55.63, 109.94, 119.81, 121.12, 124.10, 124.29, 127.29, 128.54, 129.25, 129.63, 129.84, 131.42, 135.51, 140.38, 145.91, 146.62, 147.97, 165.20. MS (ESI): m/z (%)=380.95 (M$^+$, 100), 402.96 (M+Na$^+$, 95).

Methyl 2-chloro-4-((4-nitrophenyl)thio)benzoate (1)

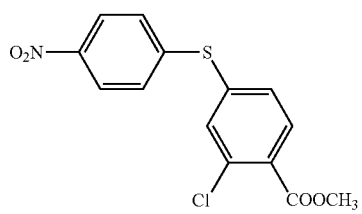

In a 50 ml oven dried two-neck round bottom flask methyl 2-chloro-4-iodobenzoate (1.0 g, 3.38 mmol) was dissolved in anhydrous DMF (15 ml) followed by anhydrous potassium carbonate (0.93 g, 6.74 mmol, 2.0 equiv.) and catalyst copper iodide (32.09 mg, 0.169 mmol, 5 mol %) and the resulted mixture was stirred for 10 minutes under nitrogen pressure. To the above mixture was added 4-nitrothiophenol (0.628 g, 4.05 mmol, 1.2 equiv.) dissolved in 2 ml of anhydrous DMF and the resulted mixture was stirred at 100° C. for a period of 6 hours till TLC showed the completion of the reaction. The reaction mixture was poured in to ice-cold water followed by the extraction with EtOAc (2×15 ml). Organic extractions were combined, treated sequentially with saturated potassium carbonate solution, saturated brine solution and anhydrous sodium sulphate. The dried organic extract was adsorbed on silica gel and flash chromatography using EtOAc: petroleum ether (1:9) afforded the compound 1 as a yellow solid (0.872 g, 80% yield).

$^1$H NMR (400 MHz, CDCl$_3$, TMS) δ: 3.86 (s, 3H), 7.21-7.34 (m, 3H), 7.41 (d, 1H, J=2.29 Hz), 7.71-7.78 (m, 1H), 8.02-8.10 (m, 2H). $^{13}$C NMR (100 MHz, CDCl$_3$) δ: 52.59, 124.38, 129.70, 129.84, 132.34, 133.78, 134.90, 138.43, 143.97, 146.57, 165.23. MS (ESI): m/z (%)=346.17 (M+Na$^+$, 100), 348.17 (M+2+Na$^+$, 40).

2-chloro-4-((4-nitrophenyl)thio)benzoic Acid (2)

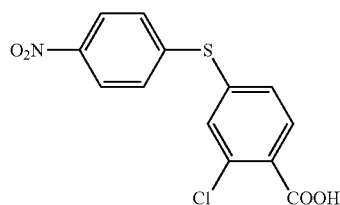

In a 25 ml round bottom flask was taken methyl ester compound 1 (0.50 g, 1.548 mmol) and dissolved in 10 ml of THF/CH$_3$OH/H$_2$O (4:2:1). To this solution lithium hydroxide hydrate (0.130 g, 3.09 mmol, 2 equiv.) was added and stirred for a period of 5 hours at room temperature. TLC (EtOAc/hexane, 1:1) showed the completion of the reaction. Organic solvents were evaporated in vacuo and the residue was diluted by adding 10 ml deionized water and the traces of unreacted starting material were removed by washing with EtOAc (2×5 ml). The aqueous layer was separated and treated with 2N HCl solution leading to the precipitation of the compound. The precipitate was filtered and dried to afford a yellow free flowing solid compound 2 (0.43 g, 90% yield).

$^1$H NMR (400 MHz, Acetone-d$_6$, TMS) δ7.52-7.55 (dd, 1H, J$_1$=1.83 Hz, J$_2$=8.24 Hz), 7.58-7.63 (m, 3H), 7.97 (d, 1H, J=8.24 Hz), 8.25 (d, 2H, J=8.70 Hz). $^{13}$C NMR (100 MHz, Acetone-d$_6$) δ: 125.24, 130.88, 131.10, 131.24, 133.34, 134.28, 134.93, 139.14, 144.66, 147.60, 165.96. MS (ESI): m/z (%)=332.10 (M+Na$^+$, 100), 334.04 (M+2+Na$^+$, 40).

Methyl 4-(2-chloro-4-((4-nitrophenyl)thio)benzamido)-3-methoxybenzoate (3)

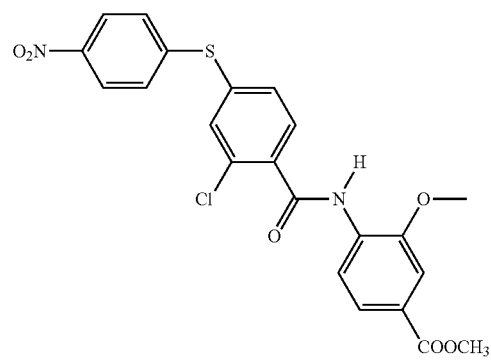

N,N-dimethylformamide (50 µl) was added to a stirred suspension of the carboxylic acid 2 (0.35 g, 1.13 mmol) and thionyl chloride (0.2 g, 1.69 mmol, 1.5 equiv) in dry benzene (5 mL) and refluxed for a period of 2 hours till a transparent solution obtained. After evaporation of benzene in vacuo, the resultant yellow solid was dissolved in dry benzene (5 mL) and added drop wise for a period of 10 minutes to a stirred mixture of methyl 4-amino-3-methoxybenzoate (0.246 g, 1.36 mmol, 1.2 equiv) and Et$_3$N (2 mL) dissolved in 5 ml of dry benzene at 0° C. The reaction mixture was gradually heated up to 75° C. for a period of 5 hours. After removal of the solvent by evaporation in vacuo, the residue was diluted with water (10 mL) and extracted with EtOAc (3×10 mL). The combined organic phase was sequentially washed with 1N HCl (10 mL), saturated solution of sodium bicarbonate (10 ml) and brine followed by treatment with anhydrous Na$_2$SO$_4$. Flash column chromatography using EtOAc: petroleum ether, (1:3) to afford the corresponding amide as a pale yellow solid 3 (0.454 g, 85% yield).

$^1$H NMR (400 MHz, CDCl$_3$, TMS) δ: 3.93 (s, 3H), 3.97 (s, 3H), 7.35-7.64 (m, 5H), 7.75 (d, 1H, J=8.24 Hz), 7.83 (d, 1H, J=7.79 Hz), 8.17 (d, 2H, J=8.70 Hz), 8.62 (d, 1H, J=8.70 Hz), 8.82 (s, 1H).
$^{13}$C NMR (100 MHz, CDCl$_3$) δ: 52.15, 56.13, 110.82, 118.99, 123.39, 124.42, 125.80, 129.45, 131.01, 131.40, 131.65, 131.89, 133.63, 134.77, 137.40, 144.31, 146.54, 147.66, 163.28, 166.56.

MS (ESI): m/z (%)=332.10 (M+Na+, 100), 334.04 (M+2+Na+, 40).

4-(2-chloro-4-((4-nitrophenyl)thio)benzamido)-3-methoxybenzoic Acid (4)

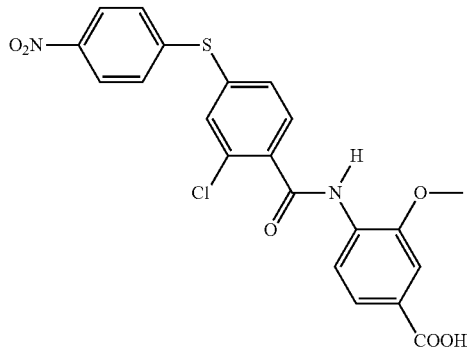

Procedure described for the synthesis of compound 2 was followed for the hydrolysis of methyl ester 3 (0.3 g) leading to the formation of carboxylic acid as a light yellow solid 4 (0.268 g, 92% yield).

$^1$H NMR (400 MHz, DMSO-$d_6$, TMS) δ: 3.89 (s, 3H), 7.42-7.78 (m, 7H), 8.15-8.32 (m, 3H), 10.02 (s, 1H).

$^{13}$C NMR (100 MHz, DMSO-$d_6$) δ: 111.63, 115.54, 121.27, 122.12, 124.51, 128.75, 130.52, 130.98, 131.29, 131.68, 133.30, 134.38, 136.85, 144.86, 145.87, 149.49, 164.68, 166.84.

MS (ESI): m/z (%)=473.18 (M+H+, 100), 475.18 (M+2+H+, 70).

2-chloro-N-(2-methoxy-4-((13-oxo-17-(2-oxohexahydro-1H-thieno[3,4-d]imidazol-4-yl)-3,6,9-trioxa-12-azaheptadecyl)carbamoyl)phenyl)-4-((4-nitrophenyl)thio)benzamide (IMA-82)

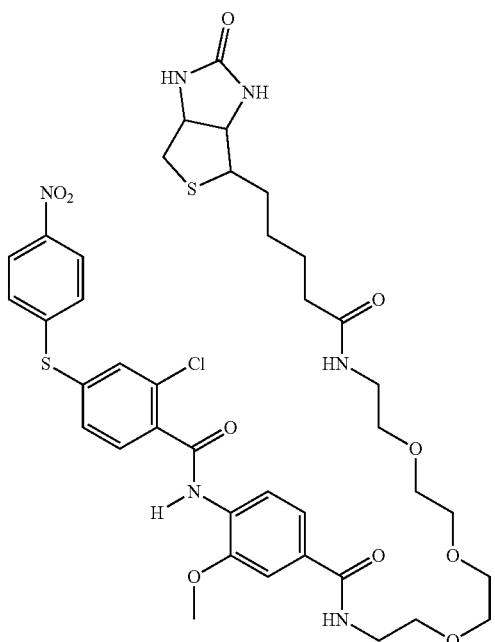

IMA-82

To a mixture of carboxylic acid 4 (50.0 mg, 0.109 mmol) and the commercially available Amine-PEG$_3$-Biotin (45.63 mg, 0.109 mmol, 1.0 equiv) in dry DCM (2.5 ml) was added EDCI (25.11 mg, 0.131 mmol, 1.2 equiv) and HOBT (17.68 mg, 0.131 mmol, 1.2 equiv) under nitrogen atmosphere. The reaction mixture was stirred for a period of 12 hours till TLC (15% methanol in DCM) showed completion of the reaction. The reaction mixture was diluted with DCM (5 ml) and quenched with deionized water (5 ml) followed by washing with 1N HCl (5 ml), saturated solution of sodium bicarbonate (5 ml) and brine. The combined solvent was dried by treatment with anhydrous sodium sulphate. Flash column chromatography using CH$_3$OH: CH$_2$Cl$_2$, (0.75:10) resulted in the formation of a light yellowish solid compound IMA-82 (0.268 g, 92% yield).

$^1$H NMR (400 MHz, CDCl$_3$, TMS) δ: 1.35-1.47 (m, 2H), 1.55-1.77 (m, 4H), 2.14-2.22 (m, 2H), 2.68-2.76 (m, 1H), 2.85-2.92 (m, 1H), 3.08-3.16 (m, 1H), 3.36-3.46 (m, 2H), 3.50-3.76 (m, 14H), 3.97 (s, 3H), 4.25-4.32 (m, 1H), 4.45-4.52 (m, 1H), 5.21 (s, 1H), 6.20 (s, 1H), 6.64 (s, 1H), 7.32-7.63 (m, 7H), 7.82 (d, 1H, J=8.24 Hz), 8.18 (d, 2H, J=8.70 Hz), 8.56 (d, 1H, J=8.24 Hz), 8.77 (s, 1H). $^{13}$C NMR (100 MHz, CDCl$_3$) δ: 25.55, 27.98, 28.12, 35.79, 38.99, 39.83, 40.43, 55.55, 56.15, 60.12, 61.71, 69.86, 69.92, 70.06, 70.28, 109.86, 118.99, 119.47, 124.39, 129.40, 129.85, 130.40, 131.02, 131.49, 131.87, 133.60, 134.82, 137.28, 144.34, 146.48, 148.11, 163.35, 164.00, 166.82, 173.48. MS (ESI): m/z (%)=881.00 (M+Na+, 100), 883.07 (M+2+Na+, 50). IR (KBr): Vmax 3185.55, 2918.40, 2863.42, 1694.52, 1682.95, 1645.33, 1634.73, 1593.25, 1574.93, 1515.14, 1464.02, 1456.30, 1335.75, 1273.06, 1133.22, 1109.11, 1085.96, 1030.02, 852.56, 759.98 cm$^{-1}$.

2-((4-nitrophenyl)thio)benzoic Acid (5)

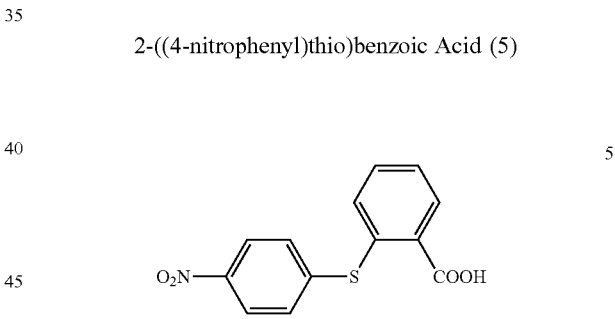

In a 50 ml oven dried two-neck round bottom flask thiosalicylic acid (1.0 g, 6.48 mmol) was dissolved in DMF (15 ml) followed by the treatment of anhydrous potassium carbonate (0.93 g, 19.45 mmol, 3.0 equiv.) and the resulted mixture was stirred for 10 minutes. To the above mixture was added slightly excess of 4-fluoronitrobenzene (1.1 g, 7.79 mmol, 1.2 equiv.) dissolved in 2 ml of DMF and the resulted mixture was stirred at 110° C. for a period of 8 hours till TLC (EtOAc: petroleum ether, 1:1) showed the completion of the reaction. The reaction mixture was poured in to ice-cold water followed by acidification using 5N HCl leading to the precipitation of crude product. The crude solid was filtered and washed several times with deionized water and petroleum ether to afford pure compound 5 as a yellow solid (1.60 g, 90% yield).

$^1$H NMR (400 MHz, Acetone-$d_6$, TMS) δ: 7.25-7.28 (dd, 1H, J$_2$=1.22 Hz, J$_2$=7.93 Hz), 7.377.55 (m, 2H), 7.61-7.66 (m, 2H), 8.03-8.07 (m, 1H), 8.23-8.28 (m, 2H). MS (ESI): m/z (%)=314.14 (M+K+).

Methyl 3-methoxy-4-(2-((4-nitrophenyl)thio)benzamido)benzoate (6)

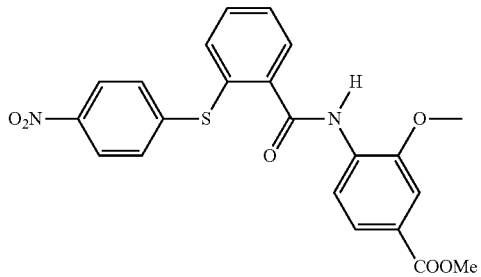

N,N-dimethylformamide (50 μl) was added to a stirred suspension of the carboxylic acid 5 (0.50 g, 1.82 mmol) and thionyl chloride (0.32 g, 2.73 mmol, 1.5 equiv) in dry benzene (5 mL) and refluxed for a period of 2 hours till a transparent solution obtained. After evaporation of benzene in vacuo, the resultant yellow solid was dissolved in dry benzene (5 mL) and added drop wise for a period of 10 minutes to a stirred mixture of methyl 4-amino-3-methoxybenzoate (0.258 g, 2.18 mmol, 1.2 equiv) and $Et_3N$ (2 mL) dissolved in 5 mL of dry benzene at 0° C. The reaction mixture was gradually heated up to 75° C. for a period of 5 hours. After removal of the solvent by evaporation in vacuo, the residue was diluted with water (10 mL) and extracted with EtOAc (3×10 mL). The combined organic phase was sequentially washed with 1N HCl (10 mL), saturated solution of sodium bicarbonate (10 ml) and brine followed by treatment with anhydrous $Na_2SO_4$. Flash column chromatography using EtOAc: petroleum ether, (1:3) to afford the corresponding amide as a pale yellow solid 6 (0.668 g, 84% yield).

$^1$H NMR (400 MHz, $CDCl_3$, TMS) δ: 3.86 (s, 3H), 3.91 (s, 3H), 7.28 (d, 2H, J=8.70 Hz), 7.50-7.60 (m, 4H), 7.67-7.71 (dd, 1H, $J_1$=1.37 Hz, $J_2$=8.70 Hz), 7.78-7.83 (m, 1H), 8.07 (d, 2H, J=9.16 Hz), 8.51 (d, 1H, J=8.24 Hz), 8.61 (s, 1H). $^{13}$C NMR (100 MHz, $CDCl_3$) δ: 52.16, 55.98, 110.71, 118.78, 123.41, 124.19, 125.62, 128.65, 129.38, 129.67, 130.10, 131.51, 131.77, 135.54, 139.69, 146.05, 146.27, 147.49, 165.39, 166.61. MS (ESI): m/z (%)=461.23 (M+Na$^+$).

3-methoxy-4-(2-((4-nitrophenyl)thio)benzamido) benzoic Acid (7)

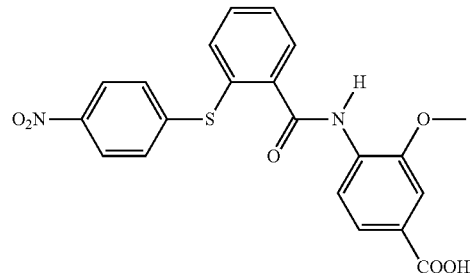

In a 25 ml round bottom flask was taken methyl ester compound 6 (0.35 g, 0.8 mmol) and dissolved in 10 ml of 1,2-dichloroethane solvent. To this solution trimethyltin hydroxide (0.867 g, 4.79 mmol, 6 equiv.) was added and the resulted mixture was refluxed at 80° C. for a period of 6 hours. TLC (EtOAc/hexane, 1:1) showed the completion of the reaction. Organic solvents were evaporated in vacuo and the residue was diluted by adding 10 ml deionized water and the traces of unreacted starting material were removed by washing with EtOAc (2×5 ml). The aqueous layer was separated and treated with 2N HCl solution leading to the precipitation of the compound. The precipitate was filtered and dried to afford a light yellow solid compound 7 (0.298 g, 88% yield).

$^1$H NMR (400 MHz, Acetone-d$_6$, TMS) δ3.82 (s, 3H), 7.38 (d, 2H, J=9.16 Hz), 7.49-7.64 (m, 5H), 7.69-7.75 (m, 1H), 8.12 (m, 3H), 9.80 (s, 1H).
MS (ESI): m/z (%)=424.97 (M+, 100), 446.94 (M+Na$^+$, 20).

3-methoxy-4-(2-((4-nitrophenyl)thio)benzamido)-N-(13-oxo-17-(2-oxohexahydro-1H-thieno[3,4-d]imidazol-4-yl)-3,6,9-trioxa-12-azaheptadecyl)benzamide (IMD-40)

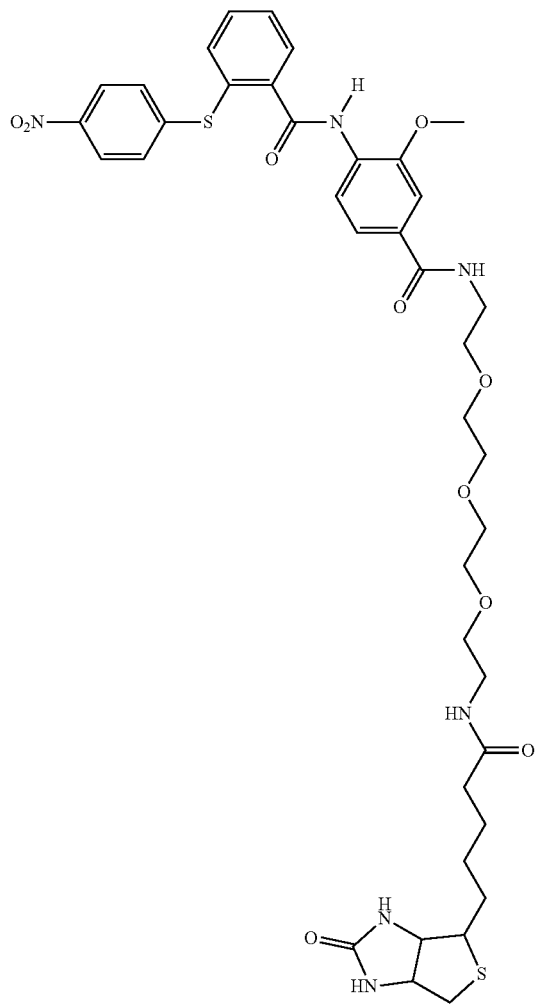

IMD-40

Procedure described for the synthesis of compound IMA-82 was followed for coupling reaction between carboxylic acid 7 (50.7 mg) and Amine-PEG3-Biotin (50.0 mg) leading to the formation of a pale yellow gummy solid IMD-40 (78.82 mg, 80% yield).

$^1$H NMR (400 MHz, CDCl$_3$, TMS) δ: 1.31-1.42 (m, 2H), 1.52-1.72 (m, 4H), 2.11-2.20 (m, 2H), 2.66-2.74 (m, 1H), 2.81-2.89 (m, 1H), 3.04-3.12 (m, 1H), 3.34-3.42 (m, 2H), 3.46-3.71 (m, 14H), 3.85 (s, 3H), 4.23-4.29 (m, 1H), 4.43-4.50 (m, 1H), 5.75 (s, 1H), 6.51 (s, 1H), 6.92 (s, 1H), 7.22-7.57 (m, 8H), 7.76-7.84 (m, 1H), 8.06 (d, 2H, J=8.70 Hz), 8.41 (d, 1H, J=8.70 Hz), 8.60 (s, 1H). $^{13}$C NMR (100 MHz, CDCl$_3$) δ: 25.49, 27.93, 28.09, 35.73, 39.01, 39.81, 40.40, 55.48, 55.95, 60.17, 61.76, 69.82, 69.89, 70.05, 70.25, 109.69, 118.72, 119.41, 124.11, 128.60, 129.30, 129.59, 129.92, 129.96, 130.12, 131.69, 135.37, 139.54, 145.92, 146.24, 147.92, 164.11, 165.40, 166.90, 173.56. MS (ESI): m/z (%)=847.52 (M+Na$^+$, 100), 848.52 (M+1+Na$^+$, 40).

Methyl 2-iodo-4-nitrobenzoate (8)

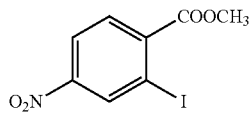

8

An oven dried 250 ml two-neck round bottom flask was discharged with 2-amino-4-nitrobenzoic acid (10.0 g, 54.94 mmol) and dissolved in 100 mL of methanol. To this solution SOCl$_2$ (12 ml) was added drop by drop using addition funnel at 0° C. The reaction mixture gradually was refluxed for a period of 8 hours using calcium sulphate guard tube. Volatiles were removed using in vacuo evaporation and the residue was quenched with deionized water. The crude residue was filtered and washed several times with saturated solution of sodium bicarbonate till TLC showed complete removal of starting carboxylic acid. The crude amino ester was dried and the resultant yellow solid amino ester (8.0 g, 40.81 mmol, 1 equiv.) was taken in a 250 ml round bottom flask and dissolved in 12 N H$_2$SO$_4$ (100 mL) at 0° C. NaNO$_2$ (3.38 g, 48.98 mmol, 1.2 equiv.) was dissolved in minimum amount of water and added drop wise to the above mixture at −10° C. Stirring was continued at the same temperature for a period of 2 hours. Urea (1 g) was added to the mixture to remove if any excess nitrous acid remained in the reaction mixture. In a separate beaker was dissolved KI (13.55 g, 81.62 mmol, 2.0 equiv.) in 20 ml of deionized water and kept stirring at a temperature of −10° C. To this solution of KI was added the diazonium hydrochloride salt obtained above at −10° C. drop wise using addition funnel. Stirring of the reaction continued for a period of 8 hours at room temperature. The reaction mixture was diluted with 100 ml of EtOAc and 100 ml of deionized water. Small amount of iodine liberated in the iodination reaction was quenched by the addition of sodium dithionite. Organic layer was separated and was sequentially treated with saturated NaHCO$_3$, saturated brine, and anhydrous Na$_2$SO$_4$ followed by the adsorption of silica gel. Flash chromatography using EtOAc: petroleum ether (1:3) afforded the iodo compound 8 as a light yellow solid (12.53 g, 70% yield).

$^1$H NMR (400 MHz, CDCl$_3$, TMS) δ3.99 (s, 3H), 7.90 (d, 1H, J=8.70 Hz), 8.22-8.28 (dd, 1H, J$_1$=2.29 Hz, J$_2$=8.24 Hz), 8.80 (d, 1H, J=2.29 Hz). $^{13}$C NMR (100 MHz, CDCl$_3$) δ: 53.11, 93.42, 122.72, 131.13, 135.80, 140.97, 148.83, 165.71.

Methyl 4-amino-2-iodobenzoate (9)

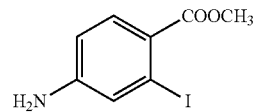

9

A solution of the compound 8 (10.0 g, 32.57 mmol) and SnCl$_2$. 2H$_2$O (22.04 g, 97.69 mmol, 3 equiv.) in EtOAc (150 mL) was refluxed for 5 hours until TLC (EtOAc/hexane, 1:1) indicated that reaction was complete. The reaction mixture was poured in a 500 ml beaker and it was diluted with 100 ml of EtOAc followed by the addition of potassium carbonate and 200 ml of deionized water and the two layer mixture was stirred for 30 minutes. The milky suspension was filtered through a short bed of CELITE® and the organic layer was separated. The combined organic layer was sequentially treated with saturated brine and anhydrous Na$_2$SO$_4$. Purification by flash column chromatography using EtOAc: petroleum ether (1:1) afforded a pale yellow solid 9 (5.86 g, 65% yield).

$^1$H NMR (400 MHz, CDCl$_3$, TMS) δ 3.86 (s, 3H), 4.01 (broad singlet, 2H), 6.58-6.64 (dd, 1H, J$_1$=2.29 Hz, J$_2$=8.70 Hz), 7.30 (d, 1H, J=2.29 Hz), 7.77 (d, 1H, J=8.24 Hz). $^{13}$C NMR (100 MHz, CDCl$_3$) δ: 51.87, 96.53, 113.44, 127.03, 132.95, 150.24, 165.92. MS (ESI): m/z (%)=300.19 (M+Na$^+$).

Methyl 4-amino-2-((4-nitrophenyl)thio)benzoate (10)

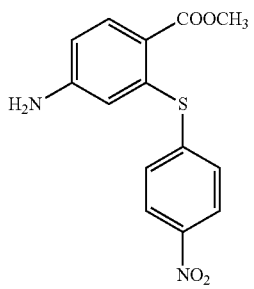

10

In a 100 ml oven dried two-neck round bottom flask compound 9 (2.5 g, 9.02 mmol) was dissolved in anhydrous dimethylethylene glycol (50 ml) followed by anhydrous potassium carbonate (2.49 g, 18.04 mmol, 2.0 equiv.) and catalyst copper iodide (85.94 mg, 0.45 mmol, 5 mol %) and the resulted mixture was stirred for 10 minutes under nitrogen pressure. To the above mixture was added 4-nitrothiophenol (1.68 g. 10.84 mmol, 1.2 equiv.) dissolved in 2 ml of anhydrous DME and the resulted mixture was stirred at 80° C. for a period of 5 hours till TLC showed the completion of the reaction. The reaction mixture was poured in to ice-cold water followed by the extraction with EtOAc (3×25 ml). Organic extractions were combined, treated sequentially with saturated potassium carbonate solution, saturated brine solution and anhydrous sodium sulphate. The dried organic extract was adsorbed on silica gel and flash chromatography using EtOAc: petroleum ether (1:1) followed by eluting with EtOAc afforded the compound 10 as a deep yellow solid (2.74 g, 88% yield).

$^1$H NMR (400 MHz, DMSO-d$_6$, TMS) δ: 3.66 (s, 3H), 5.99 (broad singlet, 2H), 6.17 (d, 1H, J=1.83 Hz), 6.40-6.44 (dd, 1H, J$_1$=2.29 Hz, J$_2$=8.70 Hz), 7.57 (d, 2H, J=8.70 Hz), 7.66 (d, 1H, J=8.24 Hz), 8.19 (d, 2H, J=8.70 Hz). $^{13}$C NMR (100 MHz, DMSO-d$_6$) δ: 51.44, 111.54, 113.95, 114.47, 124.47, 132.97, 133.09, 139.02, 144.14, 146.59, 153.22, 165.59. MS (ESI): m/z (%)=327.24 (M+Na$^+$).

Methyl 4-azido-2-((4-nitrophenyl)thio)benzoate (11)

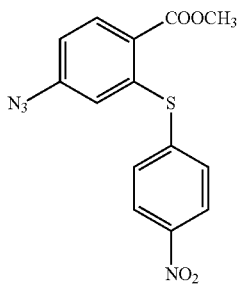

In a 100 ml round bottom flask compound 10 (1.5 g, 4.93 mmol) was dissolved in 20 ml 5N HCl at 0° C. and stirred for 30 minutes to insure the formation of hydrochloride salt. NaNO$_2$ (0.408 g, 5.91 mmol, 1.2 equiv.) was dissolved in minimum amount of water and added drop wise to the above mixture at −10° C. Stirring was continued at the same temperature for a period of 2 hours to obtain diazonium hydrochloride salt. Urea (approximately 200 mg) was added to the mixture to remove if any excess nitrous acid remained in the reaction mixture. In a separate beaker was dissolved NaN$_3$ (0.641 g, 9.86 mmol, 1.2 equiv.) in 15 ml of deionized water and kept stirring at a temperature of −10° C. To this solution of sodium azide was added the diazonium hydrochloride drop wise using addition funnel at a temperature around −10° C. Stirring of the reaction continued for a period of 8 hours at room temperature. The reaction mixture was diluted with 25 ml of EtOAc and 25 ml of deionized water. Organic layer was separated and was sequentially treated with saturated NaHCO$_3$, saturated brine, and anhydrous Na$_2$SO$_4$ followed by the adsorption of silica gel. Flash chromatography using EtOAc: petroleum ether (1:4) afforded the azide compound 11 as a light yellow solid (1.11 g, 68% yield).

$^1$H NMR (400 MHz, CDCl$_3$, TMS) δ: 3.92 (s, 3H), 6.58 (d, 1H, J=1.83 Hz), 6.92-6.97 (dd, 1H, J$_1$=2.29 Hz, J$_2$=8.24 Hz), 7.60 (d, 2H, J=9.16 Hz), 8.03 (d, 1H, J=8.24 Hz), 8.24 (d, 2H, J=8.70 Hz). $^{13}$C NMR (100 MHz, CDCl$_3$) δ: 52.46, 116.50, 119.92, 124.59, 125.19, 133.06, 133.63, 141.35, 142.64, 144.71, 147.57, 165.88. MS (ESI): m/z (%)=353.34 (M+Na$^+$).

4-azido-2-((4-nitrophenyl)thio)benzoic Acid (12)

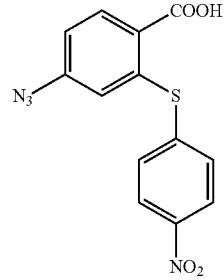

In a 25 ml round bottom flask was taken methyl ester compound 11 (0.50 g, 1.51 mmol) and dissolved in 10 ml of THF/CH$_3$OH/H$_2$O (4:2:1). To this solution lithium hydroxide hydrate (0.127 g, 3.02 mmol, 2 equiv.) was added and stirred for a period of 5 hours at room temperature. TLC (EtOAc/hexane, 1:1) showed the completion of the reaction. Organic solvents were evaporated in vacuo and the residue was diluted by adding 10 ml deionized water and the traces of unreacted starting material were removed by washing with EtOAc (2×5 ml). The aqueous layer was separated and treated with 2N HCl solution leading to the precipitation of the compound. The precipitate was filtered and dried to afford a colorless solid compound 12 (0.44 g, 92% yield).

$^1$H NMR (400 MHz, DMSO-d$_6$, TMS) δ 6.55 (d, 1H, J=1.83 Hz), 7.12-7.18 (dd, 1H, J=2.29 Hz, J$_2$=8.70 Hz), 7.71 (d, 2H, J=9.16 Hz), 8.00 (d, 1H, J=8.24 Hz), 8.27 (d, 2H, J=8.70 Hz). $^{13}$C NMR (100 MHz, DMSO-d$_6$) δ: 117.09, 119.28, 124.65, 126.03, 132.98, 133.73, 139.91, 142.29, 143.78, 147.17, 166.60. MS (ESI): m/z (%)=288.44 (M−N$_2$+Na$^+$, 50), 339.32 (M+Na$^+$, 100).

Methyl 4-(4-azido-2-((4-nitrophenyl)thio)benzamido)-3-methoxybenzoate (13)

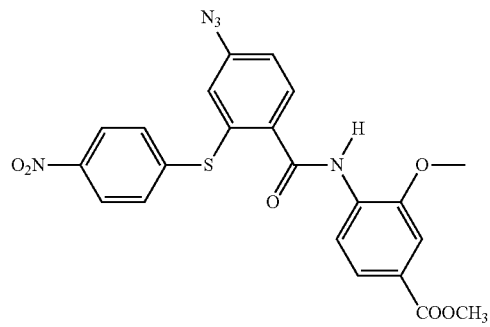

N,N-dimethylformamide (50 μl) was added to a stirred suspension of the carboxylic acid 12 (0.40 g, 1.26 mmol) and thionyl chloride (0.22 g, 1.86 mmol, 1.5 equiv) in dry benzene (5 mL) and heated up to 60° C. for a period of 2 hours till a transparent solution obtained. After evaporation of benzene in vacuo, the resultant yellow solid was dissolved in dry THF (5 mL) and added drop wise for a period of 10 minutes to a stirred mixture of methyl 4-amino-3-methoxybenzoate (0.34 g, 1.88 mmol, 1.5 equiv) and Et$_3$N (2 mL) dissolved in 5 mL of dry THF at 0° C. The reaction mixture was gradually heated up to 55° C. for a period of 5 hours. After removal of the solvent by evaporation in vacuo, the residue was diluted with water (10 mL) and extracted with EtOAc (3×10 mL). The combined organic phase was sequentially washed with 1N HCl (10 mL), saturated solution of sodium bicarbonate (10 ml) and brine followed by treatment with anhydrous $Na_2SO_4$. Flash column chromatography using EtOAc: petroleum ether, (1:3) to afford the corresponding amide as a yellow solid 13 (0.496 g, 82% yield).

$^1$H NMR (400 MHz, CDCl$_3$, TMS) δ: 3.89 (s, 3H), 3.91 (s, 3H), 7.09 (d, 1H, J=1.83 Hz), 7.14-7.18 (dd, 1H, $J_1$=2.29 Hz, $J_2$=8.24 Hz), 7.35 (d, 2H, J=9.16 Hz), 7.55 (d, 1H, J=1.83 Hz), 7.67-7.71 (dd, 1H, $J_1$=1.83 Hz, $J_2$=8.24 Hz), 7.84 (d, 1H, J=8.24 Hz), 8.11 (d, 2H, J=8.70 Hz), 8.47 (d, 1H, J=8.24 Hz), 8.74 (s, 1H). $^{13}$C NMR (100 MHz, CDCl$_3$) δ: 52.09, 55.96, 110.66, 118.68, 119.31, 123.31, 124.28, 124.53, 125.58, 129.60, 131.07, 131.38, 133.40, 134.52, 143.64, 144.56, 146.43, 147.44, 164.37, 166.50, 104091 MS (ESI): m/z (%)=437.23 (M−N$_3$+Na$^+$, 100), 474.19 (M−N$_2$+Na$^+$, 20), 502.14 (M+Na$^+$, 55).

4-(4-azido-2-((4-nitrophenyl)thio)benzamido)-3-methoxybenzoic Acid (14)

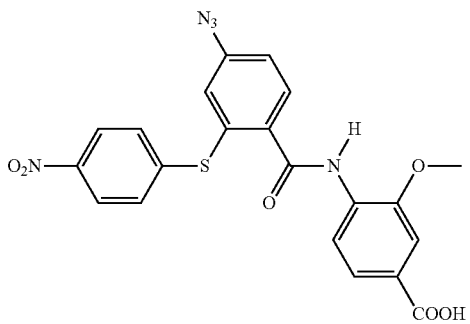

In a 25 ml round bottom flask was taken methyl ester compound 13 (0.35 g, 0.73 mmol) and dissolved in 10 ml of 1,2-dichloroethane solvent. To this solution trimethyltin hydroxide (0.792 g, 4.38 mmol, 6.0 equiv.) was refluxed at 80° C. for a period of 6 hours. TLC (EtOAc/hexane, 1:1) showed the completion of the reaction. Organic solvents were evaporated in vacuo and the residue was diluted by adding 10 ml deionized water and the traces of unreacted starting material were removed by washing with EtOAc (2×5 ml). The aqueous layer was separated and treated with 2N HCl solution leading to the precipitation of the compound. The precipitate was filtered and dried to afford a light yellow solid compound 14 (0.288 g, 85% yield).

$^1$H NMR (400 MHz, DMSO-d$_6$, TMS) δ: 3.84 (s, 3H), 7.16 (d, 1H, J=1.83 Hz), 7.31-7.37 (dd, 1H, $J_1$=2.29 Hz, $J_2$=8.24 Hz), 7.45 (d, 2H, J=9.16 Hz), 7.52 (s, 1H), 7.55 (d, 1H, J=8.70 Hz), 7.79 (d, 1H, J=8.70 Hz), 8.07 (d, 1H, J=7.33 Hz), 8.14 (d, 2H, J=9.16 Hz), 9.80 (s, 1H). $^{13}$C NMR (100 MHz, DMSO-d$_6$) δ 55.77, 111.46, 119.66, 121.09, 122.05, 124.21, 126.97, 129.19, 130.65, 131.05, 131.84, 136.38, 142.19, 145.44, 145.57, 145.69, 149.40, 165.37, 166.87. MS (ESI): m/z (%/o)=460.24 (M−N$_2$+Na$^+$, 10), 488.26 (M+Na$^+$, 100).

4-azido-N-(2-methoxy-4-((13-oxo-17-(2-oxohexahydro-1H-thieno[3,4-d]imidazol-4-yl)-3,6,9-trioxa-12-azaheptadecyl)carbamoyl)phenyl)-2-((4-nitrophenyl)thio)benzamide (IMD-55)

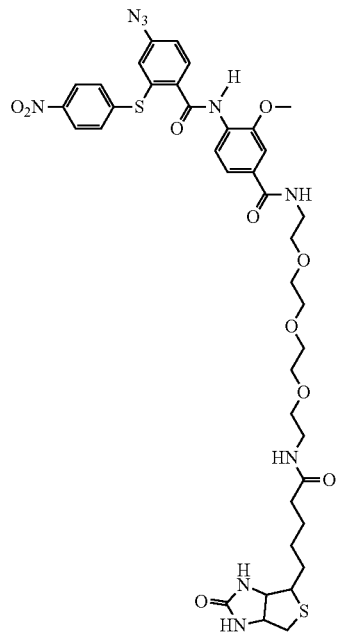

Procedure described for the synthesis of compound IMA-82 was followed for coupling reaction between carboxylic acid 14 (50.0 mg) and Amine-PEG3-Biotin (45.0 mg) leading to the formation of a yellow solid IMD-55 (78.12 mg, 84% yield).

$^1$H NMR (400 MHz, CDCl$_3$, TMS) δ: 1.24-1.37 (m, 2H), 1.45-1.68 (m, 4H), 2.04-2.14 (m, 2H), 2.55-2.68 (m, 1H), 2.74-2.84 (m, 1H), 2.98-3.06 (m, 1H), 3.26-3.36 (m, 2H), 3.41-3.68 (m, 14H), 3.81 (s, 3H), 4.16-4.23 (m, 1H), 4.35-4.44 (m, 1H), 5.66 (s, 1H), 6.45 (s, 1H), 6.78 (s, 1H), 7.00 (s, 1H), 7.08 (d, 1H, J=8.24 Hz), 7.23-7.39 (m, 4H), 7.45 (s, 1H), 7.76 (d, 1H, J=8.24 Hz), 8.02 (d, 2H, J=8.70 Hz), 8.31 (d, 1H, J=8.24 Hz), 8.66 (s, 1H). $^{13}$C NMR (100 MHz, CDCl$_3$) δ: 25.51, 27.97, 28.11, 35.77, 39.01, 39.82, 40.42, 55.50, 56.01, 60.16, 61.76, 69.87, 69.91, 70.08, 70.28, 109.74, 118.73, 119.34, 119.40, 124.31, 124.47, 129.66, 129.90, 130.18, 131.11, 133.36, 134.55, 143.61, 144.61, 146.43, 147.96, 164.09, 164.47, 166.83, 173.46. MS (ESI): m/z (%)=860.48 (M−N$_2$+Na$^+$, 63), 888.52 (M+Na$^+$, 100), 889.52 (M+1+Na$^+$, 47), 890.46 (M+2+Na$^+$, 20). IR (KBr): Vmax 3306.10, 3272.34, 3261.74, 3231.84, 3192.30, 3093.92, 3068.85, 3054.38, 2928.04, 2919.36, 2865.35, 2110.19, 1694.52, 1652.09, 1645.33, 1589.40, 1512.24, 1471.74, 1464.02, 1408.08, 1336.71, 1301.03, 126.35, 1131.29, 1108.14, 1086.92, 1030.02, 907.54, 852.56, 727.19 cm$^{-1}$.

2-methoxy-N-(13-oxo-17-(2-oxohexahydro-1H-thieno[3,4-d]imidazol-4-yl)-3,6,9-trioxa-12-azaheptadecyl)benzamide (IMD-41)

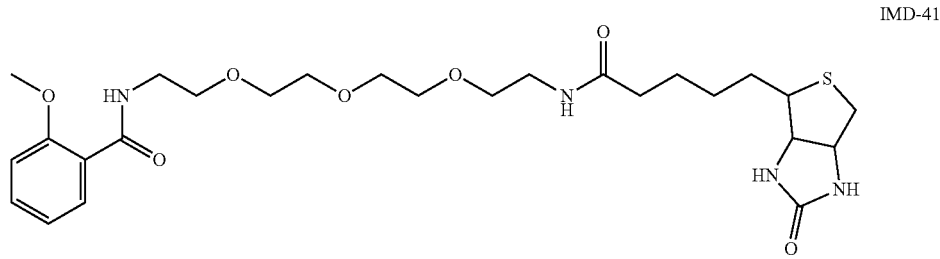 [SMILES: COc1ccccc1C(=O)NCCOCCOCCOCCNC(=O)CCCCC1SCC2NC(=O)NC21]

Procedure described for the synthesis of compound IMA-82 was followed for coupling reaction between o-anisic acid (18.2 mg) and Amine-PEG3-Biotin (50.0 mg) leading to the formation of a pale yellow gummy solid IMD-41 (51.55 mg, 78% yield).

$^1$H NMR (400 MHz, CDCl$_3$, TMS) δ: 1.33-1.45 (m, 2H), 1.55-1.76 (m, 4H), 2.14-2.24 (m, 2H), 2.67-2.91 (m, 2H), 3.05-3.13 (m, 1H), 3.35-3.44 (m, 2H), 3.48-3.72 (m, 14H), 3.95 (s, 3H), 4.23-4.31 (m, 1H), 4.42-4.50 (m, 1H), 5.71 (s, 1H), 6.51 (s, 1H), 6.91-7.11 (m, 3H), 7.40-7.48 (m, 1H), 8.13-8.18 (dd, 1H, J$_1$=1.37 Hz, J$_2$=7.79 Hz), 8.24 (s, 1H). $^{13}$C NMR (100 MHz, CDCl$_3$) δ: 25.51, 27.94, 28.10, 35.76, 39.10, 39.48, 40.43, 55.50, 55.93, 60.18, 61.77, 69.88, 69.99, 70.20, 70.33, 70.42, 111.37, 121.20, 132.04, 132.82, 157.50, 164.06, 165.52, 173.59. MS (ESI): m/z (%)=575.28 (M+Na$^+$, 100).

4-Azidobenzoic Acid (15)

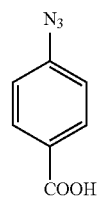

In a 100 ml round bottom flask p-aminobenzoic acid, PABA (1.0 g, 7.30 mmol) was dissolved in 15 ml 5N HCl at 0° C. and stirred for 30 minutes to insure the formation of hydrochloride salt. NaNO$_2$ (0.604 g, 8.75 mmol, 1.2 equiv.) was dissolved in minimum amount of water and added drop wise to the above mixture at −10° C. Stirring was continued at the same temperature for a period of 2 hours to obtain diazonium hydrochloride salt. Urea (approximately 200 mg) was added to the mixture to remove if any excess nitrous acid remained in the reaction mixture. In a separate beaker was dissolved NaN$_3$ (0.641 g, 10.94 mmol, 1.5 equiv.) in 15 ml of deionized water and kept stirring at a temperature of −10° C. To this solution of sodium azide was added the diazonium hydrochloride drop wise using addition funnel at a temperature around −10° C. Stirring of the reaction continued for a period of 8 hours at room temperature. The reaction mixture was diluted with 50 ml of deionized water and the mixture was filtered to get crude solid compound. This was washed several times with deionized water and petroleum ether to get dried pure colorless solid 15 (0.83 g, 70% yield).

$^1$H NMR (400 MHz, DMSO-d$_6$, TMS) δ: 7.22 (d, 2H, J=8.70 Hz), 7.96 (d, 2H, J=8.70 Hz). $^{13}$C NMR (100 MHz, DMSO-d$_6$) δ: 119.16, 127.28, 131.20, 143.94, 166.55.

4-Azido-N-(13-oxo-17-(2-oxohexahydro-1H-thieno[3,4-d]imidazol-4-yl)-3,6,9-trioxa-12-azaheptadecyl)benzamide (IMD-64)

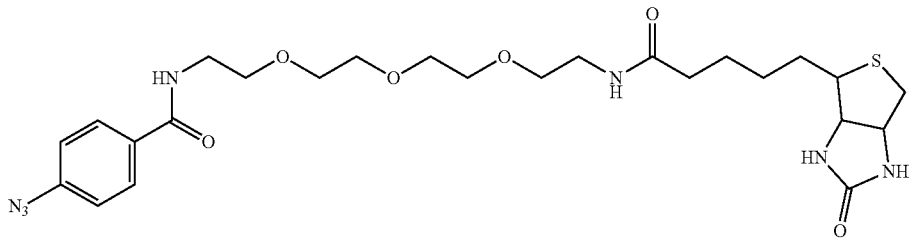

Procedure described for the synthesis of compound IMA-82 was followed for coupling reaction between the compound 15 (20.0 mg) and Amine-PEG3-Biotin (50.0 mg) leading to the formation of a pale yellow gummy solid IMD-64 (56.64 mg, 82% yield).

$^1$H NMR (400 MHz, CDCl$_3$, TMS) δ: 1.32-1.44 (m, 2H), 1.52-1.74 (m, 4H), 2.12-2.22 (m, 2H), 2.66-2.75 (m, 1H), 2.78-2.91 (m, 1H), 3.04-3.14 (m, 1H), 3.32-3.43 (m, 2H), 3.46-3.70 (m, 14H), 4.22-4.30 (m, 1H), 4.43-4.51 (m, 1H), 5.71 (s, 1H), 6.56 (s, 1H), 6.95 (s, 1H), 7.04 (d, 2H, J=8.70 Hz), 7.43 (s, 1H), 7.86 (d, 2H, J=8.24 Hz). $^{13}$C NMR (100 MHz, CDCl$_3$) δ: 25.52, 27.94, 28.08, 35.74, 39.09, 39.81, 40.43, 55.51, 60.23, 61.81, 69.88, 69.91, 70.04, 70.24, 70.27, 118.83, 128.99, 130.85, 143.15, 164.15, 166.71, 173.68. MS (ESI): m/z (%)=558.29 (M−N$_2$+Na$^+$, 100), 586.26 (M+Na$^+$, 63).

Proposed Explanation of Unrequired Amide Hydrolysis of Compounds 6 and 13 by LiOH

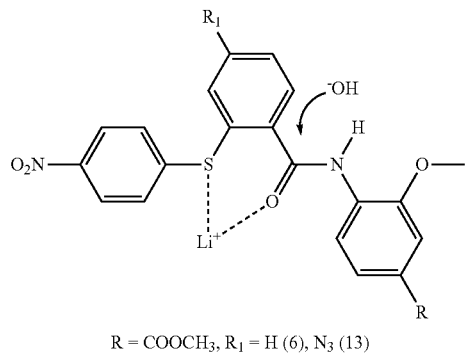

R = COOCH$_3$, R$_1$ = H (6), N$_3$ (13)

REFERENCES (EXAMPLE 1)

[1] Goff, S. P. Retrovirus restriction factors. Mol. Cell 16, 849-859 (2004); [2] Malim, M. H. & Bieniasz, P. D. HIV Restriction Factors and Mechanisms of Evasion. Cold Spring Harbor perspectives in medicine 2, a006940, (2012); [3] Wolf, D. & Goff, S. P. Host restriction factors blocking retroviral replication. Annual review of genetics 42, 143-163, (2008); [4] Albin, J. S. & Harris, R. S. Interactions of host APOBEC3 restriction factors with HIV-1 in vivo: implications for therapeutics. Expert Rev. Mol. Med. 12, e4 (2010); [5] Cullen, B. R. Role and mechanism of action of the APOBEC3 family of antiretroviral resistance factors. J. Virol. 80, 1067-1076 (2006); [6] Navarro, F. & Landau, N. R. Recent insights into HIV-1 Vif. Curr. Opin. Immunol. 16, 477-482 (2004); [7] Prohaska, K. M., Bennett, R. P., Salter, J. D. & Smith, H. C. The multifaceted roles of RNA binding in APOBEC cytidine deaminase functions. Wiley interdisciplinary reviews. RNA 5, 493-508, (2014); [8] Sheehy, A. M., Gaddis, N. C., Choi, J. D. & Malim, M. H. Isolation of a human gene that inhibits HIV-1 infection and is suppressed by the viral Vif protein. Nature 418, 646-650 (2002); [9] Marin, M., Rose, K. M., Kozak, S. L. & Kabat, D. HIV-1 Vif protein binds the editing enzyme APOBEC3G and induces its degradation. Nature Med. 9, 1398-1403 (2003); [10] Mehle, A. et al. Vif overcomes the innate antiviral activity of APOBEC3G by promoting its degradation in the ubiquitin-proteasome pathway. The Journal of biological chemistry 279, 7792-7798, (2004); [11] Mehle, A., Goncalves, J., Santa-Marta, M., McPike, M. & Gabuzda, D. Phosphorylation of a novel SOCS-box regulates assembly of the HIV-1 Vif-Cul5 complex that promotes APOBEC3G degradation. Genes Dev. 18, 2861-2866 (2004); [12] Stopak, K., de Noronha, C., Yonemoto, W. & Greene, W. C. HIV-1 Vif blocks the antiviral activity of APOBEC3G by impairing both its translation and intracellular stability. Mol. Cell 12, 591-601 (2003); [13] Yu, X. et al. Induction of APOBEC3G ubiquitination and degradation by an HIV-1 Vif-Cul5-SCF complex. Science 302, 1056-1060, (2003); [14] Yu, Y., Xiao, Z., Ehrlich, E. S., Yu, X. & Yu, X. F. Selective assembly of HIV-1 Vif-CUL5-ElonginB-ElonginC E3 ubiquitin ligase complex through a novel SOCS box and upstream cysteines. Genes Dev. 18, 2867-2872 (2004); [15] Bergeron, J. R. et al. The SOCS-box of HIV-1 Vif interacts with ElonginBC by induced-folding to recruit its Cul5-containing ubiquitin ligase complex. PLoS pathogens 6, e1000925, (2010); [16] Sheehy, A. M., Gaddis, N. C. & Malim, M. H. The antiretroviral enzyme APOBEC3G is degraded by the proteasome in response to HIV-1 Vif. Nature Med. 9, 1404-1407 (2003); [17] Ali, A. et al. Synthesis and structure-activity relationship studies of HIV-1 virion infectivity factor (Vif) inhibitors that block viral replication. ChemMedChem 7, 1217-1229, (2012); [18] Mohammed, I. et al. SAR and Lead Optimization of an HIV-1 Vif-APOBEC3G Axis Inhibitor. Acs Medicinal Chemistry Letters 3, 465-469, (2012); [19] Nathans, R. et al. Small-molecule inhibition of HIV-1 Vif. Nat Biotechnol 26, 1187-1192, (2008); [20] Taipale, M., Jarosz, D. F. & Lindquist, S. HSP90 at the hub of protein homeostasis: emerging mechanistic insights. Nature reviews. Molecular cell biology 11, 515-528, (2010); [21] Jager, S. et al. Vif hijacks CBF-beta to degrade APOBEC3G and promote HIV-1 infection. Nature 481, 371-375, (2012); [22] Zhang, W., Du, J., Evans, S. L., Yu, Y. & Yu, X. F. T-cell differentiation factor CBF-beta regulates HIV-1 Vif-mediated evasion of host restriction. Nature 481, 376-379, (2012); [23] Karagoz, G. E. & Rudiger, S. G. Hsp90 interaction with clients. Trends in biochemical sciences 40, 117-125, (2015); [24] Blagosklonny, M. V. Hsp-90-associated oncoproteins: multiple targets of geldanamycin and its analogs. Leukemia 16, 455-462, (2002); [25] Trepel, J., Mollapour, M., Giaccone, G. & Neckers, L. Targeting the dynamic HSP90 complex in cancer. Nature reviews. Cancer 10, 537-549, (2010); [26] Ehrlich, E. S. et al. Regulation of Hsp90 client proteins by a Cullin5-RING E3 ubiquitin ligase. Proceedings of the National Academy of Sciences of the United States of America 106, 20330-20335, (2009); [27] Samant, R. S., Clarke, P. A. & Workman, P. E3 ubiquitin ligase Cullin-5 modulates multiple molecular and cellular responses to heat shock protein 90 inhibition in human cancer cells. Proceedings of the National Academy of Sciences of the United States of America 111, 6834-6839, (2014).

Example 2. Triazole Based HIV-1 Vif Antagonists: Candidates for Novel A1 DS Therapeutics Peptidomimetic replacement of amide functionality in RN-18 (IC$_{50}$=6 μM), an HIV-1 Vif-APOBEC3G axis inhibitor, by peptidomimetic heterocycles has led to the discovery of a novel 1,4-disubstituted-1H-1,2,3-trizole analogue, 1d (IMA-53, IC$_{50}$=1.2 μM) with improved profile as HIV-1 replication inhibitor. Owing to the activity, metabolic stability, and synthetic feasibility of the 1,2,3-trizole scaffold, an 84 member library has been synthesized using reactions like Cham-Lam type coupling, Sonogashira reaction, copper (I) catalyzed click chemistry, and Buchwald's S-arylation. Noteworthy, among several highly potent inhibitors discovered from the library, are 5ax ($IC_{50}$=0.01 µM), 5bx ($IC_{50}$=0.2 µM), 2ey ($IC_{50}$=0.4 µM), and 5ey ($IC_{50}$=0.6 µM). Three water-soluble choline salts 2gy ($IC_{50}$=0.2 µM), 4gy ($IC_{50}$=0.7 µM), and 5gy ($IC_{50}$=0.5 µM) exhibited potent antiviral activities. Preclinical animal studies for selected compounds from the library are in progress.

Significant efforts are being made for the improvement of antiretroviral agents targeting crucial HIV-1 enzymes mainly reverse transcriptase,[1] protease,[2] and integrase.[3] But, due to the very high mutation rate in the viral genome multidrug resistance (MDR) strains of HIV is emerging, which is making the antiretroviral drugs practically ineffective.[4] In AIDS patients, MDR HIV-1 strains are not susceptible to the administration of any single drug, which necessitated the development of a combination strategy called "highly active antiretroviral therapy" (HAART)[5] HAART consists of a combination of three or more antiretroviral agents (HIV protease and reverse transcriptase inhibitors), which suppresses the MDR HIV-1 strains, reduces plasma viral load, enhances CD4+ count, and lowers the mortality rate in AIDS patients. Although significant impact was made due to HAART, the strategy has the following demerits: expensive for HIV-1 prevalent third world patients, requires life-long administration, causes serious metabolic and cardiovascular side effects, and potentially increases risk to develop resistant HIV-1 strains among non-adherent patients.[6] Due to the current problems and challenges in anti-HIV drug discovery, many research groups are now focusing on finding new druggable targets in HIV physiology using forward chemical genetics approach. This strategy relies on libraries of diverse set of drug-like chemical compounds and one such efforts resulted in the discovery of RN-18, 1a as a specific inhibitor of HIV Vif-APOBEC3G (A3G) axis.[7]

Mortality in AIDS patients is mainly due to the weakening of their immune system as HIV-1 mainly infects T lymphocytes. Nonetheless, CD4+ T lymphocytes ('non-permissive' cells) have a defensive restriction factor called APOBEC3G (A3G), which catalyzes antiviral G-to-A hypermutations in the HIV-1 DNA. In addition to the hypermutation activity, A3G exerts direct effects on reverse transcription and integration of HIV genome.[8] HIV-1 counteracts the host defensive factor by the expression of viral infectivity (Vif) protein in CD4 T lymphocytes. Vif protects the viral genome by inhibiting A3G packaging into virions and by promoting ubiquitin mediated proteosomal degradation of A3G.[9] However, HIV-1 replication does not depend on the expression of Vif protein in 'permissive' cells host cells (which do not express A3G).

RN-18 (1a) antagonizes Vif protein, enhances its degradation, increases A3G incorporation into virions and hence significantly reduces HIV-1 infectivity in T lymphocytes. RN-18 exhibits $IC_{50}$ values of 4.5 µM and 6 µM in CEM cells and H9 cells (non-permissive cells) respectively. It does not show any activity in MT4 cell line (permissive cells) a concentrations of 100 µM. This finding provided a new and unique approach against HIV and it is highly probable that this may slow down substantially the problem of drug resistance in HIV.[10]

Figure 14:
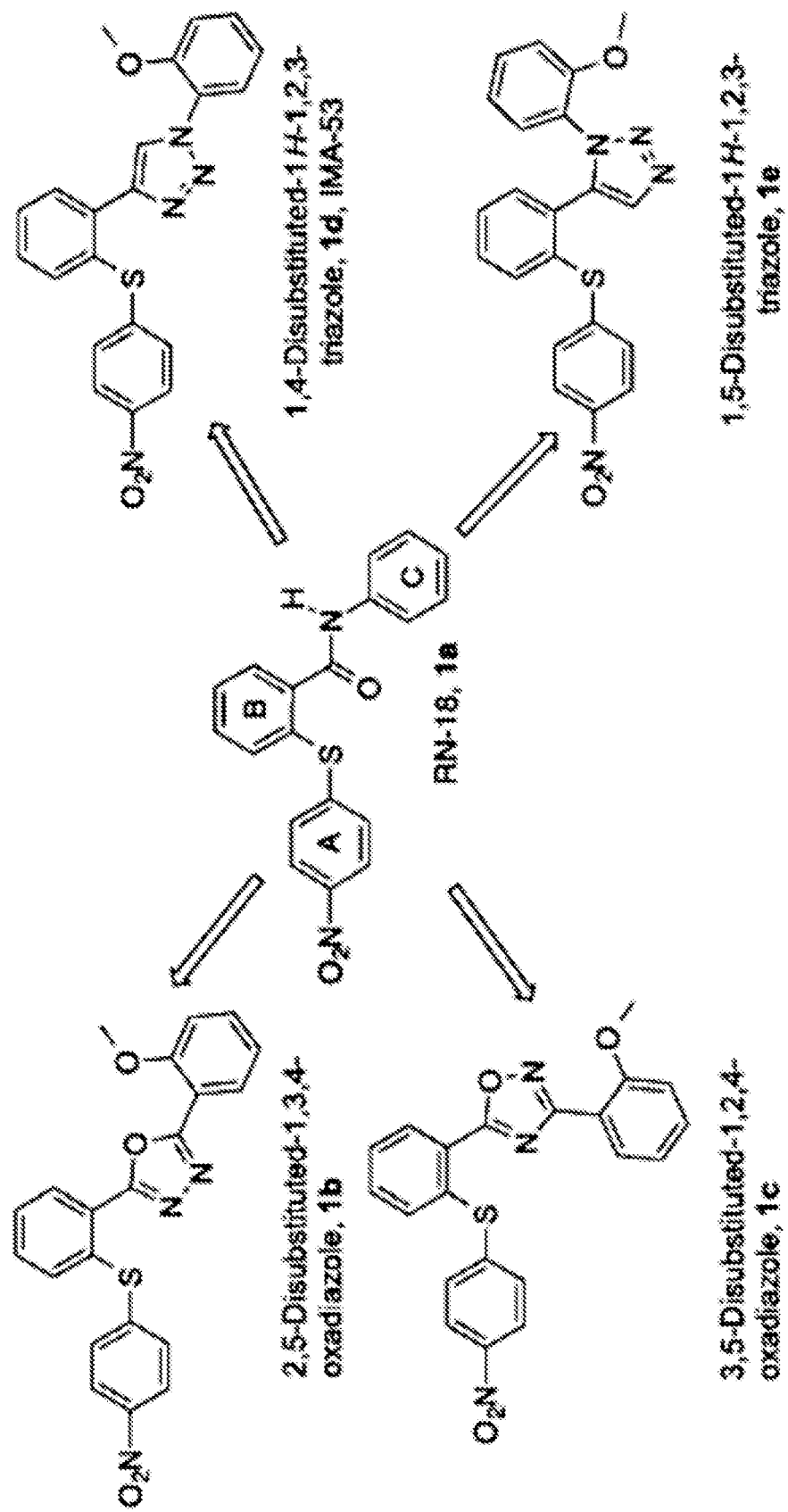
FIG. 14. Peptidomimetic analogues of 1a, RN-18. Compound 1b, 1d (IMA-53), 1c, and 1e.

Earlier we have published our preliminary SAR results of RN-18.[11] In this communication; we describe our success toward the lead optimization of RN-18 by bioisosteric replacement of amide functionality by peptidomimetic heterocyclic systems. In this study, our basic idea was to test conformationally restricted peptide surrogates in place of amide functionality in RN-18 1a aiming to improve both activity and pharmacological profile of the lead molecule. Initially, we designed and synthesized four test molecules by substituting the amide functionality in the lead molecule with peptidomimetic heterocyclic systems such as 1,3,4-oxadiazole 1b,[12] 1,2,4-oxadiazole 1c,[13] 1,4-disubstituted-1,2,3-triazole[14] 1d and 1,5-disubstituted-1,2,3-triazole 1e[15] (FIG. 14). The synthetic schemes have been given in the as Scheme 1S. The antiviral activities of the four synthesized RN-18 analogues were measured against wild-type HIV-1 both in non-permissive H9 cells and permissive MT-4 cells (See details of methods in S.I.). In all the antiviral experiments, RN-18 (1) was used as a positive control and the cells cultured without any inhibitor served as negative control. Measurements of the antiviral activity in cultured cells were repeated at least 3 times and the $IC_{50}$ values were calculated using GraFit software. The $IC_{50}$ values of the bioisosteric analogues of RN-18 are presented in Table 1. Both 1,3,4-oxadiazole 1b ($IC_{50}$=6.8 µM) and 1,2,4-oxadiazole 1c ($IC_{50}$=6.8 µM) based analogues exhibited same cell-based antiviral activity in the non-permissive H9 cells as compared with the lead molecule RN-18 ($IC_{50}$=6 µM). However, 2,5-disubstituted-1,3,4-oxadiazole 1b showed some non-specific antiviral activity with $IC_{50}$ of 50 µM in permissive MT4 cells. Whereas the 1,4-disubstituted-1,2,3-triazole based analogue 1d exhibited (Table 1) remarkably better cell-based anti-HIV activity ($IC_{50}$=1.2 µM in H9 cells) and specificity (no activity in MT4 cells). On the contrary, 1,5-disubstituted-1,2,3-triazole 1e analogue exhibited comparatively lesser potency ($IC_{50}$=15 µM in H9 cells) with some non-specific activity in the permissive cells ($IC_{50}$=25 µM in MT4 cells).

TABLE 1

$IC_{50}$ values of the peptidomimetic analogues

| Compd. | Antiviral activity ($IC_{50}$ µM) | |
|---|---|---|
| | H9 cells | MT4 cells |
| 1a, RN-18 | 6 | N.A. |
| 1b | 6.8 | 50 |
| 1c | 6.8 | N.A. |
| 1d, IMA-53 | 1.2 | N.A. |
| 1e | 15 | 25 |

N.A. = no activity 50 µM conc.

Figure 15:
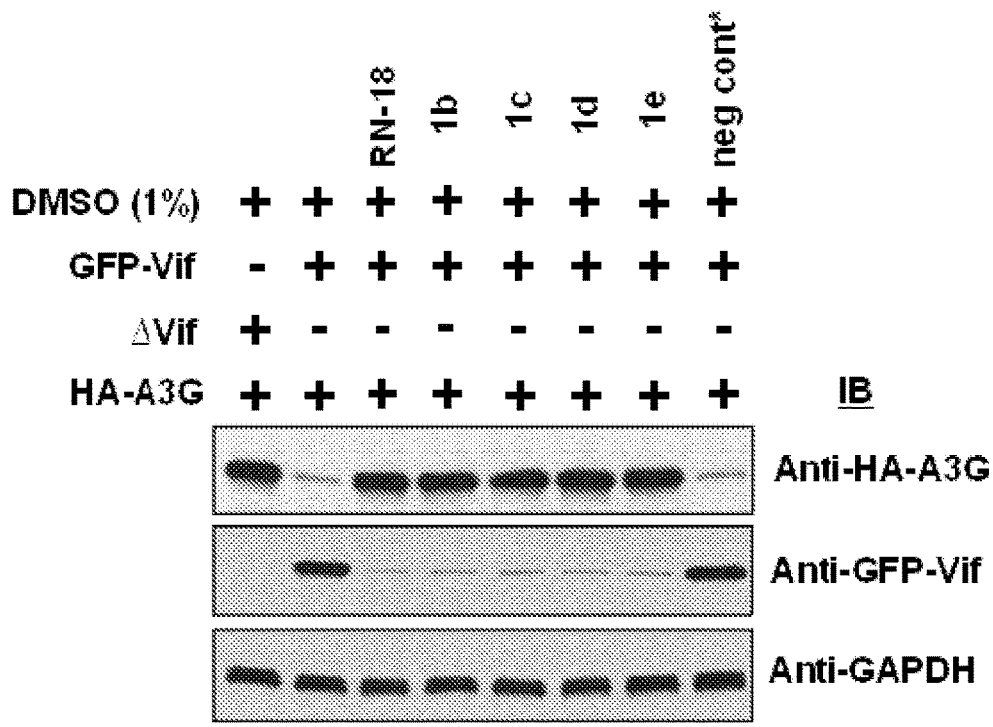
FIG. 15. Bioisosteric analogues of RN-18 enhance A3G levels and reduce Vif expression. 293FT cells co-expressing HA-tagged A3G and GFP-tagged Vif or ΔVif were grown for 16 h in the presence of (50 μM) or in the absence of compounds. Negative control (compound 8s). Cell extracts were analyzed by immunoblotting with anti-HA-A3G, anti-GFP-Vif, and anti-GAPDH antibodies.

We then checked whether the analogues could up-regulate A3G and down-regulate Vif, as was shown for RN-18.[7] 293FT cells co-expressing hemagglutinin (HA)-tagged A3G and green fluorescent protein (GFP)-tagged Vif or ΔVif were grown alone or in the presence of the compounds (50 µM) for 16 h (see S.I. for methods details). The cell extracts were then analyzed by immunoblotting with anti-HA-A3G, anti-GFP-Vif, and anti-GAPDH antibodies (FIG. 15). Surprisingly, all the peptidomimetic analogues of RN-18 exhibited up-regulation of A3G and downregulation of Vif as shown by RN-18. Hence it could be inferred that all the peptidomimetic analogues (1b, 1c, 1d and 1e) could interact with target protein of RN-18 at 50 µM concentration and exhibited the required mechanistic phenotype.

These interesting observations could also be inferred from the crystal structures of the analogues showing significant similarities in the three-dimensional orientations and planarity except the 1,5-disubstituted-1,2,3-triazole 1e analogue, which has a twisted structure (see the single crystal x-ray diffraction data attached as separate files). 1,3,4-Oxadiazole and 1,2,4-oxadiazole heterocyclic systems have both planarity and dipole moment similar to amide functionality. Similarly, 1,4-Disubstituted and 1,5-disubstituted 1,2,3-triazoles both are capable of mimicking amide functionality. They possess strong dipole moment (amide approximately 4 Debye and triazole approximately 5 Debye) beside having better H-bond accepting and H-bond donating (triazole C(5)-H or C(4)-H) capacity than an amide functionality.[16] However in the present case, 1,4-disubstituted-1,2,3-triazle 1d analogue showed both improved antiviral activity ($IC_{50}$=1.2 µM) and selectivity (no activity in MT4 cells). The x-ray crystal structure of RN-18 showed that it is a trans (Z–) amide compound and the crystal structure of 1d showed geometrical orientation similar to Z-amide.

Having discovered 1,4-disubstituted-1,2,3-triazole 1d as a potent and specific inhibitor of Vif-APOBEC3G axis, we decided to optimize it to generate anti-HIV drug candidates for clinical development. An 84-membered library was designed and synthesized in a parallel format exploring various substitution patterns in ring-A, ring-C and bridge A-B (Table 2). Synthetic schemes (see Schemes 2S to 7S), experimental procedures and characterization data of all the 84 members of the library are disclosed herein. Some of the key reactions involved in the parallel synthesis were Cham-Lam type coupling for the synthesis of aryl azides,[17] Sonogashira reaction for alkyne synthon,[18] copper (I) catalyzed click chemistry for 1,5-disubstituted-1,2,3-triazole synthesis,[19] and Buchwald's S-arylation.[20] Anti-viral activities of the library were determined against wild-type HIV-1 both in non-permissive H9 and permissive MT-4 cells. The $IC_{50}$ values for all the synthesized compounds are presented in Table 2.

TABLE 2

$IC_{50}$ values of the library $R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | $R_1$ | $R_2$ | Antiviral activity ($IC_{50}$ µM) H9 | MT4 |
|---|---|---|---|---|---|
| 2ax (1d) | S | H | NO$_2$ | 1.2 | N.A. |
| 2bx | S | H | COOCH$_3$ | N.A. | N.A. |
| 2cx | S | H | OCH$_3$ | N.T. | N.T. |
| 2dx | S | H | CF$_3$ | 2.6 | N.A. |
| 2ex | S | H | NH$_2$ | 2.5 | N.A. |
| 2fx | S | H | COOH | 1.0 | N.A. |
| 2gx | S | H | C.C.† | N.A. | N.A. |
| 2ay | SO$_2$ | H | NO$_2$ | 13.8 | N.A. |
| 2by | SO$_2$ | H | COOCH$_3$ | N.A. | N.A. |
| 2cy | SO$_2$ | H | OCH$_3$ | 4.3 | N.A. |
| 2dy | SO$_2$ | H | CF$_3$ | 4.8 | N.A. |
| 2ey | SO$_2$ | H | NH$_2$ | 0.4 | N.A. |
| 2fy | SO$_2$ | H | COOH | 8.2 | N.A. |
| 2gy | SO$_2$ | H | C.C.† | 0.2 | N.A. |
| 3ax | S | 3-OCH$_3$ | NO$_2$ | 1.1 | N.A. |
| 3bx | S | 3-OCH$_3$ | COOCH$_3$ | 8 | N.A. |
| 3cx | S | 3-OCH$_3$ | OCH$_3$ | N.T. | N.T. |
| 3dx | S | 3-OCH$_3$ | CF$_3$ | 1.9 | N.A. |
| 3ex | S | 3-OCH$_3$ | NH$_2$ | N.T. | N.T. |
| 3fx | S | 3-OCH$_3$ | COOH | 2.8 | N.A. |
| 3gx | S | 3-OCH$_3$ | C.C.† | 4.3 | N.A. |
| 3ay | SO$_2$ | 3-OCH$_3$ | NO$_2$ | N.A. | N.A. |
| 3by | SO$_2$ | 3-OCH$_3$ | COOCH$_3$ | 4.7 | N.A. |
| 3cy | SO$_2$ | 3-OCH$_3$ | OCH$_3$ | N.A. | N.A. |
| 3dy | SO$_2$ | 3-OCH$_3$ | CF$_3$ | N.A. | N.A. |
| 3ey | SO$_2$ | 3-OCH$_3$ | NH$_2$ | 12.4 | N.A. |
| 3fy | SO$_2$ | 3-OCH$_3$ | COOH | 1.4 | N.A. |
| 3gy | SO$_2$ | 3-OCH$_3$ | C.C.† | N.A. | N.A. |
| 4ax | S | 4-OCH$_3$ | NO$_2$ | N.T. | N.T. |
| 4bx | S | 4-OCH$_3$ | COOCH$_3$ | N.T. | N.T. |
| 4cx | S | 4-OCH$_3$ | OCH$_3$ | N.T. | N.T. |
| 4dx | S | 4-OCH$_3$ | CF$_3$ | N.T. | N.T. |
| 4ex | S | 4-OCH$_3$ | NH$_2$ | N.T. | N.T. |
| 4fx | S | 4-OCH$_3$ | COOH | 7.1 | N.A. |
| 4gx | S | 4-OCH$_3$ | C.C.† | N.T. | N.T. |
| 4ay | SO$_2$ | 4-OCH$_3$ | NO$_2$ | N.A. | N.A. |
| 4by | SO$_2$ | 4-OCH$_3$ | COOCH$_3$ | N.T. | N.T. |
| 4cy | SO$_2$ | 4-OCH$_3$ | OCH$_3$ | N.A. | N.A. |
| 4dy | SO$_2$ | 4-OCH$_3$ | CF$_3$ | 12 | N.A. |
| 4ey | SO$_2$ | 4-OCH$_3$ | NH$_2$ | N.T. | N.T. |
| 4fy | SO$_2$ | 4-OCH$_3$ | COOH | N.T. | N.T. |
| 4gy | SO$_2$ | 4-OCH$_3$ | C.C.† | 0.7 | N.A. |
| 5ax | S | 5-OCH$_3$ | NO$_2$ | 0.01 | N.A. |
| 5bx | S | 5-OCH$_3$ | COOCH$_3$ | 0.2 | N.A. |
| 5cx | S | 5-OCH$_3$ | OCH$_3$ | 15.7 | N.A. |
| 5dx | S | 5-OCH$_3$ | CF$_3$ | 46.4 | N.A. |
| 5ex | S | 5-OCH$_3$ | NH$_2$ | N.A. | N.A. |
| 5fx | S | 5-OCH$_3$ | COOH | 4.5 | N.A. |
| 5gx | S | 5-OCH$_3$ | C.C.† | N.T. | N.T. |
| 5ay | SO$_2$ | 5-OCH$_3$ | NO$_2$ | 1.0 | N.A. |
| 5by | SO$_2$ | 5-OCH$_3$ | COOCH$_3$ | 4.6 | N.A. |
| 5cy | SO$_2$ | 5-OCH$_3$ | OCH$_3$ | N.A. | N.A. |
| 5dy | SO$_2$ | 5-OCH$_3$ | CF$_3$ | N.T. | N.T. |
| 5ey | SO$_2$ | 5-OCH$_3$ | NH$_2$ | 0.6 | N.A. |
| 5fy | SO$_2$ | 5-OCH$_3$ | COOH | N.A. | N.A. |
| 5gy | SO$_2$ | 5-OCH$_3$ | C.C.† | 0.5 | N.A. |
| 6ax | S | 6-OCH$_3$ | NO$_2$ | N.T. | N.T. |
| 6bx | S | 6-OCH$_3$ | COOCH$_3$ | N.T. | N.T. |
| 6cx | S | 6-OCH$_3$ | OCH$_3$ | N.T. | N.T. |
| 6dx | S | 6-OCH$_3$ | CF$_3$ | N.T. | N.T. |
| 6ex | S | 6-OCH$_3$ | NH$_2$ | N.T. | N.T. |
| 6fx | S | 6-OCH$_3$ | COOH | 1.9 | N.A. |
| 6gx | S | 6-OCH$_3$ | C.C.† | 52 | N.A. |
| 6ay | SO$_2$ | 6-OCH$_3$ | NO$_2$ | N.A. | N.A. |
| 6by | SO$_2$ | 6-OCH$_3$ | COOCH$_3$ | N.A. | N.A. |

TABLE 2-continued

IC$_{50}$ values of the library

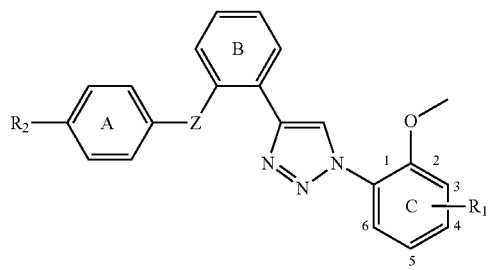

$R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | $R_1$ | $R_2$ | Antiviral activity (IC$_{50}$ μM) H9 | MT4 |
|---|---|---|---|---|---|
| 6cy | SO$_2$ | 6-OCH$_3$ | OCH$_3$ | N.A. | N.A. |
| 6dy | SO$_2$ | 6-OCH$_3$ | CF$_3$ | N.T. | N.T. |
| 6ey | SO$_2$ | 6-OCH$_3$ | NH$_2$ | 1.5 | N.A. |
| 6fy | SO$_2$ | 6-OCH$_3$ | COOH | 1.2 | N.A. |
| 6gy | SO$_2$ | 6-OCH$_3$ | C.C.[†] | N.A. | N.A. |
| 7ax | S | 6-F | NO$_2$ | 3.9 | N.A. |
| 7bx | S | 6-F | COOCH$_3$ | 7.8 | N.A. |
| 7cx | S | 6-F | OCH$_3$ | N.T. | N.T. |
| 7dx | S | 6-F | CF$_3$ | N.T. | N.T. |
| 7ex | S | 6-F | NH$_2$ | N.A. | N.A. |
| 7fx | S | 6-F | COOH | 4.9 | N.A. |
| 7gx | S | 6-F | C.C.[†] | N.T. | N.T. |
| 7ay | SO$_2$ | 6-F | NO$_2$ | N.A. | N.A. |
| 7by | SO$_2$ | 6-F | COOCH$_3$ | N.T. | N.T. |
| 7cy | SO$_2$ | 6-F | OCH$_3$ | N.A. | N.A. |
| 7dy | SO$_2$ | 6-F | CF$_3$ | N.A. | N.A. |
| 7ey | SO$_2$ | 6-F | NH$_2$ | 15 | N.A. |
| 7fy | SO$_2$ | 6-F | COOH | N.A. | N.A. |
| 7gy | SO$_2$ | 6-F | C.C.[†] | N.T. | N.T. |

Figure 16:
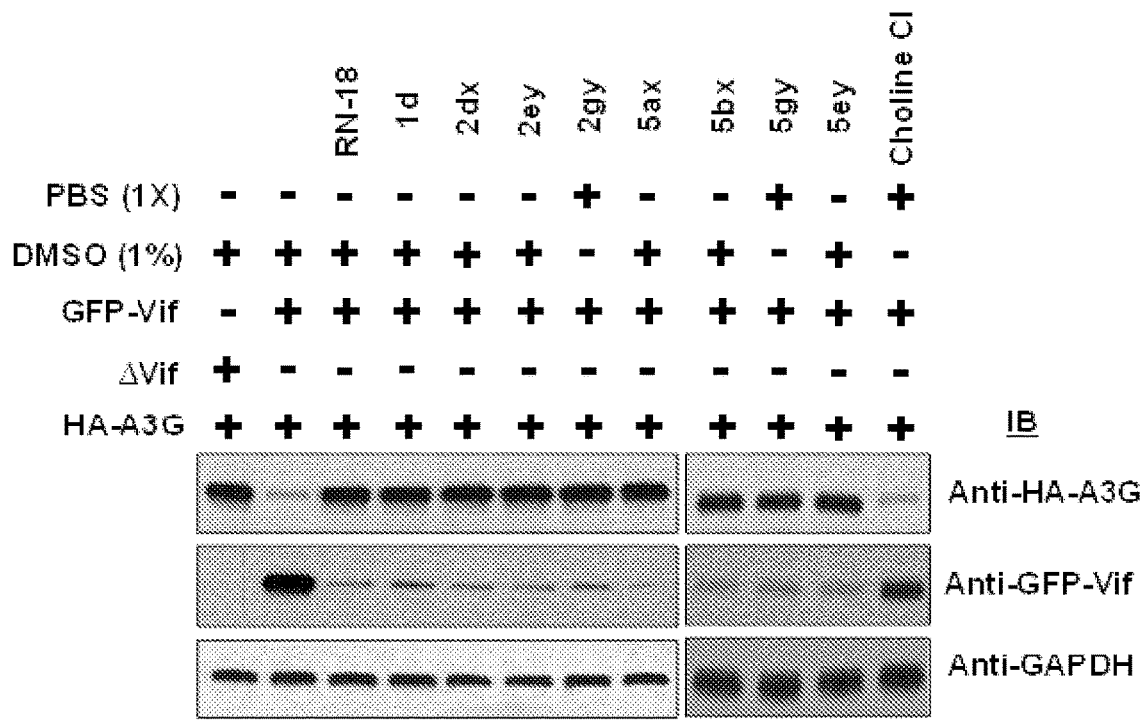
FIG. 16. Triazole based Vif antagonist small molecules enhance A3G levels and reduce Vif expression. 293FT cells co-expressing HA-tagged A3G and GFP-tagged Vif or ΔVif were grown for 16 h in the presence of (50 μM) or in the absence of compounds. Choline chloride was used as a negative control.
Figure 17A:
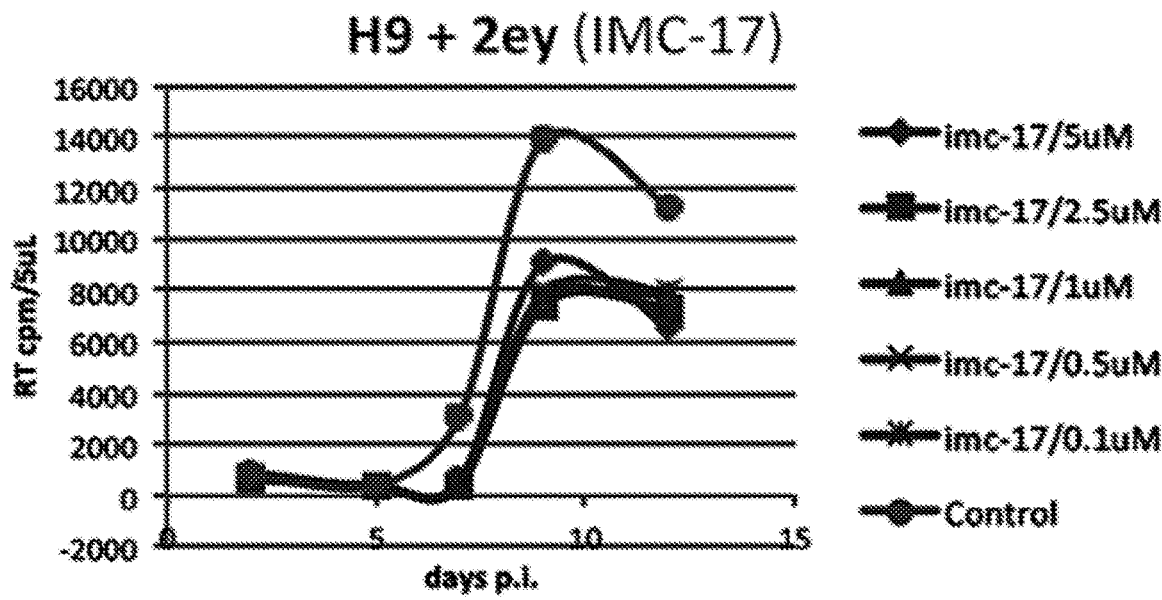
FIGS. 17A-E. Anti-HIV-1 activity graphs for compounds 2ey (IC$_{50}$ 0.4 μM) in FIGS. 17A-17B, 5ax (IC$_{50}$ 0.01 μM) in FIGS. 17C-17D, and 5bx (IC$_{50}$ 0.2 μM) in FIGS. 17E-17F, as indicated in the figure headings. The Vif antagonists inhibit HIV-1 replication selectively in non-permissive H9 cells.
Figure 17B:
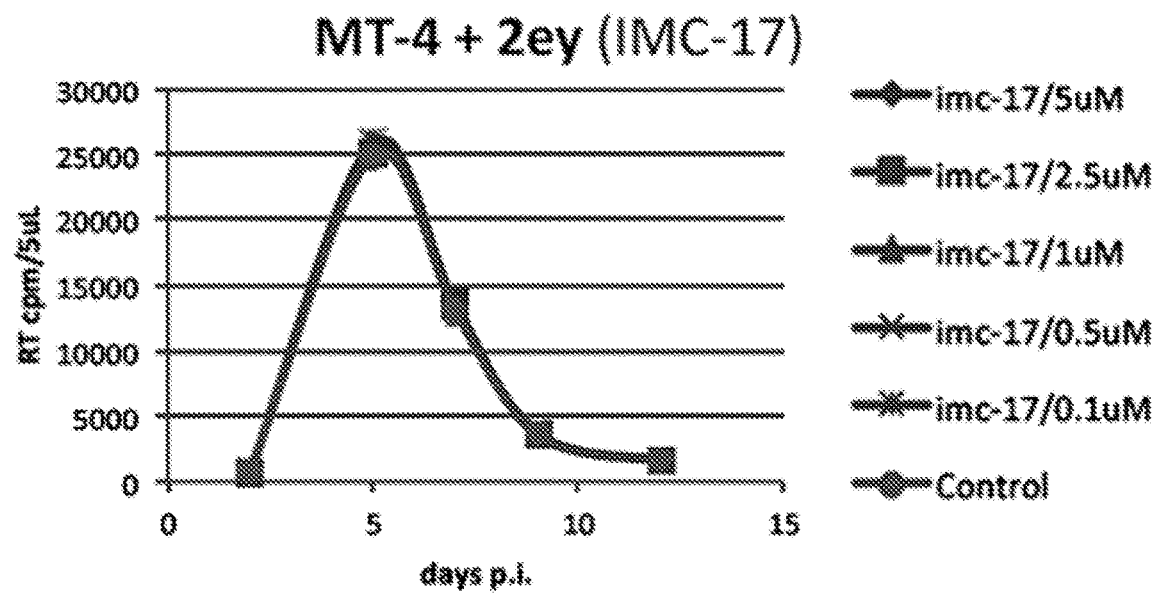
Figure 17C:
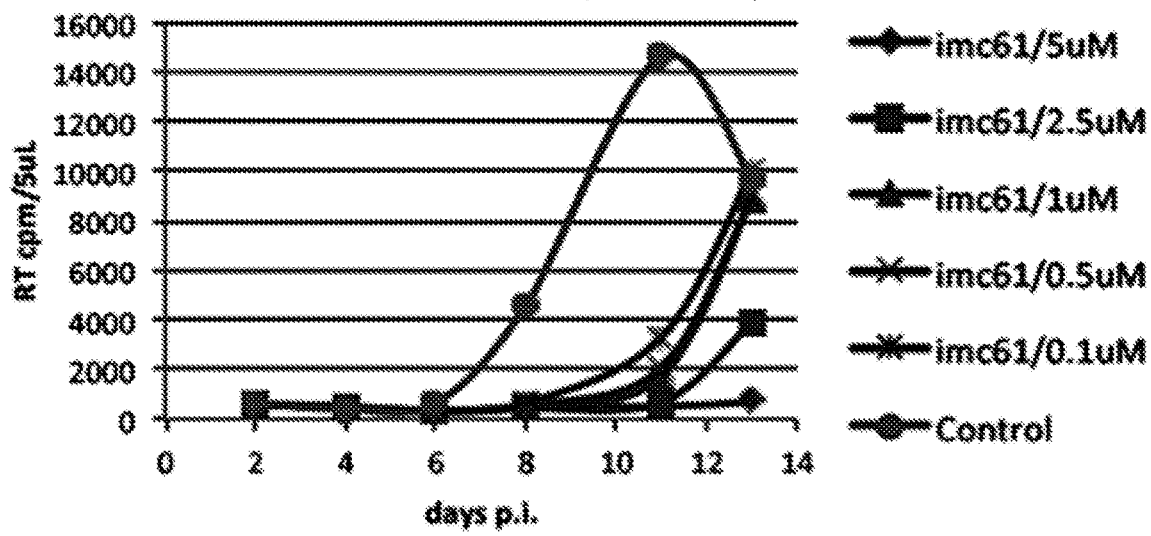
Figure 17D:
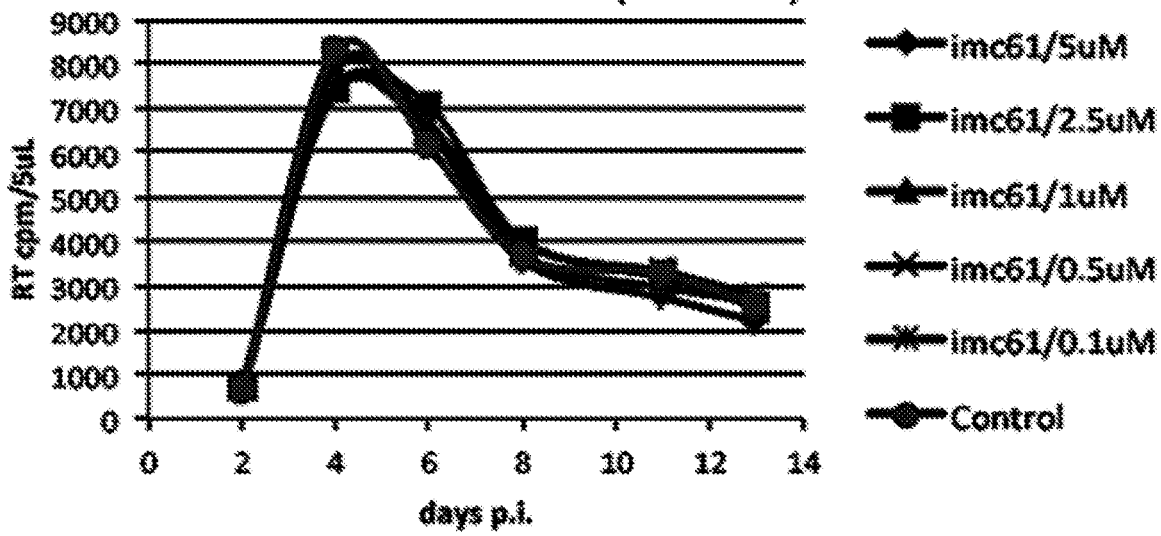
Figure 17E:
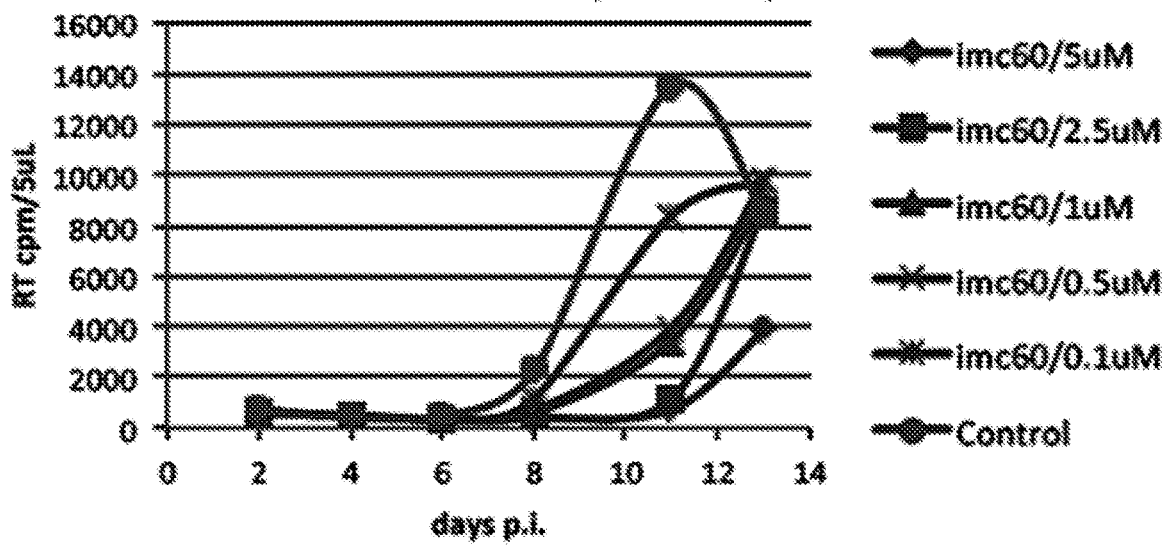
Figure 17F:
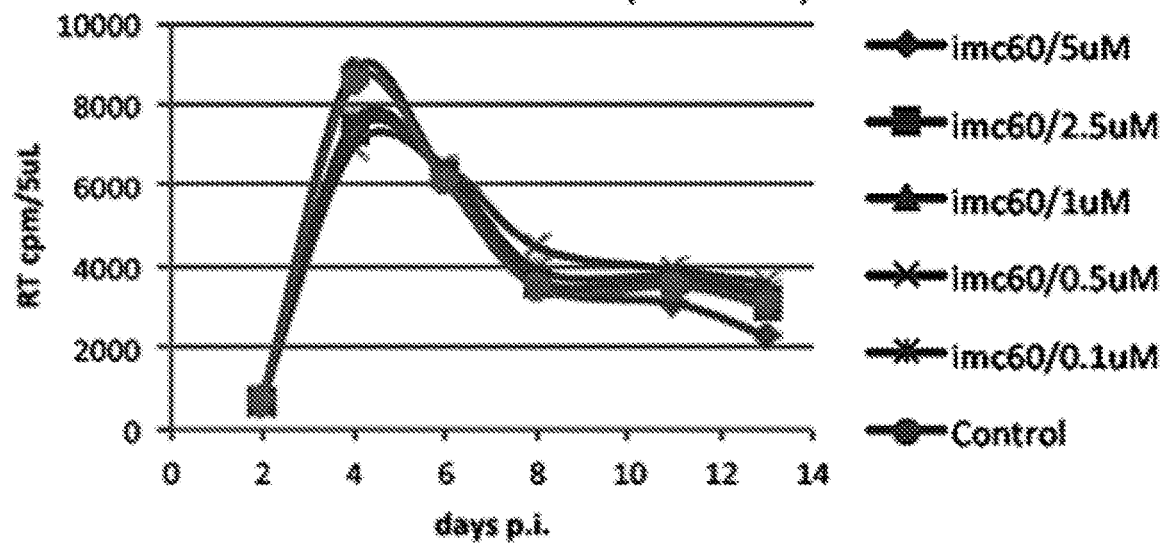

N.A. = no activity 50 μM concentration;
N.T. = not tested;
[†]Choline carboxylate For few selected compounds (2dx, 2ey, 2gy, 5ax, 5bx, 5gy and 5ey) we then determined whether the analogues could upregulate A3G and downregulate Vif in a similar manner as RN-18 and 1d do. Immunoblots for the compounds are shown in FIG. 16, which clearly show that the new inhibitors exert the anti-HIV activity via the same mechanism as of RN-18.

Of the 84 members library, about 27 compounds exhibited IC$_{50}$ values in the range of 0.01 to 5 μM in the non-permissive H9 cells. Among them, the compound 5ax (IMC-61) exhibited the most potent activity with IC$_{50}$ of 10 nM, which is about 1000 fold more potent than the original lead molecule, RN-18. Three water soluble choline salts 2gy, 4gy and 5gy exhibited IC$_{50}$ values of 0.2 μM, 0.7 μM, and 0.5 μM respectively. Similarly, compounds 2ey, 5bx, and 5ey, exhibited IC$_{50}$ values in the range of 0.2 μM to 0.6 μM and compounds 2dx, 2ex, 2fx, 3ax, 3dx, 3fx, 5ay, 6ey, 6fx, 6fy in the range of 1 μM to 3 μM. Overall, the SAR of the library showed remarkable sensitivity toward the three variables (Z-bridge, $R_1$ and $R_2$ substituents) tested in this study. Among various SAR findings made in the study few of the noteworthy ones are: sulfide (—S—) as bridge Z exhibited overall better performance compared to sulfone (—SO$_2$—) bridge (in the case of RN-18 sulfone derivative showed better activity)[11a] with triazole system as peptide mimic. However, in few cases sulfones (—SO$_2$—) showed better activities where $R_2$ substituent was either amino group or choline carboxylate. We have found safe replacements for the nitro functionality such as —COOCH$_3$, —COOH, —CF$_3$, —NH$_2$, and -choline carboxylate. Irrespective of the antiviral potency profiles in the non-permissive cells, overall the library exhibited no inhibition in the permissive cells at the measured concentrations. Pharmacological studies have been completed for the most potent compounds and few of them have been selected for preclinical studies in animal models. Pharmacological and preclinical studies will be reported elsewhere shortly.

In summary, the study has made the following three important contributions: (a) provided few potent Vif antagonists as preclinical candidates against HIV-1, (b) generated potent modulators to explore Vif-APOBEC3G cell biology and related physiology, and (c) validated the applicability of oxadiazole and triazole scaffolds as peptide bioisosteres.

General Procedures.

Reactions were performed in oven-dried round-bottom flasks and air sensitive reactions were performed under positive pressure of nitrogen. Moisture sensitive reactions were performed using calcium sulphate protected guard tubes. Stainless steel syringes were used to transfer dry solvents or moisture/air sensitive liquids. Column chromatography was performed using SINGLE StEP™ Pump and SINGLE StEP™ columns Intro Packs of various sizes made by Thomson Instrument Company. Silica gel used was 60° pore size, 40 μm, supplied by Fisher Scientific and amines were purified using neutral alumina Brockmann I of Sigma-Aldrich. Analytical thin-layer chromatography (TLC) was performed using TLC silica gel 60 F$_{254}$ aluminum sheets of EMD. TLC plates were visualized by exposure to ultraviolet light, iodine adsorbed on silica gel and by exposure to an ethanolic solution of phosphomolybdic acid (PMA) or an acidic solution of p-anisaldehyde, or a slightly basic solution of potassium permanganate. Organic extracts or solutions or eluents were concentrated using Heidolph's Hei-VAP Advantage vacuo rotavapor at temperatures below 38-40° C. Parallel synthesis was performed using Carousel 6 REACTION STATION™ purchased from Radleys Discovery Technologies. Dry-ice was used for low temperature baths in different organic solvents. Reversed-phase high performance liquid chromatography of the library compounds was performed on a Waters 2695 Separation module system equipped with an autosampler and a Waters 996 photodiode array detector. Purity analysis was performed using column, YMC-Pack Pro C18 (particle size=5 μm, pore size=12 nm, dimensions=150 mm×4.6 mm); mobile phase A, water; mobile phase B, acetonitrile. We applied the following mobile phase gradient for total 10 minutes per sample: starting from 50% B and reaches to 90% B for 2 min followed by 100% B over 10 minutes (Method A for all the compounds except water soluble choline salts). Method B for water soluble choline salts; starting from 50% A and 50% B followed by 100% A over 10 minutes. The injection volume was 10 μL and the flow rate was 1.0 mL/min. HPLC retention times (R$_T$) and purity data (%) for the compounds are given in the analytical data of the respective compounds.

Materials.

Commercial reagents and solvents (HPLC grade for purifications and anhydrous solvents for reactions) were purchased from Sigma-Aldrich, Acros Organics, Alfa Aesar, EMD, Combiblocks, Oakwoods, Toronto Research Chemicals Inc., Astatech Inc., etc.

Instrumentation.

$^1$H (proton) and $^{13}$C (carbon) nuclear magnetic spectra were recorded using 400 MHz Jeol JNM-ECS spectrometer with a 5 mm proton/multi-frequency auto-tune and auto sample changer. Proton and carbon nuclear magnetic resonance spectra are reported in parts per million (ppm) on the δ scale using the internal standard of reference as trimethylsilane (TMS). Electron-Spray Mass spectroscopy (ESI MS) was performed on Waters micromass Model ZQ 4000 using methanol solvent to dissolve samples. High-resolution Mass Spectroscopy (HRMS) was performed on Agilent Technologies 6224A Time-of-Flight Mass Spectrometer (MS-TOF). HPLC was performed using Waters 2695 Separation Module having Waters 996 photodiode array detector. X-ray diffraction structural determination was performed at University of California, San Diego (UCSD) facility using Bruker diffractometer with CCD detectors and low-temperature cryostats.

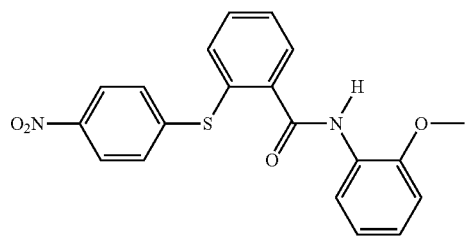

RN-18

N-(2-methoxyphenyl)-2-((4-nitrophenyl)thio)benzamide (RN-18, 1a): m. p. 143-145° C. (crystallized in DCM/methanol mixture). $^1$H NMR (400 MHz, CDCl$_3$, TMS) δ 3.71 (s, 3H), 6.77-6.81 (m, 1H), 6.86-6.92 (m, 1H), 6.96-7.02 (m, 1H), 7.21 (d, 2H, J=9.16 Hz), 7.40-7.50 (m, 3H), 7.69-7.73 (dd, 1H, J$_1$=1.83 Hz, J$_2$=7.32 Hz), 7.99 (d, 2H, J=9.16 Hz), 8.31 (s, 1H), 8.33 (d, 1H, J=7.93 Hz). $^{13}$C NMR (100 MHz, CDCl$_3$, TMS) δ 55.63, 109.94, 119.81, 121.12, 124.10, 124.29, 127.29, 128.54, 129.25, 129.63, 129.84, 131.42, 135.51, 140.38, 145.91, 146.62, 147.97, 165.20. HRMS (ESI$^+$) m/z 381.0875 (M+H)$^+$ (calcd. for C$_{20}$H$_{17}$N$_2$O$_4$S 381.0904). R$_{T, HPLC}$=5.106 min, Purity>97%.

X-ray crystal structure determination of RN-18:

Data were recorded on Bruker APEX-II CCD device using Mo-Kα radiation (wavelength=0.71073 Å) and graphite monochromator. The structure was refined using the program SHELXL-97. Crystal data: C$_{20}$H$_{16}$N$_2$O$_4$S, M=380.41, monoclinic, space group P2$_1$/c, a=7.411(3) Å, b=7.977(4) Å, c=30.044(14) Å; β=95.648(5)°; V=1767.5 (14) Å$^3$; Z=4; T=100(2) K; µ=0.213 mm$^{-1}$; Crystal size=0.33×0.10×0.06 mm$^3$. Of 15997 reflections measured to theta range 1.36 to 28.230, 6115 were independent (R$_{int}$=0.0000). Final R1=0.0420 (I>2σ (I)), wR2=0.0928, R1=0.0486, wR2=0.0964 (all data).

Synthesis of Peptidomimetic Analogues of RN-18:

Description:

Synthesis of 2,5-disubstituted-1,3,4-oxadiazole 1b was started with the initial coupling of hydrazine with 2-iodobenzoic acid (Scheme 1S-A). This sequential one pot reaction involves acid chloride formation using thionyl chloride followed by treatment with methanol at lower temperature to get in situ methyl ester of 2-iodobenzoic acid which was later refluxed in the presence of hydrazine hydrate to obtain the benzohydrazide derivative 1s quantitatively. Benzohydrazide 1s was reacted with o-anisic acid in refluxing phosphoryl chloride leading to the formation of crucial iodo intermediate 1,3,4-oxadiazole 2s. Intermediate 1,3,4-oxadiazole 2s was reacted with 4-nitrothiophenol under copper (I) catalyzed S-arylation conditions[1] leading to the formation of 2,5-disubstituted-1,3,4-oxadiazole, 1b analogue of RN-18. Synthesis of 3,5-Disubstituted-1,2,4-oxadiazole analogue 1c was started (Scheme 1S-B) with the coupling reaction between the commercially available N'-hydroxy-2-methoxybenzimidamide and 2-iodobenzoic acid using dicyclohexyldicarbodiimide in DMF solvent[2] at room temperature followed by refluxing the same reaction mixture leading to the formation of crucial iodo intermediate 1,2,4-oxadiazole 3s. S-arylation of the intermediate 3s with 4-nitrothiophenol under copper (1) catalytic conditions led to the formation of 3,5-disubstituted-1,2,4-oxadiazole, 1c. Synthesis of 1,4-disubstituted-1,2,3-triazole analogue 1d was started with the initial syntheses of two crucial synthons; 2-ethynylaniline 5s and 1-azido-2-methoxybenzene 6s (Scheme 1S-C). 2-Iodoaniline was reacted with trimethylsilylacetylene under Sonogashira reaction conditions catalyzed by bis(triphenylphosphine)palladium chloride in the presence of triethylamine base and copper iodide as co-catalyst[3] leading to the formation of TMS protected ethynylaniline 4s which was deprotected using sodium hydroxide in ethanol giving the required synthon 2-ethynylaniline 5s in quantitative yield. Azide 6s was synthesized by following a Cham-Lam type of coupling between 2-methoxyphenylboronic acid and sodium azide catalyzed by copper sulfate at room temperature in methanol.[4] Copper-catalyzed click reaction[5] between alkyne 5s and azide 6s generated triazole amine 7s quantitatively in t-butanol/water solvent system (Scheme 1S-D). Triazole amine 7s was diazotized using sodium nitrite in 5N HCl around −10° C. and concomitantly converted to iodotriazole 8s by reacting with potassium iodide at the same temperature. Copper (I) catalyzed S-arylation of iodotriazole 8s using catalytic copper iodide in DMF solvent and potassium carbonate led to the synthesis of 1d, IMA-53. 1,5-Disubstituted-1,2,3-triazole 1e analogue of RN-18 was synthesized initially by reacting alkyne 5s and azide 6s under ruthenium catalyzed click chemistry conditions using Cp*RuCl(PPh$_3$)$_2$ catalyst in benzene at 80° C.[6] leading to the formation of 1,5-disubstituted-1,2,3-triazole amine 9s quantitatively (Scheme 1S-E). Diazotization, iodination and S-arylation reaction sequences afforded 1,5-disubstituted-1,2,3-triazole 1e analogue of RN-18.

Scheme 1S$^a$; part 1:

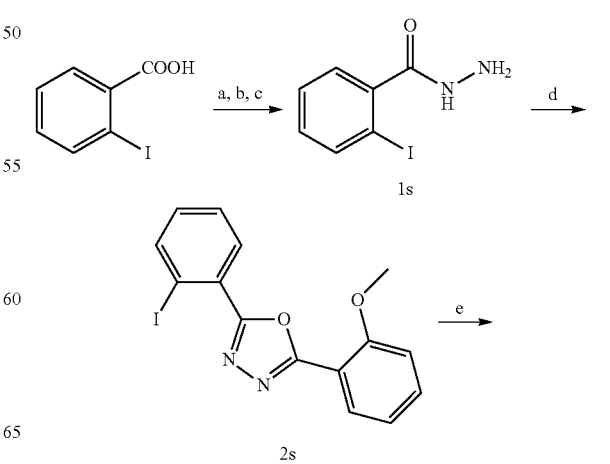

(A)

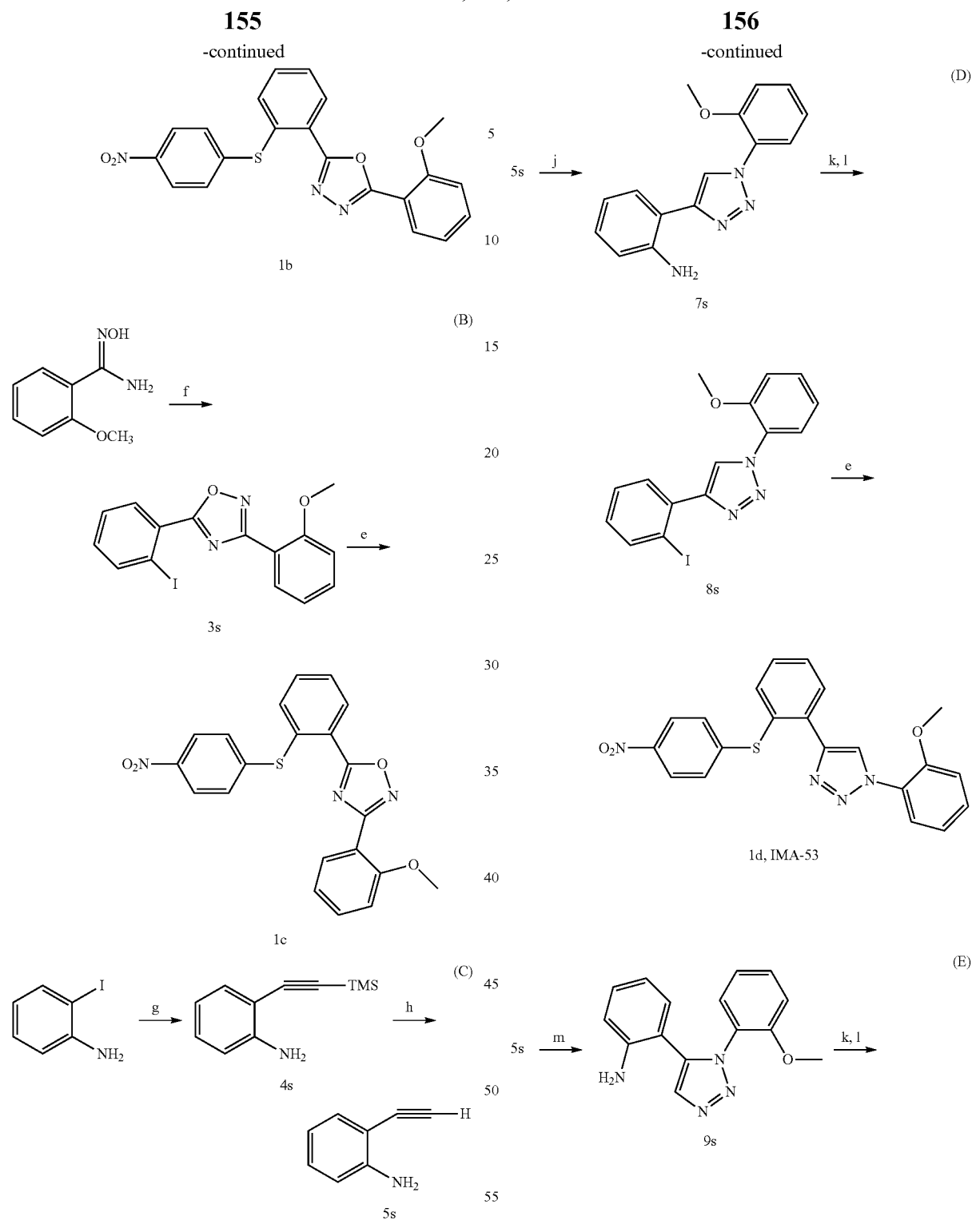
Scheme 1S[a]; part 2:
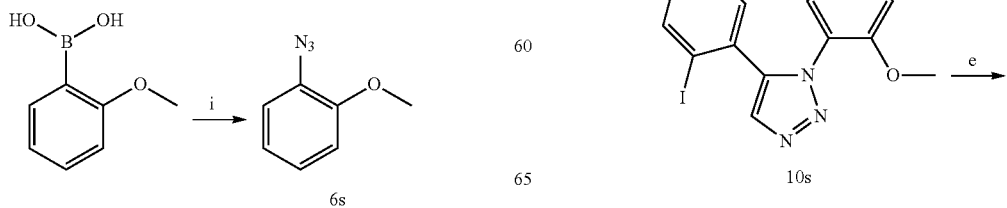

-continued

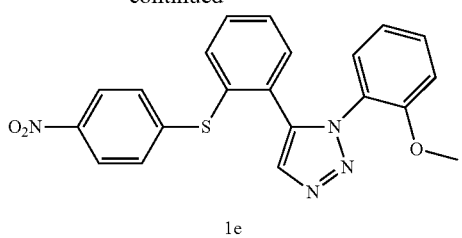

1e

<sup>a</sup>Reagents & Conditions: (a) SOCl<sub>2</sub>, cat. DMF, Benzene, 80° C., 2 h. (b) CH<sub>3</sub>OH, TEA, 0° C. - R.T., 2 h. (c) NH<sub>2</sub>NH<sub>2</sub>• H<sub>2</sub>O, 80° C., 3 h. (d) o-anisic acid, POCl<sub>3</sub>, 110° C., 8 h. (e) 4-nitrothiophenol, K<sub>2</sub>CO<sub>3</sub>, 5 mol %, CuI, DMF, 110° C., 8 h. (f) 2-iodobenzoic acid, DCC, DMF, R.T. to 100° C., 8 h. (g) Trimethylsilyl acetylene, 1 mol % PdCl<sub>2</sub>(PPh<sub>3</sub>)<sub>2</sub>, 1 mol %,CuI, NEt<sub>3</sub>, R.T., 12 h (h) NaOH (aq), ethanl/THF (1:1), R.T., 1 h (i) NaN<sub>3</sub>/10 mol % CuSO<sub>4</sub>•5H<sub>2</sub>O, CH<sub>3</sub>OH, R.T., 8 h. (j) 6s, 5 mol % CuSO<sub>4</sub> 5 H<sub>2</sub>O, 10 mol % Naascorbate, t-BuOH/H<sub>2</sub>O (1:1), R.T., overnight. (k) NaNO<sub>2</sub>, 5N HCl, -10 to -5° C. 2 h. (l) KI, -10 to -5° C., 8 h. (m) 6s, 1 mol % Cp*RuCl(PPh<sub>3</sub>)<sub>2</sub>, Benzene, 80° C., 3 h.

Experimental Procedures and Analytical Data of Scheme IS:

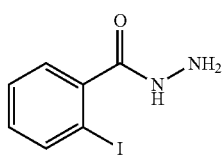

2-Iodobenzohydrazide (1s/1f)

A suspension of 2-iodobenzoic acid (2.48 g, 10 mmol, 1 equiv.) and thionyl chloride (1.43 g, 12 mmol, 1.2 equiv.) in dry benzene 25 mL was refluxed for about 2 hours at 80° C. in the presence of catalytic DMF (2 drops). Benzene and excess thionyl chloride were removed under reduced pressure to get solid acid chloride. The residue obtained was slowly treated with methanol (25 mL) at 0° C. and triethylamine (5 mL) was added followed by stirring at room temperature for 2 hours. To the above mixture hydrazine hydrate (1.0 g, 20 mmol, 2 equiv.) was added drop wise and refluxed at 80° C. for about 3 hours. TLC showed the completion of the reaction. The reaction mixture was dried under reduced pressure and extracted using EtOAc (2×25 mL). The organic extract was sequentially treated with saturated solution of NaHCO<sub>3</sub>, brine and anhydrous Na<sub>2</sub>SO<sub>4</sub>. Flash column chromatography using EtOAc:petroleum ether (1:1) afforded a colorless amorphous solid compound benzohydrazide is (1.99 g, 76% yield). <sup>1</sup>H NMR (400 MHz, CD<sub>3</sub>OD, TMS) δ 4.41 (broad singlet, 2H), 7.09-7.15 (m, 1H), 7.21-7.25 (m, 1H), 7.36-7.41 (m, 1H), 7.81-7.85 (dd, 1H, J<sub>1</sub>=0.92 Hz, J<sub>2</sub>=7.79 Hz). MS (ESI): m/z (%)=262.85 (M<sup>+</sup>, 50), 284.82 (M+Na<sup>+</sup>, 100).

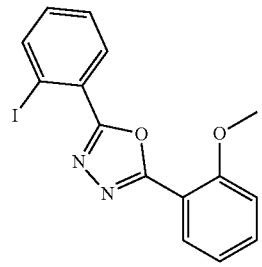

2-(2-Iodophenyl)-5-(2-methoxyphenyl)-1,3,4-oxadiazole (1g/2s)

A 50 mL oven dried round bottom flask was discharged with o-anisic acid (0.30 g, 2 mmol, 1 equiv.) and benzohydrazide 1s (0.52 g, 2 mmol, 1 equiv.) followed by the addition of 8 mL of POCl<sub>3</sub>. The suspension was refluxed at 110° C. for 8 hours till TLC showed depletion of the starting materials. The reaction mixture was poured into ice-cold water saturated solution of potassium carbonate followed by extraction using EtOAc (2×25 mL). The organic extract was sequentially treated with saturated solution of NaHCO<sub>3</sub>, brine and anhydrous Na<sub>2</sub>SO<sub>4</sub>. TLC (EtOAc:petroleum ether, 1:1) showed two new spots with almost equal intensity. Flash column chromatographic separation of the upper spot using EtOAc: petroleum ether (1:1) afforded the required colorless amorphous solid compound iodo 1,3,4-oxadiazole 2s (0.41 g, 55% yield). <sup>1</sup>H NMR (400 MHz, CDCl<sub>3</sub>, TMS) δ 4.00 (s, 3H), 7.04-7.24 (m, 3H), 7.45-7.56 (m, 2H), 7.92-7.98 (d, 1H, J=7.79 Hz), 8.03-8.10 (d, 2H, J=7.79 Hz). <sup>13</sup>C NMR (100 MHz, CDCl<sub>3</sub>, TMS) δ 56.05, 94.00, 112.00, 112.84, 120.78, 128.24, 129.43, 130.56, 131.58, 132.26, 133.22, 141.31, 158.03, 163.81, 163.91. MS (ESI): m/z (%)=378.53 (M<sup>+</sup>, 100), 400.70 (M+Na<sup>+</sup>, 70).

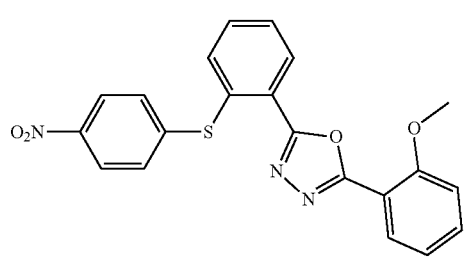

2-(2-Methoxyphenyl)-5-(2-((4-nitrophenyl)thio)phenyl)-1,3,4-oxadiazole (1b)

S-arylation procedure described for the synthesis of 1 d (see below) was followed for the synthesis of compound 1b to afford a light yellow amorphous solid (82% yield). The amorphous solid was crystallized using a mixture of DCM and methanol to afford a light yellow crystalline compound 1b. m. p. 128-130° C. <sup>1</sup>H NMR (400 MHz, CDCl<sub>3</sub>, TMS) δ

3.95 (s, 3H), 7.00-7.08 (m, 2H), 7.31-7.37 (m, 2H), 7.48-7.60 (m, 4H), 7.79-7.84 (d. 1H, J=7.79 Hz), 8.07-8.16 (m, 3H). $^{13}$C NMR (100 MHz, CDCl$_3$, TMS) δ 55.93, 111.93, 112.58, 120.66, 124.16, 126.84, 129.02, 129.20, 130.29, 131.14, 132.04, 132.52, 133.23, 134.93, 146.07, 146.10, 157.90, 162.90, 163.68. MS (ESI): m/z (a %)=405.86 (M$^+$, 100). R$_{T, HPLC}$=5.012 min, Purity>98%.

X-Ray Crystal Structure Determination of 1b:

CCDC deposition number 1449875. Data were recorded on Bruker APEX-II CCD device using Mo-Kα radiation (wavelength=0.71073 Å) and graphite monochromator. The structure was refined using the program SHELXL-97. Crystal data: C$_{21}$H$_{15}$N$_3$O$_4$S, M=405.42, orthorhombic, space group Pbca, a=7.9715(4) Å, b=12.4566(6) Å, c=37.3403(17) Å; α=90°, β=90°, γ=90°; V=3707.8(3) Å$^3$; Z=8; T=110(2) K; μ=0.210 mm$^{-1}$; Crystal size=0.33×0.30×0.27 mm$^3$. Of 17777 reflections measured to theta range 2.18 to 25.43°, 3422 were independent (R$_{int}$=0.0405). Final R1=0.0373 (I>2σ(I)), wR2=0.1090.

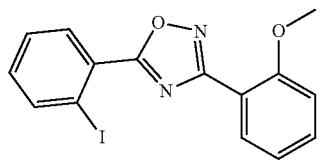

3s 5-(2-Iodophenyl)-3-(2-methoxyphenyl)-1,2,4-oxadiazole (1 h/3s): A solution of 2-iodobenzoic acid (0.99 g, 4 mmol, 1 equiv.) in dry DMF (15 mL) was cooled to 0° C. followed by the addition of dicyclohexylcarbodiimide (1.24 g, 6.0 mmol, 1.5 equiv.) under nitrogen atmosphere and stirring was continued for an hour at the same temperature. To the above mixture was added commercially available N'-hydroxy-2-methoxybenzimidamide (0.664 g, 4 mmol, 1 equiv.) and stirred for 30 minutes at 0° C. Then the reaction mixture was stirred for about 3 hours at room temperature. Gradually the reaction mixture was heated up to 110° C. and kept for a period of 8 hours. The reaction mixture was later poured into ice-cold water and diluted by EtOAc (20 mL) leading to the formation of dicyclohexylurea crystals, which were separated by filtration. Filtrate organic layer was separated and treated with saturated solution of potassium carbonate, brine and anhydrous Na$_2$SO$_4$. Flash chromatography using EtOAc: petroleum ether (1:3) afforded the required iodo 1,2,4-oxadiazole 3s as a colorless amorphous solid (1.2 g, 80% yield). $^1$H NMR (400 MHz, CDCl$_3$, TMS) δ4.02 (s, 3H), 7.05-7.15 (m, 2H), 7.20-7.27 (m, 1H), 7.46-7.55 (m, 2H), 7.96-8.01 (dd, 1H, J=1.83 Hz, J$_2$=7.79 Hz), 8.07-8.12 (m, 1H), 8.16-8.21 (m, 1H). $^{13}$C NMR (100 MHz, CDCl$_3$, TMS) δ 56.04, 94.57, 111.69, 115.74, 120.75, 128.25, 129.51, 131.60, 131.68, 132.46, 132.84, 141.63, 158.25, 167.07, 174.22. MS (ESI): m/z (%)=400.50 (M+Na$^+$, 100).

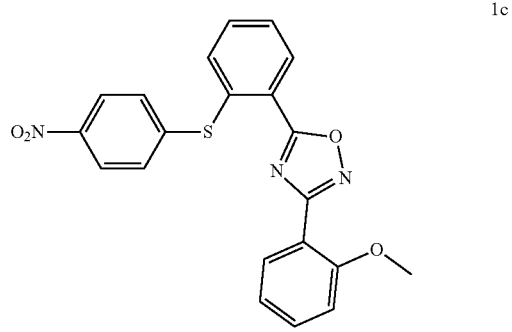 [SMILES: COc1ccccc1-c1noc(-c2ccccc2Sc2ccc([N+](=O)[O-])cc2)n1]

3-(2-Methoxyphenyl)-5-(2-((4-nitrophenyl)thio)phenyl)-1,2,4-oxadiazole (1c)

S-arylation procedure described for the synthesis of 1d was followed for the synthesis of compound 1c to afford a light yellow amorphous solid (84% yield). The amorphous solid was crystallized using a mixture of DCM and methanol to afford a light yellow crystalline compound 1c. m. p. 138° C. $^1$H NMR (400 MHz, CDCl$_3$, TMS) δ 3.98 (s, 3H), 7.04-7.10 (m, 2H), 7.37-7.43 (m, 2H), 7.45-7.57 (m, 4H), 8.02-8.05 (dd, 1H, J$_1$=1.83 Hz, J$_2$=7.79 Hz), 8.10-8.15 (m, 2H), 8.16-8.21 (m, 1H). $^{13}$C NMR (100 MHz, CDCl$_3$) 55.94, 111.63, 115.48, 120.63, 124.19, 126.30, 128.57, 130.10, 131.38, 131.54, 132.44, 132.70, 134.11, 134.17, 145.44, 146.34, 158.12, 167.06, 173.02. MS (ESI): m/z (%)=406.09 (M+H$^+$, 100), 428.07 (M+Na$^+$, 20). R$_{T, HPLC}$=5.589 min, Purity>96%.

X-Ray Crystal Structure Determination of 1c:

CCDC deposition number 1450498. Data were recorded on Bruker APEX-II CCD device using Cu-Kα radiation (wavelength=1.54178 Å) and graphite monochromator. The structure was refined using the program SHELXL-2008. Crystal data: C$_{21}$H$_{15}$N$_3$O$_4$S, M=405.42, monoclinic, space group P2$_1$/n, a=9.8728(18) Å, b=8.9138(15) Å, c=20.417(4) Å; α=90°, β=91.886 (7)°, γ=90°; V=1795.8(5) Å$^3$; Z=4; T=123(2) K; μ=1.916 mm$^{-1}$; Crystal size=0.29×0.24×0.20 mm$^3$. Of 9281 reflections measured to theta range 4.33 to 67.56°, 2996 were independent (R$_{int}$=0.0414). Final R1=0.0449 (I>2σ (I)), wR2=0.1271.

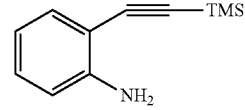

4s 2-((Trimethylsilyl)ethynyl)aniline (1i/4s)

In a 500 mL oven-dried two-necked round bottom flask 2-iodoaniline (25.0 g, 0.114 mol, 1.0 equiv) was dissolved in 250 mL of deoxygenated triethylamine. To this solution, PdCl$_2$(PPh$_3$)$_2$ catalyst (0.8 g, 1.14 mmol, 1 mol %) and copper (I) iodide co-catalyst (0.217 g, 1.14 mmol, 1 mol %) was added. The mixture was stirred for 15 minutes at room temperature under nitrogen pressure. To this mixture trimethylacetylene (11.21 g, 0.114 mol, 1.0 equiv.) was added and the reaction was allowed to stir for a period of 12 hours at room temperature. Triethylamine was removed under reduced pressure to get a crude viscous residue. The residue was dissolved in EtOAc (200 mL) treated with saturated brine, anhydrous Na₂SO₄ and adsorbed on neutral alumina followed by flash column chromatography using EtOAc: petroleum ether (1:9) afforded a pale yellow liquid compound, TMS protected 2-ethynylaniline, 4s (18.37 g, 85% yield). ¹H NMR (400 MHz, CDCl₃, TMS) δ 0.26 (s, 9H), 4.22 (broadsinglet, 2H), 6.63-6.69 (m, 2H), 7.09-7.13 (m, 1H), 7.27-7.30 (m, 1H).

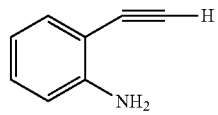

2-Ethynylaniline (1j/5s)

A 1 M aqueous solution of sodium hydroxide (2.64 g, 65.95 mmol, 1.2 equiv.) was added to a solution of 2-ethynylaniline, 4s (18.0 g, 54.96 mmol, 1 equiv.) dissolved in 200 mL of ethanol/THF (1:1). Stirring was continued at room temperature for about 1 hour till TLC showed complete disappearance of the starting material. Organic solvents were evaporated under reduced pressure and residue was diluted by adding 50 mL of distilled water and extracted using CH₂Cl₂ (2×100 mL). Organic extractions were dried over brine and anhydrous Na₂SO₄ and adsorbed on neutral alumina followed by flash column chromatography using EtOAc:petroleum ether (1:4) afforded a colorless pale yellow liquid compound, 2-ethynylaniline, 5s (6.18 g, 96% yield). ¹H NMR (400 MHz, CDCl₃, TMS) δ 3.38 (s, 1H), 4.24 (broadsinglet, 2H), 6.65-6.70 (m, 2H), 7.12-7.16 (m, 1H), 7.31-7.33 (m, 1H).

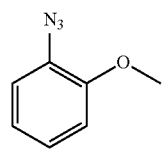

1-Azido-2-methoxybenzene (1k/6s): To a solution of 2-methoxyphenylboronic acid (1.52 g, 10 mmol, 1 equiv.) in 20 mL of methanol, sodium azide (0.78 g, 12.0 mmol, 1.2 equiv.) was added and stirred. To this mixture CuSO₄.5H₂O (0.249 g, 1 mmol, 10 mol %) was added and stirred at room temperature for about 8 hours till TLC showed completion of the reaction. Methanol was removed under reduced pressure and the residue was treated with saturated solution of sodium bicarbonate followed by extraction with CH₂Cl₂ (2×100 mL). Organic extractions were dried over saturated brine and anhydrous Na₂SO₄ and adsorbed on silica gel followed by flash column chromatography using EtOAc: petroleum ether (1:9) afforded a colorless dark brown liquid compound, 1-azido-2-methoxybenzene, 6s (1.34 g, 900/yield). ¹H NMR (400 MHz, CDCl₃, TMS) δ 3.87 (s, 3H), 6.87-6.96 (m, 2H), 7.00-7.03 (dd, 1H, J₁=1.37 Hz, J₂=7.79 Hz), 7.08-7.12 (m, 1H).

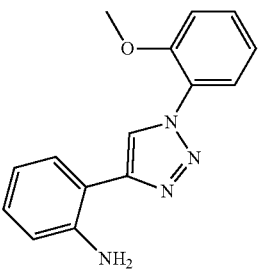

2-(1-(2-Methoxyphenyl)-1H-1,2,3-triazol-4-yl)aniline (1l/7s)

2-Ethynylaniline, 5s (0.234 g, 2 mmol, 1.0 equiv.) and 1-azido-2-methoxybenzene, 6s (0.298 g, 2 mmol, 1 equiv.) were dissolved in 10 ml of a mixture of tert-butanol and deionized water (1:1) in a 50 ml round bottom flask. To the stirred solution sodium ascorbate (39.62 mg, 0.2 mmol, 10 mol %) and CuSO₄.5H₂O (24.97 mg, 0.1 mmol, 5 mol %) was added and stirring was continued for overnight till TLC showed the completion of the reaction. t-Butanol solvent was removed under reduced pressure and the viscous residue was extracted with CH₂Cl₂ (2×10 mL). The combined organic extractions were treated with saturated brine and anhydrous Na₂SO₄ followed by adsorption on neutral alumina. Flash chromatography using EtOAc:petroleum ether (1:3) afforded the triazole amine compound 7s as a light brown amorphous solid (0.467 g, 88% yield). ¹H NMR (400 MHz, CDCl₃, TMS) δ 3.84 (s, 3H), 5.49 (broadsinglet, 2H), 6.70-6.78 (m, 2H), 7.03-7.13 (m, 3H), 7.36-7.45 (m, 2H), 7.75-7.79 (dd, 1H, J=1.83 Hz, J₂=7.79 Hz), 8.29 (s, 1H). ¹³C NMR (100 MHz, CDCl₃) δ 55.97, 112.33, 113.74, 116.69, 117.31, 121.14, 122.12, 125.43, 126.17, 127.84, 128.96, 130.22, 145.15, 147.71, 151.24. MS (ESI): m/z (%)=289.08 (M+Na⁺, 100).

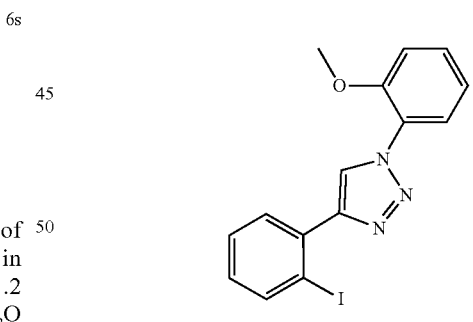

4-(2-Iodophenyl)-1-(2-methoxyphenyl)-1H-1,2,3-triazole (1m/8s)

In a 50 ml round bottom flask triazole amine 7s (0.266 g, 1 mmol) was dissolved in 10 mL 5N HCl at 0° C. and stirred for 30 minutes to insure the formation of hydrochloride salt. Sodium nitrite (82.8 mg, 1.2 mmol) was dissolved in minimum amount of water and added drop wise to the above mixture at −10° C. Stirring was continued at the same temperature for a period of 2 hours to obtain diazonium hydrochloride in situ. Urea (approximately 50 mg) was added to the reaction mixture to remove any excess nitrous acid generated in situ. In a separate beaker potassium iodide (0.249 g, 1.5 mmol) was dissolved in 5 mL of deionized water and kept stirring at a temperature of −5° C. To this solution of potassium iodide was added the diazonium hydrochloride salt drop by drop using addition funnel. Stirring of the reaction continued for a period of 8 hours at room temperature. The reaction mixture was diluted with 20 mL of EtOAc and 10 mL of deionized water. Small amount of iodine liberated in the iodination reaction was quenched by the addition of sodium dithionite. Organic layer was separated and was sequentially treated with saturated NaHCO$_3$, saturated brine, and anhydrous Na$_2$SO$_4$ followed by adsorption on silica gel. Flash chromatography using EtOAc: petroleum ether (1:3) afforded the iodo triazole compound 8s as a colorless amorphous solid (0.293 g, 78%0 yield). $^1$H NMR (400 MHz, CDCl$_3$, TMS) δ 3.90 (s, 3H), 7.02-7.15 (m, 3H), 7.39-7.47 (m, 2H), 7.85-7.99 (m, 3H), 8.73 (s, 1H). $^{13}$C NMR (100 MHz, CDCl$_3$) δ 56.14, 96.71, 112.35, 121.24, 124.78, 125.33, 125.41, 128.81, 129.59, 130.15, 130.72, 135.33, 140.22, 147.29, 151.04. MS (ESI): m/z (%)=377.95 (M+H$^+$, 100), 399.91 (M+Na$^+$, 20).

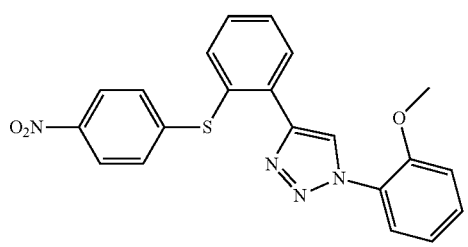

1d 1-(2-Methoxyphenyl)-4-(2-((4-nitrophenyl)thio)phenyl)-1H-1,2,3-triazole (1d, IMA-53)

In a 25 mL oven dried two-neck round bottom flask iodo triazole compound 8s (0.25 g, 0.66 mmol, 1 equiv.) was dissolved in anhydrous DMF (5 mL) followed by the addition of anhydrous potassium carbonate (0.110 g, 0.79 mmol, 1.2 equiv.) and catalyst copper iodide (6.31 mg, 0.033 mmol, 5 mol %). The resulting mixture was stirred for 10 minutes under nitrogen pressure. To the above mixture 4-nitrothiophenol (0.123 g, 0.79 mmol, 1.2 equiv.) dissolved in 2 ml of anhydrous DMF was added and stirred at 110° C. for 8 hours till TLC showed completion of the reaction. The reaction mixture was poured into ice-cold water followed by extraction with EtOAc (2×10 mL). Organic extractions were combined, treated sequentially with saturated potassium carbonate solution, saturated brine solution and anhydrous sodium sulphate. The dried organic extract was adsorbed on silica gel and flash chromatography using EtOAc: petroleum ether (1:3) afforded the compound 1d, IMA-53 as a light yellow amorphous solid (0.219 g, 82% yield). The amorphous solid was crystallized using a mixture of DCM and methanol to afford a light yellow crystalline compound 1d. m. p. 149-151° C. H NMR (400 MHz, CDCl$_3$, TMS) δ 3.75 (s, 3H), 7.03-7.14 (m, 4H), 7.39-7.48 (m, 2H), 7.61-7.70 (m, 2H), 7.75-7.78 (m, 1H), 8.01-8.06 (m, 2H), 8.34-8.38 (dd, 1H, J=1.37 Hz, J$_2$=7.79 Hz), 8.52 (s, 1H). $^{13}$C NMR (100 MHz, CDCl$_3$) δ 55.86, 112.30, 121.27, 124.13, 125.13, 125.32, 126.06, 126.17, 126.84, 129.37, 130.15, 130.64, 130.77, 135.55, 137.37, 144.09, 145.29, 147.80, 150.93. HRMS (ESI$^+$) m/z 405.0997 (M+H)$^+$ (calcd. for C$_{21}$H$_{17}$N$_4$O$_3$S 405.1016). R$_{T, HPLC}$=6.140 min, Purity>99%.

X-Ray Crystal Structure Determination of 1d:

CCDC deposition number 1450499. Data were recorded on Bruker APEX-II CCD device using Mo-Kα radiation (wavelength=0.71073 Å) and graphite monochromator. The structure was refined using the program SHELXL-2008. Crystal data: C$_{21}$H$_{16}$N$_4$O$_3$S, M=404.44, monoclinic, space group P2$_1$/c, a=11.9017(7) Å, b=15.9345(9) Å, c=10.8512 (6) Å; α=90.00°, β=115.6170(10)°, γ=90.00°; V=1855.62 (18) Å$^3$; Z=4; T=110(2) K; μ=0.207 mm$^{-1}$; Crystal size=0.42×0.38×0.36 mm$^{-1}$. Of 9488 reflections measured to theta range 1.90 to 25.35°, 3327 were independent (R$_{int}$=0.0253). Final R1=0.0335 (I>2σ (I)), wR2=0.0858.

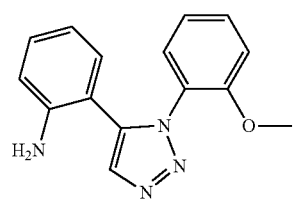

9s 2-(1-(2-Methoxyphenyl)-1H-1,2,3-triazol-5-yl)aniline (1n/9s)

2-Ethynylaniline, 5s (0.234 g, 2 mmol, 1.0 equiv.) and 1-azido-2-methoxybenzene, 6s (0.298 g, 2 mmol, 1 equiv.) were dissolved in 10 mL of anhydrous benzene in a 50 mL round bottom flask. To the above stirred solution Cp*RuCl (PPh3)2 (15.90 mg, 0.02 mmol, 1 mol %) catalyst was added and the reaction mixture was refluxed at 80° C. under nitrogen pressure for 3 hours till TLC showed the completion of the reaction. Benzene solvent was removed under reduced pressure and the viscous residue was extracted with CH$_2$Cl$_2$ (2×10 mL). The combined extractions were treated with saturated brine and anhydrous Na$_2$SO$_4$ followed by adsorption on neutral alumina. Flash chromatography using EtOAc: petroleum ether (2:3) afforded the 1,5-disubstituted triazole amine compound 9s as a light brown amorphous solid (0.488 g, 92% yield). $^1$H NMR (400 MHz, CDCl$_3$, TMS) δ 3.55 (s, 3H), 3.84 (broad singlet, 2H), 6.53-6.59 (t, 1H, J=7.33 Hz), 6.66-6.71 (d, 1H, J=8.24 Hz), 6.74-6.78 (d, 1H, J=8.24 Hz), 6.87-6.91 (d, 1H, J=8.24 Hz), 7.00-7.11 (m, 2H), 7.36-7.45 (m, 2H), 7.90 (s, 1H). $^{13}$C NMR (100 MHz, CDCl$_3$, TMS) 55.49, 112.14, 112.19, 115.39, 117.83, 120.85, 125.44, 128.20, 130.07, 130.32, 131.17, 133.02, 136.37, 144.90, 153.49. MS (ESI): m/z (%)=266.92 (M+H$^+$, 100), 289.00 (M+Na$^+$, 10).

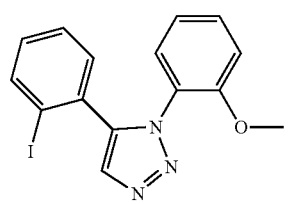

10s

5-(2-Iodophenyl)-1-(2-methoxyphenyl)-1H-1,2,3-triazole (1o/10s)

Procedure described for the synthesis of compound 8s was followed for the synthesis of compound 10s to afford a colorless amorphous solid (0.282 g, 75% yield). $^1$H NMR (400 MHz, CDCl$_3$, TMS) δ 3.56 (s, 3H), 6.82-6.87 (dd, 1H, J=0.92 Hz, J$_2$=8.24 Hz), 6.98-7.07 (m, 3H), 7.19-7.25 (m, 1H), 7.35-7.40 (m, 1H), 7.51-7.55 (dd, 1H, J$_1$=1.83 Hz, J$_2$=7.79 Hz), 7.86-7.90 (dd, 1H, J=0.92 Hz, J$_2$=7.79 Hz), 7.91 (s, 1H). $^{13}$C NMR (100 MHz, CDCl$_3$, TMS) δ 55.32, 99.15, 111.88, 120.71, 124.93, 127.59, 128.69, 130.50, 130.62, 131.28, 132.98, 133.82, 139.49, 140.56, 153.17. MS (ESI): m/z (%)=377.96 (M+H$^+$, 100), 399.95 (M+Na$^+$, 30).

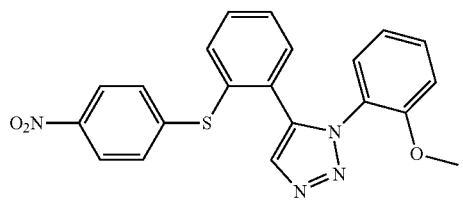

1a

1-(2-Methoxyphenyl)-5-(2-((4-nitrophenyl)thio)phenyl)-1H-1,2,3-triazole (1e)

Procedure described for the synthesis of compound 1d was followed for the synthesis of compound 1e to afford a light yellow amorphous solid (0.227 g, 85% yield). The amorphous solid was crystallized using a mixture of DCM and methanol to afford a light yellow crystalline compound 1e. m. p. 139-141° C. $^1$H NMR (400 MHz, CDCl$_3$, TMS) δ 3.54 (s, 3H), 6.80-6.85 (d, 1H, J=7.79 Hz), 6.88-6.98 (m, 3H), 7.31-7.51 (m, 6H), 7.66 (s, 1H), 7.98-8.03 (m, 2H). $^{13}$C NMR (100 MHz, CDCl$_3$) δ 55.32, 111.88, 120.71, 124.03, 125.04, 126.96, 128.62, 129.19, 130.68, 131.24, 131.32, 131.92, 132.08, 133.68, 135.62, 137.16, 145.47, 147.24, 153.17. HRMS (ESI$^+$) m/z 405.0998 (M+H)$^+$ (calcd. for C$_{21}$H$_{17}$N$_4$O$_3$S 405.1016). R$_{T, HPLC}$=4.589 min, Purity>97%.

X-Ray Crystal Structure Determination of 1e:

CCDC deposition number 1449876. Data were recorded on Bruker APEX-II CCD device using Mo-Kα radiation (wavelength=0.71073 Å) and graphite monochromator. The structure was refined using the program SHELXL-97. Crystal data: C$_{21}$H$_{16}$N$_4$O$_3$S, M=404.44, monoclinic, space group P2$_1$/c, a=9.7955(4) Å, b=11.6841(5) Å, c=16.9727(7) Å; α=90.000, β=106.3550(10)°, γ=90.00°; V=1863.95(13) Å$^3$; Z=4; T=110(2) K; μ=0.206 mm$^{-1}$; Crystal size=0.48×0.44×0.36 mm$^3$. Of 17215 reflections measured to theta range 2.15 to 25.410, 3434 were independent (R$_{int}$=0.0261). Final R1=0.0316 (I>2σ (I)), wR2=0.0858.

Scheme 2S$^a$:

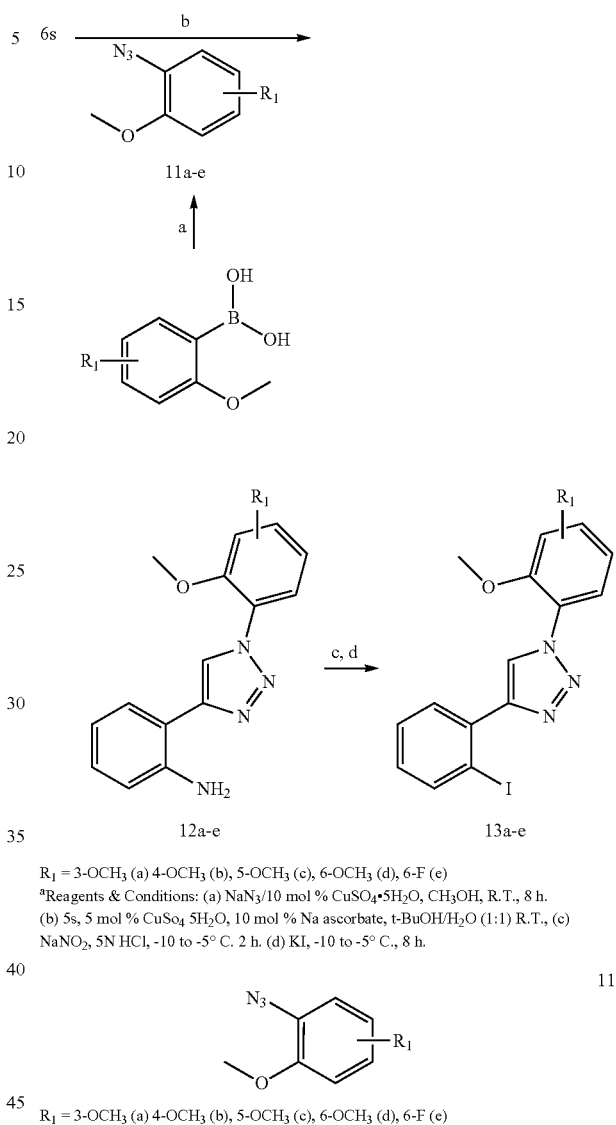

R$_1$ = 3-OCH$_3$ (a) 4-OCH$_3$ (b), 5-OCH$_3$ (c), 6-OCH$_3$ (d), 6-F (e)
$^a$Reagents & Conditions: (a) NaN$_3$/10 mol % CuSO$_4$•5H$_2$O, CH$_3$OH, R.T., 8 h.
(b) 5s, 5 mol % CuSO$_4$ 5H$_2$O, 10 mol % Na ascorbate, t-BuOH/H$_2$O (1:1) R.T., (c) NaNO$_2$, 5N HCl, -10 to -5° C. 2 h. (d) KI, -10 to -5° C., 8 h.

11

R$_1$ = 3-OCH$_3$ (a) 4-OCH$_3$ (b), 5-OCH$_3$ (c), 6-OCH$_3$ (d), 6-F (e)

Procedure described for the synthesis of 6s was followed for the syntheses of synthons 11a-e.

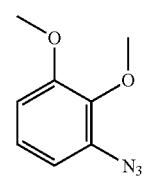

1-Azido-2,3-dimethoxybenzene (8a/11a)

$^1$H NMR (400 MHz, CDCl$_3$, TMS) δ 3.86 (s, 3H), 3.87 (s, 3H), 6.63-6.65 (dd, 1H, J$_1$=1.37 Hz, J$_2$=8.24 Hz), 6.69-6.71 (dd, 1H, J$_1$=1.37 Hz, J$_2$=8.24 Hz), 6.98-7.02 (m, 1H).

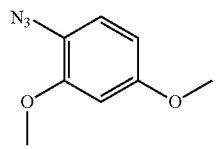

1-Azido-2,4-dimethoxybenzene (8b/11b)

¹H NMR (400 MHz, CDCl₃, TMS) δ 3.79 (s, 3H), 3.85 (s, 3H), 6.44-6.52 (m, 2H), 6.90 (dd, 1H, J=1.37 Hz, J₂=8.24 Hz).

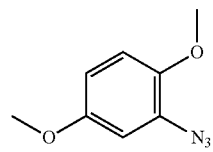

2-Azido-1,4-dimethoxybenzene (8c/11c)

¹H NMR (400 MHz, CDCl₃, TMS) δ 3.76 (s, 3H), 3.83 (s, 3H), 6.58-6.64 (m, 2H), 6.80-6.84 (m, 1H).

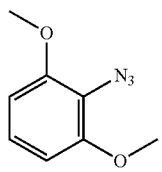

2-Azido-1,3-dimethoxybenzene (8d/11d)

¹H NMR (400 MHz, CDCl₃, TMS) δ 3.87 (s, 6H), 6.53-6.57 (m, 2H), 7.00-7.06 (m, 1H).

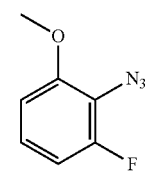

2-Azido-1-fluoro-3-methoxybenzene (8e/11e)

¹H NMR (400 MHz, CDCl₃, TMS) δ 3.88 (s, 3H), 6.65-6.73 (m, 2H), 6.98-7.04 (m, 1H).

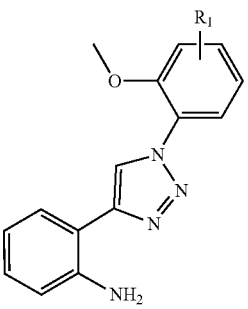

12

$R_1$=3—OCH₃ (a), 4-OCH₃ (b), 5-OCH₃ (c), 6-OCH₃ (d), 6-F (a)

Procedure described for the synthesis of 7s was followed for the syntheses of the intermediates 12a-e.

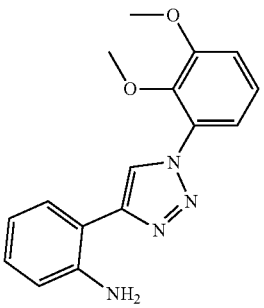 [SMILES: COc1cccc(-n2cc(-c3ccccc3N)nn2)c1OC]

2-(1-(2,3-Dimethoxyphenyl)-1H-1,2,3-triazol-4-yl) aniline (9a/12a)

¹H NMR (400 MHz, CDCl₃, TMS) δ 3.74 (s, 3H), 3.93 (s, 3H), 5.51 (broadsinglet, 2H), 6.72-6.81 (m, 2H), 7.00-7.05 (m, 1H), 7.10-7.23 (m, 2H), 7.37-7.47 (m, 2H), 8.36 (s, 1H). ¹³C NMR (100 MHz, CDCl₃) δ 56.20, 61.24, 112.86, 113.57, 116.77, 116.92, 117.42, 121.71, 124.54, 127.85, 129.10, 131.13, 141.44, 145.17, 148.14, 153.63. MS (ESI): m/z (%)=319.08 (M+Na⁺, 100).

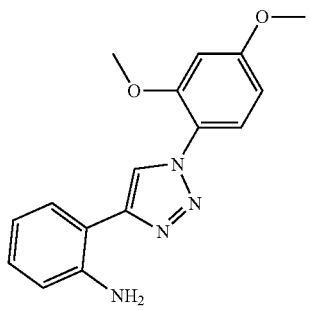 [SMILES: COc1ccc(-n2cc(-c3ccccc3N)nn2)c(OC)c1]

2-(1-(2,4-Dimethoxyphenyl)-1H-1,2,3-triazol-4-yl) aniline (9b/12b)

¹H NMR (400 MHz, CDCl₃, TMS) δ 3.85 (s, 3H), 3.86 (s, 3H), 6.59-6.63 (m, 2H), 6.72-6.80 (m, 2H), 7.10-7.15 (m,

1H), 7.41-7.44 (dd, 1H, $J_1$=1.83 Hz, $J_2$=7.79 Hz), 7.64-7.67 (m, 1H), 8.19 (s, 1H). $^{13}$C NMR (100 MHz, CDCl$_3$) δ 55.70, 55.99, 99.61, 104.81, 113.91, 116.73, 117.35, 119.90, 122.16, 126.50, 127.81, 128.92, 145.10, 147.63, 152.71, 161.29. MS (ESI): m/z (%)=319.00 (M+Na$^+$, 100).

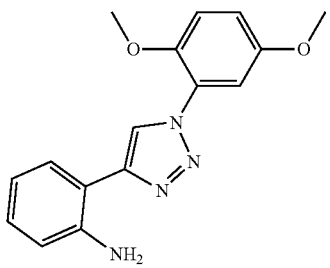 [SMILES: COc1ccc(OC)c(-n2cc(-c3ccccc3N)nn2)c1]

2-(1-(2,5-Dimethoxyphenyl)-1H-1,2,3-triazol-4-yl) aniline (9c/12c)

$^1$H NMR (400 MHz, CDCl$_3$, TMS) δ 3.80 (s, 3H), 3.82 (s, 3H), 5.49 (broadsinglet, 2H), 6.71-6.80 (m, 2H), 6.92-7.02 (m, 2H), 7.09-7.15 (m, 1H), 7.41-7.46 (m, 2H), 8.37 (s, 1H). $^{13}$C NMR (100 MHz, CDCl$_3$) δ 55.93, 56.78, 110.32, 113.72, 113.76, 115.69, 116.71, 117.34, 122.06, 126.44, 127.85, 129.01, 145.01, 145.17, 147.81, 153.87. MS (ESI): m/z (%)=319.11 (M+Na$^+$, 100).

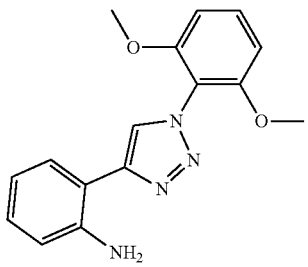 [SMILES: COc1cccc(OC)c1-n1cc(-c2ccccc2N)nn1]

2-(1-(2,6-Dimethoxyphenyl)-1H-1,2,3-triazol-4-yl) aniline (9d/12d)

$^1$H NMR (400 MHz, CDCl$_3$, TMS) δ 3.76 (s, 6H), 5.58 (broadsinglet, 2H), 6.66-6.80 (m, 4H), 7.07-7.15 (m, 1H), 7.38-7.46 (m, 2H), 7.86 (s, 1H). $^{13}$C NMR (100 MHz, CDCl$_3$) δ 56.19, 104.32, 113.91, 115.26, 116.72, 117.23, 123.33, 127.78, 128.78, 131.42, 145.12, 147.44, 155.94. MS (ESI): m/z (%)=319.00 (M+Na$^+$, 100).

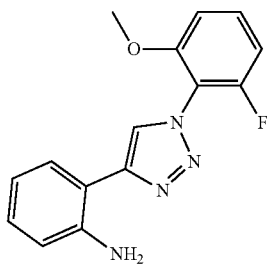 [SMILES: COc1cccc(F)c1-n1cc(-c2ccccc2N)nn1]

2-(1-(2-Fluoro-6-methoxyphenyl)-1H-1,2,3-triazol-4-yl)aniline (9e/12e)

$^1$H NMR (400 MHz, CDCl$_3$, TMS) δ 3.80 (s, 3H), 5.51 (broadsinglet, 2H), 6.70-6.80 (m, 2H), 6.83-6.91 (m, 2H), 7.10-7.15 (m, 1H), 7.39-7.46 (m, 2H), 7.94 (s, 1H). $^{13}$C NMR (100 MHz, CDCl$_3$) δ 56.50, 107.61 (1C, d, J=2.88 Hz), 108.54 (1C, d, J=20.13 Hz), 113.45, 115.02 (1C, d, J=14.38 Hz), 116.78, 117.36, 123.00, 127.87, 129.09, 131.51 (1C, d, J=10.54 Hz), 145.14, 147.74, 155.55 (1C, d, J=2.88 Hz), 157.79 (1C, d, J=253.99 Hz). MS (ESI): m/z (%)=307.19 (M+Na$^+$, 100).

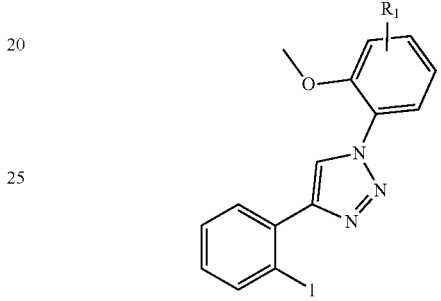

R=3-OCH$_3$ (a), 4-OCH$_3$ (b), 5-OCH$_3$ (c), 6-OCH$_3$ (d), 6-F (e)

Procedure described for the synthesis of 8s was followed for the syntheses of the intermediates 13a-e.

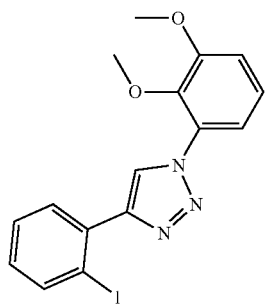

1-(2,3-Dimethoxyphenyl)-4-(2-iodophenyl)-1H-1,2,3-triazole (10a/13a)

$^1$H NMR (400 MHz, CDCl$_3$, TMS) δ 3.78 (s, 3H), 3.95 (s, 3H), 7.00-7.09 (m, 2H), 7.19-7.27 (m, 1H), 7.43-7.51 (m, 2H), 7.92-8.00 (m, 2H), 8.81 (s, 1H). $^{13}$C NMR (100 MHz, CDCl$_3$) δ 56.21, 61.39, 96.73, 112.69, 116.73, 124.43, 124.60, 128.44, 129.67, 130.69, 131.11, 135.23, 140.27, 141.14, 147.64, 153.63. MS (ESI): m/z (%)=430.40 (M+Na$^+$, 100).

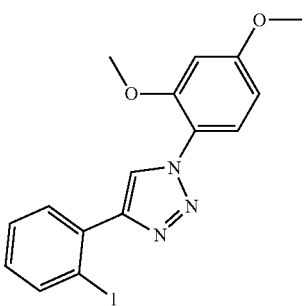

1-(2,4-Dimethoxyphenyl)-4-(2-iodophenyl)-1H-1,2,3-triazole (10b/13b)

¹H NMR (400 MHz, CDCl₃, TMS) δ 3.87 (s, 6H), 6.59-6.65 (m, 2H), 7.02-7.07 (m, 1H), 7.41-7.48 (m, 1H), 7.69-7.75 (m, 1H), 7.89-7.99 (m, 2H), 8.61 (s, 1H). ¹³C NMR (100 MHz, CDCl₃) δ 55.71, 56.10, 96.69, 99.61, 104.87, 119.95, 124.78, 126.38, 128.41, 129.53, 130.73, 135.48, 140.22, 147.18, 152.53, 161.24. MS (ESI): m/z (%)=430.51 (M+Na⁺, 100).

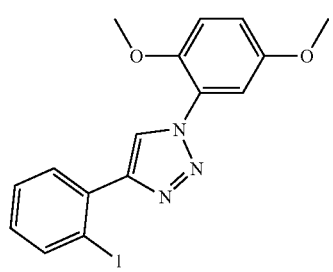

1-(2,5-Dimethoxyphenyl)-4-(2-iodophenyl)-1H-1,2,3-triazole (10c/13c)

¹H NMR (400 MHz, CDCl₃, TMS) δ 3.84 (s, 3H), 3.86 (s, 3H), 6.95-7.08 (m, 3H), 7.42-7.53 (m, 2H), 7.90-8.00 (m, 2H), 8.79 (s, 1H). ¹³C NMR (100 MHz, CDCl₃) δ 55.99, 56.79, 96.73, 110.20, 113.89, 115.71, 124.72, 126.56, 128.43, 129.62, 130.74, 135.35, 140.25, 144.86, 147.43, 153.97. MS (ESI): m/z (%)=430.25 (M+Na⁺, 100).

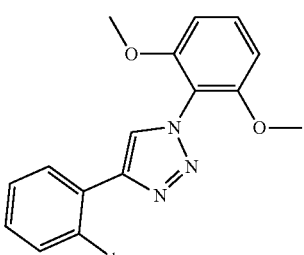

1-(2,6-Dimethoxyphenyl)-4-(2-iodophenyl)-1H-1,2,3-triazole (10d/13d)

¹H NMR (400 MHz, CDCl₃, TMS) δ 3.78 (s, 6H), 6.67-6.70 (m, 2H), 7.00-7.05 (m, 1H), 7.38-7.47 (m, 2H), 7.94-8.04 (m, 2H), 8.30 (s, 1H). ¹³C NMR (100 MHz, CDCl₃) δ 56.25, 96.62, 104.36, 115.26, 126.09, 128.35, 129.37, 130.73, 131.40, 135.52, 140.20, 146.63, 155.85. MS (ESI): m/z (%)=430.32 (M+Na⁺, 100).

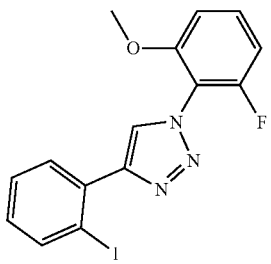

1-(2-Fluoro-6-methoxyphenyl)-4-(2-iodophenyl)-1H-1,2,3-triazole (10e/13e)

¹H NMR (400 MHz, CDCl₃, TMS) δ 3.84 (s, 1H), 6.86-6.94 (m, 2H), 7.03-7.08 (m, 1H), 7.40-7.49 (m, 2H), 7.95-8.00 (m, 2H), 8.39 (s, 1H). ¹³C NMR (100 MHz, CDCl₃): δ 56.60, 96.67, 107.65 (1C, d, J=2.88 Hz), 108.59 (1C, d, J=20.13 Hz), 115.05 (1C, d, J=14.38 Hz), 125.73, 128.44, 129.66, 130.76, 131.48 (1C, d, J=10.54 Hz), 135.09, 140.25, 147.09, 155.47 (1C, d, J=2.88 Hz), 157.76 (1C, d, J=253.99 Hz). MS (ESI): m/z (%)=418.18 (M+Na⁺, 100).

Scheme 3S*ᵃ*:

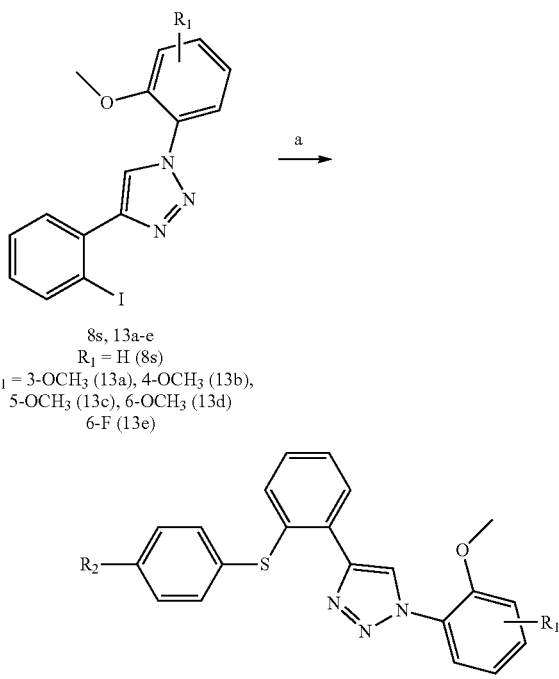

8s, 13a-e
R₁ = H (8s)
R₁ = 3-OCH₃ (13a), 4-OCH₃ (13b),
5-OCH₃ (13c), 6-OCH₃ (13d)
6-F (13e)

R₁ = H (2), 3-OCH₃ (3), 4-OCH₃ (4), 5-OCH₃ (5)
6-OCH₃ (6), 6-F (7)
R₂ = NO₂ (a), COOCH₃ (b), OCH₃ (c), CF₃ (d)
Z = S (x)

-continued

*Reagents & Conditions: (a) 4-nitrothiophenol, K$_2$CO$_3$, 5 mol %, CuI, DMF, 110-120° C., 8 h.

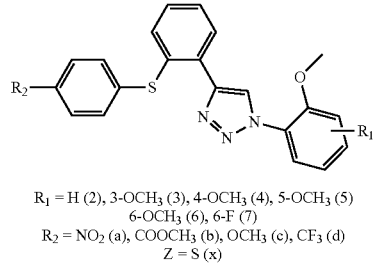

R$_1$ = H (2), 3-OCH$_3$ (3), 4-OCH$_3$ (4), 5-OCH$_3$ (5)
6-OCH$_3$ (6), 6-F (7)
R$_2$ = NO$_2$ (a), COOCH$_3$ (b), OCH$_3$ (c), CF$_3$ (d)
Z = S (x)

Procedure described for the synthesis of 1d was followed for the syntheses of the final compounds. But, for the synthesis of compounds 2cx, 3cx, 4cx, 5cx, 6cx, and 7cx the reaction temperature was kept at 120° C.

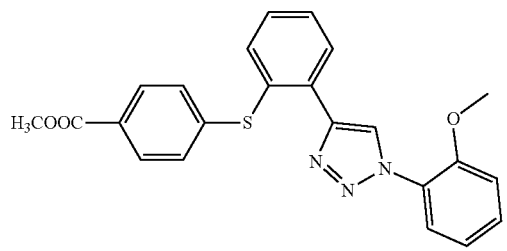

Methyl 4-((2-(1-(2-methoxyphenyl)-1H-1,2,3-triazol-4-yl)phenyl)thio)benzoate (2bx)

$^1$H NMR (400 MHz, CDCl$_3$, TMS) δ 3.71 (s, 3H), 3.84 (s, 3H), 7.00-7.12 (m, 4H), 7.35-7.41 (m, 2H), 7.53-7.63 (m, 2H), 7.74-7.78 (m, 1H), 7.82-7.87 (m, 2H), 8.32-8.36 (dd, 1H, J$_1$=1.37 Hz, J$_2$=7.79 Hz), 8.53 (s, 1H). $^{13}$C NMR (100 MHz, CDCl$_3$) δ 52.06, 55.82, 112.25, 121.19, 125.32, 126.20, 126.48, 127.24, 128.19, 129.04, 129.98, 130.02, 130.20, 130.27, 135.00, 136.82, 144.18, 144.26, 150.99, 166.58. MS (ESI): m/z (%)=440.55 (M+Na$^+$, 100). R$_{T, HPLC}$=6.067 min, Purity>96%.

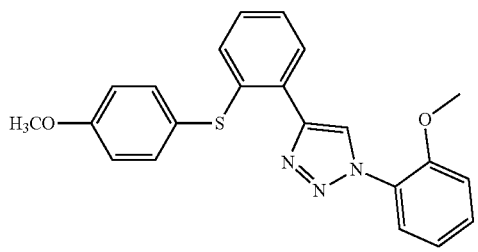 [SMILES: COc1ccc(Sc2ccccc2-c2cn(-c3ccccc3OC)nn2)cc1]

1-(2-Methoxyphenyl)-4-(2-((4-methoxyphenyl)thio)phenyl)-1H-1,2,3-triazole (2cx)

$^1$H NMR (400 MHz, CDCl$_3$, TMS) δ 3.81 (s, 3H), 3.88 (s, 3H), 6.86-6.91 (m, 2H), 7.07-7.15 (m, 3H), 7.18-7.23 (m, 1H), 7.28-7.36 (m, 3H), 7.40-7.46 (m, 1H), 7.82-7.87 (d, 1H, J=7.79 Hz), 8.09-8.12 (d, 1H, J=7.79 Hz), 8.67 (s, 1H). $^{13}$C NMR (100 MHz, CDCl$_3$) δ 55.30, 55.97, 112.26, 115.09, 121.13, 124.18, 125.30, 125.41, 125.75, 126.39, 128.44, 128.76, 129.98, 130.01, 130.12, 134.62, 135.62, 144.61, 151.12, 159.67. MS (ESI): m/z (%)=390.13 (M+H$^+$, 50), 412.09 (M+Na$^+$, 100).

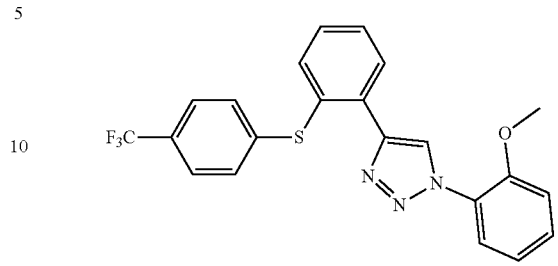

1-(2-Methoxyphenyl)-4-(2-((4-(trifluoromethyl)phenyl)thio)phenyl)-1H-1,2,3-triazole (2dx)

$^1$H NMR (400 MHz, CDCl$_3$, TMS) δ 3.73 (s, 3H), 7.03-7.19 (m, 4H), 7.37-7.47 (m, 4H), 7.55-7.62 (m, 2H), 7.77-7.80 (dd, 1H, J$_1$=1.83 Hz, J$_2$=7.79 Hz), 8.33-8.36 (dd, 1H, J$_1$=1.37 Hz, J$_2$=7.79 Hz), 8.55 (s, 1H). $^{13}$C NMR (100 MHz, CDCl$_3$) δ 55.75, 112.24, 121.19, 123.99 (1C, q, J$_1$=271.74 Hz), 125.28, 125.31, 125.88 (2C, q, J$_3$=3.82 Hz), 126.16, 127.07, 127.67 (1C, q, J$_2$=32.69 Hz), 128.22, 129.08, 129.96, 130.05, 130.28, 134.91, 136.63, 142.66, 144.23, 150.97. HRMS (ESI$^+$) m/z 428.1023 (M+H)$^+$ (calcd. for C$_{22}$H$_{17}$F$_3$N$_3$OS 428.1039). R$_{T, HPLC}$=6.039 min, Purity>97%.

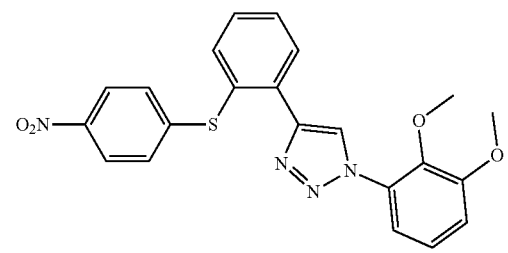 [SMILES: COc1cccc(-n2cc(-c3ccccc3Sc3ccc([N+](=O)[O-])cc3)nn2)c1OC]

1-(2,3-Dimethoxyphenyl)-4-(2-((4-nitrophenyl)thio)phenyl)-1H-1,2,3-triazole (3ax)

$^1$H NMR (400 MHz, CDCl$_3$, TMS) δ 3.54 (s, 3H), 3.93 (s, 3H), 6.98-7.21 (m, 4H), 7.36-7.49 (m, 2H), 7.62-7.70 (m, 2H), 8.00-8.05 (m, 2H), 8.36-8.41 (m, 1H), 8.64 (s, 1H). $^{13}$C NMR (100 MHz, CDCl$_3$) δ 56.11, 60.92, 112.63, 116.59, 124.15, 124.53, 124.79, 126.05, 126.80, 129.45, 130.52, 130.78, 130.86, 135.39, 137.47, 140.98, 144.37, 145.26, 147.56, 153.49. HRMS (ESI$^+$) m/z 435.1102 (M+H)$^+$ (calcd. for C$_{22}$H$_{19}$N$_4$O$_4$S 435.1122). R$_{T, HPLC}$=5.336 min, Purity>98%.

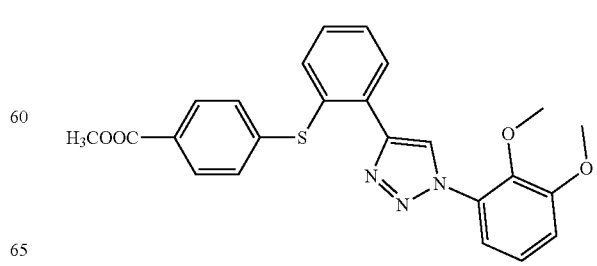

Methyl 4-((2-(1-(2,3-dimethoxyphenyl)-1H-1,2,3-triazol-4-yl)phenyl)thio)benzoate (3bx)

$^1$H NMR (400 MHz, CDCl$_3$, TMS) δ 3.53 (s, 3H), 3.86 (s, 3H), 3.92 (s, 3H), 6.97-7.00 (m, 1H), 7.08-7.12 (m, 2H), 7.15-7.20 (m, 1H), 7.37-7.42 (m, 2H), 7.55-7.64 (m, 2H), 7.83-7.87 (m, 2H), 8.35-8.39 (m, 1H), 8.69 (s, 1H). $^{13}$C NMR (100 MHz, CDCl$_3$) δ 51.90, 56.02, 60.81, 112.50, 116.53, 124.35, 124.81, 126.31, 127.13, 128.18, 129.04, 129.87, 130.05, 130.11, 130.87, 134.72, 136.76, 140.97, 143.81, 144.48, 153.43, 166.39. MS (ESI): m/z (%)=470.38 (M+Na$^+$, 100). R$_{T, HPLC}$=6.147 min, Purity>95%.

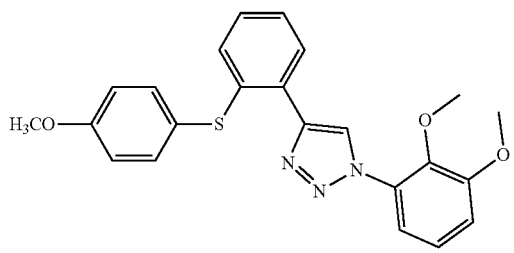 [SMILES: COc1ccc(Sc2ccccc2-c2cn(-c3cccc(OC)c3OC)nn2)cc1]

1-(2,3-Dimethoxyphenyl)-4-(2-((4-methoxyphenyl)thio)phenyl)-1H-1,2,3-triazole (3cx)

$^1$H NMR (400 MHz, CDCl$_3$, TMS) δ 3.72 (s, 3H), 3.80 (s, 3H), 3.94 (s, 3H), 6.86-6.90 (m, 2H), 6.99-7.04 (d, 1H, J=8.70 Hz), 7.07-7.11 (d, 1H, J=8.24 Hz), 7.18-7.35 (m, 5H), 7.45-7.49 (d, 1H, J=8.24 Hz), 8.09-8.13 (d, 1H, J=7.33 Hz), 8.77 (s, 1H). $^{13}$C NMR (100 MHz, CDCl$_3$) δ 55.29, 56.14, 61.16, 112.55, 115.11, 116.77, 124.01, 124.45, 124.96, 126.36, 128.52, 129.50, 129.91, 129.97, 131.17, 134.62, 135.77, 141.20, 144.93, 153.59, 159.68. MS (ESI): m/z (%)=441.72 (M+Na$^+$, 100).

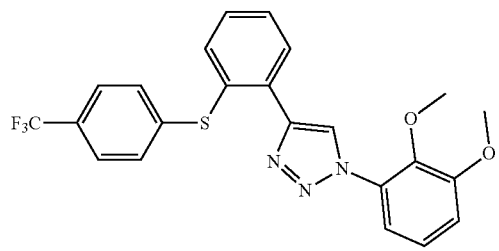 [SMILES: COc1cccc(-n2cc(-c3ccccc3Sc3ccc(C(F)(F)F)cc3)nn2)c1OC]

1-(2,3-Dimethoxyphenyl)-4-(2-((4-(trifluoromethyl)phenyl)thio)phenyl)-1H-1,2,3-triazole (3dx)

$^1$H NMR (400 MHz, CDCl$_3$, TMS) δ 3.53 (s, 3H), 3.93 (s, 3H), 6.89-7.02 (dd, 1H, J$_1$=1.37 Hz, J$_2$=8.24 Hz), 7.14-7.21 (m, 3H), 7.38-7.46 (m, 4H), 7.56-7.62 (m, 2H), 8.35-8.38 (dd, 1H, J=1.37 Hz, J$_2$=7.79 Hz), 8.70 (s, 1H). $^{13}$C NMR (100 MHz, CDCl$_3$) δ 56.12, 60.88, 112.61, 116.69, 123.97 (1C, q, J$_1$=272.20 Hz), 124.47, 124.91, 125.91 (2C, q, J$_3$=3.83 Hz), 127.05, 127.70 (1C, q, J=32.59 Hz), 128.39, 129.17, 129.94, 130.19, 130.98, 134.69, 136.65, 141.09, 142.40, 144.57, 153.52. HRMS (ESI$^+$) m/z 458.1126 (M+H)$^+$ (calcd. for C$_{23}$H$_{19}$F$_3$N$_3$O$_2$S 458.1145). R$_{T, HPLC}$=6.723 min, Purity>97%.

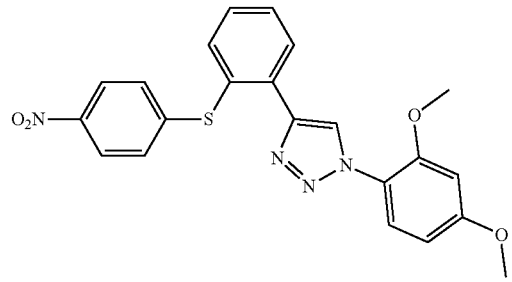

1-(2,4-Dimethoxyphenyl)-4-(2-((4-nitrophenyl)thio)phenyl)-1H-1,2,3-triazole (4ax)

$^1$H NMR (400 MHz, CDCl$_3$, TMS) δ 3.71 (s, 3H), 3.85 (s, 3H), 6.54-6.62 (m, 2H), 7.08-7.14 (m, 2H), 7.41-7.48 (m, 1H), 7.58-7.70 (m, 3H), 8.00-8.06 (m, 2H), 8.33-8.37 (m, 1H), 8.40 (s, 1H). $^{13}$C NMR (100 MHz, CDCl$_3$) δ 55.68, 55.83, 99.58, 104.83, 119.71, 124.12, 125.16, 126.19, 126.34, 126.80, 129.30, 130.62, 130.75, 135.63, 137.33, 143.97, 145.28, 147.81, 152.40, 161.25. MS (ESI): m/z (%)=457.16 (M+Na$^+$, 100).

Methyl 4-((2-(1-(2,4-dimethoxyphenyl)-1H-1,2,3-triazol-4-yl)phenyl)thio)benzoate (4bx)

$^1$H NMR (400 MHz, CDCl$_3$, TMS) δ 3.70 (s, 3H), 3.85 (s, 3H), 3.86 (s, 3H), 6.53-6.64 (m, 2H), 7.07-7.15 (m, 2H), 7.35-7.42 (m, 1H), 7.53-7.69 (m, 3H), 7.82-7.90 (m, 2H), 8.32-8.37 (dd, 1H, J$_1$=1.37 Hz, J$_2$=7.79 Hz), 8.43 (s, 1H). $^{13}$C NMR (100 MHz, CDCl$_3$) δ 52.05, 55.65, 55.79, 99.54, 104.74, 119.85, 125.32, 126.31, 126.50, 127.21, 128.16, 128.94, 129.94, 130.17, 130.22, 135.05, 136.74, 144.12, 144.17, 152.44, 161.14, 166.58. HRMS (ESI) min 448.1308 (M+H)$^+$ (calcd. for C$_{24}$H$_{22}$N$_3$O$_4$S 448.1326).

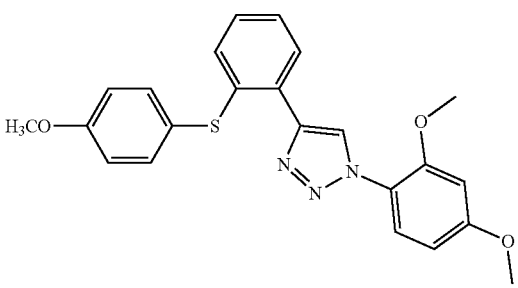 [SMILES: COc1ccc(Sc2ccccc2-c2cn(-c3ccc(OC)cc3OC)nn2)cc1]

1-(2,4-Dimethoxyphenyl)-4-(2-((4-methoxyphenyl)thio)phenyl)-1H-1,2,3-triazole (4cx)

¹H NMR (400 MHz, CDCl₃, TMS) δ 3.81 (s, 3H), 3.84 (s, 3H), 3.88 (s, 3H), 6.60-6.64 (m, 2H), 6.86-6.91 (m, 2H), 7.07-7.10 (m, 1H), 7.17-7.22 (m, 1H), 7.27-7.35 (m, 3H), 7.68-7.72 (m, 1H), 8.08-8.12 (dd, 1H, 0.1, 1.37 Hz, $J_2$=7.79 Hz), 8.55 (s, 1H). ¹³C NMR (100 MHz, CDCl₃) δ 55.34, 55.68, 55.98, 99.60, 104.73, 115.12, 120.12, 124.30, 125.38, 126.43, 126.49, 128.40, 129.61, 130.04, 130.27, 134.66, 135.59, 144.52, 152.64, 159.69, 161.51. MS (ESI): m/z (%)=420.22 (M+H⁺, 100), 442.16 (M+Na⁺, 60).

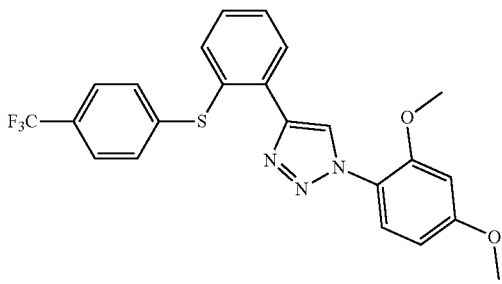 [SMILES: COc1ccc(-n2cc(-c3ccccc3Sc3ccc(C(F)(F)F)cc3)nn2)c(OC)c1]

1-(2,4-Dimethoxyphenyl)-4-(2-((4-(trifluoromethyl)phenyl)thio)phenyl)-1H-1,2,3-triazole (4dx)

¹H NMR (400 MHz, CDCl₃, TMS) δ 3.69 (s, 3H), 3.86 (s, 3H), 6.55-6.61 (m, 2H), 7.12-7.22 (m, 3H), 7.36-7.47 (m, 3H), 7.54-7.64 (m, 2H), 8.33-8.36 (dd, 1H, J=1.37 Hz, $J_2$=7.79 Hz), 8.44 (s, 1H). MS (ESI): m/z (%)=458.08 (M+H⁺, 100), 480.17 (M+Na⁺, 20).

1-(2,5-Dimethoxyphenyl)-4-(2-((4-nitrophenyl)thio)phenyl)-1H-1,2,3-triazole (5ax)

¹H NMR (400 MHz, CDCl₃, TMS) δ 3.70 (s, 3H), 3.82 (s, 3H), 6.92-7.00 (m, 2H), 7.09-7.15 (m, 2H), 7.39-7.49 (m, 2H), 7.61-7.70 (m, 2H), 8.01-8.07 (m, 2H), 8.32-8.36 (m, 1H), 8.58 (s, 1H). ¹³C NMR (100 MHz, CDCl₃) δ 55.92, 56.43, 110.10, 113.76, 115.64, 124.11, 125.06, 126.15, 126.28, 126.85, 129.39, 130.62, 130.74, 135.48, 137.36, 144.18, 144.65, 145.27, 147.78, 153.89. HRMS (ESI) m/z 435.1100 (M+H)⁺ (calcd. for C₂₂H₁₉N₄O₄S 435.1122). $R_{T,\ HPLC}$=5.904 min, Purity>95%.

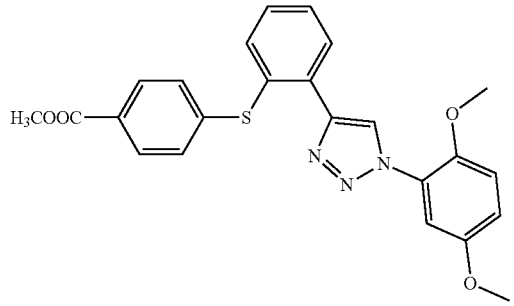

Methyl 4-((2-(1-(2,5-dimethoxyphenyl)-1H-1,2,3-triazol-4-yl)phenyl)thio)benzoate (5bx)

¹H NMR (400 MHz, CDCl₃, TMS) δ 3.67 (s, 3H), 3.82 (s, 3H), 3.86 (s, 3H), 6.91-6.99 (m, 2H), 7.08-7.13 (m, 2H), 7.37-7.42 (m, 2H), 7.54-7.64 (m, 2H), 7.84-7.88 (m, 2H), 8.32-8.36 (m, 1H), 8.61 (s, 1H). ¹³C NMR (100 MHz, CDCl₃) δ 52.05, 55.94, 56.44, 110.08, 113.76, 115.64, 125.24, 126.44, 126.48, 127.23, 128.24, 129.06, 129.96, 130.19, 130.26, 134.94, 136.81, 144.16, 144.36, 144.76, 153.88, 166.56. HRMS (ESI⁺) m/z 448.1308 (M+H)⁺ (calcd. for C₂₄H₂₂N₃O₄S 448.1326). $R_{T,\ HPLC}$=6.309 min, Purity>97%.

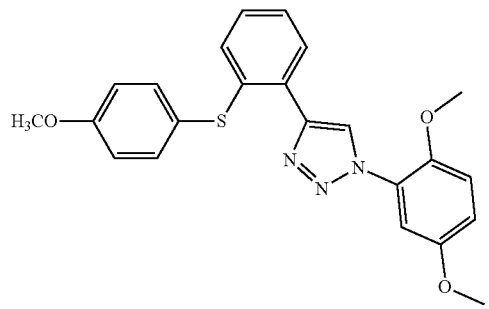 [SMILES: COc1ccc(Sc2ccccc2-c2cn(-c3cc(OC)ccc3OC)nn2)cc1]

1-(2,5-Dimethoxyphenyl)-4-(2-((4-methoxyphenyl)thio)phenyl)-1H-1,2,3-triazole (5cx)

¹H NMR (400 MHz, CDCl₃, TMS) δ 3.81 (s, 3H), 3.83 (s, 3H), 3.84 (s, 3H), 6.86-6.91 (m, 2H), 6.94-7.11 (m, 3H), 7.18-7.23 (m, 1H), 7.28-7.36 (m, 3H), 7.48-7.50 (m, 1H), 8.07-8.11 (dd, 1H, $J_1$=1.37 Hz, $J_2$=7.79 Hz), 8.72 (s, 1H). ¹³C NMR (100 MHz, CDCl₃) δ 55.32, 55.94, 56.64, 110.26, 113.81, 115.11, 115.59, 124.21, 125.26, 126.40, 126.64, 128.48, 129.61, 130.04, 130.10, 134.65, 135.70, 144.75, 144.93, 153.89, 159.69. MS (ESI): m/z (%)=420.22 (M+H⁺, 100), 442.16 (M+Na⁺, 50). $R_{T,\ HPLC}$=6.320 min, Purity>91%.

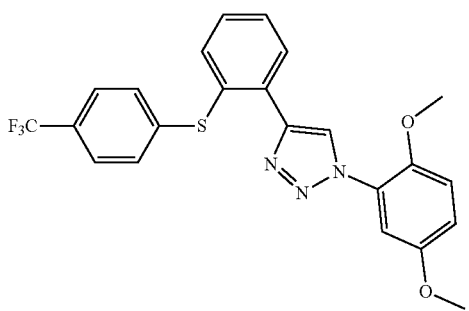 [SMILES: COc1ccc(OC)c(-n2cc(-c3ccccc3Sc3ccc(C(F)(F)F)cc3)nn2)c1]

1-(2,5-Dimethoxyphenyl)-4-(2-((4-(trifluoromethyl)phenyl)thio)phenyl)-1H-1,2,3-triazole (5dx)

¹H NMR (400 MHz, CDCl₃, TMS) δ 3.67 (s, 3H), 3.82 (s, 3H), 6.92-6.99 (m, 2H), 7.14-7.18 (m, 2H), 7.37-7.47 (m, 4H), 7.55-7.62 (m, 2H), 8.31-8.35 (dd, 1H, $J_1$=1.37 Hz, $J_2$=7.79 Hz), 8.61 (s, 1H). ¹³C NMR (100 MHz, CDCl₃) δ 55.90, 56.34, 110.11, 113.74, 115.61, 124.04 (1C, q, $J_1$ 272.00 Hz), 125.21, 125.87 (2C, q, $J_3$=3.83 Hz), 126.41, 127.08, 127.67 (1C, q, $J_2$=32.59 Hz), 128.28, 129.10, 129.94, 130.27, 134.85, 136.63, 142.66, 144.33, 144.73, 153.88. MS (ESI): m/z (%)=458.08 (M+H⁺, 100), 480.04 (M+Na⁺, 30). $R_{T, HPLC}$=6.957 min, Purity>92%.

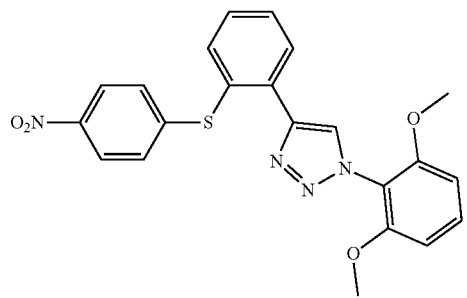 [SMILES: COc1cccc(OC)c1-n1cc(-c2ccccc2Sc2ccc([N+](=O)[O-])cc2)nn1]

1-(2,6-Dimethoxyphenyl)-4-(2-((4-nitrophenyl)thio)phenyl)-1H-1,2,3-triazole (6ax)

¹H NMR (400 MHz, CDCl₃, TMS) δ 3.66 (s, 6H), 6.62-6.65 (m, 2H), 7.08-7.12 (m, 2H), 7.36-7.45 (m, 2H), 7.61-7.68 (m, 2H), 7.99-8.03 (m, 2H), 8.13 (s, 1H), 8.44-8.48 (m, 1H). ¹³C NMR (100 MHz, CDCl₃) δ 56.09, 104.28, 115.06, 124.01, 126.18, 126.57, 126.61, 129.12, 130.54, 130.75, 131.40, 135.62, 137.28, 143.47, 145.22, 147.57, 155.78. MS (ESI): m/z (%)=434.91 (M⁺, 100), 456.93 (M+Na⁺, 40).

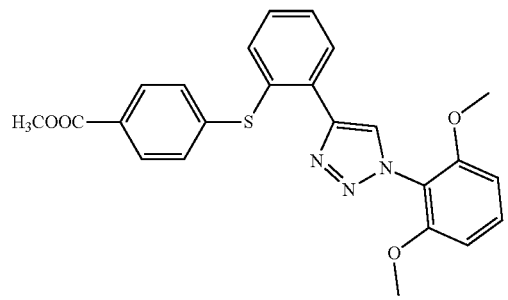

Methyl 4-((2-(1-(2,6-dimethoxyphenyl)-1H-1,2,3-triazol-4-yl)phenyl)thio)benzoate (6bx)

¹H NMR (400 MHz, CDCl₃, TMS) δ 3.67 (s, 6H), 3.86 (s, 3H), 6.62-6.66 (d, 2H, J=8.70 Hz), 7.06-7.11 (m, 2H), 7.34-7.41 (m, 2H), 7.54-7.63 (m, 2H), 7.81-7.86 (m, 2H), 8.19 (s, 1H), 8.42-8.46 (m, 1H). ¹³C NMR (100 MHz, CDCl₃) δ 51.99, 56.06, 104.23, 115.16, 126.51, 126.72, 127.07, 128.09, 128.75, 129.89, 130.06, 130.12, 131.25, 135.04, 136.66, 143.64, 143.93, 155.77, 166.59. HRMS (ESI⁺) m/z 448.1303 (M+H)⁺ (calcd. for C₂₄H₂₂N₃O₄S 448.1326). $R_{T, HPLC}$=5.804 min, Purity>97%.

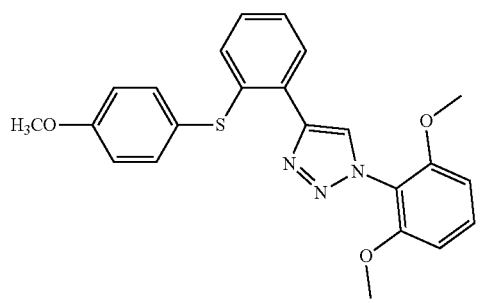 [SMILES: COc1ccc(Sc2ccccc2-c2cn(-c3c(OC)cccc3OC)nn2)cc1]

1-(2,6-Dimethoxyphenyl)-4-(2-((4-methoxyphenyl)thio)phenyl)-1H-1,2,3-triazole (6cx)

¹H NMR (400 MHz, CDCl₃, TMS) δ 3.78 (s, 3H), 3.81 (s, 6H), 6.67-6.71 (d, 2H, J=7.79 Hz), 6.85-6.90 (m, 2H), 7.07-7.10 (m, 1H), 7.16-7.21 (m, 1H), 7.28-7.35 (m, 3H), 7.38-7.43 (m, 1H), 8.20-8.24 (dd, 1H, $J_1$=1.37 Hz, $J_2$=7.79 Hz), 8.30 (s, 1H). ¹³C NMR (100 MHz, CDCl₃) δ 55.26, 56.12, 104.26, 115.01, 115.31, 124.17, 126.34, 126.69, 128.17, 129.42, 129.96, 130.28, 131.22, 134.63, 135.39, 143.96, 155.84, 159.61. MS (ESI): m/z (%)=442.51 (M+Na⁺, 100).

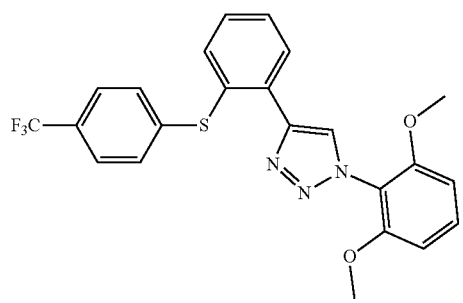 [SMILES: COc1cccc(OC)c1-n1cc(-c2ccccc2Sc2ccc(C(F)(F)F)cc2)nn1]

1-(2,6-Dimethoxyphenyl)-4-(2-((4-(trifluoromethyl)phenyl)thio)phenyl)-1H-1,2,3-triazole (6dx)

¹H NMR (400 MHz, CDCl₃, TMS) δ 3.67 (s, 6H), 6.63-6.66 (m, 2H), 7.12-7.16 (m, 2H), 7.35-7.44 (m, 4H), 7.54-7.61 (m, 2H), 8.22 (s, 1H), 8.44-8.48 (dd, 1H, $J_1$=1.37 Hz, $J_2$=7.79 Hz). ¹³C NMR (100 MHz, CDCl₃) δ 56.06, 104.28, 115.21, 124.04 (1C, q, $J_1$=272.20 Hz), 125.77 (2C, d, $J_3$=3.83 Hz), 126.71, 127.04, 127.54 (1C, q, $J_2$=32.59 Hz), 128.00, 128.83, 129.97, 130.14, 131.31, 135.06, 136.64, 142.42, 143.64, 155.83. MS (ESI): m/z (%)=480.25 (M+Na⁺, 100).

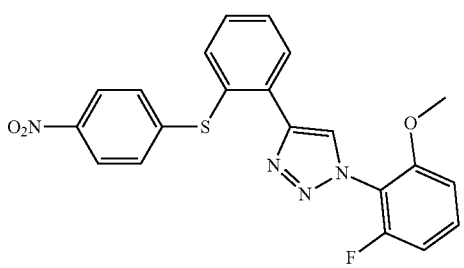 [SMILES: COc1cccc(F)c1-n1cc(-c2ccccc2Sc2ccc([N+](=O)[O-])cc2)nn1]

1-(2-Fluoro-6-methoxyphenyl)-4-(2-((4-nitrophenyl)thio)phenyl)-1H-1,2,3-triazole (7ax)

¹H NMR (400 MHz, CDCl₃, TMS) δ 3.73 (s, 3H), 6.81-6.91 (m, 2H), 7.08-7.13 (m, 2H), 7.39-7.48 (m, 2H), 7.61-7.70 (m, 2H), 8.00-8.05 (m, 2H), 8.20 (s, 1H), 8.39-8.42 (m, 1H). ¹³C NMR (100 MHz, CDCl₃) δ 56.43, 107.58 (1C, d, J=3.30 Hz), 108.56 (1C, d, J=19.95 Hz), 114.86 (1C, d, J=14.38 Hz), 124.12, 126.14, 126.25, 127.02, 129.43, 130.67, 130.78, 131.48 (1C, d, J=10.12 Hz), 135.14, 137.29, 143.90, 145.34, 147.33, 155.44 (1C, d, J=1.92 Hz), 157.68 (1C, d, J=254.95 Hz). MS (ESI): m/z (%)=423.11 (M+H⁺, 100), 445.18 (M+Na⁺, 30). R$_{T, HPLC}$=5.502 min, Purity>92%.

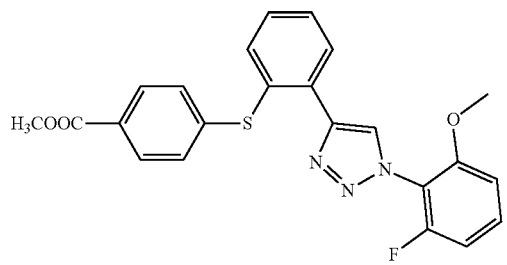

Methyl 4-((2-(1-(2-fluoro-6-methoxyphenyl)-1H-1,2,3-triazol-4-yl)phenyl)thio)benzoate (7bx)

¹H NMR (400 MHz, CDCl₃, TMS) δ 3.72 (s, 3H), 3.86 (s, 3H), 6.80-6.90 (m, 2H), 7.07-7.12 (m, 2H), 7.36-7.44 (m, 2H), 7.54-7.63 (m, 2H), 7.82-7.87 (m, 2H), 8.25 (s, 1H), 8.38-8.41 (dd, 1H, J₁=1.37 Hz, J₂=7.79 Hz). ¹³C NMR (100 MHz, CDCl₃) δ 52.01, 56.38, 107.51 (1C, d, J=3.83 Hz), 108.50 (1C, d, J=19.17 Hz), 114.95 (1C, d, J=14.38 Hz), 126.29, 126.63, 127.28, 128.46, 129.06, 129.90, 130.14, 130.23, 131.32 (1C, d, J=10.54 Hz), 134.54, 136.63, 143.71, 144.05, 155.40 (1C, d, J=2.88 Hz), 157.67 (1C, d, J=253.99 Hz), 166.56. MS (ESI): m/z (%)=458.19 (M+Na⁺, 100). R$_{T, HPLC}$=5.665 min, Purity>95%.

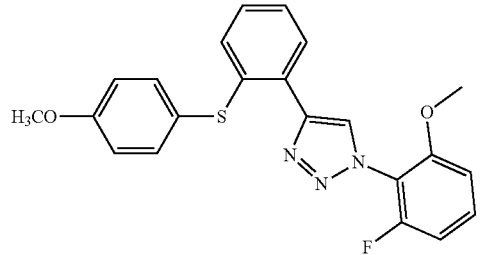 [SMILES: COc1ccc(Sc2ccccc2-c2cn(-c3c(F)cccc3OC)nn2)cc1]

1-(2-Fluoro-6-methoxyphenyl)-4-(2-((4-methoxyphenyl)thio)phenyl)-1H-1,2,3-triazole (7cx)

¹H NMR (400 MHz, CDCl₃, TMS) δ 3.81 (s, 3H), 3.83 (s, 3H), 6.85-6.94 (m, 4H), 7.08-7.12 (m, 1H), 7.18-7.23 (m, 1H), 7.29-7.35 (m, 3H), 7.41-7.48 (m, 1H), 8.17-8.20 (dd, 1H, J₁=1.37 Hz, J₂=7.79 Hz), 8.37 (s, 1H). ¹³C NMR (100 MHz, CDCl₃) δ 55.28, 56.46, 107.54 (1C, d, J=3.83 Hz), 108.48 (1C, d, J=19.98 Hz), 115.09, 115.10 (1C, d, J=14.47 Hz), 123.95, 126.30, 126.40, 128.47, 129.53, 129.80, 130.00, 131.30 (1C, d, J=10.10 Hz), 134.69, 135.65, 144.38, 155.50 (1C, d, J=2.88 Hz), 157.75 (1C, d, J=253.99 Hz), 159.70. MS (ESI): m/z (%)=442.55 (M+Na⁺, 100).

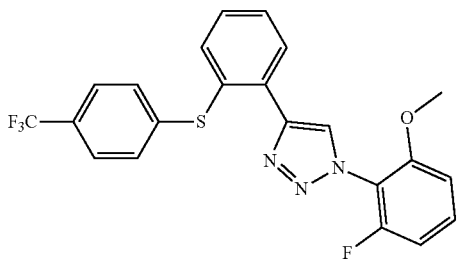 [SMILES: COc1cccc(F)c1-n1cc(-c2ccccc2Sc2ccc(C(F)(F)F)cc2)nn1]

1-(2-Fluoro-6-methoxyphenyl)-4-(2-((4-(trifluoromethyl)phenyl)thio)phenyl)-1H-1,2,3-triazole (7dx)

¹H NMR (400 MHz, CDCl₃, TMS) δ 3.72 (s, 3H), 6.81-6.91 (m, 2H), 7.13-7.17 (d, 2H, J=8.24 Hz), 7.37-7.46 (m, 4H), 7.55-7.62 (m, 2H), 8.27 (s, 1H), 8.38-8.41 (d, 1H, J=7.79 Hz). ¹³C NMR (100 MHz, CDCl₃) δ 56.41, 107.58 (1C$_{Ar-F}$, d, J=2.88 Hz), 108.58 (1C$_{Ar-F}$, d, J=20.13 Hz), 115.02 (1C$_{Ar-F}$, d, J=13.42 Hz), 124.04 (1C$_{CF3}$, q, J=272.20 Hz), 125.91 (2C$_{CF3-CAr}$, q, J₃=3.83 Hz), 126.34, 127.28, 127.81 (1C$_{CF3-CAr}$, q, J₂=32.59 Hz), 128.55, 129.18, 129.97, 130.30, 131.42 (1C$_{Ar-F}$, d, J=9.58 Hz), 134.51, 136.55, 142.25, 144.10, 155.47 (1C$_{Ar-F}$, d, J=2.88 Hz), 157.76 (1C$_{Ar-F}$, d, J=253.99 Hz). MS (ESI): m/z (%)=468.28 (M+Na⁺, 100).

Scheme 4S$^a$:

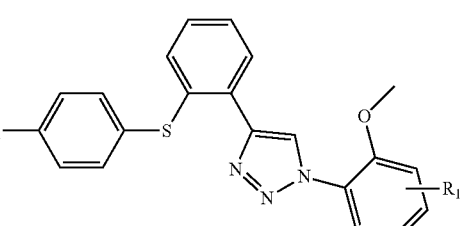

R₁ = H (2), 3-OCH₃ (3), 4-OCH₃ (4), 5-OCH₃ (5)
6-OCH₃ (6), 6-F (7)
R₂ = NO₂ (a), COOCH₃ (b), OCH₃ (c), CF₃ (d)
Z = S (x)

↓ a

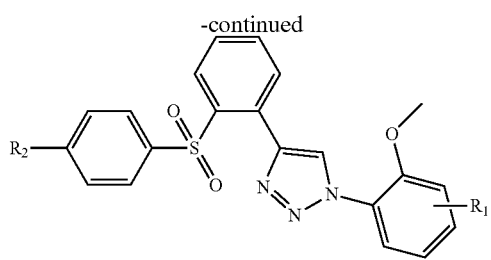

R₁ = H (2), 3-OCH₃ (3), 4-OCH₃ (4), 5-OCH₃ (5)
6-OCH₃ (6), 6-F (7)
R₂ = NO₂ (a), COOCH₃ (b), OCH₃ (c), CF₃ (d)
Z = SO₂ (y)

[a]Reagents & Conditions: (a) KMnO₄, MnO₂, DCM, R.T., overnight.

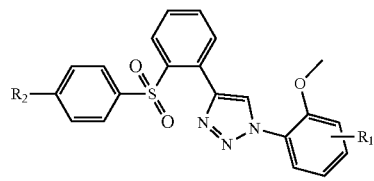

R₁ = H (2), 3-OCH₃ (3), 4-OCH₃ (4), 5-OCH₃ (5)
6-OCH₃ (6), 6-F (7)
R₂ = NO₂ (a), COOCH₃ (b), OCH₃ (c), CF₃ (d)
Z = SO₂ (y)

Typical procedure for the syntheses of sulfones:

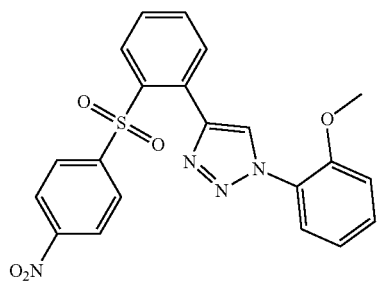 [SMILES: COc1ccccc1-n1cc(-c2ccccc2S(=O)(=O)c2ccc([N+](=O)[O-])cc2)nn1]

1-(2-Methoxyphenyl)-4-(2-((4-nitrophenyl)sulfonyl)phenyl)-1H-1,2,3-triazole (2ay)

In a 50 mL oven dried round bottom flask compound 1d (0.40 g, 1 mmol) was dissolved in dichloromethane (10 mL). Finely grounded mixture of KMnO₄ (0.5 g) and manganese dioxide (1.5 g) reagent[7] was added in small portions over a period of 15 minutes. The mixture was stirred vigorously at room temperature overnight and the reaction was monitored using TLC. The reaction mixture was filtered through a sintered glass funnel to remove the oxidant mixture. The residue was thoroughly washed with dichloromethane (3×15 mL) and the organic extract was sequentially treated with saturated brine and anhydrous Na₂SO₄ afforded a crude solid. Flash column chromatography using EtOAc:petroleum ether (1:1) afforded a light yellow amorphous compound 2ay (0.41 g, 95% yield). $^1$H NMR (400 MHz, CDCl₃, TMS) δ 4.01 (s, 3H), 7.13-7.18 (m, 2H), 7.46-7.51 (m, 1H), 7.62-7.76 (m, 6H), 8.07-8.11 (m, 2H), 8.43-8.46 (m, 1H), 8.62 (s, 1H). $^{13}$C NMR (100 MHz, CDCl₃) δ 55.96, 112.35, 121.40, 123.77, 125.44, 125.81, 128.17, 128.85, 129.06, 129.30, 130.59, 130.90, 133.44, 134.22, 138.14, 142.00, 146.09, 150.03, 151.12. MS (ESI): m/z (%)=459.05 (M+Na⁺, 100). $R_{T,\ HPLC}$=4.857 min, Purity>95%.

The same procedure was followed for the syntheses of the following sulfones:

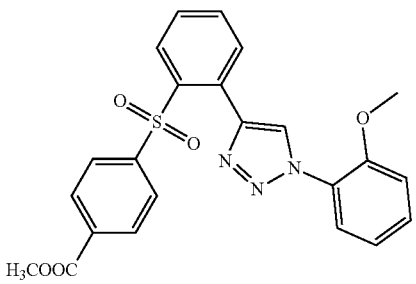

Methyl 4-((2-(1-(2-methoxyphenyl)-1H-1,2,3-triazol-4-yl)phenyl)sulfonyl)benzoate (2by)

$^1$H NMR (400 MHz, CDCl₃, TMS) δ 3.88 (s, 3H), 4.02 (s, 3H), 7.14-7.20 (m, 2H), 7.47-7.58 (m, 3H), 7.63-7.77 (m, 4H), 7.90-7.95 (m, 2H), 8.44-8.48 (m, 1H), 8.69 (s, 1H). $^{13}$C NMR (100 MHz, CDCl₃) δ 52.51, 55.91, 112.27, 121.29, 125.54, 125.96, 127.52, 128.28, 128.77, 129.13, 129.75, 130.46, 130.83, 133.28, 133.82, 134.00, 138.57, 142.09, 144.10, 151.23, 165.35. MS (ESI): m/z (%)=472.11 (M+Na⁺, 100). $R_{T,\ HPLC}$=4.704 min, Purity>96%.

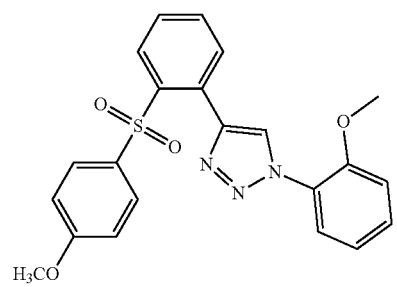 [SMILES: COc1ccc(S(=O)(=O)c2ccccc2-c2cn(-c3ccccc3OC)nn2)cc1]

1-(2-Methoxyphenyl)-4-(2-((4-methoxyphenyl)sulfonyl)phenyl)-1H-1,2,3-triazole (2cy)

$^1$H NMR (400 MHz, CDCl₃, TMS) δ 3.75 (s, 3H), 4.00 (s, 3H), 6.70-6.75 (m, 2H), 7.13-7.18 (m, 2H), 7.38-7.44 (m, 2H), 7.46-7.51 (m, 1H), 7.57-7.62 (m, 1H), 7.64-7.69 (m, 1H), 7.73-7.80 (m, 2H), 8.36-8.40 (dd, 1H, $J_1$=1.37 Hz, $J_2$=8.24 Hz), 8.74 (s, 1H). $^{13}$C NMR (100 MHz, CDCl₃) δ 55.44, 55.85, 112.25, 113.82, 121.13, 125.43, 126.04, 128.27, 128.51, 128.69, 129.73, 130.31, 130.39, 131.55, 133.03, 133.09, 139.84, 142.41, 151.24, 163.13. MS (ESI): m/z (%)=444.62 (M+Na⁺, 100). $R_{T,\ HPLC}$=4.730 min, Purity>97%.

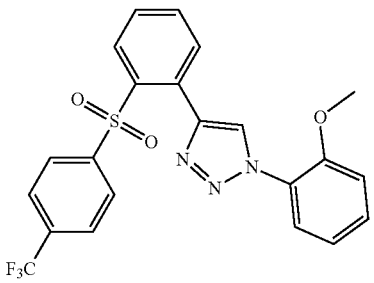 [SMILES: COc1ccccc1-n1cc(-c2ccccc2S(=O)(=O)c2ccc(C(F)(F)F)cc2)nn1]

1-(2-Methoxyphenyl)-4-(2-((4-(trifluoromethyl)phenyl)sulfonyl)phenyl)-1H-1,2,3-triazole (2dy)

$^1$H NMR (400 MHz, CDCl$_3$, TMS) δ 4.02 (s, 3H), 7.14-7.20 (m, 2H), 7.46-756 (m, 3H), 7.59-7.69 (m, 3H), 7.70-7.78 (m, 3H), 8.42-8.47 (d, 1H, J=8.24 Hz), 8.68 (s, 1H). $^{13}$C NMR (100 MHz, CDCl$_3$) δ 55.90, 112.31, 121.30, 122.96 (1C, q, J$_1$=273.16 Hz), 125.43, 125.73 (2C, q, J$_3$=3.83 Hz), 125.90, 128.08, 128.19, 128.88, 129.25, 130.48, 130.83, 133.33, 133.94, 134.57 (1C, q, J$_2$=33.55 Hz), 138.39, 142.10, 143.90, 151.18. MS (ESI): m/z (%)=482.02 (M+Na$^+$, 100). R$_{T, HPLC}$=5.070 min, Purity>98%.

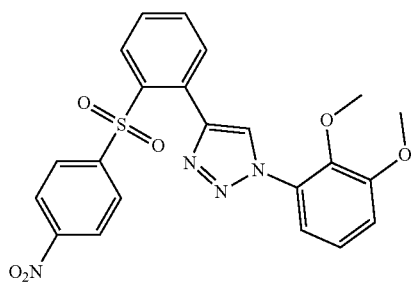 [SMILES: COc1cccc(-n2cc(-c3ccccc3S(=O)(=O)c3ccc([N+](=O)[O-])cc3)nn2)c1OC]

1-(2,3-Dimethoxyphenyl)-4-(2-((4-nitrophenyl)sulfonyl)phenyl)-1H-1,2,3-triazole (3ay)

$^1$H NMR (400 MHz, CDCl$_3$, TMS) δ 3.99 (s. 3H), 4.00 (s, 3H), 7.08-7.11 (m, 1H), 7.23-7.27 (m, 1H), 7.32-7.36 (m, 1H), 7.66-7.79 (m, 5H), 8.12-8.16 (m, 2H), 8.44-8.47 (m, 1H), 8.57 (s, 1H). $^{13}$C NMR (100 MHz, CDCl$_3$) δ 56.22, 61.51, 113.23, 116.84, 123.91, 124.46, 127.57, 128.88, 129.17, 129.46, 130.56, 130.83, 133.45, 134.22, 138.19, 141.60, 142.36, 146.15, 150.06, 153.68. MS (ESI): m/z (%)=489.03 (M+Na$^+$, 100). R$_{T, HPLC}$=4.826 min, Purity>96%.

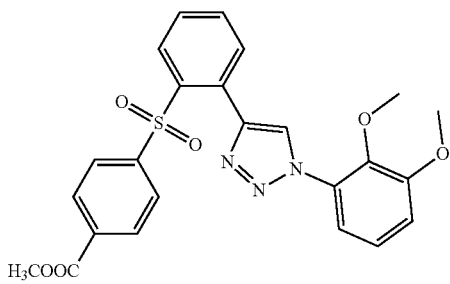

Methyl 4-((2-(1-(2,3-dimethoxyphenyl)-1H-1,2,3-triazol-4-yl)phenyl)sulfonyl)benzoate (3by)

$^1$H NMR (400 MHz, CDCl$_3$, TMS) δ 3.88 (s, 3H), 3.97 (s, 3H), 3.99 (s, 3H), 7.06-7.10 (m, 1H), 7.20-7.25 (m, 1H), 7.33-7.36 (m, 1H), 7.54-7.58 (m, 2H), 7.62-7.68 (m, 1H), 7.70-7.77 (m, 2H), 7.93-7.97 (m, 2H), 8.40-8.44 (m, 1H), 8.63 (s, 1H). $^{13}$C NMR (100 MHz, CDCl$_3$) δ 52.49, 56.21, 61.43, 113.12, 116.93, 124.33, 127.50, 127.68, 128.87, 129.26, 129.87, 130.68, 130.71, 133.26, 133.78, 134.01, 138.61, 141.63, 142.42, 144.17, 153.66, 165.35. MS (ESI): m/z (%)=502.35 (M+Na$^+$, 100). R$_{T, HPLC}$=4.889 min, Purity>95%.

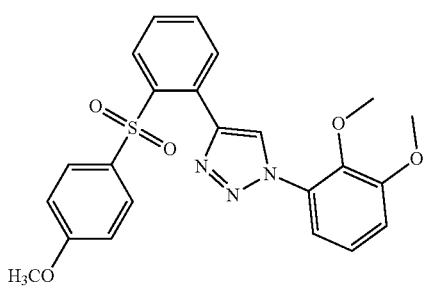 [SMILES: COc1ccc(S(=O)(=O)c2ccccc2-c2cn(-c3cccc(OC)c3OC)nn2)cc1]

1-(2,3-Dimethoxyphenyl)-4-(2-((4-methoxyphenyl)sulfonyl)phenyl)-1H-1,2,3-triazole (3cy)

$^1$H NMR (400 MHz, CDCl$_3$, TMS) δ 3.76 (s, 3H), 3.97 (s, 3H), 3.98 (s, 3H), 6.73-6.79 (m, 2H), 7.05-7.09 (m, 1H), 7.20-7.25 (m, 1H), 7.36-7.46 (m, 3H), 7.56-7.62 (m, 1H), 7.64-7.69 (m, 1H), 7.73-7.77 (m, 1H), 8.32-8.36 (m, 1H), 8.69 (m, 1H). $^{13}$C NMR (100 MHz, CDCl$_3$) δ 55.49, 56.21, 61.45, 113.01, 113.99, 116.97, 124.26, 127.73, 128.64, 128.83, 129.80, 130.30, 130.86, 131.67, 133.08, 139.97, 141.68, 142.82, 153.69, 163.19. MS (ESI): m/z (%)=474.22 (M+Na$^+$, 100). R$_{T, HPLC}$=4.813 min, Purity>95%.

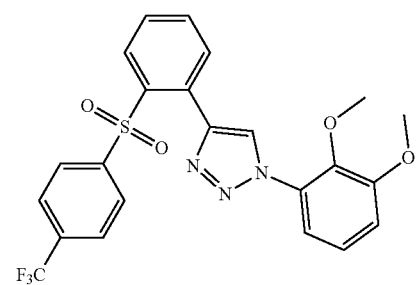 [SMILES: COc1cccc(-n2cc(-c3ccccc3S(=O)(=O)c3ccc(C(F)(F)F)cc3)nn2)c1OC]

1-(2,3-Dimethoxyphenyl)-4-(2-((4-(trifluoromethyl)phenyl)sulfonyl)phenyl)-1H-1,2,3-triazole (3dy)

$^1$H NMR (400 MHz, CDCl$_3$, TMS) δ 3.97 (s, 3H), 3.99 (s, 3H), 7.06-7.11 (m, 1H), 7.20-7.25 (m, 1H), 7.32-7.37 (m, 1H), 7.5-7.78 (m, 7H), 8.40-8.45 (d, 1H, J=7.79 Hz), 8.62 (s, 1H). $^{13}$C NMR (100 MHz, CDCl$_3$) δ 56.20, 61.46, 113.15, 116.90, 121.65 (1C, quarter merged), 124.38, 125.88 (2C, q, J$_3$=3.83 Hz), 127.61, 128.10, 129.00, 129.40, 130.72, 130.74, 133.36, 133.93, 134.60 (1C, q, J$_2$=32.59 Hz), 138.46, 141.67, 142.47, 143.97, 153.68. MS (ESI): m/z (%)=512.08 (M+Na$^+$, 100). R$_{T, HPLC}$=5.266 min, Purity>95%.

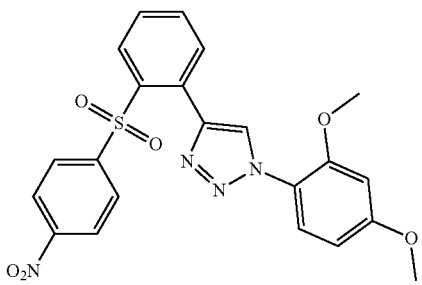 [SMILES: COc1ccc(-n2cc(-c3ccccc3S(=O)(=O)c3ccc([N+](=O)[O-])cc3)nn2)c(OC)c1]

1-(2,4-Dimethoxyphenyl)-4-(2-((4-nitrophenyl)sulfonyl)phenyl)-1H-1,2,3-triazole (4ay)

$^1$H NMR (400 MHz, CDCl$_3$, TMS) δ 3.92 (s, 3H), 3.99 (s, 3H), 6.65-6.71 (m, 2H), 7.60-7.78 (m, 6H), 8.09-8.13 (m, 2H), 8.44-8.48 (m, 1H), 8.53 (s, 1H). $^{13}$C NMR (100 MHz, CDCl$_3$) δ 55.78, 55.98, 99.71, 105.04, 119.45, 123.79, 126.45, 128.24, 128.90, 129.02, 129.30, 131.07, 133.48, 134.24, 138.15, 141.90, 146.11, 150.07, 152.56, 161.58. MS (ESI): m/z (%)=467.06 (M+H$^+$, 70), 489.06 (M+Na$^+$, 100). R$_T$. HPLC=5.126 min, Purity>95%.

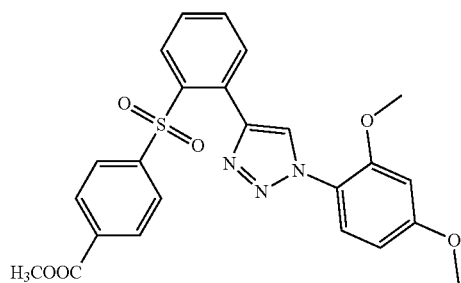

Methyl 4-((2-(1-(2,4-dimethoxyphenyl)-1H-1,2,3-triazol-4-yl)phenyl)sulfonyl)benzoate (4by)

$^1$H NMR (400 MHz, CDCl$_3$, TMS) δ 3.88 (s, 3H), 3.91 (s, 3H), 3.98 (s, 3H), 6.63-6.69 (m, 2H), 7.52-7.76 (m, 6H), 7.90-7.94 (m, 2H), 8.43-8.47 (m, 1H), 8.57 (s, 1H). $^{13}$C NMR (100 MHz, CDCl$_3$) δ 52.51, 55.74, 55.90, 99.60, 104.90, 119.58, 126.51, 127.54, 128.31, 128.71, 129.11, 129.74, 130.95, 133.28, 133.81, 133.99, 138.53, 141.96, 144.11, 152.65, 161.46, 165.37. MS (ESI): m/z (%)=502.36 (M+Na$^+$, 100).

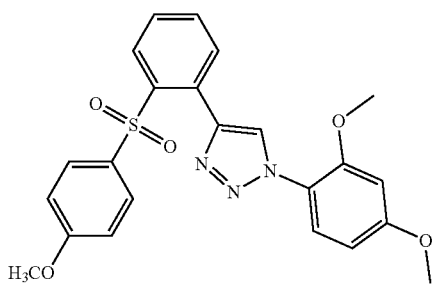 [SMILES: COc1ccc(S(=O)(=O)c2ccccc2-c2cn(-c3ccc(OC)cc3OC)nn2)cc1]

1-(2,4-Dimethoxyphenyl)-4-(2-((4-methoxyphenyl)sulfonyl)phenyl)-1H-1,2,3-triazole (4cy)

$^1$H NMR (400 MHz, CDCl$_3$, TMS) δ 3.78 (s, 3H), 3.92 (s, 3H), 3.98 (s, 3H), 6.65-6.81 (m, 4H), 7.39-7.44 (m, 2H), 7.57-7.73 (m, 4H), 8.28-8.33 (m, 1H), 8.53 (s, 1H). MS (ESI): m/z (%)=452.13 (M+H$^+$, 100), 474.11 (M+Na$^+$, 40). R$_{T,\ HPLC}$=5.156 min, Purity>97%.

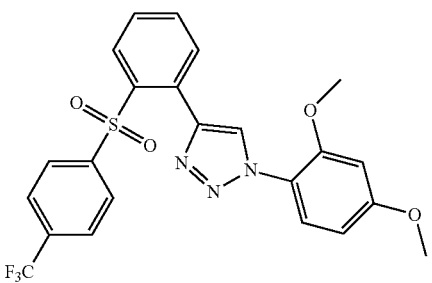 [SMILES: COc1ccc(-n2cc(-c3ccccc3S(=O)(=O)c3ccc(C(F)(F)F)cc3)nn2)c(OC)c1]

1-(2,4-Dimethoxyphenyl)-4-(2-((4-(trifluoromethyl)phenyl)sulfonyl)phenyl)-1H-1,2,3-triazole (4dy)

$^1$H NMR (400 MHz, CDCl$_3$, TMS) δ 3.91 (s, 3H), 3.97 (s, 3H), 6.64-6.70 (m, 2H), 7.51-7.56 (m, 2H), 7.59-7.68 (m, 4H), 7.71-7.76 (m, 2H), 8.42-8.46 (d, 1H, J=7.79 Hz), 8.57 (s, 1H). $^{13}$C NMR (100 MHz, CDCl$_3$) δ 55.70, 55.89, 99.60, 104.93, 119.52, 122.98 (1C, q, J$_1$=273.16 Hz), 125.71 (2C, q, J$_3$=3.72 Hz), 126.42, 128.09, 128.24, 128.82, 129.22, 130.95, 133.33, 133.39, 134.56 (1C, q, J$_2$ 32.59 Hz), 138.35, 141.97, 143.90, 152.59, 161.47. MS (ESI): m/z (%)=512.05 (M+Na$^+$, 100). R$_{T,\ HPLC}$=5.516 min, Purity>96%.

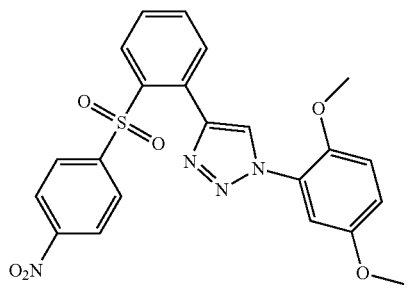 [SMILES: COc1ccc(OC)c(-n2cc(-c3ccccc3S(=O)(=O)c3ccc([N+](=O)[O-])cc3)nn2)c1]

1-(2,5-Dimethoxyphenyl)-4-(2-((4-nitrophenyl)sulfonyl)phenyl)-1H-1,2,3-triazole (5ay)

$^1$H NMR (400 MHz, CDCl$_3$, TMS) δ 3.87 (s, 3H), 3.99 (s, 3H), 7.02-7.13 (m, 2H), 7.38 (d, 1H, J=2.75 Hz), 7.66-7.79 (m, 5H), 8.08-8.14 (m, 2H), 8.45-8.49 (m, 1H), 8.69 (s, 1H). $^{13}$C NMR (100 MHz, CDCl$_3$) δ 55.99, 56.40, 110.33, 113.59, 116.11, 123.77, 125.95, 128.09, 128.88, 129.09, 129.30, 130.84, 133.41, 134.22, 138.17, 142.10, 144.89, 146.09, 150.02, 153.98. HRMS (ESI$^+$) m/z 467.0998 (M+H)$^+$ (calcd. for C$_{22}$H$_{19}$N$_4$O$_6$S 467.1020). R$_{T,\ HPLC}$=4.626 min, Purity>97%.

189

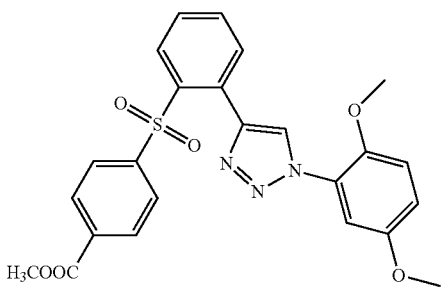

Methyl 4-((2-(1-(2,5-dimethoxyphenyl)-1H-1,2,3-triazol-4-yl)phenyl)sulfonyl)benzoate (5by)

$^1$H NMR (400 MHz, CDCl$_3$, TMS) δ 3.87 (s, 3H), 3.88 (s, 3H), 3.98 (s, 3H), 7.01-7.11 (m, 2H), 7.35-7.38 (m, 1H), 7.54-7.58 (m, 2H), 7.63-7.69 (m, 1H), 7.71-7.76 (m, 2H), 7.90-7.94 (m, 2H), 8.43-8.47 (m, 1H), 8.73 (s, 1H). $^{13}$C NMR (100 MHz, CDCl$_3$) δ 52.50, 55.99, 56.37, 110.43, 113.50, 115.99, 126.09, 127.54, 128.19, 128.80, 129.13, 129.73, 130.75, 133.23, 133.81, 133.99, 138.59, 142.17, 144.09, 145.02, 153.89, 165.34. MS (ESI): m/z (%)=502.42 (M+Na$^+$, 100). R$_{T, HPLC}$=5.040 min, Purity>95%.

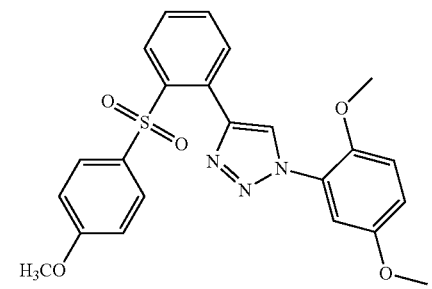 [SMILES: COc1ccc(S(=O)(=O)c2ccccc2-c2cn(-c3cc(OC)ccc3OC)nn2)cc1]

1-(2,5-Dimethoxyphenyl)-4-(2-((4-methoxyphenyl)sulfonyl)phenyl)-1H-1,2,3-triazole (5cy)

$^1$H NMR (400 MHz, CDCl$_3$, TMS) δ 3.75 (s, 3H), 3.86 (s, 3H), 3.96 (s, 3H), 6.70-6.74 (m, 2H), 6.99-7.04 (m, 1H), 7.07-7.10 (m, 1H), 7.39-7.45 (m, 3H), 7.57-7.62 (m, 1H), 7.64-7.69 (m, 1H), 7.72-7.76 (m, 1H), 8.36-8.40 (dd, 1H, J=1.37 Hz, J$_2$=7.79 Hz), 8.79 (s, 1H). $^{13}$C NMR (100 MHz, CDCl$_3$) δ 55.50, 56.01, 56.39, 110.64, 113.50, 114.62, 115.73, 126.31, 128.28, 128.58, 128.78, 129.83, 130.37, 131.03, 131.64, 133.14, 139.93, 142.56, 145.14, 153.87, 163.20. MS (ESI): m/z (%)=452.16 (M+H$^+$, 100), 474.04 (M+Na$^+$, 60). R$_{T, HPLC}$=5.198 min, Purity>90%.

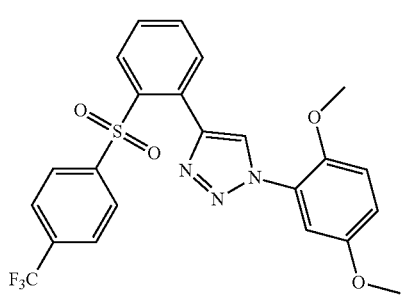 [SMILES: COc1ccc(OC)c(-n2cc(-c3ccccc3S(=O)(=O)c3ccc(C(F)(F)F)cc3)nn2)c1]

190

1-(2,5-Dimethoxyphenyl)-4-(2-((4-(trifluoromethyl)phenyl)sulfonyl)phenyl)-1H-1,2,3-triazole (5dy)

$^1$H NMR (400 MHz, CDCl$_3$, TMS) δ 3.86 (s, 3H), 3.97 (s, 3H), 7.01-7.11 (m, 2H), 7.37-7.39 (m, 1H), 7.52-7.56 (m, 2H), 7.62-7.69 (m, 3H), 7.72-7.76 (m, 2H), 8.43-8.46 (d, 1H, J=8.24 Hz), 8.72 (s, 1H). $^{13}$C NMR (100 MHz, CDCl$_3$) δ 55.96, 56.38, 110.40, 113.57, 116.00, 122.99 (1C, q, J=273.16 Hz), 125.75 (2C, q, J$_1$=3.83 Hz), 126.09, 128.13, 128.92, 129.30, 130.79, 133.33, 133.96, 134.60 (1C, q, J$_2$=32.59 Hz), 135.76, 138.44, 142.21, 143.91, 145.00, 153.94. MS (ESI): m/z (%)=490.07 (M+H$^+$, 100), 512.08 (M+Na$^+$, 100).

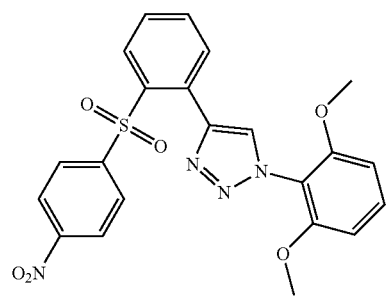 [SMILES: COc1cccc(OC)c1-n1cc(-c2ccccc2S(=O)(=O)c2ccc([N+](=O)[O-])cc2)nn1]

1-(2,6-Dimethoxyphenyl)-4-(2-((4-nitrophenyl)sulfonyl)phenyl)-1H-1,2,3-triazole (6ay)

$^1$H NMR (400 MHz, CDCl$_3$, TMS) δ 3.89 (s, 6H), 6.75-6.79 (m, 2H), 7.46-7.52 (m, 1H), 7.63-7.79 (m, 5H), 8.10-8.15 (m, 2H), 8.25 (s, 1H), 8.44-8.48 (d, 1H, J=7.79 Hz). $^{13}$C NMR (100 MHz, CDCl$_3$) δ 56.32, 104.51, 114.85, 123.82, 128.94, 129.16, 129.17, 129.83, 131.28, 131.74, 133.75, 134.19, 138.17, 141.43, 146.00, 150.14, 155.71. MS (ESI): m/z (%)=489.23 (M+Na$^+$, 100). R$_{T, HPLC}$=4.621 min, Purity>94%.

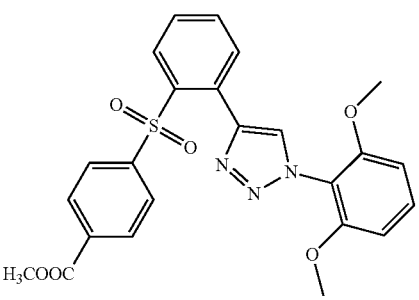

Methyl 4-((2-(1-(2,6-dimethoxyphenyl)-1H-1,2,3-triazol-4-yl)phenyl)sulfonyl)benzoate (6by)

$^1$H NMR (400 MHz, CDCl$_3$, TMS) δ 3.87 (s, 9H), 6.72-6.77 (d, 2H, J=8.70 Hz), 7.44-7.50 (m, 1H), 7.52-7.58 (m, 2H), 7.60-7.66 (m, 1H), 7.68-7.73 (m, 1H), 7.77-7.81 (m, 1H), 7.92-7.97 (m, 2H), 8.31 (s, 1H), 8.42-8.47 (m, 1H). $^{13}$C NMR (100 MHz, CDCl$_3$) δ 52.48, 56.23, 104.37, 114.96, 127.76, 128.64, 129.08, 129.81, 131.19, 131.59, 133.56, 133.76, 133.99, 138.52, 141.58, 144.11, 155.81, 165.44. MS (ESI): m/z (%)=502.55 (M+Na$^+$, 100). R$_{T, HPLC}$=4.632 min, Purity>97%.

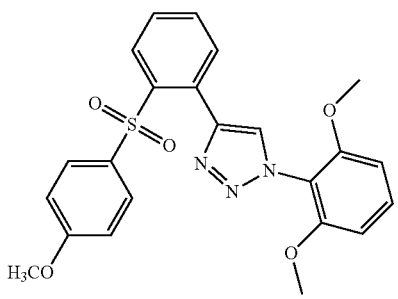 [SMILES: COc1ccc(S(=O)(=O)c2ccccc2-c2cn(-c3c(OC)cccc3OC)nn2)cc1]

1-(2,6-Dimethoxyphenyl)-4-(2-((4-methoxyphenyl)
sulfonyl)phenyl)-1H-1,2,3-triazole (6cy)

¹H NMR (400 MHz, CDCl₃, TMS) δ 3.76 (s, 3H), 3.87 (s, 6H), 6.72-6.77 (m, 4H), 7.39-7.49 (m, 3H), 7.55-7.60 (m, 1H), 7.62-7.67 (m, 1H), 7.76-7.79 (dd, 1H, $J_1$=1.37 Hz, $J_2$=7.33 Hz), 8.34 (s, 1H), 8.36-8.40 (dd, 1H, $J_1$=1.37 Hz, $J_2$=7.79 Hz). ¹³C NMR (100 MHz, CDCl₃) δ 55.46, 56.20, 104.35, 113.94, 115.09, 128.47, 128.65, 129.91, 130.03, 130.81, 131.55, 131.90, 133.04, 133.41, 140.06, 142.03, 155.89, 163.28. MS (ESI): m/z (%)=452.12 (M+H, 100), 474.09 (M+Na⁺, 40). $R_T$, HPLC=4.558 min, Purity>96%.

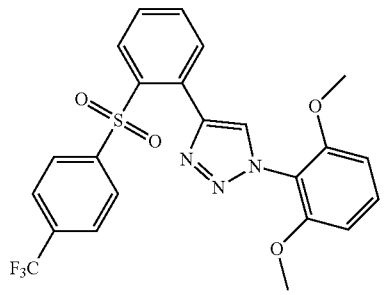 [SMILES: COc1cccc(OC)c1-n1cc(-c2ccccc2S(=O)(=O)c2ccc(C(F)(F)F)cc2)nn1]

1-(2,6-Dimethoxyphenyl)-4-(2-((4-(trifluoromethyl)
phenyl)sulfonyl)phenyl)-1H-1,2,3-triazole (6dy)

¹H NMR (400 MHz, CDCl₃, TMS) δ 3.87 (s, 6H), 6.73-6.78 (m, 2H), 7.44-7.82 (m, 8H), 8.30 (s, 1H), 8.44 (d, 1H, J=7.79 Hz). ¹³C NMR (100 MHz, CDCl₃) δ 56.25, 104.47, 114.97, 123.06 (1C, q, $J_1$=275.08 Hz), 125.77 (2C, q, J. 3.83 Hz), 128.38, 128.78, 129.19, 129.83, 131.23, 131.66, 133.65, 133.92, 134.66 (q, 1C, $J_2$=33.55 Hz), 138.46, 141.60, 143.92, 155.79. MS (ESI): m/z (%)=490.09 (M+H⁺, 100), 512.04 (M+Na⁺, 50). $R_{T, HPLC}$=5.023 min, Purity>90%.

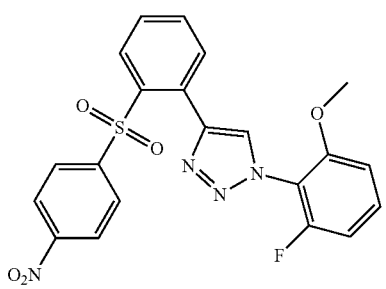 [SMILES: COc1cccc(F)c1-n1cc(-c2ccccc2S(=O)(=O)c2ccc([N+](=O)[O-])cc2)nn1]

1-(2-Fluoro-6-methoxyphenyl)-4-(2-((4-nitrophenyl)
sulfonyl)phenyl)-1H-1,2,3-triazole (7ay)

¹H NMR (400 MHz, CDCl₃, TMS) δ 3.93 (s, 3H), 6.93-7.02 (m, 2H), 7.49-7.56 (m, 1H), 7.59-7.65 (m, 2H), 7.67-7.73 (m, 1H), 7.75-7.79 (m, 2H), 8.11-8.17 (m, 2H), 8.33 (s, 1H), 8.46-8.50 (d, 1H, J=7.79 Hz). ¹³C NMR (100 MHz, CDCl₃) δ 56.59, 107.74 (1C, d, J=2.88 Hz), 108.70 (1C, d, J=19.17 Hz), 114.59 (d, 1C, J=14.38 Hz), 123.91, 128.84, 129.15, 129.29, 129.33, 130.67, 131.90 (1C, d, J=10.54 Hz), 133.63, 134.27, 138.05, 141.81, 145.86, 150.12, 155.40 (1C, d, J=2.88 Hz), 157.82 (1C, d, J=253.04 Hz). MS (ESI): m/z (%)=455.06 (M+H, 100), 477.06 (M+Na⁺, 50). $R_{T, HPLC}$=4.875 min, Purity>96%.

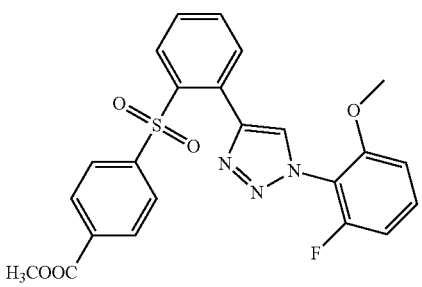

Methyl 4-((2-(1-(2-fluoro-6-methoxyphenyl)-1H-1,
2,3-triazol-4-yl)phenyl)sulfonyl)benzoate (7by)

¹H NMR (400 MHz, CDCl₃, TMS) δ 3.88 (s, 3H), 3.93 (s, 3H), 6.91-7.01 (m, 2H), 7.47-7.55 (m, 3H), 7.63-7.81 (m, 3H), 7.93-7.98 (m, 2H), 8.39 (s, 1H), 8.44-8.49 (dd, 1H, $J_1$=1.37 Hz, $J_2$=7.79 Hz). ¹³C NMR (100 MHz, CDCl₃) δ 52.50, 56.54, 107.64 (1C, d, J=2.88 Hz), 108.66 (1C, d, J=19.90 Hz), 114.75 (1C, d, J=14.80 Hz), 127.52, 128.87, 129.17, 129.37, 129.90, 130.62, 131.76 (1C, d, J=10.16 Hz), 133.46, 133.86, 134.09, 138.51, 141.96, 143.95, 155.49 (1C, d, J=1.92 Hz), 157.90 (1C, d, J=253.04 Hz), 165.37. MS (ESI): m/z (%)=468.06 (M+H⁺, 50), 490.16 (M+Na⁺, 100). $R_{T, HPLC}$=4.787 min, Purity>90%.

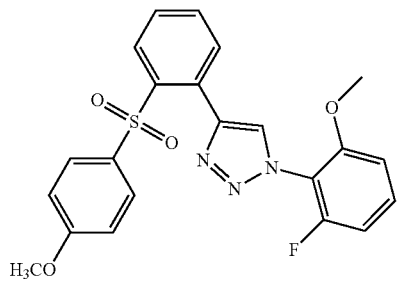 [SMILES: COc1ccc(S(=O)(=O)c2ccccc2-c2cn(-c3c(F)cccc3OC)nn2)cc1]

1-(2-Fluoro-6-methoxyphenyl)-4-(2-((4-methoxy-
phenyl)sulfonyl)phenyl)-1H-1,2,3-triazole (7cy)

¹H NMR (400 MHz, CDCl₃, TMS) δ 3.77 (s, 3H), 3.91 (s, 3H), 6.72-6.79 (m, 2H), 6.90-7.00 (m, 2H), 7.35-7.41 (m, 2H), 7.46-7.54 (m, 1H), 7.58-7.70 (m, 2H), 7.76-7.80 (m, 1H), 8.39-8.46 (m, 2H). ¹³C NMR (100 MHz, CDCl₃) δ 55.45, 56.47, 107.58 (1C, d, J=2.88 Hz), 108.60 (1C, d, J=20.13 Hz), 113.98, 114.85 (1C, d, J=14.38 Hz), 128.64, 128.71, 129.43, 129.75, 130.21, 131.47, 131.59, 131.700, 133.19 (1C, d. J=9.58 Hz), 139.86, 142.30, 155.46 (1C, d, J=2.88 Hz), 157.92 (1C, d, J=253.04 Hz), 163.25. MS (ESI): m/z (%)=440.19 (M+H, 100), 462.19 (M+Na$^+$, 100). $R_{T, HPLC}$=4.804 min, Purity>97%.

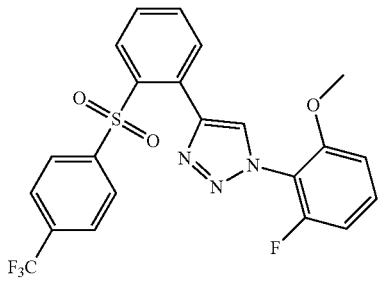 [SMILES: COc1cccc(F)c1-n1cc(-c2ccccc2S(=O)(=O)c2ccc(C(F)(F)F)cc2)nn1]

1-(2-Fluoro-6-methoxyphenyl)-4-(2-((4-(trifluoromethyl)phenyl)sulfonyl)phenyl)-1H-1,2,3-triazole (7dy)

$^1$H NMR (400 MHz, CDCl$_3$, TMS) δ 3.92 (s, 3H), 6.92-7.01 (m, 2H), 7.48-7.81 (m, 8H), 8.38 (s, 1H), 8.44-8.48 (dd, 1H, $J_1$=1.37 Hz, $J_2$=7.79 Hz). $^{13}$C NMR (100 MHz, CDCl$_3$) δ 56.51, 107.68 (1C$_{Ar-F}$, d, 1C, J=2.88 Hz), 108.64 (1C$_{Ar-F}$, d, J=20.13 Hz), 114.67 (1C$_{Ar-F}$, d, J=14.38 Hz), 122.98 (1C$_{CF3}$, q, $J_1$=273.16 Hz), 125.84 (2C$_{CF3-CAr}$, q, $J_2$=3.83 Hz), 128.06, 128.97, 129.25, 129.29, 130.60, 131.80 (1C$_{Ar-F}$, d, J=10.54 Hz), 133.49, 133.99, 134.66 (1C$_{CF3-CAr}$, Q, $J_2$=32.59 Hz), 138.32, 141.93, 143.70, 155.42 (1C$_{Ar-F}$, d, J=2.88 Hz), 157.85 (1C$_{Ar-F}$, d, J=253.04 Hz). MS (ESI): m/z (%)=478.10 (M+H$^+$, 50), 500.04 (M+Na$^+$, 100). $R_{T, HPLC}$=5.243 min, Purity>96%.

Scheme 5S$^a$;

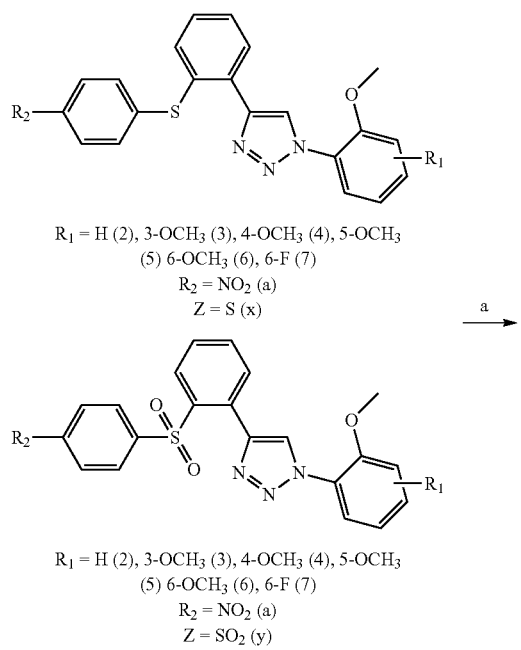

$R_1$ = H (2), 3-OCH$_3$ (3), 4-OCH$_3$ (4), 5-OCH$_3$ (5) 6-OCH$_3$ (6), 6-F (7)
$R_2$ = NO$_2$ (a)
Z = S (x)

$R_1$ = H (2), 3-OCH$_3$ (3), 4-OCH$_3$ (4), 5-OCH$_3$ (5) 6-OCH$_3$ (6), 6-F (7)
$R_2$ = NO$_2$ (a)
Z = SO$_2$ (y)

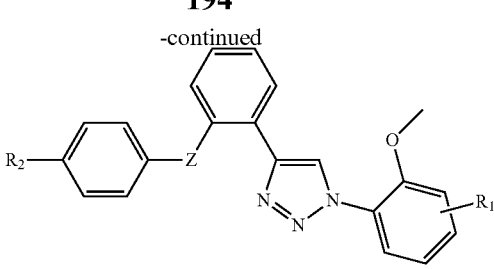

$R_1$ = H (2), 3-OCH$_3$ (3), 4-OCH$_3$ (4), 5-OCH$_3$ (5) 6-OCH$_3$ (6), 6-F (7)
$R_2$ = NH$_2$ (e)
Z = S (x), SO$_2$ (y)

$^a$Reagents & Conditions: (a) SnCl$_2$•2H$_2$O/EtOAc/80° C., 3 h

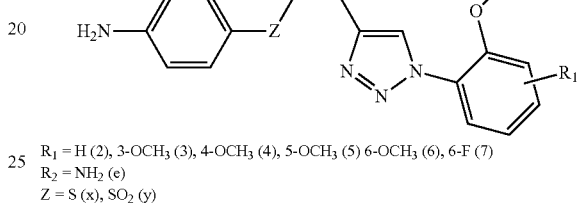

$R_1$ = H (2), 3-OCH$_3$ (3), 4-OCH$_3$ (4), 5-OCH$_3$ (5) 6-OCH$_3$ (6), 6-F (7)
$R_2$ = NH$_2$ (e)
Z = S (x), SO$_2$ (y)

Typical procedure for the syntheses of amines:

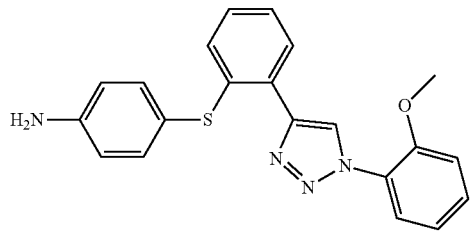 [SMILES: COc1ccccc1-n1cc(-c2ccccc2Sc2ccc(N)cc2)nn1]

4-((2-(1-(2-Methoxyphenyl)-1H-1,2,3-triazol-4-yl)phenyl)thio)aniline (2ex)

A mixture of the nitro compound 1d (0.40 g, 1 mmol, 1 equiv.) and SnCl$_2$. 2H$_2$O (0.67 g, 3 mmol, 3 equiv.) in EtOAc (10 mL) was refluxed for 3 hours until TLC (EtOAc/hexane, 1:1) indicated that reaction was complete. The reaction mixture was poured in a 50 mL beaker having an aqueous solution of potassium carbonate (10 mL). The mixture was diluted with 10 mL of EtOAc and stirred for 30 minutes. The suspension obtained was filtered through a short bed of CELITE® and the organic layer was separated using separating funnel. The combined organic layers were sequentially treated with saturated brine and anhydrous Na$_2$SO$_4$. Purification by flash column chromatography using EtOAc: petroleum ether (1:1) afforded a light yellow amorphous compound 2ex (0.24 g, 65% yield). $^1$H NMR (400 MHz, CDCl$_3$, TMS) δ 3.81 (broad singlet, 2H), 3.90 (s, 3H), 6.65-6.70 (m, 2H), 7.00-7.04 (m, 1H), 7.08-7.20 (m, 3H), 7.23-7.28 (m, 3H), 7.40-7.46 (m, 1H), 7.84-7.88 (dd, 1H, J, 1.83 Hz, $J_2$=7.79 Hz), 8.05-8.10 (dd, 1H, $J_1$=1.83 Hz, $J_2$=7.79 Hz), 8.69 (s, 1H). $^{13}$C NMR (100 MHz, CDCl$_3$) δ 56.05, 112.29, 115.98, 120.07, 121.18, 125.36, 125.52, 125.68, 126.44, 128.34, 128.62, 129.14, 129.45, 129.99, 135.77, 137.12, 144.68, 147.09, 151.21. HRMS (ESI) m/z 375.1255 (M+H)⁺ (calcd. for C₂₁H₉N₄OS 375.1274). R_{T, HPLC}=4.556 min, Purity>95%.

The same procedure was followed for the syntheses of all the remaining amines.

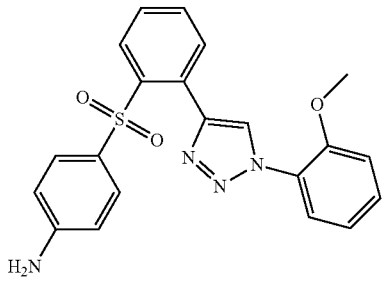 [SMILES: COc1ccccc1-n1cc(-c2ccccc2S(=O)(=O)c2ccc(N)cc2)nn1]

4-((2-(1-(2-Methoxyphenyl)-1H-1,2,3-triazol-4-yl)phenyl)sulfonyl)aniline (2ey)

¹H NMR (400 MHz, CDCl₃, TMS) δ 3.99 (s, 3H), 4.04 (broad singlet, 2H), 6.37-6.43 (m, 2H), 7.12-7.18 (m, 2H), 7.21-7.26 (m, 2H), 7.45-7.51 (m, 1H), 7.54-7.59 (m, 1H), 7.61-7.67 (m, 1H), 7.72-7.80 (m, 2H), 8.33-8.37 (m, 1H), 8.75 (s, 1H). ¹³C NMR (100 MHz, CDCl₃) δ 55.86, 112.24, 113.47, 121.10, 125.51, 126.08, 127.45, 128.37, 128.45, 128.50, 129.70, 130.16, 130.20, 132.75, 132.91, 140.49, 142.59, 151.07, 151.34. HRMS (ESI⁺) m/z 407.1149 (M+H)⁺ (calcd. for C₂₁H₁₉N₄O₃S 407.1172). R_{T, HPLC}=4.094 min, Purity>97%.

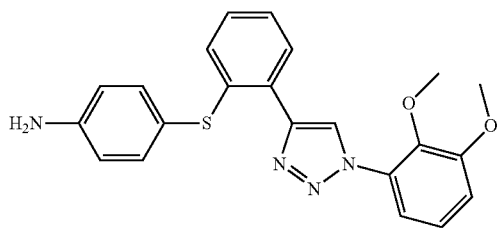 [SMILES: COc1cccc(-n2cc(-c3ccccc3Sc3ccc(N)cc3)nn2)c1OC]

4-((2-(1-(2,3-Dimethoxyphenyl)-1H-1,2,3-triazol-4-yl)phenyl)thio)aniline (3ex)

¹H NMR (400 MHz, CDCl₃, TMS) δ 3.75 (s, 3H), 3.81 (broad singlet, NH₂), 3.95 (s, 3H), 6.65-6.70 (m, 2H), 7.00-7.04 (m, 2H), 7.15-7.28 (m, 5H), 7.47-7.50 (dd, 1H, J₁=1.37 Hz, J₂=8.24 Hz), 8.06-8.09 (m, 1H), 8.78 (s, 1H). ¹³C NMR (100 MHz, CDCl₃) δ 56.15, 61.22, 112.57, 115.95, 116.80, 119.69, 124.45, 124.98, 125.58, 128.42, 128.46, 128.80, 129.33, 131.22, 135.80, 137.38, 141.25, 144.99, 147.16, 153.61. MS (ESI): m/z (%)=427.34 (M+Na⁺, 100).

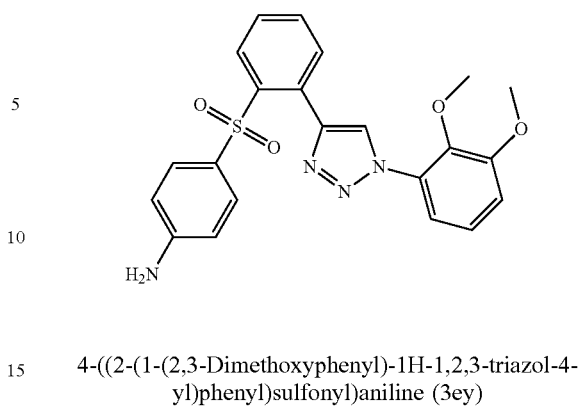

4-((2-(1-(2,3-Dimethoxyphenyl)-1H-1,2,3-triazol-4-yl)phenyl)sulfonyl)aniline (3ey)

¹H NMR (400 MHz, CDCl₃, TMS) δ 3.96 (s, 3H), 3.97 (s, 3H), 4.08 (broad singlet, 2H), 6.38-6.47 (d, 2H, J=8.70 Hz), 7.02-7.09 (d, 1H, J=8.24 Hz), 7.18-7.29 (m, 3H), 7.35-7.41 (d, 1H, J=7.79 Hz), 7.52-7.67 (m, 2H), 7.72-7.78 (d, 1H, J=7.33 Hz), 8.25-8.31 (d, 1H, J=7.79 Hz), 8.71 (s, 1H). ¹³C NMR (100 MHz, CDCl₃) 56.18, 61.40, 112.98, 113.58, 116.94, 124.21, 127.47, 127.76, 128.53, 128.57, 129.72, 129.98, 130.83, 132.69, 132.91, 140.58, 141.65, 142.95, 151.11, 153.65. MS (ESI): m/z (%)=459.49 (M+Na⁺, 100). R_{T, HPLC}=4.107 min, Purity>96%.

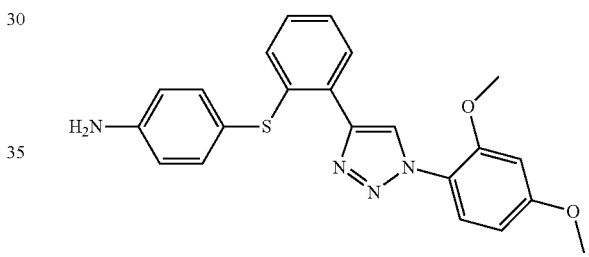

4-((2-(1-(2,4-Dimethoxyphenyl)-1H-1,2,3-triazol-4-yl)phenyl)thio)aniline (4ex)

¹H NMR (400 MHz, CDCl₃, TMS) δ 3.85 (s, 3H), 3.87 (broad singlet merged with singlet, 3H, NH₂), 6.57-6.69 (m, 4H), 6.99-7.03 (dd, 1H, J₁=0.93 Hz, J₂=7.79 Hz), 7.14-7.19 (m, 1H), 7.21-7.27 (m, 3H), 7.69-7.72 (m, 1H), 8.05-8.08 (m, 1H), 8.57 (s, 1H). ¹³C NMR (100 MHz, CDCl₃) δ 55.68, 56.00, 99.61, 104.73, 115.45, 115.98, 120.23, 125.40, 125.71, 126.51, 128.26, 128.64, 129.27, 129.44, 135.77, 137.05, 144.56, 147.04, 152.69, 161.71. MS (ESI): m/z (%)=427.19 (M+Na⁺, 100).

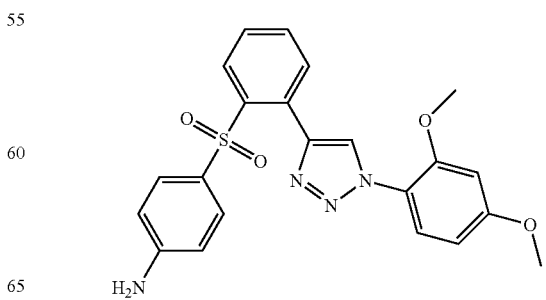

4-((2-(1-(2,4-Dimethoxyphenyl)-1H-1,2,3-triazol-4-yl)phenyl)sulfonyl)aniline (4ey)

$^1$H NMR (400 MHz, CDCl$_3$, TMS) δ 3.90 (s, 3H), 3.95 (s, 3H), 4.03 (broad singlet, NH$_2$), 6.38-6.43 (m, 2H), 6.62-6.69 (m, 2H), 7.21-7.25 (m, 2H), 7.52-7.66 (m, 3H), 7.71-7.76 (m, 1H), 8.32-8.36 (m, 1H), 8.64 (s, 1H). $^{13}$C NMR (100 MHz, CDCl$_3$) δ 55.72, 55.88, 99.52, 104.82, 113.59, 119.84, 126.55, 128.39, 128.48, 128.55, 129.82, 130.37, 131.01, 132.78, 132.99, 140.40, 142.51, 150.90, 152.86, 161.39. MS (ESI): m/z (%)=459.34 (M+Na$^+$, 100).

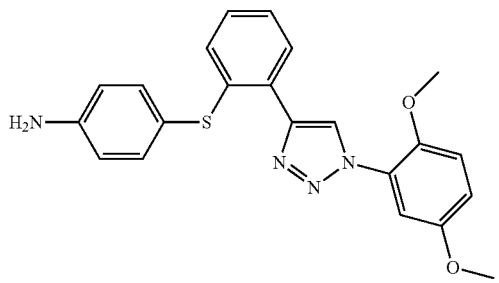 [SMILES: COc1ccc(OC)c(-n2cc(-c3ccccc3Sc3ccc(N)cc3)nn2)c1]

4-((2-(1-(2,5-Dimethoxyphenyl)-1H-1,2,3-triazol-4-yl)phenyl)thio)aniline (5ex)

$^1$H NMR (400 MHz, CDCl$_3$, TMS) δ 3.73 (s, 3H), 3.75 (s, 3H), 4.11 (broad singlet, 2H), 6.53-6.63 (m, 2H), 6.82-7.19 (m, 7H), 7.29-7.39 (m, 2H), 7.83-7.92 (m, 1H), 8.61 (s, 1H). $^{13}$C NMR (100 MHz, Acetone-d$_6$) δ 56.24, 57.09, 111.33, 115.01, 116.17, 117.45, 121.61, 125.98, 126.07, 127.51, 128.60, 129.13, 129.56, 129.98, 137.12, 139.21, 145.36, 146.16, 150.64, 154.80. MS (ESI): m/z (%)=427.66 (M+Na$^+$, 100). R$_{T, HPLC}$=5.267 min, Purity>95%.

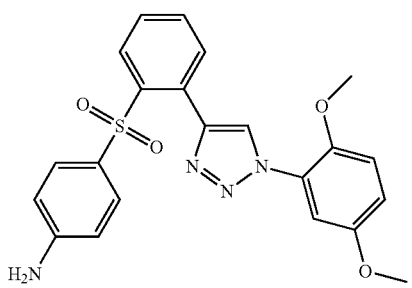 [SMILES: COc1ccc(OC)c(-n2cc(-c3ccccc3S(=O)(=O)c3ccc(N)cc3)nn2)c1]

4-((2-(1-(2,5-Dimethoxyphenyl)-1H-1,2,3-triazol-4-yl)phenyl)sulfonyl)aniline (5ey)

$^1$H NMR (400 MHz, CDCl$_3$, TMS) δ 3.86 (s, 3H), 3.95 (s, 3H), 4.02 (s, 2H), 6.78-6.43 (m, 2H), 6.98-7.10 (m, 2H), 7.23-7.27 (m, 2H), 7.39-7.42 (m, 1H), 7.53-7.59 (m, 1H), 7.61-7.66 (m, 1H), 7.72-7.76 (m, 1H), 8.32-8.36 (m, 1H), 8.80 (s, 1H). $^{13}$C NMR (100 MHz, CDCl$_3$) δ 56.01, 56.39, 110.78, 113.45, 113.61, 115.61, 126.41, 127.99, 128.37, 128.47, 128.60, 129.86, 130.24, 132.82, 132.99, 140.49, 142.71, 145.23, 150.81, 153.83. HRMS (ESI$^+$) m/z 437.1259 (M+H)$^+$ (calcd. for C$_{22}$H$_{21}$N$_4$O$_4$S 437.1278). R$_{T, HPLC}$=3.880 min, Purity>96%.

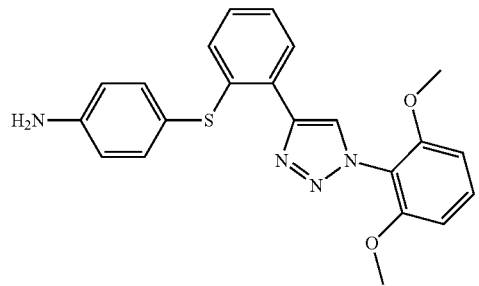 [SMILES: COc1cccc(OC)c1-n1cc(-c2ccccc2Sc2ccc(N)cc2)nn1]

4-((2-(1-(2,6-Dimethoxyphenyl)-1H-1,2,3-triazol-4-yl)phenyl)thio)amine (6ex)

$^1$H NMR (400 MHz, CDCl$_3$, TMS) δ 3.79 (s, 6H), 6.65-6.72 (m, 4H), 6.99-7.03 (m, 1H), 7.13-7.18 (m, 1H), 7.23-7.29 (m, 3H), 7.38-7.43 (m, 1H), 8.17-8.20 (m, 1H), 8.30 (s, 1H). $^{13}$C NMR (100 MHz, CDCl$_3$) δ 56.17, 104.29, 115.40, 115.92, 119.94, 125.60, 126.74, 128.07, 128.52, 129.28, 131.22, 135.80, 136.96, 144.05, 147.12, 155.91. MS (ESI): m/z (%)=427.53 (M+Na$^+$, 100).

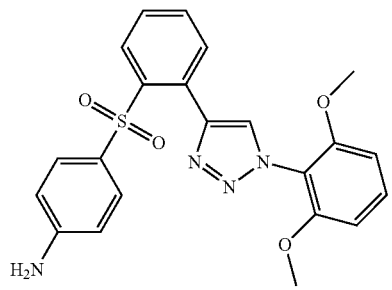 [SMILES: COc1cccc(OC)c1-n1cc(-c2ccccc2S(=O)(=O)c2ccc(N)cc2)nn1]

4-((2-(1-(2,6-Dimethoxyphenyl)-1H-1,2,3-triazol-4-yl)phenyl)sulfonyl)aniline (6ey)

$^1$H NMR (400 MHz, CDCl$_3$, TMS) δ 3.86 (s, 6H), 4.02 (broad singlet, 2H), 6.41-6.46 (m, 2H), 6.71-6.75 (d, 2H, J=8.70 Hz), 7.22-7.28 (m, 2H), 7.43-7.64 (m, 3H), 7.74-7.77 (d, 1H, J=7.33 Hz), 8.32-8.36 (m, 2H). $^{13}$C NMR (100 MHz, CDCl$_3$) δ 56.19, 104.31, 113.70, 115.11, 128.17, 128.40, 128.43, 129.94, 130.00, 130.57, 131.53, 132.67, 133.32, 140.74, 142.24, 151.02, 155.93. HRMS (ESI$^+$) m/z 437.1260 (M+H)$^+$ (calcd. for C$_{22}$H$_{21}$N$_4$O$_4$S 437.1278). R$_{T, HPLC}$=3.976 min, Purity>95%.

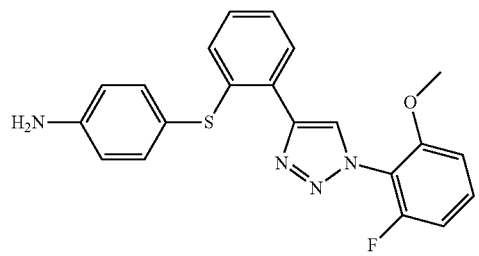 [SMILES: COc1cccc(F)c1-n1cc(-c2ccccc2Sc2ccc(N)cc2)nn1]

4-((2-(1-(2-Fluoro-6-methoxyphenyl)-1H-1,2,3-triazol-4-yl)phenyl)thio)aniline (7ex)

$^1$H NMR (400 MHz, CDCl$_3$, TMS) δ 3.82 (broad singlet, 2H), 3.83 (s, 3H), 6.64-6.69 (m, 2H), 6.84-6.94 (m, 2H), 6.99-7.04 (m, 1H), 7.14-7.20 (m, 1H), 7.21-7.28 (m, 3H), 7.40-7.47 (m, 1H), 8.13-8.17 (d, 1H, J=7.79 Hz), 8.39 (s, 1H). $^{13}$C NMR (100 MHz, CDCl$_3$) 56.49, 107.55 (1C, d, J=3.83 Hz), 108.50 (1C, d, J=20.13 Hz), 115.14 (1C, d, J=14.38 Hz), 115.95, 119.66, 125.64, 126.32, 128.37, 128.55, 128.73, 129.34, 131.30 (1C, d, J=9.58 Hz), 135.80, 137.17, 144.44, 147.18, 155.52 (1C, d, J=2.88 Hz), 157.78 (1C, d, J=253.99 Hz). MS (ESI): m/z (%)=393.11 (M+H$^+$, 100), 415.08 (M+Na$^+$, 30). R$_{T, HPLC}$=4.882 min, Purity>95%.

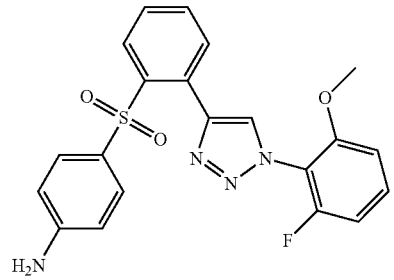 [SMILES: COc1cccc(F)c1-n1cc(-c2ccccc2S(=O)(=O)c2ccc(N)cc2)nn1]

4-((2-(1-(2-Fluoro-6-methoxyphenyl)-1H-1,2,3-triazol-4-yl)phenyl)sulfonyl)aniline (7ey)

$^1$H NMR (400 MHz, CDCl$_3$, TMS) δ 3.82 (s, 3H), 4.49 (broad singlet, 2H), 6.33-6.39 (m, 2H), 6.82-6.90 (m, 2H), 7.05-7.11 (m, 2H), 7.37-7.58 (m, 3H), 7.64-7.69 (m, 1H), 8.18-8.23 (m, 1H), 8.34 (s, 1H). MS (ESI): m/z (%)=447.42 (M+Na$^+$, 100). R$_{T, HPLC}$=4.260 min, Purity>95%.

Scheme 6S$^a$:

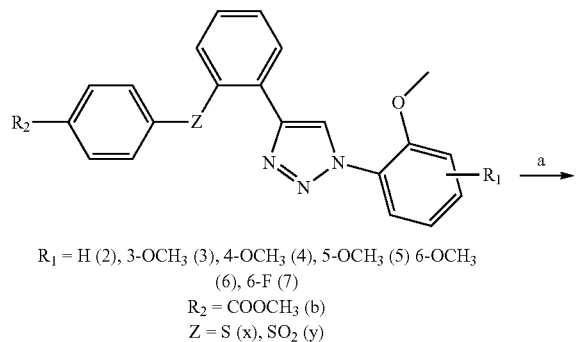

R$_1$ = H (2), 3-OCH$_3$ (3), 4-OCH$_3$ (4), 5-OCH$_3$ (5) 6-OCH$_3$ (6), 6-F (7)
R$_2$ = COOCH$_3$ (b)
Z = S (x), SO$_2$ (y)

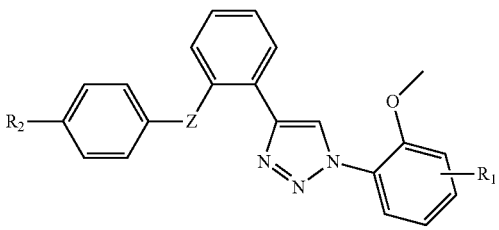

R$_1$ = H (2), 3-OCH$_3$ (3), 4-OCH$_3$ (4), 5-OCH$_3$ (5) 6-OCH$_3$ (6), 6-F (7)
R$_2$ = COOH (f)
Z = S (x), SO$_2$ (y)

$^a$Reagents & Conditions: (a) LiOH•H$_2$O, THF/CH$_3$OH/H$_2$O (4:2:1), R. T., 3 h

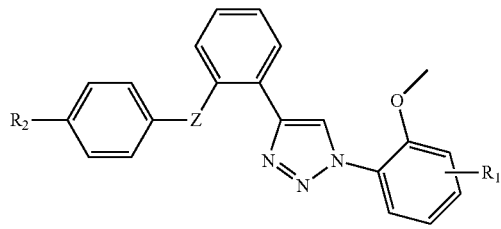

R$_1$ = H (2), 3-OCH$_3$ (3), 4-OCH$_3$ (4), 5-OCH$_3$ (5) 6-OCH$_3$ (6), 6-F (7)
R$_2$ = COOH (f)
Z = S (x), SO$_2$ (y)

Typical procedure for the syntheses of benzene carboxylic acids:

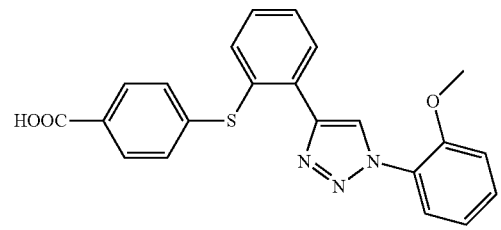 [SMILES: COc1ccccc1-n1cc(-c2ccccc2Sc2ccc(C(=O)O)cc2)nn1]

4-((2-(1-(2-Methoxyphenyl)-1H-1,2,3-triazol-4-yl)phenyl)thio)benzoic Acid (2fx)

In a 25 mL round bottom flask, methyl ester compound 2bx (0.417 g, 1 mmol, 1 equiv.) was dissolved in mL of THF/CH$_3$OH/H$_2$O (4:2:1) mixture. To this mixture lithium hydroxide hydrate (84.0 mg, 2 mmol, 2 equiv.) was added and stirred for 3 hours at room temperature. TLC (EtOAc/hexane, 1:1) showed the completion of the reaction. Organic solvents were evaporated under reduced pressure and the residue was diluted by adding 10 mL deionized water and the traces of unreacted starting material were removed by washing with EtOAc (2×5 mL). The aqueous layer was separated and treated with 1N HCl solution leading to the precipitation of the compound. The precipitate was filtered, washed with 20% DCM in hexane and dried to afford a colorless amorphous solid compound 2fx (0.38 g, 94% yield). $^1$H NMR (400 MHz, DMSO-d$_6$, TMS) δ 3.63 (s, 3H), 6.93-7.04 (m, 4H), 7.26-7.34 (m, 2H), 7.44-7.54 (m, 2H), 7.64-7.68 (m, 1H), 7.76-7.81 (m, 2H), 8.19-8.24 (m, 1H), 8.44 (s, 1H). $^{13}$C NMR (100 MHz, DMSO-d$_6$) δ 56.02, 113.10, 120.98, 125.34, 125.37, 125.61, 127.17, 128.35, 128.85, 129.51, 129.81, 130.03, 130.23, 130.74, 133.85, 135.97, 142.58, 143.81, 151.21, 166.79. HRMS (ESI$^+$) m/z 404.1043 (M+H)$^+$ (calcd. for C$_{22}$H$_8$N$_3$O$_3$S 404.1063). R$_{T, HPLC}$=1.372 min, Purity>99%.

The same procedure was followed for the syntheses of remaining carboxylic acids.

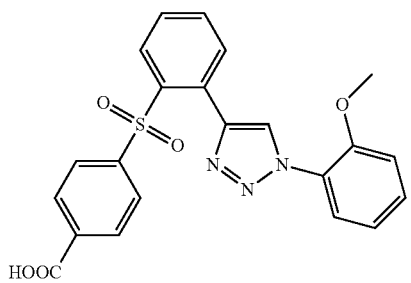 [SMILES: COc1ccccc1-n1cc(-c2ccccc2S(=O)(=O)c2ccc(C(=O)O)cc2)nn1]

4-((2-(1-(2-Methoxyphenyl)-1H-1,2,3-triazol-4-yl)phenyl)sulfonyl)benzoic acid (2fy)

$^1$H NMR (400 MHz, CDCl$_3$, TMS) δ 3.96 (s, 3H), 7.17-7.23 (m, 1H), 7.39 (d, 1H, J=8.24 Hz), 7.55-7.71 (m, 5H), 7.80-7.90 (m, 2H), 7.94 (d, 2H, J=8.70 Hz), 8.36-8.40 (dd, 1H, J=1.37 Hz, 0.1$_2$=7.79 Hz), 8.60 (s, 1H). $^{13}$C NMR (100 MHz, DMSO-d$_6$) δ 56.16, 113.18, 121.01, 125.32, 125.59, 127.45, 127.69, 129.06, 129.49, 126.76, 130.18, 130.91, 133.20, 134.31, 134.87, 138.23, 141.72, 143.67, 151.49, 165.95. MS (ESI): m/z (%)=436.14 (M+H$^+$, 100), 458.11 (M+Na$^+$, 60). R$_{T, HPLC}$=1.269 min, Purity>96%.

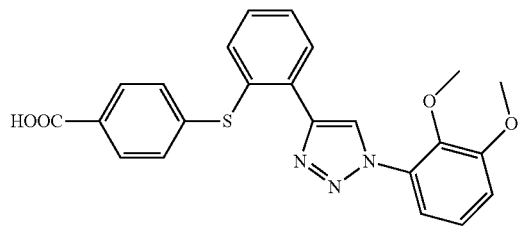 [SMILES: COc1cccc(-n2cc(-c3ccccc3Sc3ccc(C(=O)O)cc3)nn2)c1OC]

4-((2-(1-(2,3-Dimethoxyphenyl)-1H-1,2,3-triazol-4-yl)phenyl)thio)benzoic Acid (3fx)

$^1$H NMR (400 MHz, CDCl$_3$, TMS) δ 3.52 (s, 3H), 3.91 (s, 3H), 6.96-7.01 (m, 1H), 7.11 (d, 2H, J=8.24 Hz), 7.18 (t, 1H, J=8.24 Hz), 7.37-7.45 (m, 2H), 7.57-7.67 (m, 2H), 7.90 (d, 2H, J=8.70 Hz), 8.36-8.40 (m, 1H), 8.69 (s, 1H). $^{13}$C NMR (100 MHz, DMSO-d$_6$) δ 56.19, 60.66, 113.85, 116.74, 124.50, 125.22, 127.05, 128.29, 128.84, 129.59, 129.84, 130.03, 130.23, 130.33, 133.86, 136.00, 141.20, 142.53, 144.02, 153.28, 166.77. HRMS (ESI$^+$) m/z 434.1150 (M+H)$^+$ (calcd. for C$_{23}$H$_{20}$N$_3$O$_4$S 434.1169). R$_{T, HPLC}$=1.573 min, Purity>97%.

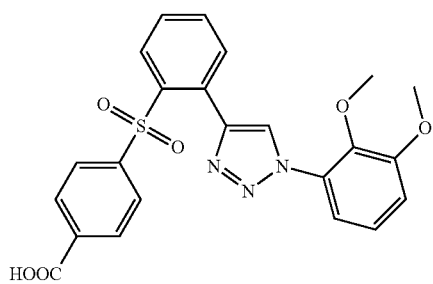 [SMILES: COc1cccc(-n2cc(-c3ccccc3S(=O)(=O)c3ccc(C(=O)O)cc3)nn2)c1OC]

4-((2-(1-(2,3-Dimethoxyphenyl)-1H-1,2,3-triazol-4-yl)phenyl)sulfonyl)benzoic Acid (3fy)

$^1$H NMR (400 MHz, Acetone-d$_6$, TMS) δ 3.97 (s, 3H), 4.01 (s, 3H), 7.26-7.37 (m, 3H), 7.71 (d, 2H, J=7.79 Hz), 7.75-7.90 (m, 3H), 8.04 (d, 2H, J=8.24 Hz), 8.41-8.45 (m, 1H), 8.66 (s, 1H). $^{13}$C NMR (100 MHz, Acetone-d$_6$) δ 56.66, 61.64, 114.43, 117.68, 125.19, 128.33, 128.56, 129.96, 130.15, 130.83, 131.66, 131.85, 134.18, 134.75, 135.43, 139.78, 142.69, 143.26, 145.53, 154.78, 166.19. HRMS (ESI$^+$) m/z 466.1051 (M+H)$^+$ (calcd. for C$_{23}$H$_{20}$N$_3$O$_6$S 466.1067). R$_{T, HPLC}$=1.376 min, Purity>98%.

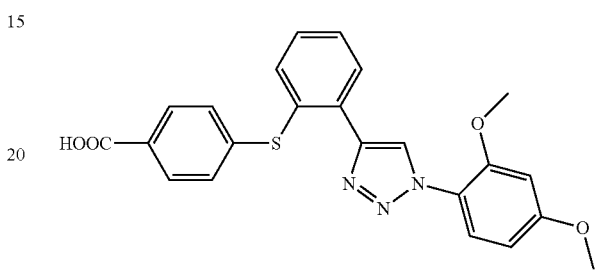

4-((2-(1-(2,4-Dimethoxyphenyl)-1H-1,2,3-triazol-4-yl)phenyl)thio)benzoic Acid (4fx)

$^1$H NMR (400 MHz, DMSO-d$_6$, TMS) δ 3.73 (s, 3H), 3.84 (s, 3H), 6.67-6.72 (dd, 1H, J$_1$=2.29 Hz, J$_2$=8.24 Hz), 6.81 (d, 1H, J=2.75 Hz), 7.18 (d, 2H, J=8.24 Hz), 7.46-7.68 (m, 4H), 7.83 (d, 2H, J=8.24 Hz), 8.10 (d, 1H, J=7.79 Hz), 8.56 (s, 1H). $^{13}$C NMR (100 MHz, DMSO-d$_6$) δ 55.73, 56.13, 99.61, 105.48, 118.87, 125.66, 126.45, 127.15, 128.31, 128.81, 129.44, 129.80, 129.97, 130.23, 133.95, 135.94, 142.63, 143.66, 152.66, 161.15, 166.78. MS (ESI): m/z (%)=434.11 (M+H$^+$, 100), 456.06 (M+Na$^+$, 100). R$_{T, HPLC}$=1.624 min, Purity>95%.

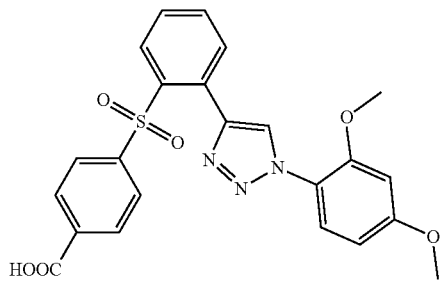 [SMILES: COc1ccc(-n2cc(-c3ccccc3S(=O)(=O)c3ccc(C(=O)O)cc3)nn2)c(OC)c1]

4-((2-(1-(2,4-Dimethoxyphenyl)-1H-1,2,3-triazol-4-yl)phenyl)sulfonyl)benzoic Acid (4fy)

$^1$H NMR (400 MHz, DMSO-d, TMS) δ 3.91 (s, 3H), 3.97 (s, 3H), 6.64-6.71 (m, 2H), 7.52-7.80 (m, 6H), 7.92-7.97 (d, 2H, J=8.70 Hz), 8.41-8.45 (d, 1H, J=8.24 Hz), 8.55 (s, 1H). $^{13}$C NMR (100 MHz, DMSO-d$_6$) δ 55.76, 56.25, 99.71, 105.52, 118.80, 126.69, 127.46, 127.78, 129.06, 129.44, 129.76, 130.33, 133.18, 134.33, 134.89, 138.16, 141.57, 143.67, 152.90, 161.29, 165.94. R$_{T, HPLC}$=1.360 min, Purity>99%.

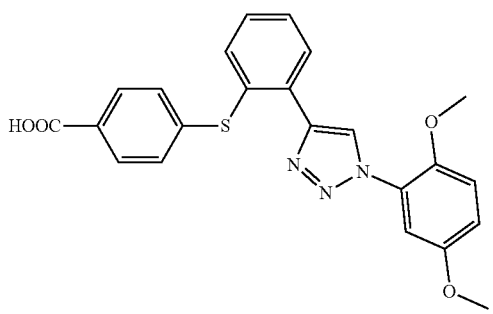 [SMILES: COc1ccc(OC)c(-n2cc(-c3ccccc3Sc3ccc(C(=O)O)cc3)nn2)c1]

4-((2-(1-(2,5-Dimethoxyphenyl)-1H-1,2,3-triazol-4-yl)phenyl)thio)benzoic Acid (5fx)

¹H NMR (400 MHz, DMSO-d₆, TMS) δ 3.68 (s, 3H), 3.82 (s, 3H), 6.92-7.01 (m, 2H), 7.09-7.13 (m, 1H), 7.36-7.41 (m, 3H), 7.54-7.64 (m, 2H), 7.86-7.91 (m, 2H), 8.28-8.33 (m, 1H), 8.60 (s, 1H). ¹³C NMR (100 MHz, DMSO-d₆) δ 55.79, 56.45, 110.51, 114.41, 115.77, 125.53, 125.60, 127.08, 128.26, 128.77, 129.54, 129.88, 130.05, 130.25, 133.87, 136.09, 142.64, 143.86, 145.03, 153.19, 166.78. MS (ESI): m/z (%)=434.08 (M+H⁺, 100), 456.08 (M+Na⁺, 50). R$_{T, HPLC}$=1.650 min, Purity>99%.

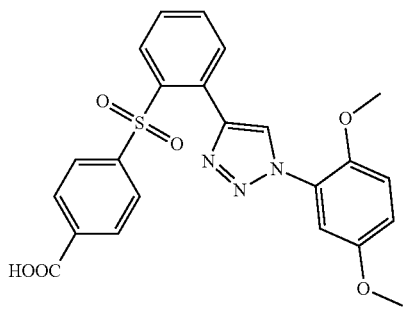 [SMILES: COc1ccc(OC)c(-n2cc(-c3ccccc3S(=O)(=O)c3ccc(C(=O)O)cc3)nn2)c1]

4-((2-(1-(2,5-Dimethoxyphenyl)-1H-1,2,3-triazol-4-yl)phenyl)sulfonyl)benzoic Acid (5fy)

¹H NMR (400 MHz, DMSO-d₆, TMS) δ 3.88 (s, 3H), 3.98 (s, 3H), 7.02-7.14 (m, 2H), 7.35-7.39 (m, 2H), 7.55-7.60 (d, 2H, J=8.70 Hz), 7.65-7.78 (m, 2H), 7.93-7.98 (d, 2H, J=8.70 Hz), 8.42-8.47 (d, 1H, J=7.33 Hz), 8.72 (s, 1H). ¹³C NMR (100 MHz, DMSO-d₆) δ 55.73, 56.60, 110.64, 114.46, 116.04, 125.53, 127.48, 127.60, 129.05, 129.54, 129.77, 130.10, 133.18, 134.35, 134.89, 138.25, 141.78, 143.65, 145.27, 153.23, 165.96. R$_{T, HPLC}$=1.517 min, Purity>99%.

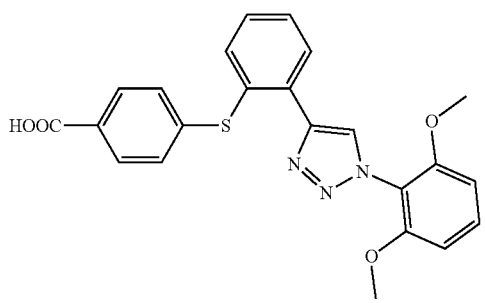 [SMILES: COc1cccc(OC)c1-n1cc(-c2ccccc2Sc2ccc(C(=O)O)cc2)nn1]

4-((2-(1-(2,6-Dimethoxyphenyl)-1H-1,2,3-triazol-4-yl)phenyl)thio)benzoic Acid (6fx)

¹H NMR (400 MHz, CDCl₃, TMS) δ 3.66 (s, 6H), 6.61-6.65 (m, 2H), 7.07-7.12 (m, 2H), 7.34-7.41 (m, 2H), 7.56-7.66 (m, 2H), 7.85-7.90 (m, 2H), 8.18 (s, 1H), 8.44-8.48 (m, 1H). ¹³C NMR (100 MHz, DMSO-d₆) δ 56.13, 104.71, 114.40, 126.95, 127.41, 128.32, 128.95, 129.20, 129.62, 129.71, 130.14, 131.75, 133.78, 135.68, 142.33, 143.18, 155.31, 166.80. HRMS (ESI) m/z 434.1149 (M+H)⁺ (calcd. for C₂₃H₂₀N₃O₄S 434.1169). R$_{T, HPLC}$=1.282 min, Purity>98%.

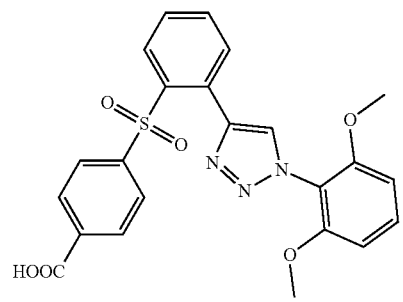 [SMILES: COc1cccc(OC)c1-n1cc(-c2ccccc2S(=O)(=O)c2ccc(C(=O)O)cc2)nn1]

4-((2-(1-(2,6-Dimethoxyphenyl)-1H-1,2,3-triazol-4-yl)phenyl)sulfonyl)benzoic Acid (6fy)

¹H NMR (400 MHz, DMSO-d₆, TMS) δ 3.87 (s, 6H), 6.72-6.78 (d, 2H, J=8.70 Hz), 7.44-7.55 (m, 4H), 7.62-7.78 (m, 2H), 7.90-7.94 (d, 2H, J=8.70 Hz), 8.27 (s, 1H), 8.44-8.48 (dd, 1H, J₁=0.92 Hz, J₂=7.79 Hz). ¹³C NMR (100 MHz, DMSO-d₆) δ 56.31, 104.82, 114.28, 127.59, 129.06, 129.20, 129.33, 129.73, 130.56, 131.90, 133.25, 134.33, 134.90, 138.06, 141.05, 143.63, 155.42, 165.98. HRMS (ESI⁺) m/Z 466.1052 (M+H)⁺ (calcd. for C₂₃H₂₀N₃O₆S 466.1067). R$_{T, HPLC}$=1.210 min, Purity>99%.

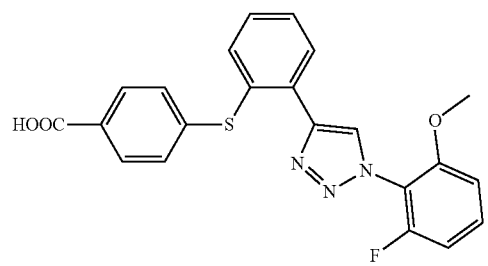 [SMILES: COc1cccc(F)c1-n1cc(-c2ccccc2Sc2ccc(C(=O)O)cc2)nn1]

4-((2-(1-(2-Fluoro-6-methoxyphenyl)-1H-1,2,3-triazol-4-yl)phenyl)thio)benzoic Acid (7fx)

¹H NMR (400 MHz, DMSO-d₆, TMS) δ 3.72 (s, 3H), 6.81-6.92 (m, 2H), 7.11 (d, 2H, J=8.24 Hz), 7.37-7.47 (m, 2H), 7.54-7.64 (m, 2H), 7.87 (d, 2H, J=8.24 Hz), 8.26 (s, 1H), 8.38 (d, 1H, J=8.24 Hz). ¹³C NMR (100 MHz, DMSO-d₆) δ 56.68, 108.13 (1C, d, J=20.13 Hz), 108.74 (1C, d, J=2.88 Hz), 114.15 (1C, d, J=15.34 Hz), 127.03, 127.66, 128.46, 129.55, 130.02, 130.17, 132.20 (1C, d, J=10.54 Hz), 133.38, 135.53, 142.21, 143.72, 155.21 (1C, d, J=2.88 Hz), 157.04 (1C, d, J=251.12 Hz), 166.82. MS (ESI): m/z (%)=422.05 (M+H⁺, 100), 444.04 (M+Na⁺, 70). R$_{T, HPLC}$=1.533 min, Purity>98%.

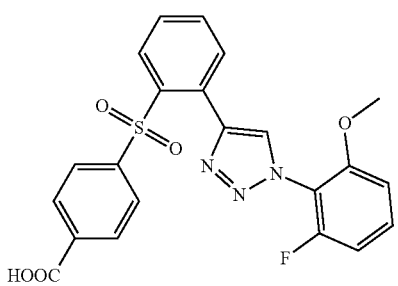 [SMILES: COc1cccc(F)c1-n1cc(-c2ccccc2S(=O)(=O)c2ccc(C(=O)O)cc2)nn1]

4-((2-(1-(2-Fluoro-6-methoxyphenyl)-1H-1,2,3-triazol-4-yl)phenyl)sulfonyl)benzoic Acid (7fy)

$^1$H NMR (400 MHz, DMSO-$d_6$, TMS) δ 3.92 (s, 3H), 7.15-7.21 (m, 1H), 7.24 (d, 1H, J=8.70 Hz), 7.60 (d, 2H, J=8.24 Hz), 7.64-7.71 (m, 2H), 7.80-7.90 (m, 2H), 7.93 (d, 2H, J=8.70 Hz), 8.37-8.41 (dd, 1H, $J_1$=1.83 Hz, $J_2$=7.79 Hz), 8.58 (s, 1H). $^{13}$C NMR (100 MHz, DMSO-$d_6$) δ 56.81, 108.22 (1C, d, J=19.17 Hz), 108.84 (1C, d, J=2.88 Hz), 114.04 (1C, d, J=15.34 Hz), 127.49, 129.09, 129.11, 129.61, 129.76, 130.07, 132.35 (1C, d, J=10.54 Hz), 133.36, 134.37, 134.93, 138.27, 141.53, 143.63, 155.28 (1C, d, J=2.88 Hz), 157.18 (1C, d, J=251.12 Hz), 165.95. $R_{T, HPLC}$=1.352 min, Purity>98%.

Scheme 7S$^a$:

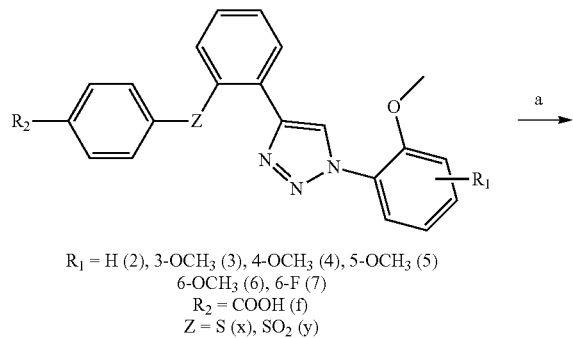

$R_1$ = H (2), 3-OCH$_3$ (3), 4-OCH$_3$ (4), 5-OCH$_3$ (5)
6-OCH$_3$ (6), 6-F (7)
$R_2$ = COOH (f)
Z = S (x), SO$_2$ (y)

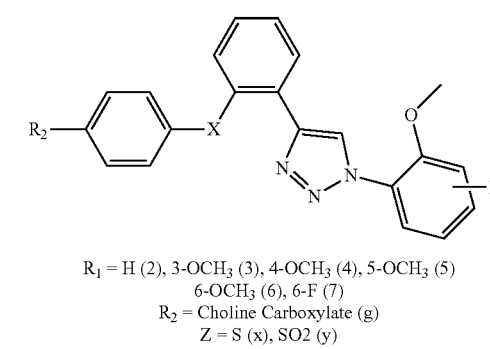

$R_1$ = H (2), 3-OCH$_3$ (3), 4-OCH$_3$ (4), 5-OCH$_3$ (5)
6-OCH$_3$ (6), 6-F (7)
$R_2$ = Choline Carboxylate (g)
Z = S (x), SO2 (y)

$^a$Reagents & Conditions: (a) 40% choline base in methanol/EtOAc or Acetone/R.T.

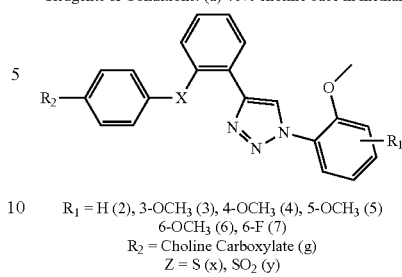

$R_1$ = H (2), 3-OCH$_3$ (3), 4-OCH$_3$ (4), 5-OCH$_3$ (5)
6-OCH$_3$ (6), 6-F (7)
$R_2$ = Choline Carboxylate (g)
Z = S (x), SO$_2$ (y)

Typical procedure for the syntheses of choline salts:

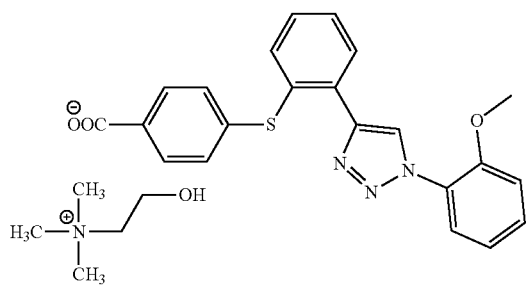

2-Hydroxy-N,N,N-trimethylethanaminium 4-((2-(1-(2-methoxyphenyl)-1H-1,2,3-triazol-4-yl)phenyl)thio)benzoate (2gx)

In a 10 mL oven dried round bottom flask carboxylic acid compound 2fx (0.20 g, 0.5 mmol, 1 equiv.) was dissolved in 5 mL of ethyl acetate and stirring was continued till transparent solution was obtained (slight warming up to 45-50° C. helped to get clear solution). To this stirred solution 0.24 mL of 2-hydroxyethyl)trimethylammonium hydroxide (0.225 g, 1.5 equiv., d=0.94 g/ml, choline base 40% w/w in methanol) was added drop by drop till turbidity was formed. The mixture was allowed to stir for a period of 30 minutes at room temperature. Organic solvents were decanted and the gummy residue obtained was washed several times with ethyl acetate (3×5 mL) by vigorous stirring to remove unreacted traces of the carboxylic acid and excess choline base. Now the gummy residue was dissolved in little amount of isopropanol following by the addition of ethyl acetate till choline salt gets precipitated. Solvents were decanted and dried in calcium chloride desiccator to afford pure choline salt as a light yellow colored gummy solid compound 2gx (0.17 g, 68% yield). $^1$H NMR (400 MHz, Acetone-$d_6$, TMS) δ 3.39 (s, 9H), 3.72-3.76 (m, 2H), 3.86 (s, 3H), 4.02-4.07 (m, 2H), 7.13-7.17 (m, 3H), 7.27-7.31 (dd, 1H, J=1.37 Hz, $J_{2=8.24}$ Hz), 7.37-7.41 (m, 1H), 7.44-7.53 (m, 3H), 7.75-7.78 (dd, 1H, J=1.37 Hz, $J_2$=7.79 Hz), 7.97-8.00 (m, 2H), 8.19-8.23 (dd, 1H, $J_1$=1.37 Hz, $J_2$=7.79 Hz), 8.74 (s, 1H). MS (ESI): m/z (%)=610.22 (M+ cholinium$^+$, 100). $R_{T, HPLC, METHOD-B}$=1.623 min, Purity>95%.

The same procedure was followed for the syntheses of the remaining choline carboxylate salts.

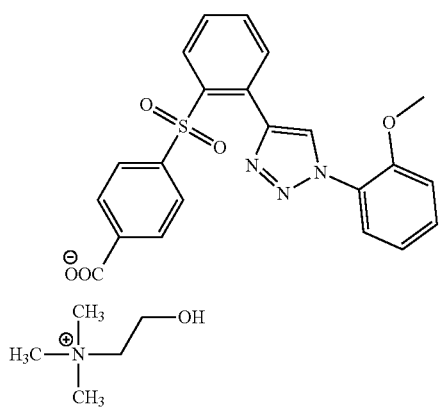

2-Hydroxy-N,N,N-trimethylethanaminium 4-((2-(1-(2-methoxyphenyl)-1H-1,2,3-triazol-4-yl)phenyl)sulfonyl)benzoate (2gy)

Light brown needles crystallized in isopropanol/ethyl acetate/n-pentane. m. p. 93° C. $^1$H NMR (400 MHz, Acetone-$d_6$, TMS) δ 3.39 (s, 9H), 3.71 (m, 2H), 4.02-4.08 (multiplet & singlet merged, 5H), 7.19-7.24 (m, 1H), 7.39 (d, 1H, J=8.24 Hz), 7.50 (d, 2H, J=8.70 Hz), 7.54-7.59 (m, 1H), 7.72-7.79 (m, 2H), 7.79-7.83 (m, 2H), 7.99 (d, 2H, J=8.24 Hz), 8.39 (d, 1H, J=8.24 Hz), 8.74 (s, 1H). $^{13}$C NMR (100 MHz, Acetone-$d_6$) δ 54.59 (3C, t, J=3.89 Hz), 56.49, 56.72, 69.22 (1C, t, J=2.58 Hz), 113.87, 122.04, 126.46, 127.12, 127.57, 128.94, 129.71, 129.94, 130.41, 131.51, 131.83, 133.93, 134.40, 140.63, 141.21, 143.24, 146.70, 152.64, 169.05. MS (ESI): m/z (%)=642.16 (M+ cholinium$^+$, 100). HRMS (ESI$^-$) m/z 434.0803 (M$^{*-}$, carboxylate ion) (calcd. for $C_{22}H_{16}N_3O_5S$ 434.0816), HRMS (ESI$^+$) m/z 104.1063 (M$^{*+}$, cholinium cation) (calcd. for $C_5H_{14}NO$ 104.1070). $R_{T, HPLC, METHOD-B}$=1.446 min, Purity>99%.

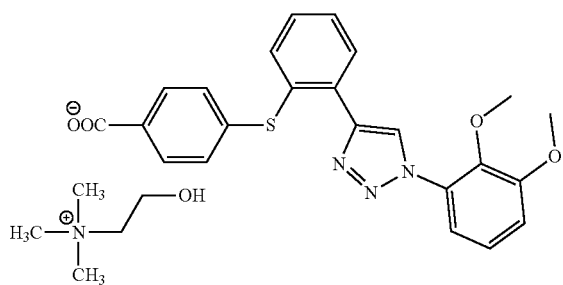

2-Hydroxy-N,N,N-trimethylethanaminium 4-((2-(1-(2,3-dimethoxyphenyl)-1H-1,2,3-triazol-4-yl)phenyl)thio)benzoate (3gx)

$^1$H NMR (400 MHz, CD$_3$OD, TMS) δ 3.19 (s, 9H), 3.44-3.48 (m, 2H), 3.59 (s, 3H), 3.92 (s, 3H), 3.95-4.00 (m, 2H), 7.07-7.11 (m, 2H), 7.16-7.27 (m, 3H), 7.41-7.46 (m, 1H), 7.52-7.59 (m, 2H), 7.79-7.84 (m, 2H), 8.05-8.10 (dd, 1H, $J_1$=1.37 Hz, $J_2$=7.79 Hz), 8.61 (s, 1H). $^{13}$C NMR (100 MHz, Acetone-$d_6$) δ 54.53 (3C, t, J=4.11 Hz), 56.39, 56.58, 61.35, 69.30 (1C, t, J=2.91 Hz), 114.13, 117.45, 125.20, 125.91, 128.92, 129.29, 129.66, 130.45, 131.45, 131.91, 133.21, 133.73, 134.74, 136.26, 141.04, 142.42, 145.36, 154.75, 170.06. MS (ESI): m/z (%)=640.35 (M+ cholinium$^+$, 100). $R_{T, HPLC, METHOD-B}$=1.568 min, Purity>99%.

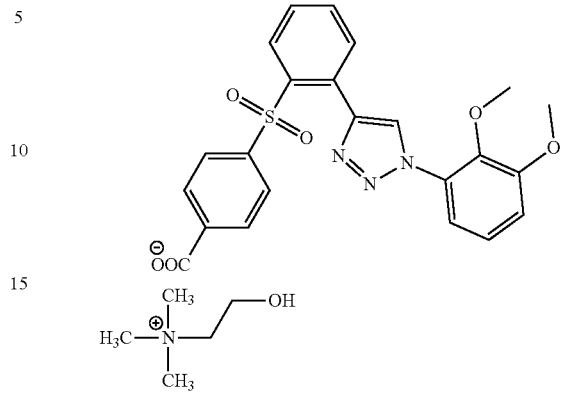

2-Hydroxy-N,N,N-trimethylethanaminium 4-((2-(1-(2,3-dimethoxyphenyl)-1H-1,2,3-triazol-4-yl)phenyl)sulfonyl)benzoate (3gy)

$^1$H NMR (400 MHz, Acetone-$d_6$, TMS) δ 3.38 (s, 9H), 3.71 (m, 2H), 3.96 (s, 3H), 4.01 (s, 3H), 4.01-4.06 (m, 2H), 7.26-7.38 (m, 3H), 7.50 (d, 2H, J=8.70 Hz), 7.72-7.77 (m, 1H), 7.79-7.83 (m, 2H), 8.00 (d, 2H, J=8.24 Hz), 8.33-8.37 (m, 1H), 8.72 (s, 1H). $^{13}$C NMR (100 MHz, CD$_3$OD) δ 54.66 (3C, t, J=3.83 Hz), 56.81, 57.03, 62.04, 69.03 (1C, t, J=2.88 Hz), 115.08, 118.23, 125.62, 128.25, 129.22, 130.28, 130.52, 130.60, 131.42, 131.79, 134.39, 134.96, 140.84, 142.82, 143.40, 143.90, 144.16, 155.18, 172.59. MS (ESI): m/z (%)=672.34 (M+ cholinium$^+$, 100). $R_{T, HPLC, METHOD-B}$=1.517 min, Purity>97%.

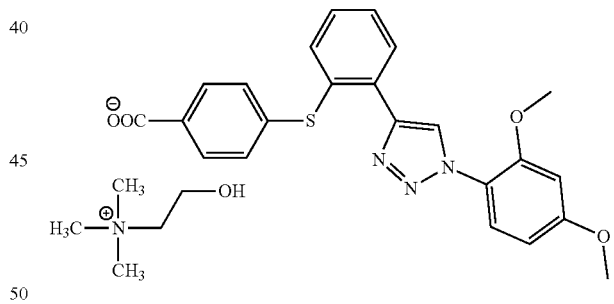

2-Hydroxy-N,N,N-trimethylethanaminium 4-((2-(1-(2,4-dimethoxyphenyl)-1H-1,2,3-triazol-4-yl)phenyl)thio)benzoate (4gx)

$^1$H NMR (400 MHz, Acetone-$d_6$, TMS) δ 3.39 (s, 9H), 3.71-3.75 (m, 2H), 3.84 (s, 3H), 3.89 (s, 3H), 4.03-4.08 (m, 2H), 6.69-6.73 (m, 1H), 6.78-6.80 (m, 1H), 7.12-7.16 (m, 2H), 7.36-7.41 (m, 1H), 7.44-7.53 (m, 2H), 7.60-7.63 (m, 1H), 7.96-8.00 (m, 2H), 8.19-8.23 (m, 1H), 8.61 (s, 1H). $^{13}$C NMR (100 MHz, Acetone-$d_6$) δ 53.95 (3C, t, J=4.07 Hz), 55.49, 55.83, 55.99, 68.54 (1C, t, J=2.84 Hz), 99.63, 105.56, 119.99, 125.79, 126.51, 128.44, 128.49, 128.91, 129.85, 130.83, 132.12, 133.58, 134.52, 136.28, 139.93, 144.34, 153.12, 161.78, 169.77. MS (ESI): m/z (%)=640.25 (M+ cholinium$^+$, 100).

209

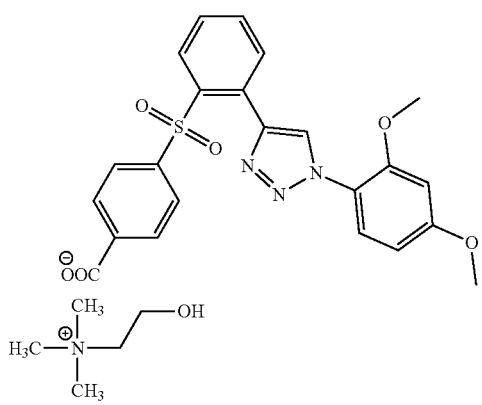

2-Hydroxy-N,N,N-trimethylethanaminium 4-((2-(1-(2,4-dimethoxyphenyl)-1H-1,2,3-triazol-4-yl)phenyl)sulfonyl)benzoate (4gy)

$^1$H NMR (400 MHz, Acetone-$d_6$, TMS) δ 3.36 (s, 9H), 3.68-3.72 (m, 2H), 3.93 (s, 3H), 4.00-4.06 (multiplet & singlet merged, 5H), 6.75-6.79 (m, 1H), 6.88-6.90 (m, 1H), 7.47-7.50 (m, 2H), 7.60-7.63 (m, 1H), 7.72-7.83 (m, 3H), 7.96-8.00 (m, 2H), 8.38-8.41 (dd, 1H, $J_1$=1.37 Hz, $J_2$=7.79 Hz), 8.60 (s, 1H). HRMS (ESI$^-$) m/z 464.0908 (M*$^-$, carboxylate ion) (calcd. for $C_{23}H_{18}N_3O_6S$ 464.0922), HRMS (ESI$^+$) m/z104.1063 (M*$^+$, cholinium cation) (calcd. for $C_5H_{14}NO$ 104.1070). $R_{T,\ HPLC,\ METHOD-B}$=1.451 min, Purity>96%.

210

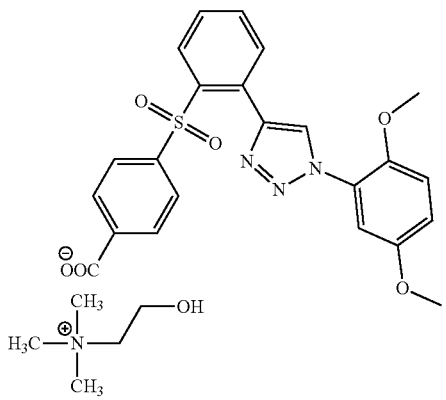

2-Hydroxy-N,N,N-trimethylethanaminium 4-((2-(1-(2,5-dimethoxyphenyl)-1H-1,2,3-triazol-4-yl)phenyl)sulfonyl)benzoate (5gy)

$^1$H NMR (400 MHz, Acetone-$d_6$, TMS) δ 3.37 (s, 9H), 3.69-3.73 (m, 2H), 3.89 (s, 3H), 4.01 (s, 3H), 4.01-4.07 (m, 2H), 7.09-7.14 (m, 1H), 7.30-7.35 (m, 2H), 7.49 (d, 2H, J=8.70 Hz), 7.73-7.85 (m, 3H), 7.968 (d, 2H, J=8.70 Hz), 8.39-8.42 (dd, 1H, $J_1$=1.37 Hz, $J_{2=7.79}$ Hz), 8.75 (s, 1H). $^{13}$C NMR (100 MHz, Acetone-$d_6$) δ 54.49 (3C, t, J=3.83 Hz), 56.35, 56.43, 57.02, 69.13, 111.33, 115.00, 116.56, 127.17, 127.44, 128.72, 129.61, 129.78, 130.27, 131.62, 133.76, 134.30, 140.49, 141.09, 143.14, 146.22, 146.41, 154.77, 168.98. MS (ESI): m/z (%)=672.34 (M+ cholinium$^+$, 100). HRMS (EST) m/z 464.0905 (M*$^+$, carboxylate ion) (calcd. for $C_{23}H_{18}N_3O_6S$ 464.0922), HRMS (ESI$^+$) m/z104.1063 (M*$^+$, cholinium cation) (calcd. for $C_5H_{14}NO$ 104.1070). $R_{T,\ HPLC,\ METHOD-B}$=1.557 min, Purity>98%.

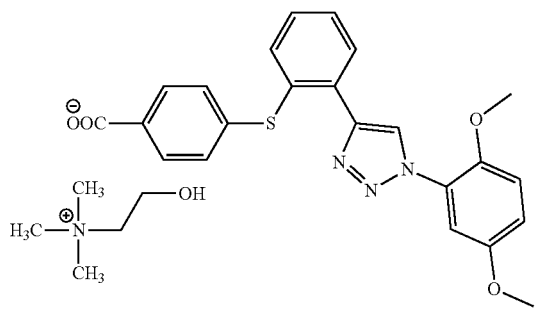

2-Hydroxy-N,N,N-trimethylethanaminium 4-((2-(1-(2,5-dimethoxyphenyl)-1H-1,2,3-triazol-4-yl)phenyl)thio)benzoate (5gx)

$^1$H NMR (400 MHz, Acetone-$d_6$, TMS) δ 3.40 (s, 9H), 3.72-3.76 (m, 2H), 3.81 (s, 3H), 3.85 (s, 3H), 4.03-4.08 (m, 2H), 7.04-7.08 (m, 1H), 7.13-7.17 (m, 2H), 7.21-7.24 (m, 1H), 7.37-7.54 (m, 4H), 7.97-8.00 (m, 2H), 8.19-8.23 (m, 1H), 8.77 (s, 1H). MS (ESI): m/z (%)=640.32 (M+ cholinium$^+$, 100).

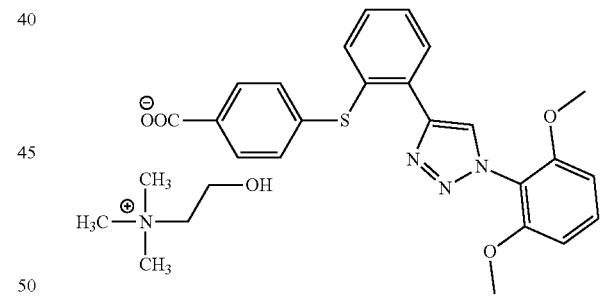

2-Hydroxy-N,N,N-trimethylethanaminium 4-((2-(1-(2,6-dimethoxyphenyl)-1H-1,2,3-triazol-4-yl)phenyl)thio)benzoate (6gx)

$^1$H NMR (400 MHz, CD$_3$OD, TMS) δ 3.18 (s, 9H), 3.44-3.48 (m, 2H), 3.71 (s, 6H), 3.95-4.00 (m, 2H), 6.80 (d, 2H, J=8.70 Hz), 7.08 (d, 2H, J=7.79 Hz), 7.37-7.57 (m, 4H), 7.81 (d, 2H, J=8.24 Hz), 8.04-8.09 (m, 1H), 8.24 (s, 1H). $^{13}$C NMR (100 MHz, CD$_3$OD) δ 54.68 (3C, t, J=3.83 Hz), 56.83, 57.04, 69.03 (1C, t, J=2.88 Hz), 105.55, 115.98, 128.68, 128.79, 130.19, 130.31, 131.00, 131.21, 132.44, 133.17, 134.82, 136.63, 137.34, 140.21, 145.42, 157.21, 174.38. MS (ESI): m/z (%)=640.40 (M+ cholinium$^+$, 100). $R_{T,\ HPLC,\ METHOD-B}$=1.595 min, Purity>99%.

211

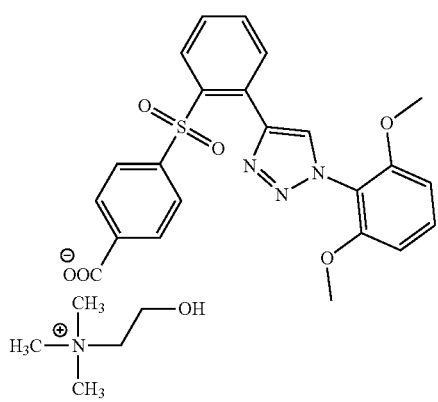

2-Hydroxy-N,N,N-trimethylethanaminium 4-((2-(1-(2,6-dimethoxyphenyl)-1H-1,2,3-triazol-4-yl)phenyl)sulfonyl)benzoate (6gy)

1H NMR (400 MHz, $CD_3OD$, TMS) δ 3.18 (s, 9H), 3.42-3.48 (m, 2H), 3.90 (s, 6H), 3.93-4.00 (m, 2H), 6.88-6.94 (d, 2H, J=8.70 Hz), 7.47-7.59 (m, 3H), 7.61-7.67 (m, 1H), 7.70-7.81 (m, 2H), 7.89-7.94 (d, 2H, J=2.88 Hz), 8.23 (s, 1H), 8.40-8.45 (dd, 1H, $J_1$=0.92 Hz, $J_2$=7.79 Hz). $^{13}C$ NMR (100 MHz, $CD_3OD$) δ 54.66 (3C, t, J=3.83 Hz), 56.97, 57.03, 69.02 (1C, t, J=2.88 Hz), 105.70, 115.86, 128.51, 130.28, 130.45, 130.60, 131.18, 131.79, 133.40, 134.55, 134.97, 140.84, 142.90, 143.27, 144.14, 157.30, 172.64. MS (ESI): m/z (%)=672.30 (M+ cholinium$^+$, 100). $R_{T, HPLC, METHOD-B}$=1.491 min, Purity>97%. $R_{T, HPLC, METHOD-B}$=1.491 min, Purity>96%.

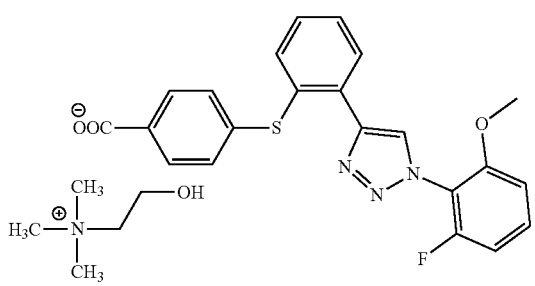

2-Hydroxy-N,N,N-trimethylethanaminium 4-((2-(1-(2-fluoro-6-methoxyphenyl)-1H-1,2,3-triazol-4-yl)phenyl)thio)benzoate (7gx)

$^1$H NMR (400 MHz, Acetone-$d_6$, TMS) δ 3.40 (s, 9H), 3.72-3.76 (m, 2H), 3.83 (s, 3H), 4.02-4.07 (m, 2H), 6.99-7.04 (m, 1H), 7.11-7.20 (m, 3H), 7.35-7.43 (m, 2H), 7.46-7.51 (m, 1H), 7.55-7.62 (m, 1H), 7.98 (d, 2H, J=8.24 Hz), 8.20-8.24 (dd, 1H, $J_1$=1.37 Hz, $J_2$=7.79 Hz), 8.59 (s, 1H). MS (ESI): m/z (%)=628.21 (M+ cholinium$^+$, 100).

212

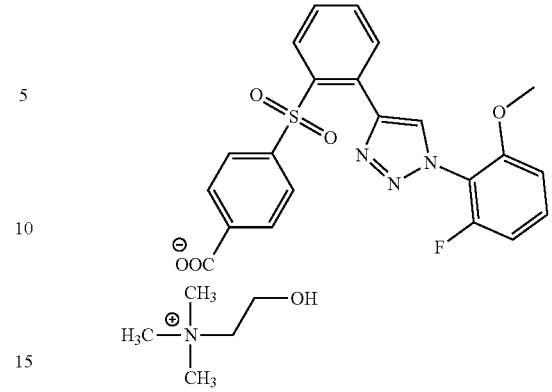

2-Hydroxy-N,N,N-trimethylethanaminium 4-((2-(1-(2-fluoro-6-methoxyphenyl)-1H-1,2,3-triazol-4-yl)phenyl)sulfonyl)benzoate (7gy)

$^1$H NMR (400 MHz, Acetone-$d_6$, TMS) δ 3.37 (s, 9H), 3.69 (m, 2H), 4.00-4.07 (multiplet & singlet merged, 5H), 7.06-7.13 (m, 1H), 7.22 (d, 1H, J=8.70 Hz), 7.49 (d, 2H, J=8.70 Hz), 7.61-7.69 (m, 1H), 7.72-7.86 (m, 3H), 8.01 (d, 2H, J=8.70 Hz), 8.42 (d, 1H, J=8.24 Hz), 8.54 (s, 1H). MS (ESI): m/z (%)=660.33 (M+ cholinium$^+$, 100).

Immunoblot Methodology: Transfection, Small Molecule Treatment and Protein analysis.

293FT cells were co-transfected with HA-APOBEC3G and pEYFP-C1-Vif or pNL-A1-ΔVif plasmid (0.5:2 molar ratio) using LIPOFECTAMINE™ 2000 (Invitrogen) in OPTI-MEM® medium. After 4 hours, the transfection mixture was replaced with complete DMEM medium without Geneticin antibiotic. Individual small molecule (RN-18, 1b, 1c, 1d, and 1e) was added to the transfected cells at 50 μM concentrations with 1% DMSO or 1×PBS. The cells were grown at 37° C. in a humidified incubator (5% $CO_2$) for 16 h. After 16 h post-incubation, the cells were washed in 1×PBS and lysed with Mammalian Protein Extraction Reagent (M-PER, Thermo) containing protease inhibitor cocktail (Roche). The total extracted protein was quantified using DC protein assay kit (Bio-Rad).

The total proteins (10 μg) were boiled with 5×SDS-PAGE sample buffer, separated in 4-200/% SDS-PAGE gel (Bio-Rad) and electroblotted onto a PVDF membrane using semi-dry electroblotter (Bio-Rad). After being blocked with 5% non-fat dry milk in 1×TBST buffer for 2 h, the membrane was exposed to primary antibody. HA-Apobec3G protein was detected by anti-HA rat polyclonal antibody (Roche) at 1:3000 dilutions. The GFP-Vif and GAPDH was detected using anti-GFP and anti-GAPDH rabbit polyclonal antibody at 1:1000 dilutions respectively (Cell Signaling). The species specific horseradish peroxidase conjugated secondary antibody was used for the respective primary antibody. The membrane was developed with the BM Chemiluminescence blotting kit (Roche).

Antiviral Activity Assay.

The antiviral activities of peptidomimetic analogues of RN-18 analogues were measured with wild-type HIV-1 in H9 cells (non-permissive) and MT-4 cells (permissive). H9 and MT4 cells (2×10$^5$ cells per well in 48-well plates) were treated overnight with differing concentrations of Vif antagonists (1 to 50 μM) in RPMI medium containing 10% fetal bovine serum. The cells were then infected with an X4-tropic HIV-1 variant (HIV-1$_{LAI}$) and maintained for further 10-15 days. Viral replication was monitored every second day by measuring reverse transcriptase (RT) activity in the culture supernatants. For this, ⅓ of the culture supernatant was replaced with an equivalent volume of fresh medium containing the appropriate compounds every second day. In all experiments, RN-18 (1) was used as a positive control and cells cultured without compound served as negative controls. Measurements of antiviral activity in cultured cells were repeated at least 3 times and the IC$_{50}$ values were calculated using GraFit software. See FIG. 17.

REFERENCES (EXAMPLE 2)

[1]. (a) Lee, W-G.; Frey, K. M.; Gallardo-Macias, R.; Spasov, K. A.; Bollini, M.; Anderson, K. S.; Jorgensen, W. L. ACS Med. Chem. Lett., 2014, 5, 1259 and references therein. (b) Tang, J.; Maddali, K.; Motifiot, M.; Sham, Y. Y.; Vince, R.; Pommier, Y.; Wang, Z. J. Med. Chem. 2011, 54, 2282 and references therein; [2]. (a) Parai, M. K.; Huggins, D. J.; Cao, H.; Nalam, M. N. L.; Ali, A.; Schiffer, C. A.; Tidor, B.; Rana, T. M. J. Med. Chem. 2012, 55, 6328. (b) Altman, M. D.; Ali, A.; Reddy, G. S. K. K.; Nalam, M. N. L.; Anjum, S. G.; Cao, H.; Chellappan, S.; Kairys, V.; Fernandes, M. X.; Gilson, M. K.; Schiffer, C. A.; Rana, T. M.; Tidor, B. J. Am. Chem. Soc. 2008, 130, 6099. (c) Ghosh, A. K.; Chapsal, B. D.; Baldridge, A.; Steffey, M. P.; Walters, D. E.; Koh, Y.; Amano, M.; Misuya, H. J. Med. Chem. 2011, 54, 622. (d) Cai, Y.; Schiffer, C. A. J. Chem. Theory Comput. 2010, 6, 1358; [3]. Hicks, C.; Gulick, R. M. Clin. Infect. Dis. 2009, 48, 931; [4]. (a) Johnson, V. A.; Brun-Vezinet, F.; Clotet, B.; Ginthard, H. F.; Kuritzkes, D. R.; Pillay, D.; Schapiro, J. M.; Richman, D. D. Topics in HIV Medicine 2010, 18, 156. (b) Ren, J.; Stammers, D. K. Virus Res. 2008, 134, 157; [5]. Spekowitz, K. A. N. Engl. J. Med. 2001, 344, 1764; [6]. Arhel, N.; Kirchhoff, F. Biochim. et Biophysic. Acta 2010, 1802, 313 and references there in; [7]. Nathans, R.; Cao, H.; Sharova, N.; All, A.; Sharkey, M.; Stranska, R.; Stevenson, M.; Rana, T. M. Nat. Biotechnol. 2008, 26, 1187; [8]. (a) Bishop, K. N.; Verma, M.; Kim, E-Y.; Wolinsky, S. M.; Malim, M. H. PLoS Pathogens 2008, 4, e1000231. (b) Luo, K.; Wang, T.; Liu, B.; Tian, C.; Xiao, Z.; Kappes, J.; Yu, X-F. J. Virol. 2007, 81, 7238. (c) Neil, S.; Bieniasz, P. J. Interferon Cytokine Res. 2009, 29, 569; [9]. Sheehy, A. M.; Gaddis, N. C.; Choi, J. D.; Malim, M. H. Nature 2002, 418, 646-650; [10]. Prochnow, C.; Bransteitter, R.; Goodman, M. F.; Chen, X. S. HIV Ther. 2009, 3, 7; [11]. (a) Mohammed, I.; Parai, M. K.; Jiang, X.; Sharova, N.; Singh, G.; Stevenson, M.; Rana, T. M. ACS Med. Chem. Lett. 2012, 3, 465. (b) Ali, A.; Wang, J.; Nathans, R. S.; Cao, H.; Sharova, N.; Steven-son, M.; Rana, T. M. ChemMedChem 2012, 7, 1217; [12]. Ko, E.; Liu, J.; Perez, L. M.; Lu, G.; Schaefer, A.; Burgess, K. J. Am. Chem. Soc. 2011, 133, 462; [13]. Borg, S.; Vollinga, R. C.; Labarre, M.; Payza, K.; Terenius, L.; Luthman, K. J. Med. Chem. 1999, 42, 4331; [14]. Lewis, W. G.; Green, L. G.; Grynszpan, F.; Radić, Carlier, P. R.; Taylor, P.; Finn, M. G.; Sharpless, K. B. Angew. Chem. Int. Ed. 2009, 41, 1053; [15]. (a) Tam, A.; Arnold, U.; Soellner, M. B.; Raines, R. T. J. Am. Chem. Soc. 2007, 129, 12670. (b) Manetsch, R.; Krasifiski, A.; Radic, Raushel, J.; Taylor, P.; Sharpless, K. B.; Kolb, H. C. J. Am. Chem. Soc. 2004, 126, 12809; [16]. Tron, G. C.; Pirali, T.; Billington, R. A.; Canonico, P. L.; Sorba, G.; Genazzani, A. A. Med. Res. Rev. 2008, 28, 278 and references therein; [17]. Grimes, K. D.; Gupte, A.; Aldrich, C. C. Synthesis 2010, 1441; [18]. Sonogashira, K.; Tohda, Y.; Hagihara, N. Tetrahedron Lett. 1975, 16, 4467; [19]. Rostovtsev, V. V.; Green, L. G.; Fokin, V. V.; Sharpless, K. B. Angew. Chem. Int. Ed. 2002, 41, 2596; [20]. Kwong, F. Y.; Buchwald, S. L. Org. Lett. 2002, 4, 3517;

REFERENCES (EXAMPLE 2, EXPERIMENTAL SECTION ONLY)

[1]. (a) Kwong, F. Y.; Buchwald, S. L. Org. Lett. 2002, 4, 3517. (b) Sperotto, E.; van Klink, G. P. M.; de Vries, J. G.; van Koten, G. J. Org. Chem. 2008, 73, 5625; [2]. (a) Liang, G.-B.; Feng, D. D. Tetrahedron Lett., 1996, 37, 6627. (b) Kumar, D.; Patel, G.; Johnson, E. O.; Shah, K. Bioorg. Med. Chem. Lett., 2009, 19, 2739; [3]. Sonogashira, K.; Tohda, Y.; Hagihara, N. Tetrahedron Lett. 1975, 16, 4467; [4]. Tao, C.-Z.; Cui, X.; Li, J.; Liu, A-X.; Liu, L.; Guo, Q-X. Tetrahedron Lett. 2007, 48, 3525; [5]. (a) Rostovtsev, V. V.; Green, L. G.; Fokin, V. V.; Sharpless, K. B. Angew. Chem. Int. Ed. 2002, 41, 2596. (b) Tornoe, C. W.; Christensen, C.; Meldal, M. J. Org. Chem. 2002, 67, 3057; [6]. Zhang, L.; Chen, X.; Xue, P.; Sun, H. H. Y.; Williams, I. D.; Sharpless, K. B.; Fokin, V. V.; Jia, G. J. Am. Chem. Soc. 2005, 127, 15998; [7]. Shabani, A.; Mirazei, P.; Naderi, S.; Lee, D. G. Tetrahedron 2004, 60, 11415.

Example 3. 1,2,3-Triazoles as Peptide Bioisosteres: Discovery of a New Class of Potent HIV-1 Vif Antagonists Compound numbers, table references, figure references, and other references set forth for Example 3 are independent of other examples.

ABBREVIATIONS

APOBEC3G (A3G), Apolipoprotein B mRNA editing enzyme catalytic polypeptide like 3G; C. C., choline carboxylate; DCM, dichloromethane; DMF, dimethylformamide; TMS, trimethylsilyl; TLC, thin-layer chromatography; THF, tetrahydrofuran; Vif, Viral infectivity factor.

RN-18-based class of Viral infectivity factor, Vif antagonists reduce viral infectivity by rescuing APOBEC3G (A3G) expression and enhancing A3G-dependent Vif degradation. Replacement of amide functionality in RN-18 (IC$_{50}$=6 µM) by isosteric heterocycles resulted in the discovery of a novel 1,4-disubstituted-1H-1,2,3-triazole, 1d (IC$_{50}$=1.2 µM) with improved profile as HIV-1 inhibitor. Among several highly potent inhibitors discovered from the 84-membered 1d based library, few note-worthy are 5ax (IC$_{50}$=0.01 µM), 5bx (0.2 µM), 2ey (0.4 µM), 5ey (0.6 µM), and 6bx (0.2 µM). Water-soluble salts 2gy, 4gy, and 5gy also exhibited potent activities.

Since the start of the AIDS epidemic in 1981, this disease has led to the death of >30 million people globally. Although the overall growth of the epidemic appears to be slowing, nearly three million new infections and an estimated 1.8 million AIDS-related deaths in 2010 are still very high. Over the past two decades, more than 25 anti-HIV drugs have been developed targeting several different stages of the virus life cycle[1]. Among these inhibitors of HIV-1 reverse transcriptase and protease, when used in combinations in the highly active antiretroviral therapy (cART), have proven to be highly effective in reducing AIDS-related mortality throughout the world[2]. However, the development of drug resistance and toxic side effects associated with cART have created a need for more potent and less toxic therapies against other viral targets and host-virus interactions[3]. Importantly, in patients on effective cART, plasma viremia can be suppressed to below detectable levels for extended intervals. The ability of cART to sustain this aviremic state has promoted the view that cART is fully suppressive and effectively stops all ongoing viral replication. Since there is rapid recrudescence of plasma viremia upon treatment interruption, regardless of the prior interval of viral suppression, there are long-lived viral reservoirs that maintain viral persistence in the face of cART. Therefore, new antiviral drugs are needed to purge drug resistant viruses from viral reservoirs.

The HIV-1 accessory protein Viral infectivity factor, Vif is essential for in vivo viral replication[4,5]. HIV-1 Vif protein targets an innate antiviral human DNA-editing enzyme, APOBEC3G (A3G)[6], which inhibits replication of retroviruses[7]. A3G catalyzes critical hypermutations in the viral DNA and acts as an innate weapon against retroviruses.[5] Cells that express A3G are 'non-permissive' for viral replication in which HIV-1 must express Vif in order to replicate. In contrast, HIV-1 replication is Vif-independent in host cells that do not express A3G (permissive cells). Since HIV-1 Vif has no known cellular homologs, this protein represents an extremely attractive, yet unrealized, target for antiviral intervention.

The RN-18-based class of small molecule Vif antagonists reduce viral infectivity by enhancing APOBEC3G-dependent Vif degradation, increasing APOBEC3G incorporation into virions, and enhancing cytidine deamination of the viral genome[8-10]. RN-18 (1a) exhibits $IC_{50}$ values of 4.5 μM and 6 μM in CEM cells and H9 cells (non-permissive cells), respectively. RN-18 does not inhibit viral infectivity in MT4 cell line (permissive cells) 100 μM demonstrating that these inhibitors are Vif-specific. These findings provided the proof of concept that the HIV-1 Vif-A3G axis is a valid target for developing small molecule-based new therapies for AIDS or for enhancing innate immunity against viruses.

We faced two major challenges for further development of RN-18-based Vif antagonists as clinical candidates: (a) potency; and (b) metabolic stability. To address these questions, we planned to explore isosteric replacement of the amide functionality in RN-18. We reasoned to test a series of conformationally restricted, biocompatible and metabolically stable isosteric heterocyclic systems. Next, based on the activity, we would select and develop a suitable bioisosteric series to improve the both activity and pharmacological profiles.

Bioisosteres have been recognized as a fundamental strategy in drug design and development of novel drug candidates. Bioisosteres have several advantages in drug development that include enhancing potency and selectivity, diversifying physical properties, altering metabolism, lowering toxicity, and creating new chemical identities for further research. However, identifying a suitable bioisostere for a specific biochemical context is quite challenging because bioisosteres are typically not exact structural mimics.

Thus, we describe the identification of small molecules that inhibit the action of the Vif protein of HIV-1. Vif is necessary for the replication of HIV-1 and promotes viral replication by neutralizing a host antiviral protein known as apobec 3. This host protein is a cytidine deaminase that introduces catastrophic levels of G to A hypermutations in viral cDNA. As such, those viral genomes are biologically incompetent. Vif eliminates apobec 3 proteins by linking them to the proteasomal machinery such that apobec 3 proteins are prematurely ubiquitylated and degradedin the proteasome.

Since apobec 3 proteins have potent antiviral activity, agents that interfere with the action of Vif would be expected to preserve apobec 3 levels in the cell and render those cells resistant to HIV-1 infection. Intriguingly, these compounds also exhibit antiviral activities against other RNA viruse including Zika and Ebola.

Current antiretroviral agents target enzymatic functions of the virus—these include reverse transcription, protease processing of viral polyporoteins and integration. HIV-1 encodes accessory proteins including Vif, vpu and nef and these proteins counteract cellular antiviral factors that otherwise would restrict viral replication. In the case of Vif, its function is to target the host factor Apobec 3 for proteasomal degradation. As viral replication is absolutely dependent on the ability of Vif to neutralize apobec 3 proteins, the Vif-apobec axis is an attractive antiviral target. Currently, there are no compounds that target the Vif/apobec axis. The agents we have developed, specifically inhibit the activity of Vif. The most definitive demonstration of this is that we have established viral variants that are resistant to these agents and the resistance is governed by a mutation in Vif. Furthermore, antiviral activity of these agents is manifest only in cells that express Apobec 3. Therefore, they exhibit exquisite antiviral target specificity. As such, there is provided the first example of a specific Vif inhibitor. To our knowledge, there is no existing art in the Vif research field with regards to inhibitors of this viral protein. In addition, no previous reference is available about Ebola and Zika viral targets in this context.

In this disclosure, we describe the successful identification of potent bioisosteric analogues of RN-18. Initially, we designed and synthesized four test molecules by substituting the amide functionality in the lead molecule with isosteric heterocyclic systems such as 1,3,4-oxadiazole[12] 1b, 1,2,4-oxadiazole[13] 1c, 1,4-disubstituted-1,2,3-triazole[14] 1d and 1,5-disubstituted-1,2,3-triazole[15] 1e (FIG. 14).

1,3,4-Oxadiazole 1b was synthesized with the coupling of hydrazine and 2-iodobenzoic acid (Scheme 3-1, A). The one pot coupling involves the formation of in situ methyl ester of 2-iodobenzoic acid, which was later refluxed in the presence of hydrazine hydrate to obtain the benzohydrazide derivative 1f quantitatively. Benzohydrazide 1f was later reacted with o-anisic acid in refluxing phosphoryl chloride leading to the formation of iodo intermediate 1,3,4-oxadiazole 1g. Intermediate 1g was reacted with 4-nitrothiophenol under copper (I) catalyzed S-arylation conditions[16] leading to the formation of compound 1b. Synthesis of 1,2,4-oxadiazole 1c was started (Scheme 3-1, B) with the coupling between the commercially available N'-hydroxy-2-methoxybenzimidamide and 2-iodobenzoic acid using dicyclohexyldicarbodiimide[17] leading to the formation of the iodo intermediate 1,2,4-oxadiazole 1 h. S-arylation of 1 h with 4-nitrothiophenol under copper (I) catalytic conditions led to the formation of 3,5-disubstituted-1,2,4-oxadiazole, 1c.

Synthesis of 1,4-disubstituted-1,2,3-triazole analogue 1d required two synthons; 2-ethynylaniline 1j, and 1-azido-2-methoxybenzene 1k (Scheme 3-1, C). 2-Iodoaniline was reacted with trimethylsilylacetylene under sonogashira reaction conditions catalyzed by bis(triphenylphosphine)palladium chloride in the presence of triethylamine base and copper iodide as co-catalyst[18] leading to the formation of TMS protected ethynylaniline 1i, which was deprotected using sodium hydroxide affording the required synthon 2-ethynylaniline 1j. Azide 1k was synthesized by following a Cham-Lam type of coupling between 2-methoxyphenylboronic acid and sodium azide catalyzed by copper sulfate at room temperature in methanol.[19] Copper-catalyzed click reaction[20] between alkyne 1j and azide 1k generated triazole amine 1l quantitatively in t-butanol/water (Scheme 3-1, D). Triazole amine 1l was diazotized using sodium nitrite in 5N HCl around −10° C. and concomitantly converted to iodotriazole 1m by reacting with potassium iodide. Copper (I) catalyzed S-arylation of iodotriazole 1m using 4-nitrothiophenol in DMF solvent and potassium carbonate led to the synthesis of 1d, IMA-53. 1,5-Disubstituted-1,2,3-triazole 1e analogue was synthesized initially by reacting alkyne 1j and azide 1k under ruthenium catalyzed click chemistry conditions using Cp*RuCl(PPh$_3$)$_2$ catalyst in benzene at 80° C.[21] leading to the formation of amine in (Scheme 3-1, E). Diazotization, iodination (1o), and S-arylation reaction sequences afforded 1,5-disubstituted-1,2,3-triazole 1e.

Scheme 3-1. Synthesis of isosteric analogues of RN-18[a]

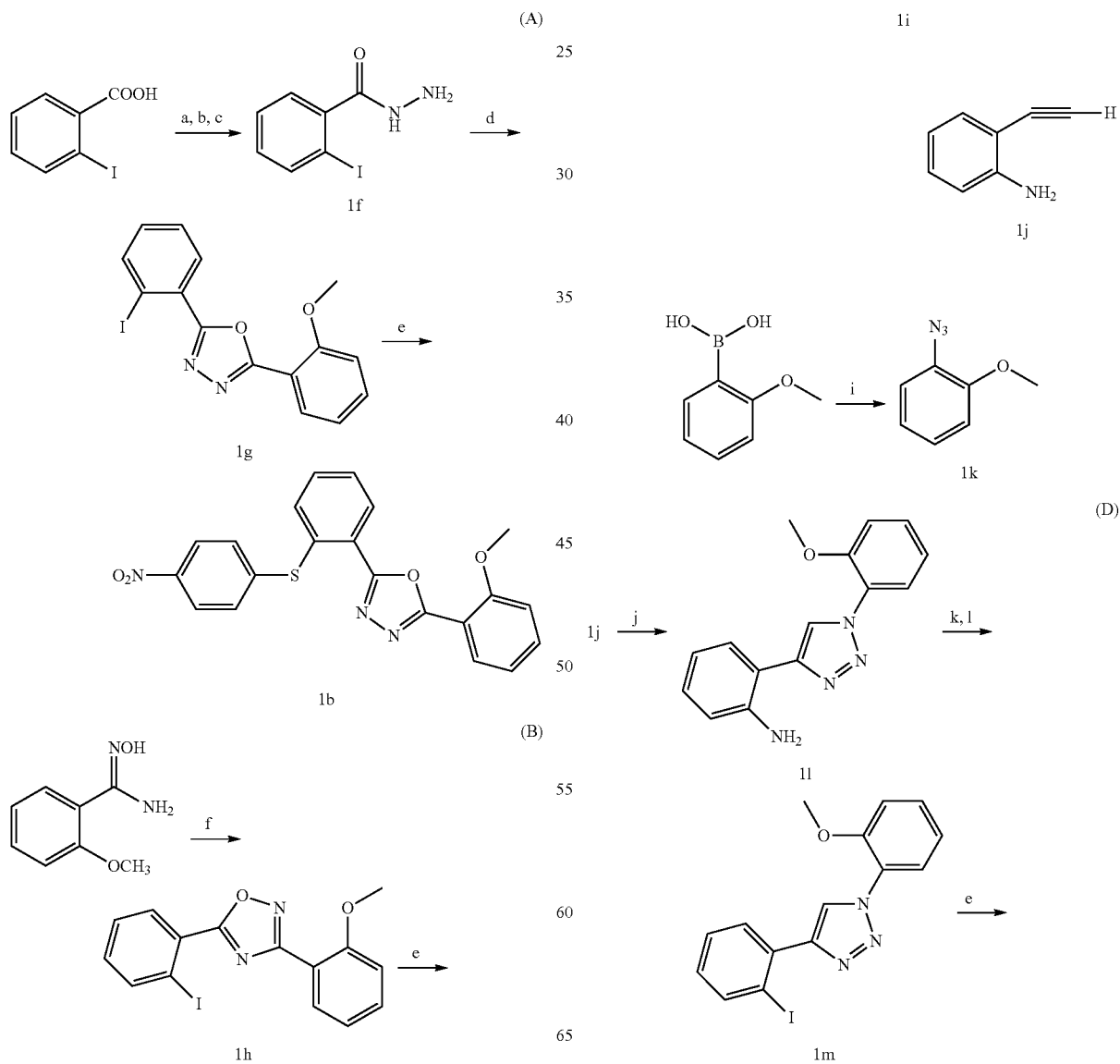
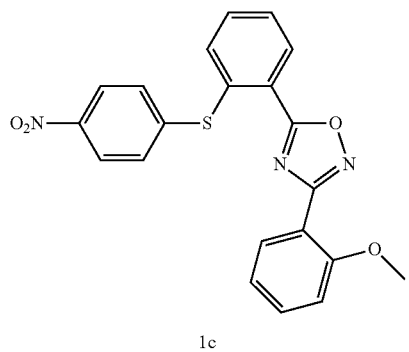

-continued

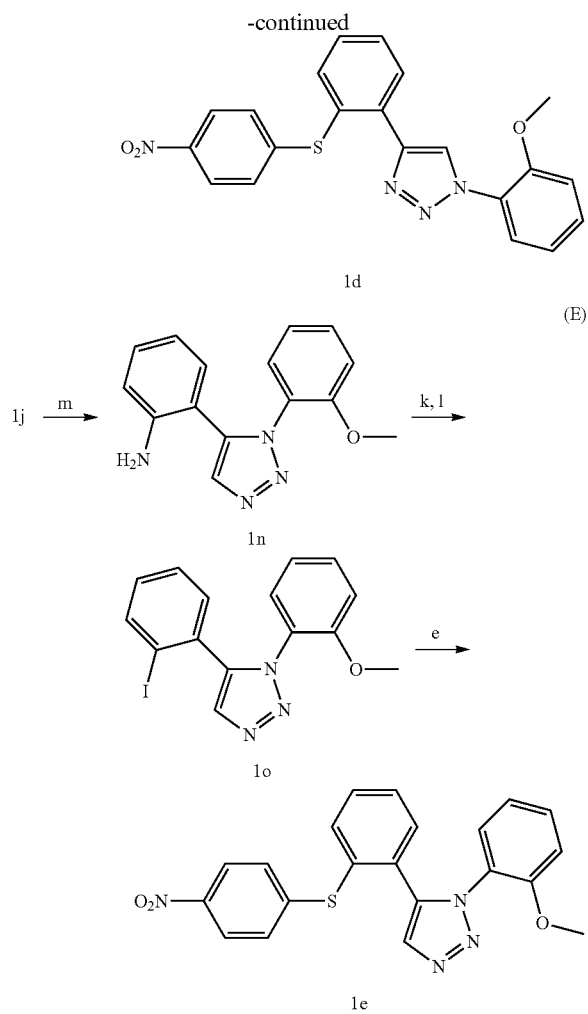

(E)

[a]Reagents and conditions: (a) SOCl$_2$, cat. DMF, benzene, 80° C., 2 h; (b) CH$_3$OH, TEA, 0° C. - rt., 2 h; (c) NH$_2$NH$_2$•H$_2$O, 80° C., 3 h; (d) o-anisic acid, POCl$_3$, 110° C., 8 h; (e) 4-nitrothiophenol, K$_2$CO$_3$, 5 mol %, CuI, DMF, 110° C., 8 h; (f) 2-iodobenzoic acid, DCC, DMF, rt to 100° C., 8 h; (g) Trimethylsilyl acetylene, 1 mol % PdCl$_2$(PPh$_3$)$_2$, 1 mol % CuI, NEt$_3$, rt, 12 h; (h) NaOH (aq), ethanol/THF (1:1), rt, 1 h; (i) NaN$_3$, 10 mol % CuSO$_4$•5H$_2$O, CH$_3$OH, rt, 8 h; (j) 1k, 5 mol % CuSO$_4$ 5H$_2$O, 10 mol % Na ascorbate, t-BuOH/H$_2$O (1:1), rt, overnight; (k) NaNO$_2$, 5N HCl, -10 to -5° C., 2 h; (l) KI, -10 to -5° C., 8 h; (m) 1k, 1 mol % Cp*RuCl(PPh$_3$)$_2$, benzene, 80° C., 3 h.

The antiviral activities of the four synthesized RN-18 analogues were measured against wild-type HIV-1 both in non-permissive H9 and permissive MT-4 cells (See details of methods in S.I.). In all the antiviral activity measurements, RN-18 (1a) was used as a positive control and the cells cultured without any inhibitor served as negative control. The IC$_{50}$ values of the bioisosteric analogues of RN-18 are presented in Table 3. Both 1,3,4-oxadiazole 1b (IC$_{50}$=6.8 μM) and 1,2,4-oxadiazole 1c (IC$_{50}$=6.8 μM) based analogues exhibited cell-based antiviral activity in the non-permissive H9 cells similar to the lead molecule RN-18 (IC$_{50}$=6 μM). Interestingly, 2,5-disubstituted-1,3,4-oxadiazole 1b showed non-specific antiviral activity with IC$_{50}$ of 50 μM in permissive MT4 cells. Whereas the 1,4-disubstituted-1,2,3-triazole based analogue 1d exhibited remarkably better cell-based anti-HIV activity (IC$_{50}$=1.2 μM in H9 cells) and specificity (no activity in MT4 cells). On the contrary, 1,5-disubstituted-1,2,3-triazole 1e analogue exhibited comparatively lesser potency (IC$_{50}$=15 μM in H9 cells) with non-specific activity in the permissive cells (IC$_{50}$=25 μM in MT4 cells).

Next, to determine the mechanism of these bioisosteres of RN-18, we analyzed Vif degradation and rescue of A3G levels in the presence these compounds and compared with RN-18. 293FT cells co-expressing hemagglutinin (HA)-tagged A3G and green fluorescent protein (GFP)-tagged Vif or ΔVif were treated with various compounds (50 μM) for 16 h (see S.I. for methods details). The cell extracts were then analyzed by immunoblotting with anti-HA-A3G, anti-GFP-Vif, and anti-GAPDH antibodies. All the bioisostere analogues of RN-18 resulted in restoring A3G levels in the presence of Vif and down-regulated Vif expression, indicating that these analogues (1b, 1c, 1d and 1e) are capable of antagonizing Vif function similar to RN-18. However, analogues 1b, and 1e also exhibited some nonspecific activity (Table 3-1).

TABLE 3

IC$_{50}$ values of the isosteric analogues of RN-18

| | Antiviral activity (IC$_{50}$ μM) | |
|---|---|---|
| Compel. | H$_9$ cells | MT$_4$ cells |
| 1a, RN-18 | 6 | N.A. |
| 1b | 6.8 | 50 |
| 1c | 6.8 | N.A. |
| 1d | 1.2 | N.A. |
| 1e | 15 | 25 |

N.A. = no activity 50 μM conc.

These observations were well in-line with the structural similarities in the 3D orientations and planarity except the 1,5-disubstituted-1,2,3-triazole 1e, which has a twisted structure. 1,3,4-Oxadiazole, and 1,2,4-oxadiazole heterocyclic systems have both planarity and dipole moment similar to amide functionality. Similarly, 1,4-disubstituted and 1,5-disubstituted 1,2,3-triazoles possess strong dipole moment beside having better H-bond accepting (N(2) and N(3)), and H-bond donating (triazole C(5)-H) capacity than an amide functionality.[22] However in the present biochemical context, 1,4-disubstituted-1,2,3-triazle 1d analogue showed both improved antiviral activity (IC$_{50}$=1.2 μM) and selectivity (no activity in MT4 cells).

Having discovered compound 1d as a potent and specific inhibitor of Vif-APOBEC3G axis, we decided to optimize the analogue to generate new class of anti-HIV drug candidates for clinical development. We designed and synthesized an 84-membered library using a parallel format exploring various substitution patterns in ring-A, ring-C, and bridge A-B in the 1d structure (Table 4). In this direction, the synthetic scheme for 1d (Scheme 3-1, D) was followed. Synthetic schemes (see Schemes 3-1S to 3-6S in Supplementary Information section), experimental procedures, and characterization data of all the 84 members of the library are disclosed herein. Anti-viral activities of the library were determined against wild-type HIV-1 both in non-permissive H9 and permissive MT-4 cells. The IC$_{50}$ values for some of the active compounds are presented in Table 4. Antiviral activities of the complete library is given in Table 5. None of the 84 compounds exhibited antiviral activities at 50 μM in non-permissive MT4 cells indicating the requirement of Vif for their function, which is quite remarkable.

TABLE 4

IC$_{50}$ values of the library

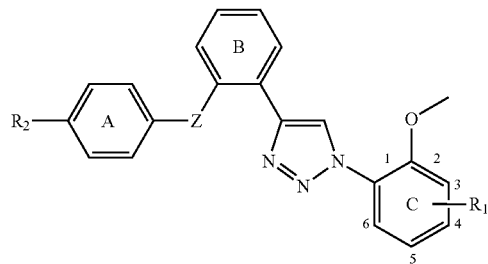

R$_1$ = H (2), 3-OCH$_3$ (3), 4-OCH$_3$ (4), 5-OCH$_3$ (5), 6-OCH$_3$ (6), 6-F (7)
R$_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | R$_1$ | R$_2$ | Antiviral activity (IC$_{50}$ µM) H9 Cells |
|---|---|---|---|---|
| 2ax (1d) | S | H | NO$_2$ | 1.2 |
| 2dx | S | H | CF$_3$ | 2.6 |
| 2ex | S | H | NH$_2$ | 7.5 |
| 2fx | S | H | COOH | 1.0 |
| 2ay | SO$_2$ | H | NO$_2$ | 13.8 |
| 2cy | SO$_2$ | H | OCH$_3$ | 4.3 |
| 2dy | SO$_2$ | H | CF$_3$ | 4.8 |
| 2ey | SO$_2$ | H | NH$_2$ | 0.4 |
| 2fy | SO$_2$ | H | COOH | 8.2 |
| 2gy | SO$_2$ | H | C.C.[†] | 0.2 |
| 3ax | S | 3-OCH$_3$ | NO$_2$ | 1.1 |
| 3bx | S | 3-OCH$_3$ | COOCH$_3$ | 8 |
| 3cx | S | 3-OCH$_3$ | OCH$_3$ | 4.7 |
| 3dx | S | 3-OCH$_3$ | CF$_3$ | 1.9 |
| 3fx | S | 3-OCH$_3$ | COOH | 2.8 |
| 3gx | S | 3-OCH$_3$ | C.C.[†] | 4.3 |
| 3by | SO$_2$ | 3-OCH$_3$ | COOCH$_3$ | 4.7 |
| 3ey | SO$_2$ | 3-OCH$_3$ | NH$_2$ | 12.4 |
| 3fy | SO$_2$ | 3-OCH$_3$ | COOH | 1.4 |
| 4fx | S | 4-OCH$_3$ | COOH | 7.1 |
| 4dy | SO$_2$ | 4-OCH$_3$ | CF$_3$ | 12 |
| 4gy | SO$_2$ | 4-OCH$_3$ | C.C.[†] | 0.7 |
| 5ax | S | 5-OCH$_3$ | NO$_2$ | 0.01 |
| 5bx | S | 5-OCH$_3$ | COOCH$_3$ | 0.2 |
| 5cx | S | 5-OCH$_3$ | OCH$_3$ | 15.7 |
| 5fx | S | 5-OCH$_3$ | COOH | 4.5 |
| 5ay | SO$_2$ | 5-OCH$_3$ | NO$_2$ | 1.0 |
| 5by | SO$_2$ | 5-OCH$_3$ | COOCH$_3$ | 4.6 |
| 5ey | SO$_2$ | 5-OCH$_3$ | NH$_2$ | 0.6 |
| 5gy | SO$_2$ | 5-OCH$_3$ | C.C.[†] | 0.5 |
| 6bx | S | 6-OCH$_3$ | COOCH$_3$ | 0.2 |
| 6ex | S | 6-OCH$_3$ | NH$_2$ | 1.5 |
| 6fx | S | 6-OCH$_3$ | COOH | 1.9 |
| 6ey | SO$_2$ | 6-OCH$_3$ | NH$_2$ | 1.5 |
| 6fy | SO$_2$ | 6-OCH$_3$ | COOH | 1.2 |
| 7ax | S | 6-F | NO$_2$ | 3.9 |
| 7bx | S | 6-F | COOCH$_3$ | 7.8 |
| 7fx | S | 6-F | COOH | 4.9 |
| 7ey | SO$_2$ | 6-F | NH$_2$ | 15 |

[†]Choline carboxylate

For few selected compounds (2dx, 2ey, 2gy, 5ax, 5bx, 5gy and 5ey) we then determined whether the analogues could upregulate A3G and downregulate Vif in a manner similar to RN-18 and 1d. Immunoblots for A3G and Vif in the presence of compounds are shown in FIG. 16, which clearly showed that the new inhibitors exert the anti-HIV activity via the same mechanism as observed for RN-18 and 1d. Of the 84 members library, about 30 compounds inhibited HIV-1 with IC$_{50}$ values in the range of 0.01 to 5 µM in the non-permissive H9 cells. Among them, the compound 5ax exhibited the most potent activity with IC$_{50}$ of 10 nM, which is about 1000 fold more potent than the original lead molecule, RN-18. Similarly, compounds 2ey, 5bx, 5ey, and 6bx exhibited IC$_{50}$ values in the range of 0.2 µM to 0.6 µM and compounds 2ax, 2dx, 2ex, 2fx, 3ax, 3dx, 3fx, 3fy, 5ay, 6ex, 6fx, 6ey, 6fy in the range of 1 µM to 3 µM. Three water soluble choline salts 2gy, 4gy and 5gy exhibited IC$_{50}$ values of 0.2 µM, 0.7 µM, and 0.5 µM, respectively. Overall, the SAR of the library showed striking sensitivity towards three the variables (Z-bridge, R$_1$ and R$_2$ substituents) tested in this study. Among various SAR findings few of the noteworthy ones are: in general sulfide (—S—) as bridge Z exhibited overall better activity compared with sulfone (—SO$_2$—) bridge (in the case of RN-18 sulfone derivative showed better activity)[9]. However, sulfones (—SO$_2$—) showed better activities when R$_2$ substituent was amino group. This study has found replacements such as —COOCH$_3$, —COOH, —CF$_3$, —NH$_2$, and -choline carboxylate for the nitro functionality in RN-18.

In summary, this study report three major findings: (a) 1,4-disubstituted-1,2,3-triazole system is a suitable bioisostere in the RN-18 context (b) discovery of a new class of potent Vif antagonists as preclinical candidates for novel AIDS therapy, and (c) generation of potent chemical modulators for perturbing and understanding Vif-APOBEC3G cell biology and physiology. Further optimization of 1,4-disubstituted-1,2,4-oxadiazole, 1c and preclinical studies for the selected 1,4-disubstituted-1,2,3-triazole based Vif antagonists are in progress.

Details of general procedures, and materials are described herein. Parallel synthesis was performed using Carousel 6 (Radleys Discovery Technologies). $^1$H and $^{13}$C NMR spectra were recorded using a 400 MHz Jeol JNM-ECS spectrometer with a 5 mm proton/multi-frequency auto-tune and auto sample changer. The spectra are reported in ppm on the δ scale using the internal reference as trimethylsilane (TMS). ESI MS was performed on Waters micromass Model ZQ 4000 using methanol. HRMS was performed on Agilent Technologies 6224A MS-TOF. Purity of the tested compounds was determined using Waters 2695 Module HPLC equipped with Waters 996 photodiode detector at 254 nm. X-ray structural determination was performed at UCSD facility using Bruker diffractometer with CCD detectors and low-temperature cryostats.

General Procedures.

Reactions were performed in oven-dried round-bottom flasks and air sensitive reactions were performed under positive pressure of nitrogen. Moisture sensitive reactions were performed using calcium sulphate protected guard tubes. Stainless steel syringes were used to transfer dry solvents or moisture/air sensitive liquids. Flash column chromatography was performed using SINGLE StEP™ Pump and SINGLE StEP™ columns Intro Packs of various sizes made by Thomson Instrument Company. Silica gel used was 60° pore size, 40 µm, supplied by Fisher Scientific and amines were purified using neutral alumina Brockmann I of Sigma-Aldrich. Analytical thin-layer chromatography (TLC) was performed using TLC silica gel 60 F$_{254}$ aluminium sheets of EMD. TLC plates were visualized by exposure to ultraviolet light, iodine adsorbed on silica gel and by exposure to an ethanolic solution of phosphomolybdic acid (PMA) or an acidic solution of p-anisaldehyde, or a slightly basic solution of potassium permanganate. Organic extracts or solutions or eluents were concentrated using Heidolph's Hei-VAP Advantage vacuo rotavapor at temperatures below 38-40° C. Dry-ice was used for low temperature baths in various organic solvents. Purity analysis was performed using column, YMC-Pack Pro C18 (particle size=5 μm, pore size=12 nm, dimensions=150 mm×4.6 mm); mobile phase A, water; mobile phase B, acetonitrile. We applied the following mobile phase gradient for total 10 minutes per sample: starting from 50, B and reaches to 90% B for 2 min followed by 100% B over 10 minutes (Method A for all the compounds except water soluble choline salts). Method B for water-soluble choline salts; starting from 50% A and 50% B followed by 100% A over 10 minutes. The injection volume was 10 μL and the flow rate was 1.0 mL/min. HPLC retention times ($R_T$) and purity data (%) for the compounds are given in the analytical data of the respective compounds.

Materials.

Commercial reagents and solvents (HPLC grade for purifications and anhydrous solvents for reactions) were purchased from Sigma-Aldrich, Acros Organics, Alfa Aesar, EMD, Combiblocks, Oakwoods, Toronto Research Chemicals Inc., Astatech Inc., etc.

Cmpd RN-18:

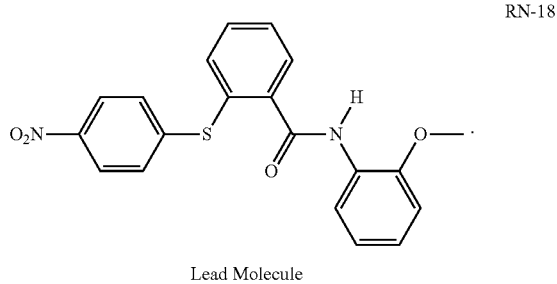 [SMILES: COc1ccccc1NC(=O)c1ccccc1Sc1ccc([N+](=O)[O-])cc1]

RN-18
Lead Molecule

N-(2-methoxyphenyl)-2-((4-nitrophenyl)thio)benzamide (1a):[1]

Melting point 143-145° C. (crystallized in DCM/methanol mixture). $R_{T, HPLC}$=5.106 min, Purity>97%.

X-Ray Crystal Structure Determination of 1a:

CCDC deposition number 1449874. Data were recorded on Bruker APEX-II CCD device using Mo-Kα radiation (wavelength=0.71073 Å) and graphite monochromator. The structure was refined using the program SHELXL-97. Crystal data: $C_{20}H_{16}N_2O_4S$, M=380.41, monoclinic, space group $P2_1/c$, a=7.411(3) Å, b=7.977(4) Å, c=30.044(14) Å; α=90.00°, β=95.648(5)°, γ=90.00°; V=1767.5(14) Å$^3$; Z=4; T=100(2) K; μ=0.213 mm$^{-1}$; Crystal size=0.33×0.10×0.06 mm$^3$. Of 15997 reflections measured to theta range 1.36 to 28.23°, 6115 were independent ($R_{int}$=0.0000). Final R1=0.0420 (I>2σ (1)), wR2=0.0964.

Figure 19:
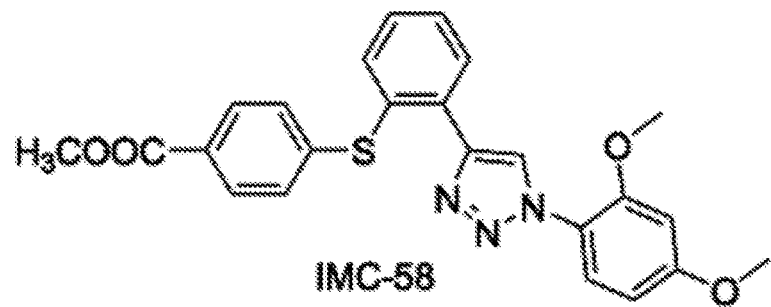
FIG. 19. A representative example of Ebola viral replication inhibition by two triazole heterocyclic compounds, IMC-58 (4bx) and IMC-68 (5ay).
Figure 19:
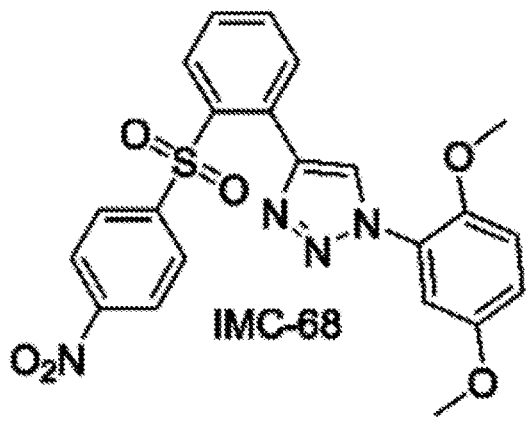
Figure 19:
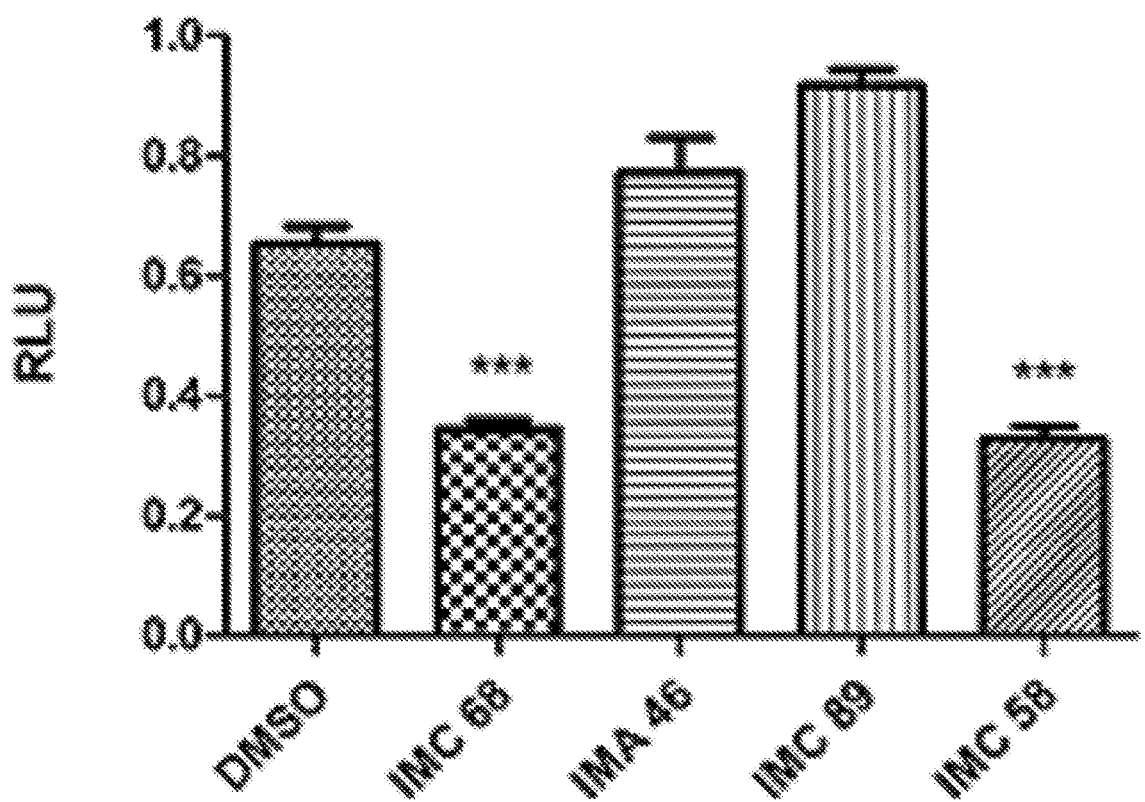
Figure 20:
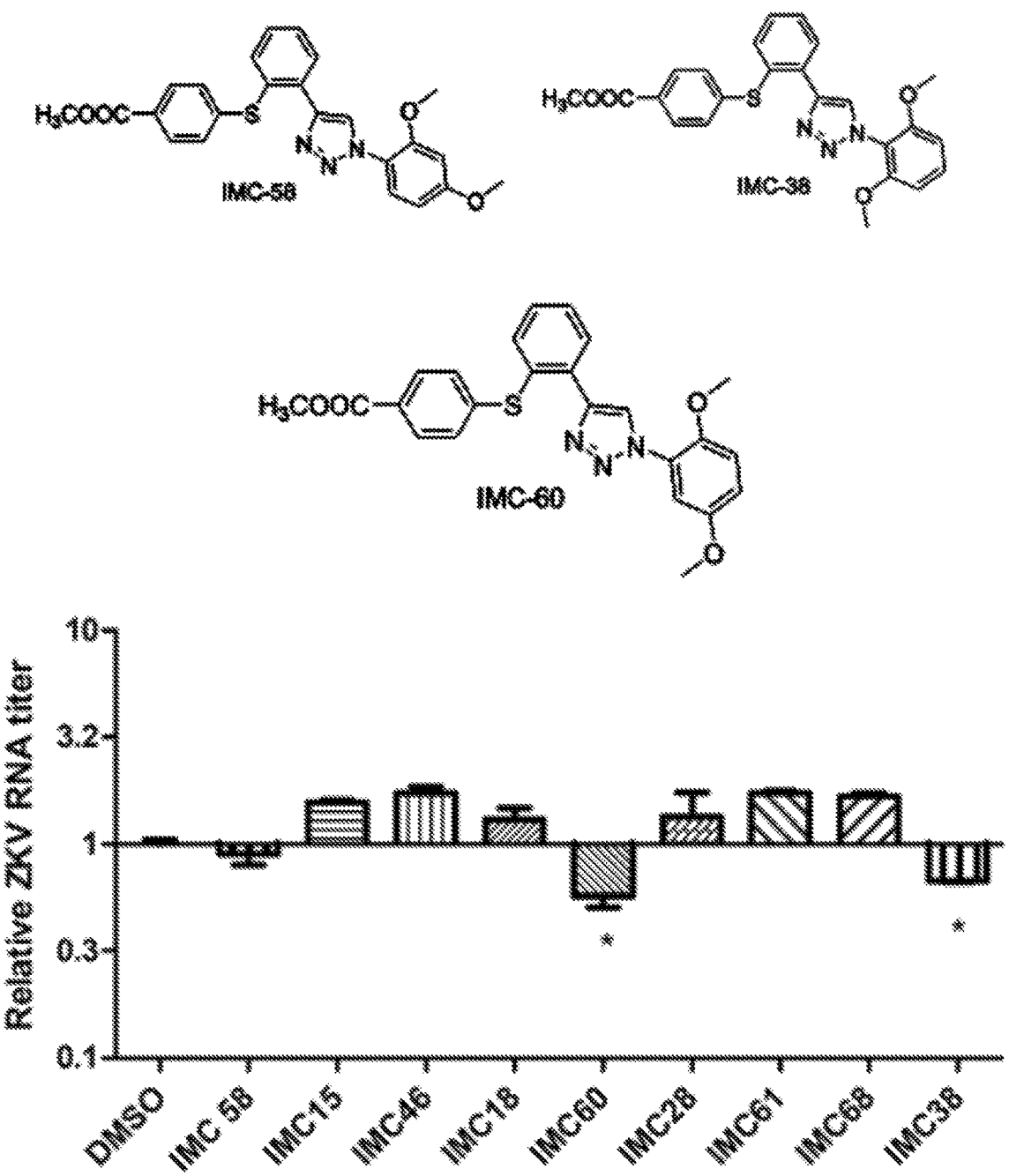
FIG. 20. A representative example of Zika viral replication inhibition by three triazole heterocyclic compounds, IMC-58 (4bx), IMC-38 (6bx), and IMC-60 (5bx).
Figure 21:
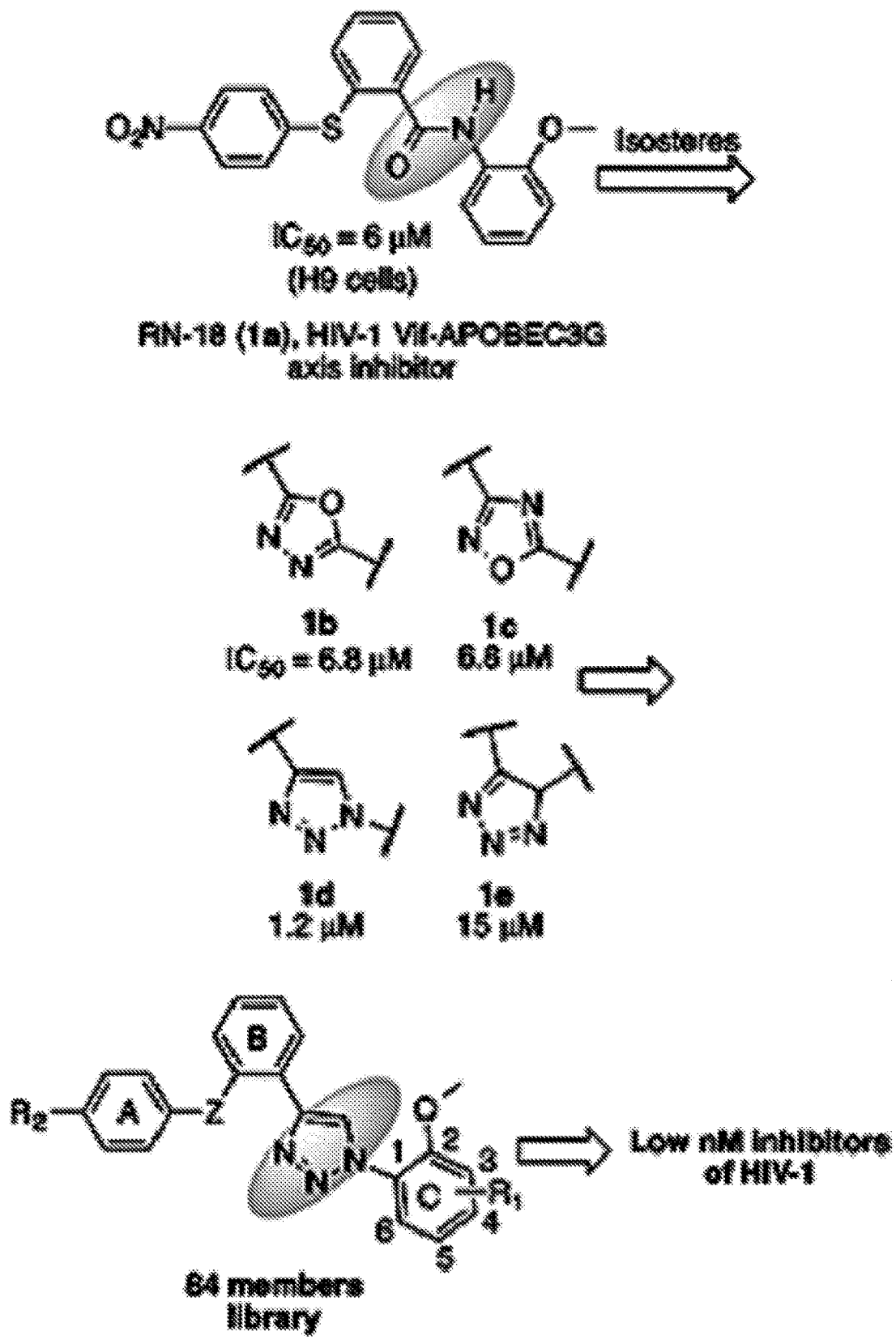
FIG. 21. Schematic overview; 1,2,3-Triazoles as amide bioisosteres. RN-18-based Viral infectivity factor, Vif antagonists reduce viral infectivity by rescuing APOBEC3G (A3G) expression and enhancing A3G-dependent Vif degradation. Replacement of amide functionality in RN-18 (IC50=6 μM) by isosteric heterocycles resulted in the discovery of a 1,2,3-trizole, 1d (IC50=1.2 μM). Several potent HIV-1 inhibitors from a 1d based library including 5ax (IC50=0.01 μM), 5bx (0.2 μM), 2ey (0.4 μM), 5ey (0.6 μM), and 6bx (0.2 μM) were identified.
Figure 22A:
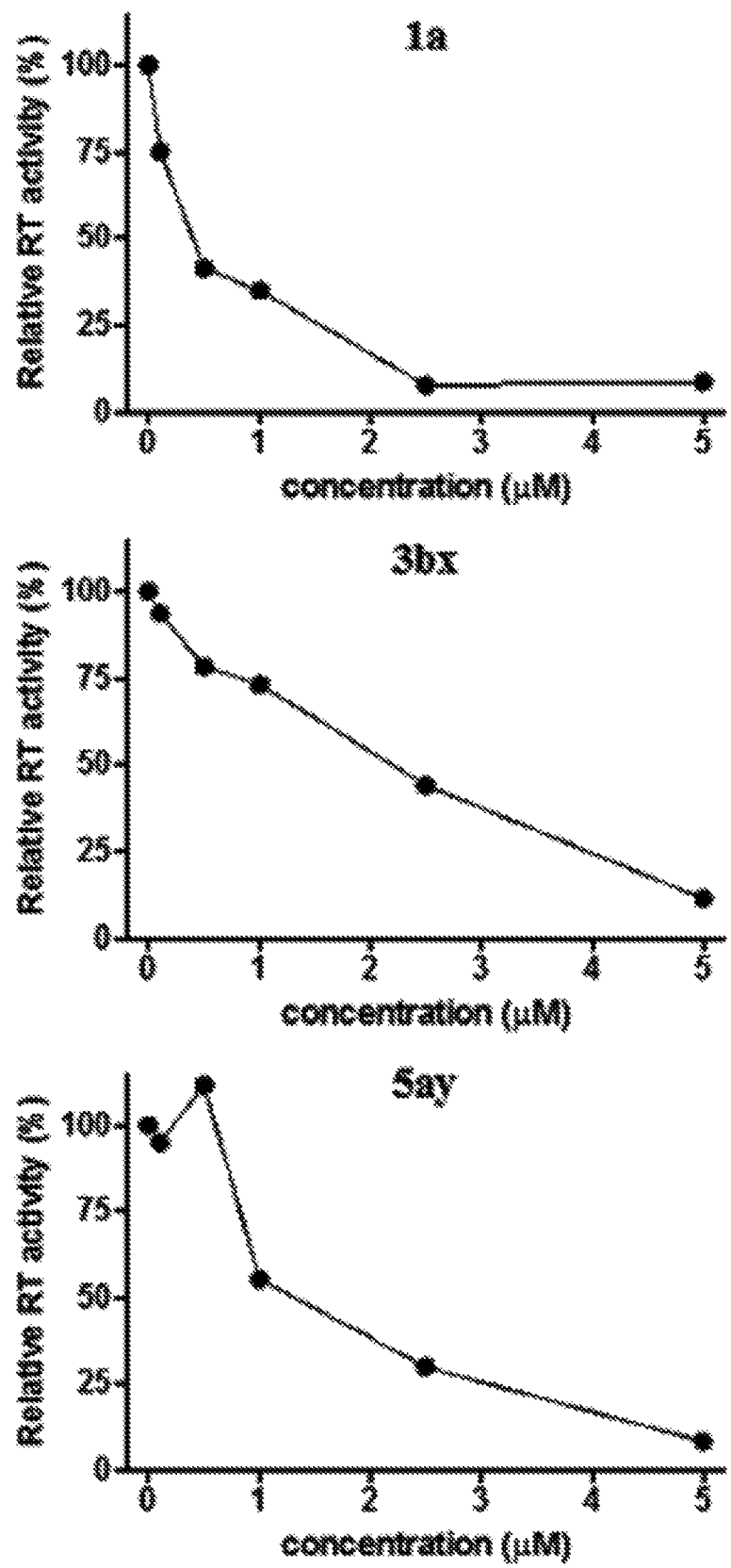
FIGS. 22A-22C. The Vif antagonists inhibit HIV-1 replication in a dose-dependent manner. H9 cells were infected with HIV-1 and the reverse transcriptase (RT) activity was measured in the supernatant of infected cells in the presence of the indicated compound at the peak of HIV replication post infection. Absolute RT activity values were normalized to the vehicle-only (0 μM) control.
Figure 22B:
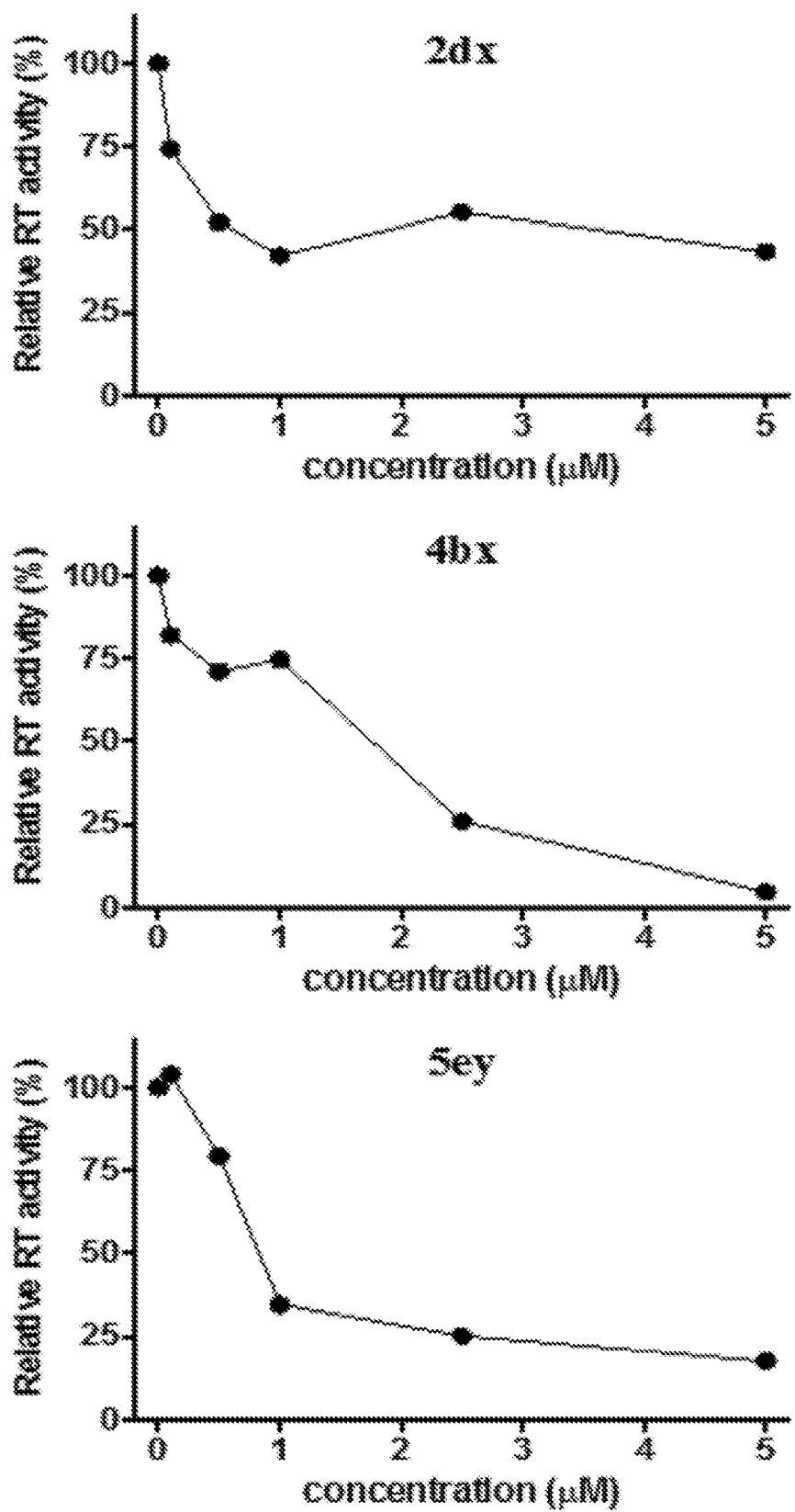
Figure 22C:
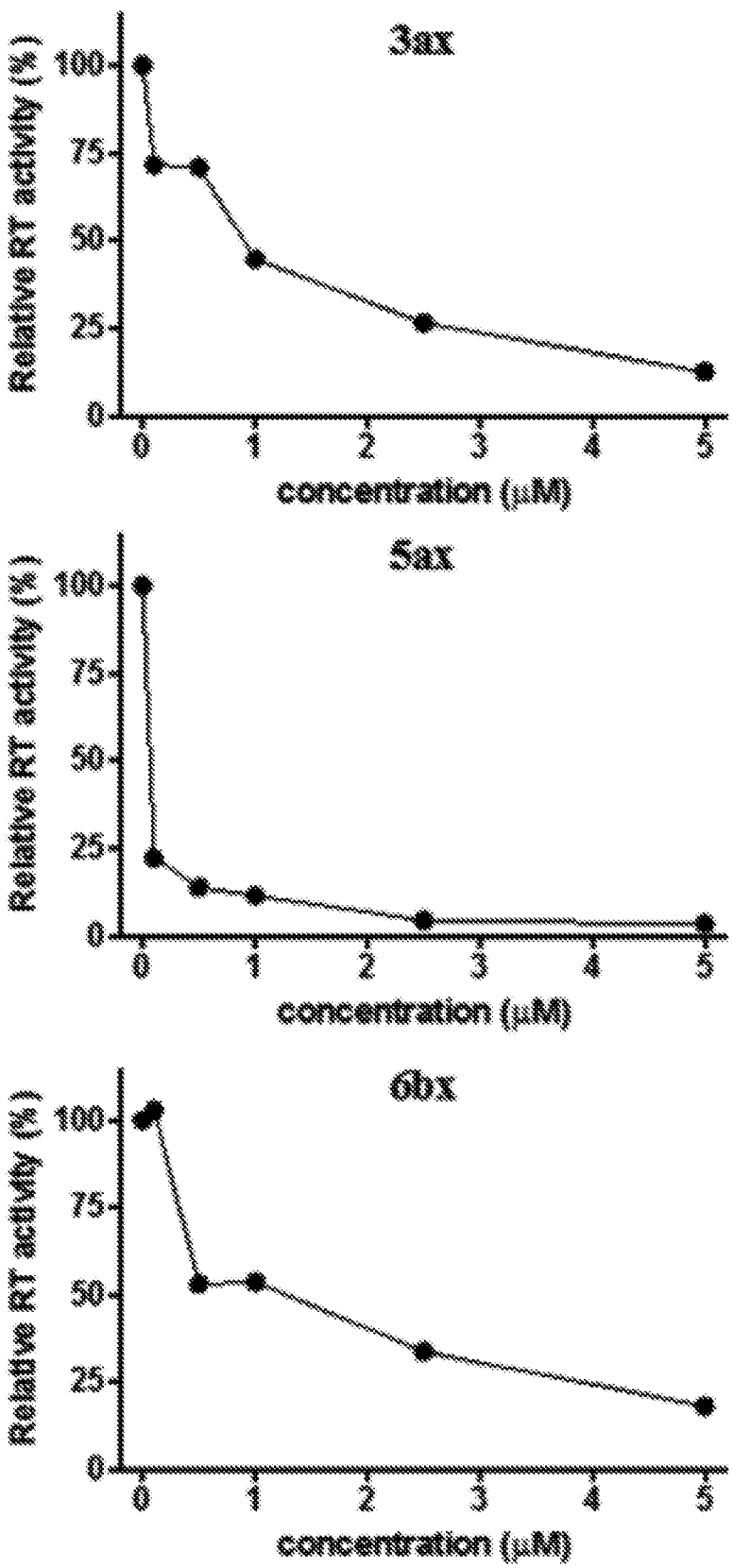
Figure 23:
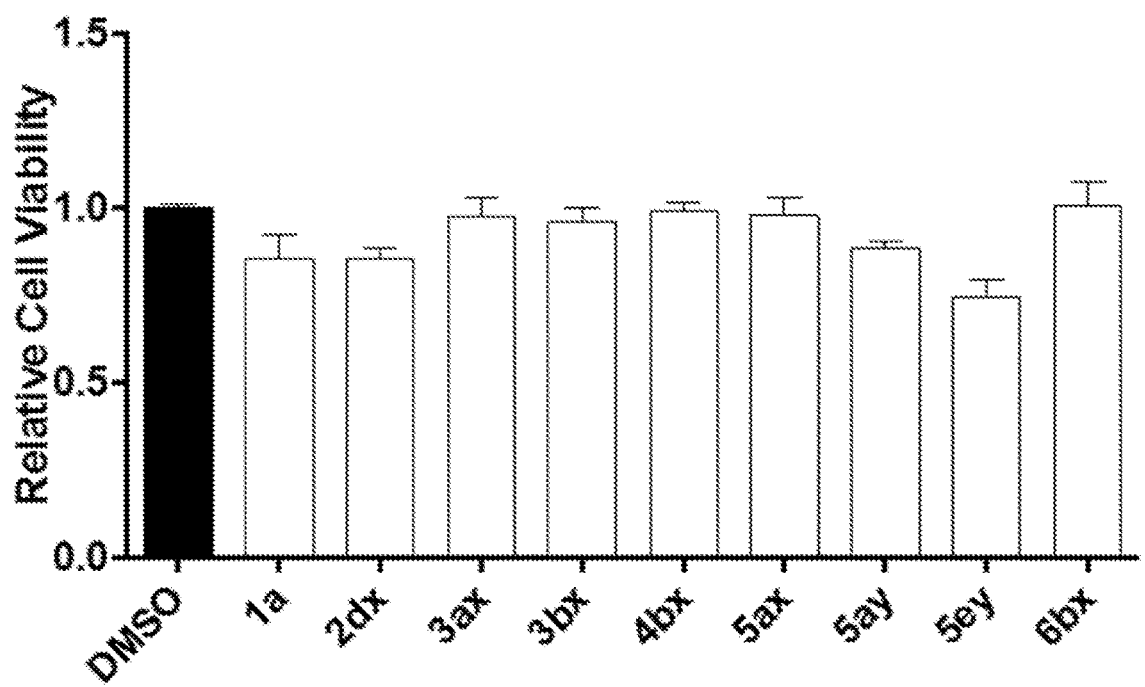
FIG. 23. MTS Cell Viability analysis of Vif antagonists 16 h post-treatment. Hela cells were treated with 50 μM of a compound or DMSO for 16 h and cell viability was assessed by Promega CellTiter 96 Aqueous One Solution Cell Proliferation Assay (MTS) relative to DMSO control.

Immunoblot Method for FIGS. 19-20: Transfection, Small Molecule Treatment and Protein Analysis.

293FT cells were co-transfected with HA-APOBEC3G and pEYFP-C1-Vif or pNL-A1-ΔVif plasmid (0.5:2 molar ratio) using Lipofectamin 2000 (Invitrogen) in Opti-MEM medium. After 4 hours, the transfection mixture was replaced with complete DMEM medium without Geneticin antibiotic. Individual small molecule (RN-18 (1a), 1b, 1c, 1d, and 1e) was added to the transfected cells at 50 μM concentrations with 1% DMSO or 1×PBS. The cells were grown at 37° C. in a humidified incubator (5% $CO_2$) for 16 h. After 16 h post-incubation, the cells were washed in 1×PBS and lysed with Mammalian Protein Extraction Reagent (M-PER, Thermo) containing protease inhibitor cocktail (Roche). The total extracted protein was quantified using DC protein assay kit (Bio-Rad).

The total proteins (10 μg) were boiled with 5×SDS-PAGE sample buffer, separated in 4-20%. SDS-PAGE gel (Bio-Rad) and electroblotted onto a PVDF membrane using semi-dry electroblotter (Bio-Rad). After being blocked with 5% non-fat dry milk in 1×TBST buffer for 2 h, the membrane was exposed to primary antibody. HA-Apobec3G protein was detected by anti-HA rat polyclonal antibody (Roche) at 1:3000 dilutions. The GFP-Vif and GAPDH was detected using anti-GFP and anti-GAPDH rabbit polyclonal antibody at 1:1000 dilutions respectively (Cell Signaling). The species specific horseradish peroxidase conjugated secondary antibody was used for the respective primary antibody. The membrane was developed with the BM Chemiluminescence blotting kit (Roche). The same procedure is following for the compounds discussed in FIG. 16.

Antiviral Activity Assay.

The antiviral activities of peptidomimetic analogues of RN-18 analogues were measured with wild-type HIV-1 in H9 cells (non-permissive) and MT-4 cells (permissive). H9 and MT4 cells (2×10$^5$ cells per well in 48-well plates) were treated overnight with differing concentrations of Vif antagonists (1 to 50 μM) in RPMI medium containing 10% fetal bovine serum. The cells were then infected with an X4-tropic HIV-1 variant (HIV-1$_{LAI}$) and maintained for further 10-15 days. Viral replication was monitored every second day by measuring reverse transcriptase (RT) activity in the culture supernatants. For this, ⅓ of the culture supernatant was replaced with an equivalent volume of fresh medium containing the appropriate compounds every second day. In all experiments, RN-18 (1) was used as a positive control and cells cultured without compound served as negative controls. Measurements of antiviral activity in cultured cells were repeated at least 3 times and the $IC_{50}$ values were calculated using GraFit software.

TABLE 5

List of the library and $IC_{50}$ values

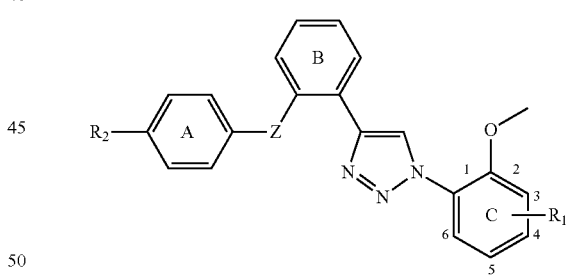

$R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | $R_1$ | $R_2$ | Antiviral activity ($IC_{50}$ μM) H9 cells |
|---|---|---|---|---|
| 2ax (1d) | S | H | NO$_2$ | 1.2 |
| 2bx | S | H | COOCH$_3$ | N.A. |
| 2cx | S | H | OCH$_3$ | 13.6 |
| 2dx | S | H | CF$_3$ | 2.6 |
| 2ex | S | H | NH$_2$ | 2.5 |
| 2fx | S | H | COOH | 1.0 |
| 2gx | S | H | C.C.[†] | N.A. |
| 2ay | SO$_2$ | H | NO$_2$ | 13.8 |
| 2by | SO$_2$ | H. | COOCH$_3$ | N.A. |
| 2cy | SO$_2$ | H | OCH$_3$ | 4.3 |

TABLE 5-continued

List of the library and IC$_{50}$ values $R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | $R_1$ | $R_2$ | Antiviral activity (IC$_{50}$ µM) H9 cells |
|---|---|---|---|---|
| 2dy | SO$_2$ | H | CF$_3$ | 4.8 |
| 2ey | SO$_2$ | H | NH$_2$ | 0.4 |
| 2fy | SO$_2$ | H | COOH | 8.2 |
| 2gy | SO$_2$ | H | C.C.† | 0.2 |
| 3ax | S | 3-OCH$_3$ | NO$_2$ | 1.1 |
| 3bx | S | 3-OCH$_3$ | COOCH$_3$ | 8 |
| 3cx | S | 3-OCH$_3$ | OCH$_3$ | 4.7 |
| 3dx | S | 3-OCH$_3$ | CF$_3$ | 1.9 |
| 3ex | S | 3-OCH$_3$ | NH$_2$ | 5.0 |
| 3fx | S | 3-OCH$_3$ | COOH | 2.8 |
| 3gx | S | 3-OCH$_3$ | C.C.† | 4.3 |
| 3ay | SO$_2$ | 3-OCH$_3$ | NO$_2$ | N.A. |
| 3by | SO$_2$ | 3-OCH$_3$ | COOCH$_3$ | 4.7 |
| 3cy | SO$_2$ | 3-OCH$_3$ | OCH$_3$ | N.A. |
| 3dy | SO$_2$ | 3-OCH$_3$ | CF$_3$ | N.A. |
| 3ey | SO$_2$ | 3-OCH$_3$ | NH$_2$ | 12.4 |
| 3fy | SO$_2$ | 3-OCH$_3$ | COOH | 1.4 |
| 3gy | SO$_2$ | 3-OCH$_3$ | C.C.† | N.A. |
| 4ax | S | 4-OCH$_3$ | NO$_2$ | N.A. |
| 4bx | S | 4-OCH$_3$ | COOCH$_3$ | 2.0 |
| 4cx | S | 4-OCH$_3$ | OCH$_3$ | N.A. |
| 4dx | S | 4-OCH$_3$ | CF$_3$ | 1.1 |
| 4ex | S | 4-OCH$_3$ | NH$_2$ | N.A. |
| 4fx | S | 4-OCH$_3$ | COOH | 7.1 |
| 4gx | S | 4-OCH$_3$ | C.C.† | N.A. |
| 4ay | SO$_2$ | 4-OCH$_3$ | NO$_2$ | N.A. |
| 4by | SO$_2$ | 4-OCH$_3$ | COOCH$_3$ | 7.6 |
| 4cy | SO$_2$ | 4-OCH$_3$ | OCH$_3$ | N.A. |
| 4dy | SO$_2$ | 4-OCH$_3$ | CF$_3$ | 12 |
| 4ey | SO$_2$ | 4-OCH$_3$ | NH$_2$ | N.A. |
| 4fy | SO$_2$ | 4-OCH$_3$ | COOH | N.A. |
| 4gy | SO$_2$ | 4-OCH$_3$ | C.C.† | 0.7 |
| 5ax | S | 5-OCH$_3$ | NO$_2$ | 0.01 |
| 5bx | S | 5-OCH$_3$ | COOCH$_3$ | 0.2 |
| 5cx | S | 5-OCH$_3$ | OCH$_3$ | 15.7 |
| 5dx | S | 5-OCH$_3$ | CF$_3$ | 46.4 |
| 5ex | S | 5-OCH$_3$ | NH$_2$ | N.A. |
| 5fx | S | 5-OCH$_3$ | COOH | 4.5 |
| 5gx | S | 5-OCH$_3$ | C.C.† | N.A. |
| 5ay | SO$_2$ | 5-OCH$_3$ | NO$_2$ | 1.0 |
| 5by | SO$_2$ | 5-OCH$_3$ | COOCH$_3$ | 4.6 |
| 5cy | SO$_2$ | 5-OCH$_3$ | OCH$_3$ | N.A. |
| 5dy | SO$_2$ | 5-OCH$_3$ | CF$_3$ | 4.3 |
| 5ey | SO$_2$ | 5-OCH$_3$ | NH$_2$ | 0.6 |
| 5fy | SO$_2$, | 5-OCH$_3$ | COOH | N.A. |
| 5gy | SO$_2$ | 5-OCH$_3$ | C.C.† | 0.5 |
| 6ax | S | 6-OCH$_3$ | NO$_2$ | 6.3 |
| 6bx | S | 6-OCH$_3$ | COOCH$_3$ | 0.2 |
| 6cx | S | 6-OCH$_3$ | OCH$_3$ | N.A. |
| 6dx | S | 6-OCH$_3$ | CF$_3$ | 5.3 |
| 6ex | S | 6-OCH$_3$ | NH$_2$ | 1.5 |
| 6fx | S | 6-OCH$_3$ | COOH | 1.9 |
| 6gx | S | 6-OCH$_3$ | C.C.† | 52 |
| 6ay | SO$_2$ | 6-OCH$_3$ | NO$_2$ | N.A. |
| 6by | SO$_2$ | 6-OCH$_3$ | COOCH$_3$ | N.A. |
| 6cy | SO$_2$ | 6-OCH$_3$ | OCH$_3$ | N.A. |
| 6dy | SO$_2$ | 6-OCH$_3$ | CF$_3$ | N.A. |
| 6ey | SO$_2$ | 6-OCH$_3$ | NH$_3$ | 1.5 |
| 6fy | SO$_2$ | 6-OCH$_3$ | COOH | 1.2 |
| 6gy | SO$_2$ | 6-OCH$_3$ | C.C.† | N.A. |
| 7ax | S | 6-F | NO$_2$ | 3.9 |
| 7bx | S | 6-F | COOCH$_3$ | 7.8 |
| 7cx | S | 6-F | OCH$_3$ | N.A. |
| 7dx | S | 6-F | CF$_3$ | 10.0 |
| 7ex | S | 6-F | NH$_2$ | N.A. |
| 7fx | S | 6-F | COOH | 4.9 |
| 7gx | S | 6-F | C.C.† | N.A. |
| 7ay | SO$_2$ | 6-F | NO$_2$ | N.A. |
| 7by | SO$_2$ | 6-F | COOCH$_3$ | N.A. |
| 7cy | SO$_2$ | 6-F | OCH$_3$ | N.A. |
| 7dy | SO$_2$ | 6-F | CF$_3$ | N.A. |
| 7ey | SO$_2$ | 6-F | NH$_2$ | 15 |
| 7fy | SO$_2$ | 6-F | COOH | N.A. |
| 7gy | SO$_2$ | 6-F | C.C.† | N.A. |

N.A. = No activity 50 µM;
†C.C. = Choline carboxylate

Supplementary Referenced (Example 3)

[1] Mohammed, I.; Parai, M. K.; Jiang, X.; Sharova, N.; Singh, G.; Stevenson, M.; Rana, T. M. SAR and Lead Optimization of an HIV-1 Vif-APOBEC3G Axis Inhibitor. ACS Med. Chem. Lett. 2012, 3, 465-469; [2] Shabani, A.; Mirazei, P.; Naderi, S.; Lee, D. G. Green oxidations. The use of potassium permanganate supported on manganese dioxide. Tetrahedron 2004, 60, 11415.

REFERENCES (EXAMPLE 3)

[1] Mehellou, Y.; Clercq, E. D. Twenty-Six Years of Anti-HIV Drug Discovery: Where Do We Stand and Where Do We Go? J. Med. Chem., 2010, 53, 521-538; [2] Thompson, M. A.; Aberg, J. A.; Cahn, P.; Montaner, J. S. G.; Rizzardini, G.; Telenti, A.; Gatell, J. M.; Giinthard, H. F.; Hammer, S. M.; Hirsch, M. S.; Jacobsen, D. M.; Reiss, P.; Richman, D. D.; Volberding, P. A.; Yeni, P.; Schooley, R. T. Antiretroviral treatment of adult HIV infection: 2010 recom-mendations of the International AIDS Society-USA panel. JAMA 2010, 304, 321-333; [3] Volderbing, P. A.; Deeks, S. G. Antiretroviral therapy and management of HIV injection. Lancet 2010, 376, 49-62; [4] Gabuzda, D. H.; Lawrence, K.; Langhoff, E.; Terwillliger, E.; Dorfman, T.; Haseltine, W. A.; Sodroski, J. Role of Vif in replication of human immunodeficiency virus type 1 in CD4+T lymphocytes. J. Virol. 1992, 66, 6489-6495; [5] Strebel, K.; Daugherty, D.; Clouse, K.; Cohen, D.; Folks, T.; Martin, M. A. The HIV A (sor) gene product is essential for virus infectivity. Nature 1987, 328, 728-730; [6] Sheehy, A. M.; Gaddis, N. C.; Choi, J. D.; Malim, M. H. Isolation of a human gene that inhibits HIV-1 infection and is suppressed by the viral Vif protein. Nature 2002, 418, 646-650; [7] Malim, M. H.; Bieniasz, P. D. HIV Restriction Factors and Mechanisms of Evasion. Cold Spring Harb. Perspect. Med. 2012, 2, a006940; [8] Ali, A.; Wang, J.; Nathans, R. S.; Cao, H.; Sharova, N.; Stevenson, M.; Rana, T. M. Synthesis and Structure-Activity Relationship Studies of HIV-1 Virion Infectivity Factor (Vif) Inhibitors that Block Viral Replication. ChemMedChem 2012, 7, 1217-1229; [9] Mohammed, I.; Parai, M. K.; Jiang, X.; Sharova, N.; Singh, G.; Stevenson, M.; Rana, T. M. SAR and Lead Optimization of an HIV-1 Vif-APOBEC3G Axis Inhibitor. ACS Med. Chem. Lett. 2012, 3, 465-469; [10] Nathans, R.; Cao, H.; Sharova, N.; Ali, A.; Sharkey, M.; Stranska, R.; Stevenson, M.; Rana, T. M. Small-molecule inhibition of HIV-1 Vif Nat. Biotechol. 2008, 26, 1187-1192; [11] Meanwell, N. A. Synopsis of Some Recent Tactical Appli-cation of Bioisosterism in Drug Design. J. Med. Chem. 2011, 54, 2529-2591; [12] Ko, E.; Liu, J.; Perez, L. M.; Lu, G.; Schaefer, A.; Burgess, K. Universal Peptidomimetics. J. Am. Chem. Soc. 2011, 133, 462-477; [13] Borg, S.; Vollinga, R. C.; Labarre, M.; Payza, K.; Terenius, L.; Luthman, K. Design, Synthesis, and Evaluation of Phe-Gly Mimetics: Heterocyclic Building Blocks of Pseudopeptides. J. Med. Chem. 1999, 42, 4331-4342; [14] Valverde, I. E.; Bauman, A.; Kluba, C. A.; Vomstein, S.; Walter, M. A.; Mindt, T. L. 1,2,3-Triazoles as Amide Bond Mim-ics: Triazole Scan Yields Protease-Resistant Peptidomimetics for Tumor Targeting. Angew. Chem. Int. Ed. 2013, 52, 8957-8960; [15] Tam, A.; Arnold, U.; Soellner, M. B.; Raines, R. T. Protein Prosthesis: 1,5-Disubstituted[1,2,3]triazoles as cis-Peptide Bond Surrogates. J. Am. Chem. Soc. 2007, 129, 12670-12671; [16] Sperotto, E.; van Klink, G. P. M.; de Vries, J. G.; van Ko-ten, G. Ligand-Free Copper-Catalyzed C-S Coupling of Aryl Iodides and Thiols. J. Org. Chem. 2008, 73, 5625-5628; [17] Liang, G.-B.; Feng, D. D. An Improved Oxadiazole Syn-thesis Using Peptide Coupling Reagents. Tetrahedron Lett., 1996, 37, 6627-6630; [18] Sonogashira, K.; Tohda, Y.; Hagihara, N. A convenient synthesis of acetylenes: catalytic substitutions of acetylenic hydrogen with bromoalkenes, iodoarenes and bromopyridines. Tetrahedron Lett. 1975, 16, 4467-4470; [19] Tao, C.-Z.; Cui, X.; Li, J.; Liu, A-X.; Liu, L.; Guo, Q-X. Copper-catalyzed Synthesis of Aryl Azides and 1-Aryl-1,2,3-Triazoles from Boronic Acids. Tetrahedron Lett. 2007, 48, 3525-3529; [20] Rostovtsev, V. V.; Green, L. G.; Fokin, V. V.; Sharpless, K. B. A Stepwise Huisgen Cycloaddition Process: Copper(I)-Catalyzed Regioselective "Ligation" of Azides and Terminal Alkynes. Angew. Chem. Int. Ed. 2002, 41, 2596-2599; [21] Zhang, L.; Chen, X.; Xue, P.; Sun, H. H. Y.; Williams, I. D.; Sharpless, K. B.; Fokin, V. V.; Jia, G. Ruthenium-Catalyzed Cycloaddition of Alkynes and Organic Azides. J. Am. Chem. Soc. 2005, 127, 15998-15999; [22] Tron, G. C.; Pirali, T.; Billington, R. A.; Canonico, P. L.; Sorba, G.; Genazzani, A. A. Click chemistry reactions in medicinal chemistry: applications of the 1,3-dipolar cycloaddition between azides and alkynes. Med. Res. Rev. 2008, 28, 278-308;

Example 4. A New Class of Broad-Spectrum Antivirals Inhibiting HIV-1, Ebola, and Zika Viruses There are described the synthesis, purification, characterization, and antiviral activities of a new class of triazole containing heterocyclic compounds. These compounds potently inhibit replication of HIV-1, Ebola, and Zika viruses. A few note-worthy compounds against HIV-1 are 5ax ($IC_{50}$=0.01 µM), 5bx (0.2 µM), 2ey (0.4 µM), 5ey (0.6 µM), and 6bx (0.2 µM). Water-soluble salts 2gy, 4gy, and 5gy also exhibited potent activities. In addition, five inhibitors for Ebola and Zika replication were identified.

Since the start of the AIDS epidemic in 1981, this disease has led to the death of >30 million people globally. Although the overall growth of the epidemic appears to be slowing, nearly three million new infections and an estimated 1.8 million AIDS-related deaths in 2010 are still very high. Over the past two decades, more than 25 anti-HIV drugs have been developed targeting several different stages of the virus life cycle[1]. Among these inhibitors of HIV-1 reverse transcriptase and protease, when used in combinations in the highly active antiretroviral therapy (cART), have proven to be highly effective in reducing AIDS-related mortality throughout the world[2]. However, the development of drug resistance and toxic side effects associated with cART have created a need for more potent and less toxic therapies against other viral targets and host-virus interactions[3]. Importantly, in patients on effective cART, plasma viremia can be suppressed to below detectable levels for extended intervals. The ability of cART to sustain this aviremic state has promoted the view that cART is fully suppressive and effectively stops all ongoing viral replication. Since there is rapid recrudescence of plasma viremia upon treatment interruption, regardless of the prior interval of viral suppression, there are long-lived viral reservoirs that maintain viral persistence in the face of cART. Therefore, new antiviral drugs are needed to purge drug resistant viruses from viral reservoirs.

Figure 18:
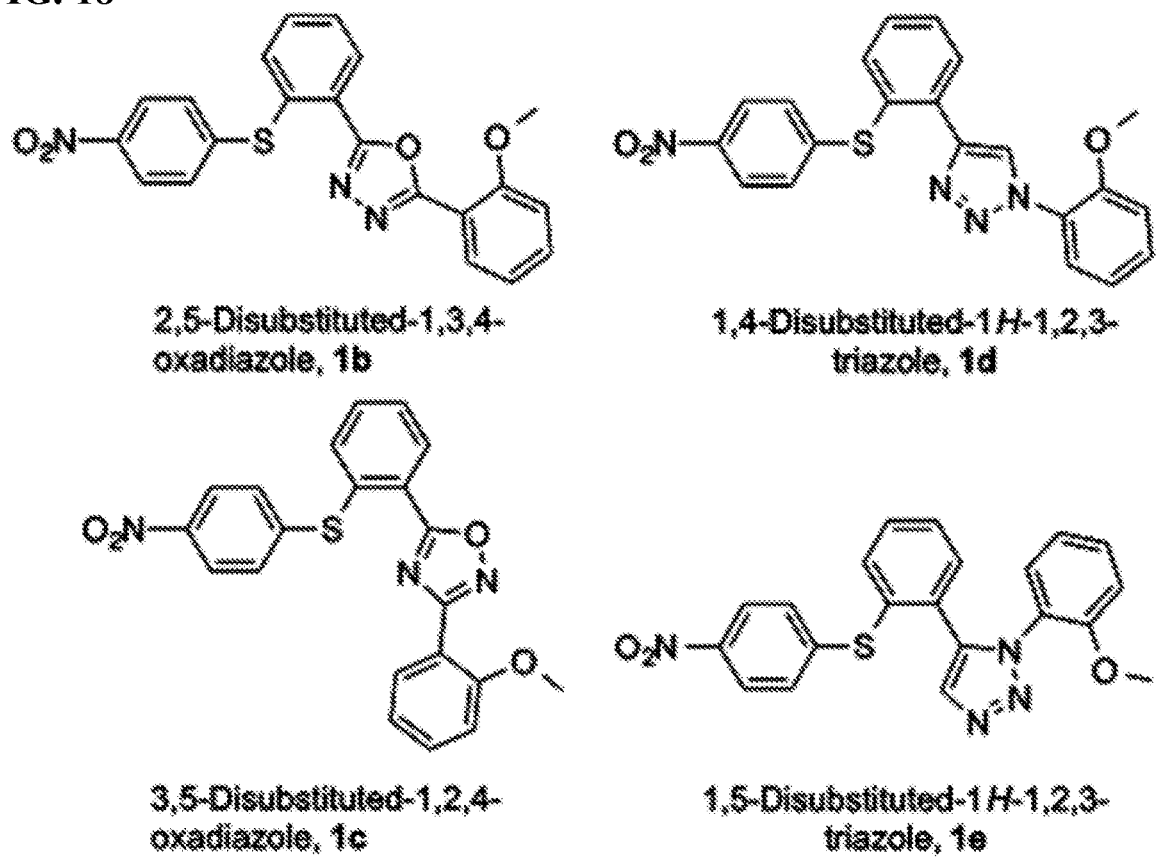
FIG. 18. Structures of novel heterocyclic compounds. SAR was performed on these parent structures and antiviral activities of compounds were determined.

We disclose the successful identification of potent triazole based heterocyclic compounds. Initially, we designed and synthesized four test molecules with isosteric heterocyclic systems such as 1,3,4-oxadiazole[12] 1b, 1,2,4-oxadiazole[13] 1c, 1,4-disubstituted-1,2,3-triazole[14] 1d and 1,5-disubstituted-1,2,3-triazole[15] 1e (FIG. 18).

1,3,4-Oxadiazole 1b was synthesized with the coupling of hydrazine and 2-iodobenzoic acid (Scheme 1, A). The one pot coupling involves the formation of in situ methyl ester of 2-iodobenzoic acid, which was later refluxed in the presence of hydrazine hydrate to obtain the benzohydrazide derivative 1f quantitatively. Benzohydrazide 1f was later reacted with o-anisic acid in refluxing phosphoryl chloride leading to the formation of iodo intermediate 1,3,4-oxadiazole 1g. Intermediate 1g was reacted with 4-nitrothiophenol under copper (I) catalyzed S-arylation conditions[16] leading to the formation of compound 1b. Synthesis of 1,2,4-oxadiazole 1c was started (Scheme 1, B) with the coupling between the commercially available N'-hydroxy-2-methoxybenzimidamide and 2-iodobenzoic acid using dicyclohexyldicarbodiimide[17] leading to the formation of the iodo intermediate 1,2,4-oxadiazole 1 h. S-arylation of 1 h with 4-nitrothiophenol under copper (I) catalytic conditions led to the formation of 3,5-disubstituted-1,2,4-oxadiazole, 1c.

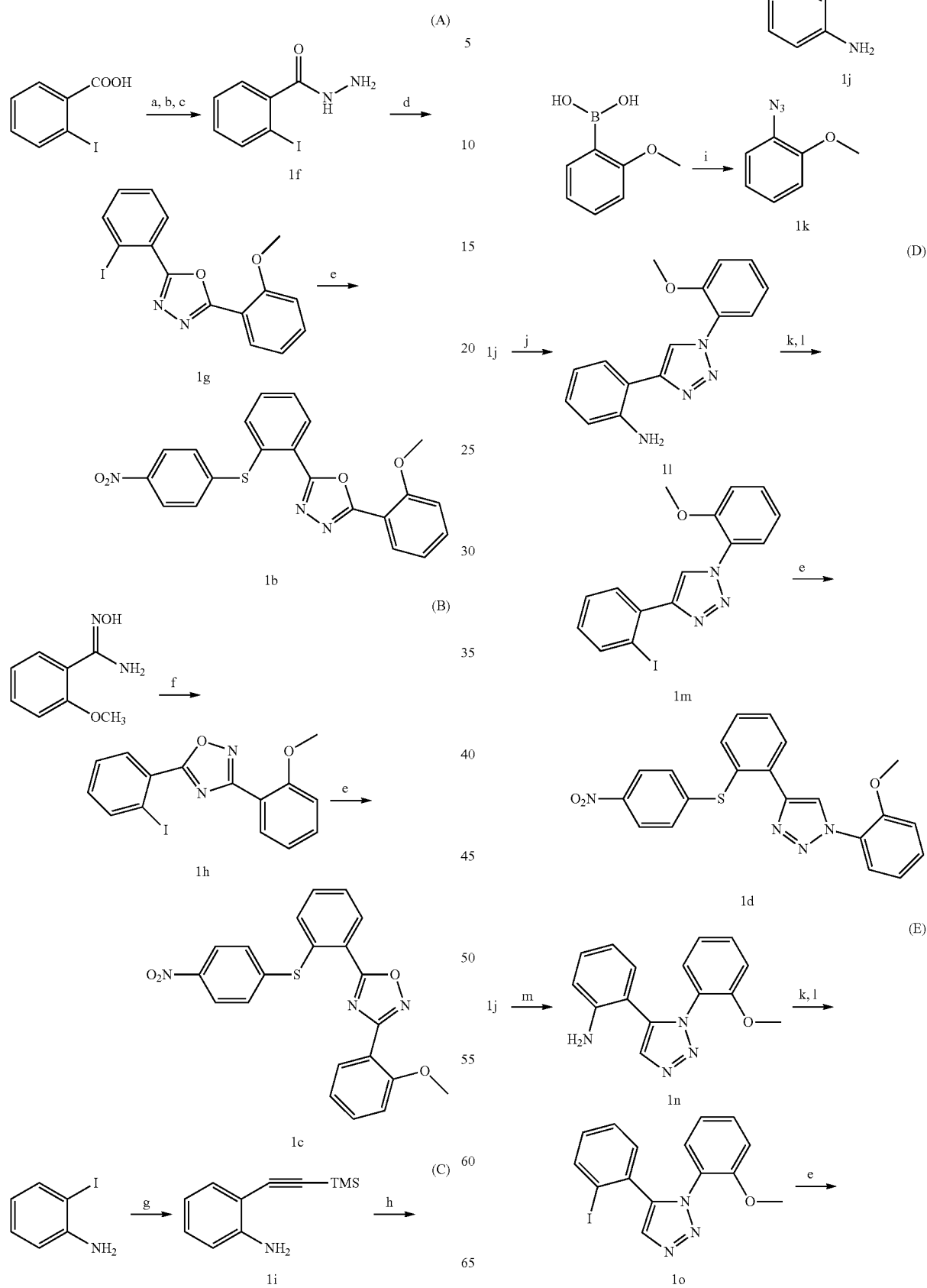
Scheme 1. Synthesis of triazole compounds.

-continued

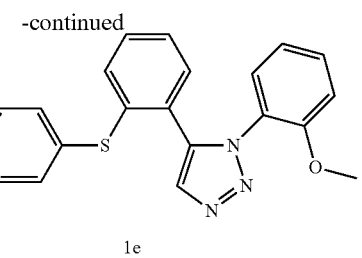

1e

<sup>a</sup>Reagents and conditions: (a) SOCl<sub>2</sub>, cat. DMF, benzene, 80° C., 2 h; (b) CH<sub>3</sub>OH, TEA, 0° C. - rt., 2 h; (c) NH<sub>2</sub>NH<sub>2</sub>•H<sub>2</sub>O, 80° C., 3 h; (d) o-anisic acid, POCl<sub>3</sub>, 110° C., 8 h; (e) 4-nitrothiophenol, K<sub>2</sub>CO<sub>3</sub>, 5 mol %, CuI, DMF, 110° C., 8 h; (f) 2-iodobenzoic acid, DCC, DMF, rt to 100° C., 8 h; (g) Trimethylsilyl acetylene, 1 mol % PdCl<sub>2</sub>(PPh<sub>3</sub>)<sub>2</sub>, 1 mol % CuI, NEt<sub>3</sub>, rt, 12 h; (h) NaOH (aq), ethanol/THF (1:1), rt, 1 h; (i) NaN<sub>3</sub>, 10 mol % CuSO<sub>4</sub>•5H<sub>2</sub>O, CH<sub>3</sub>OH, rt, 8 h; (j) 1k, 5 mol % CuSO<sub>4</sub> 5H<sub>2</sub>O, 10 mol % Na ascorbate, t-BuOH/H<sub>2</sub>O (1:1), rt, overnight; (k) NaNO<sub>2</sub>, 5N HCl, -10 to -5° C., 2 h; (l) KI, -10 to -5° C., 8 h; (m) 1k, 1 mol % Cp*RuCl(PPh<sub>3</sub>)<sub>2</sub>, benzene, 80° C., 3 h.

Synthesis of 1,4-disubstituted-1,2,3-triazole analogue 1d required two synthons; 2-ethynylaniline 1j, and 1-azido-2-methoxybenzene 1k (Scheme 1, C). 2-Iodoaniline was reacted with trimethylsilylacetylene under Sonogashira reaction conditions catalyzed by bis(triphenylphosphine) palladium chloride in the presence of triethylamine base and copper iodide as co-catalyst[18] leading to the formation of TMS protected ethynylaniline 1i, which was deprotected using sodium hydroxide affording the required synthon 2-ethynylaniline 1j. Azide 1k was synthesized by following a Cham-Lam type of coupling between 2-methoxyphenylboronic acid and sodium azide catalyzed by copper sulfate at room temperature in methanol.[19] Copper-catalyzed click reaction[20] between alkyne 1j and azide 1k generated triazole amine 1l quantitatively in t-butanol/water (Scheme 1, D). Triazole amine 1l was diazotized using sodium nitrite in 5N HCl around −10° C. and concomitantly converted to iodotriazole 1m by reacting with potassium iodide. Copper (I) catalyzed S-arylation of iodotriazole 1m using 4-nitrothiophenol in DMF solvent and potassium carbonate led to the synthesis of 1d. 1,5-Disubstituted-1,2,3-triazole 1e analogue was synthesized initially by reacting alkyne 1j and azide 1k under ruthenium catalyzed click chemistry conditions using Cp*RuCl(PPh<sub>3</sub>)<sub>2</sub> catalyst in benzene at 80° C.[21] leading to the formation of amine 1n (Scheme 1, E). Diazotization, iodination (1o), and S-arylation reaction sequences afforded 1,5-disubstituted-1,2,3-triazole 1e.

TABLE 6

IC$_{50}$ values of triazole compounds.

| Compd. | Antiviral activity (IC$_{50}$ µM) | |
|---|---|---|
| | H9 cells | MT4 cells |
| 1b | 6.8 | 50 |
| 1c | 6.8 | N.A. |
| 1d | 1.2 | N.A. |
| 1e | 15 | 25 |

N.A. = no activity 50 µM conc.

The antiviral activities of the four synthesized compounds were measured against wild-type HIV-1 both in non-permissive H9 and permissive MT-4 cells. The IC$_{50}$ values of the triazole compound library SAR are presented in Table 6. Both 1,3,4-oxadiazole 1b (IC$_{50}$=6.8 µM) and 1,2,4-oxadiazole 1c (IC$_{50}$=6.8 µM) based analogues exhibited cell-based antiviral activity in the non-permissive H9 cells. Interestingly. 2,5-disubstituted-1,3,4-oxadiazole 1b showed non-specific antiviral activity with IC$_{50}$ of 50 µM in permissive MT4 cells. Whereas the 1,4-disubstituted-1,2,3-triazole based analogue 1d exhibited remarkably better cell-based anti-HIV activity (IC$_{50}$=1.2 µM in H9 cells) and specificity (no activity in MT4 cells). On the contrary, 1,5-disubstituted-1,2,3-triazole 1e analogue exhibited comparatively lesser potency (IC$_{50}$=15 µM in H9 cells) with non-specific activity in the permissive cells (IC$_{50}$=25 µM in MT4 cells).

These observations were well in-line with the structural similarities in the 3D orientations and planarity except the 1,5-disubstituted-1,2,3-triazole 1e, which has a twisted structure. 1,3,4-Oxadiazole, and 1,2,4-oxadiazole heterocyclic systems have both planarity and dipole moment similar to amide functionality. Similarly, 1,4-disubstituted and 1,5-disubstituted 1,2,3-triazoles possess strong dipole moment beside having better H-bond accepting (N(2) and N(3)), and H-bond donating (triazole C(5)-H) capacity than an amide functionality.[22] However in the present biochemical context, 1,4-disubstituted-1,2,3-triazle 1d analogue showed both improved antiviral activity (IC$_{50}$=1.2 µM) and selectivity (no activity in MT4 cells).

Having discovered compound 1d as a potent and specific inhibitor of HIV-1, we decided to optimize the analogue to generate new class of anti-HIV drug candidates for clinical development. We designed and synthesized an 84-membered library using a parallel format exploring various substitution patterns in ring-A, ring-C, and bridge A-B in the 1d structure (Table 7). In this direction, the synthetic scheme for 1d (Scheme 1, D) was followed. Synthetic schemes (see Schemes 1S to 6S), experimental procedures, and characterization data of all the 84 members of the library are disclosed herein. Anti-viral activities of the library were determined against wild-type HIV-1 both in non-permissive H9 and permissive MT-4 cells. The IC$_{50}$ values for some of the active compounds are presented in Table 7. Antiviral activities of the complete library is given as Table 8. None of the 84 compounds exhibited antiviral activities at 50 µM in non-permissive MT4 cells indicating the requirement of Vif for their function, which is quite remarkable.

Of the 84 members library, about 30 compounds inhibited HIV-1 with IC$_{50}$ values in the range of 0.01 to 5 µM in the non-permissive H9 cells. Among them, the compound 5ax exhibited the most potent activity with IC$_{50}$ of 10 nM. Similarly, compounds 2ey, 5bx, 5ey, and 6bx exhibited IC$_{50}$ values in the range of 0.2 µM to 0.6 µM and compounds 2ax, 2dx, 2ex, 2fx, 3ax, 3dx, 3fx, 3fy, 5ay, 6ex, 6fx, 6ey, 6fy in the range of 1 µM to 3 µM. Three water soluble choline salts 2gy, 4gy and 5gy exhibited IC$_{50}$ values of 0.2 µM, 0.7 µM, and 0.5 µM, respectively. Overall, the SAR of the library showed striking sensitivity towards three the variables (Z-bridge, R$_1$ and R$_2$ substituents) tested in this study. Among various SAR findings few of the noteworthy ones are: in general sulfide (—S—) as bridge Z exhibited overall better activity compared with sulfone (—SO$_2$—) bridge. However, sulfones (—SO$_2$—) showed better activities when R$_2$ substituent was amino group. This study has found replacements such as —COOCH$_3$, —COOH, —CF$_3$, —NH$_2$, and -choline carboxylate.

TABLE 7

IC$_{50}$ values of the library.

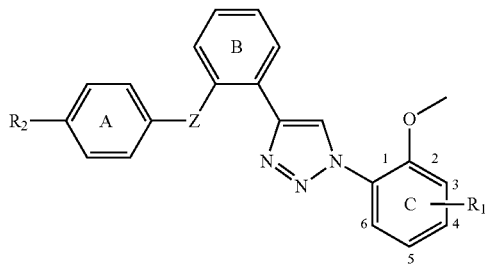

R$_1$ = H (2), 3-OCH$_3$ (3), 4-OCH$_3$ (4), 5-OCH$_3$ (5), 6-OCH$_3$ (6), 6-F (7)
R$_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | R$_1$ | R$_2$ | Antiviral activity (IC$_{50}$ μM) H9 Cells |
|---|---|---|---|---|
| 2ax (1d) | S | H | NO$_2$ | 1.2 |
| 2dx | S | H | CF$_3$ | 2.6 |
| 2ex | S | H | NH$_2$ | 2.5 |
| 2fx | S | H | COOH | 1.0 |
| 2ay | SO$_2$ | H | NO$_2$ | 13.8 |
| 2cy | SO$_2$ | H | OCH$_3$ | 4.3 |
| 2dy | SO$_2$ | H | CF$_3$ | 4.8 |
| 2ey | SO$_2$ | H | NH$_2$ | 0.4 |
| 2fy | SO$_2$ | H | COOH | 8.2 |
| 2gy | SO$_2$ | H | C.C.[†] | 0.2 |
| 3ax | S | 3-OCH$_3$ | NO$_2$ | 1.1 |
| 3bx | S | 3-OCH$_3$ | COOCH$_3$ | 8 |
| 3cx | S | 3-OCH$_3$ | OCH$_3$ | 4.7 |
| 3dx | S | 3-OCH$_3$ | CF$_3$ | 1.9 |
| 3fx | S | 3-OCH$_3$ | COOH | 2.8 |
| 3gx | S | 3-OCH$_3$ | C.C.[†] | 4.3 |
| 3by | SO$_2$ | 3-OCH$_3$ | COOCH$_3$ | 4.7 |
| 3ey | SO$_2$ | 3-OCH$_3$ | NH$_2$ | 12.4 |
| 3fy | SO$_2$ | 3-OCH$_3$ | COOH | 1.4 |
| 4fx | S | 4-OCH$_3$ | COOH | 7.1 |
| 4dy | SO$_2$ | 4-OCH$_3$ | CF$_3$ | 12 |
| 4gy | SO$_2$ | 4-OCH$_3$ | C.C.[†] | 0.7 |
| 5ax | S | 5-OCH$_3$ | NO$_2$ | 0.01 |
| 5bx | S | 5-OCH$_3$ | COOCH$_3$ | 0.2 |
| 5cx | S | 5-OCH$_3$ | OCH$_3$ | 15.7 |
| 5fx | S | 5-OCH$_3$ | COOH | 4.5 |
| 5ay | SO$_2$ | 5-OCH$_3$ | NO$_2$ | 1.0 |
| 5by | SO$_2$ | 5-OCH$_3$ | COOCH$_3$ | 4.6 |
| 5ey | SO$_2$ | 5-OCH$_3$ | NH$_2$ | 0.6 |
| 5gy | SO$_2$ | 5-OCH$_3$ | C.C.[†] | 0.5 |
| 6bx | S | 6-OCH$_3$ | COOCH$_3$ | 0.2 |
| 6ex | S | 6-OCH$_3$ | NH$_2$ | 1.5 |
| 6fx | S | 6-OCH$_3$ | COOH | 1.9 |
| 6ey | SO$_2$ | 6-OCH$_3$ | NH$_2$ | 1.5 |
| 6fy | SO$_2$ | 6-OCH$_3$ | COOH | 1.2 |
| 7ax | S | 6-F | NO$_2$ | 3.9 |
| 7bx | S | 6-F | COOCH$_3$ | 7.8 |
| 7fx | S | 6-F | COOH | 4.9 |
| 7ey | SO$_2$ | 6-F | NH$_2$ | 15 |

[†]Choline carboxylate

In summary, this study report two findings: (a) 1,4-disubstituted-1,2,3-triazole system is a suitable scaffold for antiviral compounds (b) discovery of a new class of potent preclinical candidates for novel AIDS therapy. Further optimization of 1,4-disubstituted-1,2,4-oxadiazole, 1c and preclinical studies for the selected 1,4-disubstituted-1,2,3-triazole based antivirals showed activities against ebola and Zika viruses (see sections below).

Abbreviations. C. C., choline carboxylate; DCM, dichloromethane; DMF, dimethylformamide; TMS, trimethylsilyl; TLC, thin-layer chromatography; THF, tetrahydrofuran;

Details of general procedures, and materials are described hereinbelow. Parallel synthesis was performed using Carousel 6 (Radleys Discovery Technologies). $^1$H and $^{13}$C NMR spectra were recorded using a 400 MHz Jeol JNM-ECS spectrometer with a 5 mm proton/multi-frequency auto-tune and auto sample changer. The spectra are reported in ppm on the δ scale using the internal reference as trimethylsilane (TMS). ESI MS was performed on Waters micromass Model ZQ 4000 using methanol. HRMS was performed on Agilent Technologies 6224A MS-TOF. Purity of the tested compounds was determined using Waters 2695 Module HPLC equipped with Waters 996 photodiode detector at 254 nm. X-ray structural determination was performed at UCSD facility using Bruker diffractometer with CCD detectors and low-temperature cryostats.

General Procedures.

Reactions were performed in oven-dried round-bottom flasks and air sensitive reactions were performed under positive pressure of nitrogen. Moisture sensitive reactions were performed using calcium sulphate protected guard tubes. Stainless steel syringes were used to transfer dry solvents or moisture/air sensitive liquids. Flash column chromatography was performed using SINGLE StEP™ Pump and SINGLE StEP™ columns Intro Packs of various sizes made by Thomson Instrument Company. Silica gel used was 60° pore size, 40 μm, supplied by Fisher Scientific and amines were purified using neutral alumina Brockmann I of Sigma-Aldrich. Analytical thin-layer chromatography (TLC) was performed using TLC silica gel 60 F$_{254}$ aluminium sheets of EMD. TLC plates were visualized by exposure to ultraviolet light, iodine adsorbed on silica gel and by exposure to an ethanolic solution of phosphomolybdic acid (PMA) or an acidic solution of p-anisaldehyde, or a slightly basic solution of potassium permanganate. Organic extracts or solutions or eluents were concentrated using Heidolph's Hei-VAP Advantage vacuo rotavapor at temperatures below 38-40° C. Dry-ice was used for low temperature baths in various organic solvents. Purity analysis was performed using column, YMC-Pack Pro C18 (particle size=5 μm, pore size=12 nm, dimensions=150 mm×4.6 mm); mobile phase A, water; mobile phase B, acetonitrile. We applied the following mobile phase gradient for total 10 minutes per sample: starting from 50% B and reaches to 90% B for 2 min followed by 100% B over 10 minutes (Method A for all the compounds except water soluble choline salts). Method B for water-soluble choline salts; starting from 50% A and 50% B followed by 100% A over 10 minutes. The injection volume was 10 μL and the flow rate was 1.0 mL/min. HPLC retention times (R$_T$) and purity data (%) for the compounds are given in the analytical data of the respective compounds.

Materials.

Commercial reagents and solvents (HPLC grade for purifications and anhydrous solvents for reactions) were purchased from Sigma-Aldrich, Acros Organics, Alfa Aesar, EMD, Combiblocks, Oakwoods, Toronto Research Chemicals Inc., Astatech Inc., etc.

Antiviral Activity Assay.

The antiviral activities of compounds were measured with wild-type HIV-1 in H9 cells (non-permissive) and MT-4 cells (permissive). H9 and MT4 cells (2×10$^5$ cells per well in 48-well plates) were treated overnight with differing concentrations of compounds (1 to 50 μM) in RPMI medium containing 100% fetal bovine serum. The cells were then infected with an X4-tropic HIV-1 variant (HIV-1$_{LAI}$) and maintained for further 10-15 days. Viral replication was monitored every second day by measuring reverse transcriptase (RT) activity in the culture supernatants. For this, ⅓ of the culture supernatant was replaced with an equivalent volume of fresh medium containing the appropriate compounds every second day. Measurements of antiviral activity in cultured cells were repeated at least 3 times and the $IC_{50}$ values were calculated using GraFit software.

TABLE 8

Tabulation of the library and $IC_{50}$ values.

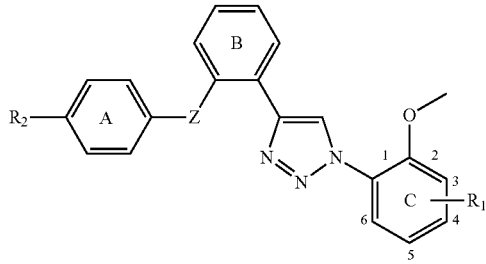

$R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | $R_1$ | $R_2$ | Antiviral activity ($IC_{50}$ μM) H9 cells |
|---|---|---|---|---|
| 2ax (1d) | S | H | NO$_2$ | 1.2 |
| 2bx | S | H | COOCH$_3$ | N.A. |
| 2cx | S | H | OCH$_3$ | 13.6 |
| 2dx | S | H | CF$_3$ | 2.6 |
| 2ex | S | H | NH$_2$ | 2.5 |
| 2fx | S | H | COOH | 1.0 |
| 2gx | S | H | C.C.[†] | N.A. |
| 2ay | SO$_2$ | H | NO$_2$ | 13.8 |
| 2by | SO$_2$ | H | COOCH$_3$ | N.A. |
| 2cy | SO$_2$ | H | OCH$_3$ | 4.3 |
| 2dy | SO$_2$ | H | CF$_3$ | 4.8 |
| 2ey | SO$_2$ | H | NH$_2$ | 0.4 |
| 2fy | SO$_2$ | H | COOH | 8.2 |
| 2gy | SO$_2$ | H | C.C.[†] | 0.2 |
| 3ax | S | 3-OCH$_3$ | NO$_2$ | 1.1 |
| 3bx | S | 3-OCH$_3$ | COOCH$_3$ | 8 |
| 3cx | S | 3-OCH$_3$ | OCH$_3$ | 4.7 |
| 3dx | S | 3-OCH$_3$ | CF$_3$ | 1.9 |
| 3ex | S | 3-OCH$_3$ | NH$_2$ | 5.0 |
| 3fx | S | 3-OCH$_3$ | COOH | 2.8 |
| 3gx | S | 3-OCH$_3$ | C.C.[†] | 4.3 |
| 3ay | SO$_2$ | 3-OCH$_3$ | NO$_2$ | N.A. |
| 3by | SO$_2$ | 3-OCH$_3$ | COOCH$_3$ | 4.7 |
| 3cy | SO$_2$ | 3-OCH$_3$ | OCH$_3$ | N.A. |
| 3dy | SO$_2$ | 3-OCH$_3$ | CF$_3$ | N.A. |
| 3ey | SO$_2$ | 3-OCH$_3$ | NH$_2$ | 12.4 |
| 3fy | SO$_2$ | 3-OCH$_3$ | COOH | 1.4 |
| 3gy | SO$_2$ | 3-OCH$_3$ | C.C.[†] | N.A. |
| 4ax | S | 4-OCH$_3$ | NO$_2$ | N.A. |
| 4bx | S | 4-OCH$_3$ | COOCH$_3$ | 2.0 |
| 4cx | S | 4-OCH$_3$ | OCH$_3$ | N.A. |
| 4dx | S | 4-OCH$_3$ | CF$_3$ | 1.1 |
| 4ex | S | 4-OCH$_3$ | NH$_2$ | N.A. |
| 4fx | S | 4-OCH$_3$ | COOH | 7.1 |
| 4gx | S | 4-OCH$_3$ | C.C.[†] | N.A. |
| 4ay | SO$_2$ | 4-OCH$_3$ | NO$_2$ | N.A. |
| 4by | SO$_2$ | 4-OCH$_3$ | COOCH$_3$ | 7.6 |
| 4cy | SO$_2$ | 4-OCH$_3$ | OCH$_3$ | N.A. |
| 4dy | SO$_2$ | 4-OCH$_3$ | CF$_3$ | 12 |
| 4ey | SO$_2$ | 4-OCH$_3$ | NH$_2$ | N.A. |
| 4fy | SO$_2$ | 4-OCH$_3$ | COOH | N.A. |
| 4gy | SO$_2$ | 4-OCH$_3$ | C.C.[†] | 0.7 |
| 5ax | S | 5-OCH$_3$ | NO$_2$ | 0.01 |
| 5bx | S | 5-OCH$_3$ | COOCH$_3$ | 0.2 |
| 5cx | S | 5-OCH$_3$ | OCH$_3$ | 15.7 |
| 5dx | S | 5-OCH$_3$ | CF$_3$ | 46.4 |
| 5ex | S | 5-OCH$_3$ | NH$_2$ | N.A. |

TABLE 8-continued

Tabulation of the library and $IC_{50}$ values.

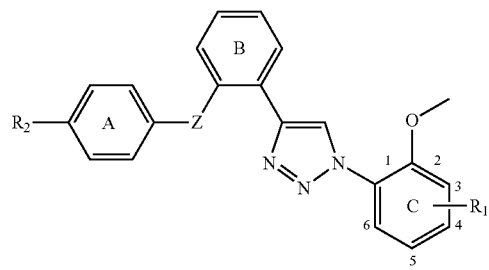

$R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Compd. | Z | $R_1$ | $R_2$ | Antiviral activity ($IC_{50}$ μM) H9 cells |
|---|---|---|---|---|
| 5fx | S | 5-OCH$_3$ | COOH | 4.5 |
| 5gx | S | 5-OCH$_3$ | C.C.[†] | N.A. |
| 5ay | SO$_2$ | 5-OCH$_3$ | NO$_2$ | 1.0 |
| 5by | SO$_2$ | 5-OCH$_3$ | COOCH$_3$ | 4.6 |
| 5cy | SO$_2$ | 5-OCH$_3$ | OCH$_3$ | N.A. |
| 5dy | SO$_2$ | 5-OCH$_3$ | CF$_3$ | 4.3 |
| 5ey | SO$_2$ | 5-OCH$_3$ | NH$_2$ | 0.6 |
| 5fy | SO$_2$ | 5-OCH$_3$ | COOH | N.A. |
| 5gy | SO$_2$ | 5-OCH$_3$ | C.C.[†] | 0.5 |
| 6ax | S | 6-OCH$_3$ | NO$_2$ | 6.3 |
| 6bx | S | 6-OCH$_3$ | COOCH$_3$ | 0.2 |
| 6cx | S | 6-OCH$_3$ | OCH$_3$ | N.A. |
| 6dx | S | 6-OCH$_3$ | CF$_3$ | 5.3 |
| 6ex | S | 6-OCH$_3$ | NH$_2$ | 1.5 |
| 6fx | S | 6-OCH$_3$ | COOH | 1.9 |
| 6gx | S | 6-OCH$_3$ | C.C.[†] | 52 |
| 6ay | SO$_2$ | 6-OCH$_3$ | NO$_2$ | N.A. |
| 6by | SO$_2$ | 6-OCH$_3$ | COOCH$_3$ | N.A. |
| 6cy | SO$_2$ | 6-OCH$_3$ | OCH$_3$ | N.A. |
| 6dy | SO$_2$ | 6-OCH$_3$ | CF$_3$ | N.A. |
| 6ey | SO$_2$ | 6-OCH$_3$ | NH$_2$ | 1.5 |
| 6fy | SO$_2$ | 6-OCH$_3$ | COOH | 1.2 |
| 6gy | SO$_2$ | 6-OCH$_3$ | C.C.[†] | N.A. |
| 7ax | S | 6-F | NO$_2$ | 3.9 |
| 7bx | S | 6-F | COOCH$_3$ | 7.8 |
| 7cx | S | 6-F | OCH$_3$ | N.A. |
| 7dx | S | 6-F | CF$_3$ | 10.0 |
| 7ex | S | 6-F | NH$_2$ | N.A. |
| 7fx | S | 6-F | COOH | 4.9 |
| 7gx | S | 6-F | C.C.[†] | N.A. |
| 7ay | SO$_2$ | 6-F | NO$_2$ | N.A. |
| 7by | SO$_2$ | 6-F | COOCH$_3$ | N.A. |
| 7cy | SO$_2$ | 6-F | OCH$_3$ | N.A. |
| 7dy | SO$_2$ | 6-F | CF$_3$ | N.A. |
| 7ey | SO$_2$ | 6-F | NH$_2$ | 15 |
| 7fy | SO$_2$ | 6-F | COOH | N.A. |
| 7gy | SO$_2$ | 6-F | C.C.[†] | N.A. |

N.A. = No activity 50 μM;
[†]C.C. = Choline carboxylate

TABLE 9

Summary Tabulation of the library and IC$_{50}$ values.

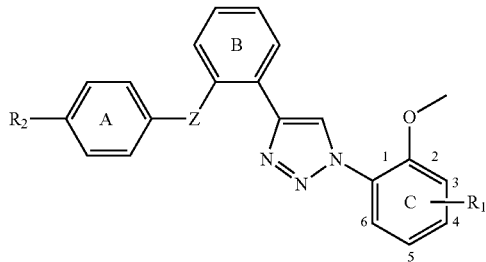

$R_1$ = H (2), 3-OCH$_3$ (3), 4-OCH$_3$ (4), 5-OCH$_3$ (5), 6-OCH$_3$ (6), 6-F (7)
$R_2$ = NO$_2$ (a), COOCH$_3$ (b), OCH$_3$ (c), CF$_3$ (d), NH$_2$ (e), COOH (f)
Choline carboxylate (g)
Z = S (x), SO$_2$ (y)

| Cmpd | Z | R1 | R$_2$ | Antiviral activity (IC$_{50}$ μM) H9 cells | Antiviral activity (IC$_{50}$ μM) MT4 cells |
|---|---|---|---|---|---|
| 2ax (1d) | S | H | NO$_2$ | 1.2 | N.A. |
| 2ay | SO$_2$ | H | NO$_2$ | 13.8 | N.A. |
| 2bx | S | H | COOCH$_3$ | N.A. | N.A. |
| 2by | SO$_2$ | H | COOCH$_3$ | N.A. | N.A. |
| 2cx | S | H | OCH$_3$ | 13.6 | N.T. |
| 2cy | SO$_2$ | H | OCH$_3$ | 4.3 | N.A. |
| 2dx | S | H | CF$_3$ | 2.6 | N.A. |
| 2dy | SO$_2$ | H | CF$_3$ | 4.8 | N.A. |
| 2ex | S | H | NH$_2$ | 2.5 | N.A. |
| 2ey | SO$_2$ | H | NH$_2$ | 0.4 | N.A. |
| 2fx | S | H | COOH | 1 | N.A. |
| 2fy | SO$_2$ | H | COOH | 8.2 | N.A. |
| 2gx | S | H | C.C.[†] | N.A. | N.A. |
| 2gy | SO$_2$ | H | C.C.[†] | 0.2 | N.A. |
| 3ax | S | 3-OCH$_3$ | NO$_2$ | 1.1 | N.A. |
| 3ay | SO$_2$ | 3-OCH$_3$ | NO$_2$ | N.A. | N.A. |
| 3bx | S | 3-OCH$_3$ | COOCH$_3$ | 8 | N.A. |
| 3by | SO$_2$ | 3-OCH$_3$ | COOCH$_3$ | 4.7 | N.A. |
| 3cx | S | 3-OCH$_3$ | OCH$_3$ | 4.7 | N.T. |
| 3cy | SO$_2$ | 3-OCH$_3$ | OCH$_3$ | N.A. | N.A. |
| 3dx | S | 3-OCH$_3$ | CF$_3$ | 1.9 | N.A. |
| 3dy | SO$_2$ | 3-OCH$_3$ | CF$_3$ | N.A. | N.A. |
| 3ex | S | 3-OCH$_3$ | NH$_2$ | 5 | N.T. |
| 3ey | SO$_2$ | 3-OCH$_3$ | NH$_2$ | 12.4 | N.A. |
| 3fx | S | 3-OCH$_3$ | COOH | 2.8 | N.A. |
| 3fy | SO$_2$ | 3-OCH$_3$ | COOH | 1.4 | N.A. |
| 3gx | S | 3-OCH$_3$ | C.C.[†] | 4.3 | N.A. |
| 3gy | SO$_2$ | 3-OCH$_3$ | C.C.[†] | N.A. | N.A. |
| 4ax | S | 4-OCH$_3$ | NO$_2$ | N.A. | N.T. |
| 4ay | SO$_2$ | 4-OCH$_3$ | NO$_2$ | N.A. | N.A. |
| 4bx | S | 4-OCH$_3$ | COOCH$_3$ | 2 | N.T. |
| 4by | SO$_2$ | 4-OCH$_3$ | COOCH$_3$ | 7.6 | N.T. |
| 4cx | S | 4-OCH$_3$ | OCH$_3$ | N.A. | N.T. |
| 4cy | SO$_2$ | 4-OCH$_3$ | OCH$_3$ | N.A. | N.A. |
| 4dx | S | 4-OCH$_3$ | CF$_3$ | 1.1 | N.T. |
| 4dy | SO$_2$ | 4-OCH$_3$ | CF$_3$ | 12 | N.A. |
| 4ex | S | 4-OCH$_3$ | NH$_2$ | N.A. | N.T. |
| 4ey | SO$_2$ | 4-OCH$_3$ | NH$_2$ | N.A. | N.T. |
| 4fx | S | 4-OCH$_3$ | COOH | 7.1 | N.A. |
| 4fy | SO$_2$ | 4-OCH$_3$ | COOH | N.A. | N.T. |
| 4gx | S | 4-OCH$_3$ | C.C.[†] | N.A. | N.T. |
| 4gy | SO$_2$ | 4-OCH$_3$ | C.C.[†] | 0.7 | N.A. |
| 5ax | S | 5-OCH$_3$ | NO$_2$ | 0.01 | N.A. |
| 5ay | SO$_2$ | 5-OCH$_3$ | NO$_2$ | 1 | N.A. |
| 5bx | S | 5-OCH$_3$ | COOCH$_3$ | 0.2 | N.A. |
| 5by | SO$_2$ | 5-OCH$_3$ | COOCH$_3$ | 4.6 | N.A. |
| 5cx | S | 5-OCH$_3$ | OCH$_3$ | 15.7 | N.A. |
| 5cy | SO$_2$ | 5-OCH$_3$ | OCH$_3$ | N.A. | N.A. |
| 5dx | S | 5-OCH$_3$ | CF$_3$ | 46.4 | N.A. |
| 5dy | SO$_2$ | 5-OCH$_3$ | CF$_3$ | 4.3 | N.T. |
| 5ex | S | 5-OCH$_3$ | NH$_2$ | N.A. | N.A. |
| 5ey | SO$_2$ | 5-OCH$_3$ | NH$_2$ | 0.6 | N.A. |
| 5fx | S | 5-OCH$_3$ | COOH | 4.5 | N.A. |
| 5fy | SO$_2$ | 5-OCH$_3$ | COOH | N.A. | N.A. |
| 5gx | S | 5-OCH$_3$ | C.C.[†] | N.A. | N.T. |
| 5gy | SO$_2$ | 5-OCH$_3$ | C.C.[†] | 0.5 | N.A. |
| 6ax | S | 6-OCH$_3$ | NO$_2$ | 6.3 | N.T. |
| 6ay | SO$_2$ | 6-OCH$_3$ | NO$_2$ | N.A. | N.A. |
| 6bx | S | 6-OCH$_3$ | COOCH$_3$ | 0.2 | N.T. |
| 6by | SO$_2$ | 6-OCH$_3$ | COOCH$_3$ | N.A. | N.A. |
| 6cx | S | 6-OCH$_3$ | OCH$_3$ | N.A. | N.T. |
| 6cy | SO$_2$ | 6-OCH$_3$ | OCH$_3$ | N.A. | N.A. |
| 6dx | S | 6-OCH$_3$ | CF$_3$ | 5.3 | N.T. |
| 6dy | SO$_2$ | 6-OCH$_3$ | CF$_3$ | N.A. | N.T. |
| 6ex | S | 6-OCH$_3$ | NH$_2$ | 1.5 | N.T. |
| 6ey | SO$_2$ | 6-OCH$_3$ | NH$_2$ | 1.5 | N.A. |
| 6fx | S | 6-OCH$_3$ | COOH | 1.9 | N.A. |
| 6fy | SO$_2$ | 6-OCH$_3$ | COOH | 1.2 | N.A. |
| 6gx | S | 6-OCH$_3$ | C.C.[†] | 52 | N.A. |
| 6gy | SO$_2$ | 6-OCH$_3$ | C.C.[†] | N.A. | N.A. |
| 7ax | S | 6-F | NO$_2$ | 3.9 | N.A. |
| 7ay | SO$_2$ | 6-F | NO$_2$ | N.A. | N.A. |
| 7bx | S | 6-F | COOCH$_3$ | 7.8 | N.A. |
| 7by | SO$_2$ | 6-F | COOCH$_3$ | N.A. | N.T. |
| 7cx | S | 6-F | OCH$_3$ | N.A. | N.T. |
| 7cy | SO$_2$ | 6-F | OCH$_3$ | N.A. | N.A. |
| 7dx | S | 6-F | CF$_3$ | 10 | N.T. |
| 7dy | SO$_2$ | 6-F | CF$_3$ | N.A. | N.A. |
| 7ex | S | 6-F | NH$_2$ | N.A. | N.A. |
| 7ey | SO$_2$ | 6-F | NH$_2$ | 15 | N.A. |
| 7fx | S | 6-F | COOH | 4.9 | N.A. |
| 7fy | SO$_2$ | 6-F | COOH | N.A. | N.A. |
| 7gx | S | 6-F | C.C.[†] | N.A. | N.T. |
| 7gy | SO$_2$ | 6-F | C.C.[†] | N.A. | N.T. |

N.A. = No activity 50 μM;
[†]C.C. = Choline carboxylate.
N.T. = not tested.

REFERENCES (EXAMPLE 4)

[1] Mehellou, Y.; Clercq, E. D. Twenty-Six Years of Anti-HIV Drug Discovery: Where Do We Stand and Where Do We Go? J. Med. Chem., 2010, 53, 521-538; [2] Thompson, M. A.; Aberg, J. A.; Cahn, P.; Montaner, J. S. G.; Rizzardini, G.; Telenti, A.; Gatell, J. M.; Ginthard, H. F.; Hammer, S. M.; Hirsch, M. S.; Jacobsen, D. M.; Reiss, P.; Richman, D. D.; Volberding, P. A.; Yeni, P.; Schooley, R. T. Antiretroviral treatment of adult HIV infection: 2010 recom-mendations of the International AIDS Society-USA panel. JAMA 2010, 304, 321-333; [3] Volderbing, P. A.; Deeks, S. G. Antiretroviral therapy and management of HIV injection. Lancet 2010, 376, 49-62; [12] Ko, E.; Liu, J.; Perez, L. M.; Lu, G.; Schaefer, A.; Burgess, K.

Universal Peptidomimetics. J. Am. Chem. Soc. 2011, 133, 462-477; [13] Borg, S.; Vollinga, R. C.; Labarre, M.; Payza, K.; Terenius, L.; Luthman, K. Design, Synthesis, and Evaluation of Phe-Gly Mimetics: Heterocyclic Building Blocks of Pseudopeptides. J. Med. Chem. 1999, 42, 4331-4342; [14] Valverde, I. E.; Bauman, A.; Kluba, C. A.; Vomstein, S.; Walter, M. A.; Mindt, T. L. 1,2,3-Triazoles as Amide Bond Mim-ics: Triazole Scan Yields Protease-Resistant Peptidomimetics for Tumor Targeting. Angew. Chem. Int. Ed. 2013, 52, 8957-8960; [15] Tam, A.; Arnold, U.; Soellner, M. B.; Raines, R. T. Protein Prosthesis: 1,5-Disubstituted[1,2,3]triazoles as cis-Peptide Bond Surrogates. J. Am. Chem. Soc. 2007, 129, 12670-12671; [16] Sperotto, E.; van Klink, G. P. M.; de Vries, J. G.; van Ko-ten, G. Ligand-Free Copper-Catalyzed C-S Coupling of Aryl Iodides and Thiols. J. Org. Chem. 2008, 73, 5625-5628; [17] Liang, G.-B.; Feng, D. D. An Improved Oxadiazole Syn-thesis Using Peptide Coupling Reagents. Tetrahedron Lett., 1996, 37, 6627-6630; [18] Sonogashira, K.; Tohda, Y.; Hagihara, N. A convenient synthesis of acetylenes: catalytic substitutions of acetylenic hydrogen with bromoalkenes, iodoarenes and bromopyridines. Tetrahedron Lett. 1975, 16, 4467-4470; [19] Tao, C.-Z.; Cui, X.; Li, J.; Liu, A-X.; Liu, L.; Guo, Q-X. Copper-catalyzed Synthesis of Aryl Azides and 1-Aryl-1,2,3-Triazoles from Boronic Acids. Tetrahedron Lett. 2007, 48, 3525-3529; [20] Rostovtsev, V. V.; Green, L. G.; Fokin, V. V.; Sharpless, K. B. A Stepwise Huisgen Cycloaddition Process: Copper(I)-Catalyzed Regioselective "Ligation" of Azides and Terminal Alkynes. Angew. Chem. Int. Ed. 2002, 41, 2596-2599; [21] Zhang, L.; Chen, X.; Xue, P.; Sun, H. H. Y.; Williams, I. D.; Sharpless, K. B.; Fokin, V. V.; Jia, G. Ruthenium-Catalyzed Cycloaddition of Alkynes and Organic Azides. J. Am. Chem. Soc. 2005, 127, 15998-15999; [22] Tron, G. C.; Pirali, T.; Billington, R. A.; Canonico, P. L.; Sorba, G.; Genazzani, A. A. Click chemistry reactions in medicinal chemistry: applications of the 1,3-dipolar cycloaddition between azides and alkynes. Med. Res. Rev. 2008, 28, 278-308.

TABLE 10

SMILES notation for chemical compounds.

| Cmpd | Simplified molecular-input line-entry system (SMILES) notation |
|---|---|
| 1b | COC1=CC=CC=C1C(O2)=NN=C2C3=CC=CC=C3SC4=CC=C([N+]([O-])=O)C=C4 |
| 1c | COC1=CC=CC=C1 C2=NOC(C3=CC=CC=C3SC4=CC=C([N+]([O-])=O)C=C4)=N2 |
| 1d (2ax) | COC1=CC=CC=C1N2N=NC(C3=CC=CC=C3SC4=CC=C([N+]([O-])=O)C=C4)=C2 |
| 1e | COC1=CC=CC=C1N2C(C3=CC=CC=C3SC4=CC=C([N+]([O-])=O)C=C4)=CN=N2 |
| 2bx | COC1=CC=CC=C1N2N=NC(C3=CC=CC=C3SC4=CC=C(C(OC)=O)C=C4)=C2 |
| 2cx | COC1=CC=CC=C1N2N=NC(C3=CC=CC=C3SC4=CC=C(OC)C=C4)=C2 |
| 2dx | COC1=CC=CC=C1N2N=NC(C3=CC=CC=C3SC4=CC=C(C(F)(F)F)C=C4)=C2 |
| 2ex | NC(C=C1)=CC=C1SC2=CC=CC=C2C3=CN(C4=CC=CC=C4OC)N=N3 |
| 2fx | COC1=CC=CC=C1N2N=NC(C3=CC=CC=C3SC4=CC=C(C(O)=O)C=C4)=C2 |
| 2gx | COC1=CC=CC=C1N2N=NC(C3=CC=CC=C3SC4=CC=C(C([O-])=O)C=C4)=C2•C[N+](C)(CCO)C |
| 2ay | COC1=CC=CC=C1N2N=NC(C3=CC=CC=C3S(C4=CC=C([N+]([O-])=O)C=C4)(=O)=O)=C2 |
| 2by | COC1=CC=CC=C1N2N=NC(C3=CC=CC=C3S(C4=CC=C(C(OC)=O)C=C4)(=O)=O)=C2 |
| 2cy | COC1=CC=CC=C1N2N=NC(C3=CC=CC=C3S(C4=CC=C(OC)C=C4)(=O)=O)=C2 |
| 2dy | COC1=CC=CC=C1N2N=NC(C3=CC=CC=C3S(C4=CC=C(C(F)(F)F)C=C4)(=O)=O)=C2 |
| 2ey | NC(C=C1)=CC=C1S(C2=CC=CC=C2C3=CN(C4=CC=CC=C4OC)N=N3)(=O)=O |
| 2fy | COC1=CC=CC=C1N2N=NC(C3=CC=CC=C3S(C4=CC=C(C(O)=O)C=C4)(=O)=O)=C2 |
| 2gy | COC1=CC=CC=C1N2N=NC(C3=CC=CC=C3S(C4=CC=C(C([O-])=O)C=C4)(=O)=O)=C2•C[N+](C)(CCO)C |
| 3ax | COC1=C(OC)C=CC=C1N2N=NC(C3=CC=CC=C3SC4=CC=C([N+]([O-])=O)C=C4)=C2 |
| 3bx | COC1=C(OC)C=CC=C1N2N=NC(C3=CC=CC=C3SC4=CC=C(C(OC)=O)C=C4)=C2 |
| 3cx | COC1=C(OC)C=CC=C1N2N=NC(C3=CC=CC=C3SC4=CC=C(OC)C=C4)=C2 |
| 3dx | COC1=C(OC)C=CC=C1N2N=NC(C3=CC=CC=C3SC4=CC=C(C(F)(F)F)C=C4)=C2 |
| 3ex | NC(C=C1)=CC=C1SC2=CC=CC=C2C3=CN(C4=CC=CC(OC)=C4OC)N=N3 |
| 3fx | COC1=C(OC)C=CC=C1N2N=NC(C3=CC=CC=C3SC4=CC=C(C(O)=O)C=C4)=C2 |
| 3gx | COC1=C(OC)C=CC=C1N2N=NC(C3=CC=CC=C3SC4=CC=C(C([O-])=O)C=C4)=C2•C[N+](C)(CCO)C |
| 3ay | COC1=C(OC)C=CC=C1N2N=NC(C3=CC=CC=C3S(C4=CC=C([N+1([O-])=O)C=C4)(=O)=O)=C2 |
| 3by | COC1=C(OC)C=CC=C1N2N=NC(C3=CC=CC=C3S(C4=CC=C(C(OC)=O)C=C4)(=O)=O)=C2 |
| 3cy | COC1=C(OC)C=CC=C1N2N=NC(C3=CC=CC=C3S(C4=CC=C(OC)C=C4)(=O)=O)=C2 |
| 3dy | COC1=C(OC)C=CC=C1N2N=NC(C3=CC=CC=C3S(C4=CC=C(C(F)(F)F)C=C4)(=O)=O)=C2 |
| 3ey | NC(C=C1)=CC=C1S(C2=CC=CC=C2C3=CN(C4=CC=CC(OC)=C4OC)N=N3)(=O)=O |
| 3fy | COC1=C(OC)C=CC=C1N2N=NC(C3=CC=CC=C3S(C4=CC=C(C(O)=O)C=C4)(=O)=O)=C2 |
| 3gy | COC1=C(OC)C=CC=C1N2N=NC(C3=CC=CC=C3S(C4=CC=C(C([O-])=O)C=C4)(=O)=O)=C2•C[N+](C)(CCO)C |
| 4ax | COC1=CC(OC)=CC=C1N2N=NC(C3=CC=CC=C3SC4=CC=C([N+]([O-])=O)C=C4)=C2 |
| 4bx | COC1=CC(OC)=CC=C1N2N=NC(C3=CC=CC=C3SC4=CC=C(C(OC)=O)C=C4)=C2 |
| 4cx | COC1=CC(OC)=CC=C1N2N=NC(C3=CC=CC=C3SC4=CC=C(OC)C=C4)=C2 |
| 4dx | COC1=CC(OC)=CC=C1N2N=NC(C3=CC=CC=C3SC4=CC=C(C(F)(F)F)C=C4)=C2 |
| 4ex | NC(C=C1)=CC=C1SC2=CC=CC=C2C3=CN(C4=CC=C(OC)C=C4OC)N=N3 |
| 4fx | COC1=CC(OC)=CC=C1N2N=NC(C3=CC=CC=C3SC4=CC=C(C(O)=O)C=C4)=C2 |
| 4gx | COC1=CC(OC)=CC=C1N2N=NC(C3=CC=CC=C3S(C4=CC=C(C([O-])=O)C=C4)(=O)=O)=C2•C[N+](C)(CCO)C |
| 4ay | COC1=CC(OC)=CC=C1N2N=NC(C3=CC=CC=C3S(C4=CC=C([N+]([O-])=O)C=C4)(=O)=O)=C2 |
| 4by | COC1=CC(OC)=CC=C1N2N=NC(C3=CC=CC=C3S(C4=CC=C(C(OC)=O)C=C4)(=O)=O)=C2 |
| 4cy | COC1=CC(OC)=CC=C1N2N=NC(C3=CC=CC=C3S(C4=CC=C(OC)C=C4)(=O)=O)=C2 |
| 4dy | COC1=CC(OC)=CC=C1N2N=NC(C3=CC=CC=C3S(C4=CC=C(C(F)(F)F)C=C4)(=O)=O)=C2 |
| 4ey | NC(C=C1)=CC=C1S(C2=CC=CC=C2C3=CN(C4=CC=C(OC)C=C4OC)N=N3)(=O)=O |
| 4fy | COC1=CC(OC)=CC=C1N2N=NC(C3=CC=CC=C3S(C4=CC=C(C(O)=O)C=C4)(=O)=O)=C2 |
| 4gy | COC1=CC(OC)=CC=C1N2N=NC(C3=CC=CC=C3S(C4=CC=C(C([O-])=O)C=C4)(=O)=O)=C2•C[N+](C)(CCO)C |
| 5ax | COC1=CC=C(OC)C=C1N2N=NC(C3=CC=CC=C3SC4=CC=C([N+]([O-])=O)C=C4)=C2 |
| 5bx | COC1=CC=C(OC)C=C1N2N=NC(C3=CC=CC=C3SC4=CC=C(C(OC)=O)C=C4)=C2 |
| 5cx | COC1=CC=C(OC)C=C1N2N=NC(C3=CC=CC=C3SC4=CC=C(OC)C=C4)=C2 |
| 5dx | COC1=CC=C(OC)C=C1N2N=NC(C3=CC=CC=C3SC4=CC=C(C(F)(F)F)C=C4)=C2 |
| 5ex | NC(C=C1)=CC=C1SC2=CC=CC=C2C3=CN(C4=CC(OC)=CC=C4OC)N=N3 |

TABLE 10-continued

SMILES notation for chemical compounds.

| Cmpd | Simplified molecular-input line-entry system (SMILES) notation |
|---|---|
| 5fx | COC1=CC=C(OC)C=C1N2N=NC(C3=CC=CC=C3SC4=CC=C(C(O)=O)C=C4)=C2 |
| 5gx | COC1=CC=C(OC)C=C1N2N=NC(C3=CC=CC=C3SC4=CC=C(C([O-])=O)C=C4)=C2•C[N+](C)(CCO)C |
| 5ay | COC1=CC=C(OC)C=C1N2N=NC(C3=CC=CC=C3S(C4=CC=C([N+]([O-])=O)C=C4)(=O)=O)=C2 |
| 5by | COC1=CC=C(OC)C=C1N2N=NC(C3=CC=CC=C3S(C4=CC=C(C(OC)=O)C=C4)(=O)=O)=C2 |
| 5cy | COC1=CC=C(OC)C=C1N2N=NC(C3=CC=CC=C3S(C4=CC=C(OC)C=C4)(=O)=O)=C2 |
| 5dy | COC1=CC=C(OC)C=C1N2N=NC(C3=CC=CC=C3S(C4=CC=C(C(F)(F)F)C=C4)(=O)=O)=C2 |
| 5ey | NC(=C1)=CC=C1S(C2=CC=CC=C2C3=CN(C4=CC(OC)=CC=C4OC)N=N3)(=O)=O |
| 5fy | COC1=CC=C(OC)C=C1N2N=NC(C3=CC=CC=C3S(C4=CC=C(C(O)=O)C=C4)(=O)=O)=C2 |
| 5gy | COC1=CC=C(OC)C=C1N2N=NC(C3=CC=CC=C3S(C4=CC=C(C([O-])=O)C=C4)(=O)=O)=C2•C[N+](C)(CCO)C |
| 6ax | COC1=CC=CC(OC)=C1N2N=NC(C3=CC=CC=C3SC4=CC=C([N+]([O-])=O)C=C4)=C2 |
| 6bx | COC1=CC=CC(OC)=C1N2N=NC(C3=CC=CC=C3SC4=CC=C(C(OC)=O)C=C4)=C2 |
| 6cx | COC1=CC=CC(OC)=C1N2N=NC(C3=CC=CC=C3SC4=CC=C(OC)C=C4)=C2 |
| 6dx | COC1=CC=CC(OC)=C1N2N=NC(C3=CC=CC=C3SC4=CC=C(C(F)(F)F)C=C4)=C2 |
| 6ex | NC(=C1)=CC=C1SC2=CC=CC=C2C3=CN(C4=C(OC)C=CC=C4OC)N=N3 |
| 6fx | COC1=CC=CC(OC)=C1N2N=NC(C3=CC=CC=C3SC4=CC=C(C(O)=O)C=C4)=C2 |
| 6gx | COC1=CC=CC(OC)=C1N2N=NC(C3=CC=CC=C3SC4=CC=C(C([O-])=O)C=C4)=C2•C[N+](C)(CCO)C |
| 6ay | COC1=CC=CC(OC)=C1N2N=NC(C3=CC=CC=C3S(C4=CC=C([N+]([O-])=O)C=C4)(=O)=O)=C2 |
| 6by | COC1=CC=CC(OC)=C1N2N=NC(C3=CC=CC=C3S(C4=CC=C(C(OC)=O)C=C4)(=O)=O)=C2 |
| 6cy | COC1=CC=CC(OC)=C1N2N=NC(C3=CC=CC=C3S(C4=CC=C(OC)C=C4)(=O)=O)=C2 |
| 6dy | COC1=CC=CC(OC)=C1N2N=NC(C3=CC=CC=C3S(C4=CC=C(C(F)(F)F)C=C4)(=O)=O)=C2 |
| 6ey | NC(=C1)=CC=C1S(C2=CC=CC=C2C3=CN(C4=C(OC)C=CC=C4OC)N=N3)(=O)=O |
| 6fy | COC1=CC=CC(OC)=C1N2N=NC(C3=CC=CC=C3S(C4=CC=C(C(O)=O)C=C4)(=O)=O)=C2 |
| 6gy | COC1=CC=CC(OC)=C1N2N=NC(C3=CC=CC=C3S(C4=CC=C(C([O-])=O)C=C4)(=O)=O)=C2•C[N+](C)(CCO)C |
| 7ax | COC1=CC=CC(F)=C1N2N=NC(C3=CC=CC=C3SC4=CC=C([N+]([O-])=O)C=C4)=C2 |
| 7bx | COC1=CC=CC(F)=C1N2N=NC(C3=CC=CC=C3SC4=CC=C(C(OC)=O)C=C4)=C2 |
| 7cx | COC1=CC=CC(F)=C1N2N=NC(C3=CC=CC=C3SC4=CC=C(OC)C=C4)=C2 |
| 7dx | COC1=CC=CC(F)=C1N2N=NC(C3=CC=CC=C3SC4=CC=C(C(F)(F)F)C=C4)=C2 |
| 7ex | NC(=C1)=CC=C1SC2=CC=CC=C2C3=CN(C4=C(F)C=CC=C4OC)N=N3 |
| 7fx | COC1=CC=CC(F)=C1N2N=NC(C3=CC=CC=C3SC4=CC=C(C(O)=O)C=C4)=C2 |
| 7ay | COC1=CC=CC(F)=C1N2N=NC(C3=CC=CC=C3S(C4=CC=C([N+]([O-])=O)C=C4)(=O)=O)=C2 |
| 7by | COC1=CC=CC(F)=C1N2N=NC(C3=CC=CC=C3S(C4=CC=C(C(OC)=O)C=C4)(=O)=O)=C2 |
| 7cy | COC1=CC=CC(F)=C1N2N=NC(C3=CC=CC=C3S(C4=CC=C(OC)C=C4)(=O)=O)=C2 |
| 7dy | COC1=CC=CC(F)=C1N2N=NC(C3=CC=CC=C3S(C4=CC=C(C(F)(F)F)C=C4)(=O)=O)=C2 |
| 7ey | NC(=C1)=CC=C1S(C2=CC=CC=C2C3=CN(C4=C(F)C=CC=C4OC)N=N3)(=O)=O |
| 7fy | COC1=CC=CC(F)=C1N2N=NC(C3=CC=CC=C3S(C4=CC=C(C(O)=O)C=C4)(=O)=O)=C2 |
| 7gy | COC1=CC=CC(F)=C1N2N=NC(C3=CC=CC=C3S(C4=CC=C(C([O-])=O)C=C4)(=O)=O)=C2•C[N+](C)(CCO)C |
| 1g | COC1=CC=CC=C1C(O2)=NN=C2C3=CC=CC=C3I |
| 1h | COC1=CC=C1C2=NOC(C3=CC=CC=C3I)=N2 |
| 1l | NC1=CC=CC=C1C2=CN(C3=CC=CC=C3OC)N=N2 |
| 1m | IC1=CC=CC=C1C2=CN(C3=CC=CC=C3OC)N=N2 |
| 1n | NC1=CC=CC=C1C2=CN=NN2C3=CC=CC=C3OC |
| 1o | IC1=CC=CC=C1C2=CN=NN2C3=CC=CC=C3OC |
| 9a | NC1=CC=CC=C1C2=CN(N=N2)C3=CC=CC(OC)=C3OC |
| 9b | NC1=CC=CC=C1C2=CN(N=N2)C3=CC=C(OC)C=C3OC |
| 9c | NC1=CC=CC=C1C2=CN(N=N2)C3=CC(OC)=CC=C3OC |
| 9d | NC1=CC=CC=C1C2=CN(N=N2)C3=C(OC)C=CC=C3OC |
| 9e | NC1=CC=CC=C1C2=CN(N=N2)C3=C(F)C=CC=C3OC |
| 10a | IC1=CC=CC=C1C2=CN(N=N2)C3=CC=CC(OC)=C3OC |
| 10b | IC1=CC=CC=C1C2=ON(N=N2)C3=CC=C(OC)C=C3OC |
| 10c | IC1=CC=CC=C1C2=CN(N=N2)C3=CC(OC)=CC=C3OC |
| 10d | IC1=CC=CC=C1C2=CN(N=N2)C3=C(OC)C=CC=C3OC |
| 10e | IC1=CC=CC=C1C2=CN(N=N2)C3=C(F)C=CC=C3OC |

EMBODIMENTS

Embodiment P1

A compound with structure

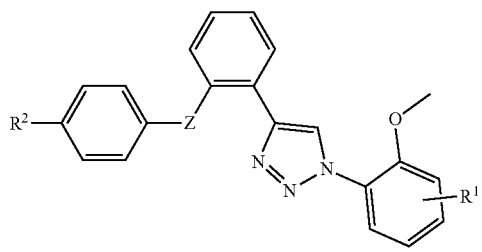

wherein

R[1] is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;

R[2] is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and Z is —S— or —SO$_2$—.

Embodiment P2

The compound of embodiment P1, wherein R$^1$ is hydrogen, halogen, or —OCH$_3$; and R$^2$ is —NO$_2$, —COOCH$_3$, —OCH$_3$, —CF$_3$, —NH$_2$, —COOH, or choline carboxylate.

Embodiment P3

A method for inhibiting Vif protein activity in a subject in need thereof, said method comprising administering an effective amount of a compound of embodiment P1 to said subject.

Embodiment P4

A compound with structure

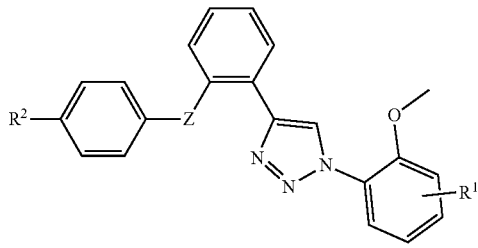

wherein
R$^1$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;
R$^2$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and Z is —S— or —SO$_2$—.

Embodiment P5

The compound of embodiment P4, wherein R$^1$ is hydrogen, halogen, or —OCH$_3$; and R$^2$ is —NO$_2$, —COOCH$_3$, —OCH$_3$, —CF$_3$, —NH$_2$, —COOH, or choline carboxylate.

Embodiment P6

The compound of embodiment P4, wherein Z is —S—.

Embodiment P7

A method for treating a viral infection, said method comprising administering to a subject in need thereof a therapeutically effective amount of a compound according to embodiment P4.

Embodiment P8

The method according to embodiment P7, wherein said viral infection is HIV-1, Ebola or Zika virus infection.

Additional Embodiments

Embodiment 1

A compound, or a pharmaceutically acceptable salt thereof, having the formula:

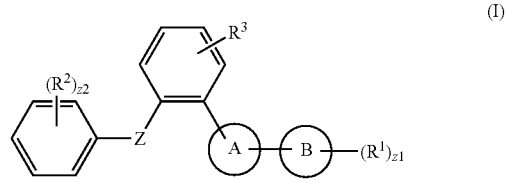

wherein
Ring A is a substituted or unsubstituted 5 membered heteroaryl;
Ring B is a phenyl or 6 membered heteroaryl;
R$^1$ is independently
halogen, —CX$^1_3$, —CHX$^1_2$, —CH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is
halogen, —CX$^2_3$, —CHX$^2_2$, —CH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is hydrogen,
halogen, —CX$^3_3$, —CHX$^3_2$, —CH$_2$X$^3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^3_3$, —OCHX$^3_2$, —OCH$_2$X$^3$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, Z is —S— or —SO$_2$—; X$^1$, X$^2$, and X$^3$ are independently —F, —Cl, —Br, or —I; and z1 and z2 are independently an integer from 0 to 5.

Embodiment 2

The compound of embodiment 1, wherein z2 is 1

Embodiment 3

The compound of one of embodiments 1 to 2, having the formula:

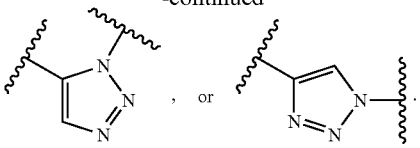

(II)

Embodiment 4

The compound of one of embodiments 1 to 3, wherein Ring A is a substituted or unsubstituted oxadiazolyl.

Embodiment 5

The compound of one of embodiments 1 to 3, wherein Ring A is a substituted or unsubstituted 1,3,4-oxadiazolyl.

Embodiment 6

The compound of one of embodiments 1 to 3, wherein Ring A is a substituted or unsubstituted 1,2,4-oxadiazolyl.

Embodiment 7

The compound of one of embodiments 1 to 3, wherein Ring A is a substituted or unsubstituted triazolyl.

Embodiment 8

The compound of one of embodiments 1 to 3, wherein Ring A is a substituted or unsubstituted 1,2,3-triazolyl.

Embodiment 9

The compound of one of embodiments 1 to 3, wherein Ring A is

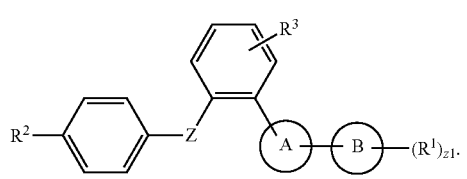

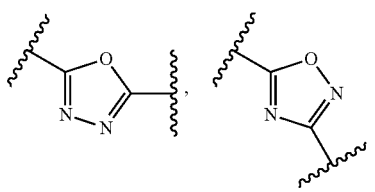

Embodiment 10

The compound of one of embodiments 1 to 9, wherein Ring B is a phenyl.

Embodiment 11

The compound of one of embodiments 1 to 9, wherein Ring B is a 6 membered heteroaryl.

Embodiment 12

The compound of one of embodiments 1 to 9, wherein Ring B is a pyridyl.

Embodiment 13

The compound of one of embodiments 1 to 9, or a pharmaceutically acceptable salt thereof, having the formula:

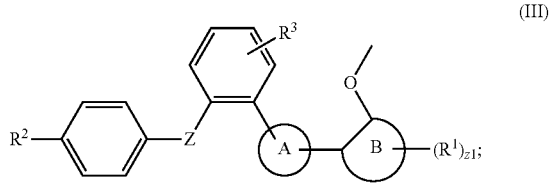

(III)

wherein z1 is an integer from 0 to 4.

Embodiment 14

The compound of one of embodiments 1 to 13, wherein Z is —S—.

Embodiment 15

The compound of one of embodiments 1 to 13, wherein Z is —SO$_2$—.

Embodiment 16

The compound of one of embodiments 1 to 15, wherein R$^3$ is hydrogen.

Embodiment 17

The compound of one of embodiments 1 to 15, wherein R$^1$ is independently halogen, —CX$^1_3$, —CHX$^1_2$, —CH$_2$X$^1$, —OH, —SH, —OCX$^1_3$, —OCHX$^1_2$, —OCH$_2$X$^1$, substi-

Embodiment 18

The compound of one of embodiments 1 to 15, wherein $R^1$ is independently —F, —$CH_3$, or —$OCH_3$.

Embodiment 19

The compound of one of embodiments 1 to 18, wherein z1 is 1.

Embodiment 20

The compound of one of embodiments 1 to 18, wherein z1 is 0.

Embodiment 21

The compound of one of embodiments 1 to 20, wherein $R^2$ is halogen, —$CX^2_3$, —$CHX^2_2$, —$CH_2X^2$, —OH, —$NH_2$, —COOH, —$CONH_2$, —$NO_2$, —SH, —$OCX^2_3$, —$OCHX^2_2$, —$OCH_2X^2$, substituted or unsubstituted $C_1$-$C_4$ alkyl, substituted or unsubstituted 2 to 4 membered heteroalkyl; or a pharmaceutically acceptable salt thereof.

Embodiment 22

The compound of one of embodiments 1 to 20, wherein $R^2$ is —$CF_3$, —$NH_2$, —COOH, —$COOCH_3$, —$NO_2$, —$OCH_3$, —$OCHX^2_2$, —$OCH_2X^2$, or —$COO^-$($HOCH_2CH_2N(CH_3)_3$).

Embodiment 23

A pharmaceutical composition comprising the compound of one of embodiments 1 to 22 and a pharmaceutically acceptable excipient.

Embodiment 24

A method of treating HIV infection in a subject in need thereof, the method comprising administering to the subject an effective amount of a compound of one of embodiments 1 to 22.

Embodiment 25

A method of treating Zika virus infection in a subject in need thereof, the method comprising administering to the subject an effective amount of a compound of one of embodiments 1 to 22.

Embodiment 26

A method of treating Ebola virus infection in a subject in need thereof, the method comprising administering to the subject an effective amount of a compound of one of embodiments 1 to 22.

Embodiment 27

A method of inhibiting Vif protein activity in a subject in need thereof, the method comprising administering an effective amount of a compound of one of embodiments 1 to 22 to the subject.

Embodiment 28

A method of increasing the level of APOBEC3G activity in a subject in need thereof, the method comprising administering an effective amount of a compound of one of embodiments 1 to 22 to the subject.

Embodiment 29

A method of inhibiting degradation of APOBEC3 family proteins in a subject in need thereof, the method comprising administering an effective amount of a compound of one of embodiments 1 to 22 to the subject.

Embodiment 30

A method of inhibiting degradation of APOBEC3G protein in a subject in need thereof, the method comprising administering an effective amount of a compound of one of embodiments 1 to 22 to the subject.

---

What is claimed is:

1. A compound, or a pharmaceutically acceptable salt thereof, having the formula:

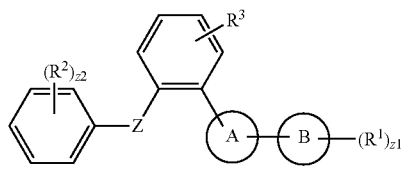

(I)

wherein
Ring A is an unsubstituted 1,3,4-oxadiazolyl, an unsubstituted 1,2,4-oxadiazolyl, or a substituted or unsubstituted 1,2,3-triazolyl;
Ring B is a phenyl or 6 membered heteroaryl;
$R^1$ is independently halogen, $—CX^1_3$, $—CHX^1_2$, $—CH_2X^1$ $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^1_3$, $—OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is independently halogen, $—CX^2_3$, $—CHX^2_2$, $—CH_2X^2$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^2_3$, $—OCHX^2_2$, $—OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is independently hydrogen, halogen, $—CX^3_3$, $—CHX^3_2$, $—CH_2X^3$, $—CN$, $—OH$, $—NH_2$, $—COOH$, —CONH$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^3_3$, —OCHX$^3_2$, —OCH$_2$X$^3$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Z is —S— or —SO$_2$—;

X$^1$, X$^2$, and X$^3$ are independently F, —Cl, —Br, or —I;

z1 is an integer from 0 to 5; and z2 is an integer from 1 to 5.

2. The compound of claim 1, wherein z2 is 1.

3. The compound of claim 1, having the formula:

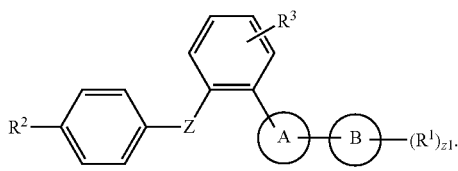

(II)

4. The compound of claim 1, wherein Ring A is

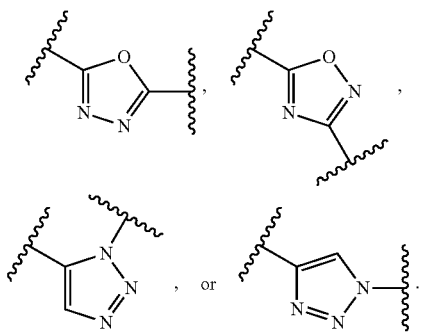

, or

5. The compound of claim 1, wherein Ring B is a phenyl.

6. A compound, or a pharmaceutically acceptable salt thereof, having the formula:

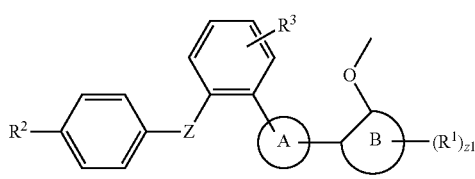

(III)

wherein z1 is an integer from 0 to 4;

Ring A is a substituted or unsubstituted 5 membered heteroaryl;

Ring B is phenyl or a 6 membered heteroaryl;

R$^1$ is independently halogen, —CX$^1_3$, —CHX$^1_2$, —CH$_2$X$^1$—CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently halogen, —CX$^2_3$, —CHX$^2_2$, —CH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^2_3$, —OCHX$^2_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently hydrogen, halogen, —CX$^3_3$, —CHX$^3_2$, —CH$_2$X$^3$, —CN, —OH, —NH$_2$, —COOH, —CONH$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^3_3$, —OCHX$^3_2$, —OCH$_2$X$^3$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Z is —S— or —SO$_2$—;

X$^1$, X$^2$, and X$^3$ are independently —F, —Cl, —Br, or —I; and z2 is an integer from 1 to 5.

7. The compound of claim 1, wherein Z is SO$_2$—.

8. The compound of claim 1, wherein R$^3$ is hydrogen.

9. The compound of claim 1, wherein R$^1$ is independently halogen, —CX$^1_3$, —CHX$^1_2$, —CH$_2$X$^1$, —OH, —OCH$_3$, —SH, —OCX$^1_3$, —OCHX$^1_2$, —OCH$_2$X$^1$, substituted or unsubstituted C$_1$-C$_4$ alkyl, or substituted or unsubstituted 2 to 4 membered heteroalkyl.

10. The compound of claim 9, wherein R$^1$ is independently —F, —CH$_3$, or —OCH$_3$.

11. The compound of claim 1, wherein z1 is 1 or 0.

12. The compound of claim 1, wherein R$^2$ is independently halogen, —CX$^2_3$, —CHX$^2_2$, —CH$_2$X$^2$, —OH, —NH$_2$, —COOH, —CONH$_2$, —NO$_2$, —SH, —OCX$^2_3$, —OCHX$^2_2$, —OCH$_2$X$^2$, substituted or unsubstituted C$_1$-C$_4$ alkyl, or substituted or unsubstituted 2 to 4 membered heteroalkyl.

13. The compound of claim 12, wherein R$^2$ is —CF$_3$, —NH$_2$, —COOH, —COOCH$_3$, —NO$_2$, —OCH$_3$, —OCHX$^2_2$, —OCH$_2$X$^2$, or —COO$^-$(HOCH$_2$CH$_2$N(CH$_3$)$_3$$^+$).

14. The compound of claim 1, wherein Ring A is a substituted or unsubstituted 1,2,3-triazolyl.

15. The compound of claim 1, or a pharmaceutically acceptable salt thereof, having the formula:

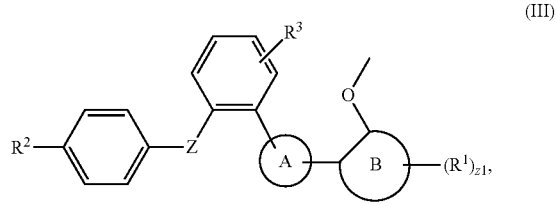

(III)

wherein z1 is an integer from 0 to 4.

16. A pharmaceutical composition comprising the compound of claim 1 and a pharmaceutically acceptable excipient.

* * * * *

SEQUENCE LISTING

```
<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60
```

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
    370                 375                 380

<210> SEQ ID NO 2
<211> LENGTH: 1848
<212> TYPE: DNA
<213> ORGANISM: Homo sapiens

<400> SEQUENCE: 2
gtgctctgct ggctcagcct ggtgtggacc cacctcccgg gcgctggctg caatgacttt     60
ctctttccct ttgcaattgc cttgggtcct gccgcacaga gcggcctgtc tttatcagag    120
gtccctctgc caggggagg gccccagaga aaaccagaaa gagggtgaga gactgaggaa     180
gataaagcgt cccagggcct cctacaccag cgcctgagca ggaagcggga ggggccatga    240
ctacgaggcc ctgggaggtc actttaggga gggctgtcct aaaaccagaa gcttggagca    300

```
gaaagtgaaa ccctggtgct ccagacaaag atcttagtcg ggactagccg gccaaggatg    360
aagcctcact tcagaaacac agtggagcga atgtatcgag acacattctc ctacaacttt    420
tataatagac ccatcctttc tcgtcggaat accgtctggc tgtgctacga agtgaaaaca    480
aagggtccct caaggccccc tttggacgca aagatctttc gaggccaggt gtattccgaa    540
cttaagtacc acccagagat gagattcttc cactggttca gcaagtggag gaagctgcat    600
cgtgaccagg agtatgaggt cacctggtac atatcctgga gcccctgcac aaagtgtaca    660
agggatatgg ccacgttcct ggccgaggac ccgaaggtta ccctgaccat ctttgttgcc    720
cgcctctact acttctggga cccagattac caggaggcgc ttcgcagcct gtgtcagaaa    780
agagacggtc cgcgtgccac catgaagatc atgaattatg acgaatttca gcactgttgg    840
agcaagttcg tgtacagcca aagagagcta tttgagcctt ggaataatct gcctaaatat    900
tatatattac tgcacatcat gctggggag attctcagac actcgatgga tccacccaca    960
ttcactttca actttaacaa tgaaccttgg gtcagaggac ggcatgagac ttacctgtgt    1020
tatgaggtgg agcgcatgca caatgacacc tgggtcctgc tgaaccagcg caggggcttt    1080
ctatgcaacc aggctccaca taaacacggt ttccttgaag gccgccatgc agagctgtgc    1140
ttcctggacg tgattccctt ttggaagctg gacctgacc aggactacag ggttacctgc    1200
ttcacctcct ggagccctg cttcagctgt gcccaggaaa tggctaaatt catttcaaaa    1260
aacaaacacg tgagcctgtg catcttcact gcccgcatct atgatgatca aggaagatgt    1320
caggaggggc tgcgcaccct ggccgaggct ggggccaaaa tttcaataat gacatacagt    1380
gaatttaagc actgctggga caccttttgtg gaccaccagg gatgtccctt ccagccctgg    1440
gatggactag atgagcacag ccaagacctg agtgggaggc tgcgggccat tctccagaat    1500
caggaaaact gaaggatggg cctcagtctc taaggaaggc agagacctgg gttgagcctc    1560
agaataaaag atcttcttcc aagaaatgca aacaggctgt tcaccaccat ctccagctga    1620
tcacagacac cagcaaagca atgcactcct gaccaagtag attcttttaa aaattagagt    1680
gcattacttt gaatcaaaaa tttatttata tttcaagaat aaagtactaa gattgtgctc    1740
aatacacaga aaagtttcaa acctactaat ccagcgacaa tttgaatcgg ttttgtaggt    1800
agaggaataa aatgaaatac taaatctttc tgtaaaaaaa aaaaaaaa                 1848
```